(12) United States Patent
Vyas et al.

(10) Patent No.: US 10,191,055 B2
(45) Date of Patent: Jan. 29, 2019

(54) DETECTION OF ACUTE MYELOID LEUKAEMIA (AML) LEUKAEMIC STEM CELLS (LSC)

(71) Applicant: Isis Innovation Limited, Oxford (GB)

(72) Inventors: Paresh Vyas, Oxford (GB); Lynn Quek, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 252 days.

(21) Appl. No.: 14/934,276

(22) Filed: Nov. 6, 2015

(65) Prior Publication Data

US 2016/0146821 A1 May 26, 2016

Related U.S. Application Data

(60) Provisional application No. 62/084,756, filed on Nov. 26, 2014.

(51) Int. Cl.
*C12Q 1/6886* (2018.01)
*A61K 35/545* (2015.01)
*G01N 33/574* (2006.01)

(52) U.S. Cl.
CPC ..... *G01N 33/57426* (2013.01); *A61K 35/545* (2013.01); *C12Q 1/6886* (2013.01); *G01N 2333/70596* (2013.01); *G01N 2800/52* (2013.01)

(58) Field of Classification Search
CPC ... G01N 33/57426; G01N 2333/70596; G01N 2800/52; A61K 35/545; C12Q 1/6886
See application file for complete search history.

(56) References Cited

U.S. PATENT DOCUMENTS

| 9,789,135 | B2 * | 10/2017 | Turner | C12N 5/0647 |
| 2010/0047217 | A1 * | 2/2010 | Refaeli | C12N 5/0641 424/93.21 |
| 2013/0337474 | A1 | 12/2013 | Vyas | |
| 2015/0299315 | A1 * | 10/2015 | Chronopoulou | C12N 5/0647 435/7.24 |

FOREIGN PATENT DOCUMENTS

| WO | 2014/066271 A1 | 5/2014 |
| WO | 2014/151994 A1 | 9/2014 |

OTHER PUBLICATIONS

Bruedigam et al. Inhibition of Telomerase is a Novel and Effective Therapy in MLL-Rearranged Acute Myeloid Leukemia (AML), Blood, 122: 2887 (Nov. 2013).*
Tiu et al. Differential Expression of SLAM Family Receptor Markers in Normal Human Hematopoietic Stem Cells and Their Malignant Counterpart in MDS and AML, Blood, 108:1897 (2006).*
International Search Report, European Patent Office, International Application No. PCT/GB2015/053363, dated Apr. 4, 2016.
Cramer et al., RAD52-Dependent Synthetic Lethality Eradicates Leukemia Stem Cells, 54th ASH Annual Meeting and Exposition (Atlanta, GA), American Society of Hematology (2012).
Oancea et al., T(13; 17)-PML/RAR-Induced Leukemogenesis: Long-Term Repopulating Hematopoietic Stem Cells as the Initial Target and More Mature Progenitors as the Potential Targets for Final Leukemic Transformation, 51st ASH Annual Meeting and Exposition (New Orleans, LA), American Society of Hematology (2009).
Oancea et al., "Hierarchical" Induction and "Stochastic" Maintenance of Leukemia in an In Vivo Model of t(6;9) Positive Acute Myeloid Leukemia, 51st ASH Annual Meeting and Exposition (New Orleans, LA), American Society of Hematology (2009).
Quek et al., Functional and Genetic Heterogeneity of Distinct Leukemic Stem Cell Populations in CD34—Human Acute Myeloid Leukemia; 56th ASH Annual Meeting and Exposition (San Francisco, CA), American Society of Hematology (Nov. 7, 2014).

* cited by examiner

*Primary Examiner* — Gailene Gabel
(74) *Attorney, Agent, or Firm* — Nevrivy Patent Law Group P.L.L.C.

(57) ABSTRACT

The present invention relates to diagnostic screens, gene expression profiles, methods and kits for detection of acute myeloid leukaemia leukaemic stem cells. Diagnostic and prognostic methods based on said diagnostic screens and/or gene expression profiles also form part of the invention.

5 Claims, 15 Drawing Sheets
Specification includes a Sequence Listing.

FIG. 1A n=49

| | |
|---|---|
| median age (range) | 55.8 years (3.1-90) |
| male: female | 36:13 |
| mean blast % + SD (range) | 72.0 + 17.2 (12-92) |
| Immunophenotype | |
| mean CD34+ % + SD (range) | 0.5 + 0.3 (0.0-1.5) |
| | |
| Karyotype (no. of samples/ total analysed (%)) | |
| normal karyotype | 21/38 (55%) |
| favourable karyotype* | 3/38 (8%) |
| Intermediate karyotype* | 8/38 (21%) |
| adverse karyotype* | 6/38 (16%) |
| karyotype not available | 11/49 (22%) |
| Mutational profile (no. of samples/ total analysed (%)) | |
| NPM1 mt | 29/49 (59%) |
| FLT3 ITD | 12/49 (25%) |
| FLT3 other | 3/49 (6%) |
| NPM1 mt/ FLT3 WT | 15/49 (31%) |
| NPM1 WT/ FLT3 ITD | 1/49 (2%) |
| NPM1 mt/ FLT3 ITD | 11/49 (22%) |
| NPM1 mt/ FLT3 D835Y | 1/49 (2%) |
| IDH1 | 9/49 (18%) |
| IDH2 | 10/49 (20%) |
| DNMT3A | 9/49 (18%) |

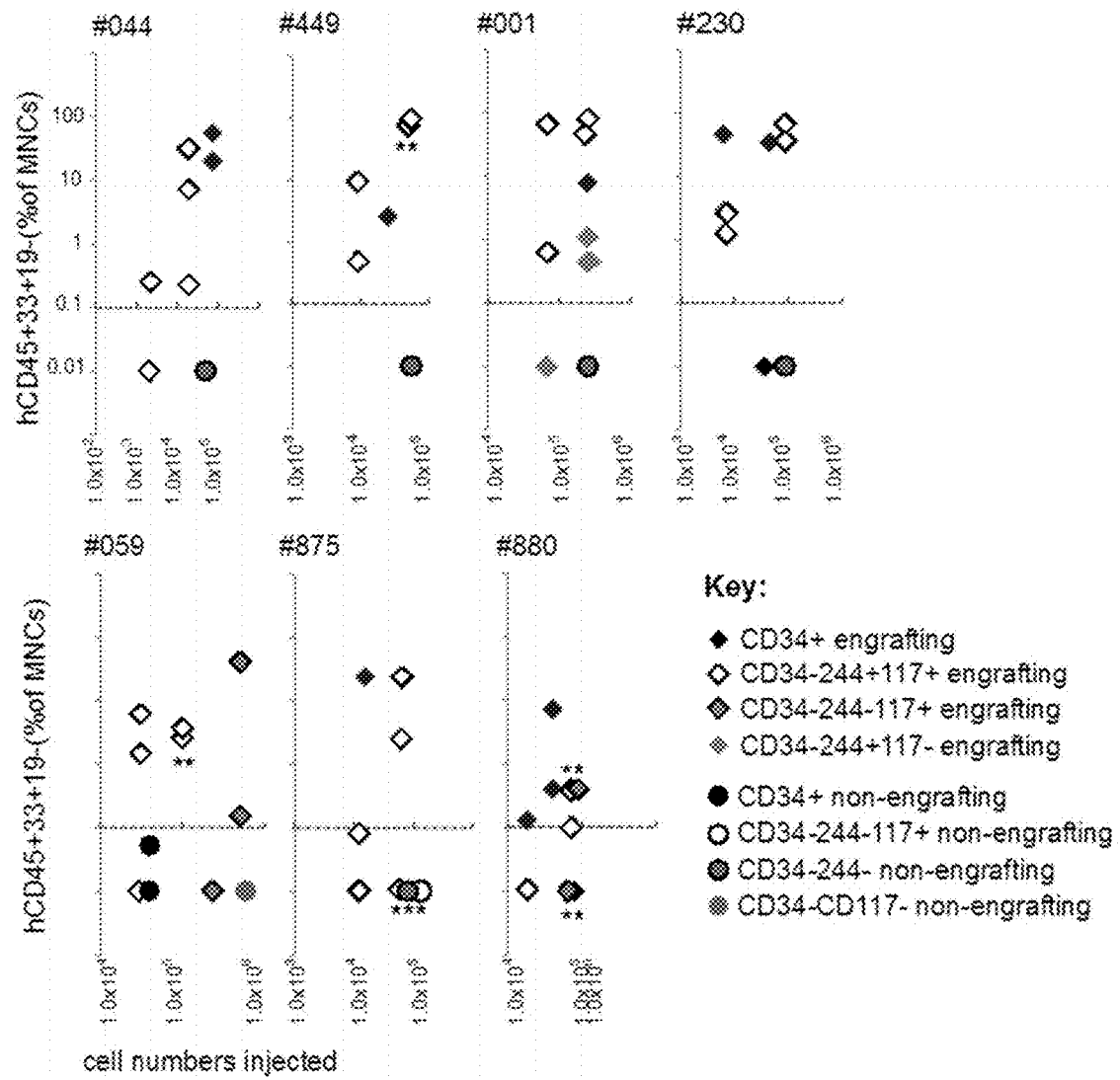

FIG. 2F

| Patient sample | | #001 | #449 | #880 | #1037 | #1037 | #1037 |
|---|---|---|---|---|---|---|---|
| Sorted population injected into primary mouse | CD34+ | | | | + | | |
| | CD34- 244+117+ | + | + | + | | + | |
| | CD34- 244-117+ | | | | | | + |
| Engrafted population in primary mouse, injected into secondary mouse | CD34+ | + | + | + | + | + | + |
| | CD34- 244+117+ | + | + | + | + | + | + |
| | CD34- 244-117+ | | | + | | | |
| engraftment in secondary mouse %hCD45+33+19- | CD34+ | 57.5 | 90.4 | 0.7 | 15.6 | 0.37 | 87.5 |
| | CD34- 244+117+ | 97.2 | 89.6 | 6.4 | 61.0 | 91.5 | 83.3 |
| | CD34- 244-117+ | | | 19.1 | | | |

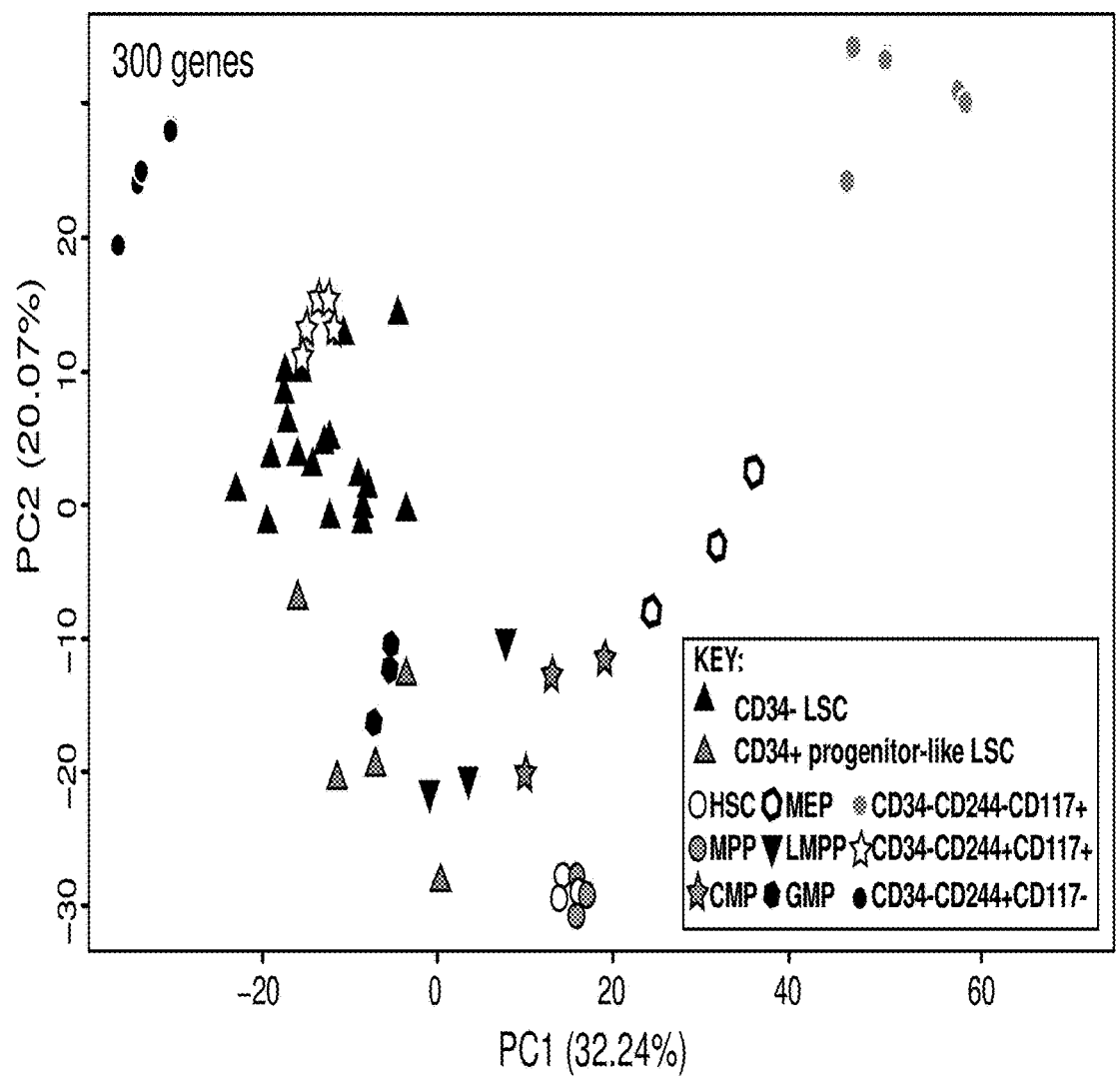

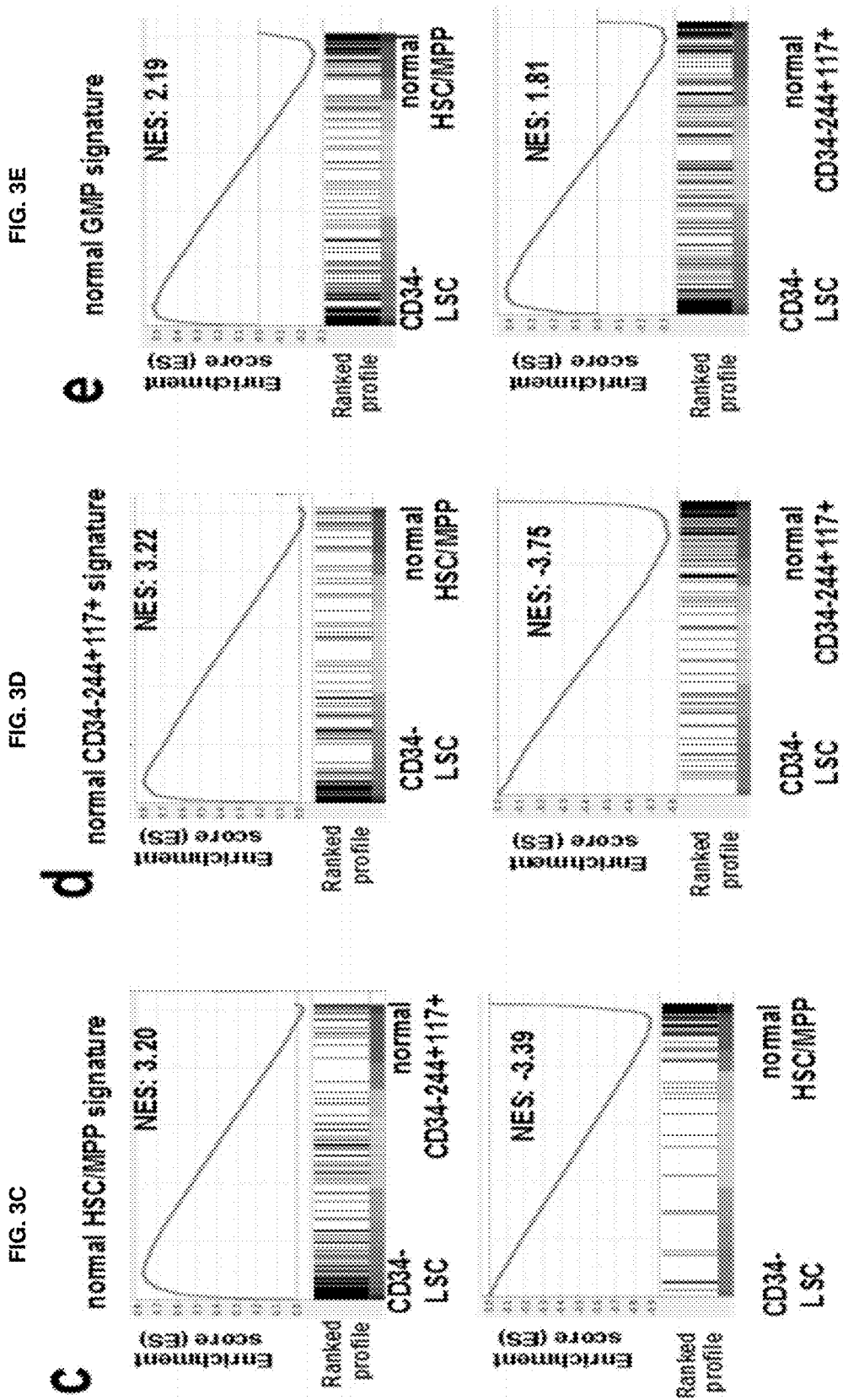

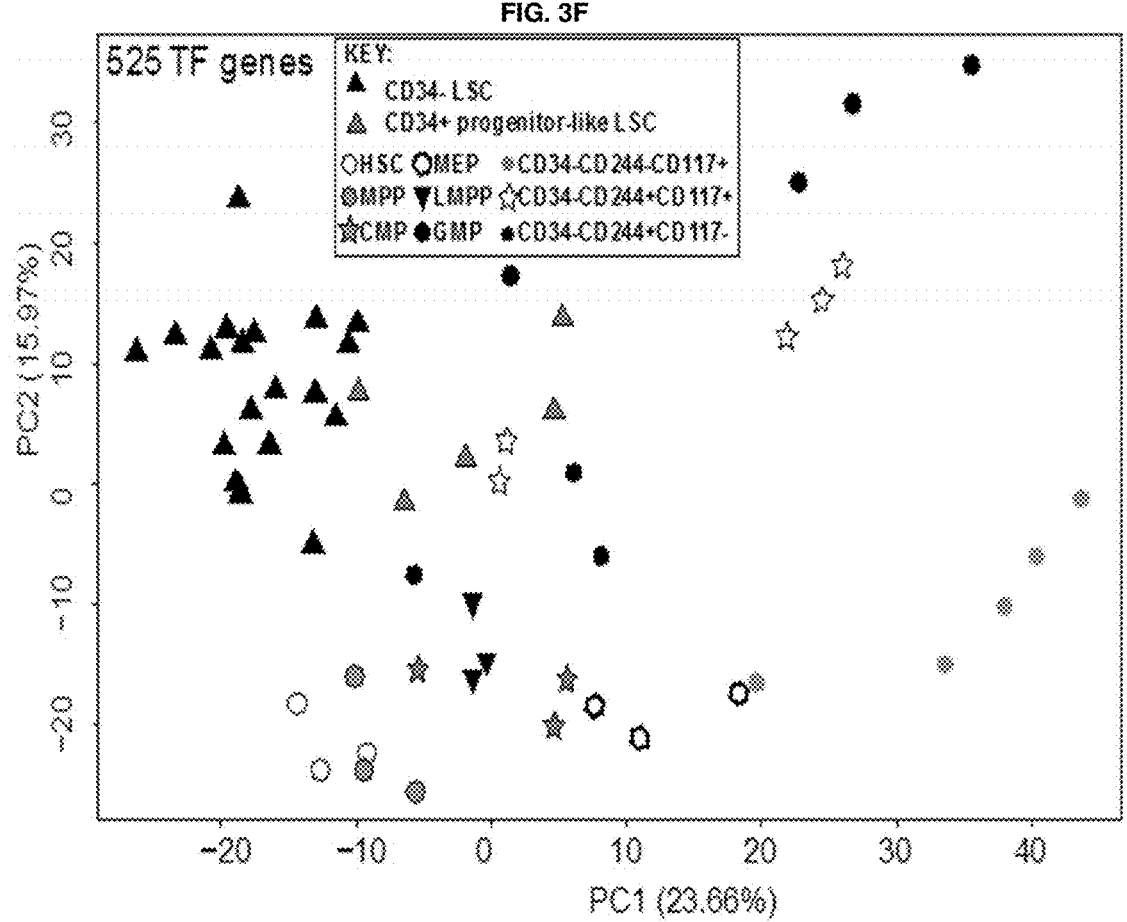

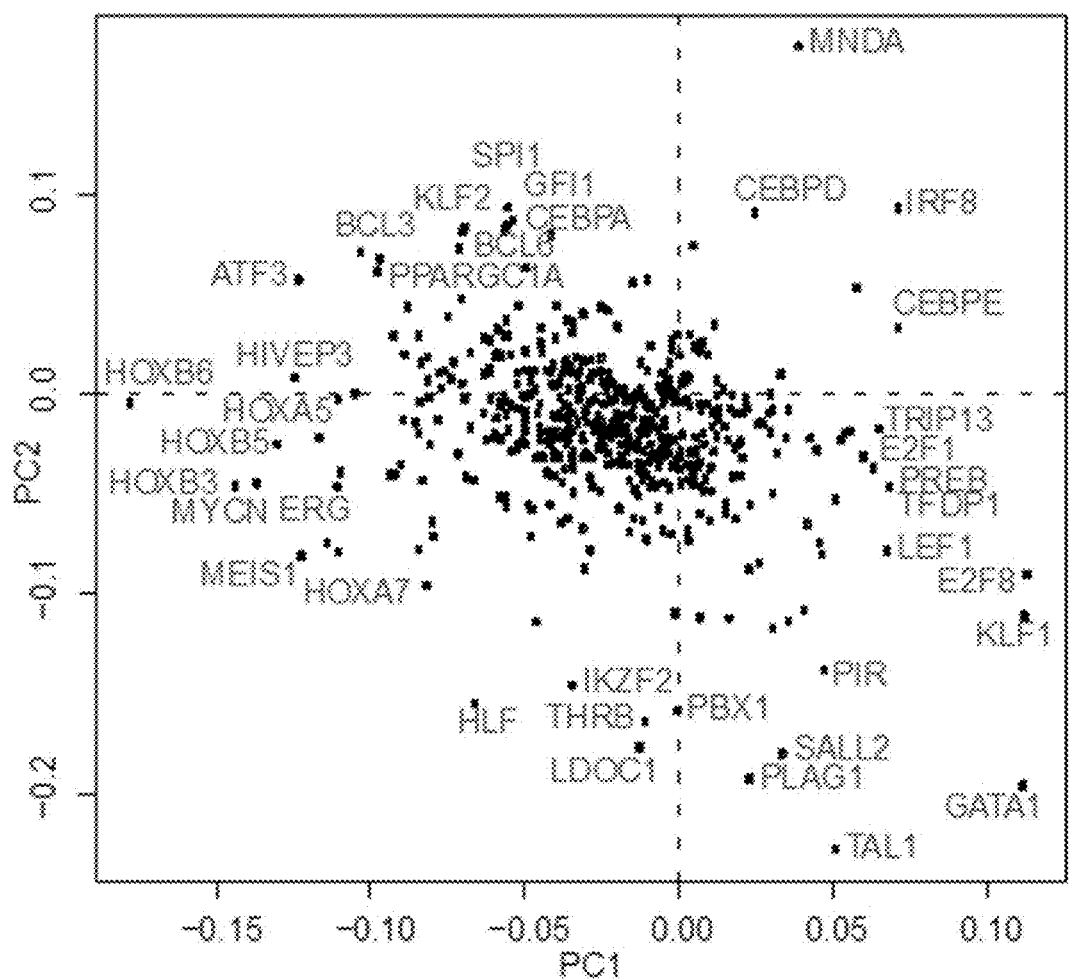

| | | |
|---|---|---|
| AFF1 | HOXA5 | MEIS1 |
| ETV5 | HOXB3 | MYCN |
| FOXO3 | HOXB5 | ZBTB16/ PLZF |
| GATA 2 | KMT2A | ZFPM2 |
| HOXA 4 | MAF | |

FIG. 4

| gene | hgnc_id | Log2 CPM | | | | | | | comparator population | CPM | log2 FC | | |
|---|---|---|---|---|---|---|---|---|---|---|---|---|---|
| | | normal HSC | normal myeloid precursors | CD34- LSC | CD34- nonLSC | SD of expression in LSC | SEM | SEM as % of mean | | FC vs comp population | log2 FC | log2 FC max | log2 FC min |
| AZU1 | 913 | -1.1 | 9.6 | 6.0 | 5.9 | 2.21 | 0.51 | 8.44% | hsc | 133.7 | 7.1 | 8.2 | 5.9 |
| CSTA | 2481 | -2.5 | 6.0 | 5.3 | 6.2 | 1.74 | 0.40 | 7.57% | hsc | 223.7 | 7.8 | 9.0 | 6.6 |
| BMI1 | 1066 | 5.6 | 3.4 | 5.0 | 1.1 | 1.94 | 0.45 | 8.95% | nonlsc | 14.6 | 3.9 | 4.5 | 3.2 |
| HOXA5 | 5106 | 3.4 | 0.8 | 4.2 | 2.5 | 0.76 | 0.17 | 4.09% | nonlsc | 3.3 | 1.7 | 1.9 | 1.6 |
| HOXB5 | 5116 | 2.8 | -3.7 | 2.6 | 0.1 | 2.28 | 0.52 | 20.32% | nonlsc | 5.6 | 2.5 | 3.5 | 1.5 |
| ITGA6 | 6142 | 5.4 | 3.1 | 4.4 | 0.5 | 1.88 | 0.43 | 9.75% | nonlsc | 14.9 | 3.9 | 4.6 | 3.2 |
| KIT | 6342 | 8.4 | 7.3 | 4.7 | 0.3 | 2.84 | 0.65 | 13.98% | nonlsc | 20.6 | 4.4 | 5.6 | 3.2 |
| ARID5B | 17362 | 6.3 | 1.3 | 5.7 | 6.3 | 1.46 | 0.33 | 5.85% | myepre | 21.8 | 4.4 | 5.0 | 3.9 |
| ATF3 | 785 | 3.5 | 1.5 | 6.7 | 6.4 | 1.19 | 0.27 | 4.05% | myepre | 38.3 | 5.3 | 5.7 | 4.8 |
| CLEC11A | 10576 | 2.2 | 5.8 | 3.9 | 2.7 | 0.69 | 0.16 | 4.09% | myepre | 0.3 | 1.9 | 2.1 | -1.8 |
| ETV5 | 3494 | 4.1 | -0.2 | 4.0 | 4.7 | 2.40 | 0.55 | 13.61% | myepre | 19.4 | 4.3 | 5.4 | 3.1 |
| HIVEP3 | 13561 | 6.4 | 1.2 | 5.9 | 4.3 | 1.31 | 0.30 | 5.09% | myepre | 26.1 | 4.7 | 5.2 | 4.2 |
| HOXA3 | 5104 | 5.5 | 1.4 | 6.6 | 5.4 | 0.61 | 0.14 | 2.12% | myepre | 36.8 | 5.2 | 5.4 | 5.0 |
| HOXB3 | 5114 | 5.6 | 0.5 | 7.0 | 5.5 | 1.36 | 0.31 | 4.44% | myepre | 179.5 | 7.5 | 8.1 | 6.8 |
| HOXB6 | 5117 | 3.6 | 3.3 | 5.2 | 2.9 | 1.48 | 0.34 | 6.52% | myepre | 353.4 | 8.5 | 9.5 | 7.4 |
| MEIS1 | 7000 | 9.9 | 4.4 | 9.3 | 9.8 | 0.66 | 0.15 | 1.62% | myepre | 30.1 | 4.9 | 5.1 | 4.8 |
| MYCN | 7559 | 2.1 | 3.6 | 2.8 | 1.4 | 3.11 | 0.71 | 25.59% | myepre | 83.0 | 6.4 | 9.6 | 3.2 |
| NFIL3 | 7787 | 3.5 | 1.9 | 5.9 | 6.8 | 0.87 | 0.20 | 3.35% | myepre | 16.2 | 4.0 | 4.3 | 3.8 |
| PTPN14 | 9647 | 1.6 | 0.3 | 5.7 | 3.5 | 1.57 | 0.36 | 6.28% | myepre | 64.9 | 6.0 | 6.8 | 5.3 |
| RHOC | 669 | 6.3 | 1.2 | 4.4 | 0.7 | 0.89 | 0.20 | 4.67% | myepre | 9.2 | 3.2 | 3.5 | 2.9 |
| WT1 | 12796 | -1.9 | -2.8 | 4.4 | 3.4 | 2.41 | 0.55 | 12.56% | myepre | 150.0 | 7.2 | 9.0 | 5.4 |
| AEBP1 | 303 | 0.2 | -0.7 | 2.2 | 0.4 | 2.48 | 0.57 | 25.33% | myepre | 7.7 | 2.9 | 4.4 | 1.5 |
| CREB5 | 16844 | 3.3 | 1.3 | 5.6 | 4.2 | 1.09 | 0.25 | 4.48% | myepre | 19.1 | 4.3 | 4.6 | 3.9 |
| ERG | 3446 | 9.2 | 5.7 | 7.1 | 6.2 | 1.03 | 0.24 | 3.30% | myepre | 2.7 | 1.4 | 1.5 | 1.3 |
| FOSL2 | 3798 | 5.1 | 2.2 | 6.2 | 7.0 | 0.97 | 0.22 | 3.57% | myepre | 16.0 | 4.0 | 4.3 | 3.7 |
| HOXA7 | 5108 | 4.4 | 0.8 | 4.8 | 4.0 | 2.15 | 0.49 | 10.39% | myepre | 15.6 | 4.0 | 4.8 | 3.2 |
| IL11RA | 5967 | 3.4 | -0.6 | 3.0 | 0.5 | 1.62 | 0.37 | 12.49% | myepre | 12.1 | 3.6 | 4.5 | 2.7 |
| KDM7A | 22224 | 3.4 | 0.4 | 4.2 | 3.9 | 0.95 | 0.22 | 5.17% | myepre | 14.2 | 3.8 | 4.2 | 3.4 |
| KLF7 | 6350 | 6.8 | 3.9 | 6.3 | 5.8 | 0.58 | 0.13 | 2.12% | myepre | 5.0 | 2.3 | 2.4 | 2.2 |
| KLF9 | 1123 | 5.2 | 1.7 | 3.6 | 4.5 | 1.22 | 0.28 | 7.80% | myepre | 3.7 | 1.9 | 2.2 | 1.6 |
| MAFF | 6780 | 3.6 | 0.8 | 4.4 | 3.2 | 1.49 | 0.34 | 7.73% | myepre | 12.2 | 3.6 | 4.2 | 3.1 |
| STAT4 | 11365 | 5.7 | 2.2 | 4.2 | 1.8 | 1.97 | 0.45 | 10.68% | myepre | 4.0 | 2.0 | 2.4 | 1.6 |
| TOX | 18988 | 7.6 | 4.3 | 7.2 | 7.5 | 2.28 | 0.52 | 7.28% | myepre | 7.5 | 2.9 | 3.3 | 2.5 |
| ZBTB16 | 12930 | 7.1 | 4.7 | 6.9 | 5.7 | 0.87 | 0.20 | 2.91% | myepre | 4.5 | 2.2 | 2.3 | 2.1 |

SEQUENCE LISTING

```
<160> NUMBER OF SEQ ID NOS: 81

<210> SEQ ID NO 1
<211> LENGTH: 328
<212> TYPE: PRT
<213> ORGANISM: Homo sapiens

<400> SEQUENCE: 1

Met Leu Val Arg Arg Gly Ala Arg Ala Gly Pro Arg Met Pro Arg Gly
1               5                   10                  15

Trp Thr Ala Leu Cys Leu Leu Ser Leu Leu Pro Ser Gly Phe Met Ser
            20                  25                  30

Leu Asp Asn Asn Gly Thr Ala Thr Pro Glu Leu Pro Thr Gln Gly Thr
        35                  40                  45

Phe Ser Asn Val Ser Thr Asn Val Ser Tyr Gln Glu Thr Thr Thr Pro
    50                  55                  60

Ser Thr Leu Gly Ser Thr Ser Leu His Pro Val Ser Gln His Gly Asn
65                  70                  75                  80

Glu Ala Thr Thr Asn Ile Thr Glu Thr Thr Val Lys Phe Thr Ser Thr
                85                  90                  95

Ser Val Ile Thr Ser Val Tyr Gly Asn Thr Asn Ser Ser Val Gln Ser
            100                 105                 110

Gln Thr Ser Val Ile Ser Thr Val Phe Thr Thr Pro Ala Asn Val Ser
        115                 120                 125

Thr Pro Glu Thr Thr Leu Lys Pro Ser Leu Ser Pro Gly Asn Val Ser
    130                 135                 140

Asp Leu Ser Thr Thr Ser Thr Ser Leu Ala Thr Ser Pro Thr Lys Pro
145                 150                 155                 160

Tyr Thr Ser Ser Ser Pro Ile Leu Ser Asp Ile Lys Ala Glu Ile Lys
                165                 170                 175

Cys Ser Gly Ile Arg Glu Val Lys Leu Thr Gln Gly Ile Cys Leu Glu
            180                 185                 190

Gln Asn Lys Thr Ser Ser Cys Ala Glu Phe Lys Lys Asp Arg Gly Glu
        195                 200                 205

Gly Leu Ala Arg Val Leu Cys Gly Glu Glu Gln Ala Asp Ala Asp Ala
    210                 215                 220

Gly Ala Gln Val Cys Ser Leu Leu Leu Ala Gln Ser Glu Val Arg Pro
225                 230                 235                 240

Gln Cys Leu Leu Leu Val Leu Ala Asn Arg Thr Glu Ile Ser Ser Lys
                245                 250                 255

Leu Gln Leu Met Lys Lys His Gln Ser Asp Leu Lys Lys Leu Gly Ile
            260                 265                 270
```

```
Leu Asp Phe Thr Glu Gln Asp Val Ala Ser His Gln Ser Tyr Ser Gln
            275                 280                 285

Lys Thr Leu Ile Ala Leu Val Thr Ser Gly Ala Leu Leu Ala Val Leu
    290                 295                 300

Gly Ile Thr Gly Tyr Phe Leu Met Asn Arg Arg Ser Trp Ser Pro Thr
305                 310                 315                 320

Gly Glu Arg Leu Glu Leu Glu Pro
                325

<210> SEQ ID NO 2
<211> LENGTH: 243
<212> TYPE: PRT
<213> ORGANISM: Homo sapiens

<400> SEQUENCE: 2

Met Cys Ser Arg Gly Trp Asp Ser Cys Leu Ala Leu Glu Leu Leu Leu
1               5                   10                  15

Leu Pro Leu Ser Leu Leu Val Thr Ser Ile Gln Gly His Leu Val His
            20                  25                  30

Met Thr Val Val Ser Gly Ser Asn Val Thr Leu Asn Ile Ser Glu Ser
        35                  40                  45

Leu Pro Glu Asn Tyr Lys Gln Leu Thr Trp Phe Tyr Thr Phe Asp Gln
    50                  55                  60

Lys Ile Val Glu Trp Asp Ser Arg Lys Ser Lys Tyr Phe Glu Ser Lys
65                  70                  75                  80

Phe Lys Gly Arg Val Arg Leu Asp Pro Gln Ser Gly Ala Leu Tyr Ile
                85                  90                  95

Ser Lys Val Gln Lys Glu Asp Asn Ser Thr Tyr Ile Met Arg Val Leu
            100                 105                 110

Lys Lys Thr Gly Asn Glu Gln Glu Trp Lys Ile Lys Leu Gln Val Leu
        115                 120                 125

Asp Pro Val Pro Lys Pro Val Ile Lys Ile Glu Lys Ile Glu Asp Met
    130                 135                 140

Asp Asp Asn Cys Tyr Leu Lys Leu Ser Cys Val Ile Pro Gly Glu Ser
145                 150                 155                 160

Val Asn Tyr Thr Trp Tyr Gly Asp Lys Arg Pro Leu Pro Lys Glu Leu
                165                 170                 175

Gln Asn Ser Val Leu Glu Thr Thr Leu Met Pro His Asn Tyr Ser Arg
            180                 185                 190

Cys Tyr Thr Cys Gln Val Ser Asn Ser Val Ser Ser Lys Asn Gly Thr
        195                 200                 205

Val Cys Leu Ser Pro Pro Cys Thr Leu Ala Arg Ser Phe Gly Val Glu
    210                 215                 220

Trp Ile Ala Ser Trp Leu Val Val Thr Val Pro Thr Ile Leu Gly Leu
225                 230                 235                 240

Leu Leu Thr

<210> SEQ ID NO 3
<211> LENGTH: 972
<212> TYPE: PRT
<213> ORGANISM: Homo sapiens

<400> SEQUENCE: 3

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
```

```
                 20                  25                  30
Glu Pro Ser Pro Pro Ser Ile His Pro Gly Lys Ser Asp Leu Ile Val
             35                  40                  45
Arg Val Gly Asp Glu Ile Arg Leu Leu Cys Thr Asp Pro Gly Phe Val
         50                  55                  60
Lys Trp Thr Phe Glu Ile Leu Asp Glu Thr Asn Glu Asn Lys Gln Asn
 65                  70                  75                  80
Glu Trp Ile Thr Glu Lys Ala Glu Ala Thr Asn Thr Gly Lys Tyr Thr
                 85                  90                  95
Cys Thr Asn Lys His Gly Leu Ser Asn Ser Ile Tyr Val Phe Val Arg
             100                 105                 110
Asp Pro Ala Lys Leu Phe Leu Val Asp Arg Ser Leu Tyr Gly Lys Glu
             115                 120                 125
Asp Asn Asp Thr Leu Val Arg Cys Pro Leu Thr Asp Pro Glu Val Thr
             130                 135                 140
Asn Tyr Ser Leu Lys Gly Cys Gln Gly Lys Pro Leu Pro Lys Asp Leu
145                 150                 155                 160
Arg Phe Ile Pro Asp Pro Lys Ala Gly Ile Met Ile Lys Ser Val Lys
                 165                 170                 175
Arg Ala Tyr His Arg Leu Cys Leu His Cys Ser Val Asp Gln Glu Gly
             180                 185                 190
Lys Ser Val Leu Ser Glu Lys Phe Ile Leu Lys Val Arg Pro Ala Phe
             195                 200                 205
Lys Ala Val Pro Val Val Ser Val Ser Lys Ala Ser Tyr Leu Leu Arg
             210                 215                 220
Glu Gly Glu Glu Phe Thr Val Thr Cys Thr Ile Lys Asp Val Ser Ser
225                 230                 235                 240
Ser Val Tyr Ser Thr Trp Lys Arg Glu Asn Ser Gln Thr Lys Leu Gln
                 245                 250                 255
Glu Lys Tyr Asn Ser Trp His His Gly Asp Phe Asn Tyr Glu Arg Gln
             260                 265                 270
Ala Thr Leu Thr Ile Ser Ser Ala Arg Val Asn Asp Ser Gly Val Phe
             275                 280                 285
Met Cys Tyr Ala Asn Asn Thr Phe Gly Ser Ala Asn Val Thr Thr Thr
     290                 295                 300
Leu Glu Val Val Asp Lys Gly Phe Ile Asn Ile Phe Pro Met Ile Asn
305                 310                 315                 320
Thr Thr Val Phe Val Asn Asp Gly Glu Asn Val Asp Leu Ile Val Glu
                 325                 330                 335
Tyr Glu Ala Phe Pro Lys Pro Glu His Gln Gln Trp Ile Tyr Met Asn
             340                 345                 350
Arg Thr Phe Thr Asp Lys Trp Glu Asp Tyr Pro Lys Ser Glu Asn Glu
             355                 360                 365
Ser Asn Ile Arg Tyr Val Ser Glu Leu His Leu Thr Arg Leu Lys Gly
             370                 375                 380
Thr Glu Gly Gly Thr Tyr Thr Phe Leu Val Ser Asn Ser Asp Val Asn
385                 390                 395                 400
Ala Ala Ile Ala Phe Asn Val Tyr Val Asn Thr Lys Pro Glu Ile Leu
                 405                 410                 415
Thr Tyr Asp Arg Leu Val Asn Gly Met Leu Gln Cys Val Ala Ala Gly
             420                 425                 430
Phe Pro Glu Pro Thr Ile Asp Trp Tyr Phe Cys Pro Gly Thr Glu Gln
             435                 440                 445
```

-continued

Arg Cys Ser Ala Ser Val Leu Pro Val Asp Val Gln Thr Leu Asn Ser
    450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
                485                 490                 495

Val Gly Lys Thr Ser Ala Tyr Phe Asn Phe Ala Phe Lys Glu Gln Ile
            500                 505                 510

His Pro His Thr Leu Phe Thr Pro Leu Leu Ile Gly Phe Val Ile Val
        515                 520                 525

Ala Gly Met Met Cys Ile Ile Val Met Ile Leu Thr Tyr Lys Tyr Leu
    530                 535                 540

Gln Lys Pro Met Tyr Glu Val Gln Trp Lys Val Val Glu Glu Ile Asn
545                 550                 555                 560

Gly Asn Asn Tyr Val Tyr Ile Asp Pro Thr Gln Leu Pro Tyr Asp His
                565                 570                 575

Lys Trp Glu Phe Pro Arg Asn Arg Leu Ser Phe Gly Lys Thr Leu Gly
            580                 585                 590

Ala Gly Ala Phe Gly Lys Val Val Glu Ala Thr Ala Tyr Gly Leu Ile
        595                 600                 605

Lys Ser Asp Ala Ala Met Thr Val Ala Val Lys Met Leu Lys Pro Ser
    610                 615                 620

Ala His Leu Thr Glu Arg Glu Ala Leu Met Ser Glu Leu Lys Val Leu
625                 630                 635                 640

Ser Tyr Leu Gly Asn His Met Asn Ile Val Asn Leu Leu Gly Ala Cys
                645                 650                 655

Thr Ile Gly Gly Pro Thr Leu Val Ile Thr Glu Tyr Cys Cys Tyr Gly
            660                 665                 670

Asp Leu Leu Asn Phe Leu Arg Arg Lys Arg Asp Ser Phe Ile Cys Ser
        675                 680                 685

Lys Gln Glu Asp His Ala Glu Ala Ala Leu Tyr Lys Asn Leu Leu His
    690                 695                 700

Ser Lys Glu Ser Ser Cys Ser Asp Ser Thr Asn Glu Tyr Met Asp Met
705                 710                 715                 720

Lys Pro Gly Val Ser Tyr Val Val Pro Thr Lys Ala Asp Lys Arg Arg
                725                 730                 735

Ser Val Arg Ile Gly Ser Tyr Ile Glu Arg Asp Val Thr Pro Ala Ile
            740                 745                 750

Met Glu Asp Asp Glu Leu Ala Leu Asp Leu Glu Asp Leu Leu Ser Phe
        755                 760                 765

Ser Tyr Gln Val Ala Lys Gly Met Ala Phe Leu Ala Ser Lys Asn Cys
    770                 775                 780

Ile His Arg Asp Leu Ala Ala Arg Asn Ile Leu Leu Thr His Gly Arg
785                 790                 795                 800

Ile Thr Lys Ile Cys Asp Phe Gly Leu Ala Arg Asp Ile Lys Asn Asp
                805                 810                 815

Ser Asn Tyr Val Val Lys Gly Asn Ala Arg Leu Pro Val Lys Trp Met
            820                 825                 830

Ala Pro Glu Ser Ile Phe Asn Cys Val Tyr Thr Phe Glu Ser Asp Val
        835                 840                 845

Trp Ser Tyr Gly Ile Phe Leu Trp Glu Leu Phe Ser Leu Gly Ser Ser
    850                 855                 860

```
Pro Tyr Pro Gly Met Pro Val Asp Ser Lys Phe Tyr Lys Met Ile Lys
865                 870                 875                 880

Glu Gly Phe Arg Met Leu Ser Pro Glu His Ala Pro Ala Glu Met Tyr
            885                 890                 895

Asp Ile Met Lys Thr Cys Trp Asp Ala Asp Pro Leu Lys Arg Pro Thr
        900                 905                 910

Phe Lys Gln Ile Val Gln Leu Ile Glu Lys Gln Ile Ser Glu Ser Thr
    915                 920                 925

Asn His Ile Tyr Ser Asn Leu Ala Asn Cys Ser Pro Asn Arg Gln Lys
930                 935                 940

Pro Val Val Asp His Ser Val Arg Ile Asn Ser Val Gly Ser Thr Ala
945                 950                 955                 960

Ser Ser Ser Gln Pro Leu Leu Val His Asp Asp Val
                965                 970

<210> SEQ ID NO 4
<211> LENGTH: 335
<212> TYPE: PRT
<213> ORGANISM: Homo sapiens

<400> SEQUENCE: 4

Met Asp Pro Lys Gly Leu Leu Ser Leu Thr Phe Val Leu Phe Leu Ser
1               5                   10                  15

Leu Ala Phe Gly Ala Ser Tyr Gly Thr Gly Gly Arg Met Met Asn Cys
            20                  25                  30

Pro Lys Ile Leu Arg Gln Leu Gly Ser Lys Val Leu Leu Pro Leu Thr
        35                  40                  45

Tyr Glu Arg Ile Asn Lys Ser Met Asn Lys Ser Ile His Ile Val Val
    50                  55                  60

Thr Met Ala Lys Ser Leu Glu Asn Ser Val Glu Asn Lys Ile Val Ser
65                  70                  75                  80

Leu Asp Pro Ser Glu Ala Gly Pro Pro Arg Tyr Leu Gly Asp Arg Tyr
                85                  90                  95

Lys Phe Tyr Leu Glu Asn Leu Thr Leu Gly Ile Arg Glu Ser Arg Lys
            100                 105                 110

Glu Asp Glu Gly Trp Tyr Leu Met Thr Leu Glu Lys Asn Val Ser Val
        115                 120                 125

Gln Arg Phe Cys Leu Gln Leu Arg Leu Tyr Glu Gln Val Ser Thr Pro
    130                 135                 140

Glu Ile Lys Val Leu Asn Lys Thr Gln Glu Asn Gly Thr Cys Thr Leu
145                 150                 155                 160

Ile Leu Gly Cys Thr Val Glu Lys Gly Asp His Val Ala Tyr Ser Trp
                165                 170                 175

Ser Glu Lys Ala Gly Thr His Pro Leu Asn Pro Ala Asn Ser Ser His
            180                 185                 190

Leu Leu Ser Leu Thr Leu Gly Pro Gln His Ala Asp Asn Ile Tyr Ile
        195                 200                 205

Cys Thr Val Ser Asn Pro Ile Ser Asn Asn Ser Gln Thr Phe Ser Pro
    210                 215                 220

Trp Pro Gly Cys Arg Thr Asp Pro Ser Glu Thr Lys Pro Trp Ala Val
225                 230                 235                 240

Tyr Ala Gly Leu Leu Gly Gly Val Ile Met Ile Leu Ile Met Val Val
                245                 250                 255

Ile Leu Gln Leu Arg Arg Arg Gly Lys Thr Asn His Tyr Gln Thr Thr
            260                 265                 270
```

```
Val Glu Lys Lys Ser Leu Thr Ile Tyr Ala Gln Val Gln Lys Pro Gly
            275                 280                 285

Pro Leu Gln Lys Lys Leu Asp Ser Phe Pro Ala Gln Asp Pro Cys Thr
290                 295                 300

Thr Ile Tyr Val Ala Ala Thr Glu Pro Val Pro Glu Ser Val Gln Glu
305                 310                 315                 320

Thr Asn Ser Ile Thr Val Tyr Ala Ser Val Thr Leu Pro Glu Ser
                325                 330                 335

<210> SEQ ID NO 5
<211> LENGTH: 365
<212> TYPE: PRT
<213> ORGANISM: Homo sapiens

<400> SEQUENCE: 5

Met Leu Gly Gln Val Val Thr Leu Ile Leu Leu Leu Leu Leu Lys Val
1               5                   10                  15

Tyr Gln Gly Lys Gly Cys Gln Gly Ser Ala Asp His Val Val Ser Ile
                20                  25                  30

Ser Gly Val Pro Leu Gln Leu Gln Pro Asn Ser Ile Gln Thr Lys Val
            35                  40                  45

Asp Ser Ile Ala Trp Lys Lys Leu Leu Pro Ser Gln Asn Gly Phe His
50                  55                  60

His Ile Leu Lys Trp Glu Asn Gly Ser Leu Pro Ser Asn Thr Ser Asn
65                  70                  75                  80

Asp Arg Phe Ser Phe Ile Val Lys Asn Leu Ser Leu Leu Ile Lys Ala
                85                  90                  95

Ala Gln Gln Gln Asp Ser Gly Leu Tyr Cys Leu Glu Val Thr Ser Ile
                100                 105                 110

Ser Gly Lys Val Gln Thr Ala Thr Phe Gln Val Phe Val Phe Asp Lys
            115                 120                 125

Val Glu Lys Pro Arg Leu Gln Gly Gln Gly Lys Ile Leu Asp Arg Gly
130                 135                 140

Arg Cys Gln Val Ala Leu Ser Cys Leu Val Ser Arg Asp Gly Asn Val
145                 150                 155                 160

Ser Tyr Ala Trp Tyr Arg Gly Ser Lys Leu Ile Gln Thr Ala Gly Asn
                165                 170                 175

Leu Thr Tyr Leu Asp Glu Glu Val Asp Ile Asn Gly Thr His Thr Tyr
            180                 185                 190

Thr Cys Asn Val Ser Asn Pro Val Ser Trp Glu Ser His Thr Leu Asn
        195                 200                 205

Leu Thr Gln Asp Cys Gln Asn Ala His Gln Glu Phe Arg Phe Trp Pro
210                 215                 220

Phe Leu Val Ile Ile Val Ile Leu Ser Ala Leu Phe Leu Gly Thr Leu
225                 230                 235                 240

Ala Cys Phe Cys Val Trp Arg Arg Lys Arg Lys Glu Lys Gln Ser Glu
                245                 250                 255

Thr Ser Pro Lys Glu Phe Leu Thr Ile Tyr Glu Asp Val Lys Asp Leu
            260                 265                 270

Lys Thr Arg Arg Asn His Glu Gln Glu Gln Thr Phe Pro Gly Gly Gly
                275                 280                 285

Ser Thr Ile Tyr Ser Met Ile Gln Ser Gln Ser Ser Ala Pro Thr Ser
            290                 295                 300

Gln Glu Pro Ala Tyr Thr Leu Tyr Ser Leu Ile Gln Pro Ser Arg Lys
```

```
            305                 310                 315                 320
Ser Gly Ser Arg Lys Arg Asn His Ser Pro Ser Phe Asn Ser Thr Ile
                325                 330                 335

Tyr Glu Val Ile Gly Lys Ser Gln Pro Lys Ala Gln Asn Pro Ala Arg
                340                 345                 350

Leu Ser Arg Lys Glu Leu Glu Asn Phe Asp Val Tyr Ser
                355                 360                 365

<210> SEQ ID NO 6
<211> LENGTH: 360
<212> TYPE: PRT
<213> ORGANISM: Homo sapiens

<400> SEQUENCE: 6

Met Ser Phe Pro Cys Lys Phe Val Ala Ser Phe Leu Leu Ile Phe Asn
1               5                   10                  15

Val Ser Ser Lys Gly Ala Val Ser Lys Glu Ile Thr Asn Ala Leu Glu
                20                  25                  30

Thr Trp Gly Ala Leu Gly Gln Asp Ile Asn Leu Asp Ile Pro Ser Phe
            35                  40                  45

Gln Met Ser Asp Asp Ile Asp Asp Ile Lys Trp Glu Lys Thr Ser Asp
        50                  55                  60

Lys Lys Lys Ile Ala Gln Phe Arg Lys Glu Lys Glu Thr Phe Lys Glu
65                  70                  75                  80

Lys Asp Thr Tyr Lys Leu Phe Lys Asn Gly Thr Leu Lys Ile Lys His
                85                  90                  95

Leu Lys Thr Asp Asp Gln Asp Ile Tyr Lys Val Ser Ile Tyr Asp Thr
            100                 105                 110

Lys Gly Lys Asn Val Leu Glu Lys Ile Phe Asp Leu Lys Ile Gln Glu
        115                 120                 125

Arg Val Ser Lys Pro Lys Ile Ser Trp Thr Cys Ile Asn Thr Thr Leu
130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
                165                 170                 175

Thr Thr Ser Leu Ser Ala Lys Phe Lys Cys Thr Ala Gly Asn Lys Val
            180                 185                 190

Ser Lys Glu Ser Ser Val Glu Pro Val Ser Cys Pro Glu Lys Gly Leu
        195                 200                 205

Asp Ile Tyr Leu Ile Ile Gly Ile Cys Gly Gly Gly Ser Leu Leu Met
    210                 215                 220

Val Phe Val Ala Leu Leu Val Phe Tyr Ile Thr Lys Arg Lys Lys Gln
225                 230                 235                 240

Arg Ser Arg Arg Asn Asp Glu Glu Leu Glu Thr Arg Ala His Arg Val
                245                 250                 255

Ala Thr Glu Glu Arg Gly Arg Lys Pro His Gln Ile Pro Ala Ser Thr
            260                 265                 270

Pro Gln Asn Pro Ala Thr Ser Gln His Pro Pro Pro Pro Gly His
        275                 280                 285

Arg Ser Gln Ala Pro Ser His Arg Pro Pro Pro Pro Gly His Arg Val
    290                 295                 300

Gln His Gln Pro Gln Lys Arg Pro Pro Ala Pro Ser Gly Thr Gln Val
305                 310                 315                 320
```

His Gln Gln Lys Gly Pro Pro Leu Pro Arg Pro Val Gln Pro Lys
            325                 330                 335

Pro Pro Met Gly Gln Gln Lys Thr His Cys Pro Leu Pro Leu Ile Lys
        340                 345                 350

Lys Asp Arg Asn Cys Leu Phe Gln
        355                 360

<210> SEQ ID NO 7
<211> LENGTH: 207
<212> TYPE: PRT
<213> ORGANISM: Homo sapiens

<400> SEQUENCE: 7

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 8
<211> LENGTH: 458
<212> TYPE: PRT
<213> ORGANISM: Homo sapiens

<400> SEQUENCE: 8

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

```
Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Gln Ala Glu Arg Met
            420                 425                 430

Ser Gln Ile Lys Arg Leu Leu Ser Glu Lys Lys Thr Cys Gln Cys Pro
    435                 440                 445

His Arg Phe Gln Lys Thr Cys Ser Pro Ile
    450                 455

<210> SEQ ID NO 9
<211> LENGTH: 235
<212> TYPE: PRT
<213> ORGANISM: Homo sapiens

<400> SEQUENCE: 9
```

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
                35                  40                  45

Asn Pro Thr Ser Gly Cys Ser Trp Leu Phe Gln Pro Arg Gly Ala Ala
        50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Cys
                100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
        130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
                180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
210                 215                 220

Gly Asp Lys Pro Ser Leu Ser Ala Arg Tyr Val
225                 230                 235

<210> SEQ ID NO 10
<211> LENGTH: 750
<212> TYPE: PRT
<213> ORGANISM: Homo sapiens

<400> SEQUENCE: 10

Met Gly Lys Ser Glu Ser Gln Met Asp Ile Thr Asp Ile Asn Thr Pro
1               5                   10                  15

Lys Pro Lys Lys Lys Gln Arg Trp Thr Pro Leu Glu Ile Ser Leu Ser
                20                  25                  30

Val Leu Val Leu Leu Leu Thr Ile Ile Ala Val Thr Met Ile Ala Leu
                35                  40                  45

Tyr Ala Thr Tyr Asp Asp Gly Ile Cys Lys Ser Ser Asp Cys Ile Lys
        50                  55                  60

Ser Ala Ala Arg Leu Ile Gln Asn Met Asp Ala Thr Thr Glu Pro Cys
65                  70                  75                  80

Thr Asp Phe Phe Lys Tyr Ala Cys Gly Gly Trp Leu Lys Arg Asn Val
                85                  90                  95

Ile Pro Glu Thr Ser Ser Arg Tyr Gly Asn Phe Asp Ile Leu Arg Asp
                100                 105                 110

Glu Leu Glu Val Val Leu Lys Asp Val Leu Gln Glu Pro Lys Thr Glu
        115                 120                 125

Asp Ile Val Ala Val Gln Lys Ala Lys Ala Leu Tyr Arg Ser Cys Ile

```
            130                 135                 140
Asn Glu Ser Ala Ile Asp Ser Arg Gly Gly Glu Pro Leu Leu Lys Leu
145                 150                 155                 160

Leu Pro Asp Ile Tyr Gly Trp Pro Val Ala Thr Glu Asn Trp Glu Gln
                165                 170                 175

Lys Tyr Gly Ala Ser Trp Thr Ala Glu Lys Ala Ile Ala Gln Leu Asn
            180                 185                 190

Ser Lys Tyr Gly Lys Lys Val Leu Ile Asn Leu Phe Val Gly Thr Asp
                195                 200                 205

Asp Lys Asn Ser Val Asn His Val Ile His Ile Asp Gln Pro Arg Leu
            210                 215                 220

Gly Leu Pro Ser Arg Asp Tyr Tyr Glu Cys Thr Gly Ile Tyr Lys Glu
225                 230                 235                 240

Ala Cys Thr Ala Tyr Val Asp Phe Met Ile Ser Val Ala Arg Leu Ile
                245                 250                 255

Arg Gln Glu Glu Arg Leu Pro Ile Asp Glu Asn Gln Leu Ala Leu Glu
                260                 265                 270

Met Asn Lys Val Met Glu Leu Glu Lys Glu Ile Ala Asn Ala Thr Ala
            275                 280                 285

Lys Pro Glu Asp Arg Asn Asp Pro Met Leu Leu Tyr Asn Lys Met Thr
290                 295                 300

Leu Ala Gln Ile Gln Asn Asn Phe Ser Leu Glu Ile Asn Gly Lys Pro
305                 310                 315                 320

Phe Ser Trp Leu Asn Phe Thr Asn Glu Ile Met Ser Thr Val Asn Ile
                325                 330                 335

Ser Ile Thr Asn Glu Glu Asp Val Val Val Tyr Ala Pro Glu Tyr Leu
                340                 345                 350

Thr Lys Leu Lys Pro Ile Leu Thr Lys Tyr Ser Ala Arg Asp Leu Gln
                355                 360                 365

Asn Leu Met Ser Trp Arg Phe Ile Met Asp Leu Val Ser Ser Leu Ser
            370                 375                 380

Arg Thr Tyr Lys Glu Ser Arg Asn Ala Phe Arg Lys Ala Leu Tyr Gly
385                 390                 395                 400

Thr Thr Ser Glu Thr Ala Thr Trp Arg Arg Cys Ala Asn Tyr Val Asn
                405                 410                 415

Gly Asn Met Glu Asn Ala Val Gly Arg Leu Tyr Val Glu Ala Ala Phe
            420                 425                 430

Ala Gly Glu Ser Lys His Val Val Glu Asp Leu Ile Ala Gln Ile Arg
                435                 440                 445

Glu Val Phe Ile Gln Thr Leu Asp Asp Leu Thr Trp Met Asp Ala Glu
450                 455                 460

Thr Lys Lys Arg Ala Glu Lys Ala Leu Ala Ile Lys Glu Arg Ile
465                 470                 475                 480

Gly Tyr Pro Asp Ile Val Ser Asn Asp Lys Leu Asn Asn Glu
                485                 490                 495

Tyr Leu Glu Leu Asn Tyr Lys Glu Asp Glu Tyr Phe Glu Asn Ile Ile
                500                 505                 510

Gln Asn Leu Lys Phe Ser Gln Ser Lys Gln Leu Lys Lys Leu Arg Glu
            515                 520                 525

Lys Val Asp Lys Asp Glu Trp Ile Ser Gly Ala Val Val Asn Ala
            530                 535                 540

Phe Tyr Ser Ser Gly Arg Asn Gln Ile Val Phe Pro Ala Gly Ile Leu
545                 550                 555                 560
```

```
Gln Pro Pro Phe Phe Ser Ala Gln Gln Ser Asn Ser Leu Asn Tyr Gly
                565                 570                 575

Gly Ile Gly Met Val Ile Gly His Glu Ile Thr His Gly Phe Asp Asp
            580                 585                 590

Asn Gly Arg Asn Phe Asn Lys Asp Gly Asp Leu Val Asp Trp Trp Thr
        595                 600                 605

Gln Gln Ser Ala Ser Asn Phe Lys Glu Gln Ser Gln Cys Met Val Tyr
    610                 615                 620

Gln Tyr Gly Asn Phe Ser Trp Asp Leu Ala Gly Gln His Leu Asn
625                 630                 635                 640

Gly Ile Asn Thr Leu Gly Glu Asn Ile Ala Asp Asn Gly Gly Leu Gly
            645                 650                 655

Gln Ala Tyr Arg Ala Tyr Gln Asn Tyr Ile Lys Lys Asn Gly Glu Glu
            660                 665                 670

Lys Leu Leu Pro Gly Leu Asp Leu Asn His Lys Gln Leu Phe Phe Leu
        675                 680                 685

Asn Phe Ala Gln Val Trp Cys Gly Thr Tyr Arg Pro Glu Tyr Ala Val
690                 695                 700

Asn Ser Ile Lys Thr Asp Val His Ser Pro Gly Asn Phe Arg Ile Ile
705                 710                 715                 720

Gly Thr Leu Gln Asn Ser Ala Glu Phe Ser Glu Ala Phe His Cys Arg
            725                 730                 735

Lys Asn Ser Tyr Met Asn Pro Glu Lys Lys Cys Arg Val Trp
        740                 745                 750

<210> SEQ ID NO 11
<211> LENGTH: 556
<212> TYPE: PRT
<213> ORGANISM: Homo sapiens

<400> SEQUENCE: 11

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ser
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
```

```
            180                 185                 190
Gly Ser Thr Leu Trp Leu Ser Cys Gly Val Pro Asp Ser Val Ser
            195                 200                 205
Arg Gly Pro Leu Ser Trp Thr His Val His Pro Lys Gly Pro Lys Ser
        210                 215                 220
Leu Leu Ser Leu Glu Leu Lys Asp Asp Arg Pro Ala Arg Asp Met Trp
225                 230                 235                 240
Val Met Glu Thr Gly Leu Leu Pro Arg Ala Thr Ala Gln Asp Ala
                245                 250                 255
Gly Lys Tyr Tyr Cys His Arg Gly Asn Leu Thr Met Ser Phe His Leu
            260                 265                 270
Glu Ile Thr Ala Arg Pro Val Leu Trp His Trp Leu Leu Arg Thr Gly
        275                 280                 285
Gly Trp Lys Val Ser Ala Val Thr Leu Ala Tyr Leu Ile Phe Cys Leu
        290                 295                 300
Cys Ser Leu Val Gly Ile Leu His Leu Gln Arg Ala Leu Val Leu Arg
305                 310                 315                 320
Arg Lys Arg Lys Arg Met Thr Asp Pro Thr Arg Arg Phe Phe Lys Val
                325                 330                 335
Thr Pro Pro Pro Gly Ser Gly Pro Gln Asn Gln Tyr Gly Asn Val Leu
                340                 345                 350
Ser Leu Pro Thr Pro Thr Ser Gly Leu Gly Arg Ala Gln Arg Trp Ala
            355                 360                 365
Ala Gly Leu Gly Gly Thr Ala Pro Ser Tyr Gly Asn Pro Ser Ser Asp
        370                 375                 380
Val Gln Ala Asp Gly Ala Leu Gly Ser Arg Ser Pro Pro Gly Val Gly
385                 390                 395                 400
Pro Glu Glu Glu Gly Glu Gly Tyr Glu Glu Pro Asp Ser Glu Glu
                405                 410                 415
Asp Ser Glu Phe Tyr Glu Asn Asp Ser Asn Leu Gly Gln Asp Gln Leu
            420                 425                 430
Ser Gln Asp Gly Ser Gly Tyr Glu Asn Pro Glu Asp Glu Pro Leu Gly
        435                 440                 445
Pro Glu Asp Glu Asp Ser Phe Ser Asn Ala Glu Ser Tyr Glu Asn Glu
        450                 455                 460
Asp Glu Glu Leu Thr Gln Pro Val Ala Arg Thr Met Asp Phe Leu Ser
465                 470                 475                 480
Pro His Gly Ser Ala Trp Asp Pro Ser Arg Glu Ala Thr Ser Leu Gly
                485                 490                 495
Ser Gln Ser Tyr Glu Asp Met Arg Gly Ile Leu Tyr Ala Ala Pro Gln
            500                 505                 510
Leu Arg Ser Ile Arg Gly Gln Pro Gly Pro Asn His Glu Glu Asp Ala
        515                 520                 525
Asp Ser Tyr Glu Asn Met Asp Asn Pro Asp Gly Pro Asp Pro Ala Trp
        530                 535                 540
Gly Gly Gly Gly Arg Met Gly Thr Trp Ser Thr Arg
545                 550                 555

<210> SEQ ID NO 12
<211> LENGTH: 297
<212> TYPE: PRT
<213> ORGANISM: Homo sapiens

<400> SEQUENCE: 12
```

```
Met Thr Thr Pro Arg Asn Ser Val Asn Gly Thr Phe Pro Ala Glu Pro
1               5                   10                  15

Met Lys Gly Pro Ile Ala Met Gln Ser Gly Lys Pro Leu Phe Arg
            20                  25                  30

Arg Met Ser Ser Leu Val Gly Pro Thr Gln Ser Phe Phe Met Arg Glu
            35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
            115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Gln Glu Leu Val Ile
    195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
            275                 280                 285

Ser Pro Ile Glu Asn Asp Ser Ser Pro
    290                 295

<210> SEQ ID NO 13
<211> LENGTH: 150
<212> TYPE: PRT
<213> ORGANISM: Homo sapiens

<400> SEQUENCE: 13

Met Tyr Gly Lys Ile Ile Phe Val Leu Leu Leu Ser Ala Ile Val Ser
1               5                   10                  15

Ile Ser Ala Ser Ser Thr Thr Gly Val Ala Met His Thr Ser Thr Ser
            20                  25                  30

Ser Ser Val Thr Lys Ser Tyr Ile Ser Ser Gln Thr Asn Asp Thr His
            35                  40                  45

Lys Arg Asp Thr Tyr Ala Ala Thr Pro Arg Ala His Glu Val Ser Glu
    50                  55                  60

Ile Ser Val Arg Thr Val Tyr Pro Pro Glu Glu Glu Thr Gly Glu Arg
65                  70                  75                  80
```

Val Gln Leu Ala His His Phe Ser Glu Pro Glu Ile Thr Leu Ile Ile
            85                  90                  95

Phe Gly Val Met Ala Gly Val Ile Gly Thr Ile Leu Leu Ile Ser Tyr
                100                 105                 110

Gly Ile Arg Arg Leu Ile Lys Lys Ser Pro Ser Asp Val Lys Pro Leu
            115                 120                 125

Pro Ser Pro Asp Thr Asp Val Pro Leu Ser Ser Val Glu Ile Glu Asn
    130                 135                 140

Pro Glu Thr Ser Asp Gln
145                 150

<210> SEQ ID NO 14
<211> LENGTH: 7948
<212> TYPE: DNA
<213> ORGANISM: Homo sapiens

<400> SEQUENCE: 14
agatgcacag tggagctcgc taccctcct ctcctccaaa atctcatca gacgatatcc      60 cagacaggag cggttagaga gagaggaatc acatctccac acagttttag ggtgcttttt    120 attttacaa atcttcttgt gtgttttttg ccttgatcca tcctcttccc gccgagatcg    180 tatgcgcct ttctctcgat tatgaatttg atcaatccat ctttggaaga aaacccacat    240
agttttttca ggagctgaaa attgagtcgt tatagaaata ttaggacata ttttcaatca    300
tttcggtgcc cgaagggagg caagagctca gttttatatt gagacattac gccggctgaa    360
ggcagagaat gcgtttccct gccaggacct gatgcaatcc attcaagcca caagtttgg     420 agagaatgtt gagttcaatc aattcagaac gtcgagatgg agcccaactc actccagtgg    480
gtcggctcac cgtgtggctt gcacggacct tacattttct acaaggcttt tcaattccac    540
cttgaaggca aaccaagaat tttgtccctt ggcgactttt tctttgtaag atgtacgcca    600
aaggatccga tttgcatagc ggagctccag ctgttgtggg aagagaggac cagccggcaa    660
cttttatcca gctctaaact ttatttcctc ccagaagaca ctccccaggg cagaaatagc    720
gaccatggcg aggatgaagt cattgctgtt tccgaaaagg tgattgtgaa gcttgaagac    780
ctggtcaagt gggtacattc tgatttctcc aagtggagat gtggcttcca cgctggacca    840
gtgaaaactg aggccttggg aaggaatgga cagaaggaag ctctgctgaa gtacaggcag    900
tcaaccctaa acagtggact caacttcaaa gacgttctca aggagaaggc agacctgggg    960
gaggacgagg aagaaacgaa cgtgatagtt ctcagctacc cccagtactg ccggtaccgc   1020
tcgatgctga acgcatcca ggataagcca tcttccattc taacggacca gtttgcattg   1080
gccctggggg gcattgcagt ggtcagcagg aaccctcaga tcctgtactg tcgggacacc   1140
tttgaccacc cgactctcat agaaaacgag agtatatgcg atgagtttgc gccaaatctt   1200
aaaggcagac cacgcaaaaa gaaaccatgc ccacaaagaa gagattcatt cagtggtgtt   1260
aaggattcca acaacaattc cgatggcaaa gccgttgcca aggtgaaatg tgaggccagg   1320
tcagccttga ccaagccgaa gaataaccat aactgtaaaa aagtctcaaa tgaagaaaaa   1380
ccaaaggttg ccattggtga agagtgcagg gcagatgaac aagccttctt ggtggcactt   1440
tataaataca tgaaagaaag gaaaacgccg atagaacgaa tacctatttt aggttttaaa   1500
cagattaacc tttggactat gtttcaagct gctcaaaaac tgggaggata tgaaacaata   1560
acagcccgcc gtcagtggaa acatatttat gatgaattag gcggtaatcc tgggagcacc   1620
agcgctgcca cttgtacccg cagacattat gaaagattaa tcctaccata tgaaagattt   1680

```
attaaaggag aagaagataa gccctgcct ccaatcaaac ctcggaaaca ggagaacagt   1740
tcacaggaaa atgagaacaa aacaaaagta tctggaacca aacgcatcaa acatgaaata   1800
cctaaaagca agaaagaaaa agaaaatgcc ccaaagcccc aggatgcagc agaggtttca   1860
tcagagcaag aaaaagaaca agagacttta ataagccaga aaagcatccc tgagcctctc   1920
ccagcagcag acatgaagaa aaaaatagaa gggtatcagg aattttcagc gaagcccctg   1980
gcatccagag tagacccaga gaaggacaac gaaacagacc aaggttccaa cagtgagaag   2040
gtggcagagg aggcgggaga gaaggggccc acacctccac tcccaagtgc tcctctggcc   2100
ccagaaaaag attcagcctt ggtccctggg gccagcaaac agccactcac ctctcctagt   2160
gccctggtgg actcaaaaca agaatccaaa ctgtgctgtt ttacagagag ccctgaaagt   2220 gaacccaag aagcatcctt ccccagcttc cccaccacac agccaccgct ggcaaaccag   2280
aatgagacgg aggatgacaa actgcccgcc atggcagatt acattgccaa ctgcaccgtg   2340
aaggtggacc agctgggcag tgacgacatc acaatgcgc tcaagcagac cccaaaggtc   2400
cttgtggtcc agtcgtttga catgttcaaa gacaaagacc tgactgggcc catgaacgag   2460
aaccatggac ttaattacac gcccctgctc tactctaggg gcaacccagg catcatgtcc   2520
ccactggcca agaaaaagct tttgtcccaa gtgagtgggg ccagcctctc cagcagctac   2580
ccttatggct ccccacccc tttgatcagc aaaaagaaac tgattgctag ggatgacttg   2640
tgttccagtt tgtcccagac ccaccatggc caaagcactg accatatggc ggtcagccgg   2700
ccatcagtga ttcagcacgt ccagagtttc agaagcaagc cctcggaaga gagaaagacc   2760
atcaatgaca tctttaagca tgagaaactg agtcgatcag atccccaccg ctgcagcttc   2820
tccaagcatc accttaaccc ccttgctgac tcctacgtcc tgaagcaaga aattcaggag   2880
ggcaaggata aactcttaga gaaaagggcc ctcccccatt cccacatgcc tagcttcctg   2940
gctgacttct actcgtcccc tcatctccat agcctctaca gacacaccga gcaccatctt   3000
cataatgaac agacatccaa ataccttcc agggacatgt acagggaatc ggaaaacagt   3060
tcttttcctt cccacagaca ccaagaaaag ctccatgtaa attatctcac gtccctgcac   3120
ctgcaagaca aaaagtcggc ggcagcagaa gcccctacgg atgatcagcc tacagatctg   3180
agccttccca agaacccgca caaacctacc ggcaaggtcc tgggcctggc tcattccacc   3240
acagggcccc aggagagcaa aggcatctcc cagttccagg tcttaggcag ccagagtcga   3300
gactgtcacc ccaaagcctg tcgggtatca cccatgacca tgtcaggccc taaaaaatac   3360
cctgaatcgc tttcaagatc aggaaaacct caccatgtga gactggagaa tttcaggaag   3420
atggaaggca tggtccaccc aatcctgcac cggaaaatga gcccgcagaa cattggggcg   3480
gcgcggccga tcaagcgcag cctggaggat ttggaccttg tgattgcagg gaaaaaggcc   3540
cgggcagtgt ctcccttaga cccatccaag gaggtctctg ggaaggagaa ggcctctgag   3600
caggagagtg aaggcagcaa agcagcgcac ggtgggcatt ccggggcgg atcagaaggc   3660 cacaagcttc ccctctcctc ccctatcttc ccaggtctgt attccgggag cctgtgtaac   3720
tcgggcctca actccaggct cccggctggg tattctcatt ctctgcagta cttgaaaaac   3780
cagactgtgc tttctccact catgcagccc ctggctttcc actcgcttgt gatgcaaaga   3840 ggaatttta catcaccgac aaattctcag cagctgtaca gacacttggc tgcggctaca   3900
cctgtaggaa gttcatatgg ggacttttg cataacagca tttacccttt agctgctata   3960
aatcctcaag ctgcctttcc atcttcccag ctgtcatccg tgcaccccag tacaaaactg   4020
```

```
taggctcagc tctgcccagc agtccaaagc ggcatggcca acagagcttc actccttacc    4080
caggagtgct ggcttataga gttagaagtc agtatttctt ctaatctgag gctatgatca    4140
gtcccagctg taggggccca gaggggaggt gaacatgcct gattttttgtg ggacaactct    4200
agcccacaaa ctgactggct ggtgagtctt gactcccttc aacacagat gcccaggcac    4260
ctccagatca ttcacttcgc acgtgggcct tgtgaaggga tttgtgaata tccaggaaga    4320
acttagagga ccccatctga gttcggatgg tcaggaaaca atctgggcaa aaaagaggca    4380
ggcatttcaa aggaagggc aaggaagact ggcaaacaga tggcaaggga tgcccctctt    4440
tttcataaaa ctctccaagg ttcaatcaat gcaatgtata gtgaaacttc aatagatctt    4500
tcattttgac actattaaac aatccagaga agtaaacact gttaaattga ctgtatatat    4560
ttgcttctta aaactacctg tatcactgtt tgctcaccta atttatatac aggtagttcc    4620
attttctccc agttccttct cgtctttttt tttttttttt tttttttttt tattaaatgg    4680
tattgctttt gtttgcaggt ctttttgttt ttgttttgtt tttgaggctg actgactgtc    4740
ctagttgttg tgtgtttgta atttttccac atcttatttt gagcagcttt gggtggtaaa    4800
gttattgttt acaaattgaa gcaactgatt ctagtggaac aaatgaaaaa gaaacagtca    4860
agcacacaat agtgcaaaga acgttccttt gtagatccgc aacttaagga ttttgttcct    4920
cataaatggc atagttgaaa gagcttatac actgcttacc cagccaaatg ctttgctttg    4980
aagtattggg ttctgtgaaa atattgagca ttgtacttac cttatctagg ctgtgaaact    5040
gtcctacata ccagagaatc ataaaaacaa aaacctcact ggcagcaagc tgccgaataa    5100
caacagagtc tagaggacat atttgtgggc tgcacagata ttttaggaat ttcagaaatt    5160
agaacaggag ccaaaatgat ttacattggc gttggcactg attcctttaa atggtctggg    5220
aaagggggtt gggaagagga tggagctcaa ctggccagaa gaggagcagc tgcagtcctg    5280
atagcttctc tagcctcggt cttttgagtg ataagtagtc atgttgtttt catccagttg    5340
gtttcttgtc attcccaaga agaatctccc aggccacatc tttggggata actgacatac    5400
tggattagcc ttttcaaaag aaaagtcatc ctatttggtt ttatgggggtg tgagttttgt    5460
gtgtacacac acagaaacat gtaaggtggt ttgggtcatg ttttttaacca cctggcaata    5520
cagtccactt tctggtttct tttattgtgg gaagtaaatg gtcaagctgc tcaggcagtg    5580
aaaagatgtg gagaatgtcc gttgtcattc ttgccactgt attccatttg ctaccgagat    5640
ataacattaa ggtggacaca ttttctaact gtattaatta aaagtcaatg gatacagaga    5700
gtggattttc tccccaagtc ccatccctgc tgaagaccgc ttggatgaac tccccaaccc    5760
actgtgcccc tcccgcaaca ctaccagtag actttagaac catagttaac taagtctttt    5820
acctctgaga tacttaattc tgggaaaatt ggtgacaatt ttcaacttct aaataggtaa    5880
ctcgactgca aaataatcaa aactgataac aatgaaactg cggctcttaa acaaagccat    5940
gcatgccgtg catttgtatt gaaatgtctc catgatatga agccaaatat tcaatgtaac    6000
atacttaata tccaaaggtg gaaacaaaag aatgtagaga tccagtgtta agagttccat    6060
ttgcttcaat taattatttta ccttcctgtg gaataatata tatatatata tttaatagaa    6120
ccatagatag actagtagaa tttagattat aaatgtgtga gtgcagatta tcctgctatt    6180
gcacaagcta gagggggggaa aaatctcaat tccagctggc aagatgctag ccaggacaca    6240
tataagaaag ttgcactaga ttgaatggtc acagaatcgg aggacatgga agaaaaagga    6300
aacttcggtg gttctgcagc agacatgggc taggtcatat gtggtttcta tgagttcgtg    6360
tctcaaaaaa aaaaggaggg ggggcatctg tccccggtgg agctcaccta tttggaatat    6420
```

```
gggcatttg tttttccac tgcaatgatt tcagtctggt ttcatcatgt tggaattcga     6480
tcacaccatt ttcaaacaat gttaacatag tccagctttt gttttctca tctcttctga    6540 gaggagactc actgtttctg tctgaggaag ctcataccct cggcaaaaca tcaggacaaa    6600
taaagagaaa tgggggtacg cattcccaac agaagcagtg tgttatttgt tttaaaactc    6660
tgaacagaga tcttggaaat ctttcaaaaa gaccattgaa ttcttcattg gctgagaacg    6720
acgttttaaa atgtcttaaa taaggctttg tttgcattgt ttgagttcaa ggggccttat    6780
tattgaatgg aattgcacaa gcctttcttt gtgcaatcaa accattgtta ttggtagttc    6840
tgtaaaggaa actgtggaat cgaattggca gtggagtcat aaatctattt actgagtgtg    6900
gcttccaaga aatgttgcaa ttcaaaatgc actaagtctg tgatttattg gagatttgga    6960
gattctaaat aatatttta aaaaacttcc atgcaacttc tggtttaatg tttggcaact     7020
ccacatgata aaaaataaa acagcccaa ccgagtttcg gaattaagta ttcttctagt     7080
aagtgattca aacttgtaat atttgccaca ggactgactt atttatttac tagctagaag    7140
ctcttaagtt cacttgttta tcagggcata tacagaaggg tttgttaaaa ctcgatgtta    7200
actttacaac tttctgacct ggtgcatgaa ttctcaagta ctgtatttca ctgtgttggt    7260
gtgtctgatg gaaatttcga ggtggtccca caaaaatatt ttatgtagtg tgccttcaaa    7320
gagaaccatt tatttctctt cacttatcgt cccacaaagt cacatttggt ggtggtcagc    7380
caagtcgcat ctggtctagt tttactcttg tcccaatttt aaagagaaat gggaatgagt    7440
ttgccctggt gagacccata ccattgcaat gattatcttg agcacttaaa gtccagtgtt    7500
ggctgttagt gtatttgata ttctgcctgt ctcctcatgg ttgaaatatg tctgaagaat    7560
agcagcataa tctcttggct gtttatactt ttttaaactt tcctgtgttg taaatattgt    7620
atacttttgg tgattccagc tatgtaacct ctatgctctg taaggtgatt atttgtatat    7680
agcaacatgg cccagtgata ttatatagtt tcccaatgga gaggttattg agtaaccttt    7740
gcattagttt aaacactacc agaagaatgc tgagccaact ataaacactc aattttgtat    7800
gttttccaaa ttgtacttat tactgctttt gatactgtat tacgtgccaa tagtttccca    7860
atcacatagc aggcaagaga tattttgtac ttttgatcc actgtaatat ttaataaaaa    7920
atgttactat ctgtttcctt taaaaaaa                                        7948
```

<210> SEQ ID NO 15
<211> LENGTH: 2088
<212> TYPE: DNA
<213> ORGANISM: Homo sapiens

<400> SEQUENCE: 15

```
tccgctccgt tcggccggtt ctcccgggaa gctattaata gcattacgtc agcctgggac      60
tggcaacacg gagtaaacga ccgcgccgcc agcctgaggg ctataaaagg ggtgatgcaa     120
cgctctccaa gccacagtcg cacgcagcca ggcgcgcact gcacagctct cttctctcgc     180
cgccgcccga gcgcacccct cagcccgcgc gccggccgtg agtcctcggt gctcgcccgc     240
cggccagaca aacagcccgc ccgaccccgt cccgaccctg gccgcccccga gcggagcctg     300 gagcaaaatg atgcttcaac acccaggcca ggtctctgcc tcggaagtga gtgcttctgc     360
catcgtcccc tgcctgtccc ctcctgggtc actggtgttt gaggatttg ctaacctgac      420 gcccttgtc aaggaagagc tgaggtttgc catccagaac aagcacctct gccaccggat     480
gtcctctgcg ctggaatcag tcactgtcag cgacagaccc ctcggggtgt ccatcacaaa     540
```

```
agccgaggta gcccctgaag aagatgaaag gaaaagagg cgacgagaaa gaaataagat    600
tgcagctgca aagtgccgaa acaagaagaa ggagaagacg gagtgcctgc agaaagagtc    660
ggagaagctg gaaagtgtga atgctgaact gaaggctcag attgaggagc tcaagaacga    720
gaagcagcat ttgatataca tgctcaacct tcatcggccc acgtgtattg tccgggctca    780
gaatgggagg actccagaag atgagagaaa cctctttatc aacagataa aagaaggaac    840 attgcagagc taagcagtcg tggtatgggg gcgactgggg agtcctcatt gaatcctcat    900
tttataccca aaaccctgaa gccattggag agctgtcttc ctgtgtacct ctagaatccc    960
agcagcagag aaccatcaag gcgggagggc ctgcagtgat tcagcaggcc cttcccattc   1020
tgccccagag tgggtcttgg accagggcaa gtgcatcttt gcctcaactc caggatttag   1080
gccttaacac actggccatt cttatgttcc agatggcccc cagctggtgt cctgcccgcc   1140
tttcatctgg attctacaaa aaaccaggat gcccaccgtt aggattcagg cagcagtgtc   1200
tgtacctcgg gtgggaggga tggggccatc tccttcaccg tggctaccat tgtcactcgt   1260
aggggatgtg gagtgagaac agcatttagt gaagttgtgc aacggccagg ttgtgctttt   1320
ctagcaaata tgctgttatg tccagaaatt gtgtgtgcaa gaaaactagg caatgtactc   1380
ttccgatgtt tgtgtcacac aacactgatg tgactttttat atgctttttc tcagatctgg   1440
tttctaagag ttttgggggg cggggctgtc accacgtgca gtatctcaag atattcaggt   1500
ggccagaaga gcttgtcagc aagaggagga cagaattctc ccagcgttaa cacaaaatcc   1560
atgggcagta tgatggcagg tcctctgttg caaactcagt tccaaagtca caggaagaaa   1620
gcagaaagtt caacttccaa agggttagga ctctccactc aatgtcttag gtcaggagtt   1680
gtgtctaggc tggaagagcc aaagaatatt ccattttcct ttccttgtgg ttgaaaacca   1740
cagtcagtgg agagatgttt ggaaaccaca gtcagtggag cctgggtggt acccaggctt   1800
tagcattatt ggatgtcaat agcattgttt ttgtcatgta gctgttttaa gaaatctggc   1860
ccagggtgtt tgcagctgtg agaagtcact cacactggcc acaaggacgc tggctactgt   1920
ctattaaaat tctgatgttt ctgtgaaatt tcagagtgt ttaattgtac tcaatggtat   1980
cattacaatt ttctgtaaga gaaaatatta cttatttatc ctagtattcc taacctgtca   2040
gaataataaa tattggaacc aagacatggt aaacaaaaaa aaaaaaaa              2088

<210> SEQ ID NO 16
<211> LENGTH: 912
<212> TYPE: DNA
<213> ORGANISM: Homo sapiens

<400> SEQUENCE: 16
acagacctgc cccgccatga cccggctgac agtcctggcc ctgctggctg gtctgctggc     60
gtcctcgagg gccggctcca gccccctttt ggacatcgtt ggcggccgga aggcgaggcc    120
ccgccagttc ccgttcctgg cctccattca gaatcaaggc aggcacttct gcggggtgc    180 cctgatccat gcccgcttcg tgatgaccgc ggccagctgc ttccaaagcc agaacccgg    240 ggttagcacc gtggtgctgg gtgcctatga cctgaggcgg cgggagaggc agtcccgcca    300
gacgttttcc atcagcagca tgagcgagaa tggctacgac cccagcagaa acctgaacga    360
cctgatgctg cttcagctgg accgtgaggc caacctcacc agcagcgtga cgatactgcc    420
actgcctctg cagaacgcca cggtggaagc cggcaccaga tgccaggtgg ccggctgggg    480
gagccagcgc agtgggggc gtctctcccg tttttcccagg tttgtcaacg tgactgtgac    540
ccccgaggac cagtgtcgcc ccaacaacgt gtgcaccggt gtgctcaccc gccgcggtgg    600
```

| | |
|---|---|
| catctgcaat ggggacgggg gcaccccct cgtctgcgag ggcctggccc acggcgtggc | 660 |
| ctccttttcc ctggggccct gtggccgagg ccctgacttc ttcacccgag tggcgctctt | 720 |
| ccgagactgg atcgatggtg ttctcaacaa cccgggaccg gggccagcct agggggggcct | 780 |
| gtgacctccc atggagccca gccccgccct ccacacctcc ggcgctccgc acccacctcc | 840 |
| cacggccccg cccctgcccc cgctccggcc agaggggccc tggctgtaat aaagaagccg | 900 |
| atctctcctc tg | 912 |

<210> SEQ ID NO 17
<211> LENGTH: 3435
<212> TYPE: DNA
<213> ORGANISM: Homo sapiens

<400> SEQUENCE: 17

| | |
|---|---|
| acagcaacta tgaaataatc gtagtatgag aggcagagat cggggcgaga caatggggat | 60 |
| gtgggcgcgg gagccccgtt ccggcttagc agcacctccc agccccgcag aataaaaccg | 120 |
| atcgcgcccc ctccgcgcgc gccctccccc gagtgcggag cggaggagg cggcggcggc | 180 |
| cgaggaggag gaggaggagg ccccggagga ggaggcgttg gaggtcgagg cggaggcgga | 240 |
| ggaggaggag gccgaggcgc cggaggaggc cgaggcgccg gagcaggagg aggccggccg | 300 |
| gaggcggcat gagacgagcg tggcggccgc ggctgctcgg ggccgcgctg gttgcccatt | 360 |
| gacagcggcg tctgcagctc gcttcaagat ggccgcttgg ctcgcattca tttttctgctg | 420 |
| aacgactttt aactttcatt gtcttttccg cccgcttcga tcgcctcgcg ccggctgctc | 480 |
| tttccgggat ttttttatcaa gcagaaatgc atcgaacaac gagaatcaag atcactgagc | 540 |
| taaatcccca cctgatgtgt gtgctttgtg gagggtactt cattgatgcc acaaccataa | 600 |
| tagaatgtct acattccttc tgtaaaacgt gtattgttcg ttacctggag accagcaagt | 660 |
| attgtcctat ttgtgatgtc caagttcaca agaccagacc actactgaat ataaggtcag | 720 |
| ataaaactct ccaagatatt gtatacaaat tagttccagg gcttttcaaa aatgaaatga | 780 |
| agagaagaag ggattttat gcagctcatc cttctgctga tgctgccaat ggctctaatg | 840 |
| aagatagagg agaggttgca gatgaagata agagaattat aactgatgat gagataataa | 900 |
| gcttatccat tgaattcttt gaccagaaca gattggatcg gaaagtaaac aaagacaaag | 960 |
| agaaatctaa ggaggaggtg aatgataaaa gatacttacg atgcccagca gcaatgactg | 1020 |
| tgatgcactt aagaaagttt ctcagaagta aaatggacat acctaatact ttccagattg | 1080 |
| atgtcatgta tgaggaggaa cctttaaagg attattatac actaatggat attgcctaca | 1140 |
| tttatacctg gagaaggaat ggtccacttc cattgaaata cagagttcga cctacttgta | 1200 |
| aaagaatgaa gatcagtcac cagagagatg gactgacaaa tgctggagaa ctggaaagtg | 1260 |
| actctgggag tgacaaggcc aacagcccag caggaggtat tccctccacc tcttcttgtt | 1320 |
| tgcctagccc cagtactcca gtgcagtctc ctcatccaca gtttcctcac atttccagta | 1380 |
| ctatgaatgg aaccagcaac agccccagcg gtaaccacca atcttctttt gccaatagac | 1440 |
| ctcgaaaatc atcagtaaat gggtcatcag caacttcttc tggttgatac ctgagactgt | 1500 |
| taaggaaaaa aatttaaac ccctgattta tatagatatc ttcatgccat tacagctttc | 1560 |
| tagatgctaa tacatgtgac tatcgtccaa tttgctttct tttgtagtga cattaaattt | 1620 |
| ggctataaaa gatggactac atgtgatact cctatggacg ttaattgaaa agaaagattg | 1680 |
| ttgttataaa gaattggttt cttggaaagc aggcaagact ttttctctgt gttaggaaag | 1740 |

| | |
|---|---|
| atgggaaatg gtttctgtaa ccattgtttg gatttggaag tactctgcag tggacataag | 1800 |
| cattgggcca tagtttgtta atctcaacta acgcctacat tacattctcc ttgatcgttc | 1860 |
| ttgttattac gctgttttgt gaacctgtag aaaacaagtg cttttatct tgaaattcaa | 1920 |
| ccaacggaaa gaatatgcat agaataatgc attctatgta gccatgtcac tgtgaataac | 1980 |
| gatttcttgc atatttagcc attttgattc ctgtttgatt tatacttctc tgttgctacg | 2040 |
| caaaaccgat caaagaaaag tgaacttcag ttttacaatc tgtatgccta aaagcgggta | 2100 |
| ctaccgttta ttttactgac ttgtttaaat gattcgcttt tgtaagaatc agatggcatt | 2160 |
| atgcttgttg tacaatgcca tattggtata tgacataaca ggaaacagta ttgtatgata | 2220 |
| tatttataaa tgctataaag aaatattgtg tttcatgcat tcagaaatga ttgttaaaat | 2280 |
| tctcccaact ggttcgacct tgcagatac ccataaccta tgttgagcct tgcttaccag | 2340 |
| caaagaatat ttttaatgtg gatatctaat tctaaagtct gttccattag aagcaattgg | 2400 |
| cacatctttc tatactttat atacttttct ccagtaatac atgtttactt taaagattgt | 2460 |
| tgcagtgaag aaaaaccttt aactgagaaa tatggaaacc gtcttaattt tccattggct | 2520 |
| atgatggaat taatattgta tttaaaaat gcatattgat cactataatt ctaaaacaat | 2580 |
| tttttaaata aaccagcagg ttgctaaaag aaggcatttt atctaaagtt attttaatag | 2640 |
| gtggtatagc agtaatttta aatttaagag ttgcttttac agttaacaat ggaatatgcc | 2700 |
| ttctctgcta tgtctgaaaa tagaagctat ttattatgag cttctacagg tatttttaaa | 2760 |
| tagagcaagc atgttgaatt taaaatatga ataaccccac ccaacaattt tcagtttatt | 2820 |
| ttttgctttg gtcgaacttg gtgtgtgttc atcacccatc agttatttgt gagggtgttt | 2880 |
| attctatatg aatattgttt catgtttgta tgggaaaatt gtagctaaac atttcattgt | 2940 |
| ccccagtctg caaagaagc acaattctat tgctttgtct tgcttatagt cattaaatca | 3000 |
| ttacttttac atatattgct gttacttctg cttttctttaa aaatatagta aaggatgttt | 3060 |
| tatgaagtca caagatacat atattttttat tttgacctaa atttgtacag tcccattgta | 3120 |
| agtgttgttt ctaattatag atgtaaaatg aaatttcatt tgtaattgga aaaaatccaa | 3180 |
| taaaaaggat attcatttag aaaatagcta agatctttaa taaaaatttg atatgaaaag | 3240 |
| cacaatgtgc agaagttatg gaaaacctat agaggattac aacaggtaaa cgttaaagag | 3300 |
| aatacattgc tgacttatag tgatgtggct aagaagtaca tgctttgttg taaaattgct | 3360 |
| tgaaagccca ttgaaagatg tatctgttta tttacagtct ttgaagtaaa agttaccaat | 3420 |
| gtttgccaat aaaaa | 3435 |

<210> SEQ ID NO 18
<211> LENGTH: 1423
<212> TYPE: DNA
<213> ORGANISM: Homo sapiens

<400> SEQUENCE: 18

| | |
|---|---|
| gaccaacgga ccggacagag acgaggagag gaacaggaag agagaagctg ggagaatcgg | 60 |
| gaacctgggg gctagtgacc tgcacacagg gcagggcac tcggcagttc ccagaggcca | 120 |
| cccctcccac cccagacatc cagacatctg gaactttggg tgccaagagt ccagcttaat | 180 |
| gcaggcagcc tggctttgg gggctttggt ggtccccag ctcttgggct ttggccatgg | 240 |
| ggctcgggga gcagagaggg agtgggaggg aggctgggga ggtgcccagg aggaggagcg | 300 |
| ggagagggag gccctgatgc tgaagcatct gcaggaagcc ctaggactgc ctgctgggag | 360 |
| gggggatgag aatcctgccg gaactgttga gggaaaagag gactgggaga tggaggagga | 420 |

| | |
|---|---|
| ccaggggagg gaagaggagg aggaagcaac gccaacccca tcctccggcc ccagcccctc | 480 |
| tcccacccct gaggacatcg tcacttacat cctgggccgc ctggccggcc tggacgcagg | 540 |
| cctgcaccag ctgcacgtcc gtctgcacgc gttggacacc cgcgtggtcg agctgaccca | 600 |
| ggggctgcgg cagctgcgga acgcggcagg cgacacccgc gatgccgtgc aagccctgca | 660 |
| ggaggcgcag ggtcgcgccg agcgcgagca cggccgcttg gagggctgcc tgaaggggct | 720 |
| gcgcctgggc cacaagtgct tcctgctctc gcgcgacttc gaagctcagg cggcggcgca | 780 |
| ggcgcggtgc acggcgcggg gcgggagcct ggcgcagccg gcagaccgcc agcagatgga | 840 |
| ggcgctcact cggtacctgc gcgcggcgct cgctccctac aactggcccg tgtggctggg | 900 |
| cgtgcacgat cggcgcgccg agggcctcta cctcttcgaa aacggccagc gcgtgtcctt | 960 |
| cttcgcctgg catcgctcac cccgcccgga gctcggcgcc cagcccagcg cctcgccgca | 1020 |
| tccgctcagc ccggaccagc ccaacggtgg cacgctcgag aactgcgtgg cgcaggcctc | 1080 |
| tgacgacggc tcctggtggg accacgactg ccagcggcgt ctctactacg tctgcgagtt | 1140 |
| cccctctag cggggccggt accccgcctc cctgcccatc ccaccacccg gcctttccct | 1200 |
| gcgccgtgcc caccctcctc cggaatctcc cttcccttcc tggccacgaa tggcagcgtc | 1260 |
| ctccccgacc cccagtctgg gcgcttctgg gagggctctt gcggtgccgg cactcctcct | 1320 |
| tgttagtgtc tttccttgaa ggggcgggca ccaggctagg tccggtgcca ataaatcctt | 1380 |
| gtggaatctg acttgagggg cagtgaaaaa aaaaaaaaa aaa | 1423 |

<210> SEQ ID NO 19
<211> LENGTH: 838
<212> TYPE: DNA
<213> ORGANISM: Homo sapiens

<400> SEQUENCE: 19

| | |
|---|---|
| tgctgtttgt ggaaaataaa gcattctata ggcggagcta gtgaacgcct cttttaaaac | 60 |
| acgagtctcc acacttccct gttcactttg gttccagcat cctgtccagc aaagaagcaa | 120 |
| tcagccaaaa tgatacctgg aggcttatct gaggccaaac ccgccactcc agaaatccag | 180 |
| gagattgttg ataaggttaa accacagctt gaagaaaaaa caaatgagac ttacggaaaa | 240 |
| ttggaagctg tgcagtataa aactcaagtt gttgctggaa caaattacta cattaaggta | 300 |
| cgagcaggtg ataataaata tatgcacttg aaagtattca aagtcttcc cggacaaaat | 360 |
| gaggacttgg tacttactgg ataccaggtt gacaaaaaca aggatgacga gctgacgggc | 420 |
| ttttagcagc atgtacccaa agtgttctga ttccttcaac tggctactga gtcatgatcc | 480 |
| ttgctgataa atataaccat caataaagaa gcattctttt ccaaagaaat tatttcttca | 540 |
| attatttctc atttattgta ttaagcagaa attacctttt ctttctcaaa atcagtgtta | 600 |
| ttgctttaga gtataaactc catataaatt gatggcaatt ggaaatctta taaaaactag | 660 |
| tcaagcctaa tgcaactggc taaggatag taccacctc accccacca taggcaggct | 720 |
| ggatcgtgga ctatcaattc accagcctcc ttgttccctg tggctgctga taacccaaca | 780 |
| ttccatctct accctcatac ttcaaaatta aatcaagtat tttacaaaaa aaaaaaaa | 838 |

<210> SEQ ID NO 20
<211> LENGTH: 4102
<212> TYPE: DNA
<213> ORGANISM: Homo sapiens

<400> SEQUENCE: 20

```
agcctggttg gcagctgcgg cgcagagtcc agccgctggt gcgcggagcg gttcaccgtc    60
ttcggagcgg ttcggcccag cctttcgccc aggcgcccag gcccgctgcg cgcgtgcgtg   120
agcgcgcctg cgccgccggg gccgctgcaa ggggaggaga gaggccgcct caggaggatc   180
ccttttcccc cagaaattac tcaatgctga aacctctcaa agtggtatta gagacgctga   240
aagcaccatg gacgggtttt atgatcagca agtccctttt atggtcccag ggaaatctcg   300
atctgaggaa tgcagagggc ggcctgtgat tgacagaaag aggaagtttt tggacacaga   360
tctggctcac gattctgaag agctatttca ggatctcagt caacttcaag aggcttggtt   420
agctgaagca caagttcctg atgatgaaca gtttgtccca gattttcagt ctgataacct   480
ggtgcttcat gccccacctc caaccaagat caaacgggag ctgcacagcc cctcctctga   540
gctgtcgtct tgtagccatg agcaggctct tggtgctaac tatggagaaa agtgcctcta   600
caactattgt gcctatgata ggaagcctcc ctctgggttc aagccattaa cccctcctac   660 aaccccctc tcacccaccc atcagaatcc cctatttccc ccactcagg caactctgcc   720 cacctcaggg catgccctg cagctggccc agttcaaggt gtgggcccg ccccgcccc   780 ccattcgctt ccagagcctg gaccacagca gcaaacattt gcggtccccc gaccaccaca   840
tcagcccctg cagatgccaa agatgatgcc tgaaaaccag tatccatcag aacagagatt   900
tcagagacaa ctgtctgaac cctgccaccc cttccctcct cagccaggag ttcctggaga   960
taatcgcccc agttaccatc ggcaaatgtc agaacctatt gtccctgcag ctcccccgcc  1020
ccctcaggga ttcaaacaag aataccatga cccactctat gaacatgggg tcccgggcat  1080 gccagggcc ccagcacacg ggttccagtc accaatggga atcaagcagg agcctcggga  1140
ttactgcgtc gattcagaag tgcctaactg ccagtcatcc tacatgagag ggggttattt  1200
ctccagcagc catgaaggtt tttcatatga aaaagatccc cgattatact ttgacgacac  1260
ttgtgttgtg cctgagagac tggaaggcaa agtcaaacag gagcctacca tgtatcgaga  1320 ggggcccct taccagaggc gaggttccct tcagctgtgg cagttcctgg tcacccttct  1380
tgatgaccca gccaatgccc acttcattgc ctggacaggt cgaggcatgg agttcaagct  1440
gatagaaccg gaagaggttg ctcggcgctg gggcatccag aagaaccggc cagccatgaa  1500
ctatgacaag ctgagccgct ctctccgcta ttactatgaa aagggcatca tgcagaaggt  1560
ggctggagag cgatacgtct acaaatttgt ctgtgaccca gatgccctct tctccatggc  1620
tttccccgat aaccagcgtc cgttcctgaa ggcagagtcc gagtgccacc tcagcgagga  1680
ggacaccctg ccgctgaccc actttgaaga cagccccgct tacctcctgg acatggaccg  1740
ctgcagcagc ctcccctatg ccgaaggctt tgcttactaa gtttctgagt ggcggagtgg  1800
ccaaacccta gagctagcag ttcccattca ggcaaacaag ggcagtggtt ttgtttgtgt  1860
ttttggttgt tcctaaagct tgccctttga gtattatctg agaacccaa gctgtctctg  1920 gattggcacc cttaaagaca gatacattgg ctggggagtg ggaacaggga ggggcagaaa  1980
accaccaaaa ggccagtgcc tcaactcttg attctgatga ggtttctggg aagagatcaa  2040
aatggagtct ccttaccatg acaatacat gcaaagcaat atcttgttca ggttagtacc  2100
cgcaaaacgg gacatagtat gtgacaatct gcatcgatca tggactacta atgccttta  2160 catagaaggg ctctgatttg cacaatttgt tgaaaaatca caaacccata gaaaagtaag  2220
taggctaagt tggggaggct caaaccatta agggttaaaa atacatctta aacattggaa  2280
agctcttcta gctgaatctg aaatattacc ccttgtctag aaaaagggg gcagtcagaa  2340 cagctgttcc ccactccgtg gttctcaaaa tcataaacca tggctactct tgggaaccac  2400
```

```
ccggccatgt ggtcgccaag tagagcaagc cccctttctc ttcccaatca cgtggctgag    2460
tgtggatgac ttttatttta ggagaagggc gattaacact tttgacagta ttttgttttg    2520
ccctgatttg ggggattgtt ttgttttggt ggttgttttg gaaaaacagt ttataaactg    2580 attttttgtag ttttggtatt taaagcaaaa aaacgaaaaa caaaaaacaa aaacaaacct    2640
tttggtaact gtgcactgtg tcctttagcc agggccgtgc caacttatga agacactgca    2700
gcttgagagg ggctttgctg aggcttcccc ttggccatgt gaaagcccgc cttgttgcct    2760
gctttgtgct ttctgcacca gacaacctga tggaacattt gcacctgagt tgtacatttt    2820
tgaagtgtgc agggcagcct ggacacaagc ttagattctc tatgtatagt tccccgtgtt    2880
cactaacatg ccctctctgg aaagcatatg tatataacat gtgtcatgtc ctttggaaac    2940
ctggtcacct ggtgaaaacc cttgggattc ttccctgggc atgactgatg acaatttcca    3000
tttcatcagt ttgttttgtt ttcctttttc tttaaatctt ggactttaaa ccctacctgt    3060
gtgattcagt agggtttgag acttacgtgt gatactgaca ggtaagcaac agtgctagca    3120
ttctagattc ctgcctttt ttaaaaagaa attattctca ttgctgtatt atattggaaa    3180
agttttaaac aaccaagcta aagctatgtg aaagttgagc tcaaagtaga ggaaaagtta    3240
ctggtggtac cttgctgcct gctctgctgg tagaattctg tgctccccgt gacacttagt    3300
acattaagaa tgactacact gttcctcgta tgtgaaggag gcagtgctga ctccgtgagt    3360
gtgagacacg tgctttgaac tgcttttcta ttcatggagc actccatagt ctcaaactgt    3420
cccccttatg accaacagca catttgtgaa gaggttcgca gggataaggg gtgcacttta    3480
tagctatgga aacatgagat tctcctctat tggaagctaa ttagcccaca aggtggtaa    3540 acctgtagat tgggccttaa ttagcattgt actctaatca aaggactctt tctaaaccat    3600
atttatagct ttcttaacct acacatagtc tatacataga tgcatatttt accccccagct    3660 ggctagagat ttatttgttg taaatgctgt atagatttgg ttttcctttc tttacttacc    3720
ctggtttgga tttttttttt ttttctttg aatggattta tgctgtctta gcaatatgac    3780
aataatcctc tgtagcttga gctacccctc ccctgctgta acttacgtga cctgtgctgt    3840
cactgggcat aggacagcgg catcacggtt gcattcccat tggactcatg cacctcccgg    3900 atggttttg tttttttcgg gggttctttg gggtttgttt gtttgcttct tttccagagt    3960
gtggaaagtc tacagtgcag aaaggcttga acctgccagc tgatttgaaa actttccccc    4020
tgcgcagggc cgtatgcatc ctgccaagct gcgttatatt ctgtactgtg tacaataaag    4080
aagtttgctt ttcgtttacc aa                                              4102
```

<210> SEQ ID NO 21
<211> LENGTH: 12408
<212> TYPE: DNA
<213> ORGANISM: Homo sapiens

<400> SEQUENCE: 21

```
ctcacaacca gccgactctc ccattatcca gctgcctagt ttggtgcttc aatgtacatg      60
gctattccgt gtgcatatgt gtgtatacaa acacgcatgc atgcctggat ggacatacgt     120
atgcacaggt tatttttaa ggacaattct ttcaataagg tctttacccc ttacttgaaa     180
caggtgttca tgaaaaaaat gcacaaaatc ctgcctggcc ggaataattc atgaagaagg     240
ggctggatcc gtgggtcaga gaacacagga ccagttgcc atcccaaggc cgaaggcctc     300
cctccaacac agttctccaa gctctagaaa tctctgacac atcttgacca tgagaccacg     360
```

```
gctggttttt ggcaggattc gaggcacaaa cccagcagcc tcaacctagt tcatggagga    420
gcctcgcggg gtcctggcca agcaagcccg cccctctggt gggaagagcg gcgcctaggt    480
ggagggtggc tgccgtagga gtggacatga atgctggctt tcagagagaa cagcgtttca    540
gttttggtca tcggaagtgg tgccttcagc acagaagaag agcgtgattt ctcctccaag    600
gccgttgatc tccaacccag aactaaaggg gagaagagcc accccagca tccagcgtgg     660 catctcttgt gccaggacca gggatgactg ggccatggac acagatgtct ccaaccttca    720
accgtttgca tagcacacgg gggactcgtg ggggccacct gccactgcca gctgaaacaa    780
tacaatggca atactgacat ccttcatgac gtttttcccga cagacattca ggcagaaagt    840
gctggtgcgt tttctgtctg caaagtagag ggccatgcct caccaataga atagcgtggg    900
ccctgatgac ctgctccgag tccactcaca gccagtgaca cttgcaaaaa actcccaaag    960
ccgtcttggg tttggctccc acagctcttg accaatgtgg ccaaagctgg cacctcctt    1020 gggacactgg gattattcat aaatgcagcc cgccctgact ctccctgaat agcatctgaa    1080
gtctttgtga aggtcatgga tcctgaacaa agtgtcaagg gcaccaagaa ggctgaggga    1140
agtccccgga agcggctgac caaaggagag gccattcaga ccagtgtttc ttccagcgtc    1200
ccatacccag gcagcggcac agctgccacc caagagagcc ccgcccaaga gctcttagcc    1260
ccgcagccct tcccgggccc ctcatcagtt cttagggaag gctctcagga gaaaacgggc    1320
cagcagcaga agccccccaa aaggcccccc atcgaagcat ccgtccacat ctcacagctt    1380
ccgcagcacc ctctgacacc agcattcatg tcgcctggca aacctgagca tctcctggag    1440
gggtccacat ggcaactggt tgaccccatg agacctggac cctctggctc cttcgtggcc    1500
cctgggctcc atcctcagag ccagctcctt ccttcccacg cttccatcat tccccccgag    1560
gaccttcctg gagtccccaa agtcttcgtg cctcgtcctt cccaggtctc cttgaagccc    1620
acagaagagg cacacaagaa ggagaggaag cccagaagc caggcaagta catctgccag    1680
tactgcagcc ggcccgtgc caagcccagc gtgctccaga agcacattcg ctcacacaca    1740
ggtgagaggc cctacccctg cggcccctgt ggcttctcct tcaagaccaa gagtaatctc    1800
tacaagcaca ggaagtccca tgcccaccgc atcaaagcag gctggcctc aggcatgggt    1860 ggcgagatgt acccacatgg gctggagatg gagcggatcc ctggggaaga gtttgaggag    1920
cccactgagg gagaaagcac agattctgaa gaggagacta gtgccacctc tggtcaccct    1980
gcagagctct cccaagacc caagcagccc cttctctcca gcgggctata cagctctggg    2040
agccacagtt ccagccacga acgctgttcc ctgtcccagt ccagcacagc ccagtcactc    2100
gaagaccccc ctccatttgt ggaaccctca tctgagcacc cctgagcca taaacctgaa    2160 gacacccaca cgattaagca gaagctggcc ctccgcttaa gcgagaggaa gaaggtgatc    2220
gatgagcagg cgtttctgag cccaggcagc aaagggagta ctgagtctgg gtatttctct    2280
cgctccgaga gtgcagagca gcaggtcagc cccccaaaca ccaacgccaa gtcctacgct    2340
gagatcatct ttggcaagtg tgggcgaata ggacagcgga ccgccatgct gacagccacc    2400
tccacccagc ccctcctgcc cctgtccacc aagacaagc ccagcctggt gcctttgtct    2460
gtaccccgga cgcaggtgat cgagcacatc acgaagctca tcaccatcaa cgaggccgtg    2520
gtggacacca gcgagatcga cagcgtgaag ccaaggcgga gctcactgtc caggcgcagc    2580
agcatggagt cccaaaaatc cagcctctac cgggagcccc tgtcatccca cagtgagaaa    2640
accaagcctc aacaatcact gctgagcctc cagcacccgc ccagtaccgc cccccctgtg    2700
cctctcctga gaagccactc aatgccttct gccgcctgca ctatcagcac ccccaccac    2760
```

```
cccttccgag gtagctactc cttcgatgac catatcaccg actccgaagc cctgagccac    2820
agcagtcacg tgtttacctc ccaccccgg atgctgaagc gccagccggc aatcgaatta     2880
cctttgggag gggaatacag ttctgaggag cctggcccaa gcagcaaaga cacagcctcc    2940
aagccctcgg acgaagtgga acccaaggaa agcgagctta ccaaaaagac caagaagggt    3000
ttgaaaacaa aagggggtgat ctacgaatgt aacatatgtg gtgctcggta caagaaaagg   3060
gataactacg aagcccacaa aaatactac tgctcagagc ttcagatcgc aaagcccatc     3120
tctgcaggca cccacacatc tccagaagct gaaaagagtc agattgagca tgagccgtgg    3180
tcccaaatga tgcattacaa actgggaacc accctgaaac tcactccact gaggaagagg    3240
aggaaagaga agagccttgg ggacgaggaa gagccacctg cctttgagtc cacaaaaagt    3300
cagtttggca gccccgggcc atctgatgct gctcggaacc ttcccctgga gtccaccaag    3360
tcaccagcag aaccaagtaa atcagtgccc tccttggagg acccacggg cttccagcca     3420 aggactccca agccagggtc cggttcagaa tcagggaagg agaggagaac aacgtccaaa    3480
gaaatttctg tcatccagca caccagctcc tttgagaaat ctgattctct cgagcagccg    3540
agtggcttgg aaggggaaga caaacctctg gcccagttcc catcacccc acctgcccca    3600 cacggacgct ctgctcactc cctgcagcct aagttggtcc gccagcccaa cattcaggtt    3660
cctgagatcc tagtaactga ggagcctgac cggccggaca cagagccaga gccgccccct    3720
aaggaacctg agaagactga ggagttccaa tggccccagc gcagccagac acttgcccag    3780
ctcccagctg agaagctgcc acccaaaaag aagaggttgc gcctggcaga gatgcccaa    3840 tcatcagggg agtccagctt cgagtcctct gtgcctctgt ctcgcagccc gagccaggaa    3900
agcaatgtct cttttgagtgg gtccagccgc tcagcctcgt ttgagaggga tgaccatggg    3960
aaagccgagg cccccagtcc ctcatctgac atgcgcccca aaccctgggg cacccacatg    4020
ttgactgtcc ccagccacca cccacatgcc cgagagatgc ggaggtcagc ctcagagcag    4080
agccccaacg tttcccattc tgcccacatg accgagacac gcagcaaatc ctttgactat    4140
ggcagcttgt ccttgacagg cccttctgct ccagccccag tggctccacc agcgcgggtg    4200
gccccgccag agagaagaaa atgcttcttg gtgagacagg cctctctgag caggcctcca    4260
gaatctgagt tggaggttgc ccccaaggga agacaggaga gcgaagaacc acagccctca    4320
tccagtaaac cctctgccaa aagctcattg tcccagattt cctctgcggc cacctcacat    4380 ggtggaccc cggaggcaa gggcccaggg caggacaggc cccattggg gcccactgtg     4440 ccctacacag aagcactgca agtgttccac caccccgttg cccagacacc cctgcatgag    4500
aagccatacc tgcccccacc agtctcccct ttctccttcc agcatctcgt gcagcatgag    4560
ccaggacagt ctccagaatt cttctccacc caggccatgt ccagcctcct gtcctcacca    4620
tactccatgc ccccacttcc tccctcctta tttcaagccc caccgcttcc tctccagcct    4680
actgttctgc acccaggcca actccatctc ccccagctca tgcctcaccc agccaacatc    4740
cccttcaggc agccccctc cttcctcccc atgccatacc cgacctcctc agcactgtct    4800 tctgggttttt tcctgcctct gcaatcccag tttgcacttc agctccctgg tgatgtggaa    4860
agccatctgc cccagatcaa aaccagcctg ccccactgg caacaggaag tgctggcctc    4920
tcccccagca cagagtacag cagtgacatc cggctacccc ctgtggctcc cccagccagc    4980
tcctcagcac ctacatcagc tcctccactg gccctgcctg cctgtccaga caccatggtg    5040
tccctggttg tgcctgtccg tgttcagacc aatatgccgt cctatgggag cgcaatgtac    5100
```

```
accacccttt cccagatctt ggtcacccag tcccaaggca gctcagcaac tgtggcactt    5160
cccaagtttg aggaaccccc atcaaagggg acgactgtat gtggtgcaga gtgtgcatga   5220
gttgggcccg gcccttctgg gttaagtgaa gagcaaagca gagctttccc aactccatac   5280
ctgagagtgc ctgtgacatt acctgaaaga aaaggcactt ccctgtcatc agagagtatc   5340
ttgagcctgg aggggagttc atcaacagca gggggaagca aacgtgtcct ttcaccagct   5400
ggcagccttg aacttaccat ggaaacccag cagcaaaaaa gagtgaagga ggaggaggct   5460
tccaaggcag atgaaaaact tgagctggta aaccatgca gtgtggtcct taccagcacc    5520
gaggatggga agaggccaga gaaatcccac ttaggcaacc agggccaagg caggagggag   5580
ctagaaatgc tgtccagcct gtcctcagat ccatctgaca caaaggaaat tcctcccctc   5640
cctcaccctg cattgtccca tgggacagcc ccaggctcag aagctttgaa ggaatatccc   5700
cagccatctg gcaaacctca ccgaagaggg ttgaccccac tgagcgtgaa gaaagaagat   5760
tccaaggaac aacctgatct cccctccttg gcacctccga gctctctgcc tctgtcagaa   5820
acgtcctcca gaccagccaa gtcacaagaa ggtacggact caaagaaggt actgcagttc   5880
cccagcctcc acacaaccac taatgtcagt tggtgctatt taaactacat taagccaaat   5940
cacatccagc atgcagatag gaggtcctct gtttacgctg gttggtgcat aagtttgtac   6000
aaccccaacc ttccgggggt ttccactaaa gctgctttgt ccctcctgag gtctaagcag   6060
aaagtgagca aagagacata caccatggcc acagctccgc atcctgaggc aggaaggctt   6120
gtgccatcca gctcccgcaa gccccgcatg acagaggttc acctcccttc actggtttcc   6180
ccggaaggcc agaaagatct agctagagtg agaaggaag aagagaggag aggggagccg    6240
gaggaggatg ctcctgcctc ccagagaggg gagccggcga ggatcaaaat cttcgaagga   6300
gggtacaaat caaacgaaga gtatgtatat gtgcgaggcc gcggccgagg gaaatatgtt   6360
tgtgaggagt gtggaattcg ctgcaagaag cccagcatgc tgaagaaaca catccgcacc   6420
cacactgacg tccggcccta tgtgtgcaag cactgtcact ttgcttttaa aaccaaaggg   6480
aatctgacta agcacatgaa gtcgaaggcc cacagcaaaa agtgccaaga gacaggggtg   6540
ctggaggagc tggaagccga agaaggaacc agtgacgacc tgttccagga ctcggaagga   6600
cgagagggtt cagaggctgt ggaggagcac cagttttcgg acctggagga ctcggactca   6660
gactcagacc tggacgaaga cgaggatgag gatgaggagg agagccagga tgagctgtcc   6720
agaccatcct cagaggcgcc cccgcctggc ccaccacatg cactgcgggc agactcctca   6780
cccatcctgg gccctcagcc cccagatgcc ccgcctctg gcacggaggc tacacgaggc    6840
agctcggtct cggaagctga gcgcctgaca gccagcagct gctccatgtc cagccagagc   6900
atgccgggcc tccctggct gggaccggcc cctctgggct ctgtggagaa agacacaggc    6960
tcagccttga gctacaagcc tgtgtcccca agaagaccgt ggtccccaag caaagaagca   7020
ggcagccgtc caccactagc ccgcaaacac tcgctaacca aaaacgactc atctccccag   7080
cgatgctccc cggcccgaga accacaggcc tcagccccaa gcccacctgg cctgcacgtg   7140
gacccaggaa ggggcatggg cgctctcct tgtgggtctc caagacttca gctgtctcct    7200
ctcaccctct gccccctggg aagagaactg gcccctcgag cacatgtgct ctccaaactc   7260
gagggtacca ccgacccagg cctccccaga tactcgccca ccaggagatg gtctccaggt   7320
caggccgagt caccaccacg gtcagcgccg ccagggaagt gggccttggc tgggccgggc   7380
agcccctcag cggggagca tggcccaggc ttggggctgg accacgggt tctcttcccg     7440 cccgcgcctc tacctcacaa gctcctcagc agaagcccag agacctgcgc ctccccgtgg   7500
```

```
cagaaggccg agtcccgaag tccctcctgc tcacccggcc ctgctcatcc tctctcctcc    7560
cgacccttct ccgccctcca tgacttccac ggccacatcc tggcccggac agaggagaac    7620
atcttcagcc acctgcctct gcactcccag cacttgaccc gtgccccatg tcccttgatt    7680
cccatcggtg ggatccagat ggtgcaggcc cggccaggag cccaccccac cctgctgcca    7740
gggcccaccg cagcctgggt cagtggcttc tccggggtg gcagcgacct gacaggggcc    7800
cgggaggccc aggagcgagg ccgctggagt cccactgaga gctcgtcagc ctccgtgtcg    7860
cctgtggcta aggtctccaa attcacactc tcctcagagc tggagggcgg ggactacccc    7920
aaggagaggg agaggaccgg cggaggcccg ggcaggcctc ctgactggac accccatggg    7980
accggggcac ctgcagagcc cacacccacg cacagcccct gcaccccacc cgacaccttg    8040
ccccggccgc cccagggacg ccgggcagcg cagtcctgga gccccgcctt ggagtccccg    8100
cgtgcaccga ccaaccccga gccttctgcc accccgccgc tggaccgcag cagctctgtg    8160
ggctgcctgg cagaggcctc tgcccgcttc cagcccgga cgaggaacct ctccggggaa    8220
cccaggacca ggcaggactc ccccaagccc tcaggaagtg gggagcccag ggcacatcca    8280
catcagcctg aggacagggt tccccccaac gcttagcctc tctccaactg cttcagcatc    8340
tggcttccag tgtccagcaa cagacgtttc cagccacttt cctcgaatca tcccacttcc    8400
tcagccccat ctgtccctcc gtccaggagc tctcacggcc ccatctgttg taccttccca    8460
tgtatgcagt tacctgtgcc ttttctaca ccttttgttg cttaaaaaga aacaaaacaa    8520
atcacataca tacatttaaa aaaaaacaa caacccacga ggagtctgag gctgtgaata    8580
gtttatggtt ttggggaaag gctgatggtg aagcctcctg accctccccg ctgtggttgg    8640
cagccaccca ccccagaggc tggcagaggg aaagggtac actgagggag aaaggaaaag    8700
gaaacttcaa acaatataga attaaatgta aaggaagca ctcctgtgta cagatgcgat    8760
caaggttcct gtttattgcc acttcacccc cctgcccagc tcgtagccac ccctctctgc    8820
cagcagaaag gccagtgtcc ccaggcagag gggcacaaac acaggcaggt gaccccccacc    8880 caggccccag caggcaggcc cagaaaaact aatcttttcc tttttttttt tttttttttt    8940
ttttgcaaga aaataaaatg atactttcc taggatttca acacaaaata ataggtgcag    9000
gtagaaggag gagggctggc tccccaaggg ctcctggata ctctggtagt ctgagtcatg    9060
ggcccatcct ggcactccac aggtgggcag gccaccccac ccacgcaccc ccactccaga    9120
cacctccctt ctgcaccca ccctggcccc ctgggctggg aaggagccc tgactgtccg    9180 tccctggctc ccaagcccct gaccgaggcc tcactctcct gttgcctcct ctgttctaaa    9240
accaccaaac cacccacaaa ggcagaagtg gcagggcccg agccctagcg gccgttcctg    9300
agactggggt ttgggtttg tttcatcttg gtccctgggg tacaagggag cctgttcccc    9360
tcatggctgg gtttttccag ttctccacag cagaggtttg cggggaactg tttcaggacc    9420
actttgccac aggaccgttt ccccccgtcc ctgcccctgt ctccactacc caaggaaat    9480 acccacaact gtggctggtg gatacggcct ggacctgttt gctgtcttac acctctttt    9540 taaaaagaga gaggatggtg tttgatactt cacccagcca ccacagattc tttgaccta    9600 gaggattttt gaattgtcct aactcgttgg aattctccaa agcaatcagt gtgagccagt    9660
gcctcttcct tacccacatc tctactttca agaagctgcc ctgcatttcc tggggcaaaa    9720
ctctactttg taagaaaaat aataggacca gaaatttaaa tcccaaattg aactatggaa    9780
cttgaactct agcgtgttcg ccccaactgg gagaggtgag ctttttccca gtgtttcaga    9840
```

```
actgattttc tttactttct acaagggagg gcagcacagg gactacggtt gaggcccgtg    9900
aaggctgggt ttgatgccac cctatacaga gcagggacct ctctggctaa tccccagtcc    9960
tcagccaggc tgtgtgaatc aagtgcctgc cccagggctc ttgagctatt gaagctgctt   10020
gggtacagga cacagtaggt ggggagggtt aagacccttc tgtgagttcc ctgtgcgggg   10080
ctgtacttgc ctcttccaat tcgtggcctt tccctgcttg gtccctacta gacagacaaa   10140
ccagccacag tccagcctgc agccagacca ccttgttcac tcattctcct ttgcctcaga   10200
gctaagacaa aaatgagaca gaaggcaggg ctccctggga gtccactgtg ctccagggtt   10260
ctggggaatc agggttagcc agcagctcct ggctgcttcc ctcagagact agggctctca   10320
tcctccccaa gagaagcagc aagcccagcc tggaccacac tgtccatatt gctggacagt   10380
ggcctgacag aaagtgactc ctccaagtcc caggaggcca gggcttttct catccttgcc   10440
tttcagccct aacccatggg actgcccacg gattggagac ttcaagggct gaggtctggg   10500
agctgcataa agggcattgc ttcagcccag gttagaaatc tgcctgggca agctcttcct   10560
gccccagacc tacaaagcag cagaccgggg gctctggtgg actagcccct gacattggtg   10620
gggggcccca caccactcca ccccacccctg ccttccagct ctcctgggca ttttctccc   10680 tgtactcaaa cagcctaccc acccaaggtt tcctccctgg gcagcctagc aatgaacagt   10740
gcagccggca gggcagaggc ccggcagtca ccgggcccgt caggctcagg cagagaagcc   10800
acaggggcca ggagtcactg gagactattt ctaaatgatg ggggtaaatg cacaaataga   10860
atctcaccaa agggctgcct ccacattgat gccgtgccca gagggacaga accaatgcca   10920
ccagcctggg tatatgtcac tgggcacagc tctaaccccc tcctccggac tctagtcccg   10980
ctcctctgcg cacagagccc ccagcccaca ggtacacctt catgatttgg agaaagacgc   11040 tcgcccatg cacgccctcc tctgggcctt ctgccctgct cccagtcact ccaagcttc    11100 ctgtttgcct gtgatgttat tgtgcctgtt gagggaagca gcagaggagg cagtggctga   11160
cttggcacag atgcctgcta cgtgctctgt tgaaatgcgc ggggtggcca ttcctcggta   11220
cagactagtc ctggtccttg ggtgtgggca gtggggagg aaccaactgg tcgaggtttc    11280
agagccaaac cttgcctttg gttggtgagt ccttgccccc caggcctgcg ctccacgatg   11340
cctttcaccc ttggcaatct cagggccatc ctgggtagta accccactcc tctctgctcc   11400
cgcccgcacc tgtggctctc actctgggct caacccctgc aaccctccag gagcccgaca   11460
gcagccagct gcctgcactg tcgcctccgt aagctccaac ttccagaccc agaagtccct   11520
ctgcttccct ctgttggaaa aagcctaaaa gaattagctt ccagattcct ctagcccctg   11580
ctccattccc acccagtcct tctgaagagg aatgagcaat acatctgagc tggatttctc   11640
tctagtcctt tctccagaca aatccttctt aaagcaaaag tcctggctga gcacctgtcc   11700
ttggggaccg atctgccgtg tgaccagggg aagaaagttc ccgaaagcct gttccaccaa   11760
ttctgcttct gtgttgtgaa tccagtctgc tttccattag aaaaccgctt cggcacttat   11820
ggtcacttta ataaatctag tatgtaaaaa agaaagaaa gaaagaaac agaaaaaaga     11880 aacgtgcagg caaatgtaaa atacaatgct ctctgtaaga taaatatttg cctttttttc   11940
taaaaggtgt acgtattctg tatgtgaaat tgtctgtaga aagtttctat gttcttaaat   12000
ggcaatacat tccaaaaatt gtactgtaga tatgtacagc aaccgcactg ggatggggta   12060
gttttgcctg taattttatt taaactccag tttccacact tgcatcttgc aatgttggta   12120
tggtatatat cagtgcaaaa gaaaaaacaa aacagaaaca aacaaaaaaa aaaaacaaaa   12180
atccacgcag gtctaaagca cagagtctga cgtacaaaag gaaaaatgct cagtattgat   12240
```

```
gtgtgtgacc tttgttgtaa attacatctg tactgtgaat gagaagtttt tacaagtata    12300
ataattgcct ttattacagc tctggctgag tgttcagcct gaggatattt tttaaaaaaa    12360
aaagaattag catgttggaa taaatttgaa atcccaaca  taaaaaaa                 12408

<210> SEQ ID NO 22
<211> LENGTH: 3257
<212> TYPE: DNA
<213> ORGANISM: Homo sapiens

<400> SEQUENCE: 22
tctcactagc ctcagagcac tctcagaagt tcagaaacta agaccagaaa agagaagatt      60
tttagacagc tcatgaaacg gtctgcgcgg ggcggccatt ggcggcggag tgtcacgtga     120 ccgcggggge gtgccaatgt gcgccctcac gggtgtcaaa cccctgtcag agtgtgcgat     180
caagatcgtg aaacaacgcg atgcaaaaag cgacctacta cgacagctcg gcgatctacg     240
gtggctaccc ctaccaggca gccaacgggt tcgcttataa tgccaatcag cagccgtacc     300
cggcgtccgc cgctttgggc gccgacggcg agtaccaccg acccgcctgc tccctccagt     360
ctccctccag cgccggggc  caccccaagg cacacgaact gagtgaggcg tgcctgcgca     420
ccctgagcgc cccacctagc cagcctccaa gcctgggaga gccgcccctg cacccgccgc     480
cgccccaggc cgcgccccct gccccacagc cgcctcagcc cgcacctcag cccctgcac      540 ctaccctgc  cgcgccccg  cctccctctt ctgcctcccc tcctcagaat gccagcaaca     600
accctacccc tgccaacgcg gccaagagcc ccctgctcaa ctcacccaca gtggccaaac     660
aaatcttccc ctggatgaaa gagtctcgac aaaacacaaa gcagaaaacc agcagctcca     720
gctcaggcga aagctgcgct ggcgacaaga gcccgccggg gcaggcttcg tccaagcgcg     780
cgcgcacggc ctacacgagc gcgcagctgg tggagctgga gaaagagttc cacttcaacc     840
gctacctgtg ccggccgcgc cgggtggaga tggccaatct gctgaacctc actgagcgcc     900
agatcaagat ctggttccag aatcgccgca tgaagtacaa aaaggatcag aagggcaagg     960
gcatgctaac gtcatcgggg ggccagtctc caagtcgcag cccgtgcc   cccggagccg    1020 gtggctatct gaactctatg cattcgctgg tcaacagcgt cccgtatgag ccccagtcgc    1080
ccccgcccct tctccaagcc cccagggta  cctacgggct gccccccgcc tcctaccctg    1140
cgtccctgcc cagctgcgca ccccccgccac ccccacagaa gcgctacacg gcggcagggg    1200
cgggcgcagg gggcacccc  gactatgacc cgcacgctca tggcctgcag ggcaacggca    1260
gctatgggac cccacacata cagggaagcc ccgtcttcgt gggggggcagc tatgtggagc    1320 ccatgagcaa ctccgggcca gccctctttg gtctaactca cctcccccac gctgcctcgg    1380
gcgccatgga ctatggggg  gccgggccgc tgggcagcgg ccaccaccac gggccggggc    1440
ctggggagcc gcaccccacc tacacggacc ttaccggcca ccatccttct cagggaagaa    1500
ttcaggaagc acccaagctc accccacctgt gatagtgggc ttggggctac gcgccaggag    1560
agtctccccc cacccacctt ttttctttgg ttgctttttt tttttttttt ttttaggttc    1620
ttcctgccct ttccttcctt ccttttctct cttctccgcc ccgcactccg tttcccggtt    1680 tccccctcg  ttggtaaggc gttttatag  tttatgtgac gtagcaatct tggttgctgg    1740
aatggctgta tcatagcgat atttatctct tcctgctcct cgataggcca ctggccctgc    1800 acccttacc  ttctccactc tttgatcaga aacagggtat atgaacaaat tttctagtcg    1860
agttttcaat gtgaatttgt tcttacatta tggctcccga ggggaagcga ttacttttt     1920
```

```
taattttaaa ttttttttt  aattgcactt  cttgtaaaga  gtgagaaaaa  aaatcaaagg    1980
cgctttgaaa cagggggctct ctgtgcaagg atgactaagt gtacgtcttt ccgtgtgtgt    2040
atgctggtga acagtcagat ttatttatat ttttttgcaa gcattgaata atctaagttt    2100
taaatattat ttatccccat ccgttcgtat ttatattaaa gaattctgta ccctgatggt    2160
tcagaagggt tcttgggcct tttgttcaat tgtgtattgg cgtacttaga atttttttta    2220
tttgaaagag aaatataatt cctttaaacg gtaacgatac aataaaacca gagaagatcc    2280
agcttttgaa aacagtgatt taggtttgta acatccggca aaactgaaaa aaaaaatctg    2340
taaacgcgaa aaatactaga tttgtttttga gagttcttca ttccttgctg ctcacattct    2400
gagaaacaaa aagaaataaa gttttttattc tgaataatat ccgtgttaag aagggggttct    2460 ttggccgaag acgtgggtct gcgtggaatt caggccgagg cgagccggca gagcaggccg    2520
gacgcagcag ccctctggct ccagcatggg gcctggccag gctattcgcc tggaagctcg    2580
gcgaattctc aggatggcgg ctggggctcc aggcggctgc ggcagctctg gtaacgccgt    2640
gcggcgggcc agctgggctg cccggttccc agctgctgcg gaggcaggct gagggcgcag    2700
gggctgccga gtgctgtgca cggaagaaac aaagacatcc cggcccaagg cgcagcggga    2760
gcgcacaggt gccccgcggc ccagccgggg gataacgcag ggcggtcttc tgctccatgc    2820
tcttcctcgg gtcaaagcgg accaactaac gcctaaacct cggtattagc cagccgcgca    2880
gaggatgccg agcactttcc gggagcaatc ggactcctgg tctcctccgg ggatgcttcg    2940
cggtctgtta tcgcgtcagg aggaaagaat tgctccaaaa atctgcacgc ggagcgaaac    3000
agtttgaaag ggactgaggc tcacccaggt ctccagcaaa cggaggactg aactggggag    3060
agtcaccctg agccagccct tccctggact gccggaatcc cagcattagc ttcctgctga    3120
atgtagtatt tggcattctc tgaatttatt tcctctcctt cccccaccca gctttctttt    3180
tatggcccca gggggagggg gagagagcaa ggagatcggt atctttgtaa taaaactgca    3240
attttataaa tttttca                                                    3257

<210> SEQ ID NO 23
<211> LENGTH: 1657
<212> TYPE: DNA
<213> ORGANISM: Homo sapiens

<400> SEQUENCE: 23
gggtgctata gacgcacaaa cgaccgcgag ccacaaatca agcacacata tcaaaaaaca      60
aatgagctct tattttgtaa actcatttttg cggtcgctat ccaaatggcc cggactacca    120
gttgcataat tatggagatc atagttccgt gagcgagcaa ttcagggact cggcgagcat    180
gcactccggc aggtacggct acggctacaa tggcatggat ctcagcgtcg gccgctcggg    240
ctccggccac tttggctccg gagagcgcgc ccgcagctac gctgccagcg ccagcgcggc    300
gcccgccgag cccaggtaca gccagccggc cacgtccacg cactctcctc agcccgatcc    360
gctgccctgc tccgccgtgg cccccctcgcc cggcagcgac agccaccacg gcgggaaaaa    420
ctccctaagc aactccagcg gcgcctcggc cgacgccggc agcacccaca tcagcagcag    480
agagggggtt ggcacggcgt ccggagccga ggaggacgcc cctgccagca gcgagcaggc    540
gagtgcgcag agcgagccga gccggcgcc gcccgcccaa cccagatct accccctggat    600 gcgcaagctg cacataagtc atgacaacat aggcggcccg gaaggcaaaa gggcccggac    660
ggcctacacg cgctaccaga ccctggagct ggagaaggga ttccactcca ccgttacct     720 gacccgcaga aggaggattg aaatagcaca tgctctttgc ctctccgaga gacaaattaa    780
```

```
aatctggttc caaaaccgga gaatgaagtg gaaaaaagat aataagctga aaagcatgag      840
catggccgcg gcaggagggg ccttccgtcc ctgagtatct gagcgtttaa agtactgagc      900
agtattagcg gatcccgcgt agtgtcagta ctaaggtgac tttctgaaac tcccttgtgt      960
tccttctgtg aagaagccct gttctcgttg ccctaattca tctttttaatc atgagcctgt    1020 ttattgccat tatagcgcct gtataagtag atctgctttc tgttcatctc tttgtcctga    1080
atggctttgt cttgaaaaaa aatagatgtt ttaacttatt tatatgaagc aagctgtgtt    1140
acttgaagta actataacaa aaaagaaaa gagaaaaaaa aacacacaaa aagtccccct    1200
tcaatctcgt ttagtgccaa tgttgtgtgt tgcactcaag ttgtttaact gtgcatgtgc    1260
gtggaagtgt tcctgtctca atagctccaa gctgttaaag atattttat tcaaactacc    1320 tatattcctt gtgtaattaa tgctgttgta gaggtgactt gatgagacac aacttgttcg    1380
acgtgtagtg actagtgact ctgtgatgaa aactgtgact ccaagcggtg tgtccctgcg    1440
tgcctttata ggacccttg cacgaactct ggaagtggct cttataagcg cagcttcagt    1500
gatgtatgtt tttgtgaaca aagttacaaa tattgtccaa gtctggctgt tttaagcaaa    1560
ctgtgatcag cttttttttt tttttttttt tttttgtatt tgttttaag gaaaaaatac    1620 tgactggaac aaaaaataaa ctttctattg taagttc                              1657

<210> SEQ ID NO 24
<211> LENGTH: 3627
<212> TYPE: DNA
<213> ORGANISM: Homo sapiens

<400> SEQUENCE: 24
ctgggtaggg caggggaac cgacaggccg gtgtccccag ccgcaaaaga gctgctgaac        60
tgtccgttta aatgctgctg ggagactcgt aaaaaaatca tcgtggacct ggaggatgag      120
aggggcgagc tttatttcgg tcggattgcg gtgtggtggt ttagctgcaa ggggatgccg      180
cagccccagt tgaggggaa aatagttctt aaaaagcata tgccccccta aggaatgtct      240
ctaaagaacc aaatcaaagc tgctctttgg aaggtatgaa tagaatttaa aaaaaaaga      300 tttctatgga gcttaaagtt cacagccatt ctgtgtagac aagagctaag aaaaatgtga      360
gaattataca gaaaaccatt aatcacttct tttctttaaa tacgtatcct ctctccttttg    420 ttattattca acagcaaatc tccttggacc ggctgttggg ggaaaaaagt gttagccgtc      480
tctcccggat ctgcaagggg gaaaaaattt ggaaccataa agttgaaaac tttttttctct    540 cagtttggaa gaagcccttc gtcatgaatg ggatctgcag agttcgggcg agaggaggcg      600
agaggcgcaa aggaggggag atttgtcgcc tgccgctcgc tctgggctc gatgtgaata      660 tatattatgt ctgcctgttc tccctcgtc ggtggctaag gtcagccgct tggaacagac      720
cccggaggag ggggcagag aggggaggtg gggggggggg gtccggcgtg tcacgtgacc      780
cccagggttg ccaatgtccg gtcctgaggg tatcaggcct ttccaagttg ccacccactg      840
cccaggcctc acccagcgat gcagaaagcc acctactacg acaacgccgc ggctgctctc      900
ttcggaggct attcctcgta ccctggcagc aatggcttcg gcttcgatgt cccccccccaa     960 ccccccattc aggccgccac gcacctggag ggcgactacc agcgctcagc ttgctcgctg    1020
cagtccctgg gcaacgctgc cccacatgcc aagagcaagg agctcaacgg cagctgcatg    1080
aggccgggtc tggcccccga gccctgtcg gcccgcctg gctcacccc gcccagtgcc    1140 gcacctacca gtgccactag caacagcagt aatggggcg ggcccagcaa aagtggtccc    1200
```

```
ccaaagtgcg gtcccggcac caactccacc ctcaccaaac agatattccc ctggatgaaa      1260
gagtcgaggc aaacgtccaa gctgaaaaac aactcccccg gcacagcaga gggctgtggt      1320
ggcggcggcg gtggcggcgg cggcggaggc agtggtggca gcggggggcgg tggcggcggc      1380 ggcggggggag gggacaagag ccccccgggg tcggcggcgt ccaagcgggc gcggacggcg      1440
tacacgagcg cgcagctggt ggagctggag aaggagttcc attttaaccg ctacctgtgc      1500
cggcctcgcc gtgtagagat ggccaacctg ctgaacctca gcgagcggca gatcaagatc      1560
tggttccaga accggcgcat gaagtacaag aaggaccaga aggccaaggg attggcctcg      1620
tcgtcggggg gcccatctcc agccggcagc ccccgcagc ccatgcagtc cacggccggc      1680
ttcatgaacg ccttacactc catgaccccc agctacgaga gcccgtcccc acccgccttc      1740
ggtaaagccc accagaatgc ctacgcgctg ccctccaact accagccccc tctcaaaggc      1800
tgcggcgccc cgcagaagta ccctccgacc ccggcgcccg agtatgagcc gcacgtcctc      1860
caagccaacg ggggcgccta cgggacgccc accatgcagg gcagtccggt gtacgtgggc      1920
gggggcggct acgcggatcc gctgccgccc cctgccggcc cctccctcta tggcctcaac      1980 caccttctcccc atcacccttc cgggaacctg gactacaacg gggcgccccc tatggcgccc      2040
agccagcacc acgacccctg cgaacccccac cccacctaca cagacctctc ctctcaccac      2100
gcgcctcctc ctcagggtag aatccaagaa gcgcccaaat taacacacct gtgatgggaa      2160
agggcgaacg aggattaggg gatggggagg aagagagaga ctgtggagct ctgggggca      2220 acctggaggt ctgaaaagag gagccagaga aggtggtacc caggcttcct ggtcagaacc      2280
ggcctggagc tccttccctt cccctggcc tgagaggttg cttttaagtc ttccaccct      2340 tgttccatct gcctgccaac ccatcggaaa ggaatccaca tcatattgga gatgacccca      2400
tcaaccccag ggctccagca ctaccaagtt ggaattccac gcccgggagt ggggtagagg      2460
aagacgagac aggacgaggc agaaaagcac atttaaaaa ccagacaaga tggctaggcc      2520
atcaccaacc aacggactta ccttacatct ttgtaggtaa ttccccccaa atcttgattt      2580 tttttttttcc tcaattatcc tttaaaaaat aagaaacac atttcaaacc caaaaggcac      2640
aaaacacgtt cccttccaac tttcccaaaa cctcaaattt gttcccattt gaggtttatt      2700
gaggtacact tctagccccc ggttttttctg ctctagaaca ttcatatcta tacatcccac      2760
ccccatcaat tacagttttt agagggctca gggatggtga gagatcctga aagagctgcc      2820
tatattataa attatataca ttttttttta aggaaaagtg tggaggctag ggcaggcagg      2880
ttgttaggac tgaaggtttg cccattctgc tgcctccatc tcagctccag ctccatcccc      2940
ctctccacag aaagcagttg gtgacacgag gttctatact tttcttctgt tgctctcttg      3000
acttaacgtg aaaacagggt atatttgaac aaactgtccc aggcagggc tgggcagggc      3060 ctgtgtgcct tgctcagcct cctgacagga cacttttgtt gcacttagaa tttacatttt      3120
aatggatgta aaaacaactg tgagagatgt ctgggcctgc agaagtccag cattgctcaa      3180
aaaagcgtgt gttctagtga acatttcat atatatttat tggttatagc ctgttaaaat      3240 attttcttttt ttgtattatt tatccccccta cattatgtat ttatatgagg gaaaaaaagg      3300
aaaaaattgt actttttag tatttacctg ttacaaagga cattgtgttt cctgtcatgt      3360
aaaaccagct attttagtta ctattgtact ctagaaaaga gctgtagatt tatgttaaac      3420
tcgtacttac gaacaattgt aattagttct aaaaggcatg aactcagctc ctaatcgtca      3480
ctgtatagtc ctgaatttgt agaactagag ttaattccct cttggaactt tctttgttct      3540
tcagtagtta cttttttcct tacctaaaag ggttgtctgt caaacaattc ttgaataaac      3600
```

```
tttctgttat caatttttaaa aaaaaaa                                        3627
```

<210> SEQ ID NO 25
<211> LENGTH: 1830
<212> TYPE: DNA
<213> ORGANISM: Homo sapiens
<400> SEQUENCE: 25

```
gtgaagcaca gggttataac gaccacgatc cacaaatcaa gccctccaaa atcacccaaa      60
tgagctcgta ctttgtaaac tccttctcgg ggcgttatcc aaatggcccg gactatcagt     120
tgctaaatta tggcagtggc agctctctga gcggctctta cagggatccc gctgccatgc     180
acaccggctc ttacggctac aattacaatg ggatggacct cagcgtcaac cgctcctcgg     240
cctcctccag ccactttggg gcggtgggcg agagctcgcg cgccttcccc gcgcccgccc     300
aggagccccg cttcaggcaa gcggcttcga gctgctccct gtcctcgccc gagtccctgc     360
cctgcaccaa cggcgacagc cacggcgcca agccctctgc ttcgtccccc tccgaccagg     420
cgacctcagc cagctccagc gccaatttca ccgaaataga cgaggccagc gcgtcctcgg     480
agcctgagga agcggcaagc cagctaagca gccccagcct agctcgggcg cagccagagc     540
ccatggccac ctccacagcc gcgcccgagg ggcagactcc gcaaatattc ccctggatga     600
ggaagcttca catcagccat gatatgaccg ggccggacgg gaaaagggcc cggaccgcgt     660
ataccegcta ccagaccctg gagctggaaa aggagttcca cttcaaccgc tacctgaccc     720
ggcgacggcg catcgagatc gcccacgcac tctgcctgtc cgagcgccag atcaagatct     780
ggttccagaa ccggcgcatg aagtggaaga aggacaacaa attgaaaagt atgagcctgg     840
ctacagctgg cagcgccttc cagccctgag cccgcccaga ggagcccagc ggcccaagag     900
cccgtgccac ccccagccct ggcccctcca atcctccccg ctctgccgcc gccgctgggg     960
gaccggttcc cacaagcctg cctcgccttg tgttacgata tttcgtttgg tcttaggtct    1020
tcctgtggct ccctctctcc tggactggtt atcttgttat tattgttaat aataattatt    1080
attattattt tccttccatg ctcccaactc ccttctgctt gtcccaaatc cgccagtgtt    1140
tctgaatgtt tgtgtctgtg gttgcagtct ttcccccagg aaaaaaaaaa aaagaaattc    1200
gcatgtttaa tgtgaactct cccctcccca tctgtgttct aacttattta taaaaagatg    1260
atcgctgtat tttgagtttc agctggaaac ttctgtaagg ggcagcagtt gaggtggggt    1320
agtgccgcag tggggtcaag ctgagctggc ttcggagatg gagtccettt tcattctcct    1380
cctcctccct cctcactccc taggcccaag tctcctaggg gcttggtcct agggtgggaa    1440
ggggctaggg aggaccaaag ggatggtatt gagaagagag aaagaagata gtgagattta    1500
agttcctgct gcctgggtag gccccacaag gcctggtctg ggagtatacg gaaacaaaaa    1560
tgatcctcag tgcaaaatgt cttgtgtatt tctctgtgaa tccatgggtc tggctagagg    1620
gcccaaagct tgtaaatatg gggatagtct gggtcagacc catctctccc ttacccatct    1680
tgcttccaag accatttgta gtgagcgagt ggatgctgtg ctacgtgtga aatctgtctt    1740
tgcggggcct gtctcagtga ttcgcttttg gtatttgttt gtagctttcc tggaagtcaa    1800
ataaatgttt ccccccactcc aaaaaaaaaa                                    1830
```

<210> SEQ ID NO 26
<211> LENGTH: 1686
<212> TYPE: DNA
<213> ORGANISM: Homo sapiens

<400> SEQUENCE: 26

```
caccacacct aggtcggagc actgtcgtcc ttcagggctc cagcctcttg atattttgt      60
acttcagtat cagctcgata gagcaaaaga gagagaggac gagagagggg gtcagagaag     120
gggaagcaac ggctctcacg ttgggacaat attatctgga agctgaagaa gaaactgaat    180
actccttcct tcctccccac ccattccttt aaatccggag ggggaaaaaa tcccaaggtc    240
tgcaaaggcg cggcgctcgg actataaaac acaacaaatc ataaacccgg cggagcagca    300
gcggccgcgc gcgcctcccc tcccaatgag ttcctatttc gtgaactcca ccttccccgt    360
cactctggcc agcgggcagg agtccttcct gggccagcta ccgctctatt cgtcgggcta    420
tgcggacccg ctgagacatt accccgcgcc ctacgggcca gggccgggcc aggacaaggg    480
ctttgccact tcctcctatt acccgccggc gggcggtggc tacgccgag cggcgccctg      540
cgactacggg ccggcgccgg ccttctaccg cgagaaagag tcggcctgcg cactctccgg    600
cgccgacgag cagcccccgt tccaccccga gccgcgaag tcggactgcg cgcaggacaa      660
gagcgtgttc ggcgagacag aagagcagaa gtgctccact ccggtctacc cgtggatgca    720
gcggatgaat tcgtgcaaca gttcctcctt tgggcccagc ggccggcgag gccgccagac    780
atacacacgt taccagacgc tggagctgga aaggagttt cactacaatc gctacctgac      840
gcggcggcgg cgcatcgaga tcgcgcacgc cctgtgcctg acggagaggc agatcaagat    900
atggttccag aaccgacgca tgaagtgaa aaaggagagc aaactgctca gcgcgtctca      960
gctcagtgcc gaggaggagg aagaaaaaca ggccgagtga aggtgctgga aagggaggga   1020
ggacgcgagg ggaaaggcct gtggggagcc gagggcgtca gagagacccg ggaaggaagg   1080
ctctcgggtg ggggagccag gagacctgct ctccggcgca gacaggcggg gcccagcgct   1140
ctcctggacg cccccgcccg cacagctccc ggcgggtgct ctgaggcctc actactcgag   1200
cccacccagc atcccgcgcg ccccttcttc ccgaggaact cgcctcagcc tgatcaggct   1260
tcctggtgag aactgaggag cggactcact tgatgtttcc tggaagcaga gcaaaatgct   1320
cttgtccctg tcgcgtctca ttttgtccat gtccccgtg cacggttcaa tggtagattc     1380
gctgtccect cagcggggc cttgaagact ccctgatccc agacctgtcg tctctcccac     1440
cccctcccca aagccactgg aaggagcaca tactacctag aagtaagaag aggagcctca   1500
gaagaaaaca aagttctatt ttattaattt tctatgtgtt gtgtttgtag tcttgtctta   1560
gctctggacg tgaaatactt cgatgatgat gatgatgatg atgatgataa taataataat   1620
aataacaaca caacaacaa taataaagat gtgaaaactc gacgctcggt cacctcaaaa     1680
aaaaaa                                                             1686
```

<210> SEQ ID NO 27
<211> LENGTH: 5680
<212> TYPE: DNA
<213> ORGANISM: Homo sapiens

<400> SEQUENCE: 27

```
aacgggctca ttcagcggtc gcgagctgcc cgcgaggggg agcggccgga cggagagcgc      60
gacccgtccc gggggtgggg ccgggcgcag cggcgagagg aggcgaaggt ggctgcggta    120
gcagcagcgc ggcagcctcg gacccagccc ggagcgcagg gcggccgctg caggtccccg    180
ctcccctccc cgtgcgtccg cccatggccg ccgccgggca gctgtgcttg ctctacctgt    240
cggcggggct cctgtcccgg ctcggcgcag ccttcaactt ggacactcgg gaggacaacg    300
tgatccggaa atatggagac cccgggagcc tcttcggctt ctcgctggcc atgcactggc    360
```

```
aactgcagcc cgaggacaag cggctgttgc tcgtgggggc cccgcgggca gaagcgcttc    420
cactgcagag agccaacaga acgggagggc tgtacagctg cgacatcacc gcccgggggc    480
catgcacgcg gatcgagttt gataacgatg ctgaccccac gtcagaaagc aaggaagatc    540
agtggatggg ggtcaccgtc cagagccaag gtccaggggg caaggtcgtg acatgtgctc    600
accgatatga aaaaggcag catgttaata cgaagcagga atcccgagac atctttgggc     660
ggtgttatgt cctgagtcag aatctcagga ttgaagacga tatggatggg ggagattgga    720
gcttttgtga tgggcgattg agaggccatg agaaatttgg ctcttgccag caaggtgtag    780
cagctacttt tactaaagac tttcattaca ttgtatttgg accccgggt acttataact     840 ggaaagggat tgttcgtgta gagcaaaaga ataacacttt ttttgacatg aacatctttg    900
aagatgggcc ttatgaagtt ggtggagaga ctgagcatga tgaaagtctc gttcctgttc    960
ctgctaacag ttacttaggt ttttctttgg actcagggaa aggtattgtt tctaaagatg    1020
agatcacttt tgtatctggt gctcccagag ccaatcacag tggagccgtg gttttgctga    1080
agagagacat gaagtctgca catctcctcc ctgagcacat attcgatgga aaggtctgg    1140 cctcttcatt tggctatgat gtggcggtgg tggacctcaa caaggatggg tgcaagata    1200 tagttattgg agccccacag tattttgata gagatggaga agttggaggt gcagtgtatg    1260
tctacatgaa ccagcaaggc agatggaata atgtgaagcc aattcgtctt aatgaaccaa    1320
aagattctat gtttggcatt gcagtaaaaa atattggaga tattaatcaa gatggctacc    1380
cagatattgc agttggagct ccgtatgatg acttgggaaa ggttttatc tatcatggat     1440 ctgcaaatgg aataaatacc aaaccaacac aggttctcaa gggtatatca ccttatttg     1500 gatattcaat tgctggaaac atggaccttg atcgaaattc ctaccctgat gttgctgttg    1560
gttccctctc agattcagta actatttttca gatcccggcc tgtgattaat attcagaaaa    1620
ccatcacagt aactcctaac agaattgacc tccgccagaa aacagcgtgt ggggcgccta    1680
gtgggatatg cctccaggtt aaatcctgtt ttgaatatac tgctaacccc gctggttata    1740
atccttcaat atcaattgtg ggcacacttg aagctgaaaa agaaagaaga aaatctgggc    1800
tatcctcaag agttcagttt cgaaaccaag gttctgagcc caaatatact caagaactaa    1860
ctctgaagag gcagaaacag aaagtgtgca tggaggaaac cctgtggcta caggataata    1920
tcagagataa actgcgtccc attcccataa ctgcctcagt ggagatccaa gagccaagct    1980
ctcgtaggcg agtgaattca cttccagaag ttcttccaat tctgaattca gatgaaccca    2040
agacagctca tattgatgtt cacttcttaa aagagggatg tggagacgac aatgtatgta    2100
acagcaacct taaactagaa tataaatttt gcacccgaga aggaaatcaa gacaaattt     2160 cttatttacc aattcaaaaa ggtgtaccag aactagttct aaaagatcag aaggatattg    2220
ctttagaaat aacagtgaca aacagccctt ccaacccaag gaatcccaca aagatggcg    2280 atgacgccca tgaggctaaa ctgattgcaa cgtttccaga cactttaacc tattctgcat    2340
atagagaact gagggctttc cctgagaaac agttgagttg tgttgccaac cagaatggct    2400
cgcaagctga ctgtgagctc ggaaatcctt ttaaaagaaa ttcaaatgtc acttttatt    2460 tggttttaag tacaactgaa gtcacctttg acaccccaga tctggatatt aatctgaagt    2520
tagaaacaac aagcaatcaa gataatttgg ctccaattac agctaaagca aagtggtta    2580 ttgaactgct tttatcggtc tcgggagttg ctaaaccttc ccagtgtat tttgaggta     2640 cagttgttgg cgagcaagct atgaaatctg aagatgaagt gggaagttta atagagtatg    2700
```

```
aattcagggt aataaactta ggtaaacctc ttacaaacct cggcacagca accttgaaca    2760
ttcagtggcc aaaagaaatt agcaatggga aatggttgct ttatttggtg aaagtagaat    2820
ccaaaggatt ggaaaaggta acttgtgagc cacaaaagga gataaactcc ctgaacctaa    2880
cggagtctca caactcaaga aagaaacggg aaattactga aaaacagata gatgataaca    2940
gaaaattttc tttatttgct gaaagaaaat accagactct taactgtagc gtgaacgtga    3000
actgtgtgaa catcagatgc ccgctgcggg ggctggacag caaggcgtct cttattttgc    3060
gctcgaggtt atggaacagc acatttctag aggaatattc caaactgaac tacttggaca    3120
ttctcatgcg agccttcatt gatgtgactg ctgctgccga aaatatcagg ctgccaaatg    3180
caggcactca ggttcgagtg actgtgtttc cctcaaagac tgtagctcag tattcgggag    3240
taccttggtg gatcatccta gtggctattc tcgctgggat cttgatgctt gctttattag    3300
tgtttatact atggaagtgt ggattcttta aacgctctag gtacgatgac agtgttcccc    3360
gataccatgc tgtaaggatc cggaaagaag agcgagagat caaagatgaa aagtatattg    3420
ataaccttga aaaaaacag tggatcacaa agtggaacga aaatgaaagc tactcatagc    3480
ggggcctaa aaaaaaaag cttcacagta cccaaactgc ttttccaac tcagaaattc    3540
aatttggatt taaaagcctg ctcaatccct gaggactgat ttcagagtga ctacacacag    3600
tacgaaccta cagttttaac tgtggatatt gttacgtagc ctaaggctcc tgttttgcac    3660
agccaaattt aaaactgttg gaatggattt ttctttaact gccgtaattt aactttctgg    3720
gttgccttta ttttggcgt ggctgactta catcatgtgt tggggaaggg cctgcccagt    3780
tgcactcagg tgcatcctc cagatagtgt agctgaggag gcacctacac tcacctgcac    3840
taacagagtg gccgtcctaa cctcgggcct gctgcgcaga cgtccatcac gttagctgtc    3900
ccacatcaca agactatgcc attggggtag ttgtgtttca acggaaagtg ctgtcttaaa    3960
ctaaatgtgc aatagaaggt gatgttgcca tcctaccgtc ttttcctgtt tcctagctgt    4020
gtgaataccct gctcacgtca aatgcataca agtttcattc tcccttcac taaaacacac    4080
aggtgcaaca gacttgaatg ctagttatac ttatttgtat atggtattta tttttttctt    4140
tctttacaaa ccatttttgt attgactaac aggccaaaga gtctccagtt tacccttcag    4200
gttggtttaa tcaatcagaa ttagagcatg ggaggtcatc actttgacct aaattattta    4260
ctgcaaaaag aaaatcttta taaatgtacc agagagagtt gttttaataa cttatctata    4320
aactataacc tctccttcat gacagcctcc accccacaac ccaaaaggtt taagaaatag    4380
aattataact gtaaagatgt ttatttcagg cattggatat ttttttacttt agaagcctgc    4440
ataatgtttc tggatttcat actgtaacat tcaggaattc ttggagaaaa tgggtttatt    4500
cactgaactc tagtgcggtt tactcactgc tgcaaatact gtatattcag gacttgaaag    4560
aaatggtgaa tgcctatggt ggatccaaac tgatccagta taagactact gaatctgcta    4620
ccaaaacagt taatcagtga gtcgatgttc tatttttgt tttgtttcct ccctatctg    4680
tattcccaaa aattactttg gggctaattt aacaagaact ttaaattgtg ttttaattgt    4740
aaaaatggca gggggtggaa ttattactct atacattcaa cagagactga atagatatga    4800
aagctgattt ttttaatta ccatgcttca caatgttaag ttatatgggg agcaacagca    4860
aacaggtgct aatttgtttt ggatatagta taagcagtgt ctgtgttttg aaagaataga    4920
acacagtttg tagtgccact gttgtttggg gggggctttt ttcttttcgg aaatcttaaa    4980
ccttaagata ctaaggacgt tgttttggtt gtacttggaa attcttagtc acaaaatata    5040
ttttgtttac aaaaatttct gtaaaacagg ttataacagt gtttaaagtc tcagtttctt    5100
```

| | |
|---|---|
| gcttggggaa cttgtgtccc taatgtgttt agattgctag attgctaagg agctgatact | 5160 |
| ttgacagtgt ttttagacct gtgttactaa aaaaaagatg aatgtcctga aaagggtgtt | 5220 |
| gggagggtgg ttcaacaaag aaacaaagat gttatggtgt ttagatttat ggttgttaaa | 5280 |
| aatgtcatct caagtcaagt cactggtctg tttgcatttg atacattttt gtactaacta | 5340 |
| gcattgtaaa attatttcat gattagaaat tacctgtgga tatttgtata aaagtgtgaa | 5400 |
| ataaattttt tataaaagtg ttcattgttt cgtaacacag cattgtatat gtgaagcaaa | 5460 |
| ctctaaaatt ataaatgaca acctgaatta tctatttcat caaaccaaag ttcagtgttt | 5520 |
| ttatttttgg tgtctcatgt aatctcagat cagccaaaga tactagtgcc aaagcaatgg | 5580 |
| gattcggggt ttttttctgt tttcgctcta tgtaggtgat cctcaagtct ttcatttcc | 5640 |
| ttctttatga ttaaaagaaa cctacaggta tttaacaacc | 5680 |

<210> SEQ ID NO 28
<211> LENGTH: 5190
<212> TYPE: DNA
<213> ORGANISM: Homo sapiens

<400> SEQUENCE: 28

| | |
|---|---|
| tctgggggct cggctttgcc gcgctcgctg cacttgggcg agagctggaa cgtggaccag | 60 |
| agctcggatc ccatcgcagc taccgcgatg agaggcgctc gcggcgcctg ggattttctc | 120 |
| tgcgttctgc tcctactgct tcgcgtccag acaggctctt ctcaaccatc tgtgagtcca | 180 |
| ggggaaccgt ctccaccatc catccatcca ggaaaatcag acttaatagt ccgcgtgggc | 240 |
| gacgagatta ggctgttatg cactgatccg ggctttgtca aatggacttt tgagatcctg | 300 |
| gatgaaacga atgagaataa gcagaatgaa tggatcacgg aaaaggcaga agccaccaac | 360 |
| accggcaaat acacgtgcac caacaaacac ggcttaagca attccatttta tgtgtttgtt | 420 |
| agagatcctg ccaagctttt ccttgttgac cgctccttgt atgggaaaga agacaacgac | 480 |
| acgctggtcc gctgtcctct cacagaccca gaagtgacca attattccct caaggggtgc | 540 |
| caggggaagc ctcttcccaa ggacttgagg tttattcctg accccaaggc gggcatcatg | 600 |
| atcaaaagtg tgaaacgcgc ctaccatcgg ctctgtctgc attgttctgt ggaccaggag | 660 |
| ggcaagtcag tgctgtcgga aaaattcatc ctgaaagtga ggccagcctt caaagctgtg | 720 |
| cctgttgtgt ctgtgtccaa agcaagctat cttcttaggg aaggggaaga attcacagtg | 780 |
| acgtgcacaa taaaagatgt gtctagttct gtgtactcaa cgtggaaaag agaaaacagt | 840 |
| cagactaaac tacaggagaa atataatagc tggcatcacg tgacttcaa ttatgaacgt | 900 |
| caggcaacgt tgactatcag ttcagcgaga gttaatgatt ctggagtgtt catgtgttat | 960 |
| gccaataata cttttggatc agcaaatgtc acaacaacct tggaagtagt agataaagga | 1020 |
| ttcattaata tcttccccat gataaacact acagtatttg taaacgatgg agaaaatgta | 1080 |
| gatttgattg ttgaatatga agcattcccc aaacctgaac accagcagtg gatctatatg | 1140 |
| aacagaacct tcactgataa atgggaagat tatcccaagt ctgagaatga agtaatatc | 1200 |
| agatacgtaa gtgaacttca tctaacgaga ttaaaaggca ccgaaggagg cacttacaca | 1260 |
| ttcctagtgt ccaattctga cgtcaatgct gccatagcat ttaatgttta tgtgaataca | 1320 |
| aaaccagaaa tcctgactta cgacaggctc gtgaatggca tgctccaatg tgtggcagca | 1380 |
| ggattcccag agcccacaat agattggtat ttttgtccag gaactgagca gagatgctct | 1440 |
| gcttctgtac tgccagtgga tgtgcagaca ctaaactcat ctgggccacc gtttggaaag | 1500 |

```
ctagtggttc agagttctat agattctagt gcattcaagc acaatggcac ggttgaatgt    1560
aaggcttaca acgatgtggg caagacttct gcctatttta actttgcatt taaaggtaac    1620
aacaaagagc aaatccatcc ccacaccctg ttcactcctt tgctgattgg tttcgtaatc    1680
gtagctggca tgatgtgcat tattgtgatg attctgacct acaaatattt acagaaaccc    1740
atgtatgaag tacagtggaa ggttgttgag gagataaatg gaaacaatta tgtttacata    1800
gacccaacac aacttcctta tgatcacaaa tgggagtttc ccagaaacag gctgagtttt    1860
gggaaaaccc tgggtgctgg agctttcggg aaggttgttg aggcaactgc ttatggctta    1920
attaagtcag atgcggccat gactgtcgct gtaaagatgc tcaagccgag tgcccatttg    1980
acagaacggg aagccctcat gtctgaactc aaagtcctga gttaccttgg taatcacatg    2040
aatattgtga atctacttgg agcctgcacc attggagggc ccaccctggt cattacagaa    2100
tattgttgct atggtgatct ttttgaatttt ttgagaagaa aacgtgattc atttatttgt    2160
tcaaagcagg aagatcatgc agaagctgca ctttataaga atcttctgca ttcaaaggag    2220
tcttcctgca gcgatagtac taatgagtac atggacatga aacctggagt ttcttatgtt    2280
gtcccaacca aggccgacaa aaggagatct gtgagaatag gctcatacat agaaagagat    2340
gtgactcccg ccatcatgga ggatgacgag ttggccctag acttagaaga cttgctgagc    2400
ttttcttacc aggtggcaaa gggcatggct ttcctcgcct ccaagaattg tattcacaga    2460
gacttggcag ccagaaatat cctccttact catggtcgga tcacaaagat ttgtgatttt    2520
ggtctagcca gagacatcaa gaatgattct aattatgtgg ttaaaggaaa cgctcgacta    2580
cctgtgaagt ggatggcacc tgaaagcatt ttcaactgtg tatacacgtt tgaaagtgac    2640
gtctggtcct atgggatttt tctttgggag ctgttctctt taggaagcag ccctatcct    2700 ggaatgccgt cgattctaa gttctacaag atgatcaagg aaggcttccg gatgctcagc    2760
cctgaacacg cacctgctga atgtatgac ataatgaaga cttgctggga tgcagatccc    2820
ctaaaaagac caacattcaa gcaaattgtt cagctaattg agaagcagat ttcagagagc    2880
accaatcata tttactccaa cttagcaaac tgcagcccca accgacagaa gcccgtggta    2940
gaccattctg tgcggatcaa ttctgtcggc agcaccgctt cctcctccca gcctctgctt    3000
gtgcacgacg atgtctgagc agaatcagtg tttgggtcac ccctccagga atgatctctt    3060
cttttggctt ccatgatggt tatttcttt tctttcaact tgcatccaac tccaggatag    3120
tgggcacccc actgcaatcc tgtctttctg agcacacttt agtggccgat gattttgtc    3180 atcagccacc atcctattgc aaaggttcca actgtatata ttcccaatag caacgtagct    3240
tctaccatga acagaaaaca ttctgatttg gaaaagaga gggaggtatg gactgggggc    3300
cagagtcctt tccaaggctt ctccaattct gcccaaaaat atggttgata gtttacctga    3360
ataaatggta gtaatcacag ttggccttca gaaccatcca tagtagtatg atgatacaag    3420
attagaagct gaaaacctaa gtcctttatg tggaaaacag aacatcatta gaacaaagga    3480
cagagtatga acacctgggc ttaagaaatc tagtatttca tgctgggaat gagacatagg    3540
ccatgaaaaa aatgatcccc aagtgtgaac aaaagatgct cttctgtgga ccactgcatg    3600 agctttata ctaccgacct ggttttttaa tagagtttgc tattagagca ttgaattgga    3660
gagaaggcct ccctagccag cacttgtata tacgcatcta taaattgtcc gtgttcatac    3720
atttgagggg aaaacaccat aaggtttcgt ttctgtatac aacccctggca ttatgtccac    3780 tgtgtataga agtagattaa gagccatata agtttgaagg aaacagttaa taccatttt    3840 taaggaaaca atataaccac aaagcacagt ttgaacaaaa tctcctcttt tagctgatga    3900
```

```
acttattctg tagattctgt ggaacaagcc tatcagcttc agaatggcat tgtactcaat    3960
ggatttgatg ctgtttgaca aagttactga ttcactgcat ggctcccaca ggagtgggaa    4020
aacactgcca tcttagtttg gattcttatg tagcaggaaa taaagtatag gtttagcctc    4080
cttcgcaggc atgtcctgga caccgggcca gtatctatat atgtgtatgt acgtttgtat    4140
gtgtgtagac aaatatttgg aggggtattt ttgccctgag tccaagaggg tcctttagta    4200
cctgaaaagt aacttggctt tcattattag tactgctctt gtttcttttc acatagctgt    4260
ctagagtagc ttaccagaag cttccatagt ggtgcagagg aagtggaagg catcagtccc    4320
tatgtatttg cagttcacct gcacttaagg cactctgtta tttagactca tcttactgta    4380
cctgttcctt agaccttcca taatgctact gtctcactga acatttaaa ttttacccctt    4440 tagactgtag cctggatatt attcttgtag tttacctctt taaaaacaaa acaaaacaaa    4500
acaaaaaact cccctttcctc actgcccaat ataaaaggca aatgtgtaca tggcagagtt    4560
tgtgtgttgt cttgaaagat tcaggtatgt tgcctttatg gtttcccct tctacatttc    4620 ttagactaca tttagagaac tgtggccgtt atctggaagt aaccatttgc actggagttc    4680
tatgctctcg caccttttcca aagttaacag attttgggt tgtgttgtca cccaagagat    4740
tgttgtttgc catactttgt ctgaaaaatt cctttgtgtt tctattgact tcaatgatag    4800
taagaaaagt ggttgttagt tatagatgtc taggtacttc aggggcactt cattgagagt    4860
tttgtcttgg atattcttga aagtttatat ttttataatt ttttcttaca tcagatgttt    4920
ctttgcagtg gcttaatgtt tgaaattatt ttgtggcttt ttttgtaaat attgaaatgt    4980
agcaataatg tcttttgaat attcccaagc ccatgagtcc ttgaaaatat ttttttatata    5040 tacagtaact ttatgtgtaa atacataagc ggcgtaagtt taaggatgt tggtgttcca    5100 cgtgttttat tcctgtatgt tgtccaattg ttgacagttc tgaagaattc taataaaatg    5160
tacatatata aatcaaaaaa aaaaaaaaaa                                     5190

<210> SEQ ID NO 29
<211> LENGTH: 3198
<212> TYPE: DNA
<213> ORGANISM: Homo sapiens

<400> SEQUENCE: 29
atttgaggtg ttctgaccag aagaagacag agcggatgat cattcattca ccacgttgac      60
aacctcgcct gtgattgaca gctggagtgg cagaaagcca tgagatttgg tagttgggtc     120 tgagggggcgc tcttttttttt cctttctcttt cttttctttct tttttttttt ttaaactgat     180
ttttggggga gagaagatct gcttttttttt gcccccgctg ctgtcttgga acggagcgc     240 ttttatgctc agtgactcgg gcgctttgct tcaggtcccg tagaccgaag atctgggacc     300
agtagctcac gttgctggag acgttaaggg attttttcgtc gtgcttttttt ttttttttttt     360 ttttttttcc ggggggagttt gaatatttgt ttcttttcac actggcctta aagaggatat     420
attagaagtt gaagtaggaa gggagccaga gaggccgatg gcgcaaaggt acgacgatct     480
accccattac gggggcatgg atggagtagg catcccctcc acgatgtatg ggaccccgca     540
tgcagccagg tccatgcagc cggtccacca cctgaaccac gggcctcctc tgcactcgca     600
tcagtacccg cacacagctc ataccaacgc catggccccc agcatgggct cctctgtcaa     660
tgacgcttta aagagagata aagatgccat ttatggacac cccctcttcc ctctcttagc     720
actgattttt gagaaatgtg aattagctac ttgtaccccc cgcgagccgg gggtggcggg     780
```

| | |
|---|---|
| cggggacgtc tgctcgtcag agtcattcaa tgaagatata gccgtgttcg ccaaacagat | 840 |
| tcgcgcagaa aaacctctat tttcttctaa tccagaactg gataacttga tgattcaagc | 900 |
| catacaagta ttaaggtttc atctattgga attagagaag gtacacgaat tatgtgacaa | 960 |
| tttctgccac cggtatatta gctgtttgaa agggaaaatg cctatcgatt tggtgataga | 1020 |
| cgatagagaa ggaggatcaa atcagacag tgaagatata acaagatcag caaatctaac | 1080 |
| tgaccagccc tcttggaaca gagatcatga tgacacggca tctactcgtt caggaggaac | 1140 |
| cccaggccct tccagcggtg ccacacgtc acacagtggg gacaacagca gtgagcaagg | 1200 |
| tgatggcttg gacaacagtg tagcttcccc cagcacaggt gacgatgatg accctgataa | 1260 |
| ggacaaaaag cgtcacaaaa agcgtggcat ctttcccaaa gtagccacaa atatcatgag | 1320 |
| ggcgtggctg ttccagcatc taacacaccc ttacccttct gaagaacaga aaaagcagtt | 1380 |
| ggcacaagac acgggactca ccatccttca agtgaacaat tggtttatta atgcccggag | 1440 |
| aagaatagtg cagcccatga tagaccagtc caaccgagca gtaagtcaag gaacaccta | 1500 |
| taatcctgat ggacagccca tgggaggttt cgtaatggac ggtcagcaac atatgggaat | 1560 |
| tagagcacca ggacctatga gtggaatggg catgaatatg ggcatggagg ggcagtggca | 1620 |
| ctacatgtaa ccttcatcta gttaaccaat cgcaaagcaa gggggaaggc tgcaaagtat | 1680 |
| gccaggggag tatgtagccc ggggtggtcc aatgggtgtg agtatgggac agccaagtta | 1740 |
| tacccaaccc cagatgcccc cccatcctgc tcagctgcgt catgggcccc ccatgcatac | 1800 |
| gtacattcct ggacaccctc accacccaac agtgatgatg catggaggac cgccccaccc | 1860 |
| tggaatgcca atgtcagcat caagcccac agttcttaat acaggagacc caacaatgag | 1920 |
| tggacaagtc atggacattc atgctcagta gcttaaggga atatgcattg tctgcaatgg | 1980 |
| tgactgattt caaatcatgt ttttttctgca atgactgtgg agttccattc ttggcatcta | 2040 |
| ctctggacca aggagcatcc ctaattcttc atagggacct ttaaaaagca ggaaatacca | 2100 |
| actgaagtca atttggggga catgctaat aactatataa gacattaaga gaacaaagag | 2160 |
| tgaaatattg taaatgctat tatactgtta tccatattac gttgtttctt atagatttt | 2220 |
| taaaaaaat gtgaaatttt tccacactat gtgtgttgtt tccatagctc ttcacttcct | 2280 |
| ccagaagcct ccttacatta aaaagcctta cagttatcct gcaagggaca ggaaggtctg | 2340 |
| atttgcagga ttttttagagc attaaaataa ctatcaggca gaagaatctt tcttctcgcc | 2400 |
| taggatttca gccatgcgcg cgctctctct cttttctctct cttttcctct ctctccctct | 2460 |
| ttctagcctg gggcttgaat ttgcatgtct aattcattta ctcaccatat ttgaattggc | 2520 |
| ctgaacagat gtaaatcggg aaggatggga aaaactgcag tcatcaacaa tgattaatca | 2580 |
| gctgttgcag gcagtgtctt aaggagactg gtaggaggag gcatggaaac caaaaggccg | 2640 |
| tgtgtttaga agcctaattg tcacatcaag catcattgtc cccatgcaac aaccaccacc | 2700 |
| ttatacatca cttcctgttt taagcagctc taaaacatag actgaagatt tatttttaat | 2760 |
| atgttgactt tatttctgag caaagcatcg gtcatgtgtg tattttttca tagtcccacc | 2820 |
| ttggagcatt tatgtagaca ttgtaaataa attttgtgca aaaggactg gaaaaatgaa | 2880 |
| ctgtattatt gcaatttttt tttgtaaaag tagcagtttg gtatgagttg gcatgcatac | 2940 |
| aagatttact aagtgggata agctaattat acttttgtt gtggataaac aaatgcttgt | 3000 |
| tgatagcctt tttctatcaa gaaaccaagg agctaattat taataacaat cattgcacac | 3060 |
| tgagtcttag cgtttctgat ggaaacagtt tggattgtat aataacgcca agcccagttg | 3120 |
| tagtcgtttg agtgcagtaa tgaaatctga atctaaaata aaaacaagat tatttttgtc | 3180 |

```
aaaaaaaaaa aaaaaaaa                                                     3198

<210> SEQ ID NO 30
<211> LENGTH: 3046
<212> TYPE: DNA
<213> ORGANISM: Homo sapiens

<400> SEQUENCE: 30
gctttcctct cctttctccc tccccttgt ctgcgccaca gcccccttct ctccccgccc         60
cccgggtgtg tcagattttt cagttaataa tatcccccga gcttcaaagc gcaggctgtg       120
acagtcatct gtctggacgc gctgggtgga tgcgggggc tcctgggaac tgtgttggag        180
ccgagcaagc gctagccagg cgcaagcgcg cacagactgt agccatccga ggacaccccc       240 gccccccgg cccacccgga cacccgcg cagaatcgcc tccggatccc ctgcagtcgg          300
cgggaggtaa ggagcagggc ttgcaaaccg cccggcgccc agggaagcga cgagcgccgg       360
ggcaaggcaa gccctggacg ggattgcgac gtgcgcaccg ggcgcccta tatgcccggg       420 ggactgtttc tgcttccgaa acaaaaccat ctctgggttt cccagaaaaa gccagttcca       480
gccccgaagg catcctggct agaggagacc cgccctaatc cttttgcagc ccttaccggg       540
gggagtaatg gcttctgcga aaagaaattc cctcggctct agaagatctg tctgtgtttg       600
agctgtcgga gagccgtgtt ggaggtcggc gccggccccc gccttccgcg cccccacgg       660 gaaggaagca ccccggtat taaaacgaac ggggcggaaa gaagccctca gtcgccggcc      720
gggaggcgag ccgatgccga gctgctccac gtccaccatg ccgggcatga tctgcaagaa      780
cccagacctc gagtttgact cgctacagcc ctgcttctac ccggacgaag atgacttcta      840
cttcggcggc cccgactcga cccccccggg ggaggacatc tggaagaagt ttgagctgct      900
gcccacgccc ccgctgtcgc ccagccgtgg cttcgcggag cacagctccg agcccccgag      960
ctgggtcacg gagatgctgc ttgagaacga gctgtggggc agcccggccg aggaggacgc     1020
gttcggcctg ggggactgg gtggcctcac ccccaacccg gtcatcctcc aggactgcat      1080
gtggagcggc ttctccgccc gcgagaagct ggagcgcgcc gtgagcgaga agctgcagca     1140
cggccgcggg ccgccaaccg ccggttccac cgcccagtcc ccgggagccg cgccgccag     1200 ccctgcgggt cgcgggcacg gcggggctgc gggagccggc cgcgccgggg ccgccctgcc    1260
cgccgagctc gcccacccgg ccgccgagtg cgtggatccc gccgtggtct tcccctttcc    1320
cgtgaacaag cgcgagccag cgcccgtgcc cgcagccccg gccagtgccc ggcggcggg     1380 ccctgcggtc gcctcgggg cgggtattgc cgccccagcc ggggcccgg gggtcgcccc     1440 tccgcgccca ggcggccgcc agaccagcgg cggcgaccac aaggccctca gtacctccgg    1500
agaggacacc ctgagcgatt cagatgatga agatgatgaa gaggaagatg aagaggaaga    1560
aatcgacgtg gtcactgtgg agaagcggcg ttcctcctcc aacaccaagg ctgtcaccac    1620
attcaccatc actgtgcgtc caagaacgc agccctgggt cccggagggg ctcagtccag    1680
cgagctgatc ctcaaaacgat gccttcccat ccaccagcag cacaactatg ccgcccctc    1740 tccctacgtg gagagtgagg atgcaccccc acagaagaag ataaagagcg aggcgtcccc    1800
acgtccgctc aagagtgtca tccccccaaa ggctaagagc ttgagccccc gaaactctga    1860
ctcggaggac agtgagcgtc gcagaaacca caacatcctg gagcgccagc gccgcaacga    1920
ccttcggtcc agctttctca cgctcaggga ccacgtgccg gagttggtaa agaatgagaa    1980
ggccgccaag gtggtcattt tgaaaaaggc cactgagtat gtccactccc tccaggccga    2040
```

```
ggagcaccag cttttgctgg aaaaggaaaa attgcaggca agacagcagc agttgctaaa      2100
gaaaattgaa cacgctcgga cttgctagac gcttctcaaa actggacagt cactgccact      2160
ttgcacattt tgattttttt tttaaacaaa cattgtgttg acattaagaa tgttggttta      2220
ctttcaaatc ggtccctgt cgagttcggc tctgggtggg cagtaggacc accagtgtgg       2280
ggttctgctg ggaccttgga gagcctgcat cccaggatgc tgggtggccc tgcagcctcc      2340
tccacctcac ctccatgaca gcgctaaacg ttggtgacgg ttgggagcct ctggggctgt      2400
tgaagtcacc ttgtgtgttc caagtttcca acaacagaa agtcattcct tctttttaaa       2460
atggtgctta agttccagca gatgccacat aaggggtttg ccatttgata cccctgggga      2520
acatttctgt aaataccatt gacacatccg ccttttgtat acatcctggg taatgagagg      2580
tggcttttgc ggccagtatt agactggaag ttcataccta agtactgtaa taatacctca      2640
atgtttgagg agcatgtttt gtatacaaat atattgttaa tctctgttat gtactgtact      2700
aattcttaca ctgcctgtat actttagtat gacgctgata cataactaaa tttgatactt      2760
atattttcgt atgaaaatga gttgtgaaag ttttgagtag atattacttt atcacttttt      2820
gaactaagaa actttgtaa agaaatttac tatatatata tgccttttc ctagcctgtt       2880 tcttcctgtt aatgtatttg ttcatgtttg gtgcatagaa ctgggtaaat gcaaagttct      2940
gtgtttaatt tcttcaaaat gtatatattt agtgctgcat cttatagcac tttgaaatac      3000
ctcatgttta tgaaataaa tagcttaaaa ttaaatgaaa aaaaa                       3046

<210> SEQ ID NO 31
<211> LENGTH: 2247
<212> TYPE: DNA
<213> ORGANISM: Homo sapiens

<400> SEQUENCE: 31
aattgtgcag ggggcggtgt ttgtgcgtgg agctttccct cccggctccg ggccgtcgcg       60
gctctcggga gaggcgccgg gacatttaa tcgctgcctc cgccgcgcag ccctgcgcag       120
ctgcccggcc gcgccaaccc cttccccgcc gcagcgcgcc ccgagtgttg gcagcttgcc      180
agccgccacc ccccgccttc cctcctgccc accccaaggt agagggctcc tctcgggagt      240
gtgcggggaa ggggaggccg aggtccgggc cacgcccggg tagccgcaac ccgcagtgct      300
cagtcggcaa caggtagccc agcaggctgc ggctctcagg aagacaaaaa gcgcctctgc      360
gagcaaataa cgaaggaggc ccaacttcat tcaataagga gcctgacgga tttatcccag      420
acggtagaac aaaaggaaga atattgatgg attttaaacc agagttttta aagagcttga      480
gaatacgggg aaattaattt gttctcctac acacatagat agggtaaggt tgtttctgat      540
gcagctgaga aaaatgcaga ccgtcaaaaa ggagcaggcg tctcttgatg ccagtagcaa      600
tgtggacaag atgatggtcc ttaattctgc tttaacggaa gtgtcagaag actccacaac      660
aggtgaggag ctgcttctca gtgaaggaag tgtgggaag acaaatctt ctgcatgtcg       720 gaggaaacgg gaattcattc ctgatgaaaa gaaagatgct atgtattggg aaaaaaggcg      780 gaaaataat gaagctgcca aaagatctcg tgagaagcgt cgactgaatg acctggtttt      840
agagaacaaa ctaattgcac tgggagaaga aaacgccact ttaaaagctg agctgctttc      900
actaaaatta agtttggtt taattagctc cacagcatat gctcaagaga ttcagaaact       960
cagtaattct acagctgtgt actttcaaga ttaccagact tccaaatcca atgtgagttc      1020
atttgtggac gagcacgaac cctcgatggt gtcaagtagt tgtatttctg tcattaaaca      1080
ctctccacaa agctcgctgt ccgatgtttc agaagtgtcc tcagtagaac acacgcagga      1140
```

```
gagctctgtg cagggaagct gcagaagtcc tgaaaacaag ttccagatta tcaagcaaga    1200
gccgatggaa ttagagagct acacaaggga gccaagagat gaccgaggct cttacacagc    1260
gtccatctat caaaactata tggggaattc tttctctggg tactcacact ctcccccact    1320
actgcaagtc aaccgatcct ccagcaactc cccgagaacg tcggaaactg atgatggtgt    1380
ggtaggaaag tcatctgatg gagaagacga gcaacaggtc cccaagggcc ccatccattc    1440
tccagttgaa ctcaagcatg tgcatgcaac tgtggttaaa gttccagaag tgaattcctc    1500
tgccttgcca cacaagctcc ggatcaaagc caaagccatg cagatcaaag tagaagcctt    1560
tgataatgaa tttgaggcca cgcaaaaact ttcctcacct attgacatga catctaaaag    1620
acatttcgaa ctcgaaaagc atagtgcccc aagtatggta cattcttctc ttactccttt    1680
ctcagtgcaa gtgactaaca ttcaagattg gtctctcaaa tcggagcact ggcatcaaaa    1740
agaactgagt ggcaaaactc agaatagttt caaaactgga gttgttgaaa tgaaagacag    1800
tggctacaaa gtttctgacc cagagaactt gtatttgaag caggggatag caaacttatc    1860
tgcagaggtt gtctcactca agagacttat agccacacaa ccaatctctg cttcagactc    1920
tgggtaaatt actactgagt aagagctggg catttagaaa gatgtcattt gcaatagagc    1980
agtccatttt gtattatgct gaattttcac tggacctgtg atgtcatttc actgtgatgt    2040
gcacatgttg tctgtttggt gtcttttgt gcacagatta tgatgaagat tagattgtgt    2100
tatcactctg cctgtgtata gtcagatagt ccatgcgaag gctgtatata ttgaacatta    2160
tttttgttgt tctattataa agtgtgtaag ttaccagttt caataaagga ttggtgacaa    2220
acacagaaaa aaaaaaaaaa aaaaaaa                                         2247

<210> SEQ ID NO 32
<211> LENGTH: 13443
<212> TYPE: DNA
<213> ORGANISM: Homo sapiens

<400> SEQUENCE: 32
actcgcacgg cccctttcctc cctcctctcc cggccgctcg catttcctgc cgctctggct     60
ctcccggccc ctcaaagttc tttccaactt ttttctcggcg gagtgagcgc agcgggcgca    120
gactcggggg caggttgctg tgcttctccg ggctcagccg cctgctctcc tggctcaggt    180
cctcggggag ccctagacag acatcaagtg ccactggcg ctccttcccc tcccagctga    240
gccatcctcc ccggcctcct cgggcgggac agcccgtgc ttaggttttt ctccttttct    300 ccccccggtgc gcctctgctc ggactctcgc gccgggatcg cggcggaaac ctccctcccc    360
tttcgcctcc tgcggctcct tcccttcgcc cctcctccgc cagtcactgg aatcaattcc    420
gtggggaatc ggctccgccg ccgcgaagga cagccttttcc gcgcgggact ccggggcgcc    480 acggggggcca tgtaagcagc tatcttccag agggccacac tgggcatgga caccttttc    540 cctgcctgga ggagcacagg tgatagtgta attttccagt cacgaaactg ctaaggccat    600 ctcagggcg tgtgcgccag gataggcggg cggcgtccga ggaccacata gccatgcctt    660
ttggtctgaa gctccgccgg acacggcgct acaacgtcct gagcaagaac tgctttgtca    720
cacggattcg cctgctggac agcaatgtta tcgagtgcac gctgtcggtg gaaagcacag    780
ggcaagaatg cctggaggct gtggcccaga ggctggagct gcgagagacg cactactttg    840
gcctttggtt tctcagcaag agccagcaag cacgatgggg ggagctggag aaacctctga    900
agaaacatct ggacaaattc gctaatgagc ctttgctttt ctttggagtc atgttctatg    960
```

-continued

```
tgccaaatgt gtcatggctt cagcaagagg ccacaagata tcagtattac ctgcaagtca    1020
aaaaagatgt gcttgaaggg cgattacgat gtacattgga ccaggtgatt cggctagccg    1080
gcctagctgt gcaagctgat tttggagact ataatcagtt tgattctcaa gatttcctca    1140
gagagtatgt gctatttcct atggatttgg ccctggaaga ggctgttctg gaggagctga    1200
cccagaaggt agcccaagaa cacaaagccc acagtggaat cctgccagca gaagctgaac    1260
tgatgtacat caatgaagtt gaacgtttgg atggatttgg acaggaaatc ttccctgtaa    1320
aggacaatca tggaaactgt gtacaccttg gcattttctt tatggggatt tcgtgagga    1380 acagaattgg aagacaagcg gtaatataca ggtggaatga catgggaat atcactcata    1440 acaagtcgac cattctagtg gagctcatca acaaagaaga gactgccctc tttcacacgg    1500
atgatatcga aaatgccaag tatatttctc ggttgtttgc cacacgacac aagttttaca    1560
aacaaaacaa aatctgcact gaacagtcaa attctccacc ccccatcaga cgccagccca    1620
cctggagccg atcctctctg cccaggcagc agccgtacat cctgcctccc gttcacgtcc    1680
agtgtggtga gcactactcg gaaacgcaca cctcgcaaga cagcatttttt catgggaatg    1740 aagaagcctt gtattgcaac tctcacaaca gcctggactt aaattattta aatggcactg    1800
tcaccaatgg cagcgtgtgt agcgttcaca gcgtcaactc cctcaactgc tcgcaaagtt    1860
tcatccaggc ctcccctgta tcctccaacc tcagtatccc tgggagtgac atcatgcggg    1920
ccgactacat cccgagccac cggcacacgc gatcatcgt gccctcgtac aggccaaccc    1980
ccgattatga cagtcatg cgccagatga agagggggat cctgcataca gacagccaga    2040
gccagtctct gagaaacctc aacattatca cacccatgc ctacaaccag ccagaggatc    2100
tggtgtacag ccaaccggag atgcgggaga ggcacccccta cactgtccct tatgggccac    2160
agggggtcta cagcaacaaa cttgtcagtc catctgacca gggaacccca aagaataatg    2220
tggtaccaag caagccgggg gcaagcgcca tctcgcacac ggtgagcacc ccagagctgg    2280
ccaacatgca gctgcagggc agccataact acagcacggc ccacatgctt aagaactatc    2340
tcttcaggcc accgccccc tacccacggc cacgacctgc caccagcacc cagacctgg    2400 ccagccaccg ccacaagtac gtcagcgca gcagcccgga cctggtgacc cggaaggtgc    2460
agctctcggt gaagaccttc caagaggaca gctctccggt ggttcatcag tctctccagg    2520
aggtgagcga gcccctcacg gccaccaagc caccgcgcac tgtgaacaag cgccacagcc    2580
tggaggtgat gaacagcatg gtgcgggca tggaggccat gacgctcaag tcgctccacc    2640
tccccatggc tcgccgcaac acgctccggg agcaggacc gccgaggag gggtcaggca    2700 gccacgaggt cccccagctc cctcagtatc accacaagaa gaccttctct gatgccacta    2760
tgctaatcca cagcagcgag agtgaggagg aggaggagga ggctccagaa tcggtgcccc    2820
agatccccat gctccgggag aagatggagt acagtgccca gctgcaggcg gccctggccc    2880
gcatccccaa caagccccg cctgagtacc ccggtccaag gaagagtgtg agcaatgggg    2940
ctctgaggca ggaccaagcc agccttcctc ccgccatggc cagagccagg gtgctgaggc    3000
atgggccagc caaggccatc agcatgtctc ggactgaccc gccggctgtc aacgggcct    3060 ctctcggccc atccatctcg gaacccgacc tgactagtgt gaaggagcgg gtcaaaaaag    3120
agcctgtgaa ggagagacct gtgtctgaaa tgttttccct ggaagacagc attatagaga    3180
gagagatgat gatcaggaat ctagagaagc agaagatggc aggcctggag gcacagaaga    3240
ggccgctgat gttggcagca ttgaatgggc tctcggtggc tcgagtctca gggcgggaag    3300
agaatcgagt tgatgccacc cgggttccca tggacgagag gttcagaacc ctgaagaaga    3360
```

```
aactagaaga gggaatggtg ttcacagaat atgagcaaat tccaaagaaa aaggcgaatg   3420
gcattttcag cacagcagct ctgccagaaa acgccgagcg cagccgaatc cgtgaagttg   3480
tcccctatga ggagaatcga gtagagctga taccaaccaa agaaaataac acaggataca   3540
ttaatgcctc ccacatcaag gtggtggttg gcggggcaga atggcactac atagccaccc   3600
aggggcccct gccacacacg tgccacgact tctggcagat ggtgtgggag cagggagtga   3660
atgtgattgc catggtcact gcagaggagg agggtggacg aaccaaaagc caccgatact   3720
ggcccaaact aggttcaaag cacagctcag ccacctatgg caagttcaag gtcaccacga   3780
agtttcgaac ggattctgtt tgctatgcaa ccacgggctt gaaggtcaag cacctttttgt   3840 ctgggcaaga aaggacggtg tggcatttac aatatactga ctggccagat cacggctgtc   3900
cagaagatgt ccaaggattt ttatcctact tggaggagat ccagtcggtc cgtcgccata   3960
ccaacagcat gctggaaggc accaagaacc ggcacccgcc catcgtggtc cactgtagtg   4020
ctggggtggg aaggaccggc gtgctcattc tttctgagct gatgatctac tgcttggaac   4080
ataacgaaaa ggtggaagtg cccatgatgc tgaggctcct cagggagcag aggatgttca   4140
tgatccagac tatcgctcag tacaagtttg tctaccaagt cctcatccag ttcctccaaa   4200
actccagact catttaatca ccccaatcca gctcctggag gagggaccca gctccatcgc   4260
gctggaggag agtcacctcc agacaacatc tgctcccccc acaggggtgc aggtggctgg   4320
cagcaaacag gctctctgaa gacagtagcc aagattattc acacatacca tgtattattt   4380
tatatgagat aaatttatttt tttccccttt ggaataactt ttgtgaatta ttataatgca   4440
gtttccctag taatatagta cttttcattt gaaccacatc ttgactgatc tgtattgtaa   4500
tatatgtcag caggtaaggt tgcctgctgg atcattttga ggacagaggc atgagggagc   4560
acatctcttg tgaagttgca gccagatttg taaccaaccc tgaaattcat cagcttaatt   4620
catttatcag cttgattcat tcatcattca ttgcttatat ccaaagcaaa gacggtaaga   4680
aaatgaattc atcctgaaat ataaagaaaa gggtctgaag gaacaaacac gattctctta   4740 tatttttgggg ctcatgagcc ttgatagaca gtttcctctc gtcttcattt ccaccccctca   4800 tcctcagtag tctcctctcc cccacgcccc accccaactt cccccccaag cttgagttaa   4860
agacagaata gctaaagaca gtgctgcctt tacaatgcag taattgccat ctttggggcc   4920
gaaagacaag ctctgtgttg tgcttttctt gaccacccct tatcctgggc tctggagctt   4980
gtgtttccct gctggcgact gtaccttggg tatttgttgc tacctctcct gtttgctcag   5040
taggaccctg tctggtggca ttgaggctct ggaccagacc atctgtgcag ttaaggctct   5100
accctgattg agagaggata gcagacctag aaagagaaag gagttgggca gggcctttga   5160
ggattgtgtt tttcaggcag ggccttgatg atcattgttt tttatttaaa taagatgtgt   5220
gtgctggaca gagacctaaa agttgaggtc actaagtcat tggaaaggcc atcaaggaaa   5280
cagatgggga agctgatttta tgggagctgt aaggcattta gctacataac aggggtcctg   5340
gccaggaaac acatcaaatg tgaccccgc tgtgctgata tcatcttcag gctttggtct   5400
gcaagatcag aattaatccc actcgggacc ccatagtcca aacttggggc cacttgatga   5460
acgatggtag aattgtcatt ggcagagccc tgtgcttctt tccttttctt cataaaatcc   5520
actcgctggt cagttatctt cactttgaag cccagttctt agtttcttcc tatggcttca   5580
ttggtcagtg tccttctgaa tttccaagga tggtacacaa taaatcatgt tttgtacttt   5640
tttcctctta ctgcatttttg ggggatttat cattctatgt ctaccttttc ttgagtacag   5700
```

```
ctttgatatg cacctgttgt tacgtggtga tgggaagtca caggcgtgct ctttctagtt    5760
aatttgatgc cacatcttcc ttgtcttttc agcttgggaa aaaggcggca gtggaggaag    5820
gcatggaatg cccacagtgg tcagttcaaa gaacaaacgt gcaattaaaa aactgtagtc    5880
agccaggcac ggtggttcac acctgtaatc ccagcacttt gaaaggccaa ggcgggcaga    5940
ttgcttgagc taaggagttc gagaccagcc tgagcaacat gatgaaaccc cgtctctaca    6000
aaaagtacaa aaattagcca ggcgtggtgg tatgccctgg tagtcccagc tgctcgggag    6060
gctgaggcag gaggatcacc tgattctaag aattcgagac tgcagtgagc cgtgatcttg    6120
ccactgtagt ccaggctggg ctacggagag accctgcctc aaaaaaaaaa aaaaaaaaag    6180
gaaaaaggt tgtcaagaaa aactagatgt taggagaaag gaaaatttaa ttgcagtttt     6240
ttttcttaga attgactgct gtgagagttc catatgcctt tcttcattgc tgcttttgtc    6300
ccccgtgagc taaaagatg gagtgacatc aaatcaacca gaaaaagtat gcctttgtga     6360
catcccatca ccacatgcca acaggtatat attccccatt aagttcttcg gaataggaat    6420
cctctgtttc aacctggcca ggtgttgtgg tggctgtact ctagttagac tcggaatatc    6480
tggggatgga gggcttcccc tgtgtcttct acttcaaggt ctgaaggctc agtgaaggag    6540
tataatctgc tgatctttgt agattctgga gttttgttgt atgtcctgga agaaacccca   6600
ttagtattac atgtattttc agtgaacaga gcttataacc cttattataa gaagctcatc    6660
aataagcaaa aagatacttg tttcctttcc ttggaggttt ttccatcctt gggatattct    6720
gctgttaggg atgttttagc aagtggtctc agttactggt ttattgcgtg atgaacaaca    6780
tcagtattta tcttttatct ctaagcccca aggtgggcac tgttagaata tgtctcatgt    6840
ggacagcata tagatctggt gcgtctttga ggtcgtcaga gctcatgggc ttccctgaaa    6900
ttcatccact gtccctgccg tatgctacgg gaatattcat tagtgtacaa aatgcaggga    6960
ggaagtaggt ttaatattca acttctagc caaagtttat attgaaaccc aaaagaaaac     7020
atttaagagt tgttccacat atttcacttt taaaaacaaa tgccttgggt tctttagcac     7080
atttgcatt ccttttcaca tctccagtaa atgccaacat atctcctgtt aaattagcag     7140
cagccattta aagtcctttc ggtggcatct gcataataat tgcccagaga tgctttatat    7200
ctgggaagca agccaaggaa taaaccttga agcaaagtgt attaaattag ttatctagtt    7260
agagcttttg gaatgatttc ctgatgatgt atcaagtctg aagctggagc tgtcagtgtc    7320
tattgctgca gtttggattt gaagggagaa aatgtaaaat ggaggaaaaa aaagttacca    7380
tctcacaaca aagccatcaa acatttttcca gccgctgttt tcgaggtttt ccagttgaac    7440
tgtttggttt ctttcatcca cactcatttg gatacattga cccgaggtat tcatccttgt    7500
ttactgtggt ccctgaatca tggggctga atttgatgtc ttcatccttg agatgagcct     7560
gctggcttag ctgaggaatg tcctgctgag gtttcttagg tttccttggg ttctaaggat    7620
atactggata taccatcttt tagcaagagt atctggtagc atttacagat agcatagaca    7680
ttggtatgca cttctttccc cagataggaa gtaaggagg atttagttgc atgaaaaaag     7740
gatgttaaac attgattaca taggagtaaa gatgaatgag ctgcaatatt cagtcggagc    7800
taaacaataa gatcagggaa ggtaaaaata cctatgtgga atattttgaa tcgtaagctt    7860
ttgaggagct taaattgaga gaattttact tttaattttg tagattgaga agaggaaccg    7920
cttttttaaaa ttatagctaa actgtcattg ttttcctaag agtcacttgg ccatctctgg   7980
cccctctttt catcagcctg aagagagggt ctttgtagac tgctgagggt gggccttgta    8040
ggacttgacc atggcttaca cctacttaac ctttatcctg cttctttca gcttgtgctt     8100
```

```
ttcagttata aactccagtg ggtacagcag gctggccttt tcatccagct gattattttt    8160
ccagcttaat atagattgac ccatatgaaa tttccaataa tggaccatat tttctgcaaa    8220
tagacagtac tcgcatggat cacctatatc ttcccctga tacactgtgg gtcccaacac    8280
cagatgtcat ttctccagag cagtgctaat gaacacaaaa ggtataccct gggtggccca    8340
gctcttttca cgaacgtgct gccctgctca tagtgatcct tgcatcactt ggtgaatggg    8400
ccatctcctg ggacatggaa gttgcagagg tagatagtgc actgcagctt ctcttaagcc    8460
ggattggcca tcaggcatat cactctggag ttttagctg ctgtcctttc ccgatgaaca    8520
gtctgtatta gctgacctca gcctacttgt tacgtgacgt atgggtccca aaagtgtcct    8580
ttgtcaaaaa gcagaatgtg ccttctagtc tccctttccc catctaatgg tgtattcgat    8640
ggtgaagatg agtacagttg accaccccta tctgtgggtt ccacatccct atattcaacc    8700
aagtacagat tgaaaaatat ttggggaaga ggggaaaccc acaaagttcc aaaaagcaaa    8760
agttgaattt gccacatgct gaatactaca ttgaattcac acaaatgaag tgatgtgtag    8820
gcattgagtt aggtattgta aataatctag agatgattta agtatgcaa gagatgtgca    8880 taggttatat gcaaatactg tgctatttta tataaaagac ttgaacatcc atggattctg    8940
gtattctcag agggtccttg attgcccct ttggtaaagg acaactattt cgttactgat    9000
tttcgtttgg ggaagatctg tcaatcccct gaggtgcggg ggttgggggg atggagggta    9060
cagggcattc taggatgtgt gccagggagc acagattcaa gggatgggat tgagtcagac    9120
ctgtgttctt actcagtgtc agaaataact ctgtggagct cctagagtaa gacatttccg    9180
gaagcaccac ataattactg ttgggctctt agggtagccc ttttagggaa ttgagcattc    9240 ccatgttta ccaacaatta ttctgctgct gtgttttatt atattgccaa tggttttgag    9300
acactcatca tgctcttatt tagtgatttc ttttcatgag cagagcaaca gctcatccag    9360 catggttcc aaatggagaa atttgggtct tctgtagaaa ccacacaaat tctccaatgg    9420
cctacagcct tatggttggc acactagttg gccctatagg gtggaaataa agctgtaaga    9480
tgttaaactg catttgatac ttctcttgaa cgctgagcaa ggaagcaaaa tagttcttgt    9540
ctttacttaa gcttctaaga cattttgggg caaaggacct tacagatggc gtctgttgaa    9600
agtaacagca acgtgccagg gagaaatgtg ggggaaatct catcaaattc tgccacctca    9660
aatgtgttgt ccagaagtca gtgttattca ggggccctg tgaaacttga ccaccagctt    9720
gcgccatcaa cactcagcct ttatccagcc tgctctcagc ttttgtgttt ctgttagaaa    9780
ctcagatagg taagtatttt tattcagtag actacctttc ttatcttttc agcttaatat    9840
agctgcatct tctttctcaa agccaaacta agatattctc tattaaaatg tccatgagcc    9900
tagcattgag tgtctggcat ccatcaattt catagactgg aaaatgattg ttgtttggta    9960
cagtaaagaa gaggatgtgc atcagttcct accgtttgca gctttgtttt tagccttccc   10020
attttaaaaa taaattcaag gacattgagt tacaaggcag gagggctgga gctactgggc   10080
agcctgaata tgacaagcat ttgtgtggaa agtcattgct ccttctgcca cactttgggc   10140
catcaggatc attctttccc agaagtgcca taaacttgct caaaagtttc tataaatggg   10200
aagagggaga ggaaggattt ttgcatcagt cctgaagttg ctatccaaaa gttctctgtt   10260
tcacaaataa ttttctgaac tctggaatgc ctctcctact ccctgcctcc ctttctgtaa   10320
tgtcagagtg atggaaacca ccaagtggca tgctagggaa agcctgcagc agtgttggag   10380
tctatttcac cctagctcat agttttaaac tgtcttcact gttgaggtag agcttgatga   10440
```

```
atgtcatgga ttatgatgtg tggtttatca tatttgcctg gatttgctga tcaaaagcac    10500
catcttccct cgcctgctgc tggcagcctt tccttgcctt gcttgttagc agagcattct    10560
gcttacccat gtggctccca gagttagcag ccccggctct tggatttctt gattcttctc    10620
ccctgtgatc tcagaggtgc tgcagaggac attcccctttt agagcaagtc atgtttctat   10680
tcaggccaca aaactgggat gtacatgcag tgactttggt gttccttgtc ttgttcaggg    10740
gaacgggtgg gactgttgtg tgctgtcacc ctcttcattc catgagcacc ttgttcactt    10800
agggtctgct gcctttttttt ttttctttttt ctttttttttt tttttttag tttttgagat   10860 cgtgtctcac tcctgttgcg caggctggag tgcagcctcc aaagtagctg ggattatagg    10920
cgtgcaccac cacacccggc taattttttat atttttagta gagacggggt tttgccatgt    10980
tggccagact ggtctcaaac ctctgacctc gtgatgaccc ccctcggcct cccaaagtgc    11040
tgggattaca cccagcctct gctgccttttt catatttccc catctgcttt atggatcaac    11100
tctcaacagt acactttttc tttttcttac ctacccctatg agtgcaaccc agatgtaaga    11160
gttaatcctc gtcagagaat cattgcctta aacctctcag aaatatgtaa ttaggaaatc    11220 ttatttttaat ttttttaaaaa ttgcttgtat agtttcaaag aataagatct ggcaaatggc   11280
cagatgtggt ggctcacacc tgtaatcaaa ccagcacttt gggaggctga ggcaggcaga    11340
tcacctgagg tcaggcgttc aagaccagcc tggccaacat ggtgaaatcc cgtctctact    11400
aaaaatacaa aaaaaaaaaa aaaaaaaaaa attagccagg catggtggca catgcctgta    11460
atcccagcta ctcaggaggc tgaggcagga taattgcttg aacccgggag gtggaggttg    11520
cagtgagccg agatcatgcc actgcactcc agcctgggca acagagtgag actttgtctc    11580
aaaaaaaaaa aaaaaaaaaa aaaagatct ggcggatgaa aataaccaga atgaaaatag     11640
ctagaaaact cagcaagcag gaagctccct ttctcaccct tttgttccct tgccgataga    11700
atcagtcact attagaaaaa atgaaagacg ctctgtttaa aacaatgatg acagcagtac    11760
ttaatatgta tttcgaggtg aacttatata gattgagaga ggctgcattt ggcagactga    11820
tgtataggaa gacccatttg tttctagctt ctccctgcag ggaaaatgct ttcgtcatta    11880
tagcctcttt acacagactg gccattctag tgaaacaggt ggtaaacctt tgggctgccc    11940
agaaacattt tatctgtttt cacttaccta ggaagtgggaa agattagcgg gtcatccaaa   12000
atctgtatgt aagctatctt catttcttc cccaaccttc tcctcctggg aaacacaaat     12060
gctatctcat ctgacaaaag gttttagagg ataaagctga aagattgga ttgggatctt     12120 tttgtggctt ggggcggagc cttttgctaa aatctcaaga atgctgcttt gagtttagct    12180
agggtggctc tcagaactgg ggtgcctggc attctcagca tttctcaggg gcctcccacc    12240
tctgacaact gcagtgttag ctaatacata ccttgagcat agaactgaat gctgtaattc    12300 agagccatttt tttttttcaa cttgaacatt gtacaatttt actgcaattt cctttgaact   12360
ttcttgccac tgtttggaat cttaaaaatt cattagcctt ctcctttctg acataaagct    12420
actcttcatc agagatgagt tcctatgtat gtcctttgtt ccttcaatag ctaattaatg    12480
tgcttgagga tacttcagtg gaaaaaagg tttaaatatg caaattacta ataaatgtgt     12540
aaccttatgt aacttgtgtt acatcaagta acaagctaat ctagtttgtt tcactggact    12600
aggcttgtgc tccctacttc agtattttga tgctttcctt gatctttgtt tcacaaaatg    12660
ttgtgaattt tggtatcatt caaaacaaat gacatttatt aggtttcatt ttgaaacgat    12720
gtacagacaa gtccccaact tagaaaccgg tttgttctta aggttcttgc gtcagcccat    12780
agaagcccac tgacctccac cacagcccaa atggagggct gtgatagcca gatctggttg    12840
```

```
gcttttgtgg gctgacccag acatttaatc accatctctt atgttgttgc cgtaagaaat   12900
gcattccagg ttgggacttg ggatcctgag agcacattcg cccctgtgg tggccgcttg    12960 ccaccttgca agatggaagc ccagtctcct tactaccaaa ctgtagttgt aagcagaggg   13020
aggggtgaga tgtttatagg acattcccta agctggggag tgattttat cactattcat    13080 gtcaactgta ctttggtata gactccctat caatttaata atatgaaaag cctaaaataa   13140
aactatgcat gctattctat gtgctatttt atatcagtaa ataagcttat gcttgccagt   13200
tgtatacaca gttatgaggt gtatagaact gactttgaca gtattttttg cactgttttcc  13260 tatctgtttt tataaagtct tatttagata ttggaccttg ttgatgttct cactgccctt   13320
gtgcttgcta taaatgtttt catatgtgcc tttacaaatg tgagatcttt attctaacct   13380 tttttttgtaa aagatatcta ttgatttcca tatgcaataa accttttttt cagagaaaag  13440
tta                                                                 13443
```

<210> SEQ ID NO 33
<211> LENGTH: 1415
<212> TYPE: DNA
<213> ORGANISM: Homo sapiens

<400> SEQUENCE: 33

```
attgaaggct gggcagagtc tgagtccacc cgggtcgtgc tcccccgct cgccggctc       60 ctccgcagtc caggaatctc cccgtggctc tccccgacct ggaggggtgg acgcccctgg    120
cccccagtcc ccggcctgcg gaggggggccg gtggctgcgg ccctgcgcgg ggccggggcg   180
ggccgagcca agggccgccc ccggccgacc ctcccctgc cgggcccgcc ctcccgccg     240 cggcgctgga ggagggcggg gcggggccct ggggtcagtc tgagcctccg gcaccggccg   300
cgcagctgga ggcggcggag cggaagcctt gacttcatct cagctccaga gcccgccctc   360
tcttcctgca gcctgggaac ttcagccggc tggagcccca ccatggctgc aatccgaaag   420
aagctggtga tcgttgggga tggtgcctgt gggaagacct gcctcctcat cgtcttcagc   480
aaggatcagt ttccggaggt ctacgtccct actgtctttg agaactatat tgcggacatt   540
gaggtggacg gcaagcaggt ggagctggct ctgtgggaca cagcagggca ggaagactat   600
gatcgactgc ggcctctctc ctacccggac actgatgtca tcctcatgtg cttctccatc   660
gacagccctg acagcctgga aaacattcct gagaagtgga ccccagaggt gaagcacttc   720
tgccccaacg tgcccatcat cctggtgggg aataagaagg acctgaggca agacgagcac   780
accaggagag agctggccaa gatgaagcag gagcccgttc ggtctgagga aggccgggac   840
atggcgaacc ggatcagtgc ctttggctac cttgagtgct cagccaagac caaggaggga   900
gtgcgggagg tgtttgagat ggccactcgg gctggcctcc aggtccgcaa gaacaagcgt   960
cggaggggct gtcccattct ctgagatccc caaggccttt cctacatgcc cctccctttc    1020 acagggtac agaaattatc cccctacaac cccagcctcc tgagggctcc atgctgaagg   1080
ctcccatttt cagttccctc ctgcccagga ctgcattgtt ttctagcccc gaggtggtgg   1140
cacgggccct cctcccagc gctctgggag ccacgcctat gcctgccct tcctcagggc    1200 ccctggggat cttgccccct tgaccttcc ccaaaggatg gtcacacacc agcactttat    1260
acacttctgg ctcacaggaa agtgtctgca gtaggggacc cagagtccca ggcccctgga   1320
gttgttttcg gcaggggcct tgtctctcac tgcatttggt cagggggca tgaataaagg    1380 ctacaggctc caacgtgaaa aaaaaaaaa aaaa                                1415
```

<210> SEQ ID NO 34
<211> LENGTH: 2977
<212> TYPE: DNA
<213> ORGANISM: Homo sapiens

<400> SEQUENCE: 34

```
agctgggta aggagttcaa ggcagcgccc acaccgggg gctctccgca acccgaccgc      60
ctgtccgctc ccccacttcc cgccctccct cccacctact cattcaccca cccacccacc     120
cagagccggg acggcagccc aggcgccggg gccccgccgt ctcctcgccg cgatcctgga     180
cttcctcttg ctgcaggacc cggcttccac gtgtgtcccg gagccggcgt ctcagcacac     240
gctccgctcc gggcctgggt gcctacagca gccagagcag cagggagtcc gggacccggg     300
cggcatctgg gccaagttag cgccgccga ggccagcgct gaacgtctcc agggccggag      360
gagccgcggg gcgtccgggt ctgagccgca gcaaatgggc tccgacgtgc gggacctgaa     420
cgcgctgctg cccgccgtcc cctccctggg tggcggcggc ggctgtgccc tgcctgtgag     480
cggcgcggcg cagtgggcgc cggtgctgga cttggcgccc ccgggcgctt cggcttacgg     540
gtcgttgggc ggccccgcgc cgccaccggc tccgccgcca ccccgccgc cgccgcctca      600
ctccttcatc aaacaggagc cgagctgggg cggcgcggag ccgcacgagg agcagtgcct     660
gagcgccttc actgtccact tttcggccca gttcactggc acagccggag cctgtcgcta     720
cgggcccttc ggtcctcctc cgcccagcca ggcgtcatcc ggccaggcca ggatgtttcc     780
taacgcgccc tacctgccca gctgcctcga gagccagccc gctattcgca atcagggtta     840
cagcacggtc accttcgacg ggacgcccag ctacggtcac acgccctcgc accatgcggc     900
gcagttcccc aaccactcat tcaagcatga ggatcccatg gccagcagg gctcgctggg     960
tgagcagcag tactcggtgc cgccccggt ctatggctgc cacacccca ccgacagctg     1020
caccggcagc caggctttgc tgctgaggac gccctacagc agtgacaatt tataccaaat     1080
gacatcccag cttgaatgca tgacctggaa tcagatgaac ttaggagcca ccttaaaggg     1140
ccacagcaca gggtacgaga gcgataacca cacaacgccc atcctctgcg gagcccaata     1200
cagaatacac acgcacggtg tcttcagagg cattcaggat gtgcgacgtg tgcctggagt     1260
agccccgact cttgtacggt cggcatctga gaccagtgag aaacgcccct tcatgtgtgc     1320
ttacccaggc tgcaataaga gatattttaa gctgtccac ttacgatgc acagcaggaa      1380
gcacactggt gagaaaccat accagtgtga cttcaaggac tgtgaacgaa ggttttctcg     1440
ttcagaccag ctcaaaagac accaaaggag acatacaggt gtgaaaccat tccagtgtaa     1500
aacttgtcag cgaaagttct cccggtccga ccacctgaag acccacacca ggactcatac     1560
aggtgaaaag cccttcagct gtcggtggcc aagttgtcag aaaagtttg cccggtcaga     1620
tgaattagtc cgccatcaca acatgcatca gagaaacatg accaaactcc agctggcgct     1680
ttgaggggtc tccctcgggg accgttcagt gtcccaggca gcacagtgtg tgaactgctt     1740
tcaagtctga ctctccactc ctcctcacta aaaaggaaac ttcagttgat cttcttcatc     1800
caacttccaa gacaagatac cggtgcttct ggaaactacc aggtgtgcct ggaagagttg     1860
gtctctgccc tgcctacttt tagttgactc acaggccctg gagaagcagc taacaatgtc     1920
tggttagtta aaagcccatt gccatttggt gtggattttc tactgtaaga agagccatag     1980
ctgatcatgt cccctgacc cttcccttct tttttttatgc tcgttttcgc tggggatgga     2040
attattgtac cattttctat catggaatat ttataggcca gggcatgtgt atgtgtctgc     2100
taatgtaaac tttgtcatgg tttccattta ctaacagcaa cagcaagaaa taaatcagag     2160
```

```
agcaaggcat cggggtgaa tcttgtctaa cattcccgag gtcagccagg ctgctaacct   2220
ggaaagcagg atgtagttct gccaggcaac ttttaaagct catgcatttc aagcagctga   2280
agaaaaaatc agaactaacc agtacctctg tatagaaatc taaaagaatt ttaccattca   2340
gttaattcaa tgtgaacact ggcacactgc tcttaagaaa ctatgaagat ctgagatttt   2400
tttgtgtatg ttttttgactc ttttgagtgg taatcatatg tgtctttata gatgtacata   2460
cctccttgca caaatggagg ggaattcatt ttcatcactg ggagtgtcct tagtgtataa   2520
aaaccatgct ggtatatggc ttcaagttgt aaaaatgaaa gtgactttaa aagaaaatag   2580
gggatggtcc aggatctcca ctgataagac tgttttttaag taacttaagg acctttgggt   2640
ctacaagtat atgtgaaaaa aatgagactt actgggtgag gaaatccatt gtttaaagat   2700
ggtcgtgtgt gtgtgtgtgt gtgtgtgtgt gtgtgtgttg tgttgtgttt tgttttttaa   2760
gggagggaat ttattattta ccgttgcttg aaattactgt gtaaatatat gtctgataat   2820
gatttgctct ttgacaacta aaattaggac tgtataagta ctagatgcat cactgggtgt   2880
tgatcttaca agatattgat gataacactt aaaattgtaa cctgcatttt tcactttgct   2940
ctcaattaaa gtctattcaa aaggaaaaaa aaaaaaa                            2977

<210> SEQ ID NO 35
<211> LENGTH: 4102
<212> TYPE: DNA
<213> ORGANISM: Homo sapiens

<400> SEQUENCE: 35
cggctatccg cgcgggagtg cgccacgcgg ggccggagcg cctattagcc gccaggacct     60
cggagcgccc cgaccacccc tgagcccctc tggcttcgga gccccccagc accccttccc    120
gggtcccctc gcccacccta atccactctc cctcccttc ccggattccc tcgctcaccc    180
catcctctct cccgcccctt cctggattcc ctcacccgtc tcgatcccct ctccgcccctt   240 tcccagagac ccagagcccc tgaccccccg cgccctcccc ggagcccccc gcgcgtgccg    300
cggccatggc ggccgtgcgc ggggcgcccc tgctcagctg cctcctggcg ttgctggccc    360
tgtgccctgg agggcgcccg cagacggtgc tgaccgacga cgagatcgag gagttcctcg    420
agggcttcct gtcagagcta gaacctgagc cccggaggga cgacgtggag gccccgccgc    480
ctcccgagcc caccccgcgg gtccgaaaag cccaggcggg gggcaagcca ggaagcggc     540 cagggacggc cgcagaagtg cctccggaaa agaccaaaga caaagggaag aaaggcaaga    600
aagacaaagg ccccaaggtg cccaaggagt ccttggaggg gtccccccagg ccgcccaaga   660 aggggaagga gaagccaccc aaggccacca agaagcccaa ggagaagcca cctaaggcca    720
ccaagaagcc caaggagaag ccaccaaggg ccaccaagaa gccaaagagg aagccaccca    780
aggccaccaa gaagcccccg tcagggaaga ggccccccat tctggctccc tcagaaaccc    840
tggagtggcc actgccccca cccccagccc ctggccccga ggagctaccc caggagggag   900
gggcgcccct ctcaaataac tggcagaatc caggagagga cccatgtgt gaggcacggg     960 agcaccagcc tgagccggag gaggagacccg agcaacccac actggactac aatgaccaga   1020
tcgagaggga ggactatgag gactttgagt acattcggcg ccagaagcaa cccaggccac   1080
ccccaagcag aaggaggagg cccgagcggg tctggccaga gccccctgag gagaaggccc   1140
cggccccagc cccggaggag aggattgagc ctcctgtgaa gcctctgctg ccccccgctgc   1200 cccctgacta tggtgatggt tacgtgatcc ccaactacga tgacatggac tattactttg    1260
```

```
ggcctcctcc gccccagaag cccgatgctg agcgccagac agacgaagag aaggaggagc    1320
tgaagaaacc caaaaaggag gacagcagcc ccaaggagga gaccgacaag tgggcagtgg    1380
agaagggcaa ggaccacaaa gagccccgaa agggcgagga gttggaggag gagtggacgc    1440
ctacggagaa agtcaagtgt ccccccattg ggatggagtc acaccgtatt gaggacaacc    1500
agatccgagc ctcctccatg ctgcgccacg gcctggggc acagcgcggc cggctcaaca     1560
tgcagaccgg tgccactgag gacgactact atgatggtgc gtggtgtgcc gaggacgatg    1620
ccaggaccca gtggatagag gtggacacca ggaggactac ccggttcaca ggcgtcatca    1680
cccagggcag agactccagc atccatgacg attttgtgac caccttcttc gtgggcttca    1740
gcaatgacag ccagacatgg gtgatgtaca ccaacggcta tgaggaaatg acctttcatg    1800
ggaacgtgga caaggacaca cccgtgctga gtgagctccc agagccggtg gtggctcgtt    1860
tcatccgcat ctacccactc acctggaatg gcagcctgtg catgcgcctg gaggtgctgg    1920
ggtgctctgt ggcccctgtc tacagctact acgcacagaa tgaggtggtg gccaccgatg    1980
acctggattt ccggcaccac agctacaagg acatgcgcca gctcatgaag gtggtgaacg    2040
aggagtgccc caccatcacc cgcacttaca gcctgggcaa gagctcacga ggcctcaaga    2100
tctatgccat ggagatctca gacaaccctg gggagcatga actgggggag cccgagttcc    2160
gctacactgc tgggatccat ggcaacgagg tgctgggccg agagctgttg ctgctgctca    2220
tgcagtacct gtgccgagag taccgcgatg ggaacccacg tgtgcgcagc ctggtgcagg    2280
acacacgcat ccacctggtg ccctcactga accctgatgg ctacgaggtg cagcgcagag    2340
tgggctcaga gtttgggaac tgggcgctgg gactgtggac tgaggagggc tttgacatct    2400
ttgaagattt cccggatctc aactctgtgc tctgggagc tgaggagagg aaatgggtcc     2460
cctaccgggt ccccaacaat aacttgccca tccctgaacg ctaccttcg ccagatgcca     2520 cggtatccac ggaggtccgg gccatcattg cctggatgga aagaacccc ttcgtgctgg     2580 gagcaaatct gaacgcggc gagcggctag tatcctaccc ctacgatatg gcccgcacgc     2640
ctacccagga gcagctgctg gccgcagcca tggcagcagc ccgggggag gatgaggacg     2700 aggtctccga ggcccaggag actccagacc acgccatctt ccggtggctt gccatctcct    2760
tcgcctccgc acacctcacc ttgaccgagc cctaccgcgg aggctgccaa gcccaggact    2820
acaccggcgg catgggcatc gtcaacgggg ccaagtggaa ccccggacc gggactatca     2880 atgacttcag ttacctgcat accaactgcc tggagctctc cttctacctg ggctgtgaca    2940
agttccctca tgagagtgag ctgccccgcg agtgggagaa caacaaggag gcgctgctca    3000
ccttcatgga gcaggtgcac cgcggcatta agggggtggt gacggacgag caaggcatcc    3060
ccattgccaa cgccaccatc tctgtgagtg gcattaatca cggcgtgaag acagccagtg    3120
gtggtgatta ctggcgaatc ttgaacccgg gtgagtaccg cgtgacagcc cacgcggagg    3180
gctacacccc gagcgccaag acctgcaatg ttgactatga catcgggc actcagtgca     3240 acttcatcct ggctcgctcc aactggaagc gcatccggga gatcatgcc atgaacggga     3300 accggcctat cccacacata gacccatcgc gccctatgac cccccaacag cgacgcctgc    3360
agcagcgacg cctacaacac cgcctgcggc ttcgggcaca gatgcggctg cggcgcctca    3420
acgccaccac caccctaggc ccccacactg tgcctccac gctgcccct gccctgcca      3480 ccaccctgag cactaccata gagccctggg gcctcatacc gccaaccacc gctggctggg    3540
aggagtcgga gactgagacc tacacagagg tggtgacaga gtttgggacc gaggtggagc    3600
ccgagtttgg gaccaaggtg gagcccgagt ttgagaccca gttggagcct gagtttgaga    3660
```

```
cccagctgga acccgagttt gaggaagagg aggaggagga gaaagaggag gagatagcca    3720
ctggccaggc attcccttc acaacagtag agacctacac agtgaacttt ggggacttct    3780
gagatcagcg tcctaccaag accccagccc aactcaagct acagcagcag cacttcccaa    3840
gcctgctgac cacagtcaca tcacccatca gcacatggaa ggcccctggt atggacactg    3900
aaaggaaggg ctggtcctgc cccttgagg gggtgcaaac atgactggga cctaagagcc    3960
agaggctgtg tagaggctcc tgctccacct gccagtctcg taagagatgg ggttgctgca    4020
gtgttggagt aggggcagag ggagggagcc aaggtcactc caataaaaca agctcatggc    4080
acggacaaaa aaaaaaaaaa aa                                            4102

<210> SEQ ID NO 36
<211> LENGTH: 8532
<212> TYPE: DNA
<213> ORGANISM: Homo sapiens

<400> SEQUENCE: 36
aacatttaca acaaagttga ttctgtgtag ggttggaggc tagacagttc cacaaatttt      60
tagtcacatt ttccatgtca gttaaatcta gggagttcaa gactactgga aaaattagtc     120
tcattactaa aagaaactta gagaccgagg gaggtaccag agtctaggag gtacctctgg     180
gttgcagaag taattgtaaa ataccagacc tgttctttt actaaaagct agtttcacta     240
tcttctggtc tgaaatactg aggcaaatac tcaagactta ttttcttcct aatcttgctg     300
gtgaaacaga agttactaga aagaaaggaa gaaaaaactt gatttggtga ctgcaggaag     360
caacacgttg ctgcttttat tctacagata atgatttatg aggaatccaa gatgaatttg     420
gagcaggaga ggccgtttgt ctgcagtgcc ccaggctgct cccagcgctt cccaacagag     480
gaccatctga tgattcatag gcacaaacat gaaatgactt tgaagtttcc ttcaataaaa     540
acagacaata tgttatcaga tcaaactccg accccaacga gattcctgaa gaactgcgag     600
gaggtgggcc tcttcagcga gctggactgc tccctggagc acgagttcag gaaggctcag     660
gaagaggaga gcagcaagcg gaatatctcg atgcataatg cagttggtgg ggccatgacg     720
gggcccggaa ctcaccagct tagcagcgct cggctgccca accatgacac caacgttgtg     780
attcagcaag ccatgccgtc gcctcagtcc agctctgtca tcactcaggc accttccacc     840
aaccgccaga tcgggcctgt cccaggctct ctatcttctc tgctacatct ccacaacaga     900
cagagacagc ccatgccagc ctccatgcct gggaccctgc ccaacccctac aatgccagga     960 tcttccgccg tcttgatgcc aatggagcga caaatgtcag tgaactccag catcatgggg    1020
atgcaaggtc caaatctcag caaccctgt gcttctcccc aggtccagcc aatgcattca    1080
gaagccaaaa tgaggttgaa ggctgcattg actcaccacc ctgctgccat gtcaaatggg    1140
aacatgaaca ccatgggaca catgatggag atgatgggct cccggcagga ccagacgcca    1200
caccatcaca tgcactcgca cccgcatcag caccagacac tgccaccca tcacccttac    1260 ccacaccagc accagcaccc agcacaccat cctcacccctc aaccccatca ccagcagaac    1320
catccacatc accactccca ttcccaccttt catgcacacc cagcacatca ccagacctcg    1380
ccacatccgc cctgcacac cggcaaccaa gcacaggttt caccagcaac acaacagatg    1440
cagccaaccc agacaataca gccaccccag cccacagggg ggcgccggcg aagggtggta    1500
gacgaggatc cggacgagag gcggcggaaa tttctggaac ggaaccggc agctgccacc    1560 cgctgcagac agaagaggaa ggtctgggtg atgtcattgg aaaagaaagc agaagaactc    1620
```

```
acccagacaa acatgcagct tcagaatgaa gtgtctatgt tgaaaaatga ggtggcccag   1680
ctgaaacagt tgttgttaac acataaagac tgcccaataa cagccatgca gaaagaatca   1740
caaggatatc taagtccaga gagtagccct cctgctagtc ctgtcccagc ttgctcccag   1800
caacaagtca tccagcataa taccatcact acttcctcat cggtcagcga ggtggtagga   1860
agctccaccc tcagccagct caccactcac agaacagacc tgaatccgat tctttaaaat   1920
gcaccatcag acctggcctc caagaagagc tgtagcgtac catgcgtcct ttcttttaag   1980
ggcattttta gaattaactc agacctggaa gactcctcag ttcttcaaag actggctttc   2040
atttttatag ttattatgga aatgttgtct tttatactta gttatataag aaaaaaggga   2100
gttatgcaat taatatctat cagcttggga aacgctttgg tgcttttctc cagttttctg   2160
gtaccagtta cttgtttata aactgaacct tttctgtata tagccatggt ttcattctta   2220
tcagtccaac cctttgcctg aaacattgaa tcttgttaaa ccacagcтттt tagctaaaat   2280 gaggtatacc tagatgtcaa gtaagacaga tccaaggtaa ctgggtagga aatcttttga   2340
catcttaact catgttgagt tgtgctgtg gtgtcaccag aattccagat aaacacacag   2400
cctttcccat accttttttt tcttactat aaaatattat aagatccatt gatgtccaaa   2460
taataccacc aagcatctct tcacctctcc tcctcttggt ccacttgcta atgcccagtt   2520

ttcttctcca tttccacttt tcttaggct ccctatttac tattcatttt gacttccttc   2580
tgtttatttt tttcccttt agcattgcat gtgaataaga aaataatgtt taagaaaaa   2640 aaaaaaaag caaacctcca aaacgtggac ctaaccattg cttcacttac acttcaccca   2700
cagctggagt tcattcaact cttgctttc acaaatagt aaccaggaga tgtttaatgt   2760
gcctgattta atgtttttaa taatcacagc aaatgaaagg тgгтттagтт ataagtgaag   2820 catggttgaa taccagctgg ggagacacta gggaagggag ctttgtaagc cttgattgcg   2880
aaagtccaaa ttttgatgtg gggctataac atgacaccct tggattgcga ctggttttat   2940
acggcctgcc tataacgttg aaaatccatg tactacataa taattcagaa gggctctatt   3000
cactacacag attacattgt tcaatcatca gctgctaata gcctaagatt tatttttttt   3060

ttttcttaa gcctatggaa ccggctttgc tgttctgggg ggtgaaaata gactaactac   3120
tggagaaaca aagagagaaa gaaaacccag tgtttccata ggggcacttt tagccttccc   3180
acaacagtta agcactcttt gactgctgaa ggaaccccat ggatgaggtg caggctactt   3240 cactcтттттт тттттcттттт tgagacagag tctcacctat tgcccagact gaagtgcagt   3300
ggtgcgatca tggatcactg cagcagcatc ctccgagttc aagctatcct tccacctccg   3360
cctcctgagt agctgggacc acaggttcac ataaccatgc ctggctaatt таттттттact   3420

тттатттттаa aataaaagat gaggtctgtc ttatgttgcc caggctggtc tcaaactatc   3480
ctacttcttc ctcccaaagt gttgggatta taggtgtgag ccactgcacc cagcctactt   3540
cactcttctg aattattctg atttattttc aacaactttt tgaacttgc ccgtgataca   3600 aagcagatag tccctgaacc acagtcgtgc ctccttgaaa caagccattc tactgtgcta   3660 aтgтттттaат atcacatctc acaaataaca ggggtgaatg tttctctcta gcaatctagg   3720
caggtgctgg tgtttcatct ccatttgaat gcttgacctc taatgtgtg tgtgtgtgtg   3780 tgtgtgtgtg tgtgtgttca tgggttttaa aagaacagta тттттacaaaa ggtgtagctt   3840

ttataagagt gcagaaaagg gaaggatgtg tttttttctc tcactatagt ataagaatct   3900 atttggaga aaaaagaaa aтатgaggggт ctcgaagcat gattttata taactagttt   3960 cagttttatc taataactta cттттттaaат caatatttat caacaatctt tccttgtatg   4020
```

```
cagtgctttc aaaagatggt tttgagtgtc cagtgaaact tatgacttgg atatatggtt    4080
gaagaatcaa aacaaaagca aaaaaaaaaa gcaaaaaaag aaaagagaaa aaaagaaaaa    4140
atgcaaatgg aataattttc tattatattt tagacaaaca tatcattttc gagtatttta    4200
aatactgaat tcatagttgt tgtttttttaa attccaacag taacagctga atggtttaat    4260
ctgactggct tcctaagaaa tgtttaagac tcagctttaa aaagaagtta acattcatat    4320
ctctgttttg aaatcaaaaa tcatatttca aaattctttc ctaggaccat ctatgtgtct    4380
cccctcccct ccacaaaaag gagaaagagt gcattaaaat gtttagttgg gttttttaat    4440
ttttaatttt tatgttatgt tttgctttgt tttaagtaaa caaaaatttt tctttctttta    4500 ctgcatgcat agcacttaat aaaatggatt tttaaaaaat ccactagtaa tatcagaatg    4560
tccagggagt gactgtcact acaatgatgg tttagtttac ttctgttcca ccttttgatt    4620
gaaatattta gttgttaggc tgaaagcctc ggcagttaag aacttgcctg agttttcttc    4680
gttcagcaac ttgacagttt gactgatgtg cattatatat agctcaatta tgtctgtttt    4740
ttatgctaag taggaaaacc aaccacacac attagcaaac cggcctcaac atataattag    4800
aataaactgt cttcttgttc tactcagggc ctttaggtgt gttcattcac ggtatggaaa    4860
tacagtaaat gaaagattcc aactagttgt cagtgcttct tgaaattcca aacagaaaga    4920
tacattggtc aaatccaaca cttggcttat caatattaag tcttttacct aaaggcccag    4980
ccgtcaccag acaacagaat aatcaatctg cctgaaaatc cctcctcctt gtcctacact    5040
ttttgcctgt ttgggagaat atctttgtac tccattctcc tccctcagcc agttactggg    5100
tcacccatcc atgtgttcat gaatcaatca tcacggcctg cagagcacct gtcctaagga    5160
gggaaaatcc tgtcacactg cctctcccca ttcgtgtgtg gttttcttga tcggtgagat    5220
ctgtctctga agtcactgcc agcctccctg ggaacgtcta tagtgcctcc cctgccttat    5280
gtgatgggag ttaacaactc agataagtac acctgagagc atttctatca ggtaaactgt    5340
cacttaaatg gaggtgtcca catcttaatt gtttctcctt gacacatttc tcaatccacg    5400
aagccaggag aggtagagtg aaaatcccag ccatggatga atgtactaat ttgaaagcca    5460
agtgttaagt cggatgtttt cccgttacac tactactcag ccctctcctg cggccacatc    5520
aacggatgca agtcacagtc ttaacacagc ctgtgggaga caagcagttt gtgtgctcac    5580
agtatatatt atagtaatta gggtgactta gagcaaatac tcttcagatc ctatgtagtc    5640
agtgaaacaa aatggagagc gtattctgat agaaggacgt cgacggtgaa tgttctggtg    5700
gttgttgcct gttaagtaaa ctttagtgtg taagttgagt ttgtcattaa aatcataaac    5760
cagctgcggt aacagacaag cctttggctg gggagtttta agcctcggta actgctataa    5820
aactagccat ccagttagga tagaatgtgt ttctttctgg ttaaaaaaag gaaaaaccat    5880
ctaagaaaat atatatgtat gtatgtgtgt atacagtgga attcaaagga ccaaagcaaa    5940
atttgaacag gaatctatta atttagaatt ttataagata tttattaata aatgttattt    6000
ttaaacattc catttgaaca gtattctgta ggatctactt gttttttaaag tgttagtcca    6060 taataaacta ctatagttat gtgtattttc atttttcagg gttcaaatg gctattctcc    6120 atcatttggt ggaaatgttt gcttagatct ctgtgcatag acatttcaag gatttttatt    6180
gctctgtgag ttatttttta atcaacattc tgaacagttt ttttaaaaca tttatttctg    6240
tgtgttcatt tttaaagtaa gctctttcat ttaggaagca gagttcagct aaagggaatc    6300
agtaactcta actggaacag ctttcttgta gaagtgtaaa aacagcttca tctctgcctc    6360
```

| | |
|---|---:|
| tctccacccc accccaattt cctagaaagc cttgcactat tcagctccct tagtgctttt | 6420 |
| tgtcccttcc cgaacaatat gcagtagctt taagccattc aagctccatt atgcagtata | 6480 |
| tctgagaagg gaaaggaaac aacccattta aatttgaata aaaccgtgcc tatgcgaaca | 6540 |
| gtagcaattt agaatctctt ttctgctttt aaaataattt atatttaaaa attgcactt | 6600 |
| agcttttga tcccttgta tttctcttat tctctttcta acctcttctc tgtcctcaaa | 6660 |
| cttgcctttg ctctccttta caatacccccc caccccctcct ccaaggctct gagcggcatc | 6720 |
| atttaaaata ctttacagat atttgcacca ggtacattta tgtgcgtcca ttggtagcac | 6780 |
| agctgagacc tgtgtctcac atcagcctag gtgaagccta ctacaagaat gccaaggaga | 6840 |
| agagccagta cactatatgg tttatactct ttatccctt attcatagca tgttttttaa | 6900 |
| aaatgttata ttatgcaaca gatgtgaggc agcagctaag ctatacttaa gaattttctc | 6960 |
| tcaccttcca aaccaaagtg tcctgaataa gccaggagac ttattctttt gtgcaccctg | 7020 |
| gtgcacatct gactgttgtc ctagccatag actctctgag gccactgaaa gaacagtggc | 7080 |
| cctatcgatt tcattcctag gtctcaaaaa tacaatgttg ccttgtaaca taattaggga | 7140 |
| cagcacctct atttcacaat tataatctaa ggtaggataa gacgacacag cagcaataaa | 7200 |
| cttacaagta aaattcaata ccaaaacaaa cacaagaaaa tttaaaaaac aaaaaaccta | 7260 |
| gctcatcatg ttgtgaaaat gaaaagtga atgtccattc aaaatatttt actatttctt | 7320 |
| gtggagtttt tcagtgatgt aatgcttgta gccaaattgc ttaaagagtg tttatatatt | 7380 |
| tttttcctta taaattgtct atttttaaa aaagctattt aaccacagct gaagtggggg | 7440 |
| gtaaggccaa attgccaaca cttgttaaaa gattaatact cttaagtggc actctgatac | 7500 |
| ctttccaact tgtcatcaga aaggaatcaa taattaccaa ctgttgtatt tagaccaact | 7560 |
| tacaatatct agctcattag aagccaggat ctagaaagct ccttctaagc catttaagat | 7620 |
| attcttacat tgagcttcat attatagaac tttataggat tggatatttt acaatagaat | 7680 |
| aatttagcct caggactgag aatgtggaag ctgaataaat tagctttaaa tacatcatta | 7740 |
| aaatcttatg cacaataagc tcattagatt ctagttttct cctttagaat accaatgcca | 7800 |
| cagacactac aggagataat gaaaggtatc agttgtgttg agtggaggga gtttaagaga | 7860 |
| aaggacccctt cccaaccagc agccagtaga aaatacaacc tactcacctt tttcccttct | 7920 |
| aagttctgct aaatcacatc tgcctcatag agaaaggaat gttgcctttg agaactgtct | 7980 |
| tggagaacag ataagcttga aatgttctct ctagagagga catagggttt gggatcctct | 8040 |
| gaaaaggccc agaaaaatag ctcagttcaa atacaatgtt ctaggacaat tggaatataa | 8100 |
| atattgtcca aaaatataat taaaagaaaa aagtttagca ctgtgtaaag taagtgttaa | 8160 |
| ctgaggaagt cccaaaaagg tgctgtcact ttaagttctg gacttggggt tctttgtatt | 8220 |
| tgtaaacagc aaagcatttg tgtttgtttg tctatttgta aagcaaccac cttccttatt | 8280 |
| ggaaggagaa aaaaggggt acatacatgt aaatacttgc tgcagcattt aatatgttta | 8340 |
| attttgtgtt aagctttttg ttgcatcgtg aacacattta ttgttaccaa tggacaatga | 8400 |
| gttcattaag actgttcaac taggtcagat ttttacatct cttctagca agaagagaca | 8460 |
| agattttgtg catttgtaca aatgttaata tcactgcaat tccaatataa taaagcactc | 8520 |
| aaatgcaaat aa | 8532 |

<210> SEQ ID NO 37
<211> LENGTH: 4945
<212> TYPE: DNA
<213> ORGANISM: Homo sapiens

<400> SEQUENCE: 37

```
ttcatttccc agacttagca caatctcatc cgctctaaac aacctcatca aaactacttt        60
ctggtcagag agaagcaata attattatta acatttatta acgatcaata aacttgatcg       120
cattatggcc agcactatta aggaagcctt atcagttgtg agtgaggacc agtcgttgtt       180
tgagtgtgcc tacggaacgc cacacctggc taagacagag atgaccgcgt cctcctccag       240
cgactatgga cagacttcca agatgagccc acgcgtccct cagcaggatt ggctgtctca       300
acccccagcc agggtcacca tcaaaatgga atgtaaccct agccaggtga atggctcaag       360
gaactctcct gatgaatgca gtgtggccaa aggcgggaag atggtgggca gcccagacac       420
cgttgggatg aactacggca gctacatgga ggagaagcac atgccacccc caaacatgac       480
cacgaacgag cgcagagtta tcgtgccagc agatcctacg ctatggagta cagaccatgt       540
gcggcagtgg ctggagtggg cggtgaaaga atatggcctt ccagacgtca acatcttgtt       600
attccagaac atcgatggga aggaactgtg caagatgacc aaggacgact tccagaggct       660
cacccccagc tacaacgccg acatccttct ctcacatctc cactacctca gagagactcc       720
tcttccacat ttgacttcag atgatgttga taaagcctta caaaactctc cacggttaat       780
gcatgctaga aacacagggg gtgcagcttt tattttccca aatacttcag tatatcctga       840
agctacgcaa agaattacaa ctaggccaga tttaccatat gagcccccca ggagatcagc       900
ctggaccggt cacggccacc ccacgcccca gtcgaaagct gctcaaccat ctccttccac       960
agtgcccaaa actgaagacc agcgtcctca gttagatcct tatcagattc ttggaccaac      1020
aagtagccgc cttgcaaatc caggcagtgg ccagatccag ctttggcagt tcctcctgga      1080
gctcctgtcg acagctccaa actccagctg catcacctgg gaaggcacca acggggagtt      1140
caagatgacg gatcccgacg aggtggcccg gcgctgggga gagcggaaga gcaaacccaa      1200
catgaactac gataagctca gccgcgcccct ccgttactac tatgacaaga acatcatgac      1260
caaggtccat gggaagcgct acgcctacaa gttcgacttc cacgggatcg cccaggccct      1320
ccagccccac cccccggagt catctctgta caagtacccc tcagacctcc cgtacatggg      1380
ctcctatcac gcccacccac agaagatgaa ctttgtggcg ccccaccctc cagccctccc      1440
cgtgacatct tccagttttt ttgctgcccc aaacccatac tggaattcac caactggggg      1500
tatataccccc aacactaggc tccccaccag ccatatgcct tctcatctgg gcacttacta      1560
ctaaagacct ggcggaggct tttcccatca gcgtgcattc accagcccat cgccacaaac      1620
tctatcggag aacatgaatc aaaagtgcct caagaggaat gaaaaaagct ttactggggc      1680
tggggaagga agccggggaa gagatccaaa gactcttggg agggagttac tgaagtctta      1740
ctacagaaat gaggaggatg ctaaaaatgt cacgaatatg gacatatcat ctgtggactg      1800
accttgtaaa agacagtgta tgtagaagca tgaagtctta aggacaaagt gccaagaaa       1860
gtggtcttaa gaaatgtata aactttagag tagagtttgg aatcccacta atgcaaactg      1920
ggatgaaact aaagcaatag aaacaacaca gttttgacct aacataccgt ttataatgcc      1980
atttttaagga aaactacctg tatttaaaaa tagaaacata tcaaaaacaa gagaaaagac      2040
acgagagaga ctgtggccca tcaacagacg ttgatatgca actgcatggc atgtgctgtt      2100
ttggttgaaa tcaaatacat tccgtttgat ggacagctgt cagctttctc aaactgtgaa      2160
gatgacccaa agtttccaac tcctttacag tattaccggg actatgaact aaaaggtggg      2220
actgaggatg tgtatagagt gagcgtgtga ttgtagacag aggggtgaag aaggaggagg      2280
```

```
aagaggcaga gaaggaggag accagggctg ggaaagaaac ttctcaagca atgaagactg    2340
gactcaggac atttggggac tgtgtacaat gagttatgga gactcgaggg ttcatgcagt    2400
cagtgttata ccaaacccag tgttaggaga aaggacacag cgtaatggag aaagggaag     2460 tagtagaatt cagaaacaaa aatgcgcatc tctttctttg tttgtcaaat gaaaatttta    2520
actggaattg tctgatattt aagagaaaca ttcaggacct catcattatg tgggggcttt    2580
gttctccaca gggtcaggta agagatggcc ttcttggctg ccacaatcag aaatcacgca    2640 ggcatttttgg gtaggcggcc tccagttttc ctttgagtcg cgaacgctgt gcgtttgtca   2700
gaatgaagta tacaagtcaa tgttttccc ccttttata taataattat ataacttatg     2760
catttataca ctacgagttg atctcggcca gccaaagaca cacgacaaaa gagacaatcg    2820
atataatgtg gccttgaatt ttaactctgt atgcttaatg tttacaatat gaagttatta    2880
gttcttagaa tgcagaatgt atgtaataaa ataagcttgg cctagcatgg caaatcagat    2940
ttatacagga gtctgcattt gcacttttttt tagtgactaa agttgcttaa tgaaaacatg   3000
tgctgaatgt tgtggatttt gtgttataat ttactttgtc caggaacttg tgcaagggag    3060
agccaaggaa ataggatgtt tggcacccaa atggcgtcag cctctccagg tccttcttgc    3120
ctcccctcct gtcttttatt tctagcccct tttggaacag aaggacccccg ggtttcacat   3180 tggagcctcc atatttatgc ctggaatgga aagaggccta tgaagctggg gttgtcattg    3240
agaaattcta gttcagcacc tggtcacaaa tcacccttaa ttcctgctat gattaaaata    3300
catttgttga acagtgaaca agctaccact cgtaaggcaa actgtattat tactggcaaa    3360
taaagcgtca tggatagctg caatttctca ctttacagaa acaagggata acgtctagat    3420
ttgctgcggg gtttctcttt caggagctct cactaggtag acagctttag tcctgctaca    3480
tcagagttac ctgggcactg tggcttggga ttcactagcc ctgagcctga tgttgctggc    3540
tatcccttga agacaatgtt tatttccata atctagagtc agtttccctg gcatcttttt    3600
ctttgaatca caaatgctgc caaccttggt ccaggtgaag gcaactcaaa aggtgaaaat    3660
acaaggtgac cgtgcgaagg cgctagccga acatcttag ctgaataggt ttctgaactg     3720
gcccttttca tagctgtttc agggcctgtt tttttcacgt tgcagtcctt ttgctatgat    3780
tatgtgaagt tgccaaacct ctgtgctgtg atgttttgg cagtgggctt tgaagtcggc     3840
aggacacgat taccaatgct cctgacaccc cgtgtcattt ggattagacg gagcccaacc    3900
atccatcatt ttgcagcagc ctgggaaggc ccacaaagtg cccgtatctc cttagggaaa    3960
ataaataaat acaatcatga aagctggcag ttaggctgac ccaaactgtg ctaatgaaa     4020 agatcagtca ttttttatttt ggaatgcaaa gtcaagacac acctacattc ttcatagaaa   4080
tacacattta cttggataat cactcagttc tctcttcaag actgtctcat gagcaagatc    4140
ataaaaacaa gacatgatta tcatattcaa ttttaacaga tgttttccat tagatccctc    4200
aaccctccac ccccagtcca ggttattagc aagtcttatg agcaactggg ataattttgg    4260
ataacatgat aatactgagt tccttcaaat acataattct taaattgttt caaaatggca    4320
ttaactctct gttactgttg taatctaatt ccaaagcccc ctccaggtca tattcataat    4380
tgcatgaacc ttttctctct gtttgtccct gtctcttggc ttgccctgat gtatactcag    4440
actcctgtac aatcttactc ctgctggcaa gagatttgtc ttcttttctt gtcttcaatt    4500
ggctttcggg ccttgtatgt ggtaaaatca ccaaatcaca gtcaagactg tgttttttgtt  4560 cctagtttga tgcccttatg tcccggaggg gttcacaaag tgcttgtca ggactgctgc     4620 agttagaagg ctcactgctt ctcctaagcc ttctgcacag atgtggcacc tgcaacccag    4680
```

| | |
|---|---|
| gagcaggagc cggaggagct gccctctgac agcaggtgca gcagagatgg ctacagctca | 4740 |
| ggagctggga aggtgatggg gcacagggaa agcacagatg ttctgcagcg ccccaaagtg | 4800 |
| acccattgcc tggagaaaga aagaaaata tttttttaaaa agctagttta tttagcttct | 4860 |
| cattaattca ttcaaataaa gtcgtgaggt gactaattag agaataaaaa ttactttgga | 4920 |
| ctactcaaaa atacaccaaa aaaaa | 4945 |

<210> SEQ ID NO 38
<211> LENGTH: 4015
<212> TYPE: DNA
<213> ORGANISM: Homo sapiens

<400> SEQUENCE: 38

| | |
|---|---|
| cgaacgagcg gcgctcggcg gggacagaaa gagggagaga gagagagaga gagagggaga | 60 |
| ggcgcggccg ggcgaggcgg gcccgtccgg gagcgggctc cggggaaggg gtgcgggtct | 120 |
| gggcgccgga gcggggagcg gggccgcgtc cctctcagcg ccagctctac ttgagcccca | 180 |
| cgagccgctg tccccctggc gcgctcgggg ccgcgggacg ggcgcacgcc gccttctcct | 240 |
| agtcaagtat ccgagccgcc ccgaaactcg ggcggcgagt cggccacggg aagtttattc | 300 |
| tccggctcct tttctaaaag gaagaaacag aagtttctcc cagcggacag cttttctttc | 360 |
| cgccttttg gccctgtctg aaatcggggg tccccagggc tggcaggcca ggctcgctgg | 420 |
| gctcctaatc ttttttttaa tttccaattt ttgattgggc cgtgggtccc cgctgagctc | 480 |
| cggctgcgcg cggggggcggg agggcgcgcg caggggaggg accgagagac gcgccgactt | 540 |
| tttagaggga gggatcgggt ggacaactgg tcccgcggcg ctcgcagagc cggaaagaag | 600 |
| tgctgtaagg gacgctcggg ggacgctgtt cctgaggtgt cgccgcctcc ctgtcctcgc | 660 |
| cctccgcggt gggggagaaa cccaggagcg aagcccagag cccgcggcgc ggccggcgga | 720 |
| cgaacgagcg cgcagcagcc ggtgcgcggc cgcggcgagg gcggggggaag aaaaacaccc | 780 |
| tgtttcctct ccggccccca ccgcggatca tgtaccagga ttatcccggg aactttgaca | 840 |
| cctcgtcccg gggcagcagc ggctctcctg cgcacgccga gtcctactcc agcggcggcg | 900 |
| gcggccagca gaaattccgg gtagatatgc ctggctcagg cagtgcattc atccccacca | 960 |
| tcaacgccat cacgaccagc caggacctgc agtggatggt gcagcccaca gtgatcacct | 1020 |
| ccatgtccaa cccataccct cgctcgcacc cctacagccc cctgccgggc ctggcctctg | 1080 |
| tccctggaca catggcccct ccaagacctg gcgtgatcaa gaccattggc accaccgtgg | 1140 |
| gccgcaggag agagatgag cagctgtctc ctgaagagga ggagaagcgt cgcatccggc | 1200 |
| gggagaggaa caagctggct gcagccaagt gccggaaccg acgccgggag ctgacagaga | 1260 |
| agctgcaggc ggagacagag gagctggagg aggagaagtc aggcctgcag aaggagattg | 1320 |
| ctgagctgca gaaggagaag gagaagctgg agttcatgtt ggtggctcac ggcccagtgt | 1380 |
| gcaagattag ccccgaggag cgccgatcgc ccccagcccc tggctgcag cccatgcgca | 1440 |
| gtggggggtgg ctcggtgggc gctgtagtgg tgaaacagga gccctggaa gaggacagcc | 1500 |
| cctcgtcctc gtcggcgggg ctggacaagg cccagcgctc tgtcatcaag cccatcagca | 1560 |
| ttgctggggg cttctacggt gaggagcccc tgcacacccc catcgtggtg acctccacac | 1620 |
| ctgctgtcac tccgggcacc tcgaacctcg tcttcaccta tcctagcgtc ctggagcagg | 1680 |
| agtcacccgc atctcctcc gaatcctgct ccaaggctca ccgcagaagc agtagcagcg | 1740 |
| gggaccaatc atcagactcc ttgaactccc ccactctgct ggctctgtaa cccagtgcac | 1800 |

```
ctccctcccc agctccggag ggggtcctcc tcgctcctcc ttcccaggga ccagcacctt    1860
caagcgctcc agggccgtga gggcaagagg gggacctgcc accagggagc ttcctggctc    1920
tgggggaccc aggtgggact tagcagtgag tattggaaga cttgggttga tctcttagaa    1980
gccatgggac ctcctccctc attcatcttg caagcaaatc ccatttcttg aaaagccttg    2040
gagaactcgg tttggtagac ttggacatct ctctggcttc tgaagagcct gaagctggcc    2100
tggaccattc ctgtcccttt gttaccatac tgtctctgga gtgatggtgt ccttccctgc    2160
cccaccacgc atgctcagtg ccttttggtt tcaccttccc tcgacttgac cctttcctcc    2220
cccagcgtca gtttcactcc ctcttggttt ttatcaaatt tgccatgaca tttcatctgg    2280
gtggtctgaa tattaaagct cttcatttct ggagatgggg cagcaggtgg ctcttctgct    2340
ggggctgact tgtccagaag gggacaaagt gcaatacaga gccttcccta ccctgacgcc    2400
tcccagtcat catctccaga actcccagcg gggctccctg agctctcaag agatgctgc    2460 catcactggg aggctcagag gacccttcct gcccaccttc ggagacggct tctggaggaa    2520
cggcttggcc agaagacagg gtgtgagtga gacagtgggg cacaggttgg gtttgccaaa    2580
cgcctaatta ccaggccagg aagcatgcca acaaagccac acgggtgtcc tagccagctt    2640
cccttcacct ggtgtcttga gtagggcgtc tcctgtaatt actgccttgc cattctgccc    2700
ctggaccctt ctctccggac cagggaggcg tccctcccta ggagccacac attatactcc    2760
aagtccctgc cgggctccgc cttccccca ccctggctct caggggtgacg ccacccacag    2820 agatttaatg agcgtgggcc tggaccttcc ccagatgctg ccaggcagcc cctccccaag    2880
cctcaaagaa gcatttgctg aggatggaga ggcaggggag ggaggcggga ggccgtcact    2940
ggagtggcgt ctgcagcagc tgctgcccca gcacccgctc agcctgtcct ggctgctcac    3000
ctccccgcag ggcaccgggc cttcctgcc ctctgtggtc atctgccacc tgctggatca    3060
agtgctttct cttttacact cccctgtccc caccccagtg cactcttctg gcccaggcag    3120
caagcaagct gtgaacagct ggcctgagct gtcgctgtgg cttgtggctc atgcgccatt    3180
cctggttgtc tgttgaatct ttctggctgc tggaattgga gataggatgt tttgcttccc    3240
actgcaggag agctgccccc tttcacgggg ttggggaagg gtcccccctgg cctccagcag    3300 gagcacagct cagcagggtc cctgctgccc accctctga gccttttctc cccagggtat    3360
ggctcctgct gagtttcttg tccagcaggg ccttgacagg aatccaggga gtagctcctg    3420
gccagaacca gcctctgcgg ggcttgtgct ctgcaaagac tctgctgctg gggattcagc    3480
tctagaggtc acagtatcct cgtttgaaag ataattaaga tcccccgtgg agaaagcagt    3540
gacacattca cacagctgtt ccctcgcatg ttatttcatg aacatgacct gttttcgtgc    3600
actagacaca cagagtggaa cagccgtatg cttaaagtac atgggccagt gggactggaa    3660
gtgacctgta caagtgatgc agaaaggagg gtttcaaaga aaaaggattt tgtttaaaat    3720
actttaaaaa tgttatttcc tgcatcccytt ggctgtgatg cccctctccc gatttcccag    3780
gggctctggg agggacccytt ctaagaagat tgggcagttg ggtttctggc ttgagatgaa    3840
tccaagcagc agaatgagcc aggagtagca ggagatgggc aaagaaaact ggggtgcact    3900
cagctctcac aggggtaatc atctcaagtg gtatttgtag ccaagtggga gctattttct    3960
tttttgtgca tatagatatt tcttaaatga aaaaaaaaa aaaaaaaaa aaaaa           4015

<210> SEQ ID NO 39
<211> LENGTH: 2018
<212> TYPE: DNA
<213> ORGANISM: Homo sapiens
```

<400> SEQUENCE: 39

```
gtgctgcggc gagctccgtc caaaagaaaa tggggtttgg tgtaaatctg ggggtgtaat        60
gttatcatat atcactctac ctcgtaaaac cgacactgaa agctgccgga caacaaatca       120
caggtcaaaa ttatgagttc ttcgtattat gtgaacgcgc tttttagcaa atatacggcg       180
ggggcttctc tgttccaaaa tgccgagccg acttcttgct cctttgctcc caactcacag       240
agaagcggct acggggcggg cgccggcgcc ttcgcctcga ccgttccggg cttatacaat       300
gtcaacagcc ccctttatca gagccccttt gcgtccggct acggctgggc gccgacgcc        360
tacggcaacc tgcccgcgc ctcctacgac caaaacatcc ccgggctctg cagtgacctc       420
gccaaaggcg cctgcgacaa gacggacgag ggcgcgctgc atggcgcggc tgaggccaat       480
ttccgcatct accccctggat gcggtcttca ggacctgaca ggaagcgggg ccgccagacc       540
tacacgcgct accagacgct ggagctggag aaggagttcc acttcaaccg ctacctgacg       600
cggcgccgcc gcattgaaat cgcccacgcg ctctgcctca ccgagcgcca gattaagatc       660
tggttccaga accgccgcat gaagtggaag aaagagcata aggacgaagg tccgactgcc       720
gccgcagctc ccgagggcgc cgtgccctct gccgccgcca ctgctgccgc ggacaaggcc       780
gacgaggagg acgatgatga agaagaggaa gacgaggagg aatgaggggc cgatccgggg       840
ccctctctgc accggacagt cggaaaagcg tctttaagag actcactggt tttacttaca       900
aaaatgggaa aaataaaaga aaatgtaaaa aacaaaaaca aaacaaaaa agcaacccag        960
tccccaacct gcactctacc cacccccatc acctactcca gctcccaact tttgtggact      1020
gagcggccgc agagactggg tcgccttgga ttccctctgc ctccgaggac cccaaaagac      1080
acccccaacc ccaggccagc cggccctgct ctggcgcgtc caaaatacta cctagcacag      1140
gcctctgctc gaggcacccc caaactacct atgtatccag ccccagaggg cctccattcc      1200
caggaagtcc ctatgtatcc caacactggc agacacccag caccaccctc ccagacccgc      1260
aagaaagtga atctcactac tacctactcc cctaaaacta cctattttgt gctggctggc      1320
ttgcctgcta cctagtgccg actgctccca ggcaagtccc ctgctgctta cagcccgcag      1380
cttttggggt ccctgaggct gccctgagaa tgtgctgagg tccaggatca gggtattggc      1440
atctatttaa atcgaaaaat aatatattta ttccaaaaag catcctaagt gcttgcaccc      1500
tagaatcaat ccctccttct ctggcttggc acccacagct caggcccatc aaccccccact      1560
tctggagggg aatgttcctg agctggctgc agatctgtgg gttagcttct gcttagcagg      1620
actgtggaga tgcttccagc ttcgctgtcc tttcctctgg ctcctgtatc ttactgttca      1680
gctgtgttaa atatgtacgc cctgatgttt cctataatag cagatactgt atatttgaac      1740
aagattttt tttatcattt ctatagtctt ggagttcatt tgtaaggcag tgtcttgact      1800
tggaaaggat gtgttaatgg ggtgactttg tagcatggta tgttgtcttg agttaactgt      1860
agtgggtggg gaggtccaat gccctccgca atgcccttca tctcctgtgt tgtcctgtac      1920
cctgctcagc tccatcctgg ggttcaggga aggcacactt cccagcccag ctgtgtttta      1980
tgtaaccgaa aataaagatg cgtggtgaca aagaaaaa                              2018
```

<210> SEQ ID NO 40
<211> LENGTH: 1728
<212> TYPE: DNA
<213> ORGANISM: Homo sapiens

<400> SEQUENCE: 40

| | |
|---|---|
| agagggcgag ggcgagggca gagggcgctg gcggcagcgg ccgcggaaga tgagcagcag | 60 |
| ctgctcaggg ctgagcaggg tcctggtggc cgtggctaca gccctggtgt ctgcctcctc | 120 |
| cccctgcccc caggcctggg gcccccagg ggtccagtat gggcagccag gcaggtccgt | 180 |
| gaagctgtgt tgtcctggag tgactgccgg ggacccagtg tcctggtttc gggatgggga | 240 |
| gccaaagctg ctccagggac ctgactctgg gctagggcat gaactggtcc tggcccaggc | 300 |
| agacagcact gatgagggca cctacatctg ccagaccctg gatggtgcac ttgggggcac | 360 |
| agtgaccctg cagctgggct accctccagc ccgccctgtt gtctcctgcc aagcagccga | 420 |
| ctatgagaac ttctcttgca cttggagtcc cagccagatc agcggtttac ccacccgcta | 480 |
| cctcacctcc tacaggaaga gacagtcct aggagctgat agccagagga ggagtccatc | 540 |
| cacagggccc tggccatgcc cacaggatcc cctaggggct gccgctgtg ttgtccacgg | 600 |
| ggctgagttc tggagccagt accggattaa tgtgactgag gtgaacccac tgggtgccag | 660 |
| cacacgcctg ctggatgtga gcttgcagag catcttgcgc cctgaccac cccagggcct | 720 |
| gcgggtagag tcagtaccag gttaccccg acgcctgcga gccagctgga catacctgc | 780 |
| ctcctggccg tgccagcccc acttcctgct caagttccgt ttgcagtacc gtccggcgca | 840 |
| gcatccagcc tggtccacgg tggagccagc tggactggag gaggtgatca cagatgctgt | 900 |
| ggctgggctg ccccatgctg tacgagtcag tgcccgggac tttctagatg ctggcacctg | 960 |
| gagcacctgg agcccggagg cctggggaac tccgagcact gggaccatac caaaggagat | 1020 |
| accagcatgg ggccagctac acacgcagcc agaggtggag cctcaggtgg acagccctgc | 1080 |
| tcctccaagg ccctcccctcc aaccacaccc tcggctactt gatcacaggg actctgtgga | 1140 |
| gcaggtagct gtgctggcgt ctttgggaat cctttctttc ctgggactgg tggctggggc | 1200 |
| cctggcactg ggctctggc tgaggctgag acggggtggg aaggatggat ccccaaagcc | 1260 |
| tgggttcttg gcctcagtga ttccagtgga caggcgtcca ggagctccaa acctgtagag | 1320 |
| gacccaggag ggcttcggca gattccacct ataattctgt cttgctggtg tggatagaaa | 1380 |
| ccaggcagga cagtagatcc ctatggttgg atctcagctg gaagttctgt ttggagccca | 1440 |
| tttctgtgag accctgtatt tcaaatttgc agctgaaagg tgcttgtacc tctgatttca | 1500 |
| ccccagagtt ggagttctgc tcaaggaacg tgtgtaatgt gtacatctgt gtccatgtgt | 1560 |
| gaccatgtgt ctgtgaggca gggaacatgt attctctgca tgcatgtatg taggtgcctg | 1620 |
| gggagtgtgt gtgggtcctt ggctcttggc ctttcccctt gcaggggttg tgcaggtgtg | 1680 |
| aataaagaga ataaggaagt tcttggagat tatactcaga aaaaaaaa | 1728 |

<210> SEQ ID NO 41
<211> LENGTH: 9178
<212> TYPE: DNA
<213> ORGANISM: Homo sapiens

<400> SEQUENCE: 41

| | |
|---|---|
| aaagatggcc ggagcggcgg cggcggtggc cgcgggagca gcagctggag ccgccgcggc | 60 |
| agccgtgtcg gtggcggctc ccggccgggc ctcggcgcct ccgccgcccc cgcccgtgta | 120 |
| ctgtgtgtgc cggcagccgt acgacgtgaa ccgcttcatg atcgagtgcg atatctgcaa | 180 |
| ggactggttc cacggcagct gtgttggagt agaagaacat catgctgttg acattgacct | 240 |
| gtatcactgt cccaactgtg cagttttaca tggttcctcc ttgatgaaaa aaggaggaa | 300 |
| ctggcacaga catgactaca cagaaattga tgatggttcc aaaccagtgc aagctggaac | 360 |
| tagaactttc attaaggaat tacgctctcg agtcttccca agtgccgatg aaataattat | 420 |

```
aaagatgcat ggcagccagc tgacacaaag atatctggag aaacatggat ttgatgtccc    480
tattatggtc ccaaaattag atgatctagg actcaggctc ccttcaccta cattttctgt    540
gatggatgtg aacgttatg taggtggtga caaagtgata gatgtcattg atgtggcgag     600
gcaggcagac agcaaaatga cacttcacaa ttatgttaaa tacttcatga atcctaacag    660
accaaaagtg ttaaatgtga tcagccttga attttcagat acaaagatgt ctgaattggt    720
ggaggtccct gatatagcca aaaaactttc ctgggtggaa aattattggc cagatgattc    780
agtctttccc aagccatttg ttcagaaata ttgcttaatg ggagttcaag acagctatac    840
agatttccac attgacttcg gtggaacttc agtctggtac catgtcctct ggggtgagaa    900 gatttttat ttaataaagc caacagatga aaatttggca cgttatgaat cttggagttc     960
atctgtgacc cagagtgagg tgttctttgg agataaggtg gataaatgct acaaatgtgt    1020
ggtaaagcag ggacatacct tatttgttcc tacagggtgg atccatgctg tgctcacttc    1080
tcaggactgt atggcttttg gggggaactt cctgcacaac cttaacattg gcatgcagct    1140
caggtgttat gagatggaga aaaggctaaa acaccagat cttttcaaat tccctttctt     1200
tgaagccata tgttggtttg tagccaaaaa cttgctggaa accctgaaag aactgagaga    1260
agatggtttc cagcctcaaa cttacctagt acagggagtg aaagcactgc atactgcttt    1320
aaaattatgg atgaaaaaag aacttgtatc tgaacatgcc tttgaaattc cagacaatgt    1380
tagacctgga caccttatta agaactttc taaagtaatt cgagcaatag aggaggaaaa     1440
cggcaaacca gttaaatctc agggaattcc tattgtgtgt ccagtttcac gatcctcaaa    1500
tgaagcaact tccccatacc attcccgaag aaagatgagg aaacttcgag atcataatgt    1560
ccgaactcct tctaacctag acatcctaga gctccacaca agggaggtcc tcaaaagatt    1620
agagatgtgt ccatgggaag aggacatctt gagctctaaa ctgaatggaa aattcaacaa    1680
acatctccaa ccatcctcca cagtacctga atggagagcg aaagataatg atctacgatt    1740
actgctgaca aatggaagaa taattaaaga tgaaaggcag ccctttgcag atcaaagtct    1800
ttatacagca gatagtgaaa atgaagagga taaagaagg acaaaaaagg caaaaatgaa     1860
gatagaagag agttcaggag tagagggagt ggaacatgaa gaatctcaaa aaccactgaa    1920
tgggtttttt acacgtgtga atcagaact caggagtaga tcatcaggat attctgatat     1980
ttctgagtca gaagactccg gacccgagtg cactgcactg aaaagtatct ttaccactga    2040
agagtctgaa agttcaggtg atgaaaagaa acaagaaata acatccaact ttaaggagga    2100
atctaatgtg atgaggaact tccttcaaaa gagccagaag ccatctagaa gtgaaattcc    2160
aattaaaagg gaatgtccta cctcgacgag cacagaggaa gaagctattc agggcatgct    2220
gtctatggca gggttgcact attccacgtg tttacaaagg caaatacaaa gcacagactg    2280
cagtggtgaa agaaactctc tccaggatcc cagcagctgc catggcagta accatgaggt    2340
taggcagttg tatcgctatg ataaaccagt ggaatgtgga taccatgtca agactgaaga    2400
tccagacttg aggacttcct cctggattaa acagtttgat acttccagat tcatcctca     2460 ggatctaagt agaagccaga aatgcatcag aaaggaaggt tcatcagaaa ttagtcagag    2520
ggtacaaagt aggaattatg tggacagcag cggctcaagc cttcagaatg aaagtatat    2580 gcagaattca aacctgactt cggggggcgtg ccagataagt aatggcagtc taagcccaga    2640
aaggccagtt ggtgaaactt ccttctcggt gccccttcac cccaccaaga gaccggcatc    2700
aaatccacca cctatcagca accaggcaac aaaaggtaaa cgtccaaaaa aaggaatggc    2760
```

```
aacagccaaa caacgtcttg ggaagatcct taagttgaac agaaatggcc atgcacgttt    2820
ctttgtgtga cagagctgct gttgcagcca ttcttccctt tggagaccag tctaggggtg    2880
caggagcctg gagcttccgc tgtcccctg cctggagcag tttgtgtgta tagtaagaac    2940
actgcccgaa gaacagaatg aacctgatgc tgcattttca ctgtgccaca cccactcagc    3000
aataaccatt ttggacctgg tgggggagag gaagaaggag ggtagaacct taaaaagaga    3060
ccttgaactg gaagggtct cttgtcaggg cttgaatttt attttgttgt tggtagtgtc    3120
ttgatgtatt ttcagtggta gggtaaagaa ttatcaataa tttatttaac agattttttt    3180
ttaaagttaa cagcttttaa attctttttt taaagctatt tatttggaag atttctggag    3240
aaatatctca ctaatttaga tgtaagaatg tgaaggtttt taaattattt ttgatagtgt    3300
gtgtgttaca tgtggggaag ggccacagta acagtaacta gtctggactc ttaaatttga    3360
tattcaggtt aaagtcttaa acagggattt gatgcattaa ttattttaaa ttaagatgta    3420
tatgaaaatc atttttatttt atatatttca tgtgtttttt ataagctatt agcttcgctt    3480
ttgctaacat ccaaggtgca tactgttatc caggttgatt accttatatc ccaccttccc    3540
tctgcactcc ccatcatttt gtgatgaccc agtaagactc ttctctttgc agggaaacac    3600
tttcgtagcc aatgtgtaag aactccatga agatccctc atttctcatt tcgtttgaca    3660
ttgtgatttt cttctcaaca ttaaaaaaaa taggcttttg catttcattt tctgctgatg    3720
atatctgggt cccaaagaga gcagctttaa tatattttc ctacttgtgg gaaagtatt    3780 ataagtttgg ttaaattgtc atgtttatag ttttccaag tacatttgta actacagcag    3840
gccttcttcg tactgctgct gttggacaac aggactggca cctgctgcag aggttatacc    3900
ttatgatact tttatgctcc atacctgatt tgttgggaaa tgttatttag gatattcaaa    3960
tctgcatcat aagccgtaat ataataggat taatactaca ttaagttgta tagaagcaag    4020
catgttggaa tagatctttt gtgtgtattt acttttttta tttcttaatt ttctaaagaa    4080
ttacttaaga tatggatttg gagtaaaatg ggtgcttttg gcagtttctt ccatctatcc    4140
taacctgacc agtacatatt gaggttaagt atctggttaa actttaaggt attcatttat    4200
ctcctttatg tatgatttt actaaatgcc agttttcatt tgcttatagt agcttctatt    4260
ttcccttttt tccatccatg gcataaaaat aagtgatttc tggggtggg gcagaaatgt    4320 tcccaagtct gacaatagag catttacaa attcctacaa agaaaatata ggcaaataga    4380
taaaatttat ttttatggag aagaaatatg gccatattat ggatttgtct ttttttttact    4440 cagcaagata gcaggactta cccttctcta ttaagtatca cttgaattgc taagaagaaa    4500
aaagtctgta ccatcatctt tcatggttgc attcaaatgt atattttcaa agagaaatac    4560
ttcttgtgtc cccattccaa aatgtcatgg gataaatatg aaatagttta tgaagtagcc    4620
tttctggttc agagtgactg gaccaaagtc tgaatcttat ctgggtatca ggaaaaagaa    4680
tttttatgga aatccttagt gtctataaac aacccgtgta aaccctgtct acactatgcc    4740
aaaaccagtg gaaagatggg tagagtcatc ttatctcagg atgtcaaaaa tctgggtttg    4800
actgattccc ctaccttccc acacagtata ttcttgtgat ttttgctttt ctgtagatcc    4860
tgagtcggtg ttacaatagt catgttttta ttttgggtta agaaatacga ggtgtaagag    4920
ctataatttc cttttcgtgt tatatcatga tctgggtttt cttttttcct ttacgttttt    4980
cacagctctt gagtattttc tatttttttc tttagtcaca aaaattaaaa ttaaactttta    5040 ttttatgaa ttaaaatgaa atttaattta tttttatgaa ttaaaattgt ggccagtatc    5100
cactgtgtcc ttaggctgag aagtactaat ttggagtagc ccgtgtgtgg aattctaaag    5160
```

```
tgaaggtact gtggattcat ttttagtagt tttagcccct taataagtgg ctaagttaga    5220
aaactttcag cgaggtaata gaaccacttg aatagaatcc atgtgtcttt ttctgaattg    5280
gtgaaaattc ggccactgat ccagtgactc ctggtcaaac gtcttataac attactggcc    5340
ataatgcatc cctttatctc atggaaatgg ctgaactttg tggtagctgc tgcgagtacc    5400
tgggcttaac agtaatagag aacctcattt ataccataca gacacagcaa cttaggaaga    5460
cagcactgat agcatttagc tagttgtaac caaatacaaa tatgtaaaat tgagaattat    5520
gattaacata tgcaacttta gtaataggaa tagatgataa ttttcctgta ttgtttcaaa    5580
taagtgactg ttcagctggg atccattgga ttataattta caatgtcaca taatattatg    5640
cttttcaata ttgatgagtg atgtaaacaa tataaagttg gcagtttgta gtagttcagt    5700
atcctagaaa tacattgaac ttcataagta tcagttcatt tttaagcata cagaattgaa    5760
gattctgact gaaatcataa actcagagga aacaagccca tctttatcac taattactta    5820
gcttgaatac ttttctattt ttaaataatc ctaattattg ccttttcaat tatagtctac    5880
tgtatttatt tatatgggat caacaggtat ttatcaaaca tctactgtgt gcccagcact    5940
acctagtact gttggggaac atcaatttgc agttgtggtc tctgcccttg aaggtatctt    6000
ctccaggaaa ttagcagtat tattttcact tctaagcaaa catgagcaaa agaggacctg    6060
ttcattaaaa aacatgctga ctttttttagt ttcaactgag atatgccact gtagaagtga    6120
aagtaatttc acaattaaag aaatgcttca acttggtaat taatatggtc atacagggac    6180
ttggtgtagc atgcaaggaa gcagaagacc tgggcttttg tcgaagttct gccatttagg    6240
tatcagctgt gtaaccttga ataagtcact taactctttc tcttagtttt ctcatttgta    6300
aatttggatt aaagtgttta ttatgataat caattaagaa aatctcttaa cacttcatac    6360
atacagagaa cttatcatta agttaaaact ggcaattaat gcacctttat atatatttt    6420 aaatgaaaac taatactatt catgatgttt attttatatc aaatatatgc ccagggcatg    6480
ctactttaaa aatccgagga atctccaaca aggtgctgga ttaaaatcag atttcgtgct    6540
tgaagtggaa gaaaatgaa gttgtttatg gataagagag tgagaatgtg tatcctcaag    6600
tacgttaaga tgatttaact gaaagatggc tttaggtttt tcttgaagaa ttaggaaagt    6660
accatcccca cagattcagc atactcttca ggtactagat aaaggtgaag gaagtcatgg    6720
aattaaaatg acttagcaac tccccaggga acttgtgggg agaatgaggt ggttagaaag    6780
gtgagaatgc acaaagacag ctctgggttg ggtaccaaca gtttgcttgg tagaagaaa    6840 ccagtgtagg aaaggagacg ccaccagaca tcttcaacag acaagattct ttctgccttt    6900
ttcaaaagat gctctctgca gcagtaagac tatagataga gttgattgga atatcatgtg    6960
acccagtatg ctactgctag gcataattat caaaaattca ttttttctcat taaatattgt    7020 taattgctcg ccacataaag agaagctaga gctcaccagt cttggtggtg tcctagacct    7080
tcctctaaag cagtcttggg aagctggatc atcagatctt tagcctagac agagtgtcgc    7140
tggtaaataa aggagacaca ggtaacccag agtggacagt gatttgcgtg gggagacaca    7200
gtggatctgg ggcctctgat actttgcttc ctaaaacagc ccccagtttt cggcttgccc    7260
tatgagatga tgttcatgtg cttccttgaa accaggtgga agaaagggg aagaattaat    7320 tttctcattc tgttgctgtt gaacgtaatg taatcttaat actgtagcct tcctagaagc    7380
ccttccctct ttttcatgct gtaaagtcaa atatttgata tccttaacat aaatttttaaa    7440 aattaaggtc attaggaagc aaatgtctat ttccaaagca atgagcttgt tgtgactgtg    7500
```

-continued

| | | | | |
|---|---|---|---|---|
| attttattct | tctatagtat | ttttttcctc | attttaactg | agaggagaaa ataatactct | 7560 |
| tttgcaatat | ccttaggttc | tccccttccc | cctggtgccc | cttctagtgt cttaagactt | 7620 |
| tgtcttaaca | agtataacat | tacattttgt | tgttaaaacc | tttcgaaact gtattcagtg | 7680 |
| attcttccaa | gtttatctgc | tctgcactat | ttcactaata | aaccctggct accacgtagc | 7740 |
| ccttgatctc | caagtagttt | acctatgcaa | gacctgtgac | actctgaatt cacttctctt | 7800 |
| tctttcagaa | agtagtcata | aatggagctt | aattataaag | gtaaaacttg tctccaacca | 7860 |
| gtttcatttt | ggccatttct | ttttcaaaat | gtcagctgtt | ttcctccaag attttccacc | 7920 |
| aaaacaatga | tcataagtgc | tggaatatat | aatactttgc | aggcataaaa taacccagac | 7980 |
| atactctcat | atttctttgg | tgtattttgg | ttggtaaaac | ttaccagcat taaatgtaaa | 8040 |
| atataatgag | gagttaattc | cttacctaga | actatttctt | ccttttaaga ttcataagta | 8100 |
| acctttattt | tttacagagc | tacgtataac | ttccacatta | cagtcaggga cctgaggtgt | 8160 |
| aacttactaa | gtgaaccccaa | aggttatttt | atcttgcaaa | agaaacctaa accaaactaa | 8220 |
| gggccttaca | gtttatggtt | agactgaatc | aaaagctata | acctcaatttt ttccaaaaac | 8280 |
| agcttctgac | tgcaaaagca | agtcatacag | ttgttaggta | tgaaatagca ctgatcagga | 8340 |
| aatgcatctt | cgcagatggt | atttccttca | gaaaagactt | ttctactttt aatataaatt | 8400 |
| aagccataac | agtttcatgc | tgtggaaaga | gggtgaaaag | gttcatttta agagattata | 8460 |
| taatatgaac | tttcacattt | actgtgaaat | gtctaacttt | gccagtgctt cagcaagttt | 8520 |
| ttttggggggg | tgatggggag | gggtagtatt | ggttttagag | gtttcaaatc tgtgaacttt | 8580 |
| ggagagggga | cagttgttgg | ctctggtatt | tactagtttt | gtagtaacgt tttgctagcc | 8640 |
| tgactgactt | ttcttactgg | tttttatgcc | cacggtccga | ggggactgtt cttcttgttg | 8700 |
| ggggtgtctg | cggaatagcg | tctcgtcttg | tttgtatagg | cagtcaatgt gtgtgacatg | 8760 |
| tgtgtccttt | cagtccggaa | gcccactgtg | tgacaatggc | gtggggtgtg ctgggaggt | 8820 |
| ggggtgctga | agcttgaaga | gcatttcttt | gctgattcat | aacagtattt cccatctttt | 8880 |
| gcctgcaggc | agggaaagtg | tacagtattt | attttgtttc | tgttttactt taaatttgta | 8940 |
| agtcttaag | tagcttacat | tgattattat | aggggaggac | aagtgacttg tttaaagttg | 9000 |
| tatttagtat | tcttttccaat | ttctgtattt | taaaatattg | aaattaaaat tgtattactt | 9060 |
| ctgttttgat | tttttttagca | cttagtgtat | ttttttgctca | ttttgtttga aagtataaat | 9120 |
| gttgaaaatt | gtataaaatg | cgtccttgaa | agaaaaagaa | tctgaattct atatccaa | 9178 |

<210> SEQ ID NO 42
<211> LENGTH: 8433
<212> TYPE: DNA
<213> ORGANISM: Homo sapiens

<400> SEQUENCE: 42

| | | | | |
|---|---|---|---|---|
| agagaagcga | tcgcgagaga | aaaaaatgca | acctcccaaa | ataaagagca aagattgcat | 60 |
| taggagcgaa | cagcgctgca | gaaatagatg | gcagcttcgt | gtcagtgagt ttgcatcccc | 120 |
| cttcctgatc | cacgagctgg | agtgattaga | gccctggaag | ggaattgtta ctcccgtgga | 180 |
| gaagtcccct | tttcctggca | gtcgtctgca | ctgtacacgc | tggatgcctc tctccatcca | 240 |
| ccccactcac | tcgctcctct | ctcacctcct | ctctccctct | cctgcattga ttttttttttt | 300 |
| tccttttag | ttgactgaaa | caaaacaaaa | caaaagggcc | actggatgtc tgccttcttg | 360 |
| gggggtgagc | cagacagact | gacaaacaaa | cagccccaac | tgtgttcggg ggagggtttc | 420 |
| gcctcccgtt | ttgcccggca | gcagcagcat | ggacgtgttg | gctagttata gtatattcca | 480 |

```
ggagctacaa cttgtccacg acaccggcta cttctcagct ttaccatccc tggaggagac    540
ctggcagcag acatgccttg aattggaacg ctacctacag acggagcccc ggaggatctc    600
agagaccttt ggtgaggact tggactgttt cctccacgct tcccctcccc cgtgcattga    660
ggaaagcttc cgtcgcttag accccctgct gctccccgtg aagcggcca tctgtgagaa    720 gagctcggca gtggacatct tgctctctcg ggacaagttg ctatctgaga cctgcctcag    780
cctccagccg gccagctctt ctctagacag ctacacagcc gtcaaccagg cccagctcaa    840
cgcagtgacc tcattaacgc ccccatcgtc ccctgagctc agccgccatc tggtcaaaac    900
ctcacaaact ctctctgccg tggatggcac ggtgacgttg aaactggtgg ccaagaaggc    960
tgctctcagc tccgtaaagg tgggaggggt cgcaacagct gcagcagccg tgacggctgc   1020
gggggccgtt aagagtggac agagcgacag tgaccaagga gggctagggg ctgaagcatg   1080
tcccgaaaac aagaagaggg ttcaccgctg tcagtttaac gggtgccgga agtttatac    1140 aaaaagctcc cacttaaagg cccaccagag gactcacaca ggtgagaagc cttataagtg   1200
ctcatgggag ggatgtgagt ggcgttttgc acgaagcgat gagctcacga ggcactacag   1260
gaaacacaca ggtgcaaagc ccttcaaatg caaccactgc gacaggtgtt tttccaggtc   1320
tgaccatctt gccctccaca tgaagagaca tatctaaaaa accgaaaggc cagagttgcc   1380
atggcatcgg ctagtgtcta aaggaaacgc catgaggcag ggggctggac ttcaggcggg   1440
gacccattgc ctcgcagaag aaagttctca cttataaacc tctgtacaca cacacacaca   1500
cacacacata tacacacact cacagaccca cacacataca cactgtcatg cactcaacta   1560
tatttaaaat atatacgtct attctttatg ccttgcccta gccagatgga agaagatgaa   1620
gaaggaaacc aggtgaactc agcaaggcag actggctgct tacttcagca ctattggaat   1680
tatttcccgc tgttgccaat ggaaatcaaa gaaaatggat gtgacgtctg tgcaggtgga   1740
cggcagtccg aggggcttat ttcacttgct tctcagtgca acttgatagg agaatccagc   1800
atcttaaagt tgcatatgtg tagcactaat gttcttttt aaatagttgg gggaaaatga   1860
cctagaaaac caaattgcag tttggtagcc aaaattaact cttggtttat ttgtcctttg   1920
tgtgtgaaaa gtcctactat tccgtgcgtc agacttcctc acagaactgt tgactggttt   1980
tggttcttag tactattgag atctttcgcg tcgatcccaa cggccttagc ggcggcagac   2040
tggaataaca ccttacacct ttctggcctg catttctgta gacttcactc tcaagggagg   2100
agttttcttt tcttacgttt tgacttttgc acaccatatg cactagggat tctggaaact   2160
tctagcatga ctgcaaagtg gccaagagaa taaagtcctt gatgataaat cacagtatat   2220
cccttgagcc tcaccttatt gccagtgcta gatttttct ttttaatctc tccgttttg    2280 ctaacgaaaa cttgaaaagc ttatttggaa gcttaaatgt tttatctttt ctccatggac   2340
taaacctctc caggactctc tcggcacctg gatgtccagc tctcgaagca gccagtcaga   2400
tgggacatca cagttctctc atcctccttg aggcatgatg acctcagctc atagtgatca   2460
accgttgtgc tgtgtgtcat tgctaccca taaccagtta cagcatagat gtcgctagtc     2520
tcagagggca gctgcgtatt taatttaact ctggtttatg acctgacaaa agccaaaaa    2580 tatcactctt tccaggagtg gggaaaactg aggatgcctc ccaagtctag tggcttcaca   2640
aaagatcatc ctgtcttctc tgtcatgccc actgagctcc tattcccta cgtgttacaa    2700 tacacaattt aaaacgccat gtgggagtg aagggttgac attaaggaa aaggttgagg     2760 tgtttctctc atgggctgtc taaaaggaga gacacgtttc tttctttcct ttttttttg    2820
```

```
gctaggccca ccatgacttg tgacctagaa cccccaggat taacagaggc ctcacattta    2880
ctctgcaagc tgactccaaa ggagtctaca gtccttactt gtcatgccac actcacacat    2940
ccagtagtgg tctctatcta cccgcattcc tagctagctg gcactggcct caactccaaa    3000
gactgccttt aggaccatca aatggcctat gcaagcaagc ggggtggtta ttaggacaga    3060
ttgtatattt tgtatattct gggaccatcc cttcaagaca cgtctataaa acaaaaatgg    3120
cgcttggtcc acacacggtt gctgctccct cctaccagct ggctcccctc ctgtcctcct    3180
ttgactgttt gactcattga ctgttaaaat gccacccccat acatatttgg gatgcaaaac    3240
tgaagtcaaa aggaaataat ataagaaaca caaacacata tatgcacagca accttcaaga    3300
tctgggtttt cagcttctctg caaccttgt tttcactgaa atgttgaaac tactcgtctg    3360
agggcaaagg aacctcctca caaatgctat agctgccaat tggacacttg ggcatttcg     3420
aggtctggcc ctaagaattt actttctcct tttcctttt tctatttaga ccaaaaaaaa     3480
caaaaacaaa aacaaaaaaa aaacaaaat aatacaaaac gaaaaaaaaa gaaagaacac     3540
ccgttaacac acacgcgcac acacacacaa atctgtcca tttgccggag gcaattgtat      3600
gtatgttagt tggagggtat taaaaatcag ttttattcca aagatttaaa actagacatg    3660
acttaaaaac aatttctgga gcactgcttg ctgacaatct cgtagttctc tgctgcattt    3720
gagtgcattt tgtggccagt ccatcagggc gtaccatggg attatatttg aatgtgtggt    3780
gcatccttcc tggatgaagg atgtgtgagg gaccttgaac ctcagctgta ttaaactgta    3840
gcgcctccag tcagtgcact agatgaaact tttagacacc ctgaattctg ttggttcctt    3900
tcttttcctt tatgtagcag cctccagcat gaatgcacgc acacgccagt gatggcatta    3960
agccatggcc accacgattt gcaaatgttc tctcccaagc tggagctgct cttgcctctc    4020
gaatgctatt attaagggtt tataatactt aatttaattt tcgaactgac caatgcaagg    4080
ctctattaaa aagaaagttt aaaaaatgca aaagagtaat cattgcttgt ttgctcccta    4140
ttttcatctg tggtctcatt tgaatgtggc agaacaaagg ccctttggtc ctcatcagtg    4200
tctgaaatgt tcagtaattt ctctctcttt tgtatcagtg aggtcctttg taatctgctc    4260
ctgacctttc ttggagcagg gtgcattgaa actcaatggt ggtgcttgct tgcttcagag    4320
tcatttgttg actgtgagaa ttggcctaag aatttggtgg gtgctaagtg gatggctttg    4380
aaactgttct tctttagccg agttgacacc tgtgaatgat gaccagtcct gatcattttg    4440
gaaatggatt tgtaataaaa cgtccatcac ctctgcagtg gcagagatgg ttactaagag    4500
ccgctagagc gagcaggttt tccaagaagt aacctgaaga cattttgctc ccaagaggac    4560
tggttattta aaacagtgca ttaatggaca tttgaaacac attaaacccc tttctcattt    4620
cagttgttac ctcctaaccc tccaggggat cccaaatttg aaaggaaaaa cccggcctgg    4680
tgtttctggt ggtgtcctaa caagcacgct tttatccagg gttcagattt gttcatgtag    4740
aaaaagagtt tctaagccac tgacaatttt tttttttgt aatttcaaat tatacttctt    4800
tctcctgcca catgactgta agtcatagac atggaaacct gaaattataa tgctgctcct    4860
agctactggc ctcctgcccc acccatggtt aatggctcag ctcaatgcct ggtggtaatg    4920
agtattatgt ccagaaaaag agatgttcag attccatgac aaagctgcat ttttgtaaaa    4980
atattggaga ccccaaaatg aacttcatgc tgaccatttc ctcctctctg tgtgctttcc    5040
cttgcaaagc ccttcaaata tcctcttctc tcgacgccat ctcctctcca cctgcacctc    5100
ttgtgccctt tgtacatctt tgattgcctg atgataacag ggtaaaagga cagccaacct    5160
catgcctgat tagcagaact gaatcctagt tttaaaaaat cttctctggc ttcagagaag    5220
```

```
attttataag gacttttgtt tgggataagc tttccagatt atccatgtct atttgcatca   5280
aaggggaaag aaatggggct tttggatggc tcttccagtg cattcggaac attgcctctt   5340
gcctttattc ctgcatttta tggcaaagcc aaaagaaact caagttgcaa gaacaaaacc   5400
cagtgactcg ttttgatggt tcaaaatggt ttcctttatg gaagtcactt cataaaatgt   5460
taagtaaaaa gtgggaagtg cttctgtctt ctcttttgca tgagttgctt ttaggagcag   5520
gaagaaggta ggcaaagtaa gataaagatg caacacattt aactacaaaa atcaggttca   5580 tttttttagtt tattagaatt ttttttgaaat cttaagaggg ccagcatttc tggctacaat   5640
tttgcaccca gaacattgcc aaaatgaaca ttcagtaaat agaacctgat tgaaatttac   5700
tcctggaagc tttcctttgc attttcggga agtggccacc tgccaagcgc aagagttggg   5760
gggcaggagg ggaggactca aattcagggt gtctggatta aatttcggtg aacatggtga   5820
tatctcagtt tgaaaactag agggcctatc ctgagtatac atcaatgtct ctttgatggc   5880
ctactttcct cagtgaggat ctttgggaat acttgagatg gaacaacaga aatgtgtgaa   5940
aggaagcaga aacttcttgt aaataacgtg acctcccacg acgaactgcc tgaggcttca   6000
gggttttttc ttgcttttaa cactcttaaa tctcctctgt tggttcctaa tagatcccag   6060
aaaagggaaa aataaagctg cagttaactt tcttatgtgc atccttccaa tagagtactg   6120 tattttttcag gtgttttgca tttaacataa aagtcctcgg gaaacaggtg tcaaaaacag   6180
agagagaaat cctgggccat cacttcacaa atatcccaaa caagatattc ttttcaaaca   6240
gggctccctc tcagtggtca tgagggaagg ttgataatgt tctttgttgg ggactgttta   6300 tacaatttt ttcaactgt gagctttgga atcgtaactt gctgtgagtc cagcttctgt   6360
ctactgccat aagatggacc ccacgtcagc ataatgaggg tggtatatat gctcgcacct   6420
agacatgcgc atatgtacct gtcgtacctt cacggaagga aaacaggcta ctgacgtttc   6480
ggaggagtag ccaccagtgc ctaatatctt ttgggggga tggatgctta taattgccag   6540
tatatcgaaa ccacactggg agttccacat agcggggagg ggttgggggt gggcagaggg   6600
gacattttaa acctaggcct ttggactgga ggcagaacga tttctgcaaa cctaggtcct   6660
gaaggctttg gggcttattg gctggttctc aacctttttg ttttttcttc ccagcatgca   6720 ttcctatct aaacccagac ttagtttaat ttccttatct ttcacttctg cttcattcca   6780
gggaggaaaa atacacctgt taatggccaa gatctccttg ctaacacaga ggcaaaaata   6840
aatgtctaat gttttgaag cctccccttc ctttccacaa gccccaccc gccccgcgt   6900 caagctcctt ctcccacttc ctactcccac acaacttccc agccactgaa acttttcttt   6960
caaatctcta ttatcctctt aacagttgct tgaataaatt tattttgca ctatacattt   7020 tcttttttgcc agatgtgtct aacaagtgtg tttggagaga cctactccca gccccgtctc   7080
cttccccgcc tccccccgtc acattctctc aggccttctc tggtatttat aatatatcac   7140
agaagtaccc agtcttatag ccctcggtta tgccttttt tgacatttta ttttttttaa   7200 gcttttata tatatatata taaaatata ttactttgtc aagttttttt gctgtacaaa   7260
agtcttaaga tttaaaacta ttatttgtat tatatgatgg tggtatgtta atgttacaaa   7320
attattaatg aagaaaaaat ttattttgt tactggtctg tttcataatt cttttttaaa   7380
ttggtatatt gtaagatatc tatgcaaaaa atgttatgtg acgcattttt atttaagaat   7440
gtaatatgtg taataaacag tagaatgtgt ttggccttgg aatactttac tgtatttctc   7500
cttagcttgt ttcactgggg aaaaaaatct tcgaaagacg caagtgggta cttacatact   7560
```

-continued

| | |
|---|---|
| tcgtgaaagt tttctttctt ggagaaaggg aaagcaaaag gttgtattag gttatcttcg | 7620 |
| tttgggaagt tgtgtgtgtg tgtgcgtatg tgtgtatttt atagtttcat tgaggcagct | 7680 |
| caatgcccaa ataagggtca ctgagtttat ttcttcaagg ggaaaaggg agccaattgt | 7740 |
| tggagattat gaaaagcaat attttagaat gatagagatt acaagatgtt atttgtttag | 7800 |
| ggggttggga gaggcttatt gaaagcggtt tatttggcga gagaaggagg cagtttgttc | 7860 |
| tgggatggtg tttaatagga acctattggg aaaggatctt tgaagcagtc tgtgaaggag | 7920 |
| gaagggtaaa gatcagaggg aataatttag gtgagggta ggggcagta aaatgacagg | 7980 |
| aggtggttgg agtggggagg aaatgggtaa ccggaagcca ggaaatccag ctggctgtgg | 8040 |
| agagtacaaa aaactagatg gaaatacaag cagcttcaga cccagagaag agagggagat | 8100 |
| gaaagcccca gggaaaattc tcagaactga aaagaaaagt actaaaatct ctgccacaca | 8160 |
| cgacttccag gaaagagcat caccagtaag gaggaaggta gagaacccag ctggtggtgt | 8220 |
| cgcctcagca tcccgagctc agcgattccc cgagagaagt ggtgtcattc acaggaaaca | 8280 |
| gcagtaaaac acatttgtca catgggacac agcagtagtc aagctttctt tgcattcttt | 8340 |
| ggacttacag aagtggatac ggtggtgaat aacctctatc cctaatcaaa tgaatctgac | 8400 |
| aagaaacttt ccaataaatg tttactttag aaa | 8433 |

<210> SEQ ID NO 43
<211> LENGTH: 5208
<212> TYPE: DNA
<213> ORGANISM: Homo sapiens

<400> SEQUENCE: 43

| | |
|---|---|
| cttactcatt tgtgtttatt cttggactta tcctgacata atgggttttt tttaattata | 60 |
| gattcacact gcatttattc atcacccctg tcctctcatc cataactcaa atttactacc | 120 |
| agcaacacaa aatacaaaga tgtgtccagt ttcactacag ctcttcgcgt ttacaagtgt | 180 |
| cgagcgcttg ctttcggaac gcccttgtga ttggccgagc caatgccagt gacatcaacc | 240 |
| aacttacttt tgattggaag gctggttgct gggactgtag cgtttgcagg aagtcactta | 300 |
| actgtttggg agctggaaaa ccgaagctga agttctcttt tgccatagga acgagcgcaa | 360 |
| ctgactagga aagatgtgtc ccaaagctcc gcaagctgga acgtgagcca ggaggcccgg | 420 |
| accggccacg ggaccgcgag gcactccgaa agtgtgcggc tgccccttcc ctgcctccca | 480 |
| gctgttaccc ttttaaatgt cagtgttcga ggctgtaggg gtagcacgag gcagcgaaac | 540 |
| ggaacagtcg gattggccgc acgcctcagt tctagacgca cctctccacc gaaggccgtt | 600 |
| ctgactggca gggggagaaa gtaaacagag ttgaatcacc ctccccactg gccaattgga | 660 |
| gggggtttgg tttgtgacgt gatgggattc tgcgaaattg ttactgagca agagaatgcc | 720 |
| ggaacggtgc ggaccggccg gagcagggt tcagaagccg tcagtggact cgggaaaaag | 780 |
| tgtctcttag acctgcgct cggcgggacc ctcgccaccc gcgtcgggt gatcgggtga | 840 |
| atgtcctggg gctttggctc gacggcgagg cggccgaggg cgtgcacctc tcttgcagtt | 900 |
| tcctctccca gcgcctcggg ggcgttttca gtcgaataaa cttgcgaccg ccacgtgtgg | 960 |
| catctttcca agggagccgg ctcagagggg ccggcgcgcc cgtcggggga tcgcggccgg | 1020 |
| cgcggggcag gggcggcggc tagaggcggc ggcgcggcgg agcccggggc cgtggatgct | 1080 |
| gcgtgcggag gcgctgccgg ttacgtaaag atgaggggct gaggtcgcct cggcgctcct | 1140 |
| gcgagtcgga agcgccccgc gccccgcccc ccttggccgc cgcgccgtgc cgcgccgcgc | 1200 |
| cgcgctcgtc gtccgaggcc agggcagggc gagccgaacc tccgcagcca ccgccaagtt | 1260 |

-continued

```
tgtccgcgcc gcctgggctg ccgtcgcccg caccatgtcc gcggccgcct acatggactt    1320
cgtggctgcc cagtgtctgg tttccatttc gaaccgcgct gcggtgccgg agcatggggt    1380
cgctccggac gccgagcggc tgcgactacc tgagcgcgag gtgaccaagg agcacggtga    1440
cccgggggac acctggaagg attactgcac actggtcacc atcgccaaga gcttgttgga    1500
cctgaacaag taccgaccca tccagacccc ctccgtgtgc agcgacagtc tggaaagtcc    1560
agatgaggat atgggatccg acagcgacgt gaccaccgaa tctgggtcga gtccttccca    1620
cagcccggag gagagacagg atcctggcag cgcgcccagc ccgctctccc tcctccatcc    1680
tggagtggct gcgaagggga aacacgcctc cgaaaagagg cacaagtgcc ctacagtggg    1740
ctgtgggaaa gtctatggaa atcctccca tctcaaagcc cattacagag tgcatacagg     1800
tgaacggccc tttccctgca cgtggccaga ctgccttaaa aagttctccc gctcagacga    1860
gctgacccgc cactaccgga cccacactgg ggaaaagcag ttccgctgtc cgctgtgtga    1920
gaagcgcttc atgaggagtg accacctcac aaagcacgcc cggcggcaca ccgagttcca    1980
ccccagcatg atcaagcgat cgaaaaaggc gctggccaac gctttgtgag gtgctgcccg    2040
tggaagccag ggaggggatgg accccgaaag gacaaaagta ctcccaggaa acagacgcgt    2100
gaaaactgag ccccagaaga ggcacacttg acggcacagg aagtcactgc tctttggtca    2160
atattctgat tttcctctcc ctgcattgtt tttaaaaagc acattgtagc ctaagatcaa    2220
agtcaacaac actcggtccc cttgaagagg caactctctg aacccgtctc tgactgttgg    2280
agggaaggca aatgcttttg ggttttttgg ttttttgttt tgttttttt tctccttta     2340
ttttttgcg gggagggta gggagtgggt gggggggagg ggggtaaggc caagactggg     2400
gtagaatttt aaagattcaa cactggtgta catatgtccg ctgggtgagt tgacctgtgg    2460
cctcgcacag tgattctggg cccttatgc ttgctgtctc tcagaattgt tttcttacct    2520
tttaatgtaa tgacgagtgt gcttcagttt gtttagcaaa accactctct tgaatcacgt    2580
taacttttga gattaaaaaa aaaaacgcca tagcacagct gtcttatgc aagcaagagc    2640
acatctactc cagcatgatc tgtcatctaa agacttgaaa acaaaaaaca gttacttata    2700
gtcaatgggt aagcagagtc tgaatttata ctaatcaaga caaaccttg aaaggttaca    2760
ctaagtacag aactttttaaa ccttgctttg tatgagttgt acttttgaa cataagctgc    2820
acttttattt tctaatgcag aggatgaata agttaaatac atgctttgag gatagaagca    2880
gatgttctgt ttggcaccac gttataatct gcttattta caatatacac gtttccctaa     2940
gaaatcatgg cagagatgtg agggcagaat atacacaaca gatgctgaag gagaaggagg    3000
gtagtgtttt gcaaaagaaa aagaaaagaa ccaacagaat tttaactcta ttaactttc    3060
caaatttttcc tatgctttta gttaacatca ttattgtatc ctaatgccac tagggagag    3120
agcttttgac tctgttgggt tttatttgaa tgtgtgcata acagtaatga gatctggaaa    3180
cacctatttt ttgggggaaaa aggtttgttg gtctccttcc tgtgttccta caaaactccc    3240
actctcaggt gcaagagtta tgtagaagga aagggagctg aaataggaac agaaaaatca    3300
accccctataa ctagtgaaca ccaagggaaa ataccacaat gatttcagag gagactctgc    3360
aaaatcgtcc cttgtggaga atgcaggcaa catggaatac taggaatgaa atcacatcac    3420
tgtatctttt acatcaatag cctcaccact aatatatctt gtatctaggt gtctataatg    3480
gctgaaacca ctcatccat ctatgccatt tacctgaaaa cttaactgtg gcctttatga     3540
ggccagaaaa gtgaactgag tttcgtagt taagacctca aatgagggga gtcagcagtg     3600
```

| | |
|---|---|
| atcatggggg aaatgtttac atttttttt tcttcagaag taacgctttc tgatgatttt | 3660 |
| atctgatatt taaaacaggg agctatggtg cactctagtt tatacttgcg ctctgaaatg | 3720 |
| tgtaaacata gggtgcctac ctatttcacc tgacccatac tcgtttctga ttcagaatca | 3780 |
| gtgtgggctc ctgcagtggg cgcgggtcac ggctgactcc aacttccaat acaacagcca | 3840 |
| tcactagcac agtgtttttt tgtttaacca acgtagttgt attagtagtt ctataaagag | 3900 |
| aactgctttt aacattaggg actgggagca gtccatggga taaaaaggaa agtgttttct | 3960 |
| cacgagaaaa catgtcagga aaaataaaga acactttcta cctctgtttc agattttttga | 4020 |
| aacacttatt ttaaaccaaa ttttaatttc tgtgtccaaa ataagtttta aggacatctg | 4080 |
| ttcttccata cgaaataggt taggctgcct atttctcact gagctcatgg aatggttctg | 4140 |
| cttatgatac tctgcacgct gccttttagt gagtgaggag tttggggttg cctagcaact | 4200 |
| tgctaacttg taaaaagtca tctttccctc acagaaagaa acgaaagaaa gcaaagcaaa | 4260 |
| gtcagtgaaa gacaatcttt atagtttcag gagtaaatct aaatgtggct tttgtcaagc | 4320 |
| acttagatgg atataaatgc agcaacttgt tttaaaaaaa tgcacaattt acttcccaaa | 4380 |
| aaagttgtta cttgcctttt caagttgttg acaaacacac atttgatatt ctcttatatg | 4440 |
| ttatagtaat gtaacgtata aactcaagcc ttttttattct ttgtgattaa atcctgtttt | 4500 |
| aaaatgtcac aaaacaggaa ccagcattct aattagattt actatatcaa gatatggttc | 4560 |
| aaataggact actagagttc attgaacact aaaactatga aacaattact ttttatatta | 4620 |
| aaaagaccat ggatttaact tatgaaaatc caaatgcagg atagtaattt ttgtttactt | 4680 |
| ttttaaccaa actgaatttt tgaaagacta ttgcaggtgt ttaaaaagaa agaaaagttg | 4740 |
| ttttatctaa tactgtaagt agttgtcata ttctggaaaa tttaatagtt ttagagttaa | 4800 |
| gatatctcct ctctttggtt agggaagaag aaagcccttc accattgtgg aatgatgccc | 4860 |
| tggctttaag gtttagctcc acatcatgct tctcttgaga attctatttg gtagttacaa | 4920 |
| ttacagaaac tgattagttt gtcagtttgc agatagattt agcacagtac tcatcactcg | 4980 |
| gatagattga gatgttcttt cacatcagat gatctgtaac actgtaagat actgatcttt | 5040 |
| acaactgttt aatcagtttt attttttgtac agtattagtg acctaagtta ttttgctgtc | 5100 |
| ccgttttttgt aaatcaaatg aaattataaa agaggattct gacagtaggt attttgtaca | 5160 |
| tatgtatata tgttgtccaa ataaaaataa taaatgataa agactgaa | 5208 |

<210> SEQ ID NO 44
<211> LENGTH: 2383
<212> TYPE: DNA
<213> ORGANISM: Homo sapiens

<400> SEQUENCE: 44

| | |
|---|---|
| cgggtcggtg acgtcaccgc atgactgggt ttttatgaat gaaaggaatc ctgtgagtga | 60 |
| gtaattccgg gaagctcgcc ttacaactcc gcgcggcctc ggcccccctgc gccgcccgcc | 120 |
| ccacaacaaa actcagcgca gcgctcccgg gcgcccggtt cagagcgacc tgcggctcag | 180 |
| agcggagggg agactgaccg gagcgcggat cgggacagcg gccgggacag cggcgagacg | 240 |
| cgcgtgtgtg agcgcgccgg accaagcggg cccagaagcg gatcaagcga gagctgagcg | 300 |
| agaacacgcc gcacctgtcg gacgaggcgc tgatggggct gtcggtgcgc gagctgaacc | 360 |
| ggcatctgcg cgggctctcc gccgaggagg tgacacggct caagcagcgg cgccgcacac | 420 |
| tcaaaaaccg tggctacgcc gccagctgcc gcgtgaagcg cgtgtgccag aaggaggagc | 480 |
| tgcagaagca gaagtcggag ctggagcgcg aggtggacaa gctggcgcgc gagaacgccg | 540 |

-continued

```
ccatgcgcct ggagctcgac gcgctgcgcg gcaagtgcga ggcgctgcag ggcttcgcgc      600
gctccgtggc cgccgcccgc gggcccgcca cgctcgtggc gccggccagc gtcatcacca      660
tcgtcaagtc cacccccggc tcggggtctg gccccgccca cggcccggac ccgcccacg       720 gcccggcctc ctgctcctag tgcccgcccc cgccatgcct cagccacgcc cctccggcct      780
cagctccctc cccaaagtgc ctgagcgccg cctctgtgcc caggtcccat ttctctgcag      840
cactggcccc ttggtgcaca cacattccct tcgtgggccc tgtcttcctc ttgcagcccc      900
ccaaactggg accgaatgac cctgggaagg ggaacttggg taggttgggg atggggcaga      960
ggtctggatc tgggatcgcc cttggctgaa agtttagcct ttttagattg agagatacag     1020
agccggctta gagaacagct gttggggag aagagggcac ccctcatctt ggaaactgct      1080
cttattgtgc caatatgccc tccaaaccct cccaggattc aaagctaggt ttggctgtct     1140
gtgacttacg ggaccgtcct gctgagaaat tgcactgaag agatgccccc acctctggtt     1200
gggcctgggt gtgcctggcc ttccgaaact aaaagagtgg gtgggaagac tagtgaaacc     1260
cagttcacgg atggggaaac aggcctgagg tcacatttca cttagtggtt gtgttgggac     1320
caaaacctgg gtgtcctcac tgctgccctg agtccagcca tggttttcag ggggacagtg     1380
gacagggact cagaaatgtg gtgggagggc ctccctggct tgggagaccg ctctctgcaa     1440
gggaggggga gagaagcaga gggagagaga aggtgacacg gatggaagag tgggaaggag     1500
ctggcctggc tcagccctag gctgtccctg cagccagggt gtccgggggc tggccagtca     1560
gagaaagggg gccatggact gctgtggcaa tagggagac aaggagacag accctgcagt      1620
cctactacag tctggagtgg ggtcctaaga agaagggtcc cacctcaacc cctgtcagtg     1680
tccactgtgg ggtgggggct gacccctgcc tttgattgtc attctcctgg gaagcccagt     1740
ctcagtccct cccccaacac tgtccacact gcccctcccc actgtttatt tattgcacgg     1800
atctaagtta ttctccccag ccagagcccg agctcctgct ccctgggaaa agtggcgtat     1860
ggccctgagc tgggctttat atttatatc tgcaaataaa tcacatttta tcttatattt      1920
agggaaagcc ggagagcaac aacaaaaaat gtttaagccg ggcgcggtgg ctcacatctg     1980
taatcccagc actttgggag tccaaggagg gggatcgctt gagtccagga gtttgagacc     2040
agcctggaca acatggtgaa acccatctc tacaaaaaat acaaaaatta gccatgcatg      2100
gtggctcatg cctgtagtcc cagctacttg ggaggctgag gcaggaggat cacttaagcc     2160
cagaaggcag aggttgtagt gagctgagat cgcaccactg cactccagcc tgggcaacat     2220
agcaaaatcc tgtctcaaaa aaaaagttaa aaaatattgc ccggctccta gaatttattt     2280
atttcctgac ttacagcaag cgagttatcg tcttctgtat tttgtagact ttctaaataa     2340
agtcaaattc tttcttttc cacagagaat aaaaaaaaaa aaa                        2383
```

<210> SEQ ID NO 45
<211> LENGTH: 2840
<212> TYPE: DNA
<213> ORGANISM: Homo sapiens

<400> SEQUENCE: 45

```
tttttcctgg cactgctgag ccacctgcag ttgcgagagc cgctgggagg gataagaggg       60
aagaggacgc ccggtgaagg ggctccagcc tggcagtttc tgcgtgttag catttctaga      120
atagagtggg tgggaactga cccaagtaaa gtcccagaga ctcgaacact gacgcacagg      180
aaagcctcaa gtgggaggag aaatgcaaat cccctactga tgatggcgtc agcggctttc      240
```

```
tcctagggac tgtgaggggc gcttctgact ttggacttga gcactgcctg ggacctgtgc      300
tgagagagcg ctagcatgtc tcagtggaat caagtccaac agttagaaat caagtttttg      360
gagcaggtgg atcaattcta tgatgacaac tttcccatgg aaattcggca tctgttggcc      420
caatggattg aaaatcaaga ctgggaggca gcttctaaca atgaaaccat ggcaacgatt      480
cttcttcaaa acttgttaat acaactggat gaacagttag gtcgtgtttc caagagaaaa      540
aacctactct tgatacacaa tctaaaaaga attaggaagg tccttcaggg aaaatttcat      600
ggaaatccaa tgcatgtagc tgtggttatt tcaaactgtt aagggaaga gaggagaata      660 ttggctgcag ccaacatgcc tgtccagggg cctctagaga atccttaca aagttcttca      720 gtttcagaaa gacagaggaa tgtggagcac aaagtggctg ccattaaaaa cagtgtgcag      780
atgacagaac aagataccaa atacttagaa gatctgcaag acgaatttga ctacaggtat      840
aaaacaattc agacaatgga tcagagtgac aagaatagtg ccatggtgaa tcaggaagtt      900
ttgacactgc aggaaatgct taacagcctc gatttcaaga gaaaggaggc tctcagtaaa      960
atgacccaaa tcatccatga gacagacctg ttaatgaaca ccatgctcat agaagagctg     1020
caagactgga agcggcggca gcaaatcgcc tgcatcgggg gtccactcca caatgggctc     1080
gaccagcttc agaactgctt tacactattg gcagaaagtc ttttccaact gagaaggcaa     1140
ttggagaaac tagaggagca atctaccaaa atgacatatg aaggtgatcc cattccaatg     1200
caaagaactc acatgctaga aagagtcacc ttcttgatct acaacctttt caagaactca     1260
tttgtggttg agcgacagcc atgtatgcca acccacccte agaggccgtt ggtacttaaa     1320
accctaattc agttcactgt aaaactaagg ctactaataa aattgccaga actaaactat     1380
caggtaaagg ttaaggcatc aattgacaag aatgtttcaa ctctaagcaa ccgaagattt     1440
gtactttgtg aactaatgt caaagccatg tctattgaag aatcttccaa tgggagtctc     1500
tcagtagaat ttcgacattt gcaaccaaag gaaatgaagt ccagtgctgg aggtaaagga     1560
aatgagggct gtcacatggt gactgaagaa cttcattcca taacgtttga aacacagatc     1620
tgcctctatg gcctgaccat agatttggag accagctcat tgcctgtggt gatgatttcc     1680
aatgtcagtc agttacctaa tgcttgggca tccatcattt ggtacaacgt gtcaaccaac     1740
gattcccaga acttggtttt ctttaataat cctccacctg ccacattgag tcaactactg     1800
gaggtgatga ctggcagtt ttcatcgtac gttggtcgtg gtcttaactc agatcaactc     1860
catatgctgg cagagaagct tacagtccaa tctagctaca gtgatggtca cctcacctgg     1920
gccaagttct gcaaggaaca tttacctggt aaatcattta ccttttggac atggcttgaa     1980
gcaatattgg atctaattaa gaaacacatt cttccccttt ggattgatgg gtatgtcatg     2040
ggctttgtta gcaaagagaa ggaacggctg ttgctaaagg ataaaatgcc tggcacctttt     2100 ttattaagat tcagtgaaag ccatctcgga ggaataactt tcacctgggt ggaccattct     2160
gaaagtgggg aagtgagatt ccactctgta gaaccctaca ataaaggccg gttgtctgct     2220
ctgccattcg ctgacatcct gcgagactac aaagttatta tggctgaaaa cattcctgaa     2280
aaccctctga agtacctata tcctgacatt cccaaagaca aagccttcgg taaacactac     2340
agctctcagc cttgcgaagt ttcaagacca acagaaaggg gtgacaaagg ttatgttcct     2400
tctgttttta tccccatctc aacaatccga agtgattcaa cagagccaca ttctccatca     2460
gaccttcttc ccatgtctcc aagtgtgtat gcggtgttga gagaaaacct gagtcccaca     2520
acaattgaaa ctgcaatgaa gtctccttat tctgctgaat gacaggataa actctgacgc     2580
accaagaaag gaagcaaatg aaaaagttta aagactgttc tttgcccaat aaccacattt     2640
```

| | |
|---|---:|
| tatttcttca gctttgtaaa taccaggttc taggaaatgt ttgacatctg aagctctctt | 2700 |
| cacactcccg tggcactcct caattgggag tgttgtgact gaaatgcttg aaaccaaagc | 2760 |
| ttcagataaa cttgcaagat aagacaactt taagaaacca gtgttaataa caatattaac | 2820 |
| agaagaaaaa aaaaaaaaaa | 2840 |

<210> SEQ ID NO 46
<211> LENGTH: 4131
<212> TYPE: DNA
<213> ORGANISM: Homo sapiens

<400> SEQUENCE: 46

| | |
|---|---:|
| ggtgcgcgcc gcggcttggg ggagagttga gcgcttttcc cccctctttt tttttttttt | 60 |
| cctcttcttc ttaaacaaac cacaaacgga tgtgagggaa ggaaggtgtt tcttttactc | 120 |
| ctgagcccag acacctcact ctgttccgtc taagcttgtt ttgctgaaca cttttttttta | 180 |
| aaaaaggaaa aagaaaagga gttgcttgat gtgagagtga aatggacgta agattttatc | 240 |
| cacctccagc ccagcccgcc gctgcgcccg acgctccctg tctgggacct tctccctgcc | 300 |
| tggacccocta ctattgcaac aagtttgacg gtgagaacat gtatatgagc atgacagagc | 360 |
| cgagccagga ctatgtgcca gccagccagt cctaccctgg tccaagcctg gaaagtgaag | 420 |
| acttcaacat tccaccaatt actcctcctt ccctcccaga ccactcgctg gtgcacctga | 480 |
| atgaagttga gtctggttac cattctctgt gtcaccccat gaaccataat ggcctgctac | 540 |
| catttcatcc acaaaacatg gacctccctg aaatcacagt ctccaatatg ctgggccagg | 600 |
| atggaacact gctttctaat tccatttctg tgatgccaga tatacgaaac ccagaaggaa | 660 |
| ctcagtacag ttcccatcct cagatggcag ccatgagacc aaggggccag cctgcagaca | 720 |
| tcaggcagca gccaggaatg atgccacatg ccagctgac taccattaac cagtcacagc | 780 |
| taagtgctca acttggtttg aatatgggag gaagcaatgt tccccacaac tcaccatctc | 840 |
| cacctggaag caagtctgca actccttcac catccagttc agtgcatgaa gatgaaggcg | 900 |
| atgataccte taagatcaat ggtgagagaa gcggcctgc ctctgatatg gggaaaaaac | 960 |
| caaaaactcc caaaaagaag aagaagaagg atcccaatga gccccagaag cctgtgtctg | 1020 |
| cctatgcgtt attctttcgt gatactcagg ccgccatcaa gggccaaaat ccaaacgcta | 1080 |
| cctttggcga agtctctaaa attgtggctt caatgtggga cggtttagga gaagagcaaa | 1140 |
| aacaggtcta taaaagaaa accgaggctg cgaagaagga gtacctgaag caactcgcag | 1200 |
| catacagagc cagccttgta tccaagagct acagtgaacc tgttgacgtg aagacatctc | 1260 |
| aacctcctca gctgatcaat tcgaagccgt cggtgttcca tgggcccagc caggcccact | 1320 |
| cggccctgta cctaagttcc cactatcacc aacaaccggg aatgaatcct cacctaactg | 1380 |
| ccatgcatcc tagtctcccc aggaacatag cccccaagcc gaataaccaa atgccagtga | 1440 |
| ctgtctctat agcaaacatg gctgtgtccc ctcctcctcc cctccagatc agcccgcctc | 1500 |
| ttcaccagca tctcaacatg cagcagcacc agccgctcac catgcagcag cccttggga | 1560 |
| accagctccc catgcaggtc cagtctgcct tacactcacc caccatgcag caaggattta | 1620 |
| ctcttcaacc cgactatcag actattatca atcctacatc tacagctgca caagttgtca | 1680 |
| cccaggcaat ggagtatgtg cgttcggggt gcagaaatcc tccccacaa ccggtggact | 1740 |
| ggaataacga ctactgcagt agtggggca tgcagagga caaagcactg taccttactt | 1800 |
| gagaatctga acacctcttc tttccactga ggaattcagg gaagtgtttt caccatggat | 1860 |

```
tgctttgtac agtcaaggca gttctccatt ttattagaaa atacaagttg ctaagcactt    1920
aggaccattt gagcttgtgg gtcacccact ctggaagaaa tagtcatgct tctttattat    1980 tttttaatc ctttatggac attgtttttc ttcttccctg aaggaaattt ggaccattca     2040
gattttatgt tggttttttg ctgtgaagtg ctgcgctcta gtaactgcct tagcaactgt    2100
agatgtctcg gataaaagtc ctggattttc cattggtttt cataatgggt gtttatatga    2160
aactactaaa gactttttaa atggcttgat gtagcagtca tagcaagttt gtaaatagca    2220
tctatgttac actctcctag agtataaaat gtgaatgttt ttgtagctaa attgtaattg    2280
aaactggctc attccagttt attgatttca caatagggt taaattggca acattcata     2340 tttttacttc attttaaaa caactgactg atagttctat attttcaaaa tatttgaaaa     2400
taaaaagtat tcccaagtga ttttaattta aaacaaatt ggctttgtct cattgatcag     2460
acaaaaagaa actagtatta agggaagcgc aaacacattt attttgtact gcagaaaaat    2520 tgctttttg tatcacttt tgtgtaatgg ttagtaaatg tcatttaagt ccttttatgt      2580
ataaaactgc caaatgctta cctggtattt tattagatgc agaaacagat tggaaacagc    2640
taaattacaa cttttacata tggctctgtc ttattgtttc ttcatactgt gtctgtattt    2700
aatctttttt tatggaacct gttgcgccta tttatgaaat aataaatata ggtgtttgta    2760
agtaaatttg ttagtatttg aaagaggttt ctttgatgtt ttaactttg ctggcaaaaa     2820 aaaattcacg cttggtgtga atactttatt atttagtttt tacagtaaca tgaataaagc    2880
caaacctgct tttcatttag cagcaaatta agtaaccag tccttatttc tgcatttctt     2940
tggttgatgc aaacaaaaaa ctattatatt taagaacttt atttcttcat acgacataac    3000
agaattgccc tccaagtcac acaagctcca agactaaaca acagacagg tcctctgtct     3060 taaaaaggtt acttcttggt tctcagctgg ttctagtcaa ttctgaacca ccacccccg     3120 ccccccgcaa aaaagtaaaa gtcaaaccaa acttcctcaa gctgcatgct tttcacaaaa    3180
tccagaaagc atttaagaat tgaactaggg gctggaagaa gtgaaaggga agcatctaaa    3240
aatgaaaggt gagtaaccag atagcaaaag aaaagggaaa gccatccaaa tttgaaagct    3300
gttgatagaa attgagattc ttgctgtctt ttgtgcctct acaagctact actcattcca    3360
gaattcctgg gtcttccaag aggattctta aggtaccaga gatttgctag ggaaccaaaa    3420
gtgcttgaga atctgcctga gggcttgcat agctttcaca ttaaaaaaag aaaaagctag    3480
cagatttact ccttttttagg ggatcatatc aagaaagtta gtctggttgg aaaccaagag   3540
aatggctgat gtctctttct tggaatatgt gaaataaatt tagcagttta actaaataca    3600
aatatatgca ttgtgtaatc cactcagaat taaacagaca aaaggtatgc ttgctttgga   3660
atgattttag gcattgtaca accttgaatc acttgagcat gtaataacta ataaataatg    3720
cagatccatg tgattattaa aatgactgta gctgagagct ctaattttcc tgtcttgaaa    3780
ctgtataaga actcatgtga ttaagttcac agtttattgt ttgtctgttt agtattttag    3840
aaatatacca gcactactaa ttaactaatg tcttttattt attatattat gataaagtaa    3900
aaatttcact tgcattaagt ctaaactgag aaggtaatta ctgggaggag aatgagcagc    3960
tttgactttg acaggcggtt tgtgcaggaa agcacagtgc cgtgttgttt acagcttttc    4020
tagagcagct gtgcgaccag ggtagagagt gttgaaattc aataccaaat acagtaaaaa    4080
caaatgtaaa taaagaaaaa cacatcatca ataaaactgt tattatgcgt g             4131

<210> SEQ ID NO 47
<211> LENGTH: 2417
```

<212> TYPE: DNA
<213> ORGANISM: Homo sapiens

<400> SEQUENCE: 47

| | |
|---|---|
| gcagcagaga ggagttgagg gcgatgagag cgggtactgc gaactgccgg gcgatgctgt | 60 |
| cgctgccgcc gtgatacgga gagcaacagt tccccagcaa cacccctccc cgacacaggc | 120 |
| acacaccccc cgacaggcac gcacacccac cccacagtgc ccggctcggc tgcgcctcct | 180 |
| ctattggccc aggaagccca cccagccccg ccacgcagag cccagaagga aagaaagcct | 240 |
| catgcctgag ccgaggggag caccatggat ctgacaaaaa tgggcatgat ccagctgcag | 300 |
| aaccctagcc accccacggg gctactgtgc aaggccaacc agatgcggct ggccgggact | 360 |
| tgtgcgatg tggtcatcat ggtggacagc caggagttcc acgcccaccg gacggtgctg | 420 |
| gcctgcacca gcaagatgtt tgagatcctc ttccaccgca atagtcaaca ctatactttg | 480 |
| gacttcctct cgccaaagac cttccagcag attctggagt atgcatatac agccacgctg | 540 |
| caagccaagg cggaggacct ggatgacctg ctgtatgcgg ccgagatcct ggagatcgag | 600 |
| tacctggagg aacagtgcct gaagatgctg agaccatcc aggcctcaga cgacaatgac | 660 |
| acggaggcca ccatggccga tggcggggcc gaggaagaag aggaccgcaa ggctcggtac | 720 |
| ctcaagaaca tcttcatctc gaagcattcc agcgaggaga gtgggtatgc cagtgtggct | 780 |
| ggacagagcc tccctgggcc catggtggac cagagcccctt cagtctccac ttcatttggt | 840 |
| ctttcagcca tgagtcccac caaggctgca gtggacagtt tgatgaccat aggacagtct | 900 |
| ctcctgcagg gaactcttca gccacctgca gggcccgagg agccaactct ggctgggggt | 960 |
| gggcggcacc ctggggtggc tgaggtgaag acggagatga tgcaggtgga tgaggtgccc | 1020 |
| agccaggaca gccctgggggc agccgagtcc agcatctcag agggatgggg ggacaaggtt | 1080 |
| gaggaaagag gcaaagaggg gcctgggacc ccgactcgaa gcagcgtcat caccagtgct | 1140 |
| agggagctac actatgggcg agaggagagt gccgagcagg tgccacccccc agctgaggct | 1200 |
| ggccaggccc ccactggccg acctgagcac ccagcacccc cgcctgagaa gcatctgggc | 1260 |
| atctactccg tgttgcccaa ccacaaggct gacgctgtat tgagcatgcc gtcttccgtg | 1320 |
| acctctggcc tccacgtgca gcctgccctg gctgtctcca tggacttcag cacctatggg | 1380 |
| gggctgctgc ccagggcttt catccagagg gagctgttca gcaagctggg ggagctggct | 1440 |
| gtgggcatga agtcagagag ccggaccatc ggagagcagt gcagcgtgtg tggggtcgag | 1500 |
| cttcctgata cgaggctgt ggagcagcac aggaagctgc acagtgggat gaagacgtac | 1560 |
| gggtgcgagc tctgcgggaa gcggttcctg gatagtttgc ggctgagaat gcacttactg | 1620 |
| gctcattcag cgggtgccaa agcctttgtc tgtgatcagt gcggtgcaca gttttcgaag | 1680 |
| gaggatgccc tggagacaca caggcagacc catactggca ctgacatggc cgtcttctgt | 1740 |
| ctgctgtgtg ggaagcgctt ccaggcgcag agcgcactgc agcagcacat ggaggtccac | 1800 |
| gcgggcgtgc gcagctacat ctgcagtgag tgcaaccgca ccttccccag ccacacggct | 1860 |
| ctcaaacgcc acctgcgctc acatacaggc gaccacccct acgagtgtga gttctgtggc | 1920 |
| agctgcttcc gggatgagag cactcaag agccacaaac gcatccacac gggtgagaaa | 1980 |
| ccctacgagt gcaatggctg tggcaagaag ttcagcctca gcatcagct ggagacgcac | 2040 |
| tatagggtgc acacaggtga aagcccttt gagtgtaagc tctgccacca gcgctcccgg | 2100 |
| gactactcgg ccatgatcaa gcacctgaga acgcacaacg gcgcctcgcc ctaccagtgc | 2160 |
| accatctgca cagagtactg ccccagcctc tcctccatgc agaagcacat gaagggccac | 2220 |

```
aagcccgagg agatcccgcc cgactggagg atagagaaga cgtacctcta cctgtgctat    2280
gtgtgaaggg aggcccgcgg cggtggagcc gagcggggag ccaggaaaga agagttggag    2340
tgagatgaag gaaggactat gacaaataaa aaggaaaag aaaaaaaaaa acagaaggaa     2400
aaggaaaaaa aaaaaaa                                                   2417
```

<210> SEQ ID NO 48
<211> LENGTH: 1188
<212> TYPE: PRT
<213> ORGANISM: Homo sapiens

<400> SEQUENCE: 48

```
Met Glu Pro Asn Ser Leu Gln Trp Val Gly Ser Pro Cys Gly Leu His
1               5                   10                  15
Gly Pro Tyr Ile Phe Tyr Lys Ala Phe Gln Phe His Leu Glu Gly Lys
            20                  25                  30
Pro Arg Ile Leu Ser Leu Gly Asp Phe Phe Phe Val Arg Cys Thr Pro
        35                  40                  45
Lys Asp Pro Ile Cys Ile Ala Glu Leu Gln Leu Leu Trp Glu Arg
    50                  55                  60
Thr Ser Arg Gln Leu Leu Ser Ser Ser Lys Leu Tyr Phe Leu Pro Glu
65                  70                  75                  80
Asp Thr Pro Gln Gly Arg Asn Ser Asp His Gly Glu Asp Glu Val Ile
                85                  90                  95
Ala Val Ser Glu Lys Val Ile Val Lys Leu Glu Asp Leu Val Lys Trp
            100                 105                 110
Val His Ser Asp Phe Ser Lys Trp Arg Cys Gly Phe His Ala Gly Pro
        115                 120                 125
Val Lys Thr Glu Ala Leu Gly Arg Asn Gly Gln Lys Glu Ala Leu Leu
    130                 135                 140
Lys Tyr Arg Gln Ser Thr Leu Asn Ser Gly Leu Asn Phe Lys Asp Val
145                 150                 155                 160
Leu Lys Glu Lys Ala Asp Leu Gly Glu Asp Glu Glu Thr Asn Val
                165                 170                 175
Ile Val Leu Ser Tyr Pro Gln Tyr Cys Arg Tyr Arg Ser Met Leu Lys
            180                 185                 190
Arg Ile Gln Asp Lys Pro Ser Ser Ile Leu Thr Asp Gln Phe Ala Leu
        195                 200                 205
Ala Leu Gly Gly Ile Ala Val Val Ser Arg Asn Pro Gln Ile Leu Tyr
    210                 215                 220
Cys Arg Asp Thr Phe Asp His Pro Thr Leu Ile Glu Asn Glu Ser Ile
225                 230                 235                 240
Cys Asp Glu Phe Ala Pro Asn Leu Lys Gly Arg Pro Arg Lys Lys
                245                 250                 255
Pro Cys Pro Gln Arg Arg Asp Ser Phe Ser Gly Val Lys Asp Ser Asn
            260                 265                 270
Asn Asn Ser Asp Gly Lys Ala Val Ala Lys Val Lys Cys Glu Ala Arg
        275                 280                 285
Ser Ala Leu Thr Lys Pro Lys Asn Asn His Asn Cys Lys Lys Val Ser
    290                 295                 300
Asn Glu Glu Lys Pro Lys Val Ala Ile Gly Glu Glu Cys Arg Ala Asp
305                 310                 315                 320
Glu Gln Ala Phe Leu Val Ala Leu Tyr Lys Tyr Met Lys Glu Arg Lys
                325                 330                 335
```

```
Thr Pro Ile Glu Arg Ile Pro Tyr Leu Gly Phe Lys Gln Ile Asn Leu
            340                 345                 350

Trp Thr Met Phe Gln Ala Ala Gln Lys Leu Gly Gly Tyr Glu Thr Ile
            355                 360                 365

Thr Ala Arg Arg Gln Trp Lys His Ile Tyr Asp Glu Leu Gly Gly Asn
            370                 375                 380

Pro Gly Ser Thr Ser Ala Ala Thr Cys Thr Arg Arg His Tyr Glu Arg
385                 390                 395                 400

Leu Ile Leu Pro Tyr Glu Arg Phe Ile Lys Gly Glu Asp Lys Pro
                405                 410                 415

Leu Pro Pro Ile Lys Pro Arg Lys Gln Glu Asn Ser Ser Gln Glu Asn
            420                 425                 430

Glu Asn Lys Thr Lys Val Ser Gly Thr Lys Arg Ile Lys His Glu Ile
            435                 440                 445

Pro Lys Ser Lys Lys Glu Lys Glu Asn Ala Pro Lys Pro Gln Asp Ala
            450                 455                 460

Ala Glu Val Ser Ser Glu Gln Glu Lys Glu Gln Glu Thr Leu Ile Ser
465                 470                 475                 480

Gln Lys Ser Ile Pro Glu Pro Leu Pro Ala Ala Asp Met Lys Lys Lys
            485                 490                 495

Ile Glu Gly Tyr Gln Glu Phe Ser Ala Lys Pro Leu Ala Ser Arg Val
            500                 505                 510

Asp Pro Glu Lys Asp Asn Glu Thr Asp Gln Gly Ser Asn Ser Glu Lys
            515                 520                 525

Val Ala Glu Glu Ala Gly Glu Lys Gly Pro Thr Pro Pro Leu Pro Ser
530                 535                 540

Ala Pro Leu Ala Pro Glu Lys Asp Ser Ala Leu Val Pro Gly Ala Ser
545                 550                 555                 560

Lys Gln Pro Leu Thr Ser Pro Ser Ala Leu Val Asp Ser Lys Gln Glu
            565                 570                 575

Ser Lys Leu Cys Cys Phe Thr Glu Ser Pro Glu Ser Glu Pro Gln Glu
            580                 585                 590

Ala Ser Phe Pro Ser Phe Pro Thr Thr Gln Pro Pro Leu Ala Asn Gln
            595                 600                 605

Asn Glu Thr Glu Asp Asp Lys Leu Pro Ala Met Ala Asp Tyr Ile Ala
            610                 615                 620

Asn Cys Thr Val Lys Val Asp Gln Leu Gly Ser Asp Asp Ile His Asn
625                 630                 635                 640

Ala Leu Lys Gln Thr Pro Lys Val Leu Val Gln Ser Phe Asp Met
            645                 650                 655

Phe Lys Asp Lys Asp Leu Thr Gly Pro Met Asn Glu Asn His Gly Leu
            660                 665                 670

Asn Tyr Thr Pro Leu Leu Tyr Ser Arg Gly Asn Pro Gly Ile Met Ser
            675                 680                 685

Pro Leu Ala Lys Lys Leu Leu Ser Gln Val Ser Gly Ala Ser Leu
            690                 695                 700

Ser Ser Ser Tyr Pro Tyr Gly Ser Pro Pro Leu Ile Ser Lys Lys
705                 710                 715                 720

Lys Leu Ile Ala Arg Asp Asp Leu Cys Ser Ser Leu Ser Gln Thr His
            725                 730                 735

His Gly Gln Ser Thr Asp His Met Ala Val Ser Arg Pro Ser Val Ile
            740                 745                 750

Gln His Val Gln Ser Phe Arg Ser Lys Pro Ser Glu Glu Arg Lys Thr
```

-continued

```
            755                 760                 765
Ile Asn Asp Ile Phe Lys His Glu Lys Leu Ser Arg Ser Asp Pro His
        770                 775                 780
Arg Cys Ser Phe Ser Lys His Leu Asn Pro Leu Ala Asp Ser Tyr
785                 790                 795                 800
Val Leu Lys Gln Glu Ile Gln Glu Gly Lys Asp Lys Leu Leu Glu Lys
                    805                 810                 815
Arg Ala Leu Pro His Ser His Met Pro Ser Phe Leu Ala Asp Phe Tyr
                820                 825                 830
Ser Ser Pro His Leu His Ser Leu Tyr Arg His Thr Glu His His Leu
            835                 840                 845
His Asn Glu Gln Thr Ser Lys Tyr Pro Ser Arg Asp Met Tyr Arg Glu
850                 855                 860
Ser Glu Asn Ser Ser Phe Pro Ser His Arg His Gln Glu Lys Leu His
865                 870                 875                 880
Val Asn Tyr Leu Thr Ser Leu His Leu Gln Asp Lys Lys Ser Ala Ala
                    885                 890                 895
Ala Glu Ala Pro Thr Asp Asp Gln Pro Thr Asp Leu Ser Leu Pro Lys
                900                 905                 910
Asn Pro His Lys Pro Thr Gly Lys Val Leu Gly Leu Ala His Ser Thr
            915                 920                 925
Thr Gly Pro Gln Glu Ser Lys Gly Ile Ser Gln Phe Gln Val Leu Gly
        930                 935                 940
Ser Gln Ser Arg Asp Cys His Pro Lys Ala Cys Arg Val Ser Pro Met
945                 950                 955                 960
Thr Met Ser Gly Pro Lys Lys Tyr Pro Glu Ser Leu Ser Arg Ser Gly
                    965                 970                 975
Lys Pro His His Val Arg Leu Glu Asn Phe Arg Lys Met Glu Gly Met
                980                 985                 990
Val His Pro Ile Leu His Arg Lys Met Ser Pro Gln Asn Ile Gly Ala
            995                1000                1005
Ala Arg Pro Ile Lys Arg Ser Leu Glu Asp Leu Asp Leu Val Ile
        1010                1015                1020
Ala Gly Lys Lys Ala Arg Ala Val Ser Pro Leu Asp Pro Ser Lys
        1025                1030                1035
Glu Val Ser Gly Lys Glu Lys Ala Ser Glu Gln Glu Ser Glu Gly
        1040                1045                1050
Ser Lys Ala Ala His Gly Gly His Ser Gly Gly Gly Ser Glu Gly
        1055                1060                1065
His Lys Leu Pro Leu Ser Ser Pro Ile Phe Pro Gly Leu Tyr Ser
        1070                1075                1080
Gly Ser Leu Cys Asn Ser Gly Leu Asn Ser Arg Leu Pro Ala Gly
        1085                1090                1095
Tyr Ser His Ser Leu Gln Tyr Leu Lys Asn Gln Thr Val Leu Ser
        1100                1105                1110
Pro Leu Met Gln Pro Leu Ala Phe His Ser Leu Val Met Gln Arg
        1115                1120                1125
Gly Ile Phe Thr Ser Pro Thr Asn Ser Gln Gln Leu Tyr Arg His
        1130                1135                1140
Leu Ala Ala Ala Thr Pro Val Gly Ser Ser Tyr Gly Asp Leu Leu
        1145                1150                1155
His Asn Ser Ile Tyr Pro Leu Ala Ala Ile Asn Pro Gln Ala Ala
        1160                1165                1170
```

Phe Pro Ser Ser Gln Leu Ser Ser Val His Pro Ser Thr Lys Leu
    1175                1180                1185

<210> SEQ ID NO 49
<211> LENGTH: 181
<212> TYPE: PRT
<213> ORGANISM: Homo sapiens

<400> SEQUENCE: 49

Met Met Leu Gln His Pro Gly Gln Val Ser Ala Ser Glu Val Ser Ala
1               5                   10                  15

Ser Ala Ile Val Pro Cys Leu Ser Pro Pro Gly Ser Leu Val Phe Glu
            20                  25                  30

Asp Phe Ala Asn Leu Thr Pro Phe Val Lys Glu Glu Leu Arg Phe Ala
        35                  40                  45

Ile Gln Asn Lys His Leu Cys His Arg Met Ser Ser Ala Leu Glu Ser
    50                  55                  60

Val Thr Val Ser Asp Arg Pro Leu Gly Val Ser Ile Thr Lys Ala Glu
65                  70                  75                  80

Val Ala Pro Glu Glu Asp Glu Arg Lys Lys Arg Arg Glu Arg Asn
                85                  90                  95

Lys Ile Ala Ala Ala Lys Cys Arg Asn Lys Lys Lys Glu Lys Thr Glu
            100                 105                 110

Cys Leu Gln Lys Glu Ser Glu Lys Leu Glu Ser Val Asn Ala Glu Leu
        115                 120                 125

Lys Ala Gln Ile Glu Glu Leu Lys Asn Glu Lys Gln His Leu Ile Tyr
    130                 135                 140

Met Leu Asn Leu His Arg Pro Thr Cys Ile Val Arg Ala Gln Asn Gly
145                 150                 155                 160

Arg Thr Pro Glu Asp Glu Arg Asn Leu Phe Ile Gln Gln Ile Lys Glu
                165                 170                 175

Gly Thr Leu Gln Ser
            180

<210> SEQ ID NO 50
<211> LENGTH: 251
<212> TYPE: PRT
<213> ORGANISM: Homo sapiens

<400> SEQUENCE: 50

Met Thr Arg Leu Thr Val Leu Ala Leu Ala Gly Leu Leu Ala Ser
1               5                   10                  15

Ser Arg Ala Gly Ser Ser Pro Leu Leu Asp Ile Val Gly Gly Arg Lys
            20                  25                  30

Ala Arg Pro Arg Gln Phe Pro Leu Ala Ser Ile Gln Asn Gln Gly
        35                  40                  45

Arg His Phe Cys Gly Gly Ala Leu Ile His Ala Arg Phe Val Met Thr
    50                  55                  60

Ala Ala Ser Cys Phe Gln Ser Gln Asn Pro Gly Val Ser Thr Val Val
65                  70                  75                  80

Leu Gly Ala Tyr Asp Leu Arg Arg Arg Glu Arg Gln Ser Arg Gln Thr
                85                  90                  95

Phe Ser Ile Ser Ser Met Ser Glu Asn Gly Tyr Asp Pro Gln Gln Asn
            100                 105                 110

Leu Asn Asp Leu Met Leu Leu Gln Leu Asp Arg Glu Ala Asn Leu Thr
        115                 120                 125

Ser Ser Val Thr Ile Leu Pro Leu Pro Leu Gln Asn Ala Thr Val Glu
130                 135                 140

Ala Gly Thr Arg Cys Gln Val Ala Gly Trp Gly Ser Gln Arg Ser Gly
145                 150                 155                 160

Gly Arg Leu Ser Arg Phe Pro Arg Phe Val Asn Val Thr Val Thr Pro
                165                 170                 175

Glu Asp Gln Cys Arg Pro Asn Asn Val Cys Thr Gly Val Leu Thr Arg
                180                 185                 190

Arg Gly Gly Ile Cys Asn Gly Asp Gly Gly Thr Pro Leu Val Cys Glu
                195                 200                 205

Gly Leu Ala His Gly Val Ala Ser Phe Ser Leu Gly Pro Cys Gly Arg
210                 215                 220

Gly Pro Asp Phe Phe Thr Arg Val Ala Leu Phe Arg Asp Trp Ile Asp
225                 230                 235                 240

Gly Val Leu Asn Asn Pro Gly Pro Gly Pro Ala
                245                 250

<210> SEQ ID NO 51
<211> LENGTH: 326
<212> TYPE: PRT
<213> ORGANISM: Homo sapiens

<400> SEQUENCE: 51

Met His Arg Thr Thr Arg Ile Lys Ile Thr Glu Leu Asn Pro His Leu
1               5                   10                  15

Met Cys Val Leu Cys Gly Gly Tyr Phe Ile Asp Ala Thr Thr Ile Ile
                20                  25                  30

Glu Cys Leu His Ser Phe Cys Lys Thr Cys Ile Val Arg Tyr Leu Glu
            35                  40                  45

Thr Ser Lys Tyr Cys Pro Ile Cys Asp Val Gln Val His Lys Thr Arg
50                  55                  60

Pro Leu Leu Asn Ile Arg Ser Asp Lys Thr Leu Gln Asp Ile Val Tyr
65                  70                  75                  80

Lys Leu Val Pro Gly Leu Phe Lys Asn Glu Met Lys Arg Arg Arg Asp
                85                  90                  95

Phe Tyr Ala Ala His Pro Ser Ala Asp Ala Ala Asn Gly Ser Asn Glu
                100                 105                 110

Asp Arg Gly Glu Val Ala Asp Glu Asp Lys Arg Ile Ile Thr Asp Asp
            115                 120                 125

Glu Ile Ile Ser Leu Ser Ile Glu Phe Phe Asp Gln Asn Arg Leu Asp
130                 135                 140

Arg Lys Val Asn Lys Asp Lys Glu Lys Ser Lys Glu Glu Val Asn Asp
145                 150                 155                 160

Lys Arg Tyr Leu Arg Cys Pro Ala Ala Met Thr Val Met His Leu Arg
                165                 170                 175

Lys Phe Leu Arg Ser Lys Met Asp Ile Pro Asn Thr Phe Gln Ile Asp
                180                 185                 190

Val Met Tyr Glu Glu Glu Pro Leu Lys Asp Tyr Tyr Thr Leu Met Asp
            195                 200                 205

Ile Ala Tyr Ile Tyr Thr Trp Arg Arg Asn Gly Pro Leu Pro Leu Lys
210                 215                 220

Tyr Arg Val Arg Pro Thr Cys Lys Arg Met Lys Ile Ser His Gln Arg
225                 230                 235                 240

Asp Gly Leu Thr Asn Ala Gly Glu Leu Glu Ser Asp Ser Gly Ser Asp

```
                    245                 250                 255
Lys Ala Asn Ser Pro Ala Gly Gly Ile Pro Ser Thr Ser Ser Cys Leu
                260                 265                 270

Pro Ser Pro Ser Thr Pro Val Gln Ser Pro His Pro Gln Phe Pro His
            275                 280                 285

Ile Ser Ser Thr Met Asn Gly Thr Ser Asn Ser Pro Ser Gly Asn His
        290                 295                 300

Gln Ser Ser Phe Ala Asn Arg Pro Arg Lys Ser Ser Val Asn Gly Ser
305                 310                 315                 320

Ser Ala Thr Ser Ser Gly
                325

<210> SEQ ID NO 52
<211> LENGTH: 323
<212> TYPE: PRT
<213> ORGANISM: Homo sapiens

<400> SEQUENCE: 52

Met Gln Ala Ala Trp Leu Leu Gly Ala Leu Val Val Pro Gln Leu Leu
1               5                   10                  15

Gly Phe Gly His Gly Ala Arg Gly Ala Glu Arg Glu Trp Glu Gly Gly
            20                  25                  30

Trp Gly Gly Ala Gln Glu Glu Arg Glu Arg Glu Ala Leu Met Leu
        35                  40                  45

Lys His Leu Gln Glu Ala Leu Gly Leu Pro Ala Gly Arg Gly Asp Glu
    50                  55                  60

Asn Pro Ala Gly Thr Val Glu Gly Lys Glu Asp Trp Glu Met Glu Glu
65                  70                  75                  80

Asp Gln Gly Glu Glu Glu Glu Glu Ala Thr Pro Thr Pro Ser Ser
                85                  90                  95

Gly Pro Ser Pro Ser Pro Thr Pro Glu Asp Ile Val Thr Tyr Ile Leu
            100                 105                 110

Gly Arg Leu Ala Gly Leu Asp Ala Gly Leu His Gln Leu His Val Arg
        115                 120                 125

Leu His Ala Leu Asp Thr Arg Val Val Glu Leu Thr Gln Gly Leu Arg
    130                 135                 140

Gln Leu Arg Asn Ala Ala Gly Asp Thr Arg Asp Ala Val Gln Ala Leu
145                 150                 155                 160

Gln Glu Ala Gln Gly Arg Ala Glu Arg Glu His Gly Arg Leu Glu Gly
                165                 170                 175

Cys Leu Lys Gly Leu Arg Leu Gly His Lys Cys Phe Leu Leu Ser Arg
            180                 185                 190

Asp Phe Glu Ala Gln Ala Ala Gln Ala Arg Cys Thr Ala Arg Gly
        195                 200                 205

Gly Ser Leu Ala Gln Pro Ala Asp Arg Gln Gln Met Glu Ala Leu Thr
    210                 215                 220

Arg Tyr Leu Arg Ala Ala Leu Ala Pro Tyr Asn Trp Pro Val Trp Leu
225                 230                 235                 240

Gly Val His Asp Arg Arg Ala Glu Gly Leu Tyr Leu Phe Glu Asn Gly
                245                 250                 255

Gln Arg Val Ser Phe Phe Ala Trp His Arg Ser Pro Arg Pro Glu Leu
            260                 265                 270

Gly Ala Gln Pro Ser Ala Ser Pro His Pro Leu Ser Pro Asp Gln Pro
        275                 280                 285
```

```
Asn Gly Gly Thr Leu Glu Asn Cys Val Ala Gln Ala Ser Asp Asp Gly
            290                 295                 300

Ser Trp Trp Asp His Asp Cys Gln Arg Arg Leu Tyr Tyr Val Cys Glu
305                 310                 315                 320

Phe Pro Phe

<210> SEQ ID NO 53
<211> LENGTH: 98
<212> TYPE: PRT
<213> ORGANISM: Homo sapiens

<400> SEQUENCE: 53

Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Val
        35                  40                  45

Ala Gly Thr Asn Tyr Tyr Ile Lys Val Arg Ala Gly Asp Asn Lys Tyr
    50                  55                  60

Met His Leu Lys Val Phe Lys Ser Leu Pro Gly Gln Asn Glu Asp Leu
65                  70                  75                  80

Val Leu Thr Gly Tyr Gln Val Asp Lys Asn Lys Asp Asp Glu Leu Thr
                85                  90                  95

Gly Phe

<210> SEQ ID NO 54
<211> LENGTH: 510
<212> TYPE: PRT
<213> ORGANISM: Homo sapiens

<400> SEQUENCE: 54

Met Asp Gly Phe Tyr Asp Gln Gln Val Pro Phe Met Val Pro Gly Lys
1               5                   10                  15

Ser Arg Ser Glu Glu Cys Arg Gly Arg Pro Val Ile Asp Arg Lys Arg
            20                  25                  30

Lys Phe Leu Asp Thr Asp Leu Ala His Asp Ser Glu Glu Leu Phe Gln
        35                  40                  45

Asp Leu Ser Gln Leu Gln Glu Ala Trp Leu Ala Glu Ala Gln Val Pro
    50                  55                  60

Asp Asp Glu Gln Phe Val Pro Asp Phe Gln Ser Asp Asn Leu Val Leu
65                  70                  75                  80

His Ala Pro Pro Pro Thr Lys Ile Lys Arg Glu Leu His Ser Pro Ser
                85                  90                  95

Ser Glu Leu Ser Ser Cys Ser His Glu Gln Ala Leu Gly Ala Asn Tyr
            100                 105                 110

Gly Glu Lys Cys Leu Tyr Asn Tyr Cys Ala Tyr Asp Arg Lys Pro Pro
        115                 120                 125

Ser Gly Phe Lys Pro Leu Thr Pro Thr Thr Pro Leu Ser Pro Thr
    130                 135                 140

His Gln Asn Pro Leu Phe Pro Pro Gln Ala Thr Leu Pro Thr Ser
145                 150                 155                 160

Gly His Ala Pro Ala Gly Pro Val Gln Gly Val Gly Pro Ala Pro
                165                 170                 175

Ala Pro His Ser Leu Pro Glu Pro Gly Pro Gln Gln Thr Phe Ala
            180                 185                 190
```

Val Pro Arg Pro Pro His Gln Pro Leu Gln Met Pro Lys Met Met Pro
    195                 200                 205

Glu Asn Gln Tyr Pro Ser Glu Gln Arg Phe Gln Arg Gln Leu Ser Glu
    210                 215                 220

Pro Cys His Pro Phe Pro Pro Gln Pro Gly Val Pro Gly Asp Asn Arg
225                 230                 235                 240

Pro Ser Tyr His Arg Gln Met Ser Glu Pro Ile Val Pro Ala Ala Pro
            245                 250                 255

Pro Pro Pro Gln Gly Phe Lys Gln Glu Tyr His Asp Pro Leu Tyr Glu
            260                 265                 270

His Gly Val Pro Gly Met Pro Gly Pro Ala His Gly Phe Gln Ser
    275                 280                 285

Pro Met Gly Ile Lys Gln Glu Pro Arg Asp Tyr Cys Val Asp Ser Glu
    290                 295                 300

Val Pro Asn Cys Gln Ser Ser Tyr Met Arg Gly Gly Tyr Phe Ser Ser
305                 310                 315                 320

Ser His Glu Gly Phe Ser Tyr Glu Lys Asp Pro Arg Leu Tyr Phe Asp
            325                 330                 335

Asp Thr Cys Val Val Pro Glu Arg Leu Glu Gly Lys Val Lys Gln Glu
            340                 345                 350

Pro Thr Met Tyr Arg Glu Gly Pro Pro Tyr Gln Arg Arg Gly Ser Leu
    355                 360                 365

Gln Leu Trp Gln Phe Leu Val Thr Leu Leu Asp Asp Pro Ala Asn Ala
    370                 375                 380

His Phe Ile Ala Trp Thr Gly Arg Gly Met Glu Phe Lys Leu Ile Glu
385                 390                 395                 400

Pro Glu Glu Val Ala Arg Arg Trp Gly Ile Gln Lys Asn Arg Pro Ala
            405                 410                 415

Met Asn Tyr Asp Lys Leu Ser Arg Ser Leu Arg Tyr Tyr Glu Lys
            420                 425                 430

Gly Ile Met Gln Lys Val Ala Gly Glu Arg Tyr Val Tyr Lys Phe Val
    435                 440                 445

Cys Asp Pro Asp Ala Leu Phe Ser Met Ala Phe Pro Asp Asn Gln Arg
    450                 455                 460

Pro Phe Leu Lys Ala Glu Ser Glu Cys His Leu Ser Glu Glu Asp Thr
465                 470                 475                 480

Leu Pro Leu Thr His Phe Glu Asp Ser Pro Ala Tyr Leu Leu Asp Met
            485                 490                 495

Asp Arg Cys Ser Ser Leu Pro Tyr Ala Glu Gly Phe Ala Tyr
            500                 505                 510

<210> SEQ ID NO 55
<211> LENGTH: 2406
<212> TYPE: PRT
<213> ORGANISM: Homo sapiens

<400> SEQUENCE: 55

Met Asp Pro Glu Gln Ser Val Lys Gly Thr Lys Lys Ala Glu Gly Ser
1               5                   10                  15

Pro Arg Lys Arg Leu Thr Lys Gly Glu Ala Ile Gln Thr Ser Val Ser
            20                  25                  30

Ser Ser Val Pro Tyr Pro Gly Ser Gly Thr Ala Thr Gln Glu Ser
        35                  40                  45

Pro Ala Gln Glu Leu Leu Ala Pro Gln Pro Phe Pro Gly Pro Ser Ser

-continued

```
                    50                  55                  60
Val Leu Arg Glu Gly Ser Gln Glu Lys Thr Gly Gln Gln Lys Pro
 65                  70                  75                  80

Pro Lys Arg Pro Pro Ile Glu Ala Ser Val His Ile Ser Gln Leu Pro
                 85                  90                  95

Gln His Pro Leu Thr Pro Ala Phe Met Ser Pro Gly Lys Pro Glu His
                100                 105                 110

Leu Leu Glu Gly Ser Thr Trp Gln Leu Val Asp Pro Met Arg Pro Gly
                115                 120                 125

Pro Ser Gly Ser Phe Val Ala Pro Gly Leu His Pro Gln Ser Gln Leu
                130                 135                 140

Leu Pro Ser His Ala Ser Ile Ile Pro Pro Glu Asp Leu Pro Gly Val
145                 150                 155                 160

Pro Lys Val Phe Val Pro Arg Pro Ser Gln Val Ser Leu Lys Pro Thr
                165                 170                 175

Glu Glu Ala His Lys Lys Glu Arg Lys Pro Gln Lys Pro Gly Lys Tyr
                180                 185                 190

Ile Cys Gln Tyr Cys Ser Arg Pro Cys Ala Lys Pro Ser Val Leu Gln
                195                 200                 205

Lys His Ile Arg Ser His Thr Gly Glu Arg Pro Tyr Pro Cys Gly Pro
210                 215                 220

Cys Gly Phe Ser Phe Lys Thr Lys Ser Asn Leu Tyr Lys His Arg Lys
225                 230                 235                 240

Ser His Ala His Arg Ile Lys Ala Gly Leu Ala Ser Gly Met Gly Gly
                245                 250                 255

Glu Met Tyr Pro His Gly Leu Glu Met Glu Arg Ile Pro Gly Glu Glu
                260                 265                 270

Phe Glu Glu Pro Thr Glu Gly Ser Thr Asp Ser Glu Glu Thr
                275                 280                 285

Ser Ala Thr Ser Gly His Pro Ala Glu Leu Ser Pro Arg Pro Lys Gln
                290                 295                 300

Pro Leu Leu Ser Ser Gly Leu Tyr Ser Ser Gly Ser His Ser Ser Ser
305                 310                 315                 320

His Glu Arg Cys Ser Leu Ser Gln Ser Ser Thr Ala Gln Ser Leu Glu
                325                 330                 335

Asp Pro Pro Pro Phe Val Glu Pro Ser Ser Glu His Pro Leu Ser His
                340                 345                 350

Lys Pro Glu Asp Thr His Thr Ile Lys Gln Lys Leu Ala Leu Arg Leu
                355                 360                 365

Ser Glu Arg Lys Lys Val Ile Asp Glu Gln Ala Phe Leu Ser Pro Gly
370                 375                 380

Ser Lys Gly Ser Thr Glu Ser Gly Tyr Phe Ser Arg Ser Glu Ser Ala
385                 390                 395                 400

Glu Gln Gln Val Ser Pro Pro Asn Thr Asn Ala Lys Ser Tyr Ala Glu
                405                 410                 415

Ile Ile Phe Gly Lys Cys Gly Arg Ile Gly Gln Arg Thr Ala Met Leu
                420                 425                 430

Thr Ala Thr Ser Thr Gln Pro Leu Leu Pro Leu Ser Thr Glu Asp Lys
                435                 440                 445

Pro Ser Leu Val Pro Leu Ser Val Pro Arg Thr Gln Val Ile Glu His
                450                 455                 460

Ile Thr Lys Leu Ile Thr Ile Asn Glu Ala Val Val Asp Thr Ser Glu
465                 470                 475                 480
```

```
Ile Asp Ser Val Lys Pro Arg Arg Ser Ser Leu Ser Arg Arg Ser Ser
                485                 490                 495

Met Glu Ser Pro Lys Ser Ser Leu Tyr Arg Glu Pro Leu Ser Ser His
                500                 505                 510

Ser Glu Lys Thr Lys Pro Glu Gln Ser Leu Leu Ser Leu Gln His Pro
                515                 520                 525

Pro Ser Thr Ala Pro Pro Val Pro Leu Leu Arg Ser His Ser Met Pro
                530                 535                 540

Ser Ala Ala Cys Thr Ile Ser Thr Pro His His Pro Phe Arg Gly Ser
545                 550                 555                 560

Tyr Ser Phe Asp Asp His Ile Thr Asp Ser Glu Ala Leu Ser His Ser
                565                 570                 575

Ser His Val Phe Thr Ser His Pro Arg Met Leu Lys Arg Gln Pro Ala
                580                 585                 590

Ile Glu Leu Pro Leu Gly Gly Glu Tyr Ser Ser Glu Glu Pro Gly Pro
                595                 600                 605

Ser Ser Lys Asp Thr Ala Ser Lys Pro Ser Asp Glu Val Glu Pro Lys
                610                 615                 620

Glu Ser Glu Leu Thr Lys Lys Thr Lys Gly Leu Lys Thr Lys Gly
625                 630                 635                 640

Val Ile Tyr Glu Cys Asn Ile Cys Gly Ala Arg Tyr Lys Lys Arg Asp
                645                 650                 655

Asn Tyr Glu Ala His Lys Lys Tyr Tyr Cys Ser Glu Leu Gln Ile Ala
                660                 665                 670

Lys Pro Ile Ser Ala Gly Thr His Thr Ser Pro Glu Ala Glu Lys Ser
                675                 680                 685

Gln Ile Glu His Glu Pro Trp Ser Gln Met Met His Tyr Lys Leu Gly
                690                 695                 700

Thr Thr Leu Glu Leu Thr Pro Leu Arg Lys Arg Arg Lys Glu Lys Ser
705                 710                 715                 720

Leu Gly Asp Glu Glu Pro Pro Ala Phe Glu Ser Thr Lys Ser Gln
                725                 730                 735

Phe Gly Ser Pro Gly Pro Ser Asp Ala Ala Arg Asn Leu Pro Leu Glu
                740                 745                 750

Ser Thr Lys Ser Pro Ala Glu Pro Ser Lys Ser Val Pro Ser Leu Glu
                755                 760                 765

Gly Pro Thr Gly Phe Gln Pro Arg Thr Pro Lys Pro Gly Ser Gly Ser
                770                 775                 780

Glu Ser Gly Lys Glu Arg Thr Thr Ser Lys Glu Ile Ser Val Ile
785                 790                 795                 800

Gln His Thr Ser Ser Phe Glu Lys Ser Asp Ser Leu Glu Gln Pro Ser
                805                 810                 815

Gly Leu Glu Gly Glu Asp Lys Pro Leu Ala Gln Phe Pro Ser Pro
                820                 825                 830

Pro Ala Pro His Gly Arg Ser Ala His Ser Leu Gln Pro Lys Leu Val
                835                 840                 845

Arg Gln Pro Asn Ile Gln Val Pro Glu Ile Leu Val Thr Glu Glu Pro
                850                 855                 860

Asp Arg Pro Asp Thr Glu Pro Glu Pro Pro Lys Glu Pro Glu Lys
865                 870                 875                 880

Thr Glu Glu Phe Gln Trp Pro Gln Arg Ser Gln Thr Leu Ala Gln Leu
                885                 890                 895
```

```
Pro Ala Glu Lys Leu Pro Pro Lys Lys Arg Leu Arg Leu Ala Glu
                900                 905                 910

Met Ala Gln Ser Ser Gly Glu Ser Ser Phe Glu Ser Val Pro Leu
                915                 920                 925

Ser Arg Ser Pro Ser Gln Glu Ser Asn Val Ser Leu Ser Gly Ser Ser
930                 935                 940

Arg Ser Ala Ser Phe Glu Arg Asp Asp His Gly Lys Ala Glu Ala Pro
945                 950                 955                 960

Ser Pro Ser Ser Asp Met Arg Pro Lys Pro Leu Gly Thr His Met Leu
                965                 970                 975

Thr Val Pro Ser His His Pro His Ala Arg Glu Met Arg Arg Ser Ala
                980                 985                 990

Ser Glu Gln Ser Pro Asn Val Ser His Ser Ala His Met Thr Glu Thr
                995                 1000                1005

Arg Ser Lys Ser Phe Asp Tyr Gly Ser Leu Ser Leu Thr Gly Pro
        1010                1015                1020

Ser Ala Pro Ala Pro Val Ala Pro Pro Ala Arg Val Ala Pro Pro
        1025                1030                1035

Glu Arg Arg Lys Cys Phe Leu Val Arg Gln Ala Ser Leu Ser Arg
        1040                1045                1050

Pro Pro Glu Ser Glu Leu Glu Val Ala Pro Lys Gly Arg Gln Glu
        1055                1060                1065

Ser Glu Glu Pro Gln Pro Ser Ser Ser Lys Pro Ser Ala Lys Ser
        1070                1075                1080

Ser Leu Ser Gln Ile Ser Ser Ala Ala Thr Ser His Gly Gly Pro
        1085                1090                1095

Pro Gly Gly Lys Gly Pro Gly Gln Asp Arg Pro Pro Leu Gly Pro
        1100                1105                1110

Thr Val Pro Tyr Thr Glu Ala Leu Gln Val Phe His His Pro Val
        1115                1120                1125

Ala Gln Thr Pro Leu His Glu Lys Pro Tyr Leu Pro Pro Pro Val
        1130                1135                1140

Ser Leu Phe Ser Phe Gln His Leu Val Gln His Glu Pro Gly Gln
        1145                1150                1155

Ser Pro Glu Phe Phe Ser Thr Gln Ala Met Ser Ser Leu Leu Ser
        1160                1165                1170

Ser Pro Tyr Ser Met Pro Pro Leu Pro Pro Ser Leu Phe Gln Ala
        1175                1180                1185

Pro Pro Leu Pro Leu Gln Pro Thr Val Leu His Pro Gly Gln Leu
        1190                1195                1200

His Leu Pro Gln Leu Met Pro His Pro Ala Asn Ile Pro Phe Arg
        1205                1210                1215

Gln Pro Pro Ser Phe Leu Pro Met Pro Tyr Pro Thr Ser Ser Ala
        1220                1225                1230

Leu Ser Ser Gly Phe Phe Leu Pro Leu Gln Ser Gln Phe Ala Leu
        1235                1240                1245

Gln Leu Pro Gly Asp Val Glu Ser His Leu Pro Gln Ile Lys Thr
        1250                1255                1260

Ser Leu Ala Pro Leu Ala Thr Gly Ser Ala Gly Leu Ser Pro Ser
        1265                1270                1275

Thr Glu Tyr Ser Ser Asp Ile Arg Leu Pro Pro Val Ala Pro Pro
        1280                1285                1290

Ala Ser Ser Ser Ala Pro Thr Ser Ala Pro Pro Leu Ala Leu Pro
```

```
                 1295                1300                1305
Ala Cys Pro Asp Thr Met Val Ser Leu Val Val Pro Val Arg Val
    1310                1315                1320
Gln Thr Asn Met Pro Ser Tyr Gly Ser Ala Met Tyr Thr Thr Leu
    1325                1330                1335
Ser Gln Ile Leu Val Thr Gln Ser Gln Gly Ser Ser Ala Thr Val
    1340                1345                1350
Ala Leu Pro Lys Phe Glu Glu Pro Pro Ser Lys Gly Thr Thr Val
    1355                1360                1365
Cys Gly Ala Asp Val His Glu Val Gly Pro Gly Pro Ser Gly Leu
    1370                1375                1380
Ser Glu Glu Gln Ser Arg Ala Phe Pro Thr Pro Tyr Leu Arg Val
    1385                1390                1395
Pro Val Thr Leu Pro Glu Arg Lys Gly Thr Gly Ser Leu Ser Ser Glu
    1400                1405                1410
Ser Ile Leu Ser Leu Glu Gly Ser Ser Ser Thr Ala Gly Gly Ser
    1415                1420                1425
Lys Arg Val Leu Ser Pro Ala Gly Ser Leu Glu Leu Thr Met Glu
    1430                1435                1440
Thr Gln Gln Gln Lys Arg Val Lys Glu Glu Ala Ser Lys Ala
    1445                1450                1455
Asp Glu Lys Leu Glu Leu Val Lys Pro Cys Ser Val Val Leu Thr
    1460                1465                1470
Ser Thr Glu Asp Gly Lys Arg Pro Glu Lys Ser His Leu Gly Asn
    1475                1480                1485
Gln Gly Gln Gly Arg Arg Glu Leu Glu Met Leu Ser Ser Leu Ser
    1490                1495                1500
Ser Asp Pro Ser Asp Thr Lys Glu Ile Pro Pro Leu Pro His Pro
    1505                1510                1515
Ala Leu Ser His Gly Thr Ala Pro Gly Ser Glu Ala Leu Lys Glu
    1520                1525                1530
Tyr Pro Gln Pro Ser Gly Lys Pro His Arg Arg Gly Leu Thr Pro
    1535                1540                1545
Leu Ser Val Lys Lys Glu Asp Ser Lys Glu Gln Pro Asp Leu Pro
    1550                1555                1560
Ser Leu Ala Pro Pro Ser Ser Leu Pro Leu Ser Glu Thr Ser Ser
    1565                1570                1575
Arg Pro Ala Lys Ser Gln Glu Gly Thr Asp Ser Lys Lys Val Leu
    1580                1585                1590
Gln Phe Pro Ser Leu His Thr Thr Thr Asn Val Ser Trp Cys Tyr
    1595                1600                1605
Leu Asn Tyr Ile Lys Pro Asn His Ile Gln His Ala Asp Arg Arg
    1610                1615                1620
Ser Ser Val Tyr Ala Gly Trp Cys Ile Ser Leu Tyr Asn Pro Asn
    1625                1630                1635
Leu Pro Gly Val Ser Thr Lys Ala Ala Leu Ser Leu Leu Arg Ser
    1640                1645                1650
Lys Gln Lys Val Ser Lys Glu Thr Tyr Thr Met Ala Thr Ala Pro
    1655                1660                1665
His Pro Glu Ala Gly Arg Leu Val Pro Ser Ser Ser Arg Lys Pro
    1670                1675                1680
Arg Met Thr Glu Val His Leu Pro Ser Leu Val Ser Pro Glu Gly
    1685                1690                1695
```

```
Gln Lys Asp Leu Ala Arg Val Glu Lys Glu Glu Arg Arg Gly
    1700                1705            1710

Glu Pro Glu Glu Asp Ala Pro Ala Ser Gln Arg Gly Glu Pro Ala
    1715                1720            1725

Arg Ile Lys Ile Phe Glu Gly Gly Tyr Lys Ser Asn Glu Glu Tyr
    1730                1735            1740

Val Tyr Val Arg Gly Arg Gly Arg Gly Lys Tyr Val Cys Glu Glu
    1745                1750            1755

Cys Gly Ile Arg Cys Lys Lys Pro Ser Met Leu Lys Lys His Ile
    1760                1765            1770

Arg Thr His Thr Asp Val Arg Pro Tyr Val Cys Lys His Cys His
    1775                1780            1785

Phe Ala Phe Lys Thr Lys Gly Asn Leu Thr Lys His Met Lys Ser
    1790                1795            1800

Lys Ala His Ser Lys Lys Cys Gln Glu Thr Gly Val Leu Glu Glu
    1805                1810            1815

Leu Glu Ala Glu Glu Gly Thr Ser Asp Asp Leu Phe Gln Asp Ser
    1820                1825            1830

Glu Gly Arg Glu Gly Ser Glu Ala Val Glu Glu His Gln Phe Ser
    1835                1840            1845

Asp Leu Glu Asp Ser Asp Ser Asp Ser Asp Leu Asp Glu Asp Glu
    1850                1855            1860

Asp Glu Asp Glu Glu Glu Ser Gln Asp Glu Leu Ser Arg Pro Ser
    1865                1870            1875

Ser Glu Ala Pro Pro Pro Gly Pro Pro His Ala Leu Arg Ala Asp
    1880                1885            1890

Ser Ser Pro Ile Leu Gly Pro Gln Pro Pro Asp Ala Pro Ala Ser
    1895                1900            1905

Gly Thr Glu Ala Thr Arg Gly Ser Ser Val Ser Glu Ala Glu Arg
    1910                1915            1920

Leu Thr Ala Ser Ser Cys Ser Met Ser Ser Gln Ser Met Pro Gly
    1925                1930            1935

Leu Pro Trp Leu Gly Pro Ala Pro Leu Gly Ser Val Glu Lys Asp
    1940                1945            1950

Thr Gly Ser Ala Leu Ser Tyr Lys Pro Val Ser Pro Arg Arg Pro
    1955                1960            1965

Trp Ser Pro Ser Lys Glu Ala Gly Ser Arg Pro Pro Leu Ala Arg
    1970                1975            1980

Lys His Ser Leu Thr Lys Asn Asp Ser Ser Pro Gln Arg Cys Ser
    1985                1990            1995

Pro Ala Arg Glu Pro Gln Ala Ser Ala Pro Ser Pro Pro Gly Leu
    2000                2005            2010

His Val Asp Pro Gly Arg Gly Met Gly Ala Leu Pro Cys Gly Ser
    2015                2020            2025

Pro Arg Leu Gln Leu Ser Pro Leu Thr Leu Cys Pro Leu Gly Arg
    2030                2035            2040

Glu Leu Ala Pro Arg Ala His Val Leu Ser Lys Leu Glu Gly Thr
    2045                2050            2055

Thr Asp Pro Gly Leu Pro Arg Tyr Ser Pro Thr Arg Arg Trp Ser
    2060                2065            2070

Pro Gly Gln Ala Glu Ser Pro Pro Arg Ser Ala Pro Pro Gly Lys
    2075                2080            2085
```

```
Trp Ala Leu Ala Gly Pro Gly Ser Pro Ser Ala Gly Glu His Gly
    2090            2095            2100

Pro Gly Leu Gly Leu Asp Pro Arg Val Leu Phe Pro Pro Ala Pro
    2105            2110            2115

Leu Pro His Lys Leu Leu Ser Arg Ser Pro Glu Thr Cys Ala Ser
    2120            2125            2130

Pro Trp Gln Lys Ala Glu Ser Arg Ser Pro Ser Cys Ser Pro Gly
    2135            2140            2145

Pro Ala His Pro Leu Ser Ser Arg Pro Phe Ser Ala Leu His Asp
    2150            2155            2160

Phe His Gly His Ile Leu Ala Arg Thr Glu Glu Asn Ile Phe Ser
    2165            2170            2175

His Leu Pro Leu His Ser Gln His Leu Thr Arg Ala Pro Cys Pro
    2180            2185            2190

Leu Ile Pro Ile Gly Gly Ile Gln Met Val Gln Ala Arg Pro Gly
    2195            2200            2205

Ala His Pro Thr Leu Leu Pro Gly Pro Thr Ala Ala Trp Val Ser
    2210            2215            2220

Gly Phe Ser Gly Gly Ser Asp Leu Thr Gly Ala Arg Glu Ala
    2225            2230            2235

Gln Glu Arg Gly Arg Trp Ser Pro Thr Glu Ser Ser Ala Ser
    2240            2245            2250

Val Ser Pro Val Ala Lys Val Ser Lys Phe Thr Leu Ser Ser Glu
    2255            2260            2265

Leu Glu Gly Gly Asp Tyr Pro Lys Glu Arg Glu Arg Thr Gly Gly
    2270            2275            2280

Gly Pro Gly Arg Pro Pro Asp Trp Thr Pro His Gly Thr Gly Ala
    2285            2290            2295

Pro Ala Glu Pro Thr Pro Thr His Ser Pro Cys Thr Pro Pro Asp
    2300            2305            2310

Thr Leu Pro Arg Pro Pro Gln Gly Arg Arg Ala Ala Gln Ser Trp
    2315            2320            2325

Ser Pro Arg Leu Glu Ser Pro Arg Ala Pro Thr Asn Pro Glu Pro
    2330            2335            2340

Ser Ala Thr Pro Pro Leu Asp Arg Ser Ser Val Gly Cys Leu
    2345            2350            2355

Ala Glu Ala Ser Ala Arg Phe Pro Ala Arg Thr Arg Asn Leu Ser
    2360            2365            2370

Gly Glu Pro Arg Thr Arg Gln Asp Ser Pro Lys Pro Ser Gly Ser
    2375            2380            2385

Gly Glu Pro Arg Ala His Pro His Gln Pro Glu Asp Arg Val Pro
    2390            2395            2400

Pro Asn Ala
    2405

<210> SEQ ID NO 56
<211> LENGTH: 443
<212> TYPE: PRT
<213> ORGANISM: Homo sapiens

<400> SEQUENCE: 56

Met Gln Lys Ala Thr Tyr Tyr Asp Ser Ser Ala Ile Tyr Gly Gly Tyr
1               5                   10                  15

Pro Tyr Gln Ala Ala Asn Gly Phe Ala Tyr Asn Ala Asn Gln Gln Pro
            20                  25                  30
```

```
Tyr Pro Ala Ser Ala Ala Leu Gly Ala Asp Gly Glu Tyr His Arg Pro
        35                  40                  45

Ala Cys Ser Leu Gln Ser Pro Ser Ser Ala Gly Gly His Pro Lys Ala
 50                      55                  60

His Glu Leu Ser Glu Ala Cys Leu Arg Thr Leu Ser Ala Pro Pro Ser
 65                  70                  75                  80

Gln Pro Pro Ser Leu Gly Glu Pro Pro Leu His Pro Pro Pro Pro Gln
                 85                  90                  95

Ala Ala Pro Pro Ala Pro Gln Pro Pro Gln Pro Ala Pro Gln Pro Pro
             100                 105                 110

Ala Pro Thr Pro Ala Ala Pro Pro Pro Ser Ser Ala Ser Pro Pro
             115                 120                 125

Gln Asn Ala Ser Asn Asn Pro Thr Pro Ala Asn Ala Ala Lys Ser Pro
             130                 135                 140

Leu Leu Asn Ser Pro Thr Val Ala Lys Gln Ile Phe Pro Trp Met Lys
145                 150                 155                 160

Glu Ser Arg Gln Asn Thr Lys Gln Lys Thr Ser Ser Ser Ser Ser Gly
                 165                 170                 175

Glu Ser Cys Ala Gly Asp Lys Ser Pro Pro Gly Gln Ala Ser Ser Lys
             180                 185                 190

Arg Ala Arg Thr Ala Tyr Thr Ser Ala Gln Leu Val Glu Leu Glu Lys
             195                 200                 205

Glu Phe His Phe Asn Arg Tyr Leu Cys Arg Pro Arg Arg Val Glu Met
             210                 215                 220

Ala Asn Leu Leu Asn Leu Thr Glu Arg Gln Ile Lys Ile Trp Phe Gln
225                 230                 235                 240

Asn Arg Arg Met Lys Tyr Lys Lys Asp Gln Lys Gly Lys Gly Met Leu
                 245                 250                 255

Thr Ser Ser Gly Gly Gln Ser Pro Ser Arg Ser Pro Val Pro Pro Gly
             260                 265                 270

Ala Gly Gly Tyr Leu Asn Ser Met His Ser Leu Val Asn Ser Val Pro
             275                 280                 285

Tyr Glu Pro Gln Ser Pro Pro Phe Ser Lys Pro Pro Gln Gly Thr
             290                 295                 300

Tyr Gly Leu Pro Pro Ala Ser Tyr Pro Ala Ser Leu Pro Ser Cys Ala
305                 310                 315                 320

Pro Pro Pro Pro Gln Lys Arg Tyr Thr Ala Ala Gly Ala Gly Ala
                 325                 330                 335

Gly Gly Thr Pro Asp Tyr Asp Pro His Ala His Gly Leu Gln Gly Asn
             340                 345                 350

Gly Ser Tyr Gly Thr Pro His Ile Gln Gly Ser Pro Val Phe Val Gly
             355                 360                 365

Gly Ser Tyr Val Glu Pro Met Ser Asn Ser Gly Pro Ala Leu Phe Gly
             370                 375                 380

Leu Thr His Leu Pro His Ala Ala Ser Gly Ala Met Asp Tyr Gly Gly
385                 390                 395                 400

Ala Gly Pro Leu Gly Ser Gly His His His Gly Pro Gly Pro Gly Glu
             405                 410                 415

Pro His Pro Thr Tyr Thr Asp Leu Thr Gly His His Pro Ser Gln Gly
             420                 425                 430

Arg Ile Gln Glu Ala Pro Lys Leu Thr His Leu
             435                 440
```

<210> SEQ ID NO 57
<211> LENGTH: 233
<212> TYPE: PRT
<213> ORGANISM: Homo sapiens

<400> SEQUENCE: 57

```
Met Ser Ser Tyr Phe Val Asn Pro Thr Phe Pro Gly Ser Leu Pro Ser
1               5                   10                  15

Gly Gln Asp Ser Phe Leu Gly Gln Leu Pro Leu Tyr Gln Ala Gly Tyr
                20                  25                  30

Asp Ala Leu Arg Pro Phe Pro Ala Ser Tyr Gly Ala Ser Ser Leu Pro
            35                  40                  45

Asp Lys Thr Tyr Thr Ser Pro Cys Phe Tyr Gln Gln Ser Asn Ser Val
50                  55                  60

Leu Ala Cys Asn Arg Ala Ser Tyr Glu Tyr Gly Ala Ser Cys Phe Tyr
65                  70                  75                  80

Ser Asp Lys Asp Leu Ser Gly Ala Ser Pro Gly Ser Gly Lys Gln
                85                  90                  95

Arg Gly Pro Gly Asp Tyr Leu His Phe Ser Pro Glu Gln Tyr Lys
                100                 105                 110

Pro Asp Ser Ser Gly Gln Gly Lys Ala Leu His Asp Glu Gly Ala
            115                 120                 125

Asp Arg Lys Tyr Thr Ser Pro Val Tyr Pro Trp Met Gln Arg Met Asn
130                 135                 140

Ser Cys Ala Gly Ala Val Tyr Gly Ser His Gly Arg Arg Gly Arg Gln
145                 150                 155                 160

Thr Tyr Thr Arg Tyr Gln Thr Leu Glu Leu Glu Lys Glu Phe His Phe
                165                 170                 175

Asn Arg Tyr Leu Thr Arg Arg Arg Ile Glu Ile Ala Asn Ala Leu
                180                 185                 190

Cys Leu Thr Glu Arg Gln Ile Lys Ile Trp Phe Gln Asn Arg Arg Met
            195                 200                 205

Lys Trp Lys Lys Glu Asn Lys Leu Ile Asn Ser Thr Gln Pro Ser Gly
        210                 215                 220

Glu Asp Ser Glu Ala Lys Ala Gly Glu
225                 230
```

<210> SEQ ID NO 58
<211> LENGTH: 431
<212> TYPE: PRT
<213> ORGANISM: Homo sapiens

<400> SEQUENCE: 58

```
Met Gln Lys Ala Thr Tyr Tyr Asp Asn Ala Ala Ala Leu Phe Gly
1               5                   10                  15

Gly Tyr Ser Ser Tyr Pro Gly Ser Asn Gly Phe Gly Phe Asp Val Pro
                20                  25                  30

Pro Gln Pro Pro Phe Gln Ala Ala Thr His Leu Glu Gly Asp Tyr Gln
            35                  40                  45

Arg Ser Ala Cys Ser Leu Gln Ser Leu Gly Asn Ala Ala Pro His Ala
50                  55                  60

Lys Ser Lys Glu Leu Asn Gly Ser Cys Met Arg Pro Gly Leu Ala Pro
65                  70                  75                  80

Glu Pro Leu Ser Ala Pro Pro Gly Ser Pro Pro Ser Ala Ala Pro
                85                  90                  95
```

```
Thr Ser Ala Thr Ser Asn Ser Ser Asn Gly Gly Pro Ser Lys Ser
            100                 105                 110

Gly Pro Pro Lys Cys Gly Pro Gly Thr Asn Ser Thr Leu Thr Lys Gln
        115                 120                 125

Ile Phe Pro Trp Met Lys Glu Ser Arg Gln Thr Ser Lys Leu Lys Asn
        130                 135                 140

Asn Ser Pro Gly Thr Ala Glu Gly Cys Gly Gly Gly Gly Gly Gly Gly
145                 150                 155                 160

Gly Gly Gly Gly Ser Gly Gly Ser Gly Gly Gly Gly Gly Gly Gly Gly
                165                 170                 175

Gly Gly Asp Lys Ser Pro Pro Gly Ser Ala Ala Ser Lys Arg Ala Arg
        180                 185                 190

Thr Ala Tyr Thr Ser Ala Gln Leu Val Glu Leu Glu Lys Glu Phe His
        195                 200                 205

Phe Asn Arg Tyr Leu Cys Arg Pro Arg Arg Val Glu Met Ala Asn Leu
        210                 215                 220

Leu Asn Leu Ser Glu Arg Gln Ile Lys Ile Trp Phe Gln Asn Arg Arg
225                 230                 235                 240

Met Lys Tyr Lys Lys Asp Gln Lys Ala Lys Gly Leu Ala Ser Ser Ser
                245                 250                 255

Gly Gly Pro Ser Pro Ala Gly Ser Pro Pro Gln Pro Met Gln Ser Thr
        260                 265                 270

Ala Gly Phe Met Asn Ala Leu His Ser Met Thr Pro Ser Tyr Glu Ser
        275                 280                 285

Pro Ser Pro Pro Ala Phe Gly Lys Ala His Gln Asn Ala Tyr Ala Leu
        290                 295                 300

Pro Ser Asn Tyr Gln Pro Pro Leu Lys Gly Cys Gly Ala Pro Gln Lys
305                 310                 315                 320

Tyr Pro Pro Thr Pro Ala Pro Glu Tyr Glu Pro His Val Leu Gln Ala
                325                 330                 335

Asn Gly Gly Ala Tyr Gly Thr Pro Thr Met Gln Gly Ser Pro Val Tyr
        340                 345                 350

Val Gly Gly Gly Gly Tyr Ala Asp Pro Leu Pro Pro Pro Ala Gly Pro
        355                 360                 365

Ser Leu Tyr Gly Leu Asn His Leu Ser His His Pro Ser Gly Asn Leu
        370                 375                 380

Asp Tyr Asn Gly Ala Pro Pro Met Ala Pro Ser Gln His His Gly Pro
385                 390                 395                 400

Cys Glu Pro His Pro Thr Tyr Thr Asp Leu Ser Ser His His Ala Pro
                405                 410                 415

Pro Pro Gln Gly Arg Ile Gln Glu Ala Pro Lys Leu Thr His Leu
        420                 425                 430

<210> SEQ ID NO 59
<211> LENGTH: 269
<212> TYPE: PRT
<213> ORGANISM: Homo sapiens

<400> SEQUENCE: 59

Met Ser Ser Tyr Phe Val Asn Ser Phe Ser Gly Arg Tyr Pro Asn Gly
1               5                   10                  15

Pro Asp Tyr Gln Leu Leu Asn Tyr Gly Ser Gly Ser Ser Leu Ser Gly
            20                  25                  30

Ser Tyr Arg Asp Pro Ala Ala Met His Thr Gly Ser Tyr Gly Tyr Asn
        35                  40                  45
```

```
Tyr Asn Gly Met Asp Leu Ser Val Asn Arg Ser Ser Ala Ser Ser Ser
         50                  55                  60

His Phe Gly Ala Val Gly Glu Ser Ser Arg Ala Phe Pro Ala Pro Ala
 65                  70                  75                  80

Gln Glu Pro Arg Phe Arg Gln Ala Ala Ser Ser Cys Ser Leu Ser Ser
                 85                  90                  95

Pro Glu Ser Leu Pro Cys Thr Asn Gly Asp Ser His Gly Ala Lys Pro
                100                 105                 110

Ser Ala Ser Ser Pro Ser Asp Gln Ala Thr Ser Ala Ser Ser Ser Ala
            115                 120                 125

Asn Phe Thr Glu Ile Asp Glu Ala Ser Ala Ser Glu Pro Glu Glu
        130                 135                 140

Ala Ala Ser Gln Leu Ser Ser Pro Ser Leu Ala Arg Ala Gln Pro Glu
145                 150                 155                 160

Pro Met Ala Thr Ser Thr Ala Ala Pro Glu Gly Gln Thr Pro Gln Ile
                165                 170                 175

Phe Pro Trp Met Arg Lys Leu His Ile Ser His Asp Met Thr Gly Pro
                180                 185                 190

Asp Gly Lys Arg Ala Arg Thr Ala Tyr Thr Arg Tyr Gln Thr Leu Glu
            195                 200                 205

Leu Glu Lys Glu Phe His Phe Asn Arg Tyr Leu Thr Arg Arg Arg Arg
210                 215                 220

Ile Glu Ile Ala His Ala Leu Cys Leu Ser Glu Arg Gln Ile Lys Ile
225                 230                 235                 240

Trp Phe Gln Asn Arg Arg Met Lys Trp Lys Lys Asp Asn Lys Leu Lys
                245                 250                 255

Ser Met Ser Leu Ala Thr Ala Gly Ser Ala Phe Gln Pro
            260                 265

<210> SEQ ID NO 60
<211> LENGTH: 224
<212> TYPE: PRT
<213> ORGANISM: Homo sapiens

<400> SEQUENCE: 60

Met Ser Ser Tyr Phe Val Asn Ser Thr Phe Pro Val Thr Leu Ala Ser
 1               5                  10                  15

Gly Gln Glu Ser Phe Leu Gly Gln Leu Pro Leu Tyr Ser Ser Gly Tyr
                20                  25                  30

Ala Asp Pro Leu Arg His Tyr Pro Ala Pro Tyr Gly Pro Gly Pro Gly
             35                  40                  45

Gln Asp Lys Gly Phe Ala Thr Ser Ser Tyr Tyr Pro Pro Ala Gly Gly
         50                  55                  60

Gly Tyr Gly Arg Ala Ala Pro Cys Asp Tyr Gly Pro Ala Pro Ala Phe
 65                  70                  75                  80

Tyr Arg Glu Lys Glu Ser Ala Cys Ala Leu Ser Gly Ala Asp Glu Gln
                 85                  90                  95

Pro Pro Phe His Pro Glu Pro Arg Lys Ser Asp Cys Ala Gln Asp Lys
                100                 105                 110

Ser Val Phe Gly Glu Thr Glu Gln Lys Cys Ser Thr Pro Val Tyr
             115                 120                 125

Pro Trp Met Gln Arg Met Asn Ser Cys Asn Ser Ser Ser Phe Gly Pro
            130                 135                 140

Ser Gly Arg Arg Gly Arg Gln Thr Tyr Thr Arg Tyr Gln Thr Leu Glu
```

```
145                 150                 155                 160
Leu Glu Lys Glu Phe His Tyr Asn Arg Tyr Leu Thr Arg Arg Arg
                165                 170                 175

Ile Glu Ile Ala His Ala Leu Cys Leu Thr Glu Arg Gln Ile Lys Ile
            180                 185                 190

Trp Phe Gln Asn Arg Arg Met Lys Trp Lys Lys Glu Lys Leu Leu
            195                 200                 205

Ser Ala Ser Gln Leu Ser Ala Glu Glu Glu Glu Lys Gln Ala Glu
    210                 215                 220
```

<210> SEQ ID NO 61
<211> LENGTH: 1091
<212> TYPE: PRT
<213> ORGANISM: Homo sapiens

<400> SEQUENCE: 61

```
Met Ala Ala Ala Gly Gln Leu Cys Leu Leu Tyr Leu Ser Ala Gly Leu
1               5                   10                  15

Leu Ser Arg Leu Gly Ala Ala Phe Asn Leu Asp Thr Arg Glu Asp Asn
                20                  25                  30

Val Ile Arg Lys Tyr Gly Asp Pro Gly Ser Leu Phe Gly Phe Ser Leu
            35                  40                  45

Ala Met His Trp Gln Leu Gln Pro Glu Asp Lys Arg Leu Leu Leu Val
        50                  55                  60

Gly Ala Pro Arg Ala Glu Ala Leu Pro Leu Gln Arg Ala Asn Arg Thr
65                  70                  75                  80

Gly Gly Leu Tyr Ser Cys Asp Ile Thr Ala Arg Gly Pro Cys Thr Arg
                85                  90                  95

Ile Glu Phe Asp Asn Asp Ala Asp Pro Thr Ser Glu Ser Lys Glu Asp
            100                 105                 110

Gln Trp Met Gly Val Thr Val Gln Ser Gln Gly Pro Gly Gly Lys Val
        115                 120                 125

Val Thr Cys Ala His Arg Tyr Glu Lys Arg Gln His Val Asn Thr Lys
130                 135                 140

Gln Glu Ser Arg Asp Ile Phe Gly Arg Cys Tyr Val Leu Ser Gln Asn
145                 150                 155                 160

Leu Arg Ile Glu Asp Asp Met Asp Gly Gly Asp Trp Ser Phe Cys Asp
                165                 170                 175

Gly Arg Leu Arg Gly His Glu Lys Phe Gly Ser Cys Gln Gln Gly Val
            180                 185                 190

Ala Ala Thr Phe Thr Lys Asp Phe His Tyr Ile Val Phe Gly Ala Pro
        195                 200                 205

Gly Thr Tyr Asn Trp Lys Gly Ile Val Arg Val Glu Gln Lys Asn Asn
    210                 215                 220

Thr Phe Phe Asp Met Asn Ile Phe Glu Asp Gly Pro Tyr Glu Val Gly
225                 230                 235                 240

Gly Glu Thr Glu His Asp Glu Ser Leu Val Pro Val Pro Ala Asn Ser
                245                 250                 255

Tyr Leu Gly Phe Ser Leu Asp Ser Gly Lys Gly Ile Val Ser Lys Asp
            260                 265                 270

Glu Ile Thr Phe Val Ser Gly Ala Pro Arg Ala Asn His Ser Gly Ala
        275                 280                 285

Val Val Leu Leu Lys Arg Asp Met Lys Ser Ala His Leu Leu Pro Glu
    290                 295                 300
```

```
His Ile Phe Asp Gly Glu Gly Leu Ala Ser Ser Phe Gly Tyr Asp Val
305                 310                 315                 320

Ala Val Val Asp Leu Asn Lys Asp Gly Trp Gln Asp Ile Val Ile Gly
            325                 330                 335

Ala Pro Gln Tyr Phe Asp Arg Asp Gly Glu Val Gly Gly Ala Val Tyr
        340                 345                 350

Val Tyr Met Asn Gln Gln Gly Arg Trp Asn Asn Val Lys Pro Ile Arg
    355                 360                 365

Leu Asn Gly Thr Lys Asp Ser Met Phe Gly Ile Ala Val Lys Asn Ile
370                 375                 380

Gly Asp Ile Asn Gln Asp Gly Tyr Pro Asp Ile Ala Val Gly Ala Pro
385                 390                 395                 400

Tyr Asp Asp Leu Gly Lys Val Phe Ile Tyr His Gly Ser Ala Asn Gly
            405                 410                 415

Ile Asn Thr Lys Pro Thr Gln Val Leu Lys Gly Ile Ser Pro Tyr Phe
        420                 425                 430

Gly Tyr Ser Ile Ala Gly Asn Met Asp Leu Asp Arg Asn Ser Tyr Pro
    435                 440                 445

Asp Val Ala Val Gly Ser Leu Ser Asp Ser Val Thr Ile Phe Arg Ser
450                 455                 460

Arg Pro Val Ile Asn Ile Gln Lys Thr Ile Thr Val Thr Pro Asn Arg
465                 470                 475                 480

Ile Asp Leu Arg Gln Lys Thr Ala Cys Gly Ala Pro Ser Gly Ile Cys
            485                 490                 495

Leu Gln Val Lys Ser Cys Phe Glu Tyr Thr Ala Asn Pro Ala Gly Tyr
        500                 505                 510

Asn Pro Ser Ile Ser Ile Val Gly Thr Leu Glu Ala Glu Lys Glu Arg
    515                 520                 525

Arg Lys Ser Gly Leu Ser Ser Arg Val Gln Phe Arg Asn Gln Gly Ser
530                 535                 540

Glu Pro Lys Tyr Thr Gln Glu Leu Thr Leu Lys Arg Gln Lys Gln Lys
545                 550                 555                 560

Val Cys Met Glu Glu Thr Leu Trp Leu Gln Asp Asn Ile Arg Asp Lys
            565                 570                 575

Leu Arg Pro Ile Pro Ile Thr Ala Ser Val Glu Ile Gln Glu Pro Ser
        580                 585                 590

Ser Arg Arg Arg Val Asn Ser Leu Pro Glu Val Leu Pro Ile Leu Asn
    595                 600                 605

Ser Asp Glu Pro Lys Thr Ala His Ile Asp Val His Phe Leu Lys Glu
610                 615                 620

Gly Cys Gly Asp Asp Asn Val Cys Asn Ser Asn Leu Lys Leu Glu Tyr
625                 630                 635                 640

Lys Phe Cys Thr Arg Glu Gly Asn Gln Asp Lys Phe Ser Tyr Leu Pro
            645                 650                 655

Ile Gln Lys Gly Val Pro Glu Leu Val Leu Lys Asp Gln Lys Asp Ile
        660                 665                 670

Ala Leu Glu Ile Thr Val Thr Asn Ser Pro Ser Asn Pro Arg Asn Pro
    675                 680                 685

Thr Lys Asp Gly Asp Asp Ala His Glu Ala Lys Leu Ile Ala Thr Phe
690                 695                 700

Pro Asp Thr Leu Thr Tyr Ser Ala Tyr Arg Glu Leu Arg Ala Phe Pro
705                 710                 715                 720

Glu Lys Gln Leu Ser Cys Val Ala Asn Gln Asn Gly Ser Gln Ala Asp
```

```
                    725                 730                 735
Cys Glu Leu Gly Asn Pro Phe Lys Arg Asn Ser Asn Val Thr Phe Tyr
            740                 745                 750

Leu Val Leu Ser Thr Thr Glu Val Thr Phe Asp Thr Pro Asp Leu Asp
            755                 760                 765

Ile Asn Leu Lys Leu Glu Thr Thr Ser Asn Gln Asp Asn Leu Ala Pro
            770                 775                 780

Ile Thr Ala Lys Ala Lys Val Val Ile Glu Leu Leu Ser Val Ser
785                 790                 795                 800

Gly Val Ala Lys Pro Ser Gln Val Tyr Phe Gly Gly Thr Val Gly
                805                 810                 815

Glu Gln Ala Met Lys Ser Glu Asp Glu Val Gly Ser Leu Ile Glu Tyr
            820                 825                 830

Glu Phe Arg Val Ile Asn Leu Gly Lys Pro Leu Thr Asn Leu Gly Thr
            835                 840                 845

Ala Thr Leu Asn Ile Gln Trp Pro Lys Glu Ile Ser Asn Gly Lys Trp
850                 855                 860

Leu Leu Tyr Leu Val Lys Val Glu Ser Lys Gly Leu Glu Lys Val Thr
865                 870                 875                 880

Cys Glu Pro Gln Lys Glu Ile Asn Ser Leu Asn Leu Thr Glu Ser His
                885                 890                 895

Asn Ser Arg Lys Lys Arg Glu Ile Thr Glu Lys Gln Ile Asp Asp Asn
                900                 905                 910

Arg Lys Phe Ser Leu Phe Ala Glu Arg Lys Tyr Gln Thr Leu Asn Cys
                915                 920                 925

Ser Val Asn Val Asn Cys Val Asn Ile Arg Cys Pro Leu Arg Gly Leu
930                 935                 940

Asp Ser Lys Ala Ser Leu Ile Leu Arg Ser Arg Leu Trp Asn Ser Thr
945                 950                 955                 960

Phe Leu Glu Glu Tyr Ser Lys Leu Asn Tyr Leu Asp Ile Leu Met Arg
                965                 970                 975

Ala Phe Ile Asp Val Thr Ala Ala Glu Asn Ile Arg Leu Pro Asn
            980                 985                 990

Ala Gly Thr Gln Val Arg Val Thr Val Phe Pro Ser Lys Thr Val Ala
            995                 1000                1005

Gln Tyr Ser Gly Val Pro Trp Trp Ile Ile Leu Val Ala Ile Leu
            1010                1015                1020

Ala Gly Ile Leu Met Leu Ala Leu Leu Val Phe Ile Leu Trp Lys
            1025                1030                1035

Cys Gly Phe Phe Lys Arg Ser Arg Tyr Asp Asp Ser Val Pro Arg
            1040                1045                1050

Tyr His Ala Val Arg Ile Arg Lys Glu Glu Arg Glu Ile Lys Asp
            1055                1060                1065

Glu Lys Tyr Ile Asp Asn Leu Glu Lys Lys Gln Trp Ile Thr Lys
            1070                1075                1080

Trp Asn Glu Asn Glu Ser Tyr Ser
            1085                1090
```

<210> SEQ ID NO 62
<211> LENGTH: 976
<212> TYPE: PRT
<213> ORGANISM: Homo sapiens

<400> SEQUENCE: 62

```
Met Arg Gly Ala Arg Gly Ala Trp Asp Phe Leu Cys Val Leu Leu Leu
1               5                   10                  15
Leu Leu Arg Val Gln Thr Gly Ser Ser Gln Pro Ser Val Ser Pro Gly
            20                  25                  30
Glu Pro Ser Pro Ser Ile His Pro Gly Lys Ser Asp Leu Ile Val
        35                  40                  45
Arg Val Gly Asp Glu Ile Arg Leu Leu Cys Thr Asp Pro Gly Phe Val
    50                  55                  60
Lys Trp Thr Phe Glu Ile Leu Asp Glu Thr Asn Glu Asn Lys Gln Asn
65                  70                  75                  80
Glu Trp Ile Thr Glu Lys Ala Glu Ala Thr Asn Thr Gly Lys Tyr Thr
                85                  90                  95
Cys Thr Asn Lys His Gly Leu Ser Asn Ser Ile Tyr Val Phe Val Arg
            100                 105                 110
Asp Pro Ala Lys Leu Phe Leu Val Asp Arg Ser Leu Tyr Gly Lys Glu
            115                 120                 125
Asp Asn Asp Thr Leu Val Arg Cys Pro Leu Thr Asp Pro Glu Val Thr
145                 150                 155                 160
Asn Tyr Ser Leu Lys Gly Cys Gln Gly Lys Pro Leu Pro Lys Asp Leu
145                 150                 155                 160
Arg Phe Ile Pro Asp Pro Lys Ala Gly Ile Met Ile Lys Ser Val Lys
                165                 170                 175
Arg Ala Tyr His Arg Leu Cys Leu His Cys Ser Val Asp Gln Glu Gly
            180                 185                 190
Lys Ser Val Leu Ser Glu Lys Phe Ile Leu Lys Val Arg Pro Ala Phe
    195                 200                 205
Lys Ala Val Pro Val Val Ser Val Ser Lys Ala Ser Tyr Leu Leu Arg
210                 215                 220
Glu Gly Glu Glu Phe Thr Val Thr Cys Thr Ile Lys Asp Val Ser Ser
225                 230                 235                 240
Ser Val Tyr Ser Thr Trp Lys Arg Glu Asn Ser Gln Thr Lys Leu Gln
                245                 250                 255
Glu Lys Tyr Asn Ser Trp His His Gly Asp Phe Asn Tyr Glu Arg Gln
            260                 265                 270
Ala Thr Leu Thr Ile Ser Ser Ala Arg Val Asn Asp Ser Gly Val Phe
        275                 280                 285
Met Cys Tyr Ala Asn Asn Thr Phe Gly Ser Ala Asn Val Thr Thr Thr
    290                 295                 300
Leu Glu Val Val Asp Lys Gly Phe Ile Asn Ile Phe Pro Met Ile Asn
305                 310                 315                 320
Thr Thr Val Phe Val Asn Asp Gly Glu Asn Val Asp Leu Ile Val Glu
                325                 330                 335
Tyr Glu Ala Phe Pro Lys Pro Glu His Gln Gln Trp Ile Tyr Met Asn
            340                 345                 350
Arg Thr Phe Thr Asp Lys Trp Glu Asp Tyr Pro Lys Ser Glu Asn Glu
        355                 360                 365
Ser Asn Ile Arg Tyr Val Ser Glu Leu His Leu Thr Arg Leu Lys Gly
    370                 375                 380
Thr Glu Gly Gly Thr Tyr Thr Phe Leu Val Ser Asn Ser Asp Val Asn
385                 390                 395                 400
Ala Ala Ile Ala Phe Asn Val Tyr Val Asn Thr Lys Pro Glu Ile Leu
                405                 410                 415
Thr Tyr Asp Arg Leu Val Asn Gly Met Leu Gln Cys Val Ala Ala Gly
```

-continued

```
            420                 425                 430
Phe Pro Glu Pro Thr Ile Asp Trp Tyr Phe Cys Pro Gly Thr Glu Gln
            435                 440                 445
Arg Cys Ser Ala Ser Val Leu Pro Val Asp Val Gln Thr Leu Asn Ser
450                 455                 460
Ser Gly Pro Pro Phe Gly Lys Leu Val Val Gln Ser Ser Ile Asp Ser
465                 470                 475                 480
Ser Ala Phe Lys His Asn Gly Thr Val Glu Cys Lys Ala Tyr Asn Asp
                485                 490                 495
Val Gly Lys Thr Ser Ala Tyr Phe Asn Phe Ala Phe Lys Gly Asn Asn
                500                 505                 510
Lys Glu Gln Ile His Pro His Thr Leu Phe Thr Pro Leu Leu Ile Gly
                515                 520                 525
Phe Val Ile Val Ala Gly Met Met Cys Ile Ile Val Met Ile Leu Thr
                530                 535                 540
Tyr Lys Tyr Leu Gln Lys Pro Met Tyr Glu Val Gln Trp Lys Val Val
545                 550                 555                 560
Glu Glu Ile Asn Gly Asn Asn Tyr Val Tyr Ile Asp Pro Thr Gln Leu
                565                 570                 575
Pro Tyr Asp His Lys Trp Glu Phe Pro Arg Asn Arg Leu Ser Phe Gly
                580                 585                 590
Lys Thr Leu Gly Ala Gly Ala Phe Gly Lys Val Val Glu Ala Thr Ala
                595                 600                 605
Tyr Gly Leu Ile Lys Ser Asp Ala Ala Met Thr Val Ala Val Lys Met
                610                 615                 620
Leu Lys Pro Ser Ala His Leu Thr Glu Arg Glu Ala Leu Met Ser Glu
625                 630                 635                 640
Leu Lys Val Leu Ser Tyr Leu Gly Asn His Met Asn Ile Val Asn Leu
                645                 650                 655
Leu Gly Ala Cys Thr Ile Gly Gly Pro Thr Leu Val Ile Thr Glu Tyr
                660                 665                 670
Cys Cys Tyr Gly Asp Leu Leu Asn Phe Leu Arg Arg Lys Arg Asp Ser
                675                 680                 685
Phe Ile Cys Ser Lys Gln Glu Asp His Ala Glu Ala Ala Leu Tyr Lys
                690                 695                 700
Asn Leu Leu His Ser Lys Glu Ser Ser Cys Ser Asp Ser Thr Asn Glu
705                 710                 715                 720
Tyr Met Asp Met Lys Pro Gly Val Ser Tyr Val Val Pro Thr Lys Ala
                725                 730                 735
Asp Lys Arg Arg Ser Val Arg Ile Gly Ser Tyr Ile Glu Arg Asp Val
                740                 745                 750
Thr Pro Ala Ile Met Glu Asp Asp Glu Leu Ala Leu Asp Leu Glu Asp
                755                 760                 765
Leu Leu Ser Phe Ser Tyr Gln Val Ala Lys Gly Met Ala Phe Leu Ala
                770                 775                 780
Ser Lys Asn Cys Ile His Arg Asp Leu Ala Ala Arg Asn Ile Leu Leu
785                 790                 795                 800
Thr His Gly Arg Ile Thr Lys Ile Cys Asp Phe Gly Leu Ala Arg Asp
                805                 810                 815
Ile Lys Asn Asp Ser Asn Tyr Val Val Lys Gly Asn Ala Arg Leu Pro
                820                 825                 830
Val Lys Trp Met Ala Pro Glu Ser Ile Phe Asn Cys Val Tyr Thr Phe
                835                 840                 845
```

-continued

```
Glu Ser Asp Val Trp Ser Tyr Gly Ile Phe Leu Trp Glu Leu Phe Ser
            850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
        915                 920                 925

Ser Glu Ser Thr Asn His Ile Tyr Ser Asn Leu Ala Asn Cys Ser Pro
    930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975

<210> SEQ ID NO 63
<211> LENGTH: 390
<212> TYPE: PRT
<213> ORGANISM: Homo sapiens

<400> SEQUENCE: 63

Met Ala Gln Arg Tyr Asp Asp Leu Pro His Tyr Gly Gly Met Asp Gly
1               5                   10                  15

Val Gly Ile Pro Ser Thr Met Tyr Gly Asp Pro His Ala Ala Arg Ser
            20                  25                  30

Met Gln Pro Val His His Leu Asn His Gly Pro Pro Leu His Ser His
        35                  40                  45

Gln Tyr Pro His Thr Ala His Thr Asn Ala Met Ala Pro Ser Met Gly
    50                  55                  60

Ser Ser Val Asn Asp Ala Leu Lys Arg Asp Lys Asp Ala Ile Tyr Gly
65                  70                  75                  80

His Pro Leu Phe Pro Leu Leu Ala Leu Ile Phe Glu Lys Cys Glu Leu
                85                  90                  95

Ala Thr Cys Thr Pro Arg Glu Pro Gly Val Ala Gly Gly Asp Val Cys
            100                 105                 110

Ser Ser Glu Ser Phe Asn Glu Asp Ile Ala Val Phe Ala Lys Gln Ile
        115                 120                 125

Arg Ala Glu Lys Pro Leu Phe Ser Ser Asn Pro Glu Leu Asp Asn Leu
    130                 135                 140

Met Ile Gln Ala Ile Gln Val Leu Arg Phe His Leu Leu Glu Leu Glu
145                 150                 155                 160

Lys Val His Glu Leu Cys Asp Asn Phe Cys His Arg Tyr Ile Ser Cys
                165                 170                 175

Leu Lys Gly Lys Met Pro Ile Asp Leu Val Ile Asp Asp Arg Glu Gly
            180                 185                 190

Gly Ser Lys Ser Asp Ser Glu Asp Ile Thr Arg Ser Ala Asn Leu Thr
        195                 200                 205

Asp Gln Pro Ser Trp Asn Arg Asp His Asp Asp Thr Ala Ser Thr Arg
    210                 215                 220

Ser Gly Gly Thr Pro Gly Pro Ser Ser Gly Gly His Thr Ser His Ser
225                 230                 235                 240

Gly Asp Asn Ser Ser Glu Gln Gly Asp Gly Leu Asp Asn Ser Val Ala
```

```
                    245                 250                 255
Ser Pro Ser Thr Gly Asp Asp Asp Pro Asp Lys Asp Lys Lys Arg
            260                 265                 270

His Lys Lys Arg Gly Ile Phe Pro Lys Val Ala Thr Asn Ile Met Arg
        275                 280                 285

Ala Trp Leu Phe Gln His Leu Thr His Pro Tyr Pro Ser Glu Glu Gln
    290                 295                 300

Lys Lys Gln Leu Ala Gln Asp Thr Gly Leu Thr Ile Leu Gln Val Asn
305                 310                 315                 320

Asn Trp Phe Ile Asn Ala Arg Arg Ile Val Gln Pro Met Ile Asp
                325                 330                 335

Gln Ser Asn Arg Ala Val Ser Gln Gly Thr Pro Tyr Asn Pro Asp Gly
            340                 345                 350

Gln Pro Met Gly Gly Phe Val Met Asp Gly Gln His Met Gly Ile
            355                 360                 365

Arg Ala Pro Gly Pro Met Ser Gly Met Gly Met Asn Met Gly Met Glu
        370                 375                 380

Gly Gln Trp His Tyr Met
385                 390

<210> SEQ ID NO 64
<211> LENGTH: 464
<212> TYPE: PRT
<213> ORGANISM: Homo sapiens

<400> SEQUENCE: 64

Met Pro Ser Cys Ser Thr Ser Thr Met Pro Gly Met Ile Cys Lys Asn
1               5                   10                  15

Pro Asp Leu Glu Phe Asp Ser Leu Gln Pro Cys Phe Tyr Pro Asp Glu
            20                  25                  30

Asp Asp Phe Tyr Phe Gly Gly Pro Asp Ser Thr Pro Pro Gly Glu Asp
        35                  40                  45

Ile Trp Lys Lys Phe Glu Leu Leu Pro Thr Pro Pro Leu Ser Pro Ser
50                  55                  60

Arg Gly Phe Ala Glu His Ser Ser Glu Pro Pro Ser Trp Val Thr Glu
65                  70                  75                  80

Met Leu Leu Glu Asn Glu Leu Trp Gly Ser Pro Ala Glu Glu Asp Ala
                85                  90                  95

Phe Gly Leu Gly Gly Leu Gly Gly Leu Thr Pro Asn Pro Val Ile Leu
            100                 105                 110

Gln Asp Cys Met Trp Ser Gly Phe Ser Ala Arg Glu Lys Leu Glu Arg
        115                 120                 125

Ala Val Ser Glu Lys Leu Gln His Gly Arg Gly Pro Pro Thr Ala Gly
    130                 135                 140

Ser Thr Ala Gln Ser Pro Gly Ala Gly Ala Ala Ser Pro Ala Gly Arg
145                 150                 155                 160

Gly His Gly Gly Ala Ala Gly Ala Gly Arg Ala Gly Ala Ala Leu Pro
                165                 170                 175

Ala Glu Leu Ala His Pro Ala Ala Glu Cys Val Asp Pro Ala Val Val
            180                 185                 190

Phe Pro Phe Pro Val Asn Lys Arg Glu Pro Ala Pro Val Pro Ala Ala
        195                 200                 205

Pro Ala Ser Ala Pro Ala Ala Gly Pro Ala Val Ala Ser Gly Ala Gly
    210                 215                 220
```

Ile Ala Ala Pro Ala Gly Ala Pro Gly Val Ala Pro Arg Pro Gly
225                 230                 235                 240

Gly Arg Gln Thr Ser Gly Gly Asp His Lys Ala Leu Ser Thr Ser Gly
            245                 250                 255

Glu Asp Thr Leu Ser Asp Ser Asp Glu Asp Glu Glu Glu Asp
        260                 265                 270

Glu Glu Glu Glu Ile Asp Val Val Thr Val Glu Lys Arg Arg Ser Ser
        275                 280                 285

Ser Asn Thr Lys Ala Val Thr Thr Phe Thr Ile Thr Val Arg Pro Lys
    290                 295                 300

Asn Ala Ala Leu Gly Pro Gly Arg Ala Gln Ser Ser Glu Leu Ile Leu
305                 310                 315                 320

Lys Arg Cys Leu Pro Ile His Gln Gln His Asn Tyr Ala Ala Pro Ser
                325                 330                 335

Pro Tyr Val Glu Ser Glu Asp Ala Pro Pro Gln Lys Lys Ile Lys Ser
                340                 345                 350

Glu Ala Ser Pro Arg Pro Leu Lys Ser Val Ile Pro Pro Lys Ala Lys
        355                 360                 365

Ser Leu Ser Pro Arg Asn Ser Asp Ser Glu Asp Ser Glu Arg Arg Arg
    370                 375                 380

Asn His Asn Ile Leu Glu Arg Gln Arg Arg Asn Asp Leu Arg Ser Ser
385                 390                 395                 400

Phe Leu Thr Leu Arg Asp His Val Pro Glu Leu Val Lys Asn Glu Lys
                405                 410                 415

Ala Ala Lys Val Val Ile Leu Lys Lys Ala Thr Glu Tyr Val His Ser
            420                 425                 430

Leu Gln Ala Glu Glu His Gln Leu Leu Leu Glu Lys Glu Lys Leu Gln
        435                 440                 445

Ala Arg Gln Gln Gln Leu Leu Lys Ile Glu His Ala Arg Thr Cys
        450                 455                 460

<210> SEQ ID NO 65
<211> LENGTH: 462
<212> TYPE: PRT
<213> ORGANISM: Homo sapiens

<400> SEQUENCE: 65

Met Gln Leu Arg Lys Met Gln Thr Val Lys Lys Glu Gln Ala Ser Leu
1               5                   10                  15

Asp Ala Ser Ser Asn Val Asp Lys Met Met Val Leu Asn Ser Ala Leu
            20                  25                  30

Thr Glu Val Ser Glu Asp Ser Thr Thr Gly Glu Glu Leu Leu Leu Ser
        35                  40                  45

Glu Gly Ser Val Gly Lys Asn Lys Ser Ser Ala Cys Arg Arg Lys Arg
    50                  55                  60

Glu Phe Ile Pro Asp Glu Lys Lys Asp Ala Met Tyr Trp Glu Lys Arg
65                  70                  75                  80

Arg Lys Asn Asn Glu Ala Ala Lys Arg Ser Arg Glu Lys Arg Arg Leu
                85                  90                  95

Asn Asp Leu Val Leu Glu Asn Lys Leu Ile Ala Leu Gly Glu Glu Asn
            100                 105                 110

Ala Thr Leu Lys Ala Glu Leu Leu Ser Leu Lys Leu Lys Phe Gly Leu
        115                 120                 125

Ile Ser Ser Thr Ala Tyr Ala Gln Glu Ile Gln Lys Leu Ser Asn Ser
    130                 135                 140

-continued

```
Thr Ala Val Tyr Phe Gln Asp Tyr Gln Thr Ser Lys Ser Asn Val Ser
145                 150                 155                 160

Ser Phe Val Asp Glu His Glu Pro Ser Met Val Ser Ser Cys Ile
            165                 170                 175

Ser Val Ile Lys His Ser Pro Gln Ser Ser Leu Ser Asp Val Ser Glu
            180                 185                 190

Val Ser Ser Val Glu His Thr Gln Glu Ser Ser Val Gln Gly Ser Cys
            195                 200                 205

Arg Ser Pro Glu Asn Lys Phe Gln Ile Ile Lys Gln Glu Pro Met Glu
            210                 215                 220

Leu Glu Ser Tyr Thr Arg Glu Pro Arg Asp Asp Arg Gly Ser Tyr Thr
225                 230                 235                 240

Ala Ser Ile Tyr Gln Asn Tyr Met Gly Asn Ser Phe Ser Gly Tyr Ser
                245                 250                 255

His Ser Pro Pro Leu Leu Gln Val Asn Arg Ser Ser Ser Asn Ser Pro
            260                 265                 270

Arg Thr Ser Glu Thr Asp Asp Gly Val Val Gly Lys Ser Ser Asp Gly
            275                 280                 285

Glu Asp Glu Gln Gln Val Pro Lys Gly Pro Ile His Ser Pro Val Glu
290                 295                 300

Leu Lys His Val His Ala Thr Val Val Lys Val Pro Glu Val Asn Ser
305                 310                 315                 320

Ser Ala Leu Pro His Lys Leu Arg Ile Lys Ala Lys Ala Met Gln Ile
                325                 330                 335

Lys Val Glu Ala Phe Asp Asn Glu Phe Glu Ala Thr Gln Lys Leu Ser
                340                 345                 350

Ser Pro Ile Asp Met Thr Ser Lys Arg His Phe Glu Leu Glu Lys His
            355                 360                 365

Ser Ala Pro Ser Met Val His Ser Ser Leu Thr Pro Phe Ser Val Gln
            370                 375                 380

Val Thr Asn Ile Gln Asp Trp Ser Leu Lys Ser Glu His Trp His Gln
385                 390                 395                 400

Lys Glu Leu Ser Gly Lys Thr Gln Asn Ser Phe Lys Thr Gly Val Val
                405                 410                 415

Glu Met Lys Asp Ser Gly Tyr Lys Val Ser Asp Pro Glu Asn Leu Tyr
            420                 425                 430

Leu Lys Gln Gly Ile Ala Asn Leu Ser Ala Glu Val Val Ser Leu Lys
            435                 440                 445

Arg Leu Ile Ala Thr Gln Pro Ile Ser Ala Ser Asp Ser Gly
450                 455                 460

<210> SEQ ID NO 66
<211> LENGTH: 1187
<212> TYPE: PRT
<213> ORGANISM: Homo sapiens

<400> SEQUENCE: 66

Met Pro Phe Gly Leu Lys Leu Arg Arg Thr Arg Arg Tyr Asn Val Leu
1               5                   10                  15

Ser Lys Asn Cys Phe Val Thr Arg Ile Arg Leu Leu Asp Ser Asn Val
                20                  25                  30

Ile Glu Cys Thr Leu Ser Val Glu Ser Thr Gly Gln Glu Cys Leu Glu
            35                  40                  45

Ala Val Ala Gln Arg Leu Glu Leu Arg Glu Thr His Tyr Phe Gly Leu
```

```
                50                  55                  60
Trp Phe Leu Ser Lys Ser Gln Gln Ala Arg Trp Val Glu Leu Glu Lys
65                  70                  75                  80

Pro Leu Lys Lys His Leu Asp Lys Phe Ala Asn Glu Pro Leu Leu Phe
                85                  90                  95

Phe Gly Val Met Phe Tyr Val Pro Asn Val Ser Trp Leu Gln Gln Glu
                100                 105                 110

Ala Thr Arg Tyr Gln Tyr Tyr Leu Gln Val Lys Lys Asp Val Leu Glu
                115                 120                 125

Gly Arg Leu Arg Cys Thr Leu Asp Gln Val Ile Arg Leu Ala Gly Leu
                130                 135                 140

Ala Val Gln Ala Asp Phe Gly Asp Tyr Asn Gln Phe Asp Ser Gln Asp
145                 150                 155                 160

Phe Leu Arg Glu Tyr Val Leu Phe Pro Met Asp Leu Ala Leu Glu Glu
                165                 170                 175

Ala Val Leu Glu Glu Leu Thr Gln Lys Val Ala Gln Glu His Lys Ala
                180                 185                 190

His Ser Gly Ile Leu Pro Ala Glu Ala Glu Leu Met Tyr Ile Asn Glu
                195                 200                 205

Val Glu Arg Leu Asp Gly Phe Gly Gln Glu Ile Phe Pro Val Lys Asp
210                 215                 220

Asn His Gly Asn Cys Val His Leu Gly Ile Phe Phe Met Gly Ile Phe
225                 230                 235                 240

Val Arg Asn Arg Ile Gly Arg Gln Ala Val Ile Tyr Arg Trp Asn Asp
                245                 250                 255

Met Gly Asn Ile Thr His Asn Lys Ser Thr Ile Leu Val Glu Leu Ile
                260                 265                 270

Asn Lys Glu Glu Thr Ala Leu Phe His Thr Asp Asp Ile Glu Asn Ala
                275                 280                 285

Lys Tyr Ile Ser Arg Leu Phe Ala Thr Arg His Lys Phe Tyr Lys Gln
                290                 295                 300

Asn Lys Ile Cys Thr Glu Gln Ser Asn Ser Pro Pro Ile Arg Arg
305                 310                 315                 320

Gln Pro Thr Trp Ser Arg Ser Ser Leu Pro Arg Gln Pro Tyr Ile
                325                 330                 335

Leu Pro Pro Val His Val Gln Cys Gly Glu His Tyr Ser Glu Thr His
                340                 345                 350

Thr Ser Gln Asp Ser Ile Phe His Gly Asn Glu Glu Ala Leu Tyr Cys
                355                 360                 365

Asn Ser His Asn Ser Leu Asp Leu Asn Tyr Leu Asn Gly Thr Val Thr
370                 375                 380

Asn Gly Ser Val Cys Ser Val His Ser Val Asn Ser Leu Asn Cys Ser
385                 390                 395                 400

Gln Ser Phe Ile Gln Ala Ser Pro Val Ser Ser Asn Leu Ser Ile Pro
                405                 410                 415

Gly Ser Asp Ile Met Arg Ala Asp Tyr Ile Pro Ser His Arg His Ser
                420                 425                 430

Ala Ile Ile Val Pro Ser Tyr Arg Pro Thr Pro Asp Tyr Glu Thr Val
                435                 440                 445

Met Arg Gln Met Lys Arg Gly Ile Leu His Thr Asp Ser Gln Ser Gln
                450                 455                 460

Ser Leu Arg Asn Leu Asn Ile Ile Asn Thr His Ala Tyr Asn Gln Pro
465                 470                 475                 480
```

-continued

```
Glu Asp Leu Val Tyr Ser Gln Pro Glu Met Arg Arg His Pro Tyr
                485                 490                 495
Thr Val Pro Tyr Gly Pro Gln Gly Val Tyr Ser Asn Lys Leu Val Ser
                500                 505                 510
Pro Ser Asp Gln Arg Asn Pro Lys Asn Asn Val Val Pro Ser Lys Pro
                515                 520                 525
Gly Ala Ser Ala Ile Ser His Thr Val Ser Thr Pro Glu Leu Ala Asn
                530                 535                 540
Met Gln Leu Gln Gly Ser His Asn Tyr Ser Thr Ala His Met Leu Lys
545                 550                 555                 560
Asn Tyr Leu Phe Arg Pro Pro Pro Tyr Pro Arg Pro Arg Pro Ala
                565                 570                 575
Thr Ser Thr Pro Asp Leu Ala Ser His Arg His Lys Tyr Val Ser Gly
                580                 585                 590
Ser Ser Pro Asp Leu Val Thr Arg Lys Val Gln Leu Ser Val Lys Thr
                595                 600                 605
Phe Gln Glu Asp Ser Ser Pro Val His Gln Ser Leu Gln Glu Val
                610                 615                 620
Ser Glu Pro Leu Thr Ala Thr Lys His His Gly Thr Val Asn Lys Arg
625                 630                 635                 640
His Ser Leu Glu Val Met Asn Ser Met Val Arg Gly Met Glu Ala Met
                645                 650                 655
Thr Leu Lys Ser Leu His Leu Pro Met Ala Arg Arg Asn Thr Leu Arg
                660                 665                 670
Glu Gln Gly Pro Pro Glu Gly Ser Gly Ser His Glu Val Pro Gln
                675                 680                 685
Leu Pro Gln Tyr His His Lys Lys Thr Phe Ser Asp Ala Thr Met Leu
                690                 695                 700
Ile His Ser Ser Glu Ser Glu Glu Glu Glu Ala Pro Glu Ser
705                 710                 715                 720
Val Pro Gln Ile Pro Met Leu Arg Glu Lys Met Glu Tyr Ser Ala Gln
                725                 730                 735
Leu Gln Ala Ala Leu Ala Arg Ile Pro Asn Lys Pro Pro Glu Tyr
                740                 745                 750
Pro Gly Pro Arg Lys Ser Val Ser Asn Gly Ala Leu Arg Gln Asp Gln
                755                 760                 765
Ala Ser Leu Pro Pro Ala Met Ala Arg Ala Arg Val Leu Arg His Gly
                770                 775                 780
Pro Ala Lys Ala Ile Ser Met Ser Arg Thr Asp Pro Pro Ala Val Asn
785                 790                 795                 800
Gly Ala Ser Leu Gly Pro Ser Ile Ser Glu Pro Asp Leu Thr Ser Val
                805                 810                 815
Lys Glu Arg Val Lys Lys Glu Pro Val Lys Glu Arg Pro Val Ser Glu
                820                 825                 830
Met Phe Ser Leu Glu Asp Ser Ile Ile Glu Arg Glu Met Ile Arg
                835                 840                 845
Asn Leu Glu Lys Gln Lys Met Ala Gly Leu Ala Gln Lys Arg Pro
                850                 855                 860
Leu Met Leu Ala Ala Leu Asn Gly Leu Ser Val Ala Arg Val Ser Gly
865                 870                 875                 880
Arg Glu Glu Asn Arg Val Asp Ala Thr Arg Val Pro Met Asp Glu Arg
                885                 890                 895
```

Phe Arg Thr Leu Lys Lys Lys Leu Glu Gly Met Val Phe Thr Glu
              900             905             910

Tyr Glu Gln Ile Pro Lys Lys Ala Asn Gly Ile Phe Ser Thr Ala
        915             920             925

Ala Leu Pro Glu Asn Ala Glu Arg Ser Arg Ile Arg Glu Val Val Pro
    930             935             940

Tyr Glu Glu Asn Arg Val Glu Leu Ile Pro Thr Lys Glu Asn Asn Thr
945             950             955             960

Gly Tyr Ile Asn Ala Ser His Ile Lys Val Val Val Gly Gly Ala Glu
            965             970             975

Trp His Tyr Ile Ala Thr Gln Gly Pro Leu Pro His Thr Cys His Asp
        980             985             990

Phe Trp Gln Met Val Trp Glu Gln Gly Val Asn Val Ile Ala Met Val
        995             1000            1005

Thr Ala Glu Glu Glu Gly Gly Arg Thr Lys Ser His Arg Tyr Trp
    1010            1015            1020

Pro Lys Leu Gly Ser Lys His Ser Ser Ala Thr Tyr Gly Lys Phe
    1025            1030            1035

Lys Val Thr Thr Lys Phe Arg Thr Asp Ser Val Cys Tyr Ala Thr
    1040            1045            1050

Thr Gly Leu Lys Val Lys His Leu Leu Ser Gly Gln Glu Arg Thr
    1055            1060            1065

Val Trp His Leu Gln Tyr Thr Asp Trp Pro Asp His Gly Cys Pro
    1070            1075            1080

Glu Asp Val Gln Gly Phe Leu Ser Tyr Leu Glu Glu Ile Gln Ser
    1085            1090            1095

Val Arg Arg His Thr Asn Ser Met Leu Glu Gly Thr Lys Asn Arg
    1100            1105            1110

His Pro Pro Ile Val Val His Cys Ser Ala Gly Val Gly Arg Thr
    1115            1120            1125

Gly Val Leu Ile Leu Ser Glu Leu Met Ile Tyr Cys Leu Glu His
    1130            1135            1140

Asn Glu Lys Val Glu Val Pro Met Met Leu Arg Leu Leu Arg Glu
    1145            1150            1155

Gln Arg Met Phe Met Ile Gln Thr Ile Ala Gln Tyr Lys Phe Val
    1160            1165            1170

Tyr Gln Val Leu Ile Gln Phe Leu Gln Asn Ser Arg Leu Ile
    1175            1180            1185

<210> SEQ ID NO 67
<211> LENGTH: 193
<212> TYPE: PRT
<213> ORGANISM: Homo sapiens

<400> SEQUENCE: 67

Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Ile Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Gln Asp Glu His Thr Arg
        115                 120                 125

Arg Glu Leu Ala Lys Met Lys Gln Glu Pro Val Arg Ser Glu Glu Gly
    130                 135                 140

Arg Asp Met Ala Asn Arg Ile Ser Ala Phe Gly Tyr Leu Glu Cys Ser
145                 150                 155                 160

Ala Lys Thr Lys Glu Gly Val Arg Glu Val Phe Glu Met Ala Thr Arg
                165                 170                 175

Ala Gly Leu Gln Val Arg Lys Asn Lys Arg Arg Arg Gly Cys Pro Ile
            180                 185                 190

Leu

<210> SEQ ID NO 68
<211> LENGTH: 168
<212> TYPE: PRT
<213> ORGANISM: Homo sapiens

<400> SEQUENCE: 68

Met Gly His His His His His His His His Ser Ser Gly His
1               5                   10                  15

Ile Glu Gly Arg His Met Arg Arg Val Pro Gly Val Ala Pro Thr Leu
            20                  25                  30

Val Arg Ser Ala Ser Glu Thr Ser Glu Lys Arg Pro Phe Met Cys Ala
        35                  40                  45

Tyr Pro Gly Cys Asn Lys Arg Tyr Phe Lys Leu Ser His Leu Gln Met
    50                  55                  60

His Ser Arg Lys His Thr Gly Glu Lys Pro Tyr Gln Cys Asp Phe Lys
65                  70                  75                  80

Asp Cys Glu Arg Arg Phe Phe Arg Ser Asp Gln Leu Lys Arg His Gln
                85                  90                  95

Arg Arg His Thr Gly Val Lys Pro Phe Gln Cys Lys Thr Cys Gln Arg
            100                 105                 110

Lys Phe Ser Arg Ser Asp His Leu Lys Thr His Thr Arg Thr His Thr
        115                 120                 125

Gly Glu Lys Pro Phe Ser Cys Arg Trp Pro Ser Cys Gln Lys Lys Phe
    130                 135                 140

Ala Arg Ser Asp Glu Leu Val Arg His His Asn Met His Gln Arg Asn
145                 150                 155                 160

Met Thr Lys Leu Gln Leu Ala Leu
                165

<210> SEQ ID NO 69
<211> LENGTH: 1158
<212> TYPE: PRT
<213> ORGANISM: Homo sapiens

<400> SEQUENCE: 69

Met Ala Ala Val Arg Gly Ala Pro Leu Leu Ser Cys Leu Leu Ala Leu
1               5                   10                  15

Leu Ala Leu Cys Pro Gly Gly Arg Pro Gln Thr Val Leu Thr Asp Asp
            20                  25                  30

-continued

```
Glu Ile Glu Glu Phe Leu Gly Phe Leu Ser Glu Leu Glu Pro Glu
             35                  40                  45

Pro Arg Glu Asp Asp Val Glu Ala Pro Pro Glu Pro Thr Pro
 50                  55                  60

Arg Val Arg Lys Ala Gln Ala Gly Gly Lys Pro Gly Lys Arg Pro Gly
 65                  70                  75                  80

Thr Ala Ala Glu Val Pro Pro Glu Lys Thr Lys Asp Lys Gly Lys Lys
                 85                  90                  95

Gly Lys Lys Asp Lys Gly Pro Lys Val Pro Lys Glu Ser Leu Glu Gly
                100                 105                 110

Ser Pro Arg Pro Pro Lys Lys Gly Lys Glu Lys Pro Pro Lys Ala Thr
             115                 120                 125

Lys Lys Pro Lys Glu Lys Pro Pro Lys Ala Thr Lys Lys Pro Lys Glu
 130                 135                 140

Lys Pro Pro Lys Ala Thr Lys Lys Pro Lys Glu Lys Pro Pro Lys Ala
 145                 150                 155                 160

Thr Lys Lys Pro Pro Ser Gly Lys Arg Pro Pro Ile Leu Ala Pro Ser
                 165                 170                 175

Glu Thr Leu Glu Trp Pro Leu Pro Pro Pro Ser Pro Gly Pro Glu
             180                 185                 190

Glu Leu Pro Gln Glu Gly Gly Ala Pro Leu Ser Asn Asn Trp Gln Asn
             195                 200                 205

Pro Gly Glu Glu Thr His Val Glu Ala Arg Glu His Gln Pro Glu Pro
 210                 215                 220

Glu Glu Glu Thr Glu Gln Pro Thr Leu Asp Tyr Asn Asp Gln Ile Glu
 225                 230                 235                 240

Arg Glu Asp Tyr Glu Asp Phe Glu Tyr Ile Arg Arg Gln Lys Gln Pro
                 245                 250                 255

Arg Pro Pro Pro Ser Arg Arg Arg Pro Glu Arg Val Trp Pro Glu
             260                 265                 270

Pro Pro Glu Glu Lys Ala Pro Ala Pro Ala Pro Glu Glu Arg Ile Glu
             275                 280                 285

Pro Pro Val Lys Pro Leu Leu Pro Pro Leu Pro Pro Asp Tyr Gly Asp
 290                 295                 300

Gly Tyr Val Ile Pro Asn Tyr Asp Asp Met Asp Tyr Tyr Phe Gly Pro
 305                 310                 315                 320

Pro Pro Pro Gln Lys Pro Asp Ala Glu Arg Gln Thr Asp Glu Glu Lys
                 325                 330                 335

Glu Glu Leu Lys Lys Pro Lys Lys Glu Asp Ser Ser Pro Lys Glu Glu
             340                 345                 350

Thr Asp Lys Trp Ala Val Glu Lys Gly Lys Asp His Lys Glu Pro Arg
                 355                 360                 365

Lys Gly Glu Glu Leu Glu Glu Trp Thr Pro Thr Glu Lys Val Lys
             370                 375                 380

Cys Pro Pro Ile Gly Met Glu Ser His Arg Ile Glu Asp Asn Gln Ile
 385                 390                 395                 400

Arg Ala Ser Ser Met Leu Arg His Gly Leu Gly Ala Gln Arg Gly Arg
                 405                 410                 415

Leu Asn Met Gln Thr Gly Ala Thr Glu Asp Tyr Tyr Asp Gly Ala
             420                 425                 430

Trp Cys Ala Glu Asp Asp Ala Arg Thr Gln Trp Ile Glu Val Asp Thr
 435                 440                 445

Arg Arg Thr Thr Arg Phe Thr Gly Val Ile Thr Gln Gly Arg Asp Ser
```

```
                  450             455             460
Ser Ile His Asp Asp Phe Val Thr Thr Phe Phe Val Gly Phe Ser Asn
465                 470                 475                 480

Asp Ser Gln Thr Trp Val Met Tyr Thr Asn Gly Tyr Glu Glu Met Thr
                485                 490                 495

Phe His Gly Asn Val Asp Lys Asp Thr Pro Val Leu Ser Glu Leu Pro
                500                 505                 510

Glu Pro Val Val Ala Arg Phe Ile Arg Ile Tyr Pro Leu Thr Trp Asn
                515                 520                 525

Gly Ser Leu Cys Met Arg Leu Glu Val Leu Gly Cys Ser Val Ala Pro
                530                 535                 540

Val Tyr Ser Tyr Tyr Ala Gln Asn Glu Val Val Ala Thr Asp Asp Leu
545                 550                 555                 560

Asp Phe Arg His His Ser Tyr Lys Asp Met Arg Gln Leu Met Lys Val
                565                 570                 575

Val Asn Glu Glu Cys Pro Thr Ile Thr Arg Thr Tyr Ser Leu Gly Lys
                580                 585                 590

Ser Ser Arg Gly Leu Lys Ile Tyr Ala Met Glu Ile Ser Asp Asn Pro
                595                 600                 605

Gly Glu His Glu Leu Gly Glu Pro Glu Phe Arg Tyr Thr Ala Gly Ile
                610                 615                 620

His Gly Asn Glu Val Leu Gly Arg Glu Leu Leu Leu Leu Leu Met Gln
625                 630                 635                 640

Tyr Leu Cys Arg Glu Tyr Arg Asp Gly Asn Pro Arg Val Arg Ser Leu
                645                 650                 655

Val Gln Asp Thr Arg Ile His Leu Val Pro Ser Leu Asn Pro Asp Gly
                660                 665                 670

Tyr Glu Val Ala Ala Gln Met Gly Ser Glu Phe Gly Asn Trp Ala Leu
                675                 680                 685

Gly Leu Trp Thr Glu Glu Gly Phe Asp Ile Phe Glu Asp Phe Pro Asp
                690                 695                 700

Leu Asn Ser Val Leu Trp Gly Ala Glu Glu Arg Lys Trp Val Pro Tyr
705                 710                 715                 720

Arg Val Pro Asn Asn Asn Leu Pro Ile Pro Glu Arg Tyr Leu Ser Pro
                725                 730                 735

Asp Ala Thr Val Ser Thr Glu Val Arg Ala Ile Ile Ala Trp Met Glu
                740                 745                 750

Lys Asn Pro Phe Val Leu Gly Ala Asn Leu Asn Gly Gly Glu Arg Leu
                755                 760                 765

Val Ser Tyr Pro Tyr Asp Met Ala Arg Thr Pro Thr Gln Glu Gln Leu
770                 775                 780

Leu Ala Ala Ala Met Ala Ala Arg Gly Glu Asp Glu Asp Glu Val
785                 790                 795                 800

Ser Glu Ala Gln Glu Thr Pro Asp His Ala Ile Phe Arg Trp Leu Ala
                805                 810                 815

Ile Ser Phe Ala Ser Ala His Leu Thr Leu Thr Glu Pro Tyr Arg Gly
                820                 825                 830

Gly Cys Gln Ala Gln Asp Tyr Thr Gly Met Gly Ile Val Asn Gly
                835                 840                 845

Ala Lys Trp Asn Pro Arg Thr Gly Thr Ile Asn Asp Phe Ser Tyr Leu
                850                 855                 860

His Thr Asn Cys Leu Glu Leu Ser Phe Tyr Leu Gly Cys Asp Lys Phe
865                 870                 875                 880
```

-continued

```
Pro His Glu Ser Glu Leu Pro Arg Glu Trp Glu Asn Asn Lys Glu Ala
            885                 890                 895

Leu Leu Thr Phe Met Glu Gln Val His Arg Gly Ile Lys Gly Val Val
            900                 905                 910

Thr Asp Glu Gln Gly Ile Pro Ile Ala Asn Ala Thr Ile Ser Val Ser
            915                 920                 925

Gly Ile Asn His Gly Val Lys Thr Ala Ser Gly Gly Asp Tyr Trp Arg
    930                 935                 940

Ile Leu Asn Pro Gly Glu Tyr Arg Val Thr Ala His Ala Glu Gly Tyr
945                 950                 955                 960

Thr Pro Ser Ala Lys Thr Cys Asn Val Asp Tyr Asp Ile Gly Ala Thr
                965                 970                 975

Gln Cys Asn Phe Ile Leu Ala Arg Ser Asn Trp Lys Arg Ile Arg Glu
            980                 985                 990

Ile Met Ala Met Asn Gly Asn Arg  Pro Ile Pro His Ile  Asp Pro Ser
            995                 1000                1005

Arg Pro Met Thr Pro Gln Gln  Arg Arg Leu Gln Gln  Arg Arg Leu
    1010                1015                1020

Gln His  Arg Leu Arg Leu Arg  Ala Gln Met Arg Leu  Arg Arg Leu
    1025                1030                1035

Asn Ala  Thr Thr Thr Leu Gly  Pro His Thr Val Pro  Pro Thr Leu
    1040                1045                1050

Pro Pro  Ala Pro Ala Thr Thr  Leu Ser Thr Thr Ile  Glu Pro Trp
    1055                1060                1065

Gly Leu  Ile Pro Pro Thr Thr  Ala Gly Trp Glu Glu  Ser Glu Thr
    1070                1075                1080

Glu Thr  Tyr Thr Glu Val Val  Thr Glu Phe Gly Thr  Glu Val Glu
    1085                1090                1095

Pro Glu  Phe Gly Thr Lys Val  Glu Pro Glu Phe Glu  Thr Gln Leu
    1100                1105                1110

Glu Pro  Glu Phe Glu Thr Gln  Leu Glu Pro Glu Phe  Glu Glu Glu
    1115                1120                1125

Glu Glu  Glu Glu Lys Glu Glu  Glu Ile Ala Thr Gly  Gln Ala Phe
    1130                1135                1140

Pro Phe  Thr Thr Val Glu Thr  Tyr Thr Val Asn Phe  Gly Asp Phe
    1145                1150                1155
```

<210> SEQ ID NO 70
<211> LENGTH: 501
<212> TYPE: PRT
<213> ORGANISM: Homo sapiens

<400> SEQUENCE: 70

```
Met Asn Leu Glu Gln Glu Arg Pro Phe Val Cys Ser Ala Pro Gly Cys
1               5                   10                  15

Ser Gln Arg Phe Pro Thr Glu Asp His Leu Met Ile His Arg His Lys
            20                  25                  30

His Glu Met Thr Leu Lys Phe Pro Ser Ile Lys Thr Asp Asn Met Leu
        35                  40                  45

Ser Asp Gln Thr Pro Thr Pro Thr Arg Phe Leu Lys Asn Cys Glu Glu
    50                  55                  60

Val Gly Leu Phe Ser Glu Leu Asp Cys Ser Leu Glu His Glu Phe Arg
65                  70                  75                  80

Lys Ala Gln Glu Glu Glu Ser Ser Lys Arg Asn Ile Ser Met His Asn
```

```
                    85                  90                  95
Ala Val Gly Gly Ala Met Thr Gly Pro Gly Thr His Gln Leu Ser Ser
                100                 105                 110

Ala Arg Leu Pro Asn His Asp Thr Asn Val Val Ile Gln Gln Ala Met
                115                 120                 125

Pro Ser Pro Gln Ser Ser Val Ile Thr Gln Ala Pro Ser Thr Asn
130                 135                 140

Arg Gln Ile Gly Pro Val Pro Gly Ser Leu Ser Ser Leu Leu His Leu
145                 150                 155                 160

His Asn Arg Gln Arg Gln Pro Met Pro Ala Ser Met Pro Gly Thr Leu
                165                 170                 175

Pro Asn Pro Thr Met Pro Gly Ser Ser Ala Val Leu Met Pro Met Glu
                180                 185                 190

Arg Gln Met Ser Val Asn Ser Ser Ile Met Gly Met Gln Gly Pro Asn
                195                 200                 205

Leu Ser Asn Pro Cys Ala Ser Pro Gln Val Gln Pro Met His Ser Glu
                210                 215                 220

Ala Lys Met Arg Leu Lys Ala Ala Leu Thr His His Pro Ala Ala Met
225                 230                 235                 240

Ser Asn Gly Asn Met Asn Thr Met Gly His Met Met Glu Met Met Gly
                245                 250                 255

Ser Arg Gln Asp Gln Thr Pro His His His Met His Ser His Pro His
                260                 265                 270

Gln His Gln Thr Leu Pro Pro His His Pro Tyr Pro His Gln His Gln
                275                 280                 285

His Pro Ala His His Pro His Pro Gln Pro His His Gln Gln Asn His
                290                 295                 300

Pro His His His Ser His Ser His Leu His Ala His Pro Ala His His
305                 310                 315                 320

Gln Thr Ser Pro His Pro Pro Leu His Thr Gly Asn Gln Ala Gln Val
                325                 330                 335

Ser Pro Ala Thr Gln Gln Met Gln Pro Thr Gln Thr Ile Gln Pro Pro
                340                 345                 350

Gln Pro Thr Gly Gly Arg Arg Arg Val Val Asp Glu Asp Pro Asp
                355                 360                 365

Glu Arg Arg Arg Lys Phe Leu Glu Arg Asn Arg Ala Ala Ala Thr Arg
                370                 375                 380

Cys Arg Gln Lys Arg Lys Val Trp Val Met Ser Leu Glu Lys Lys Ala
385                 390                 395                 400

Glu Glu Leu Thr Gln Thr Asn Met Gln Leu Gln Asn Glu Val Ser Met
                405                 410                 415

Leu Lys Asn Glu Val Ala Gln Leu Lys Gln Leu Leu Thr His Lys
                420                 425                 430

Asp Cys Pro Ile Thr Ala Met Gln Lys Glu Ser Gln Gly Tyr Leu Ser
                435                 440                 445

Pro Glu Ser Ser Pro Pro Ala Ser Pro Val Pro Ala Cys Ser Gln Gln
                450                 455                 460

Gln Val Ile Gln His Asn Thr Ile Thr Thr Ser Ser Ser Val Ser Glu
465                 470                 475                 480

Val Val Gly Ser Ser Thr Leu Ser Gln Leu Thr Thr His Arg Thr Asp
                485                 490                 495

Leu Asn Pro Ile Leu
                500
```

<210> SEQ ID NO 71
<211> LENGTH: 479
<212> TYPE: PRT
<213> ORGANISM: Homo sapiens

<400> SEQUENCE: 71

Met Ala Ser Thr Ile Lys Glu Ala Leu Ser Val Val Ser Glu Asp Gln
1               5                   10                  15

Ser Leu Phe Glu Cys Ala Tyr Gly Thr Pro His Leu Ala Lys Thr Glu
            20                  25                  30

Met Thr Ala Ser Ser Ser Ser Asp Tyr Gly Gln Thr Ser Lys Met Ser
        35                  40                  45

Pro Arg Val Pro Gln Gln Asp Trp Leu Ser Gln Pro Pro Ala Arg Val
    50                  55                  60

Thr Ile Lys Met Glu Cys Asn Pro Ser Gln Val Asn Gly Ser Arg Asn
65                  70                  75                  80

Ser Pro Asp Glu Cys Ser Val Ala Lys Gly Gly Lys Met Val Gly Ser
                85                  90                  95

Pro Asp Thr Val Gly Met Asn Tyr Gly Ser Tyr Met Glu Glu Lys His
            100                 105                 110

Met Pro Pro Pro Asn Met Thr Thr Asn Glu Arg Arg Val Ile Val Pro
        115                 120                 125

Ala Asp Pro Thr Leu Trp Ser Thr Asp His Val Arg Gln Trp Leu Glu
    130                 135                 140

Trp Ala Val Lys Glu Tyr Gly Leu Pro Asp Val Asn Ile Leu Leu Phe
145                 150                 155                 160

Gln Asn Ile Asp Gly Lys Glu Leu Cys Lys Met Thr Lys Asp Asp Phe
                165                 170                 175

Gln Arg Leu Thr Pro Ser Tyr Asn Ala Asp Ile Leu Leu Ser His Leu
            180                 185                 190

His Tyr Leu Arg Glu Thr Pro Leu Pro His Leu Thr Ser Asp Asp Val
        195                 200                 205

Asp Lys Ala Leu Gln Asn Ser Pro Arg Leu Met His Ala Arg Asn Thr
    210                 215                 220

Gly Gly Ala Ala Phe Ile Phe Pro Asn Thr Ser Val Tyr Pro Glu Ala
225                 230                 235                 240

Thr Gln Arg Ile Thr Thr Arg Pro Asp Leu Pro Tyr Glu Pro Pro Arg
                245                 250                 255

Arg Ser Ala Trp Thr Gly His Gly His Pro Thr Pro Gln Ser Lys Ala
            260                 265                 270

Ala Gln Pro Ser Pro Ser Thr Val Pro Lys Thr Glu Asp Gln Arg Pro
        275                 280                 285

Gln Leu Asp Pro Tyr Gln Ile Leu Gly Pro Thr Ser Ser Arg Leu Ala
    290                 295                 300

Asn Pro Gly Ser Gly Gln Ile Gln Leu Trp Gln Phe Leu Leu Glu Leu
305                 310                 315                 320

Leu Ser Asp Ser Ser Asn Ser Ser Cys Ile Thr Trp Glu Gly Thr Asn
                325                 330                 335

Gly Glu Phe Lys Met Thr Asp Pro Asp Glu Val Ala Arg Arg Trp Gly
            340                 345                 350

Glu Arg Lys Ser Lys Pro Asn Met Asn Tyr Asp Lys Leu Ser Arg Ala
        355                 360                 365

Leu Arg Tyr Tyr Tyr Asp Lys Asn Ile Met Thr Lys Val His Gly Lys

```
                 370              375              380
Arg Tyr Ala Tyr Lys Phe Asp Phe His Gly Ile Ala Gln Ala Leu Gln
385                 390                 395                 400

Pro His Pro Pro Glu Ser Ser Leu Tyr Lys Tyr Pro Ser Asp Leu Pro
                405                 410                 415

Tyr Met Gly Ser Tyr His Ala His Pro Gln Lys Met Asn Phe Val Ala
            420                 425                 430

Pro His Pro Pro Ala Leu Pro Val Thr Ser Ser Phe Phe Ala Ala
            435                 440                 445

Pro Asn Pro Tyr Trp Asn Ser Pro Thr Gly Gly Ile Tyr Pro Asn Thr
        450                 455                 460

Arg Leu Pro Thr Ser His Met Pro Ser His Leu Gly Thr Tyr Tyr
465                 470                 475

<210> SEQ ID NO 72
<211> LENGTH: 326
<212> TYPE: PRT
<213> ORGANISM: Homo sapiens

<400> SEQUENCE: 72

Met Tyr Gln Asp Tyr Pro Gly Asn Phe Asp Thr Ser Ser Arg Gly Ser
1               5                   10                  15

Ser Gly Ser Pro Ala His Ala Glu Ser Tyr Ser Ser Gly Gly Gly Gly
            20                  25                  30

Gln Gln Lys Phe Arg Val Asp Met Pro Gly Ser Gly Ser Ala Phe Ile
        35                  40                  45

Pro Thr Ile Asn Ala Ile Thr Thr Ser Gln Asp Leu Gln Trp Met Val
50                  55                  60

Gln Pro Thr Val Ile Thr Ser Met Ser Asn Pro Tyr Pro Arg Ser His
65                  70                  75                  80

Pro Tyr Ser Pro Leu Pro Gly Leu Ala Ser Val Pro Gly His Met Ala
                85                  90                  95

Leu Pro Arg Pro Gly Val Ile Lys Thr Ile Gly Thr Thr Val Gly Arg
            100                 105                 110

Arg Arg Arg Asp Glu Gln Leu Ser Pro Glu Glu Glu Lys Arg Arg
        115                 120                 125

Ile Arg Arg Glu Arg Asn Lys Leu Ala Ala Ala Lys Cys Arg Asn Arg
130                 135                 140

Arg Arg Glu Leu Thr Glu Lys Leu Gln Ala Glu Thr Glu Glu Leu Glu
145                 150                 155                 160

Glu Glu Lys Ser Gly Leu Gln Lys Glu Ile Ala Glu Leu Gln Lys Glu
                165                 170                 175

Lys Glu Lys Leu Glu Phe Met Leu Val Ala His Gly Pro Val Cys Lys
            180                 185                 190

Ile Ser Pro Glu Glu Arg Arg Ser Pro Pro Ala Pro Gly Leu Gln Pro
        195                 200                 205

Met Arg Ser Gly Gly Gly Ser Val Gly Ala Val Val Lys Gln Glu
210                 215                 220

Pro Leu Glu Glu Asp Ser Pro Ser Ser Ser Ala Gly Leu Asp Lys
225                 230                 235                 240

Ala Gln Arg Ser Val Ile Lys Pro Ile Ser Ile Ala Gly Gly Phe Tyr
                245                 250                 255

Gly Glu Glu Pro Leu His Thr Pro Ile Val Val Thr Ser Thr Pro Ala
            260                 265                 270
```

```
Val Thr Pro Gly Thr Ser Asn Leu Val Phe Thr Tyr Pro Ser Val Leu
            275                 280                 285

Glu Gln Glu Ser Pro Ala Ser Pro Ser Glu Ser Cys Ser Lys Ala His
    290                 295                 300

Arg Arg Ser Ser Ser Gly Asp Gln Ser Ser Asp Ser Leu Asn Ser
305                 310                 315                 320

Pro Thr Leu Leu Ala Leu
                325

<210> SEQ ID NO 73
<211> LENGTH: 230
<212> TYPE: PRT
<213> ORGANISM: Homo sapiens

<400> SEQUENCE: 73

Met Ser Ser Ser Tyr Tyr Val Asn Ala Leu Phe Ser Lys Tyr Thr Ala
1               5                   10                  15

Gly Ala Ser Leu Phe Gln Asn Ala Glu Pro Thr Ser Cys Ser Phe Ala
            20                  25                  30

Pro Asn Ser Gln Arg Ser Gly Tyr Gly Ala Gly Ala Gly Ala Phe Ala
        35                  40                  45

Ser Thr Val Pro Gly Leu Tyr Asn Val Asn Ser Pro Leu Tyr Gln Ser
    50                  55                  60

Pro Phe Ala Ser Gly Tyr Gly Leu Gly Ala Asp Ala Tyr Gly Asn Leu
65                  70                  75                  80

Pro Cys Ala Ser Tyr Asp Gln Asn Ile Pro Gly Leu Cys Ser Asp Leu
                85                  90                  95

Ala Lys Gly Ala Cys Asp Lys Thr Asp Glu Gly Ala Leu His Gly Ala
            100                 105                 110

Ala Glu Ala Asn Phe Arg Ile Tyr Pro Trp Met Arg Ser Ser Gly Pro
        115                 120                 125

Asp Arg Lys Arg Gly Arg Gln Thr Tyr Thr Arg Tyr Gln Thr Leu Glu
    130                 135                 140

Leu Glu Lys Glu Phe His Phe Asn Arg Tyr Leu Thr Arg Arg Arg Arg
145                 150                 155                 160

Ile Glu Ile Ala His Ala Leu Cys Leu Thr Glu Arg Gln Ile Lys Ile
                165                 170                 175

Trp Phe Gln Asn Arg Arg Met Lys Trp Lys Lys Glu His Lys Asp Glu
            180                 185                 190

Gly Pro Thr Ala Ala Ala Pro Glu Gly Ala Val Pro Ser Ala Ala
        195                 200                 205

Ala Thr Ala Ala Ala Asp Lys Ala Asp Glu Glu Asp Asp Glu Glu
    210                 215                 220

Glu Glu Asp Glu Glu
225             230

<210> SEQ ID NO 74
<211> LENGTH: 422
<212> TYPE: PRT
<213> ORGANISM: Homo sapiens

<400> SEQUENCE: 74

Met Ser Ser Ser Cys Ser Gly Leu Ser Arg Val Leu Val Ala Val Ala
1               5                   10                  15

Thr Ala Leu Val Ser Ala Ser Ser Pro Cys Pro Gln Ala Trp Gly Pro
            20                  25                  30
```

```
Pro Gly Val Gln Tyr Gly Gln Pro Gly Arg Ser Val Lys Leu Cys Cys
             35                  40                  45

Pro Gly Val Thr Ala Gly Asp Pro Val Ser Trp Phe Arg Asp Gly Glu
 50                  55                  60

Pro Lys Leu Leu Gln Gly Pro Asp Ser Gly Leu Gly His Glu Leu Val
 65                  70                  75                  80

Leu Ala Gln Ala Asp Ser Thr Asp Glu Gly Thr Tyr Ile Cys Gln Thr
                 85                  90                  95

Leu Asp Gly Ala Leu Gly Gly Thr Val Thr Leu Gln Leu Gly Tyr Pro
            100                 105                 110

Pro Ala Arg Pro Val Val Ser Cys Gln Ala Ala Asp Tyr Glu Asn Phe
        115                 120                 125

Ser Cys Thr Trp Ser Pro Ser Gln Ile Ser Gly Leu Pro Thr Arg Tyr
130                 135                 140

Leu Thr Ser Tyr Arg Lys Lys Thr Val Leu Gly Ala Asp Ser Gln Arg
145                 150                 155                 160

Arg Ser Pro Ser Thr Gly Pro Trp Pro Cys Pro Gln Asp Pro Leu Gly
                165                 170                 175

Ala Ala Arg Cys Val Val His Gly Ala Glu Phe Trp Ser Gln Tyr Arg
            180                 185                 190

Ile Asn Val Thr Glu Val Asn Pro Leu Gly Ala Ser Thr Arg Leu Leu
        195                 200                 205

Asp Val Ser Leu Gln Ser Ile Leu Arg Pro Asp Pro Gln Gly Leu
        210                 215                 220

Arg Val Glu Ser Val Pro Gly Tyr Pro Arg Arg Leu Arg Ala Ser Trp
225                 230                 235                 240

Thr Tyr Pro Ala Ser Trp Pro Cys Gln Pro His Phe Leu Leu Lys Phe
                245                 250                 255

Arg Leu Gln Tyr Arg Pro Ala Gln His Pro Ala Trp Ser Thr Val Glu
            260                 265                 270

Pro Ala Gly Leu Glu Glu Val Ile Thr Asp Ala Val Ala Gly Leu Pro
        275                 280                 285

His Ala Val Arg Val Ser Ala Arg Asp Phe Leu Asp Ala Gly Thr Trp
290                 295                 300

Ser Thr Trp Ser Pro Glu Ala Trp Gly Thr Pro Ser Thr Gly Thr Ile
305                 310                 315                 320

Pro Lys Glu Ile Pro Ala Trp Gly Gln Leu His Thr Gln Pro Glu Val
                325                 330                 335

Glu Pro Gln Val Asp Ser Pro Ala Pro Pro Arg Pro Ser Leu Gln Pro
            340                 345                 350

His Pro Arg Leu Leu Asp His Arg Asp Ser Val Glu Gln Val Ala Val
        355                 360                 365

Leu Ala Ser Leu Gly Ile Leu Ser Phe Leu Gly Leu Val Ala Gly Ala
370                 375                 380

Leu Ala Leu Gly Leu Trp Leu Arg Leu Arg Arg Gly Gly Lys Asp Gly
385                 390                 395                 400

Ser Pro Lys Pro Gly Phe Leu Ala Ser Val Ile Pro Val Asp Arg Arg
                405                 410                 415

Pro Gly Ala Pro Asn Leu
            420

<210> SEQ ID NO 75
<211> LENGTH: 941
<212> TYPE: PRT
```

-continued

<213> ORGANISM: Homo sapiens

<400> SEQUENCE: 75

```
Met Ala Gly Ala Ala Ala Val Ala Gly Ala Ala Gly Ala
1               5                   10                  15

Ala Ala Ala Ala Val Ser Val Ala Pro Gly Arg Ala Ser Ala Pro
            20                  25                  30

Pro Pro Pro Pro Val Tyr Cys Val Cys Arg Gln Pro Tyr Asp Val
        35                  40                  45

Asn Arg Phe Met Ile Glu Cys Asp Ile Cys Lys Asp Trp Phe His Gly
    50                  55                  60

Ser Cys Val Gly Val Glu Glu His His Ala Val Asp Ile Asp Leu Tyr
65                  70                  75                  80

His Cys Pro Asn Cys Ala Val Leu His Gly Ser Ser Leu Met Lys Lys
                85                  90                  95

Arg Arg Asn Trp His Arg His Asp Tyr Thr Glu Ile Asp Asp Gly Ser
            100                 105                 110

Lys Pro Val Gln Ala Gly Thr Arg Thr Phe Ile Lys Glu Leu Arg Ser
        115                 120                 125

Arg Val Phe Pro Ser Ala Asp Glu Ile Ile Ile Lys Met His Gly Ser
    130                 135                 140

Gln Leu Thr Gln Arg Tyr Leu Glu Lys His Gly Phe Asp Val Pro Ile
145                 150                 155                 160

Met Val Pro Lys Leu Asp Asp Leu Gly Leu Arg Leu Pro Ser Pro Thr
                165                 170                 175

Phe Ser Val Met Asp Val Glu Arg Tyr Val Gly Gly Asp Lys Val Ile
            180                 185                 190

Asp Val Ile Asp Val Ala Arg Gln Ala Asp Ser Lys Met Thr Leu His
        195                 200                 205

Asn Tyr Val Lys Tyr Phe Met Asn Pro Asn Arg Pro Lys Val Leu Asn
    210                 215                 220

Val Ile Ser Leu Glu Phe Ser Asp Thr Lys Met Ser Glu Leu Val Glu
225                 230                 235                 240

Val Pro Asp Ile Ala Lys Lys Leu Ser Trp Val Glu Asn Tyr Trp Pro
                245                 250                 255

Asp Asp Ser Val Phe Pro Lys Pro Phe Val Gln Lys Tyr Cys Leu Met
            260                 265                 270

Gly Val Gln Asp Ser Tyr Thr Asp Phe His Ile Asp Phe Gly Gly Thr
        275                 280                 285

Ser Val Trp Tyr His Val Leu Trp Gly Glu Lys Ile Phe Tyr Leu Ile
    290                 295                 300

Lys Pro Thr Asp Glu Asn Leu Ala Arg Tyr Glu Ser Trp Ser Ser Ser
305                 310                 315                 320

Val Thr Gln Ser Glu Val Phe Phe Gly Asp Lys Val Asp Lys Cys Tyr
                325                 330                 335

Lys Cys Val Val Lys Gln Gly His Thr Leu Phe Val Pro Thr Gly Trp
            340                 345                 350

Ile His Ala Val Leu Thr Ser Gln Asp Cys Met Ala Phe Gly Gly Asn
        355                 360                 365

Phe Leu His Asn Leu Asn Ile Gly Met Gln Leu Arg Cys Tyr Glu Met
    370                 375                 380

Glu Lys Arg Leu Lys Thr Pro Asp Leu Phe Lys Phe Pro Phe Phe Glu
385                 390                 395                 400
```

-continued

Ala Ile Cys Trp Phe Val Ala Lys Asn Leu Leu Glu Thr Leu Lys Glu
                    405                 410                 415
Leu Arg Glu Asp Gly Phe Gln Pro Gln Thr Tyr Leu Val Gln Gly Val
            420                 425                 430
Lys Ala Leu His Thr Ala Leu Lys Leu Trp Met Lys Lys Glu Leu Val
        435                 440                 445
Ser Glu His Ala Phe Glu Ile Pro Asp Asn Val Arg Pro Gly His Leu
    450                 455                 460
Ile Lys Glu Leu Ser Lys Val Ile Arg Ala Glu Glu Glu Asn Gly
465                 470                 475                 480
Lys Pro Val Lys Ser Gln Gly Ile Pro Ile Val Cys Pro Val Ser Arg
                485                 490                 495
Ser Ser Asn Glu Ala Thr Ser Pro Tyr His Ser Arg Arg Lys Met Arg
            500                 505                 510
Lys Leu Arg Asp His Asn Val Arg Thr Pro Ser Asn Leu Asp Ile Leu
        515                 520                 525
Glu Leu His Thr Arg Glu Val Leu Lys Arg Leu Glu Met Cys Pro Trp
    530                 535                 540
Glu Glu Asp Ile Leu Ser Ser Lys Leu Asn Gly Lys Phe Asn Lys His
545                 550                 555                 560
Leu Gln Pro Ser Ser Thr Val Pro Glu Trp Arg Ala Lys Asp Asn Asp
                565                 570                 575
Leu Arg Leu Leu Leu Thr Asn Gly Arg Ile Ile Lys Asp Glu Arg Gln
            580                 585                 590
Pro Phe Ala Asp Gln Ser Leu Tyr Thr Ala Asp Ser Glu Asn Glu Glu
        595                 600                 605
Asp Lys Arg Arg Thr Lys Lys Ala Lys Met Lys Ile Glu Glu Ser Ser
    610                 615                 620
Gly Val Glu Gly Val Glu His Glu Glu Ser Gln Lys Pro Leu Asn Gly
625                 630                 635                 640
Phe Phe Thr Arg Val Lys Ser Glu Leu Arg Ser Arg Ser Ser Gly Tyr
                645                 650                 655
Ser Asp Ile Ser Glu Ser Glu Asp Ser Gly Pro Glu Cys Thr Ala Leu
            660                 665                 670
Lys Ser Ile Phe Thr Thr Glu Glu Ser Glu Ser Ser Gly Asp Glu Lys
        675                 680                 685
Lys Gln Glu Ile Thr Ser Asn Phe Lys Glu Glu Ser Asn Val Met Arg
    690                 695                 700
Asn Phe Leu Gln Lys Ser Gln Lys Pro Ser Arg Ser Glu Ile Pro Ile
705                 710                 715                 720
Lys Arg Glu Cys Pro Thr Ser Thr Ser Thr Glu Glu Glu Ala Ile Gln
                725                 730                 735
Gly Met Leu Ser Met Ala Gly Leu His Tyr Ser Thr Cys Leu Gln Arg
            740                 745                 750
Gln Ile Gln Ser Thr Asp Cys Ser Gly Glu Arg Asn Ser Leu Gln Asp
        755                 760                 765
Pro Ser Ser Cys His Gly Ser Asn His Glu Val Arg Gln Leu Tyr Arg
    770                 775                 780
Tyr Asp Lys Pro Val Glu Cys Gly Tyr His Val Lys Thr Glu Asp Pro
785                 790                 795                 800
Asp Leu Arg Thr Ser Ser Trp Ile Lys Gln Phe Asp Thr Ser Arg Phe
                805                 810                 815
His Pro Gln Asp Leu Ser Arg Ser Gln Lys Cys Ile Arg Lys Glu Gly

```
                    820                825                830
Ser Ser Glu Ile Ser Gln Arg Val Gln Ser Arg Asn Tyr Val Asp Ser
        835                840                845
Ser Gly Ser Ser Leu Gln Asn Gly Lys Tyr Met Gln Asn Ser Asn Leu
    850                855                860
Thr Ser Gly Ala Cys Gln Ile Ser Asn Gly Ser Leu Ser Pro Glu Arg
865                870                875                880
Pro Val Gly Glu Thr Ser Phe Ser Val Pro Leu His Pro Thr Lys Arg
                885                890                895
Pro Ala Ser Asn Pro Pro Ile Ser Asn Gln Ala Thr Lys Gly Lys
                900                905                910
Arg Pro Lys Lys Gly Met Ala Thr Ala Lys Gln Arg Leu Gly Lys Ile
        915                920                925
Leu Lys Leu Asn Arg Asn Gly His Ala Arg Phe Phe Val
    930                935                940
```

<210> SEQ ID NO 76
<211> LENGTH: 302
<212> TYPE: PRT
<213> ORGANISM: Homo sapiens

<400> SEQUENCE: 76

```
Met Asp Val Leu Ala Ser Tyr Ser Ile Phe Gln Glu Leu Gln Leu Val
1               5                   10                  15
His Asp Thr Gly Tyr Phe Ser Ala Leu Pro Ser Leu Glu Glu Thr Trp
                20                  25                  30
Gln Gln Thr Cys Leu Glu Leu Glu Arg Tyr Leu Gln Thr Glu Pro Arg
            35                  40                  45
Arg Ile Ser Glu Thr Phe Gly Glu Asp Leu Asp Cys Phe Leu His Ala
        50                  55                  60
Ser Pro Pro Pro Cys Ile Glu Glu Ser Phe Arg Arg Leu Asp Pro Leu
65                  70                  75                  80
Leu Leu Pro Val Glu Ala Ala Ile Cys Glu Lys Ser Ser Ala Val Asp
                85                  90                  95
Ile Leu Leu Ser Arg Asp Lys Leu Leu Ser Glu Thr Cys Leu Ser Leu
                100                 105                 110
Gln Pro Ala Ser Ser Leu Asp Ser Tyr Thr Ala Val Asn Gln Ala
            115                 120                 125
Gln Leu Asn Ala Val Thr Ser Leu Thr Pro Pro Ser Ser Pro Glu Leu
        130                 135                 140
Ser Arg His Leu Val Lys Thr Ser Gln Thr Leu Ser Ala Val Asp Gly
145                 150                 155                 160
Thr Val Thr Leu Lys Leu Val Ala Lys Lys Ala Ala Leu Ser Ser Val
                165                 170                 175
Lys Val Gly Gly Val Ala Thr Ala Ala Ala Val Thr Ala Ala Gly
                180                 185                 190
Ala Val Lys Ser Gly Gln Ser Asp Ser Asp Gln Gly Leu Gly Ala
            195                 200                 205
Glu Ala Cys Pro Glu Asn Lys Lys Arg Val His Arg Cys Gln Phe Asn
        210                 215                 220
Gly Cys Arg Lys Val Tyr Thr Lys Ser Ser His Leu Lys Ala His Gln
225                 230                 235                 240
Arg Thr His Thr Gly Glu Lys Pro Tyr Lys Cys Ser Trp Glu Gly Cys
                245                 250                 255
```

```
Glu Trp Arg Phe Ala Arg Ser Asp Glu Leu Thr Arg His Tyr Arg Lys
            260                 265                 270

His Thr Gly Ala Lys Pro Phe Lys Cys Asn His Cys Asp Arg Cys Phe
        275                 280                 285

Ser Arg Ser Asp His Leu Ala Leu His Met Lys Arg His Ile
    290                 295                 300

<210> SEQ ID NO 77
<211> LENGTH: 244
<212> TYPE: PRT
<213> ORGANISM: Homo sapiens

<400> SEQUENCE: 77

Met Ser Ala Ala Ala Tyr Met Asp Phe Val Ala Ala Gln Cys Leu Val
1               5                   10                  15

Ser Ile Ser Asn Arg Ala Ala Val Pro Glu His Gly Val Ala Pro Asp
            20                  25                  30

Ala Glu Arg Leu Arg Leu Pro Glu Arg Glu Val Thr Lys Glu His Gly
        35                  40                  45

Asp Pro Gly Asp Thr Trp Lys Asp Tyr Cys Thr Leu Val Thr Ile Ala
    50                  55                  60

Lys Ser Leu Leu Asp Leu Asn Lys Tyr Arg Pro Ile Gln Thr Pro Ser
65                  70                  75                  80

Val Cys Ser Asp Ser Leu Glu Ser Pro Asp Glu Asp Met Gly Ser Asp
                85                  90                  95

Ser Asp Val Thr Thr Glu Ser Gly Ser Ser Pro Ser His Ser Pro Glu
            100                 105                 110

Glu Arg Gln Asp Pro Gly Ser Ala Pro Ser Pro Leu Ser Leu Leu His
        115                 120                 125

Pro Gly Val Ala Ala Lys Gly Lys His Ala Ser Glu Lys Arg His Lys
    130                 135                 140

Cys Pro Tyr Ser Gly Cys Gly Lys Val Tyr Gly Lys Ser Ser His Leu
145                 150                 155                 160

Lys Ala His Tyr Arg Val His Thr Gly Glu Arg Pro Phe Pro Cys Thr
                165                 170                 175

Trp Pro Asp Cys Leu Lys Lys Phe Ser Arg Ser Asp Glu Leu Thr Arg
            180                 185                 190

His Tyr Arg Thr His Thr Gly Glu Lys Gln Phe Arg Cys Pro Leu Cys
        195                 200                 205

Glu Lys Arg Phe Met Arg Ser Asp His Leu Thr Lys His Ala Arg Arg
    210                 215                 220

His Thr Glu Phe His Pro Ser Met Ile Lys Arg Ser Lys Lys Ala Leu
225                 230                 235                 240

Ala Asn Ala Leu

<210> SEQ ID NO 78
<211> LENGTH: 164
<212> TYPE: PRT
<213> ORGANISM: Homo sapiens

<400> SEQUENCE: 78

Met Ser Val Asp Pro Leu Ser Ser Lys Ala Leu Lys Ile Lys Arg Glu
1               5                   10                  15

Leu Ser Glu Asn Thr Pro His Leu Ser Asp Glu Ala Leu Met Gly Leu
            20                  25                  30

Ser Val Arg Glu Leu Asn Arg His Leu Arg Gly Leu Ser Ala Glu Glu
```

```
            35                  40                  45
Val Thr Arg Leu Lys Gln Arg Arg Thr Leu Lys Asn Arg Gly Tyr
 50                  55                  60

Ala Ala Ser Cys Arg Val Lys Arg Val Cys Gln Lys Glu Glu Leu Gln
 65                  70                  75                  80

Lys Gln Lys Ser Glu Leu Glu Arg Glu Val Asp Lys Leu Ala Arg Glu
                 85                  90                  95

Asn Ala Ala Met Arg Leu Glu Leu Asp Ala Leu Arg Gly Lys Cys Glu
                100                 105                 110

Ala Leu Gln Gly Phe Ala Arg Ser Val Ala Ala Arg Gly Pro Ala
                115                 120                 125

Thr Leu Val Ala Pro Ala Ser Val Ile Thr Ile Val Lys Ser Thr Pro
130                 135                 140

Gly Ser Gly Ser Gly Pro Ala His Gly Pro Asp Pro Ala His Gly Pro
145                 150                 155                 160

Ala Ser Cys Ser

<210> SEQ ID NO 79
<211> LENGTH: 748
<212> TYPE: PRT
<213> ORGANISM: Homo sapiens

<400> SEQUENCE: 79

Met Ser Gln Trp Asn Gln Val Gln Gln Leu Glu Ile Lys Phe Leu Glu
  1               5                  10                  15

Gln Val Asp Gln Phe Tyr Asp Asp Asn Phe Pro Met Glu Ile Arg His
                 20                  25                  30

Leu Leu Ala Gln Trp Ile Glu Asn Gln Asp Trp Glu Ala Ala Ser Asn
             35                  40                  45

Asn Glu Thr Met Ala Thr Ile Leu Leu Gln Asn Leu Leu Ile Gln Leu
 50                  55                  60

Asp Glu Gln Leu Gly Arg Val Ser Lys Glu Lys Asn Leu Leu Leu Ile
 65                  70                  75                  80

His Asn Leu Lys Arg Ile Arg Lys Val Leu Gln Gly Lys Phe His Gly
                 85                  90                  95

Asn Pro Met His Val Ala Val Val Ile Ser Asn Cys Leu Arg Glu Glu
                100                 105                 110

Arg Arg Ile Leu Ala Ala Ala Asn Met Pro Val Gln Gly Pro Leu Glu
             115                 120                 125

Lys Ser Leu Gln Ser Ser Val Ser Glu Arg Gln Arg Asn Val Glu
130                 135                 140

His Lys Val Ala Ala Ile Lys Asn Ser Val Gln Met Thr Glu Gln Asp
145                 150                 155                 160

Thr Lys Tyr Leu Glu Asp Leu Gln Asp Glu Phe Asp Tyr Arg Tyr Lys
                165                 170                 175

Thr Ile Gln Thr Met Asp Gln Ser Asp Lys Asn Ser Ala Met Val Asn
                180                 185                 190

Gln Glu Val Leu Thr Leu Gln Glu Met Leu Asn Ser Leu Asp Phe Lys
             195                 200                 205

Arg Lys Glu Ala Leu Ser Lys Met Thr Gln Ile Ile His Glu Thr Asp
                210                 215                 220

Leu Leu Met Asn Thr Met Leu Ile Glu Glu Leu Gln Asp Trp Lys Arg
225                 230                 235                 240

Arg Gln Gln Ile Ala Cys Ile Gly Gly Pro Leu His Asn Gly Leu Asp
```

```
                    245                 250                 255
          Gln Leu Gln Asn Cys Phe Thr Leu Leu Ala Glu Ser Leu Phe Gln Leu
                        260                 265                 270
          Arg Arg Gln Leu Glu Lys Leu Glu Glu Gln Ser Thr Lys Met Thr Tyr
                        275                 280                 285
          Glu Gly Asp Pro Ile Pro Met Gln Arg Thr His Met Leu Glu Arg Val
                        290                 295                 300
          Thr Phe Leu Ile Tyr Asn Leu Phe Lys Asn Ser Phe Val Val Glu Arg
          305                 310                 315                 320
          Gln Pro Cys Met Pro Thr His Pro Gln Arg Pro Leu Val Leu Lys Thr
                        325                 330                 335
          Leu Ile Gln Phe Thr Val Lys Leu Arg Leu Leu Ile Lys Leu Pro Glu
                        340                 345                 350
          Leu Asn Tyr Gln Val Lys Val Lys Ala Ser Ile Asp Lys Asn Val Ser
                        355                 360                 365
          Thr Leu Ser Asn Arg Arg Phe Val Leu Cys Gly Thr Asn Val Lys Ala
                        370                 375                 380
          Met Ser Ile Glu Glu Ser Ser Asn Gly Ser Leu Ser Val Glu Phe Arg
          385                 390                 395                 400
          His Leu Gln Pro Lys Glu Met Lys Ser Ser Ala Gly Lys Gly Asn
                        405                 410                 415
          Glu Gly Cys His Met Val Thr Glu Glu Leu His Ser Ile Thr Phe Glu
                        420                 425                 430
          Thr Gln Ile Cys Leu Tyr Gly Leu Thr Ile Asp Leu Glu Thr Ser Ser
                        435                 440                 445
          Leu Pro Val Val Met Ile Ser Asn Val Ser Gln Leu Pro Asn Ala Trp
                        450                 455                 460
          Ala Ser Ile Ile Trp Tyr Asn Val Ser Thr Asn Asp Ser Gln Asn Leu
          465                 470                 475                 480
          Val Phe Phe Asn Asn Pro Pro Ala Thr Leu Ser Gln Leu Leu Glu
                        485                 490                 495
          Val Met Ser Trp Gln Phe Ser Ser Tyr Val Gly Arg Gly Leu Asn Ser
                        500                 505                 510
          Asp Gln Leu His Met Leu Ala Glu Lys Leu Thr Val Gln Ser Ser Tyr
                        515                 520                 525
          Ser Asp Gly His Leu Thr Trp Ala Lys Phe Cys Lys Glu His Leu Pro
                        530                 535                 540
          Gly Lys Ser Phe Thr Phe Trp Thr Trp Leu Glu Ala Ile Leu Asp Leu
          545                 550                 555                 560
          Ile Lys Lys His Ile Leu Pro Leu Trp Ile Asp Gly Tyr Val Met Gly
                        565                 570                 575
          Phe Val Ser Lys Glu Lys Glu Arg Leu Leu Leu Lys Asp Lys Met Pro
                        580                 585                 590
          Gly Thr Phe Leu Leu Arg Phe Ser Glu Ser His Leu Gly Gly Ile Thr
                        595                 600                 605
          Phe Thr Trp Val Asp His Ser Glu Ser Gly Glu Val Arg Phe His Ser
                        610                 615                 620
          Val Glu Pro Tyr Asn Lys Gly Arg Leu Ser Ala Leu Pro Phe Ala Asp
          625                 630                 635                 640
          Ile Leu Arg Asp Tyr Lys Val Ile Met Ala Glu Asn Ile Pro Glu Asn
                        645                 650                 655
          Pro Leu Lys Tyr Leu Tyr Pro Asp Ile Pro Lys Asp Lys Ala Phe Gly
                        660                 665                 670
```

```
Lys His Tyr Ser Ser Gln Pro Cys Glu Val Ser Arg Pro Thr Glu Arg
            675                 680                 685

Gly Asp Lys Gly Tyr Val Pro Ser Val Phe Ile Pro Ile Ser Thr Ile
690                 695                 700

Arg Ser Asp Ser Thr Glu Pro His Ser Pro Ser Asp Leu Leu Pro Met
705                 710                 715                 720

Ser Pro Ser Val Tyr Ala Val Leu Arg Glu Asn Leu Ser Pro Thr Thr
                725                 730                 735

Ile Glu Thr Ala Met Lys Ser Pro Tyr Ser Ala Glu
            740                 745

<210> SEQ ID NO 80
<211> LENGTH: 526
<212> TYPE: PRT
<213> ORGANISM: Homo sapiens

<400> SEQUENCE: 80

Met Asp Val Arg Phe Tyr Pro Pro Ala Gln Pro Ala Ala Ala Pro
1               5                  10                  15

Asp Ala Pro Cys Leu Gly Pro Ser Pro Cys Leu Asp Pro Tyr Tyr Cys
                20                  25                  30

Asn Lys Phe Asp Gly Glu Asn Met Tyr Met Ser Met Thr Glu Pro Ser
            35                  40                  45

Gln Asp Tyr Val Pro Ala Ser Gln Ser Tyr Pro Gly Pro Ser Leu Glu
        50                  55                  60

Ser Glu Asp Phe Asn Ile Pro Pro Ile Thr Pro Pro Ser Leu Pro Asp
65                  70                  75                  80

His Ser Leu Val His Leu Asn Glu Val Glu Ser Gly Tyr His Ser Leu
                85                  90                  95

Cys His Pro Met Asn His Asn Gly Leu Leu Pro Phe His Pro Gln Asn
                100                 105                 110

Met Asp Leu Pro Glu Ile Thr Val Ser Asn Met Leu Gly Gln Asp Gly
            115                 120                 125

Thr Leu Leu Ser Asn Ser Ile Ser Val Met Pro Asp Ile Arg Asn Pro
        130                 135                 140

Glu Gly Thr Gln Tyr Ser Ser His Pro Gln Met Ala Ala Met Arg Pro
145                 150                 155                 160

Arg Gly Gln Pro Ala Asp Ile Arg Gln Gln Pro Gly Met Met Pro His
                165                 170                 175

Gly Gln Leu Thr Thr Ile Asn Gln Ser Gln Leu Ser Ala Gln Leu Gly
            180                 185                 190

Leu Asn Met Gly Gly Ser Asn Val Pro His Asn Ser Pro Ser Pro Pro
        195                 200                 205

Gly Ser Lys Ser Ala Thr Pro Ser Pro Ser Ser Ser Val His Glu Asp
210                 215                 220

Glu Gly Asp Asp Thr Ser Lys Ile Asn Gly Gly Glu Lys Arg Pro Ala
225                 230                 235                 240

Ser Asp Met Gly Lys Lys Pro Lys Thr Pro Lys Lys Lys Lys Lys Lys
                245                 250                 255

Asp Pro Asn Glu Pro Gln Lys Pro Val Ser Ala Tyr Ala Leu Phe Phe
            260                 265                 270

Arg Asp Thr Gln Ala Ala Ile Lys Gly Gln Asn Pro Asn Ala Thr Phe
        275                 280                 285

Gly Glu Val Ser Lys Ile Val Ala Ser Met Trp Asp Gly Leu Gly Glu
```

```
            290                 295                 300
Glu Gln Lys Gln Val Tyr Lys Lys Thr Glu Ala Ala Lys Lys Glu
305                 310                 315                 320

Tyr Leu Lys Gln Leu Ala Ala Tyr Arg Ala Ser Leu Val Ser Lys Ser
                325                 330                 335

Tyr Ser Glu Pro Val Asp Val Lys Thr Ser Gln Pro Pro Gln Leu Ile
                340                 345                 350

Asn Ser Lys Pro Ser Val Phe His Gly Pro Ser Gln Ala His Ser Ala
                355                 360                 365

Leu Tyr Leu Ser Ser His Tyr His Gln Gln Pro Gly Met Asn Pro His
                370                 375                 380

Leu Thr Ala Met His Pro Ser Leu Pro Arg Asn Ile Ala Pro Lys Pro
385                 390                 395                 400

Asn Asn Gln Met Pro Val Thr Val Ser Ile Ala Asn Met Ala Val Ser
                405                 410                 415

Pro Pro Pro Pro Leu Gln Ile Ser Pro Pro Leu His Gln His Leu Asn
                420                 425                 430

Met Gln Gln His Gln Pro Leu Thr Met Gln Gln Pro Leu Gly Asn Gln
                435                 440                 445

Leu Pro Met Gln Val Gln Ser Ala Leu His Ser Pro Thr Met Gln Gln
                450                 455                 460

Gly Phe Thr Leu Gln Pro Asp Tyr Gln Thr Ile Ile Asn Pro Thr Ser
465                 470                 475                 480

Thr Ala Ala Gln Val Val Thr Gln Ala Met Glu Tyr Val Arg Ser Gly
                485                 490                 495

Cys Arg Asn Pro Pro Gln Pro Val Asp Trp Asn Asn Asp Tyr Cys
                500                 505                 510

Ser Ser Gly Gly Met Gln Arg Asp Lys Ala Leu Tyr Leu Thr
                515                 520                 525

<210> SEQ ID NO 81
<211> LENGTH: 673
<212> TYPE: PRT
<213> ORGANISM: Homo sapiens

<400> SEQUENCE: 81

Met Asp Leu Thr Lys Met Gly Met Ile Gln Leu Gln Asn Pro Ser His
1               5                   10                  15

Pro Thr Gly Leu Leu Cys Lys Ala Asn Gln Met Arg Leu Ala Gly Thr
                20                  25                  30

Leu Cys Asp Val Val Ile Met Val Asp Ser Gln Glu Phe His Ala His
                35                  40                  45

Arg Thr Val Leu Ala Cys Thr Ser Lys Met Phe Glu Ile Leu Phe His
50                  55                  60

Arg Asn Ser Gln His Tyr Thr Leu Asp Phe Leu Ser Pro Lys Thr Phe
65                  70                  75                  80

Gln Gln Ile Leu Glu Tyr Ala Tyr Thr Ala Thr Leu Gln Ala Lys Ala
                85                  90                  95

Glu Asp Leu Asp Asp Leu Leu Tyr Ala Ala Glu Ile Leu Glu Ile Glu
                100                 105                 110

Tyr Leu Glu Glu Gln Cys Leu Lys Met Leu Glu Thr Ile Gln Ala Ser
                115                 120                 125

Asp Asp Asn Asp Thr Glu Ala Thr Met Ala Asp Gly Gly Ala Glu Glu
                130                 135                 140
```

-continued

Glu Glu Asp Arg Lys Ala Arg Tyr Leu Lys Asn Ile Phe Ile Ser Lys
145                 150                 155                 160

His Ser Ser Glu Glu Ser Gly Tyr Ala Ser Val Ala Gly Gln Ser Leu
            165                 170                 175

Pro Gly Pro Met Val Asp Gln Ser Pro Ser Val Ser Thr Ser Phe Gly
            180                 185                 190

Leu Ser Ala Met Ser Pro Thr Lys Ala Ala Val Asp Ser Leu Met Thr
            195                 200                 205

Ile Gly Gln Ser Leu Leu Gln Gly Thr Leu Gln Pro Ala Gly Pro
210                 215                 220

Glu Glu Pro Thr Leu Ala Gly Gly Arg His Pro Gly Val Ala Glu
225                 230                 235                 240

Val Lys Thr Glu Met Met Gln Val Asp Glu Val Pro Ser Gln Asp Ser
                245                 250                 255

Pro Gly Ala Ala Glu Ser Ser Ile Ser Gly Gly Met Gly Asp Lys Val
            260                 265                 270

Glu Glu Arg Gly Lys Glu Gly Pro Gly Thr Pro Thr Arg Ser Ser Val
            275                 280                 285

Ile Thr Ser Ala Arg Glu Leu His Tyr Gly Arg Glu Glu Ser Ala Glu
290                 295                 300

Gln Val Pro Pro Pro Ala Glu Ala Gly Gln Ala Pro Thr Gly Arg Pro
305                 310                 315                 320

Glu His Pro Ala Pro Pro Glu Lys His Leu Gly Ile Tyr Ser Val
            325                 330                 335

Leu Pro Asn His Lys Ala Asp Ala Val Leu Ser Met Pro Ser Ser Val
            340                 345                 350

Thr Ser Gly Leu His Val Gln Pro Ala Leu Ala Val Ser Met Asp Phe
            355                 360                 365

Ser Thr Tyr Gly Gly Leu Leu Pro Gln Gly Phe Ile Gln Arg Glu Leu
            370                 375                 380

Phe Ser Lys Leu Gly Glu Leu Ala Val Gly Met Lys Ser Glu Ser Arg
385                 390                 395                 400

Thr Ile Gly Glu Gln Cys Ser Val Cys Gly Val Glu Leu Pro Asp Asn
                405                 410                 415

Glu Ala Val Glu Gln His Arg Lys Leu His Ser Gly Met Lys Thr Tyr
            420                 425                 430

Gly Cys Glu Leu Cys Gly Lys Arg Phe Leu Asp Ser Leu Arg Leu Arg
            435                 440                 445

Met His Leu Leu Ala His Ser Ala Gly Ala Lys Ala Phe Val Cys Asp
450                 455                 460

Gln Cys Gly Ala Gln Phe Ser Lys Glu Asp Ala Leu Glu Thr His Arg
465                 470                 475                 480

Gln Thr His Thr Gly Thr Asp Met Ala Val Phe Cys Leu Leu Cys Gly
            485                 490                 495

Lys Arg Phe Gln Ala Gln Ser Ala Leu Gln Gln His Met Glu Val His
            500                 505                 510

Ala Gly Val Arg Ser Tyr Ile Cys Ser Glu Cys Asn Arg Thr Phe Pro
            515                 520                 525

Ser His Thr Ala Leu Lys Arg His Leu Arg Ser His Thr Gly Asp His
            530                 535                 540

Pro Tyr Glu Cys Glu Phe Cys Gly Ser Cys Phe Arg Asp Glu Ser Thr
545                 550                 555                 560

Leu Lys Ser His Lys Arg Ile His Thr Gly Glu Lys Pro Tyr Glu Cys

-continued

```
            565                 570                 575
Asn Gly Cys Gly Lys Lys Phe Ser Leu Lys His Gln Leu Glu Thr His
            580                 585                 590

Tyr Arg Val His Thr Gly Glu Lys Pro Phe Glu Cys Lys Leu Cys His
        595                 600                 605

Gln Arg Ser Arg Asp Tyr Ser Ala Met Ile Lys His Leu Arg Thr His
    610                 615                 620

Asn Gly Ala Ser Pro Tyr Gln Cys Thr Ile Cys Thr Glu Tyr Cys Pro
625                 630                 635                 640

Ser Leu Ser Ser Met Gln Lys His Met Lys Gly His Lys Pro Glu Glu
            645                 650                 655

Ile Pro Pro Asp Trp Arg Ile Glu Lys Thr Tyr Leu Tyr Leu Cys Tyr
            660                 665                 670

Val
```

DETECTION OF ACUTE MYELOID LEUKAEMIA (AML) LEUKAEMIC STEM CELLS (LSC)

CROSS-REFERENCE TO RELATED APPLICATIONS

This application claims the benefit of U.S. Provisional Appl. 62/084,756, filed Nov. 26, 2014, the contents of which are incorporated herein by reference in their entirety.

REFERENCE TO A SEQUENCE LISTING SUBMITTED ELECTRONICALLY VIA EFS-WEB

The content of the sequence listing (Name: sequence_listing.txt; Size: (395,505 bytes; and Date of Creation: Nov. 5, 2015) electronically submitted via EFS-Web is incorporated by reference in its entirety.

BACKGROUND OF THE INVENTION

Human Acute Myeloid Leukaemia (AML) is an aggressive cancer of white blood cells and is the most common adult acute leukaemia. In more detail, AML is a cancer of the myeloid line of blood cells. It is characterized by the rapid growth of an abnormal white blood cell population. Approximately 80% of AML patients are over the age of 60 and the overall survival of this patient group lies at only approximately 5%.

AML can be classified into several subgroups. By way of example, classification according to the World Health Organization (WHO) criteria is based on examination of bone marrow aspirate or a blood sample via light microscopy. Alternatively, bone marrow or blood may be tested for chromosomal translocations by routine cytogenetic methods or fluorescent in situ hybridisation (FISH), and for specific genetic mutations (such as mutations in the FLT3, NPM1 and CEBPA genes) may be detected by polymerase chain reaction (PCR). Immunophenotyping is another method that may be used to identify the AML subtype, which involves detection of cell surface and cytoplasmic markers using flow cytometry.

Flow cytometry is a technique for counting and examining microscopic particles such as cells by suspending them in a stream of fluid and capturing the light that emerges from each cell as it passes through a laser beam. Cell surface molecules often referred to as "cluster of differentiation" (CD) molecules may be exploited in flow cytometry to characterise cell populations. For example, in fluorescence-activated cell sorting, a diagnostic antibody (labelled with a fluorophore) is employed, which binds to a surface molecule (e.g. a CD molecule) present on and characteristic of the cell population in question. Thereafter, the flourophore (attached to the antibody) is activated by a laser beam and the fluorescence signal detected by the flow cytometer. In this manner, fluorescently-labelled antibodies can be used to detect and sort cells displaying a specific CD molecule (or set of CD molecules).

Current AML therapies typically involve induction chemotherapy followed by post-induction therapy. The goal of induction chemotherapy is to reduce the amount of leukaemic cells to less than 5% of all the nucleated cells in a bone marrow sample. Regrettably, this level of reduction of leukaemic cells is not enough to prevent disease recurrence (i.e. relapse) and almost all patients relapse without post-induction therapy. Post-induction therapy typically involves further cycles of chemotherapy, and in some cases, a hematopoietic stem cell transplant that aims to eliminate minimal residual disease (MRD). MRD is the population of leukaemic cells that is recalcitrant to therapy. It is thought that this population of cells contains a sub-population of cells termed a leukaemic stem cell (LSC) population. Acute myeloid leukaemia (AML) leukaemic stem cells (LSC) are a sub-population of cells that propagate leukaemia and have self-renewal properties. They are often resistant to current treatment methods and serve to sustain disease.

Current methods used to detect MRD/LSC include real time quantitative PCR (RQ-PCR) or multi-parameter flow cytometry (MFC). However, current RQ-PCR based MRD/LSC assessment is not possible in approximately half of patients with AML.

In addition, and despite recent technical developments, there is still a lack of a validated MFC methodology demonstrating clinical utility—current sensitivity levels of MFC are at least 1 log below real time that of RQ-PCR assays.

There is, therefore, a need to provide an alternative and/or improved methods for detecting acute myeloid leukaemia leukaemic stem cells. In addition, there is a need to provide an alternative and/or improved method for diagnosis and/or prognosis of acute myeloid leukaemia. In particular, there is a need to provide an alternative and/or improved method to detect and monitor MRD/LSC for acute myeloid leukaemia.

The present invention solves one or more of the above mentioned problems.

BRIEF SUMMARY OF THE INVENTION

The present invention relates to diagnostic markers of acute myeloid leukaemia leukaemic stem cells, to a diagnostic screen based on said markers, and to the use of said screen in diagnostic, prognostic and therapeutic methods. The present invention further relates to gene expression profiles for detecting acute myeloid leukaemia leukaemic stem cells and to the use of said gene expression profiles in diagnostic, prognostic and therapeutic methods.

BRIEF DESCRIPTION OF THE SEVERAL VIEWS OF THE DRAWINGS

FIG. 1A through FIG. 1C—Characteristics of CD34− AML samples.

FIG. 1A Characteristics of 49 CD34− AML samples: patient demographics, blast %, immunophenotype, karyotype (*segregated into prognostic groups) and mutational profile. Wt: wildtype; mt: mutated.

FIG. 1B Immunophenotype analysis of CD34− samples: >98% of cells are CD34−. AML samples can be subdivided into 2 groups based on expression of CD117. Representative flow plots are shown. Numbers within flow plots indicate mean values of all samples within the group (% of parent population). Parent population is indicated above each plot.

FIG. 1C Expression of CD34, CD244 and CD117 in the 49 AML samples (% of live lineage—MNCs).

FIG. 2A through FIG. 2F—Sorting CD34− AML samples for xenotransplantation assays Where indicated, CD34+ and CD34− subpopulations are boxed. Numbers within flow plots are mean values (% of parent population). Except where indicated, the parent population is indicated above each plot.

FIG. 2A Representative FACS gating applied to all subsequent flow-sort schemes showing gating on a mononuclear blast cell gate with doublet exclusion and then a live cell gate (Hoechst negative). 2 sort methods were used to fractionate 8 AML samples: all were initially gated for lineage negative populations; following which samples #059, #449, #875, #880 and #1037 were sorted using antibodies to CD34, CD150, CD244, CD48 and CD117, and populations were purified on the basis of CD117 expression (top panel); and samples #001 and, #230 using antibodies to CD34, CD150, CD244, CD48 and CD117 where populations were purified on the basis of CD244 expression.

FIG. 2B CD34 and CD117 (in CD34− fractions) expression predict LSC activity in CD34− AML samples. Y-axis depicts mean % hCD45+33+19− cell engraftment/total live MNC. X-axis shows injected cell fraction. Red dotted line indicates threshold of engraftment (0.1% hCD45+33+19−/total live MNCs). A summary of data from 8 patient samples are shown: each data point represents mean engraftment in up to 6 mice (range 1-6) of the injected populations derived from one patient.

FIG. 2C There is no significant difference in LSC frequency between engrafting CD34+ and CD34− populations. LSC frequency was calculated from limit dilution transplant assays (LDA). Error bars indicate calculated 95% confidence interval. Data points without error bars indicate cell fractions where threshold non-engrafting cell number was not achieved. Here, lowest injected cell numbers are shown.

FIG. 2D Immunophenotype of the patient's leukemia is recapitulated in the mouse. Two representative examples #1037 and #875 show the immunophenotype in the patient sample and in the engrafted mouse. Mice injected with either CD34+ or CD34− leukemic cells engraft both CD34+ and CD34− populations. Both CD34+ and CD34− subpopulations are flow-sorted with purity. Arrows indicate gating of CD34− cells for expression of CD244 and CD117.

FIG. 2E Summary of primary engraftment experiments when different numbers of cells were injected from the populations indicated. Sorted patient AML subpopulations were annotated as engrafting or non-engrafting: at least one engrafting subpopulations in each patient sample propagates leukaemia at cell numbers lower than non-engrafting subpopulations. Results from injection of different cell populations from sample #1037 are not shown as all subpopulations engraft. '*' on the graphs denote data points where the same cell numbers were injected.

FIG. 2F CD34+ and CD34− LSCs are present in grafts regardless of whether the injected primary LSCs express CD34. This is demonstrated by serial xenotransplantation. The table shows i) sorted patient LSC populations injected (+) into primary mice (top section) whose engrafted progeny was subsequently sorted into CD34+ and CD34− populations and injected (+) into secondary mice (middle section). The mean leukaemic engraftment of secondary mice is in the lower section (mean of up to 5 mice, range 1-5).

FIG. 3A though FIG. 3H—Gene expression of LSCs are distinctive compared with normal haematopoietic and non-LSC populations.

FIG. 3A Principal component analysis (PCA) using top 300 most significant differentially expressed genes between normal BM CD34+HSC/progenitor and CD34− populations obtained by ANOVA were used to cluster normal populations and LSCs (▲). % variability in PC1 and PC2 is shown.

FIG. 3C Gene Set Enrichment Analysis (GSEA) of normal HSC/MPP signatures in profiles comparing CD34− LSCs with normal HSC/MPP or CD34−244=117+(myeloid precursor). Normalised enrichment scores (NES) are shown. All comparisons were statistically significant (false discovery rate, FDR q-value <0.001).

FIG. 3D Gene Set Enrichment Analysis (GSEA) of normal CD34− 244+117+(myeloid precursor) signatures in profiles comparing CD34− LSCs with normal HSC/MPP or CD34−244=117+(myeloid precursor). Normalised enrichment scores (NES) are shown. All comparisons were statistically significant (false discovery rate, FDR q-value <0.001).

FIG. 3E Gene Set Enrichment Analysis (GSEA) of GMP signatures in profiles comparing CD34− LSCs with normal HSC/MPP or CD34−244=117+(myeloid precursor). Normalised enrichment scores (NES) are shown. All comparisons were statistically significant (false discovery rate, FDR q-value <0.001).

FIG. 3F PCA using 525 curated, annotated transcription factor genes to cluster normal BM HSPC and precursor populations and LSCs (▲). % variability in PC1 and PC2 is shown.

FIG. 3G Loadings plot for PCA in (f). Genes contributing to most variability in PC1 and PC2 are annotated.

FIG. 4—Selection of genes whose expression in CD34− AML LSCs is distinctive compared with normal HSC, myeloid precursors and non-LSCs.

Figure 1B:
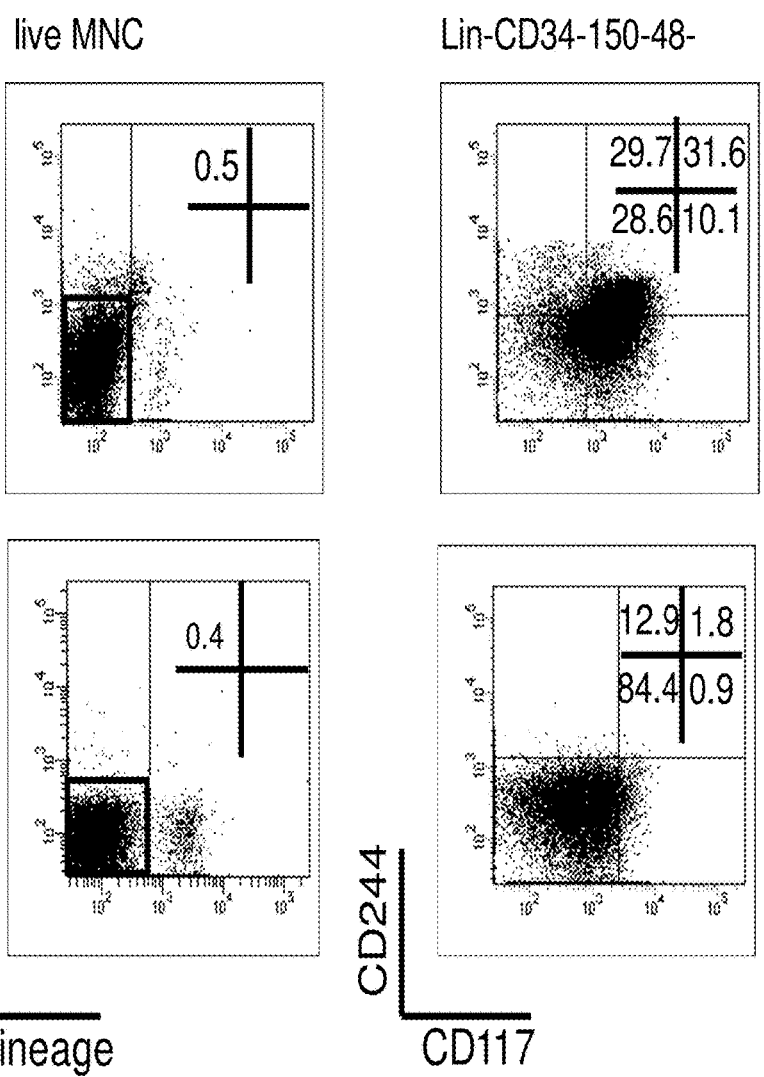

Table showing list of genes and their expression levels (log 2 counts per million) in CD34− AML LSCs (lsc) compared with normal bone marrow HSC (hsc), myeloid precursors (myepre), non-LSCs (nonlsc). (CPM=counts per million, FC=fold change, SD=standard deviation, SEM=standard error of the mean). Genes in grey boxes form a 'core' set. The range of log 2 FC calculated as mean log 2 FC+/−1.96×SEM is shown as log 2 FC min (minimum) and max (maximum).

DETAILED DESCRIPTION OF THE INVENTION

In one aspect, the invention provides a diagnostic screen for detecting acute myeloid leukaemia (AML) leukaemic stem cells (LSC), wherein said screen detects the presence (+) or absence (−), as indicated below, of the following cell surface polypeptide markers:
i) CD34−
ii) CD48−
iii) CD117+
iv) CD150−
v) CD244+ or CD244−.

A cell surface polypeptide marker may be displayed (at least in part) on the extracellular surface of a cell. Markers of the present invention may include CD34, CD48, CD117, CD150, CD244, CD2, CD3, CD4, CD8a, CD10, CD19, CD20 and/or CD235a.

The present inventors have unexpectedly found that a combination of the above-mentioned cell surface markers represents a robust diagnostic screen for acute myeloid leukaemia (AML) leukaemic stem cells (LSC). This enables detection and monitoring of AML LSC and MRD.

A screen as defined herein has many useful applications including diagnostic and prognostic applications such as in clinical guidance and for determining therapy, for patient management and for assessing treatment efficacy. In particular, the diagnostic screen of the present invention can be used as a prognostic indicator.

In one embodiment, the invention provides a diagnostic screen as defined above, wherein the marker v) is CD244+.

In another embodiment, the invention provides a diagnostic screen as defined above, wherein the marker v) is CD244−.

In one embodiment, the invention provides a diagnostic screen as defined above, further comprising one or more (or two or more, or three or more, or four or more) of the cell surface polypeptide markers selected from CD2−, CD3−, CD4−, CD8a−, CD10−, CD19−, CD20− and/or CD235a−. In one embodiment, the invention provides a diagnostic screen as defined above, comprising the cell surface polypeptide marker CD2−. In one embodiment, the invention provides a diagnostic screen as defined above, comprising the cell surface polypeptide marker CD3−. In one embodiment, the invention provides a diagnostic screen as defined above, comprising the cell surface polypeptide marker CD4−. In one embodiment, the invention provides a diagnostic screen as defined above, comprising the cell surface polypeptide marker CD8a−. In one embodiment, the invention provides a diagnostic screen as defined above, comprising the cell surface polypeptide marker CD10−. In one embodiment, the invention provides a diagnostic screen as defined above, comprising the cell surface polypeptide marker CD19−. In one embodiment, the invention provides a diagnostic screen as defined above, comprising the cell surface polypeptide marker CD20−. In one embodiment, the invention provides a diagnostic screen as defined above, comprising the cell surface polypeptide marker CD235−.

In one embodiment, the diagnostic screen comprises one or more antibodies that bind to one or more of the identified markers. Thus, said one or more antibodies may be used to confirm the presence (+) or absence (−) of said cell surface polypeptide markers. In one embodiment, the presence (+) of a marker refers to an elevation in the levels of marker in a sample above a background level. Likewise, the absence (−) of a marker refers to a reduction in the levels of a marker in a sample below a background level. In one embodiment, the elevation in the levels of marker in a sample above a background level is 1 or more (such as 2, 3, 4, 5, 6, 7, 8, 10, 15, 20, 25) fluorescence units. In one embodiment a reduction in the levels of a marker in a sample below a background level is 1 or more (such as 2, 3, 4, 5, 6, 7, 8, 10, 15, 20, 25) fluorescence units. In this regard, it would be routine for a skilled person in the art to determine the background level of marker expression in a sample. Thus, in one embodiment, said cell surface polypeptide markers may be detected by specific binding of said one or more antibodies.

In one embodiment, the screen comprises one or more antibodies that bind to one or more cell surface polypeptide markers selected from CD34, CD48, CD117, CD150, CD244, CD2, CD3, CD4, CD8a, CD10, CD19, CD20 and/or CD235a.

In one embodiment, the screen comprises a first antibody that binds to CD34, a second antibody that binds to CD48, and a third antibody that binds to CD117, a fourth antibody that binds to CD150, and a fifth antibody that binds to CD244.

Any one or more of said antibodies may bind to one of said markers and not (substantially) to any of the other markers. For example, each of the employed antibodies may bind to one of said markers and not (substantially) to any of the other markers. Alternatively, any one or more of said antibodies may bind to two, three, four, five, six, seven, eight, nine or all ten of said markers.

In one embodiment, the screen comprises five antibodies, wherein:
a first antibody that binds to CD34 and preferably not to CD48, CD117, CD150 and/or CD244;
a second antibody that binds to CD48 and preferably not to CD34, CD117, CD 150 and/or CD244;
a third antibody that binds to CD117 and preferably not to CD34, CD48, CD150 and/or CD244;
a fourth antibody that binds to CD150 and preferably not to CD34, CD48, CD117 and/or CD244; and
a fifth antibody that binds to CD 244 and preferably not to CD 34, CD48, CD117 and/or CD150.

In one embodiment, the antibodies of the present invention recognise and bind to specific epitopes of the above mentioned cell surface polypeptide markers. For example, an antibody of the present invention may bind to an epitope in the N-terminal/C-terminal/mid-region domains/extracellular domains of CD34, CD48, CD117, CD150, CD244, CD2, CD3, CD4, CD8a, CD10, CD19, CD20 and/or CD235a. The sequence of CD34, CD48, CD117, CD150, CD244, CD2, CD3, CD4, CD8a, CD10, CD19, CD20 and/or CD235a are available from the NCBI website http://www.ncbi.nlm.nih.gov/projects/genome/assembly/grc/human/index.shtml). These protein sequences are provided as SEQ ID NOs: 1-13.

In one embodiment, the antibodies of the present invention may bind to a CD34, CD48, CD117, CD150, CD244, CD2, CD3, CD4, CD8a, CD10, CD19, CD20 and/or CD235a molecules comprising an amino acid sequence having at least 80% (such at least 85%, 90%, 95%, 98%, 99% or 100%) sequence identity to SEQ ID NOs:1-13, or a fragment or variant or derivative thereof.

Conventional methods for determining nucleic acid/amino acid sequence identity are discussed in more detail later in the specification.

In one embodiment, the antibodies are polyclonal and/or monoclonal antibodies.

In one embodiment, an antibody that binds to one of the above-mentioned cell surface polypeptide markers is one capable of binding that marker with sufficient affinity such that the antibody is useful as a diagnostic/and or prognostic agent. In one embodiment, the term 'binds' is equivalent to 'specifically binds'. An antibody that binds/specifically binds to a cell surface polypeptide marker of interest is one that binds to one of the above mentioned markers with an affinity (Ka) of at least $10^4$ M.

Suitable antibodies of the present invention may include PE-Cy5 or PERCP-conjugated anti-CD34, FITC conjugated anti-CD48, PE conjugated anti-CD117, FITC conjugated anti-CD150, APC conjugated anti-CD244, CD19 Horizon V450 and APC-Alexa Fluor 750 or APC-eFluor 780 conjugated streptavidin which are available from a number of different commercial suppliers including Biolegend, BD Biosciences Europe ebioscience, Beckman Coulter, Invitrogen and/or Pharmingen.

In a preferred embodiment, the antibody is a labelled antibody, such as a fluorescently labelled antibody. Suitable labelled compounds include conventionally known labelled compounds, such as fluorescent substances such as cyanine dyes Cy3 (registered trademark of Amersham Life Science), fluorescein isothiacyanate (FITC), allophycocyanin (APC), rhodamine, Phycoerythrin (PE), PE-Cy5 (Phycoerythrin-Cy5), PE-Cy7 (Phycoerythrin-Cy7), APC-Alexa Fluor 750, APC-eFluor 780, Pacific Blue, Horizon V450 and quantum dot, biotin-conjugated; light scattering substances such as gold particles; photo-absorptive substances such as ferrite; radioactive substances such as <125> I; and enzymes such as peroxidase or alkali phosphatase.

In one embodiment of the invention, different antibodies are labelled respectively with mutually distinguishable labels. Labelling may be conducted by binding a labelled compound directly to each antibody. Preferably, the antibodies are labelled with different fluorescent dyes with different fluorescence wavelengths to enable easy discrimination from one another. For example a first antibody may be labelled in red (for example PE-Cy5), a second antibody in orange (for example PI, APC, R-PE), a third antibody in green (for example Alexa488, FITC) and so forth. Suitable labelling strategies are routine and known to a person skilled in the art. By way of example, the Lightening Link™ antibody labeling kit may be used (Innova Biosciences, UK).

Methods suitable for detection of the cell surface polypeptide markers of the present invention using labelled antibodies are conventional techniques known to those skilled in the art. For example, when a fluorescent label is used, an antibody that specifically binds to a marker may be detected by observing the emitted fluorescence colour under a microscope. A fluorescent label can also be detected by irradiating a sample with an exciting light—if the label is present, fluorescence is emitted from the sample. Thus, whether a cell is positive or negative for a particular cell surface marker may be judged by using a labelled antibody specific for said marker and observing the emitted fluorescence colour under a microscope. In a preferred embodiment of the invention, fluorescence-activated cell sorting (FACS) is used for detection of the cell surface polypeptide markers/labeled antibodies of the present invention. In other words, the one or more labelled antibodies of the present invention may bind to the one or more cell surface polypeptide markers of the present invention, thereby forming an antibody-marker/antibody-blood cell complex. In a preferred embodiment of the invention, said complex can be detected/its presence confirmed by FACS. In an alternative embodiment said complex can be detected by applying a detection agent that detects said complex. Suitable detection agents and methods are known to those skilled in the art. By way of example, a secondary antibody may be used to detect said complex and/or said complex can detected by way of an enzyme-linked immunosorbent assay (ELISA) assay. Other suitable detection methods are conventional and known to those skilled in the art.

In one aspect, the present invention provides a screen (as defined above) for use in a method of diagnosis of acute myeloid leukaemia.

In a related aspect, the invention provides a method for diagnosing acute myeloid leukaemia, said method comprising:
  i) contacting an isolated sample containing a blood cell population with a screen that identifies a blood cell/blood cell population having a cell surface phenotype comprising:
    a) CD34−;
    b) CD48−;
    c) CD117+;
    d) CD150−
    e) CD244+ or CD244−
  ii) confirming the presence of a blood cell/blood cell population that has a cell surface phenotype comprising:
    a) CD34−;
    b) CD48−;
    c) CD117+;
    d) CD150−
    e) CD244+ or CD244−.

In one embodiment, the method of diagnosis comprises:
  i) contacting an isolated sample containing a blood cell population with one or more labelled antibodies that bind to
    a) CD34−;
    b) CD48−;
    c) CD117+;
    d) CD150−
    e) CD244+ or CD244−;
  ii) detecting the presence or absence of said one or more labelled antibodies bound to a blood cell/blood cell population; and
  iii) confirming the presence of a blood cell/blood cell population having a cell surface phenotype comprising:
    a) CD34−;
    b) CD48−;
    c) CD117+;
    d) CD150−
    e) CD244+ or CD244−.

All embodiments described above for the diagnostic screen apply equally to the method of diagnosis aspect. By way of example, the latter aspect may further comprise identification of the cell surface polypeptide marker CD2−.

In another aspect, the present invention provides a screen (as defined above) for use in a method of prognosis of acute myeloid leukaemia.

In one aspect, the invention provides a method for detecting acute myeloid leukaemia (AML) leukaemic stem cells (LSC) comprising:
  i) contacting an isolated sample containing a blood cell population with a screen as defined above; and
  ii) confirming the presence of a blood cell/blood cell population that has a cell surface phenotype comprising:
    a) CD34−
    b) CD48−
    c) CD117+
    d) CD150−
    e) CD244+ or CD244−.

In one embodiment, the above method is used in a method of prognosis of acute myeloid leukaemia.

In one embodiment, the method of prognosis comprises:
  i) contacting an isolated sample containing a blood cell population with one or more labelled antibodies that bind to:
    a) CD34−;
    b) CD48−;
    c) CD117+;
    d) CD150−
    e) CD244+ or CD244−;
  ii) detecting the presence or absence of said one or more labelled antibodies bound to a blood cell/blood cell population; and
  iii) confirming the presence of a blood cell/blood cell population having a cell surface phenotype comprising:
    a) CD34−;
    b) CD48−;
    c) CD117+;
    d) CD150−
    e) CD244+ or CD244−.

All embodiments described above for the diagnostic screen apply equally to the method of prognosis aspect. By way of example, the latter aspect may further comprise identification of the cell surface polypeptide marker CD2−.

The above diagnostic screens and methods of the present invention may advantageously (a) detect AML LSC/MRD and/or provide an indication as to disease severity, (b) aid determination as to the correct course of treatment, (c) permit evaluation of response to treatment, (d) permit determination as to whether to continue or cease treatment, (e) provide a means of disease staging and/or (f) permit determination as to clinical outcome.

In other embodiments, any of the aforementioned aspects and/or embodiments and in particular the methods disclosed herein may further include treating AML and/or one or more symptoms associated with AML.

In one embodiment, the method includes administering to a patient a treatment/therapy for AML (and/or one or more symptoms thereof) if the presence of acute myeloid leukemia leukaemic stem cells is confirmed by way a diagnostic screen or methods of the present invention.

A symptom of AML may include fatigue, malaise, presence of active infection, signs and symptoms of anemia and a bleeding diathesis.

In certain embodiments, the treatment/therapy may include one or more of the following: administration of therapeutic agents such as chemotherapeutic agents, allogeneic stem cell/bone marrow transplant and radiotherapy. Typical chemotherapeutic regimens include use of anthracyclins (e.g. daunorubicin), purine analogues (e.g. fludarabine), cytarabine and epigenetic modifiers such as Azacitidine. Supportive therapies (eg. to treat one or more symptoms of AML) may also be offered in the form of blood product transfusion and antibiotic treatment of infections.

In another aspect, the present invention provides a screen (as defined above) for use in a method of identifying a therapeutic candidate for the treatment of acute myeloid leukaemia.

In a related aspect, the invention provides a method of identifying a therapeutic candidate for the treatment of acute myeloid leukaemia, said method comprising:
  i) contacting the therapeutic candidate with an isolated sample containing a population of blood cells, wherein said blood cell has a cell surface phenotype comprising:
    a) CD34−;
    b) CD48−;
    c) CD117+;
    d) CD150−
    e) CD244+ or CD244−;
  ii) incubating said therapeutic candidate with said isolated sample;
  iii) contacting said isolated sample after step ii) with a screen that identifies a blood cell having a cell surface phenotype comprising:
    a) CD34−;
    b) CD48−;
    c) CD117+;
    d) CD150−
    e) CD244+ or CD244−;
  iv) identifying blood cells by step iii) that have a cell surface phenotype comprising:
    a) CD34−;
    b) CD48−;
    c) CD117+;
    d) CD150−
    e) CD244+ or CD244−;
  v) correlating the number of blood cells identified by step iv) with the number of blood cells present in an isolated sample prior to step i) that have a cell surface phenotype comprising:
    a) CD34−;
    b) CD48−;
    c) CD117+;
    d) CD150−
    e) CD244+ or CD244−;
  vi) confirming the presence of a therapeutic candidate having anti-acute myeloid leukaemia cell activity by identifying a relative decrease in the number of blood cells in step v) after contact with the therapeutic candidate; or
    confirming the absence of a therapeutic candidate having anti-acute myeloid leukaemia cell activity by identifying no significant relative decrease in the number of blood cells in step v) after contact with the therapeutic candidate.

In one embodiment, the method of identifying a therapeutic candidate for the treatment of acute myeloid leukaemia comprises:
  i) contacting the therapeutic candidate with an isolated sample containing a population of blood cells, wherein said blood cell has a cell surface phenotype comprising:
    a) CD34−;
    b) CD48−;
    c) CD117+;
    d) CD150−
    e) CD244+ or CD244−;
  ii) incubating said therapeutic candidate with said isolated sample;
  iii) contacting said isolated sample after step ii) with one or more labelled antibodies that bind to:
    a) CD34−;
    b) CD48−;
    c) CD117+;
    d) CD150−
    e) CD244+ or CD244−;
  iv) identifying blood cells by step iii) that have a cell surface phenotype comprising:
    a) CD34−;
    b) CD48−;
    c) CD117+;
    d) CD150−
    e) CD244+ or CD244−;
  v) correlating the number of blood cells identified by step iv) with the number of blood cells present in an isolated sample prior to step i) that have a cell surface phenotype comprising:
    a) CD34−;
    b) CD48−;
    c) CD117+;
    d) CD150−
    e) CD244+ or CD244−;
  vi) confirming the presence of a therapeutic candidate having anti-acute myeloid leukaemia cell activity by identifying a relative decrease in the number of blood cells in step v) after contact with the therapeutic candidate; or
    confirming the absence of a therapeutic candidate having anti-acute myeloid leukaemia cell activity by identifying no significant relative decrease in the number of blood cells in step v) after contact with the therapeutic candidate.

All embodiments described above for the diagnostic screen and methods apply equally to the method of identifying a therapeutic candidate aspect. By way of example, the latter aspect may further comprise identification of the cell surface polypeptide marker CD2−.

In one embodiment of said methods for identifying a therapeutic candidate, the method further comprises the step of administering to a patient a therapeutic molecule identified by said method.

In another aspect, the present invention provides a screen (as defined above) for use in a method of monitoring efficacy of a therapeutic molecule in treating acute myeloid leukaemia.

In a related aspect, the invention provides a method for monitoring efficacy of a therapeutic molecule in treating acute myeloid leukaemia, said method comprising:
  i) contacting an isolated sample from a patient, wherein said patient has been administered the therapeutic molecule, with a screen that identifies a blood cell having a cell surface phenotype comprising:
    a) CD34−;
    b) CD48−;
    c) CD117+;
    d) CD150−
    e) CD244+ or CD244−;
  ii) identifying blood cells by step i) that have a cell surface phenotype comprising:
    a) CD34−;
    b) CD48−;
    c) CD117+;
    d) CD150−
    e) CD244+ or CD244−;
  iii) correlating the number of blood cells identified by step ii) with the number of blood cells present in an isolated sample taken from a patient prior to administration of the therapeutic molecule, wherein said blood cells taken prior to administration of the therapeutic molecule have a cell surface phenotype comprising:
    a) CD34−;
    b) CD48−;
    c) CD117+;
    d) CD150−
    e) CD244+ or CD244−;
  iv) confirming efficacy of the therapeutic molecule by identifying a relative decrease in the number of blood cells in step iii) after contact with the therapeutic molecule; or
    confirming the absence of efficacy of the therapeutic molecule by identifying a no significant relative decrease in the number of blood cells in step iii) after contact with the therapeutic molecule.

In one embodiment, the invention provides a method for monitoring efficacy of a therapeutic molecule in treating acute myeloid leukaemia, said method comprising:
  i) contacting an isolated sample from a patient, wherein said patient has been administered the therapeutic molecule, with a screen that comprises one or more labelled antibodies that bind to:
    a) CD34−;
    b) CD48−;
    c) CD117+;
    d) CD150−
    e) CD244+ or CD244−;
  ii) identifying blood cells by step i) that have a cell surface phenotype comprising:
    a) CD34−;
    b) CD48−;
    c) CD117+;
    d) CD150−
    e) CD244+ or CD244−;
  iii) correlating the number of blood cells identified by step ii) with the number of blood cells present in an isolated sample taken from a patient prior to administration of the therapeutic molecule, wherein said blood cells taken prior to administration of the therapeutic molecule have a cell surface phenotype comprising:
    a) CD34−;
    b) CD48−;
    c) CD117+;
    d) CD150−
    e) CD244+ or CD244−;
  iv) confirming efficacy of the therapeutic molecule by identifying a relative decrease in the number of blood cells in step iii) after contact with the therapeutic molecule; or
    confirming the absence of efficacy of the therapeutic molecule by identifying a no significant relative decrease in the number of blood cells in step iii) after contact with the therapeutic molecule.

All embodiments described above for the diagnostic screen and methods apply equally to the method for monitoring efficacy of a therapeutic molecule in treating acute myeloid leukaemia aspect. By way of example, the latter aspect may further comprise identification of the cell surface polypeptide marker CD2−.

In one embodiment of said methods for monitoring efficacy of a therapeutic molecule, the method further comprises the step of administering to a patient a therapeutically effective molecule identified by said method.

In one aspect, the invention provides a kit for detecting acute myeloid leukaemia (AML) leukaemic stem cells (LSC), said kit comprising at least one antibody that binds to a cell surface polypeptide marker selected from:
  i) CD34−
  ii) CD48−
  iii) CD117+
  iv) CD150−
  v) CD244+ or CD244−.

In one embodiment, said kit comprises a first antibody that binds to CD34, a second antibody that binds to CD48, and a third antibody that binds to CD117, a fourth antibody that binds to CD150, and a fifth antibody that binds to CD244. In one embodiment, each of said antibodies is different. In another embodiment, each of said antibodies does not substantially bind to any other marker of the present invention—for example: the first antibody does not substantially bind to any of CD48, CD117, CD150, or CD244; the second antibody does not substantially bind to any of CD34, CD117, CD150 or CD244; the third antibody does not substantially bind to any of CD34, CD48, CD150 or CD244; the fourth antibody does not substantially bind to any of CD34, CD48, CD117 or CD244; and the fifth antibody does not substantially bind to any of CD34, CD48, CD117, CD150 or CD244.

In one embodiment, the kit may further comprise instructions explaining how to use the antibodies thereof in a method of the invention.

All embodiments described above for the diagnostic screen and methods apply equally to the kit aspect. By way of example, the latter aspect may further comprise an antibody that binds to the cell surface polypeptide marker CD2. Thus, in one embodiment, said antibody may constitute a sixth antibody of the kit. In one embodiment, said sixth antibody does not substantially to any other (aforementioned) markers of the invention.

A kit of the present invention may optionally comprise suitable labels as described above (e.g. a fluorophore label) in addition to the one or more antibodies and/or other reagents. The kit may optionally contain an instruction manual instructing the user to perform the methods of the present invention.

In another aspect, the invention provides a gene expression profile for detecting/for use in detecting acute myeloid leukaemia (AML) leukaemic stem cells (LSC).

In one embodiment, the gene expression profile of the present invention comprises (or consists of) one or more (such as two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more) of ARID5B, ATF3, AZU1, BMI1, CLEC11A, CSTA, ETV5, HIVEP3, HOXA3, HOXA5, HOXB3, HOXB5, HOXB6, ITGA6, KIT, MEIS1, MYCN, NFIL3, PTPN14, RHOC and WT1. Details on said genes, including HGNC database accession numbers, are given in FIG. 7. mRNA nucleic acid sequences of said genes are provided as SEQ ID NOs: 14-34, respectively. The corresponding protein sequences are provided as SEQ ID NOs: 48-68, respectively. Thus, the gene expression profile of the present invention may comprise (or consist of) of 1 (or 2, 3, 4, 5, 6, 7, 8, 9, 10, 11, 12, 13, 14, 15, 16, 17, 18, 19, 20 or 21) of said aforementioned genes. Any and all possible combinations are embraced by the present invention.

Optionally, said gene expression profile further comprises one or more genes selected from AEBP1, CREB5, ERG, FOSL2, HOXA7, IL11RA, KDM7A, KLF7, KLF9, MAFF, STAT4, TOX and/or ZBTB16. Thus, said gene expression profile may further comprise (or consists of) one or more (such as two or more, three or more, four or more, five or more, six or more, seven or more, eight or more, nine or more, ten or more, eleven or more or twelve or more) genes selected from AEBP1, CREB5, ERG, FOSL2, HOXA7, IL11RA, KDM7A, KLF7, KLF9, MAFF, STAT4, TOX and/or ZBTB16. Details on said genes, including HGNC database accession numbers, are given in FIG. 7. mRNA nucleic acid sequences of said genes are provided as SEQ ID NOs: 35-47, respectively. The corresponding protein sequences are provided as SEQ ID NOs: 68-81, respectively. Thus, the gene expression profile of the present invention may optionally comprise (or consist of) of 1 (or 2, 3, 4, 5, 6, 7, 8, 9, 10, 11, 12, or 13) of the genes selected from AEBP1, CREB5, ERG, FOSL2, HOXA7, IL11RA, KDM7A, KLF7, KLF9, MAFF, STAT4, TOX and ZBTB16. Any and all possible combinations are embraced by the present invention.

In a preferred embodiment, the gene expression profile of the present invention comprises (or consists of) ARID5B, ATF3, AZU1, BMI1, CLEC11A, CSTA, ETV5, HIVEP3, HOXA3, HOXA5, HOXB3, HOXB5, HOXB6, ITGA6, KIT, MEIS1, MYCN, NFIL3, PTPN14, RHOC and WT1.

Optionally, said gene expression profile further comprises one or more (such as two or more, three or more, four or more, five or more, six or more, seven or more, eight or more, nine or more, ten or more, eleven or more or twelve or more) genes selected from AEBP1, CREB5, ERG, FOSL2, HOXA7, IL11RA, KDM7A, KLF7, KLF9, MAFF, STAT4, TOX and/or ZBTB16. Thus, the aforementioned preferred gene expression profile of the present invention may optionally comprise (or consist of) of 1 (or 2, 3, 4, 5, 6, 7, 8, 9, 10, 11, 12, or 13) of said aforementioned genes. Any and all possible combinations are embraced by the present invention.

Thus, in one embodiment, the gene expression profile comprises (or consists of) ARID5B, ATF3, AZU1, BMI1, CLEC11A, CSTA, ETV5, HIVEP3, HOXA3, HOXA5, HOXB3, HOXB5, HOXB6, ITGA6, KIT, MEIS1, MYCN, NFIL3, PTPN14, RHOC, WT1, AEBP1, CREB5, ERG, FOSL2, HOXA7, IL11RA, KDM7A, KLF7, KLF9, MAFF, STAT4, TOX and ZBTB16.

The present inventors have unexpectedly found that the gene expression profile of the present invention represents a 'signature' expression profile for acute myeloid leukaemia (AML) leukaemic stem cells (LSC). This enables detection and monitoring of MRD. Accordingly, said gene expression profile can be used to identify AML LSC in a sample and such information can be advantageously used in diagnostic and prognostic applications such as in clinical guidance and for determining therapy, for patient management and for assessing treatment efficacy. In particular, the gene expression profile of the present invention can be used as a prognostic indicator.

In more detail, said gene expression profile advantageously enables differentiation/discrimination between AML LSC versus non-AML LSC (including non-LSC leukaemic cells and non-LSC 'normal' cells). Said gene expression profile also enables differentiation between CD34− and CD34+LSC.

The present inventors have surprisingly noted that said genes of said gene expression profile are differentially expressed in acute myeloid leukaemia (AML) leukaemic stem cells (LSC) relative to a non-acute myeloid leukaemia leukaemic stem cell population.

Differentially expressed in the present context means an increased or decreased level of gene expression relative to a comparator population of cells, such as a non-acute myeloid leukaemia leukaemic stem cell population. Suitable comparator populations suitable for providing such a "baseline"/comparator measurement include a normal myeloid precursor cell population, an acute myeloid leukaemia non-leukaemic stem cell population and/or a normal hematopoietic stem cell (HSC) population. Thus, in one embodiment, the non-acute myeloid leukaemia leukaemic stem cell population is selected from a normal myeloid precursor cell population, an acute myeloid leukaemia non-leukaemic stem cell population and/or a normal hematopoietic stem cell (HSC) population. In one embodiment, a normal myeloid precursor cell population is Lin− CD34− CD117+CD244+.

In one embodiment, one or more of the genes of the gene expression profile of present invention are upregulated (i.e. expression is increased) in acute myeloid leukaemia (AML) leukaemic stem cells (LSC) relative to a non-acute myeloid leukaemia leukaemic stem cell population. In another embodiment, one or more of the genes of the gene expression profile of present invention are downregulated (i.e. expression is decreased) in acute myeloid leukaemia (AML) leukaemic stem cells (LSC) relative to a non-acute myeloid leukaemia leukaemic stem cell population.

In one embodiment of the present invention, ARID5B, ATF3, CLEC11A, ETV5, HIVEP3, HOXA3, HOXB3, HOXB6 MEIS1, MYCN, NFIL3, PTPN14, RHOC and WT1 are upregulated in acute myeloid leukaemia (AML) leukaemic stem cells (LSC) relative to a normal myeloid precursor cell population. The inventors have surprisingly found that said comparator cell population provides enhanced discriminatory power in relation to these specific genes. In other words, whilst other comparator cell populations may still be used, a normal myeloid precursor cell population is preferred because it provides improved discriminatory power.

In one embodiment of the present invention, BMI1, HOXA5, HOXB5, ITGA6, KIT are upregulated in acute myeloid leukaemia (AML) leukaemic stem cells (LSC) relative to an acute myeloid leukaemia non-leukaemic stem cell population. The inventors have surprisingly found that said comparator cell population provides enhanced discriminatory power in relation to these specific genes. In other words, whilst other comparator cell populations may still be used, an acute myeloid leukaemia non-leukaemic stem cell population is preferred because it provides improved discriminatory power.

In one embodiment of the present invention, AZU1 and CSTA are upregulated in acute myeloid leukaemia (AML) leukaemic stem cells (LSC) relative to a normal hematopoietic stem cell (HSC) population. The inventors have surprisingly found that said comparator cell population provides enhanced discriminatory power in relation to these specific genes. In other words, whilst other comparator cell populations may still be used, a normal hematopoietic stem cell (HSC) population is preferred because it provides improved discriminatory power.

In one embodiment of the present invention, CLEC11A is downregulated in acute myeloid leukaemia (AML) leukaemic stem cells (LSC) relative to a normal myeloid precursor cell population. The inventors have surprisingly found that said comparator cell population provides enhanced discriminatory power in relation to this specific gene. In other words, whilst other comparator cell populations may still be used, a normal myeloid precursor cell population is preferred because it provides improved discriminatory power.

Thus, in a preferred embodiment of the present invention, ARID5B, ATF3, CLEC11A, ETV5, HIVEP3, HOXA3, HOXB3, HOXB6 MEIS1, MYCN, NFIL3, PTPN14, RHOC and WT1 are upregulated in acute myeloid leukaemia (AML) leukaemic stem cells (LSC) relative to a normal myeloid precursor cell population;
  BMI1, HOXA5, HOXB5, ITGA6 and KIT are upregulated in acute myeloid leukaemia (AML) leukaemic stem cells (LSC) relative to an acute myeloid leukaemia non-leukaemic stem cell population;
  AZU1 and CSTA are upregulated in acute myeloid leukaemia (AML) leukaemic stem cells (LSC) relative to a normal hematopoietic stem cell (HSC) population; and
  CLEC11A is downregulated in acute myeloid leukaemia (AML) leukaemic stem cells (LSC) relative to a normal myeloid precursor cell population In another embodiment, the gene profile of the present invention further comprises one or more genes selected from AEBP1, CREB5, ERG, FOSL2, HOXA7, IL11RA, KDM7A, KLF7, KLF9, MAFF, STAT4, TOX and/or ZBTB16, and wherein said one or more genes is upregulated in acute myeloid leukaemia (AML) leukaemic stem cells (LSC) relative to a normal myeloid precursor cell population. The inventors have surprisingly found that said comparator cell population provides enhanced discriminatory power in relation to these specific genes. In other words, whilst other comparator cell populations may still be used, a normal myeloid precursor cell population is preferred because it provides improved discriminatory power.

Methods for assessing gene expression levels are conventional techniques known to those skilled in the art. For instance, mRNA of a target gene can be detected and quantified by e.g. Northern blotting or by quantitative reverse transcription PCR (RT-PCR). Single cell gene expression analysis may also be performed using commercially available systems (e.g. Fluidigm Dynamic Array). Alternatively, or in addition, gene expression levels can be determined by analysing protein levels e.g. by using Western blotting techniques such as ELISA-based assays. Thus, in one embodiment, gene expression levels are determined by measuring the mRNA/cDNA levels of the genes belonging to the gene expression profile of the present invention. In another embodiment, gene expression levels are determined by measuring the protein levels produced by the genes belonging to the gene expression profile of the present invention. Methods suitable for establishing a baseline or reference value for comparing gene expression levels are conventional techniques known to those skilled in the art.

In one embodiment, upregulated means an increase in gene expression by about 1.25-fold to about 10-fold or more relative to a control sample/level. In embodiments, the level of gene expression is increased by at least about 1.1-fold, 1.2-fold, 1.25-fold, 1.5-fold, 1.75-fold, 2-fold, 4-fold, 5-fold, 10-fold, 15-fold, 20-fold, 25-fold, 30-fold, 35-fold, 40-fold, 50-fold, 75-fold, 100-fold, 150-fold, 200-fold, or at least about 300-fold or more relative to a control sample/level. The fold change difference can be in absolute terms (e.g. CPM: counts per million) or Log 2CPM (a standard measure in the field) of the gene expression level in a sample. In one embodiment said fold-change is measured/is determined by in toto RNA sequencing (RNA-Seq).

In one embodiment, ARID5B, ATF3, CLEC11A, ETV5, HIVEP3, HOXA3, HOXB3, HOXB6 MEIS1, MYCN, NFIL3, PTPN14, RHOC and WT1 are upregulated in acute myeloid leukaemia (AML) leukaemic stem cells (LSC) relative to a normal myeloid precursor cell population by at least 1.25-fold, at least about 1.5-fold, at least about 2-fold, preferably at least 3-fold (Log 2CPM). In one embodiment said genes are upregulated by about 1.25-fold to about 10-fold, by about 1.5-fold to about 10-fold, about 2-fold to about 10-fold, preferably about 3-fold to about 10-fold (Log 2CPM). In one embodiment said fold-change is measured/is determined by in toto RNA sequencing (RNA-Seq).

In one embodiment, BMI1, HOXA5, HOXB5, ITGA6 and KIT are upregulated in acute myeloid leukaemia (AML) leukaemic stem cells (LSC) relative to an acute myeloid leukaemia non-leukaemic stem cell population by at least about 1.1-fold, at least about 1.2 fold, at least about 1.25-fold, preferably at least about 1.5-fold (Log 2CPM). In one embodiment said genes are upregulated by about 1.1-fold to about 6-fold, by about 1.2-fold to about 6-fold, about 1.25-fold to about 6-fold, preferably about 1.5-fold to about 6-fold (Log 2CPM). In one embodiment said fold-change is measured/is determined by in toto RNA sequencing (RNA-Seq).

In one embodiment, AZU1 and CSTA are upregulated in acute myeloid leukaemia (AML) leukaemic stem cells (LSC) relative to a normal hematopoietic stem cell (HSC) population by at least 1.5-fold, at least about 2-fold, at least about 4-fold, preferably at least 5-fold (Log 2CPM). In one embodiment said genes are upregulated by about 1.5-fold to about 9-fold, by about 2-fold to about 9-fold, about 2-fold to about 9-fold, preferably about 5-fold to about 9-fold (Log 2CPM). In one embodiment said fold-change is measured/is determined by in toto RNA sequencing (RNA-Seq).

In one embodiment, CLEC11A is downregulated in acute myeloid leukaemia (AML) leukaemic stem cells (LSC) relative to a normal myeloid precursor cell population by at least about 1.1-fold, at least about 1.2 fold, at least about 1.5-fold, preferably at least about 1.7-fold (Log 2CPM). In one embodiment said genes are downregulated by about 1.1-fold to about 3-fold, by about 1.2-fold to about 3-fold, about 1.5-fold to about 3-fold, preferably about 1.7-fold to about 3-fold (Log 2CPM). In one embodiment CLEC11A is downregulated by about 1.7-fold to about 2.1-fold (Log 2CPM). In one embodiment said fold-change is measured/is determined by in toto RNA sequencing (RNA-Seq).

In one embodiment, AEBP1, CREB5, ERG, FOSL2, HOXA7, IL11RA, KDM7A, KLF7, KLF9, MAFF, STAT4, TOX and ZBTB16 are upregulated in acute myeloid leukaemia (AML) leukaemic stem cells (LSC) relative to a normal myeloid precursor cell population by at least 1.1-fold, at least about 1.2-fold, at least about 1.25-fold, preferably at least 1.3-fold (Log 2CPM). In one embodiment said genes are upregulated by about 1.1-fold to about 5-fold, by about 1.2-fold to about 5-fold, about 1.25-fold to about 5-fold, preferably about 1.25-fold to about 5-fold (Log 2CPM). In one embodiment said fold-change is measured/is determined by in toto RNA sequencing (RNA-Seq).

The differential expression (i.e. upregulation or downregulation) of the aforementioned genes is preferably statistically significant. Statistical significance can be determined by any method known in the art. By way of example, a minimum-maximum range can be determined based on the standard error of the mean (SEM: which ranges from ~1-25% of the mean) of expression of these genes in the AML LSC population (max/min=mean+/−1.96×SEM) which provides a 95% confidence interval.

In one embodiment, the acute myeloid leukaemia (AML) leukaemic stem cells (LSC) detectable with the gene expression profile of the present invention are CD34− AML LSC.

In one aspect, the present invention provides a gene expression profile (as defined above) for use in a method of prognosis of acute myeloid leukaemia.

In a related aspect, the present invention provides a gene expression profile (as defined above) for use in a method of diagnosis of acute myeloid leukaemia.

In one aspect, the invention provides a method for detecting acute myeloid leukaemia (AML) leukaemic stem cells (LSC) comprising:
  i) determining a gene expression profile from an isolated sample containing a blood cell population, wherein said gene expression profile comprises ARID5B, ATF3, AZU1, BMI1, CLEC11A, CSTA, ETV5, HIVEP3, HOXA3, HOXA5, HOXB3, HOXB5, HOXB6, ITGA6, KIT, MEIS1, MYCN, NFIL3, PTPN14, RHOC and WT1;
  ii) confirming whether said genes are differentially expressed in said blood cell population relative to a non-acute myeloid leukaemia leukaemic stem cell population.

In one embodiment, the above method is used in a method of prognosis of acute myeloid leukaemia and/or in a method of diagnosis of acute myeloid leukaemia.

All embodiments described above for the gene expression profile apply equally to the method aspects. By way of example, the gene expression profile of the latter aspect may further comprise one or more genes selected from AEBP1, CREB5, ERG, FOSL2, HOXA7, IL11RA, KDM7A, KLF7, KLF9, MAFF, STAT4, TOX and/or ZBTB16.

In another aspect, the present invention provides a method for use in the prognosis and treatment of acute myeloid leukaemia and/or a symptom thereof comprising:
  i) determining a gene expression profile from an isolated sample containing a blood cell population obtained from a patient, wherein said gene expression profile comprises ARID5B, ATF3, AZU1, BMI1, CLEC11A, CSTA, ETV5, HIVEP3, HOXA3, HOXA5, HOXB3, HOXB5, HOXB6, ITGA6, KIT, MEIS1, MYCN, NFIL3, PTPN14, RHOC and WT1;
  ii) confirming whether said genes are differentially expressed in said blood cell population relative to a non-acute myeloid leukaemia leukaemic stem cell population;
  iii) administering to said patient a therapy for acute myeloid leukaemia (AML) and/or a symptom thereof if the presence of acute myeloid leukaemia (AML) leukaemic stem cells (LSC) is confirmed.

All embodiments described above for the gene expression profile apply equally to the method aspects. By way of example, the gene expression profile of the latter aspect may further comprise one or more genes selected from AEBP1, CREB5, ERG, FOSL2, HOXA7, IL11 RA, KDM7A, KLF7, KLF9, MAFF, STAT4, TOX and/or ZBTB16.

In one embodiment, the method includes administering to a patient a treatment/therapy for AML (and/or one or more symptoms thereof) if the presence of acute myeloid leukemia leukaemic stem cells is confirmed.

As noted above, a symptom of AML may include fatigue, malaise, presence of active infection, signs and symptoms of anemia and a bleeding diathesis.

In certain embodiments, the treatment/therapy may include one or more of the following: administration of therapeutic agents such as chemotherapeutic agents, allogeneic stem cell/bone marrow transplant and radiotherapy. Typical chemotherapeutic regimens include use of anthracyclins (e.g. daunorubicin), purine analogues (e.g. fludarabine), cytarabine and epigenetic modifiers such as Azacitidine. Supportive therapies (eg. to treat one or more symptoms of AML) may also be offered in the form of blood product transfusion and antibiotic treatment of infections.

All aspects/embodiments described above in relation to the identification of a therapeutic candidate and monitoring efficacy of a therapeutic molecule apply equally to the gene expression profile aspects/embodiments. In other words, the gene expression profile of the present invention can also be used in corresponding methods for identifying a therapeutic candidate for the treatment of acute myeloid leukaemia and/or methods for monitoring efficacy of a therapeutic molecule in treating acute myeloid leukaemia.

In one aspect, the invention provides a kit for detecting acute myeloid leukaemia (AML) leukaemic stem cells (LSC), said kit comprising one or more agents for detecting gene expression of one or more genes selected from ARID5B, ATF3, AZU1, BMI1, CLEC11A, CSTA, ETV5, HIVEP3, HOXA3, HOXA5, HOXB3, HOXB5, HOXB6, ITGA6, KIT, MEIS1, MYCN, NFIL3, PTPN14, RHOC and WT1;
  and optionally one or more genes selected from AEBP1, CREB5, ERG, FOSL2, HOXA7, IL11 RA, KDM7A, KLF7, KLF9, MAFF, STAT4, TOX and/or ZBTB16.

In one embodiment, an agent for detecting gene expression is a probe for use in quantitative RT-PCT (such as a Taqman probe). Primers or antibodies may also be used to measure gene expression levels. As discussed above, methods for assessing gene expression levels are conventional techniques known to those skilled in the art and a skilled person would readily be able to design and/or select suitable detection agents for use in inter alia the kits of the present invention.

In one embodiment, the kit may further comprise instructions explaining how to use the detection agents in a method of the invention.

All embodiments described above for the gene expression profile and related methods apply equally to the kit aspect.

In another aspect, the invention provides a method of treating acute myeloid leukaemia in a patient comprising:

i) requesting performance of a screening method of any of the screening methods described herein and/or obtaining the results of a screening method of any of the screening methods described herein; and ii) administering to said patient a therapy for acute myeloid leukaemia (AML) if the presence of acute myeloid leukaemia (AML) leukaemic stem cells (LSC) is confirmed.

In another aspect of the present invention, all of the above described aspects and embodiments apply to chronic myeloid leukaemia (CML) and/or myeldodysplastic syndromes (MDS). Thus, each and every aspect and embodiment recited above is hereby explicitly disclosed in connection with CML and/or MDS. In this regard, and without wishing to be bound by theory, it is considered that the present invention finds utility in corresponding diagnostic, prognostic and therapeutic methods for CML and/or MDS as the biomarkers of the present invention are expressed by CML and MDS cells which have transformed to Acute Myeloid Leukaemia.

Definitions

The cell surface polypeptide markers forming the diagnostic screen of the present invention can also be considered/referred to as "biomarkers". Thus, in one embodiment, the term "diagnostic marker" is equivalent and interchangeable with the term "biomarker". The genes making up the gene expression profile of the present invention may also be referred to as "biomarkers".

In one embodiment, the term 'diagnosis' is used to mean determining the incidence of AML by examining whether one or more of the cell surface polypeptide markers of the diagnostic screen is present and/or by examining whether the gene expression profile of the present invention is present in a sample. In one embodiment, diagnosis of AML embraces diagnosis of minimal residual disease (MRD). Accordingly, in one embodiment, reference herein to acute myeloid leukaemia (AML) embraces MRD.

The terms "individual", "subject", and "patient", are used interchangeably herein to refer to a mammalian subject for whom diagnosis, prognosis, treatment, therapy or disease monitoring is desired. The mammal can be a human, non-human primate, mouse, rat, dog, cat, horse or cow, but is not limited to these examples. In one preferred embodiment, the individual, subject, or patient is a human, e.g. a male or female.

In the methods of the present invention, the patient may not have been previously diagnosed as having the disease (i.e. AML). The subject may also be one who has been previously diagnosed as having the disease (i.e. AML). Alternatively, the subject may be one who does not exhibit disease risk factors or one who is asymptomatic for the disease (i.e. AML). A subject can also be one who is suffering from or is at risk of developing the disease.

In one embodiment, a sample is obtained from a patient. A suitable sample is a bone marrow or blood sample. The white blood cell population of the sample is preferably extracted or enriched prior to detection of the marker-set with antibodies of the present invention. Methods suitable for extraction of enrichment of the white blood cells from a sample are conventional techniques known to those skilled in the art. By way of example, one approach is to deplete a sample of red cells by red cell lysis. Another approach is to isolate a mononuclear by density centrifugation using a density media like Ficoll. CD34− AML samples can be purified using a lineage depletion cocktail for purification comprising CD2, CD3, CD4, CD8a, CD10, CD19, CD20 and/or CD235a. The CD34− AML samples can then be analysed using the diagnostic screen of the present invention, as defined above. In relation to the gene expression profile aspect and associated methods, a suitable sample is preferably a bone marrow sample and the gene expression of said sample is determined. In a preferred embodiment, gene expression is measured/is determined by in toto RNA sequencing (RNA-Seq).

In one embodiment, the methods referred to herein are performed in vitro. Thus, the methods of the present invention can be carried out in vitro on an isolated sampled that has been obtained from a subject. In one embodiment, the methods referred to herein are performed ex vivo.

Determining the presence or absence or relative levels of one or more biomarkers of the present invention in a sample means quantifying the biomarker by determining, for example, the relative or absolute amount of the biomarker. It will be appreciated that the assay methods do not necessarily require measurement of absolute values of biomarker, unless it is desired, because relative values are sufficient for many applications of the invention. Accordingly, determining an "effective amount" can be the (absolute) total amount of the biomarker that is detected in a sample, or it can be a "relative" amount, e.g., the difference between the biomarker detected in a sample and e.g. another constituent of the sample. In some embodiments, the effective amount of the biomarker may be expressed by its concentration in a sample, or by the concentration of an antibody that binds to the biomarker.

The present invention also encompasses, without limitation, polymorphisms, isoforms, metabolites, mutants, variants, derivatives, modifications, subunits, fragments, protein-ligand complexes and degradation products of the biomarkers of the present invention.

The protein fragments can be 2250, 2000, 1500, 1400, 1200, 1000, 800, 600, 500, 400, 200, 150, 100, 50, 25, 10 amino acids or fewer in length. The nucleic acid fragments can be 13000, 12000, 10000, 9000, 7000, 5000, 4000, 2000, 1000, 500, 250 150, 100, 50, 25, 10 nucleotides or fewer in length.

Variants of the protein biomarkers of the present invention include polypeptides with altered amino acid sequences due to amino acid substitutions, deletions, or insertions. Variant polypeptides may comprise conservative or non-conservative amino acid substitutions, deletions or additions. Variants include polypeptides that have an amino acid sequence being at least 70%, at least 80%, at least 90%, at least 95%, at least 98% or at least 99% identical to the amino acid sequences of the polypeptides disclosed herein. Variants may be allelic variants, splice variants or any other species specific homologs, paralogs, or orthologs.

Thus, in one embodiment, the CD34 molecule as referenced herein comprises an amino acid sequence having at least 80% (such at least 85%, 90%, 95%, 98%, 99% or 100%) sequence identity to SEQ ID NO: 1, or a fragment or derivative thereof. In one embodiment, the CD48 molecule as referenced herein comprises an amino acid sequence having at least 80% (such at least 85%, 90%, 95%, 98%, 99% or 100%) sequence identity to SEQ ID NO: 2, or a fragment or derivative thereof. In one embodiment, the CD117 molecule as referenced herein comprises an amino acid sequence having at least 80% (such at least 85%, 90%, 95%, 98%, 99% or 100%) sequence identity to SEQ ID NO: 3, or a fragment or derivative thereof. In one embodiment, the CD150 molecule as referenced herein comprises an amino acid sequence having at least 80% (such at least 85%, 90%, 95%, 98%, 99% or 100%) sequence identity to SEQ ID NO: 4, or a fragment or derivative thereof. In one embodiment, the CD244 molecule as referenced herein comprises an amino acid sequence having at least 80% (such at least 85%, 90%, 95%, 98%, 99% or 100%) sequence identity to SEQ ID NO: 5, or a fragment or derivative thereof. In one embodiment, the CD2 molecule as referenced herein comprises an amino acid sequence having at least 80% (such at least 85%, 90%, 95%, 98%, 99% or 100%) sequence identity to SEQ ID NO: 6, or a fragment or derivative thereof. In one embodiment, the CD3 molecule as referenced herein comprises an amino acid sequence having at least 80% (such at least 85%, 90%, 95%, 98%, 99% or 100%) sequence identity to SEQ ID NO: 7, or a fragment or derivative thereof. In one embodiment, the CD4 molecule as referenced herein comprises an amino acid sequence having at least 80% (such at least 85%, 90%, 95%, 98%, 99% or 100%) sequence identity to SEQ ID NO: 8, or a fragment or derivative thereof. In one embodiment, the CD8a molecule as referenced herein comprises an amino acid sequence having at least 80% (such at least 85%, 90%, 95%, 98%, 99% or 100%) sequence identity to SEQ ID NO: 9, or a fragment or derivative thereof. In one embodiment, the CD10 molecule as referenced herein comprises an amino acid sequence having at least 80% (such at least 85%, 90%, 95%, 98%, 99% or 100%) sequence identity to SEQ ID NO: 10, or a fragment or derivative thereof. In one embodiment, the CD19 molecule as referenced herein comprises an amino acid sequence having at least 80% (such at least 85%, 90%, 95%, 98%, 99% or 100%) sequence identity to SEQ ID NO: 11, or a fragment or derivative thereof. In one embodiment, the CD20 molecule as referenced herein comprises an amino acid sequence having at least 80% (such at least 85%, 90%, 95%, 98%, 99% or 100%) sequence identity to SEQ ID NO: 12, or a fragment or derivative thereof. In one embodiment, the CD235a molecule as referenced herein comprises an amino acid sequence having at least 80% (such at least 85%, 90%, 95%, 98%, 99% or 100%) sequence identity to SEQ ID NO: 13, or a fragment or derivative thereof.

Derivatives of the protein biomarkers of the present invention are polypeptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

Variants of the gene expression biomarkers of the present invention include sequences with altered nucleotide and/or amino acid sequences due to substitutions, deletions, and/or insertions. Variant sequences may comprise conservative or non-conservative substitutions, deletions or additions. Variants include sequences having at least 70%, at least 80%, at least 90%, at least 95%, at least 98% or at least 99% identity to the gene expression biomarker sequences of the present invention. Variants may be allelic variants, splice variants or any other species specific homologs, paralogs, or orthologs.

Thus, in one embodiment, ARID5B as referenced herein comprises a nucleotide sequence having at least 80% (such at least 85%, 90%, 95%, 98%, 99% or 100%) sequence identity to SEQ ID NO: 14, or a fragment or derivative thereof. In one embodiment, ARID5B as referenced herein comprises an amino acid sequence having at least 80% (such at least 85%, 90%, 95%, 98%, 99% or 100%) sequence identity to SEQ ID NO: 48, or a fragment or derivative thereof. In one embodiment, ATF3 as referenced herein comprises a nucleotide sequence having at least 80% (such at least 85%, 90%, 95%, 98%, 99% or 100%) sequence identity to SEQ ID NO: 15, or a fragment or derivative thereof. In one embodiment, ATF3 as referenced herein comprises an amino acid sequence having at least 80% (such at least 85%, 90%, 95%, 98%, 99% or 100%) sequence identity to SEQ ID NO: 49, or a fragment or derivative thereof. In one embodiment, AZU1 as referenced herein comprises a nucleotide sequence having at least 80% (such at least 85%, 90%, 95%, 98%, 99% or 100%) sequence identity to SEQ ID NO: 16, or a fragment or derivative thereof. In one embodiment, AZU1 as referenced herein comprises an amino acid sequence having at least 80% (such at least 85%, 90%, 95%, 98%, 99% or 100%) sequence identity to SEQ ID NO: 50, or a fragment or derivative thereof. In one embodiment, BMI1 as referenced herein comprises a nucleotide sequence having at least 80% (such at least 85%, 90%, 95%, 98%, 99% or 100%) sequence identity to SEQ ID NO: 17, or a fragment or derivative thereof. In one embodiment, BMI1 as referenced herein comprises an amino acid sequence having at least 80% (such at least 85%, 90%, 95%, 98%, 99% or 100%) sequence identity to SEQ ID NO: 51, or a fragment or derivative thereof. The same embodiments recited above also apply to the other genes of the gene expression profile of the present invention (i.e. CLEC11A, CSTA, ETV5, HIVEP3, HOXA3, HOXA5, HOXB3, HOXB5, HOXB6, ITGA6, KIT, MEIS1, MYCN, NFIL3, PTPN14, RHOC, WT1, AEBP1, CREB5, ERG, FOSL2, HOXA7, IL11RA, KDM7A, KLF7, KLF9, MAFF, STAT4, TOX and/or ZBTB16). In other words, in one embodiment, the present invention embraces the mRNA and amino acid sequences of each of said genes and any sequences having at least 80% (such at least 85%, 90%, 95%, 98%, 99% or 100%) sequence identity thereto or a fragment or derivative thereof. These embodiments should be considered disclosed in individualized fashion and are not reproduced individually for conciseness purposes.

The term "antibody" is used in the broadest sense and specifically covers monoclonal and polyclonal antibodies (and fragments thereof) so long as they exhibit the desired biological activity. In particular, an antibody is a protein including at least one or two, heavy (H) chain variable regions (abbreviated herein as VHC), and at least one or two light (L) chain variable regions (abbreviated herein as VLC). The VHC and VLC regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat, E. A., et al. Sequences of Proteins of Immunological Interest, Fifth Edition, U.S. Department of Health and Human Services, NIH Publication No. 91-3242, 1991, and Chothia, C. et al, J. Mol. Biol. 196:901-917, 1987). Preferably, each VHC and VLC is composed of three CDRs and four FRs, arranged from amino-terminus to carboxy-terminus in the following order: FRI, CDRI, FR2, DR2, FR3, CDR3, FR4. The VHC or VLC chain of the antibody can further include all or part of a heavy or light chain constant region. In one embodiment, the antibody is a tetramer of two heavy immunoglobulin chains and two light immunoglobulin chains, wherein the heavy and light immunoglobulin chains are interconnected by, e.g., disulfide bonds. The heavy chain constant region includes three domains, CHI, CH2 and CH3. The light chain constant region is comprised of one domain, CL. The variable region of the heavy and light chains contains a binding domain that interacts with an antigen. The term "antibody" includes intact immunoglobulins of types IgA, IgG, IgE, IgD, IgM (as well as subtypes thereof), wherein the light chains of the immunoglobulin may be of types kappa or lambda. The term antibody, as used herein, also refers to a portion of an antibody that binds to one of the above-mentioned markers, e.g., a molecule in which one or more immunoglobulin chains is not full length, but which binds to a marker. Examples of binding portions encompassed within the term antibody include (i) a Fab fragment, a monovalent fragment consisting of the VLC, VHC, CL and CHI domains; (ii) a F(ab')2 fragment, a bivalent fragment comprising two Fab fragments linked by a disulfide bridge at the hinge region; (iii) a Fc fragment consisting of the VHC and CHI domains; (iv) a Fv fragment consisting of the VLC and VHC domains of a single arm of an antibody, (v) a dAb fragment (Ward et al, Nature 341:544-546, 1989), which consists of a VHC domain; and (vi) an isolated complementarity determining region (CDR) having sufficient framework to bind, e.g. an antigen binding portion of a variable region. An antigen binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv); see e.g., Bird et al. (1988) Science IAI-ATi-AIβ; and Huston et al. (1988) Proc. Natl. Acad. ScL USA 85:5879-5883). Such single chain antibodies are also encompassed within the term antibody. These may be obtained using conventional techniques known to those skilled in the art, and the portions are screened for utility in the same manner as are intact antibodies.

Antibody Preparation

The antibodies of the present invention can be obtained using conventional techniques known to persons skilled in the art and their utility confirmed by conventional binding studies. By way of example, a simple binding assay is to incubate the cell expressing an antigen with the antibody. If the antibody is tagged with a fluorophore, the binding of the antibody to the antigen can be detected by FACS analysis.

Antibodies of the present invention can be raised in various animals including mice, rats, rabbits, goats, sheep, monkeys or horses. Blood isolated from these animals contains polyclonal antibodies—multiple antibodies that bind to the same antigen. Antigens may also be injected into chickens for generation of polyclonal antibodies in egg yolk. To obtain a monoclonal antibody that is specific for a single epitope of an antigen, antibody-secreting lymphocytes are isolated from an animal and immortalized by fusing them with a cancer cell line. The fused cells are called hybridomas, and will continually grow and secrete antibody in culture. Single hybridoma cells are isolated by dilution cloning to generate cell clones that all produce the same antibody; these antibodies are called monoclonal antibodies. Methods for producing monoclonal antibodies are conventional techniques known to those skilled in the art (see e.g. Making and Using Antibodies: A Practical Handbook. GC Howard. CRC Books. 2006. ISBN 0849335280). Polyclonal and monoclonal antibodies are often purified using Protein A/G or antigen-affinity chromatography.

Sequence Homology:

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Science 208-214 (1993); Align-M, see, e.g., Ivo Van Walle et al., Align-M—A New Algorithm for Multiple Alignment of Highly Divergent Sequences, 20(9) Bioinformatics: 1428-1435 (2004). Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

Alignment Scores for Determining Sequence Identity

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |

-continued

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| S | 1 | -1 | 1 | 0 | -1 | 0 | 0 | 0 | -1 | -2 | -2 | 0 | -1 | -2 | -1 | 4 |  |  |  |  |
| T | 0 | -1 | 0 | -1 | -1 | -1 | -1 | -2 | -2 | -1 | -1 | -1 | -1 | -2 | -1 | 1 | 5 |  |  |  |
| W | -3 | -3 | -4 | -4 | -2 | -2 | -3 | -2 | -2 | -3 | -2 | -3 | -1 | 1 | -4 | -3 | -2 | 11 |  |  |
| Y | -2 | -2 | -2 | -3 | -2 | -1 | -2 | -3 | 2 | -1 | -1 | -2 | -1 | 3 | -3 | -2 | -2 | 2 | 7 |  |
| V | 0 | -3 | -3 | -3 | -1 | -2 | -2 | -3 | -3 | 3 | 1 | -2 | 1 | -1 | -2 | -2 | 0 | -3 | -1 | 4 |

The percent identity is then calculated as:

$$\frac{\text{Total number of identical matches}}{[\text{length of the longer sequence plus the number of gaps introduced into the longer sequence in order to align the two sequences}]} \times 100$$

The present invention will now be described, by way of example only, with reference to the accompanying Examples and Figures, in which:
KEY TO SEQ ID NOs:
SEQ ID NO: 1 CD34 amino acid sequence
SEQ ID NO: 2 CD48 amino acid sequence
SEQ ID NO: 3 CD117 amino acid sequence
SEQ ID NO: 4 CD150 amino acid sequence
SEQ ID NO: 5 CD244 amino acid sequence
SEQ ID NO: 6 CD2 amino acid sequence
SEQ ID NO: 7 CD3 amino acid sequence
SEQ ID NO: 8 CD4 amino acid sequence
SEQ ID NO: 9 CD8a amino acid sequence
SEQ ID NO: 10 CD10 amino acid sequence
SEQ ID NO: 11 CD19 amino acid sequence
SEQ ID NO: 12 CD20 amino acid sequence
SEQ ID NO: 13 CD235a amino acid sequence
SEQ ID NO: 14 ARID5B mRNA nucleic acid sequence
SEQ ID NO: 15 ATF3 mRNA nucleic acid sequence
SEQ ID NO: 16 AZU1 mRNA nucleic acid sequence
SEQ ID NO: 17 BMI1 mRNA nucleic acid sequence
SEQ ID NO: 18 CLEC11A mRNA nucleic acid sequence
SEQ ID NO: 19 CSTA mRNA nucleic acid sequence
SEQ ID NO: 20 ETV5 mRNA nucleic acid sequence
SEQ ID NO: 21 HIVEP3 mRNA nucleic acid sequence
SEQ ID NO: 22 HOXA3 mRNA nucleic acid sequence
SEQ ID NO:23 HOXA5 mRNA nucleic acid sequence
SEQ ID NO: 24 HOXB3 mRNA nucleic acid sequence
SEQ ID NO: 25 HOXB5 mRNA nucleic acid sequence
SEQ ID NO: 26 HOXB6 mRNA nucleic acid sequence
SEQ ID NO: 27 ITGA6 mRNA nucleic acid sequence
SEQ ID NO: 28 KIT mRNA nucleic acid sequence
SEQ ID NO: 29 MEIS1 mRNA nucleic acid sequence
SEQ ID NO: 30 MYCN mRNA nucleic acid sequence
SEQ ID NO: 31 NFIL3 mRNA nucleic acid sequence
SEQ ID NO: 32 PTPN14 mRNA nucleic acid sequence
SEQ ID NO: 33 RHOC mRNA nucleic acid sequence
SEQ ID NO: 34 WT1 mRNA nucleic acid sequence
SEQ ID NO: 35 AEBP1 mRNA nucleic acid sequence
SEQ ID NO: 36 CREB5 mRNA nucleic acid sequence
SEQ ID NO: 37 ERG mRNA nucleic acid sequence
SEQ ID NO: 38 FOSL2 mRNA nucleic acid sequence
SEQ ID NO: 39 HOXA7 mRNA nucleic acid sequence
SEQ ID NO: 40 IL11RA mRNA nucleic acid sequence
SEQ ID NO: 41 KDM7A mRNA nucleic acid sequence
SEQ ID NO: 42 KLF7 mRNA nucleic acid sequence
SEQ ID NO: 43 KLF9 mRNA nucleic acid sequence
SEQ ID NO: 44 MAFF mRNA nucleic acid sequence
SEQ ID NO: 45 STAT4 mRNA nucleic acid sequence
SEQ ID NO: 46 TOX mRNA nucleic acid sequence
SEQ ID NO: 47 ZBTB16 mRNA nucleic acid sequence
SEQ ID NO: 48 ARID5B amino acid sequence
SEQ ID NO: 49 ATF3 amino acid sequence
SEQ ID NO: 50 AZU1 amino acid sequence
SEQ ID NO: 51 BMI1 amino acid sequence
SEQ ID NO: 52 CLEC11A amino acid sequence
SEQ ID NO: 53 CSTA amino acid sequence
SEQ ID NO: 54 ETV5 amino acid sequence
SEQ ID NO: 55 HIVEP3 amino acid sequence
SEQ ID NO: 56 HOXA3 amino acid sequence
SEQ ID NO:57 HOXA5 amino acid sequence
SEQ ID NO: 58 HOXB3 amino acid sequence
SEQ ID NO: 59 HOXB5 amino acid sequence
SEQ ID NO: 60 HOXB6 amino acid sequence
SEQ ID NO: 61 ITGA6 amino acid sequence
SEQ ID NO: 62 KIT amino acid sequence
SEQ ID NO: 63 MEIS1 amino acid sequence
SEQ ID NO: 64 MYCN amino acid sequence
SEQ ID NO: 65 NFIL3 amino acid sequence
SEQ ID NO: 66 PTPN14 amino acid sequence
SEQ ID NO: 67 RHOC amino acid sequence
SEQ ID NO: 68 WT1 amino acid sequence
SEQ ID NO: 69 AEBP1 amino acid sequence
SEQ ID NO: 70 CREB5 amino acid sequence
SEQ ID NO: 71 ERG amino acid sequence
SEQ ID NO: 72 FOSL2 amino acid sequence
SEQ ID NO: 73 HOXA7 amino acid sequence
SEQ ID NO: 74 IL11RA amino acid sequence
SEQ ID NO: 75 KDM7A amino acid sequence
SEQ ID NO: 76 KLF7 amino acid sequence
SEQ ID NO: 77 KLF9 amino acid sequence
SEQ ID NO: 78 MAFF amino acid sequence
SEQ ID NO: 79 STAT4 amino acid sequence
SEQ ID NO: 80 TOX amino acid sequence
SEQ ID NO: 81 ZBTB16 amino acid sequence

SEQUENCE LISTING:

SEQ ID NO: 1

```
MLVRRGARAGPRMPRGWTALCLLSLLPSGFMSLDNNGTATPELPTQGTFSNVSTNVSYQETTTPSTLGST
SLHPVSQHGNEATTNITETTVKFTSTSVITSVYGNTNSSVQSQTSVISTVFTTPANVSTPETTLKPSLSP
GNVSDLSTTSTSLATSPTKPYTSSSPILSDIKAEIKCSGIREVKLTQGICLEQNKTSSCAEFKKDRGEGL
ARVLCGEEQADADAGAQVCSLLLAQSEVRPQCLLLVLANRTEISSKLQLMKKHQSDLKKLGILDFTEQDV
ASHQSYSQKTLIALVTSGALLAVLGITGYFLMNRRSWSPTGERLELEP
```

CD48 amino acid sequence

SEQUENCE LISTING:

```
                                                          SEQ ID NO: 2
MCSRGWDSCLALELLLLPLSLLVTSIQGHLVHMTVVSGSNVTLNISESLPENYKQLTWFYTFDQKIVEWD
SRKSKYFESKFKGRVRLDPQSGALYISKVQKEDNSTYIMRVLKKTGNEQEWKIKLQVLDPVPKPVIKIEK
IEDMDDNCYLKLSCVIPGESVNYTWYGDKRPLPKELQNSVLETTLMPHNYSRCYTCQVSNSVSSKNGTVC
LSPPCTLARSFGVEWIASWLVVTVPTILGLLLT
```

CD117 amino acid sequence

```
                                                          SEQ ID NO: 3
MRGARGAWDFLCVLLLLLRVQTGSSQPSVSPGEPSPPSIHPGKSDLIVRVGDEIRLLCTDPGFVKWTFEI
LDETNENKQNEWITEKAEATNTGKYTCTNKHGLSNSIYVFVRDPAKLFLVDRSLYGKEDNDTLVRCPLTD
PEVTNYSLKGCQGKPLPKDLRFIPDPKAGIMIKSVKRAYHRLCLHCSVDQEGKSVLSEKFILKVRPAFKA
VPVVSVSKASYLLREGEEFTVTCTIKDVSSSVYSTWKRENSQTKLQEKYNSWHHGDFNYERQATLTISSA
RVNDSGVFMCYANNTFGSANVTTTLEVVDKGFINIFPMINTTVFVNDGENVDLIVEYEAFPKPEHQQWIY
MNRTFTDKWEDYPKSENESNIRYVSELHLTRLKGTEGGTYTFLVSNSDVNAAIAFNVYVNTKPEILTYDR
LVNGMLQCVAAGFPEPTIDWYFCPGTEQRCSASVLPVDVQTLNSSGPPFGKLVVQSSIDSSAFKHNGTVE
CKAYNDVGKTSAYFNFAFKEQIHPHTLFTPLLIGFVIVAGMMCIIVMILTYKYLQKPMYEVQWKVVEEIN
GNNYVYIDPTQLPYDHKWEFPRNRLSFGKTLGAGAFGKVVEATAYGLIKSDAAMTVAVKMLKPSAHLTER
EALMSELKVLSYLGNHMNIVNLLGACTIGOPTLVITEYCCYGDLLNFLRRKRDSFICSKQEDHAEEAALYK
NLLHSKESSCSDSTNEYMDMKPGVSYVVPTKADKRRSVRIGSYIERDVTPAIMEDDELALDLEDLLSFSY
QVAKGMAFLASKNCIHRDLAARNILLTHGRITKICDFGLARDIKNDSNYVVKGNARLPVKWMAPESIFNC
VYTFESDVWSYGIFLWELFSLGSSPYPGMPVDSKFYKMIKEGFRMLSPEHAPAEMYDIMKTCWDADPLKR
PTFKQIVQLIEKQISESTNHIYSNLANCSPNRQKPVVDHSVRINSVGSTASSSQPLLVHDDV
```

CD150 amino acid sequence

```
                                                          SEQ ID NO: 4
MDPKGLLSLTFVLFLSLAFGASYGTGGRMMNCPKILRQLGSKVLLPLTYERINKSMNKSIHIVVTMAKSL
ENSVENKIVSLDPSEAGPPRYLGDRYKFYLENLTLGIRESRKEDEGWYLMTLEKNVSVQRFCLQLRLYEQ
VSTPEIKVLNKTQENGTCTLILGCTVEKGDHVAYSWSEKAGTHPLNPANSSHLLSLTLGPQHADNIYICT
VSNPISNNSQTFSPWPGCRTDPSETKPWAVYAGLLGGVIMILIMVVILQLRRRGKTNHYQTTVEKKSLTI
YAQVQKPGPLQKKLDSFPAQDPCTTIYVAATEPVPESVQETNSITVYASVTLPES
```

CD244 amino acid sequence

```
                                                          SEQ ID NO: 5
MLGQVVTLILLLLLKVYQGKGCQGSADHVVSISGVPLQLQPNSIQTKVDSIAWKKLLPSQNGFHHILKWE
NGSLPSNTSNDRFSFIVKNLSLLIKAAQQQDSGLYCLEVTSISGKVQTATFQVFVFDKVEKPRLQGQGKI
LDRGRCQVALSCLVSRDGNVSYAWYRGSKLIQTAGNLTYLDEEVDINGTHTYTCNVSNPVSWESHTLNLT
QDCQNAHQEFRFWPFLVIIVILSALFLGTLACFCVWRRKRKEKQSETSPKEFLTIYEDVKDLKTRRNHEQ
EQTFPGGGSTIYSMIQSQSSAPTSQEPAYTLYSLIQPSRKSGSRKRNHSPSFNSTIYEVIGKSQPKAQNP
ARLSRKELENFDVYS
```

CD2 amino acid sequence

```
                                                          SEQ ID NO: 6
MSFPCKFVASFLLIFNVSSKGAVSKEITNALETWGALGQDINLDIPSFQMSDDIDDIKWEKTSDKKKIAQ
FRKEKETFKEKDTYKLFKNGTLKIKHLKTDDQDIYKVSIYDTKGKNVLEKIFDLKIQERVSKPKISWTCI
NTTLTCEVMNGTDPELNLYQDGKHLKLSQRVITHKWTTSLSAKFKCTAGNKVSKESSVEPVSCPEKGLDI
YLIIGICGGGSLLMVFVALLVFYITKRKKQRSRRNDEELETRAHRVATEERGRKPHQIPASTPQNPATSQ
HPPPPPGHRSQAPSHRPPPPGHRVQHPQKRPPAPSGTQVHQQKGPPLPRPRVQPKPPMGQQKTHCPLPL
IKKDRNCLFQ
```

CD3 amino acid sequence

```
                                                          SEQ ID NO: 7
MQSGTHWRVLGLCLLSVGVWGQDGNEEMGGITQTPYKVSISGTTVILTCPQYPGSEILWQHNDKNIGGDE
DDKNIGSDEDHLSLKEFSELEQSGYYVCYPRGSKPEDANFYLYLRARVCENCMEMDVMSVATIVIVDICI
TGGLLLLVYYWSKNRKAKAKPVTRGAGAGGRQRGQNKERPPPVPNPDYEPIRKGQRDLYSGLNQRRI
```

CD4 amino acid sequence

```
                                                          SEQ ID NO: 8
MNRGVPFRHLLLVLQLALLPAATQGKKVVLQKKGDTVELTCTASQKKSIQFHWKNSNQIKILGNQGSFLT
KGPSKLNDRADSRRSLWDQGNFPLIIKNLKIEDSDTYICEVEDQKEEVQLLVFGLTANSDTHLLQGQSLT
LTLESPPGSSPVSQCRSPRGKNIQGGKTLSVSQLELQDSGTWTCTVLQNQKKVEFKIDIVVLAFQKASSI
VYKKEGEQVEFSFPLAFTVEKLTGSGELWWQAERASSSKSWITFDLKNKEVSVKRVTQDPKLQMGKKLPL
HLTLPQALPQYAGSGNLTLALEAKTGKLHQEVNLVVMRATQLQKNLTCEVWGPTSPKLMLSLKLENKEAK
VSKREKAVWVLNPEAGMWQCLLSDSGQVLLESNIKVLPTWSTPVQPMALIVLGGVAGLLLFIGLGIFFCV
RCRHRRRQAERMSQIKRLLSEKKTCQCPHRFQKTCSPI
```

CD8a amino acid sequence

```
                                                          SEQ ID NO: 9
MALPVTALLLPLALLLHAARPSQFRVSPLDRTWNLGETVELKCQVLLSNPTSGCSWLFQPRGAAASPTFL
LYLSQNKPKAAEGLDTQRFSGKRLGDTFVLTLSDFRRENEGCYFCSALSNSIMYFSHFVPVFLPAKPTTT
PAPRRPPTPAPTIASQPLSLRPEACRPAAGGAVHTRGLDFACDIYIWAPLAGTCGVLLLSLVITLYCNHRN
RRRVCKCPRPVVKSGDKPSLSARYV
```

CD10 amino acid sequence (Neprilysin gene)

```
                                                          SEQ ID NO: 10
MGKSESQMDITDINTPKPKKKQRWTPLEISLSVLVLLLTIIAVTMIALYATYDDGICKSSDCIKSAARLI
QNMDATTEPCTDFFKYACGGWLKRNVIPETSSRYGNFDILRDELEVVLKDVLQEPKTEDIVAVQKAKALY
RSCINESAIDSRGGEPLLKLLPDIYGWPVATENWEQKYGASWTAEKAIAQLNSKYGKKVLINLFVGTDDK
```

```
                                     SEQUENCE LISTING:

NSVNHVIHIDQPRLGLPSRDYYECTGIYKEACTAYVDFMISVARLIRQEERLPIDENQLALEMNKVMELE
KEIANATAKPEDRNDPMLLYNKMTLAQIQNNFSLEINGKPFSWLNFTNEIMSTVNISITNEEDVVVYAPE
YLTKLKPILTKYSARDLQNLMSWRFIMDLVSSLSRTYKESRNAFRKALYGTTSETATWRRCANYVNGNME
NAVGRLYVEAAFAGESKHVVEDLIAQIREVFIQTLDDLTWMDAETKKRAEEKALAIKERIGYPDDIVSND
NKLNNEYLELNYKEDEYFENIIQNLKFSQSKQLKKLREKVDKDEWISGAAVVNAFYSSGRNQIVFPAGIL
QPPFFSAQQSNSLNYGGIGMVIGHEITHGFDDNGRNFNKDGDLVDWWTQQSASNFKEQSQCMVYQYGNFS
WDLAGGQHLNGINTLGENIADNGGLGQAYRAYQNYIKKNGEEKLLPGLDLNHKQLFFLNFAQVWCGTYRP
EYAVNSIKTDVHSPGNFRIIGTLQNSAEFSEAFHCRKNSYMNPEKKCRVW

CD19 amino acid sequence
                                                         SEQ ID NO: 11
MPPPRLLFFLLFLTPMEVRPEEPLVVKVEEGDNAVLQCLKGTSDGPTQQLTWSRESPLKPFLKSLGLPG
LGIHMRPLASWLFIFNVSQQMGGFYLCQPGPPSEKAWQPGWTVNVEGSGELFRWNVSDLGGLGCGLKNRS
SEGPSSPSGKLMSPKLYVWAKDRPEIWEGEPPCVPPRDSLNQSLSQDLTMAPGSTLWLSCGVPPDSVSRG
PLSWTHVHPKGPKSLLSLELKDDRPARDMWVMETGLLLPRATAQDAGKYYCHRGNLTMSFHLEITARPVL
WHWLLRTGGWKVSAVTLAYLIFCLCSLVGILHLQRALVLRRKRKRMTDPTRRFFKVTPPPGSGPQNQYGN
VLSLPTPTSGLGRAQRWAAGLGGTAPSYGNPSSDVQADGALGSRSPPGVGPEEEEGEGYEEPDSEEDSEF
YENDSNLGQDQLSQDGSGYENPEDEPLGPEDEDSFSNAESYENEDEELTQPVARTMDFLSPHGSAWDPSR
EATSLGSQSYEDMRGILYAAPQLRSIRGQPGPNHEEDADSYENMDNPDGPDPAWGGGGRMGTWSTR CD20 amino acid sequence
                                                         SEQ ID NO: 12
MTTPRNSVNGTFPAEPMKGPIAMQSGPKPLFRRMSSLVGPTQSFFMRESKTLGAVQIMNGLFHIALGGLL
MIPAGIYAPICVTVWYPLWGGIMYIISGSLLAATEKNSRKCLVGKMIMNSLSLFAAISGMILSIMDILN
IKISHFLKMESLNFIRAHTPYINIYNCEPANPSEKNSPSTQYCYSIQSLFLGILSVMLIFAFFQELVIAG
IVENEWKRTCSRPKSNIVLLSAEEKKEQTIEIKEEVVGLTETSSQPKNEEDIEIIPIQEEEEEETETNFP
EPPQDQESSPIENDSSP CD235a amino acid sequence (Glycophorin A gene)
                                                         SEQ ID NO: 13
MYGKIIFVLLLSAIVSISASSTTGVAMHTSTSSSVTKSYISSQTNDTHKRDTYAATPRAHEVSEISVRTV
YPPEEETGERVQLAHHFSEPEITLIIFGVMAGVIGTILLISYGIRRLIKKSPSDVKPLPSPDTDVPLSSV
EIENPETSDQ ARID5B mRNA nucleic acid sequence
                                                         SEQ ID NO: 14
AGATGCACAGTGGAGCTCGCTACCCCTCCTCTCCTCCAAAAATCTCATCAGACGATATCCCAGACAGGAG
CGGTTAGAGAGAGAGGAATCACATCTCCACACAGTTTTAGGGTGCTTTTTATTTTTACAAATCTTCTTGT
GTGTTTTTTGCCTTGATCCATCCTCTTCCCGCCGAGATCGTATGGCGCCTTTCTCTCGATTATGAATTTG
ATCAATCCATCTTTGGAAGAAAACCCACATAGTTTTTTCAGGAGCTGAAAATTGAGTCGTTATAGAAATA
TTAGGACATATTTTCAATCATTTCGGTGCCCGAAGGGAGGCAAGAGCTCAGTTTTATATTGAGACATTAC
GCCGGCTGAAGGCAGAGAATGCGTTTCCCTGCCAGGACCTGATGCAATCCATTCAAGCCAACAAGTTTGG
AGAGAATGTTGAGTTCAATCAATTCAGAACGTCGAGATGGAGCCCAACTCACTCCAGTGGGTCGGCTCAC
CGTGTGGCTTGCACGGACCTTACATTTTCTACAAGGCTTTTCAATTCCACCTTGAAGGCAAACCAAGAAT
TTTGTCCCTTGGCGACTTTTTCTTTGTAAGATGTACGCCAAAGGATCCGATTTGCATAGCGGAGCTCCAG
CTGTTGTGGGAAGAGAGGACCAGCCGGCAACTTTTATCCAGCTCTAAACTTTATTTCCTCCCAGAAGACA
CTCCCCAGGGCAGAAATAGCGACCATGGCGAGGATGAAGTCATTGCTGTTTCCGAAAGGTGATTGTGAA
GCTTGAAGACCTGGTCAAGTGGGTACATTCTGATTTCTCCAAGTGGAGATGTGGCTTCCACGCTGGACCA
GTGAAAACTGAGGCCTTGGGAAGGAATGGACAGAAGGAAGCTCTGCTGAAGTACAGGCAGTCAACCCTAA
ACAGTGGACTCAACTTCAAAGACGTTCTCAAGGAGAAGGCAGACCTGGGGGAGGACGAGGAAGAAACGAA
CGTGATAGTTCTCAGCTACCCCAGTACTGCCGGTACCGCTCGATGCTGAAACGCATCCAGGATAAGCCA
TCTTCCATTCTAACGGACCAGTTTGCATTGGCCCTGGGGGGCATTGCAGTGGTCAGCAGGAACCCTCAGA
TCCTGTACTGTCGGGACACCTTTGACCACCCGACTCTCATAGAAAACGAGAGTATGCGATGAGTTTGC
GCCAAATCTTAAAGGCAGACCACGCAAAAGAAACCATGCCCACAAAGAAGAGATTCATTCAGTGGTGTT
AAGGATTCCAACAACAATTCCGATGGCAAAGCCGTTGCCAAGGTGAAATGTGAGGCAGGTCAGCCTTGA
CCAAGCCGAAGAATAACCATAACTGTAAAAAGTCTCAAATGAAGAAAAACCAAAGGTTGCCATTGGTGA
AGAGTGCAGGGCAGATGAACAAGCCTTCTTGGTGGCACTTTATAAATACATGAAAGAAAGGAAAACGCCG
ATAGAACGAATACCCTATTTAGGTTTTAAACAGATTAACCTTTGGACTATGTTTCAAGCTGCTCAAAAAC
TGGGAGGATATGAAACAATAACAGCCCGCCGTCAGTGGAAACATATTTATGATGAATTAGGCGGTAATCC
TGGGAGCACCAGCGCTGCCACTTGTACCCGCAGACATTATGAAAGATTAATCCTACCATATGAAAGATTT
ATTAAAGGAGAAGAAGATAAGCCCCTGCCTCCAATCAAACCTCGGAAACAGGAGAACAGTTCACAGGAAA
ATGAGAACAAAACAAAAGTATCTGGAACCAAACGCATCAAACATGAAATACCTAAAAGCAAGAAAGAAAA
AGAAAATGCCCCAAAGCCCCAGGATGCAGCAGAGGTTTCATCAGAGCAAGAAAAAGAACAAGAGACTTTA
ATAAGCCAGAAAAGCATCCCTGAGCCTCTCCCAGCAGCAGACATGAAGAAAAAATAGAAGGGTATCAGG
AATTTTCAGCGAAGCCCCTGGCATCCAGAGTAGACCCAGAGAAGGACAACGAAACAGACCAAGGTTCCAA
CAGTGAGAAGGTGGCAGAGGAGGCGGGAGAGAAGGGGCCCACACCTCCACTCCCAAGTGCTCCTCTGGCG
CCAGAAAAAGATTCAGCCTTGGTCCCTGGGGCCAGCAAACAGCCACTCACCTCTCCTAGTGCCCTGGTGG
ACTCAAAACAAGAATCCAAACTGTGCTGTTTTACAGAGAGCCCTGAAAGTGAACCCAAGAAGCATCCTT
CCCCAGCTTCCCCACCACACAGCCACCGCTGGCAAACCAGAATGAGACGGAGGATGACAAACTGCCCGCC
ATGGCAGATTACATTGCCAACTGCACCGTGAAGGTGGACCAGCTGGGCAGTGACGACATCCACAATGCGC
TCAAGCAGACCCCAAAGGTCCTTGTGGTCAGTCGTTTGACATGTTCAAAGACAAAGACCTGACTGGGCC
CATGAACGAGAACCATGGACTTAATTACACGCCCCTGCTCTACTCTAGGGGCAACCCAGGCATCATGTCC
CCACTGGCCAAGAAAAAGCTTTTGTCCCAAGTGAGTGGGGCCAGCCTCTCCAGCAGCTACCCTTATGGCT
CCCCACCCCCTTTGATCAGCAAAAAGAAACTGATTGCTAGGGATGACTTGTGTTCCAGTTTGTCCCAGAC
CCACCATGGCCAAAGCACTGACCATATGGCGGTCAGCCGGCCATCAGTGATTCAGCACGTCCAGAGTTTC
AGAAGCAAGCCCTCGGAAGAGAAAGACCATCAATGACATCTTTAAGCATGAGAAACTGAGTCGATCAG
ATCCCCACCGCTGCAGCTTCTCCAAGCATCACCTTAACCCCCTTGCTGACTCCTACGTCCTGAAGCAAGA
```

SEQUENCE LISTING:

```
AATTCAGGAGGGCAAGGATAAACTCTTAGAGAAAAGGGCCCTCCCCCATTCCCACATGCCTAGCTTCCTG
GCTGACTTCTACTCGTCCCCTCATCTCCATAGCCTCTACAGACACACCGAGCACCATCTTCATAATGAAC
AGACATCCAAATACCCTTCCAGGGACATGTACAGGGAATCGGAAAACAGTTCTTTTCCTTCCCACAGACA
CCAAGAAAAGCTCCATGTAAATTATCTCACGTCCCTGCACCTGCAAGACAAAAAGTCGGCGGCAGCAGAA
GCCCCTACGGATGATCAGCCTACAGATCTGAGCCTTCCCAAGAACCCGCACAAACCTACCGGCAAGGTCC
TGGGCCTGGCTCATTCCACCACAGGGCCCCAGGAGAGCAAAGGCATCTCCCAGTTCCAGGTCTTAGGCAG
CCAGAGTCGAGACTGTCACCCCAAAGCCTGTCGGGTATCACCCATGACCATGTCAGGCCCTAAAAAATAC
CCTGAATCGCTTTCAAGATCAGGAAAACCTCACCATGTGAGACTGGAGAATTTCAGGAAGATGGAAGGCA
TGGTCCACCCAATCCTGCACCGGAAAATGAGCCCGCAGAACATTGGGGCGGCGCGGCCGATCAAGCGCAG
CCTGGAGGATTTGGACCTTGTGATTGCAGGGAAAAAGGCCCGGGCAGTGTCTCCCTTAGACCCATCCAAG
GAGGTCTCTGGGAAGGAGAAGGCCTCTGAGCAGGAGAGTGAAGGCAGCAAAGCAGCGCACGGTGGGCATT
CCGGGGCGGATCAGAAGGCCACAAGCTTCCCCTCTCCTCCCCTATCTTCCCAGGTCTGTATTCCGGGAG
CCTGTGTAACTCGGGCCTCAACTCCAGGCTCCCGGCTGGGTATTCTCATTCTCTGCAGTACTTGAAAAAC
CAGACTGTGCTTTCTCCACTCATGCAGCCCCTGGCTTTCCACTCGCTTGTGATGCAAAGAGGAATTTTTA
CATCACCGACAAATTCTCAGCAGCTGTACAGACACTTGGCTGCGGCTACACCTGTAGGAAGTTCATATGG
GGACCTTTTGCATAACAGCATTTACCCTTTAGCTGCTATAAATCCTCAAGCTGCCTTTCCATCTTCCCAG
CTGTCATCCGTGCACCCCAGTACAAAACTGTAGGCTCAGCTCTGCCCAGCAGTCCAAAGCGGCATGGCCA
ACAGAGCTTCACTCCTTACCCAGGAGTGCTGGCTTATAGAGTTAGAAGTCAGTATTTCTTCTAATCTGAG
GCTATGATCAGTCCCAGCTGTAGGGGCCCAGAGGGGAGGTGAACATGCCTGATTTTTGTGGGACAACTCT
AGCCCACAAACTGACTGGCTGGTGAGTCTTGACTCCCTTCCAACACAGATGCCCAGGCACCTCCAGATCA
TTCACTTCGCACGTGGGCCTTGTGAAGGGATTTGTGAATATCCAGGAAGAACTTAGAGGACCCCATCTGA
GTTCGGATGGTCAGGAAACAATCTGGGCAAAAAGAGGCAGGCATTTCAAAGGAAGGGGCAAGGAAGACT
GGCAAACAGATGGCAAGGGATGCCCCTCTTTTTCATAAAACTCTCCAAGGTTCAATCAATGCAATGTATA
GTGAAACTTCAATAGATCTTTCATTTTGACACTATTAAACAATCCAGAGAAGTAAACACTGTTAAATTGA
CTGTATATATTTGCTTCTTAAAACTACCTGTATCACTGTTTGCTCACCTAATTTATATACAGGTAGTTCC
ATTTTCTCCCAGTTCCTTCTCGTCTTTTTTTTTTTTTTTTTTTTTTTTTATTAAATGGTATTGCTTTT
GTTTGCAGGTCTTTTTGTTTTGTTTTGTTTTGAGGCTGACTGACTGTCCTAGTTGTTGTGTGTTTGTA
ATTTTTCCACATCTTATTTTGAGCAGCTTTGGGTGGTAAAGTTATTGTTTTACAAATTGAAGCAACTGATT
CTAGTGGAACAAATGAAAAAGAAACAGTCAAGCACACAATAGTGCAAAGAACGTTCCITTGTAGATCCGC
AACTTAAGGATTTTGTTCCTCATAAATGGCATAGTTGAAAGAGCTTATACACTGCTTACCCAGCCAAATG
CTTTGCTTTGAAGTATTGGGTTCTGTGAAAATATTGAGCATTGTACTTACCTTATCTAGGCTGTGAAACT
GTCCTACATACCAGAGAATCATAAAAACAAAAACCTCACTGGCAGCAAGCTGCCGAATAACAACAGAGTC
TAGAGGACATATTTGTGGGCTGCACAGATATTTTAGGAATTTCAGAAATTAGAACAGGAGCCAAAATGAT
TTACATTGGCGTTGGCACTGATTCCTTTAAATGGTCTGGGAAAGGGGGTTGGGAAGAGGATGGAGCTCAA
CTGGCCAGAAGAGGAGCAGCTGCAGTCCTGATAGCTTCTCTAGCCTCGGTCTTTTGAGTGATAAGTAGTC
ATGTTGTTTTCATCCAGTTGGTTTCTTGTCATTCCCAAGAAGAATCTCCCAGGCCACATCTTTGGGGATA
ACTGACATACTGGATTAGCCTTTTCAAAAGAAAAGTCATCCTATTTGGTTTTATGGGGTGTGAGTTTTGT
GTGTACACACAGAAACATGTAAGGTGGTTTGGGTCATGTTTTTACCACCTGGCAATACAGTCCACTTT
TCTGGTTTCTTTTATTGTGGGAAGTAAATGGTCAAGCTGCTCAGGCAGTGAAAAGATGTGGAGAATGTCC
GTTGTCATTCTTGCCACTGTATTCCATTTGCTACCGAGATATAACATTAAGGTGGACACATTTTCTAACT
GTATTAATTAAAGTCAATGGATACAGAGAGTGGATTTTCTCCCAAGTCCCATCCCTGCTGAAGACCGC
TTGGATGAACTCCCCAACCCACTGTGCCCCTCCCGCAACACTACCAGTAGACTTTAGAACCATAGTTAAC
TAAGTCTTTTACCTCTGAGATACTTAATTCTGGGAAAATTGGTGACAATTTTCAACTTCTAAATAGGTAA
CTCGACTGCAAAATAATCAAAACTGATAACAATGAAACTGCGGCTCTTAAACAAAGCCATGCATGCCGTG
CATTTGTATTGAAATGTCTCCATGATATGAAGCCAAATATTCAATGTAACATACTTAATATCCAAAGGTG
GAAACAAAAGAATGTAGAGATCCAGTGTTAAGAGTTCCATTTGCTTCAATTAATTATTTACCTTCCTGTG
GAATAATATATATATATATATTTAATAGAACCATAGATAGACTAGTAGAATTTAGATTATAAATGTGTGA
GTGCAGATTATTCCTGCTATTGCACAAGCTAGAGGGGGGAAAAATCTCAATTCCAGCTGGCAAGATGCTAG
CCAGGACACATATAAGAAAGTTGCACTAGATTGAATGGTCACAGAATCGGAGGACATGGAAGAAAAAGGA
AACTTCGGTGGTTCTGCAGCAGACATGGGCTAGGTCATATGTGGTTTCTATGAGTTCGTGTCTCAAAAAA
AAAAGGAGGGGGGCATCTGTCCCCGGTGGAGCTCACCTATTTGGAATATGGGGCATTTGTTTTTTCCAC
TGCAATGATTTCAGTCTGGTTTCATCATGTTGGAATTCGATCACACCATTTTCAAACAATGTTAACATAG
TCCAGCTTTTGTTTTTCTCATCTCTTCTGAGAGGAGACTCACTGTTTCTGTCTGAGGAAGCTCATACCCT
CGGCAAACATCAGGACAAATAAAGAGAAATGGGGGTACGCATTCCCAACAGAAGCAGTGTGTTATTTGT
TTTAAAACTCTGAACAGAGATCTTGGAAATCTTTCAAAAAGACCATTGAATTCTTCATTGGCTGAGAACG
ACGTTTTAAAATGTCTTAAATAAGGCTTTGTTTGCATTGTTTGAGTTCAAGGGGCCTTATTATTGAATGG
AATTGCACAAGCCTTTCTTTGTGCAATCAAACCATTGTTATTGGTAGTTCTGTAAAGGAAACTGTGGAAT
CGAATTGGCAGTGGAGTCATAAATCTATTTACTGAGTGTGGCTTCCAAGAAATGTTGCAATTCAAAATGC
ACTAAGTCTGTGATTTATTGGAGATTTGGAGATTCTAAATAATATTTTTAAAAAACTTCCATGCAACTTC
TGGTTTAATGTTTGGCAACTCCACATGATAAAAAATAAAAACAGCCCAACCGAGTTTCGGAATTAAGTA
TTCTTCTAGTAAGTGATTCAAACTTGTAATATTTGCCACAGGACTGACTTATTTATTTACTAGCTAGAAG
CTCTTAAGTTCACTTGTTTATCAGGGCATATACAGAAGGGTTTGTTAAAACTCGATGTTAACTTTACAAC
TTTCTGACCTGGTGCATGAATTCTCAAGTACTGTATTTCACTGTGTTGGTGTGTCTGATGGAAATTTCGA
GGTGGTCCCACAAAAATATTTTATGTAGTGTGCCTTCAAAGAGAACCATTTATTTCTCTTCACTTATCGT
CCCACAAAGTCACATTTGGTGGTGGTCAGCCAAGTCGCATCTGGTCTAGTTTTACTCTTGTCCCAATTTT
AAAGAGAAATGGGAATGAGTTTGCCCTGGTGAGACCCATACCATTGCAATGATTATCTTGAGCACTTAAA
GTCCAGTGTTGGCTGTTAGTGTATTTGATATTCTGCCTGTCTCCTCATGGTTGAAATATGTCTGAAGAAT
AGCAGCATAATCTCTTGGCTGTTTATACTTTTTAAACTTTCCTGTGTTGTAAATATTGTATACTTTTGG
TGATTCCAGCTATGTAACCTCTATGCTCTGTAAGGTGATTATTTGTATATAGCAACATGGCCCAGTGATA
TTATATAGTTTCCCAATGGAGAGGTTATTGAGTAACCTTTGCATTAGTTTAAACACTACCAGAAGAATGC
TGAGCCAACTATAAACACTCAATTTTGTATGTTTTCCAAATTGTACTTATTACTGCTTTTGATACTGTAT
TACGTGCCAATAGTTTCCCAATCACATAGCAGGCAAGAGATATTTTGTACTTTTTGATCCACTGTAATAT
TTAATAAAAAATGTTACTATCTGTTTCCTTTAAAAAAA
```

ATF3 mRNA nucleic acid sequence

SEQUENCE LISTING:

SEQ ID NO: 15
```
TCCGCTCCGTTCGGCCGGTTCTCCCGGGAAGCTATTAATAGCATTACGTCAGCCTGGGACTGGCAACACG
GAGTAAACGACCGCGCCGCCAGCCTGAGGGCTATAAAAGGGGTGATGCAACGCTCTCCAAGCCACAGTCG
CACGCAGCCAGGCGCGCACTGCACAGCTCTCTTCTCGCCGCCGCCCGAGCGCACCCTTCAGCCCGCGC
GCCGGCCGTGAGTCCTCGGTGCTCGCCCGCCGGCCAGACAAACAGCCCGCCCGACCCCGTCCCGACCCTG
GCCGCCCCGAGCGGAGCCTGGAGCAAAATGATGCTTCAACACCCAGGCCAGGTCTCTGCCTCGGAAGTGA
GTGCTTCTGCCATCGTCCCCTGCCTGTCCCCTCCTGGGTCACTGGTGTTTGAGGATTTTGCTAACCTGAC
GCCCTTTGTCAAGGAAGAGCTGAGGTTTGCCATCCAGAACAAGCACCTCTGCCACCGGATGTCCTCTGCG
CTGGAATCAGTCACTGTCAGCGACAGACCCCTCGGGGTGTCCATCACAAAAGCCGAGGTAGCCCCTGAAG
AAGATGAAAGGAAAAAGAGGCGACGAGAAAGAAATAAGATTGCAGCTGCAAAGTGCCGAAACAAGAAGAA
GGGAGAAGACGGAGTGCCTGCAGAAAGAGTCGGAGAAGCTGGAAAGTGTGAATGCTGAACTGAAGGCTCAG
ATTGAGGAGCTCAAGAACGAGAAGCAGCATTTGATATACATGCTCAACCTTCATCGGCCCACGTGTATTG
TCCGGGCTCAGAATGGGAGGACTCCAGAAGATGAGAGAAACCTCTTTATCCAACAGATAAAGAAGGAAC
ATTGCAGAGCTAAGCAGTCGTGGTATGGGGGCGACTGGGGAGTCCTCATTGAATCCTCATTTTATACCCA
AAACCCTGAAGCCATTGGAGAGCTGTCTTCCTGTGTACCTCTAGAATCCCAGCAGCAGAGAACCATCAAG
GCGGGAGGGCCTGCAGTGATTCAGCAGGCCCTTCCCATTCTGCCCCAGAGTGGGTCTTGGACCAGGGCAA
GTGCATCTTTGCCTCAACTCCAGGATTAGGCCTTAACACACTGGCCATTCTTATGTTCCAGATGGCCCC
CAGCTGGTGTCCTGCCCGCCTTTCATCTGGATTCTACAAAAAACCAGGATGCCCACCGTTAGGATTCAGG
CAGCAGTGTCTGTACCTCGGGTGGAGGGATGGGGCCATCTCCTTCACCGTGGCTACCATTGTCACTCGT
AGGGGATGTGGAGTGAGAACAGCATTTAGTGAAGTTGTGCAACGGCCAGGGTTTGTGCTTTCTAGCAAATA
TGCTGTTATGTCCAGAAATTGTGTGTGCAAGAAAACTAGGCAATGTACTCTTCCGATGTTTGTGTCACAC
AACACTGATGTGACTTTTATATGCTTTTTCTCAGATCTGGTTTCTAAGAGTTTTGGGGGCGGGGCTGTC
ACCACGTGCAGTATCTCAAGATATTCAGGTGGCCAGAAGAGCTTGTCAGCAAGAGGAGGACAGAATTCTC
CCAGCGTTAACACAAAATCCATGGCAGTATGATGGCAGGTCCTCTGTTGCAAACTCAGTTCCAAAGTCA
CAGGAAGAAAGCAGAAAGTTCAACTTCCAAAGGGTTAGGACTCTCCACTCAATGTCTTAGGTCAGGAGTT
GTGTCTAGGCTGGAAGAGCCAAAGAATATTCCATTTTCCTTTCCTTGTGGTTGAAAACCACAGTCAGTGG
AGAGATGTTTGGAAACCACAGTCAGTGGAGCCTGGGTGGTACCCAGGCTTTAGCATTATTGGATGTCAAT
AGCATTGTTTTGTCATGTAGCTGTTTTAAGAAATCTGGCCCAGGGTTTCTGCAGCTGTGAGAAGTCACT
CACACTGGCCACAAGGACGCTGGCTACTGTCTATTAAAATTCTGATGTTTCTGTGAAATTCTCAGAGTGT
TTAATTGTACTCAATGGTATCATTACAATTTTCTGTAAGAGAAATATTACTTATTTATCCTAGTATTCC
TAACCTGTCAGAATAATAAATATTGGAACCAAGACATGGTAAACAAAAAAAAAAAAAAA
```

AZU1 mRNA nucleic acid sequence
SEQ ID NO: 16
```
ACAGACCTGCCCCGCCATGACCCGGCTGACAGTCCTGGCCCTGCTGGCTGGTCTGCTGGCGTCCTCGAGG
GCCGGCTCCAGCCCCCTTTTGGACATCGTTGGCGGCCGGAAGGCGAGGCCCCGCCAGTTCCCGTTCCTGG
CCTCCATTCAGAATCAAGGCAGGCACTTCTGCGGGGGTGCCCTGATCCATGCCCGCTTCGTGATGACCGC
GGCCAGCTGCTTCCAAAGCCAGAACCCCGGGGTTAGCACCGTGGTGCTGGGTGCCTATGACCTGAGGCGG
CGGGAGAGGCAGTCCCGCCAGACGTTTTCCATCAGCAGCATGAGCGAGAATGGCTACGACCCCCAGCAGA
ACCTGAACGACCTGATGCTGCTTCAGCTGGACCGTGAGGCCAACCTCACCGACAGCGTGACGATACTGCC
ACTGCCTCTGCAGAACGCCACGGTGGAAGCCGGCACCAGATGCCAGGTGGCCGGCTGGGGGAGCCAGCGC
AGTGGGGGCGTCTCTCCCGTTTTCCCAGGTTTGTCAACGTGACTGTGACCCCCGAGGACCAGTGTCGCC
CCAACAACGTGTGCACCGGTGTGCTCACCCGCCGCGGTGGCATCTGCAATGGGGACGGGGGCACCCCCCT
CGTCTGCGAGGGCCTGGCCCACGGCGTGGCCTCCTTTTCCCTGGGGCCCTGTGGCCGAGGCCCTGACTTC
TTCACCCGAGTGGCGCTCTTCCGAGACTGGATCGATGGTGTTCTCAACAACCCGGGACCGGGGCCAGCCT
AGGGGGGCCTGTGACCTCCCATGGAGCCCAGCCCCGCCCTCCACACCTCCGGCGCTCCGCACCCACCTCC
CACGGCCCCGCCCCTGCCCCCGCTCCGGCCAGAGGGGCCCTGGCTGTAATAAAGAAGCCGATCTCTCCTC
TG
```

BMI1 mRNA nucleic acid sequence
SEQ ID NO: 17
```
ACAGCAACTATGAAATAATCGTAGTATGAGAGGCAGAGATCGGGGCGAGACAATGGGGATGTGGGCGCGG
GAGCCCCGTTCCGGCTTAGCAGCACCTCCCAGCCCCGCAGAATAAAACCGATCGCGCCCCTCCGCGCGC
GCCCTCCCCCGAGTGCGGAGCGGGAGGAGGCGGCGGCGGCCGAGGAGGAGGAGGAGGAGGCCCCGGAGGA
GGAGGCGTTGGAGGTCGAGGCGGAGGCGGAGGAGGAGGAGGCCGAGGCGCCGGAGGAGGCGAGGCGCCG
GAGCAGGAGGAGGCCGGCCGGAGGCGGCATGAGACGAGCGTGGCGGCCGCGGCTGCTCGGGGCCGCGCTG
GTTGCCCATTGACAGCGGCGTCTGCAGCTCGCTTCAAGATGGCCGCTTGGCTCGCATTCATTTTCTGCTG
AACGACTTTTAACTTTCATTGTCTTTTCCGCCCGCTTCGATCGCTCGCGCCGGCTGCTCTTTCCGGGAT
TTTTTATCAAGCAGAAATGCATCGAACAACGAGAATCAAGATCACTGAGCTAAATCCCCACCTGATGTGT
GTGCTTTGTGGAGGGTACTTCATTGATGCCACAACCATAATAGAATGTCTACATTCCTTCTGTAAAACGT
GTATTGTTCGTTACCTGGAGACCAGCAAGTATTGTCCTATTTGTGATGTCCAAGTTCACAAGACCAGACC
ACTACTGAATATAAGGTCAGATAAAACTCTCCAAGATATTGTATACAAATTAGTTCCAGGGCTTTTCAAA
AATGAAATGAAGAGAAGAAGGGATTTTTATGCAGCTCATCCTTCTGCTGATGCTGCCAATGGCTCTAATG
AAGATAGAGGAGAGGTTGCAGATGAAGATAAGAGAATTATAACTGATGATGAGATAATAAGCTTATCCAT
TGAATTCTTTGACCAGAACAGATTGGATCGGAAAGTAAACAAAGACAAAGAGAAATCTAAGGAGGAGGTG
AATGATAAAAGATACTTACGATGCCCAGCAGCAATGACTGTGATGCACTTAAGAAAGTTTCTCAGAAGTA
AAATGGACATACCTAATACTTTCCAGATTGATGTCATGTATGAGGAGGAACCTTTAAAGGATTATTATAC
ACTAATGGATATTGCCTACATTTATACCTGGAGAAGGAATGGTCCACTTCCATTGAAATACAGAGTTCGA
CCTACTTGTAAAAGAATGAAGATCAGTCACCAGAGAGATGGACTGACAAATGCTGGAGAACTGGAAAGTG
ACTCTGGGAGTGACAAGGCCAACAGCCCAGCAGGAGGTATTCCCTCCACCTCTTCTTGTTTGCCTAGCCC
CAGTACTCCAGTGCAGTCTCCTCATCCACAGTTTCCTCACATTTCCAGTACTATGAATGGAACCAGCAAC
AGCCCCAGCGGTAACCACCAATCTTCTTTTGCCAATAGACCTCGAAAATCATCAGTAAATGGGTCATCAG
CAACTTCTTCTGGTTGATACCTGAGACTGTTAAGGAAAAAAATTTTAAACCCCTGATTTATATAGATATC
TTCATGCCATTACAGCTTTCTAGATGCTAATACATGTGACTATCGTCCAATTTGCTTTCTTTTGTAGTGA
CATTAAATTTGGCTATAAAAGATGGACTACATGTGATACTCCTATGGACGTTAATTGAAAAGAAAGATTG
TTGTTATAAAGAATTGGTTTCTTGGAAAGCAGGCAAGACTTTTTCTCTGTGTTAGGAAAGATGGGAAATG
GTTTCTGTAACCATTGTTTGGATTTGGAAGTACTCTGCAGTGGACATAAGCATTGGGCCATAGTTTGTTA
```

```
ATCTCAACTAACGCCTACATTACATTCTCCTTGATCGTTCTTGTTATTACGCTGTTTTGTGAACCTGTAG
AAAACAAGTGCTTTTTATCTTGAAATTCAACCAACGGAAAGAATATGCATAGAATAATGCATTCTATGTA
GCCATGTCACTGTGAATAACGATTTCTTGCATATTTAGCCATTTTGATTCCTGTTTGATTTATACTTCTC
TGTTGCTACGCAAAACCGATCAAAGAAAAGTGAACTTCAGTTTTACAATCTGTATGCCTAAAAGCGGGTA
CTACCGTTTATTTTACTGACTTGTTTAAATGATTCGCTTTTGTAAGAATCAGATGGCATTATGCTTGTTG
TACAATGCCATATTGGTATATGACATAACAGGAAACAGTATTGTATGATATATTTATAAATGCTATAAAG
AAATATTGTGTTTCATGCATTCAGAAATGATTGTTAAAATTCTCCCAACTGGTTCGACCTTTGCAGATAC
CCATAACCTATGTTGAGCCTTGCTTACCAGCAAAGAATATTTTTAATGTGGATATCTAATTCTAAAGTCT
GTTCCATTAGAAGCAATTGGCACATCTTTCTATACTTTATATACTTTTCTCCAGTAATACATGTTTACTT
TAAAGATTGTTGCAGTGAAGAAAAACCTTTAACTGAGAAATATGGAAACCGTCTTAATTTTCCATTGGCT
ATGATGGAATTAATATTGTATTTTAAAAATGCATATTGATCACTATAATTCTAAAACAATTTTTTAAATA
AACCAGCAGGTTGCTAAAAGAAGGCATTTTATCTAAAGTTATTTTAATAGGTGGTATAGCAGTAATTTTA
AATTTAAGAGTTGCTTTTACAGTTAACAATGGAATATGCCTTCTCTGCTATGTCTGAAAATAGAAGCTAT
TTATTATGAGCTTCTACAGGTATTTTTAAATAGAGCAAGCATGTTGAATTTAAAATATGAATAACCCCAC
CCAACAATTTTCAGTTTATTTTTTGCTTTGGTCGAACTTGGTGTGTGTTCATCACCCATCAGTTATTTGT
GAGGGTGTTTATTCTATATGAATATTGTTTCATGTTTGTATGGGAAAATTGTAGCTAAACATTTCATTGT
CCCCAGTCTGCAAAAGAAGCACAATTCTATTGCTTTGTCTTGCTTATAGTCATTAAATCATTACTTTTAC
ATATATTGCTGTTACTTCTGCTTTCTTTAAAAATATAGTAAAGGATGTTTTATGAAGTCACAAGATACAT
ATATTTTATTTTGACCTAAATTTGTACAGTCCCATTGTAAGTGTTGTTTCTAATTATAGATGTAAAATG
AAATTTCATTTGTAATTGGAAAAAATCCAATAAAAAGGATATTCATTTAGAAAATAGCTAAGATCTTTAA
TAAAAATTTGATATGAAAAGCACAATGTGCAGAAGTTATGGAAAACCTATAGAGGATTACAACAGGTAAA
CGTTAAAGAGAATACATTGCTGACTTATAGTGATGTGGCTAAGAAGTACATGCTTTGTTGTAAAATTGCT
TGAAAGCCCATTGAAAGATGTATCTGTTTATTTACAGTCTTTGAAGTAAAAGTTACCAATGTTTGCCAAT
AAAAA

CLEC11A mRNA nucleic acid sequence
                                                        SEQ ID NO: 18
GACCAACGGACCGGACAGAGACGAGGAGAGGAACAGGAAGAGAGAAGCTGGGAGAATCGGGAACCTGGGG
GCTAGTGACCTGCACACAGGGCAGGGCACTCGGCAGTTCCCAGAGGCCACCCCTCCCACCCCAGACATC
CAGACATCTGGAACTTTGGGTGCCAAGAGTCCAGCTTAATGCAGGCAGCCTGGCTTTTGGGGGCTTTGGT
GGTCCCCCAGCTCTTGGGCTTTGGCCATGGGGCTCGGGGAGCAGAGAGGGAGTGGGAGGGAGGCTGGGGA
GGTGCCCAGGAGGAGGAGCGGGAGAGGGAGGCCCTGATGCTGAAGCATCTGCAGGAAGCCCTAGGACTGC
CTGCTGGGAGGGGGATGAGAATCCTGCCGGAACTGTTGAGGGAAAAGAGGACTGGGAGATGGAGGAGGA
CCAGGGGGAGGAAGAGGAGGAGGAAGCAACGCCAACCCCATCCTCCGGCCCCAGCCCCTCTCCCACCCCT
GAGGACATCGTCACTTACATCCTGGGCCGCCTGGCCGGCCTGGACGCAGGCCTGCACCAGCTGCACGTCC
GTCTGCACGCGTTGGACACCCGCGTGGTCGAGCTGACCCAGGGGCTGCGGCAGCTGCGGAACGCGGCAGG
CGACACCCGCGATGCCGTGCAAGCCCTGCAGGAGGCGCAGGGTCGCGCCGAGCGCGAGCACGCCGCTTG
GAGGGCTGCCTGAAGGGGCTGCGCCTGGGCCACAAGTGCTTCCTGCTCTCGCGCGACTTCGAAGCTCAGG
CGGCGGCGCAGGCGCGGTGCACGGCGCGGGGCGGGAGCCTGGCGCAGCCGGCAGACCGCCAGCAGATGGA
GGCGCTCACTCGGTACCTGCGCGCGGCGCTCGCTCCCTACAACTGGCCCGTGTGGCTGGGCGTGCACGAT
CGGCGGCGCCGAGGGCCTCTACCTCTTCGAAAACGGCCAGCGCGTGCTGTCCTTCTCGCGCTGGCATCGCTCAC
CCCGCCCCGAGCTCGGCGCCCAGCCCAGCGCCTCGCCGCATCCGCTCAGCCCGGACCAGCCCAACGGTGG
CACGCTCGAGAACTGCGTGGCGCAGGCCTCTGACGACGGCTCCTGGTGGGACCACGACTGCCAGCGGCGT
CTCTACTACGTCTGCGAGTTCCCCTTCTAGCGGGGCCGGTACCCCGCCTCCCTGCCCATCCCACCACCCG
GCCTTTCCCTGCGCCGTGCCCACCCTCCTCCGGAATCTCCCTTCCCTTGGCCACGAATGGCAGCGTC
CTCCCCGACCCCCAGTCTGGGCGCTTCTGGGAGGGCTCTTGCGGTGCCGGCACTCCTCCTTGTTAGTGTC
TTTCCTTGAAGGGGCGGGCACCAGGCTAGGTCCGGTGCCAATAAATCCTTGTGGAATCTGACTTGAGGGG
CAGTGAAAAAAAAAAAAAAAA CSTA mRNA nucleic acid sequence
                                                        SEQ ID NO: 19
TGCTGTTTGTGGAAAATAAAGCATTCTATAGGCGGAGCTAGTGAACGCCTCTTTTAAAACACGAGTCTCC
ACACTTCCCTGTTCACTTTGGTTCCAGCATCCTGTCCAGCAAAGAAGCAATCAGCCAAAATGATACCTGG
AGGCTTATCTGAGGCCAAACCCGCCACTCCAGAAATCCAGGAGATTGTTGATAAGGTTAAACCACAGCTT
GAAGAAAAAACAAATGAGACTTACGGAAAATTGGAAGCTGTGCAGTATAAAACTCAAGTTGTTGCTGGAA
CAAATTACTACATTAAGGTACGAGCAGGTGATAATAAATATATGCACTTGAAAGTATTCAAAAGTCTTCC
CGGACAAAATGAGGACTTGGTACTTACTGGATACCAGGTTGACAAAAATAAGGATGACGAGCTGACGGGC
TTTTAGCAGCATGTACCCAAAGTGTTCTGATTCCTTCAACTGGCTACTGAGTCATGATCCTTGCTGATAA
ATATAACCATCAATAAAGAAGCATTCTTTTCCAAAGAATTATTTCTTCAATTATTTCTCATTTATTGTA
TTAAGCAGAAATTACCTTTTCTTTCTCAAAATCAGTGTTATTGCTTTAGAGTATAAACTCCATATAAATT
GATGGCAATTGGAAATCTTATAAAAACTAGTCAAGCCTAATGCAACTGGCTAAAGGATAGTACCACCCTC
ACCCCCACCATAGGCAGGCTGGATCGTGGACTATCAATTCACCAGCCTCCTTGTTCCCTGTGGCTGCTGA
TAACCCAACATTCCATCTCTACCCTCATACTTCAAAATTAAATCAAGTATTTTACAAAAAAAAAAAAAA ETV5 mRNA nucleic acid sequence
                                                        SEQ ID NO: 20
AGCCTGGTTGGCAGCTGCGGCGCAGAGTCCAGCCGCTGGTGCGCGGAGCGGTTCACCGTCTTCGGAGCGG
TTCGGCCCAGCCTTTCGCCCAGGCGCCCAGGCCCGCTGCGCGCGTGCGTGAGCGCGCCTGCGCCGCCGGG
GCCGCTGCAAGGGGAGGAGAGAGGCCGCCTCAGGAGGATCCCTTTTCCCCCAGAAATTACTCAATGCTGA
AACCTCTCAAAGTGGTATTAGAGACGCTGAAAGCACCATGGACGGGTTTATGATCAGCAAGTCCCTTTT
ATGGTCCCAGGGAAATCTCGATCTGAGGAATGCAGAGGGCGGCCTGTGATTGACAGAAGAGGAAGTTTT
TGGACACAGATCTGGCTCACGATTCTGAAGAGCTATTTCAGGATCTCAGTCAACTTCAAGAGGCTTGGTT
AGCTGAAGCACAAGTTCCTGATGATGAACAGTTTGTCCCAGATTTTCAGTCTGATAACCTGGTGCTTCAT
GCCCCACCTCCAACCAAGATCAAACGGGAGCTGCACAGCCCCTCCTCTGAGCTGTCGTCTTGTAGCCATG
AGCAGGCTCTTGGTGCTAACTATGGAGAAAAGTGCCTCTACAACTATTGTGCCTATGATAGGAAGCCTCC
CTCTGGGTTCAAGCCATTAACCCCTCCTACAACCCCCCTCTCACCCACCCATCAGAATCCCCTATTTCCC
CCACCCTCAGGCAACTCTGCCCACCTCAGGGCATGCCCCTGCAGCTGGCCCAGTTCAAGGTGTGGGCCCCG
```

SEQUENCE LISTING:

```
CCCCCGCCCCCATTCGCTTCCAGAGCCTGGACCACAGCAGCAAACATTTGCGGTCCCCCGACCACCACA
TCAGCCCCTGCAGATGCCAAAGATGATGCCTGAAAACCAGTATCCATCAGAACAGAGATTTCAGAGACAA
CTGTCTGAACCCTGCCACCCCTTCCCTCCTCAGCCAGGAGTTCCTGGAGATAATCGCCCCAGTTACCATC
GGCAAATGTCAGAACCTATTGTCCCTGCAGCTCCCCCGCCCCCTCAGGGATTCAAACAAGAATACCATGA
CCCACTCTATGAACATGGGGTCCCGGGCATGCCAGGGCCCCAGCACACGGGTTCCAGTCACCAATGGGA
ATCAAGCAGGAGCCTCGGGATTACTGCGTCGATTCAGAAGTGCCTAACTGCCAGTCATCCTACATGAGAG
GGGGTTATTTCTCCAGCAGCCATGAAGGTTTTTCATATGAAAAAGATCCCCGATTATACTTTGACGACAC
TTGTGTTGTGCCTGAGAGACTGGAAGGCAAAGTCAAACAGGAGCCTACCATGTATCGAGAGGGGCCCCCT
TACCAGAGGCGAGGTTCCCTTCAGCTGTGGCAGTTCCTGGTCACCCTTCTTGATGACCCAGCCAATGCCC
ACTTCATTGCCTGGACAGGTCGAGGCATGGAGTTCAAGCTGATAGAACCGGAAGAGGTTGCTCGGCGCTG
GGGCATCCAGAAGAACCGGCCAGCCATGAACTATGACAAGCTGAGCCGCTCTCTCCGCTATTACTATGAA
AAGGGCATCATGCAGAAGGTGGCTGGAGAGCGATACGTCTACAAATTTGTCTGTGACCCAGATGCCCTCT
TCTCCATGGCTTTCCCGGATAACCAGCGTCCGTTCCTGAAGGCAGAGTCCGAGTGCCACCTCAGCGAGGA
GGACACCCTGCCGCTGACCCACTTTGAAGACAGCCCCGCTTACCTCCTGGACATGGACCGCTGCAGCAGC
CTCCCCTATGCCGAAGGCTTTGCTTACTAAGTTTCTGAGTGGCGGAGTGGCCAAACCCTAGAGCTAGCAG
TTCCCATTCAGGCAAACAAGGGCAGTGGTTTTGTTTGTTTTTGGTTGTTCCTAAAGCTTGCCCTTTGA
GTATTATCTGGAGAACCCAAGCTGTCTCTGGATTGGCACCCTTAAAGACAGATACATTGGCTGGGGAGTG
GGAACAGGGAGGGGCAGAAAACCACCAAAAGGCCAGTGCCTCAACTCTTGATTCTGATGAGGTTTCTGGG
AAGAGATCAAAATGGAGTCTCCTTACCATGGACAATACATGCAAAGCAATATCTTGTTCAGGTTAGTACC
CGCAAAACGGGACATAGTATGTGACAATCTGCATCGATCATGGACTACTAAATGCCTTTACATAGAAGGG
CTCTGATTTGCACAATTTGTTGAAAAATCACAAACCCATAGAAAAGTAAGTAGGCTAAGTTGGGGAGGCT
CAAACCATTAAGGGTTAAAAATACATCTTAAACATTGGAAAGCTCTTCTAGCTGAATCTGAAATATTACC
CCTTGTCTAGAAAAGGGGGCAGTCAGAACAGCTGTTCCCACTCCGTGGTTCTCAAAATCATAAACCA
TGGCTACTCTTGGGAACCACCCGGCCATGTGGTCGCCAAGTAGAGCAAGCCCCCTTTCTCTTCCCAATCA
CGTGGCTGAGTGTGGATGACTTTTATTTTAGGAGAAGGGCGATTAACACTTTTGACAGTATTTTGTTTTG
CCCTGATTTGGGGGATTGTTTGTTTTGGTGGTTGTTTGGAAAAACAGTTTATAAACTGATTTTGTAG
TTTTGGTATTTAAAGCAAAAAACGAAAAACAAAAAACAAAACAAACCTTTTGGTAACTGTGCACTGTG
TCCTTTAGCCAGGGCCGTGCCAACTTATGAAGACACTGCAGTCTTGAGAGGGGCTTTGCTGAGGCTTCCCC
TTGGCCATGTGAAAGCCCGCCTTGTTGCCTGCTTTGTGCTTTCTGCACCAGACAACCTGATGGAACATTT
GCACCTGAGTTGTACATTTTTGAAGTGTGCAGGGCAGCCTGGACACAAGCTTAGATTCTCTATGTATAGT
TCCCCGTGTTCACTAACATGCCCTCTCTGGAAAGCATATGTATATAACATGTGTCATGTCCTTTGGAAAC
CTGGTCACCTGGTGAAAACCCTTGGGATTCTTCCCTGGGCATGACTGATGACAATTTCCATTTCATCAGT
TTGTTTTGTTTTCCTTTTTCTTTAAATCTTGGACTTTAAACCCTACCTGTGTGATTCAGTAGGGTTTGAG
ACTTACGTGTGATACTGACAGGTAAGCAACAGTGCTAGCATTCTAGATTCCTGCCTTTTTTTAAAAAGAA
ATTATTCTCATTGCTGTATTATATTGGAAAAGTTTTAAACAACCAAGCTAAAGCTATGTGAAAGTTGAGC
TCAAAGTAGAGGGAAAAGTTACTGGTGGTACCTTGCTGCCTGCTCTGCTGATGACAATTTCTGTGCTCCCCGT
GACACTTAGTACATTAAGAATGACTACACTGTTCCTCGTATGTGAAGGAGGCAGTGCTGACTCCGTGAGT
GTGAGACACGTGCTTTGAACTGCTTTTCTATTCATGGAGCACTCCATAGTCTCAAACTGTCCCCCTTATG
ACCAACAGCACATTTGTGAAGAGGTTCGCAGGGATAAGGGGTGCACTTTATAGCTATGGAAACATGAGAT
TCTCCTCTATTGGAAGCTAATTAGCCCACCACAAAGGTGGTAAACCTGTAGATTGGGCCTTAATTAGCATTGT
ACTCTAATCAAAGGACTCTTTCTAAACATATTTATAGCTTTCTTAACCTACACATAGTCTATACATAGA
TGCATATTTTACCCCCAGCTGGCTAGAGATTTATTTGTTGTAAATGCTGTATAGATTTGGTTTTCCTTTC
TTTACTTACCCTGGTTTGGATTTTTTTTTTTTTCTTTTGAATGGATTTATGCTGTCTTAGCAATATGAC
AATAATCCTCTGTAGCTTGAGCTACCCCTCCCCTGCTGTAACTTACGTGACCTGTGCTGTCACTGGGCAT
AGGACAGCGGCATCACGGTTGCATTCCCATTGGACTCATGCACCTCCCGGATGGTTTTTGTTTTTCGG
GGGTTCTTTGGGGTTTGTTTGTTTGCTTCTTTTCCAGAGTGTGGAAAGTCTACAGTGCAGAAAGGCTTGA
ACCTGCCAGCTGATTTGAAATACTTTCCCCTGCGCAGGGCCGTATGCATCCTGCCAAGCTGCGTTATATT
CTGTACTGTGTACAATAAAGAAGTTTGCTTTTCGTTTACCAA
```

HIVEP3 mRNA nucleic acid sequence

SEQ ID NO: 21
```
CTCACAACCAGCCGACTCTCCCATTATCCAGCTGCCTAGTTTGGTGCTTCAATGTACATGGCTATTCCGT
GTGCATATGTGTGTATACAAACACGCATGCATGCCTGGATGGACATACGTATGCACAGGTTATTTTTAA
GGACAATTCTTTCAATAAGGTCTTTACCCCTTACTTGAAACAGGTGTTCATGAAAAAATGCACAAAATC
CTGCCTGGCCGGAATAATTCATGAAGAAGGGGCTGGATCCGTGGGTCAGAGAACACAGGACCAGTTTGCC
ATCCCAAGGCCGAAGGCCTCCCTCCAACACAGTTCTCCAAGCTCTAGAAATCTCTGACACATCTTGACCA
TGAGACCACGGCTGGTTTTTGGCAGGATTCGAGGCACAAACCCAGCAGCCTCAACCTAGTTCATGGAGGA
GCCTCGCGGGGTCCTGGCCAAGCAAGCCCGCCCCTCTGGTGGGAAGAGCGGCGCCTAGGTGGAGGGTGGC
TGCCGTAGGAGTGGACATGAATGCTGGCTTTCAGAGAGAACAGCGTTTCAGTTTTGGTCATCGGAAGTGG
TGCCTTCAGCACAGAAGAAGAGCGTGATTTCTCCTCCAAGGCCGTTGATCTCCAACCCAGAACTAAAGGG
GAGAAGAGCCACCCCCAGCATCCAGCGTGGCATCTCTTGTGCCAGAGACTGGGCCATGGAC
ACAGATGTCTCCAACCTTCAACCGTTTGCATAGCACACGGGGACTCGTGGGGGCCACCTGCCACTGCCA
GCTGAAACAATACAATGGCAATACTGACATCCTTCATGACGTTTTCCCGACAGACATTCAGGCAGAAAGT
GCTGGTGCGTTTTCTGTCTGCAAAGTAGAGGGCCATGCCTCACCAATAGAATAGCGTGGGCCCTGATGAC
CTGCTCCGAGTCCACTCACAGCCAGTGACACTTGCAAAAAACTCCCAAAGCCGTCTTGGGTTTGGCTCCC
ACAGCTCTTGACCAATGTGGCCAAAGCTGGACACCTCCTTGGGACTAATTCATAAAATGCAGCC
CGCCCTGACTCTCCCTGAATAGCATCTGAAGTCTTTGTGAAGGTCATGGATCCTGAACAAAGTGTCAAGG
GCACCAAGAAGGCTGAGGGAAGTCCCCGGAAGCGGCTGACCAAAGGAGAGGCCATTCAGACCAGTGTTTC
TTCCAGCGTCCCATACCCAGGCAGCGGCACAGCTGCCACCCAAGAGAGCCCCGCCCAAGAGCTCTTAGCC
CCGCAGCCCTTCCCGGGCCCCTCATCAGTTCTTAGGGAAGGCTCTCAGGAGAAACGGGCCAGCAGCAGA
AGCCCCCAAAAGGCCCCCATCGAAGCATCCGTCCACATCTCACAGCTTCCGCAGCACCCTCTGACACG
AGCATTCATGTCGCCTGGCAAACCTGAGCATCTCCTGGAGGGGTCCACATGGCAACTGGTTGACCCCATG
AGACCTGGACCCTCTGGCTCCTTCGTGGCCCCTGGGCTCCATCCTCAGAGCCAGCTCCTTCCTTCCCACG
CTTCCATCATTCCCCCCGAGGACCTTCCTGGAGTCCCCAAAGTCTTCGTGCCTCGTCCTTCCCAGGTCTC
CTTGAAGCCCACAGAAGAGGCACACAAGAAGGAGAGGAAGCCCCAGAAGCCAGGCAAGTACATCTGCCAG
TACTGCAGCCGGCCCTGTGCCAAGCCCAGCGTGCTCCAGAAGCACATTGCTCACACACAGGTGAGAGGC
CCTACCCCTGCGGCCCCTGTGGCTTCTCCTTCAAGACCAAGAGTAATCTCTACAAGCACAGGAAGTCCCA
```

SEQUENCE LISTING:

```
TGCCCACCGCATCAAAGCAGGCCTGGCCTCAGGCATGGGTGGCGAGATGTACCCACATGGGCTGGAGATG
GAGCGGATCCCTGGGGAAGAGTTTGAGGAGCCCACTGAGGGAGAAAGCACAGATTCTGAAGAGGAGACTA
GTGCCACCTCTGGTCACCCTGCAGAGCTCTCCCCAAGACCCAAGCAGCCCCTTCTCTCCAGCGGGCTATA
CAGCTCTGGGAGCCACAGTTCCAGCCACGAACGCTGTTCCCTGTCCCAGTCCAGCACAGCCCAGTCACTC
GAAGACCCCCCTCCATTTGTGGAACCCTCATCTGAGCACCCCTGAGCCATAAACCTGAAGACACCCACA
CGATTAAGCAGAAGCTGGCCCTCCGCTTAAGCGAGAGGAAGAAGGTGATCGATGAGCAGGCGTTTCTGAG
CCCAGGCAGCAAAGGGAGTACTGAGTCTGGGTATTTCTCTCGCTCCGAGAGTGCAGAGCAGCAGGTCAGC
CCCCCAAACACCAACGCCAAGTCCTACGCTGAGATCATCTTTGGCAAGTGTGGGCGAATAGGACAGCGGA
CCGCCATGCTGACAGCCACCTCCACCCAGCCCCTCCTGCCCCTGTCCACCGAAGACAAGCCCAGCCTGGT
GCCTTTGTCTGTACCCCGGACGCAGGTGATCGAGCACATCACGAAGCTCATCACCATCAACGAGGCCGTG
GTGGACACCAGCGAGATCGACAGCGTGAAGCCAAGGCGGAGCTCACTGTCCAGGCGCAGCAGCATGGAGT
CCCCAAAATCCAGCCTCTACCGGGAGCCCTGTCATCCCACAGTGAGAAAACCAAGCCTGAACAATCACT
GCTGAGCCTCCAGCACCCGCCCAGTACCGCCCCCCTGTGCCTCTCCTGAGAAGCCACTCAATGCCTTCT
GCCGCCTGCACTATCAGCACCCCCCACCACCCCTTCCGAGGTAGCTACTCCTTCGATGACCATATCACCG
ACTCCGAAGCCCTGAGCCACAGCAGTCACGTGTTTACCTCCCACCCCCGGATGCTGAAGCGCCAGCCGGC
AATCGAATTACCTTTGGGAGGGGAATACAGTTCTGAGGAGCCTGGCCCAAGCAGCAAAGACACAGCCTCC
AAGCCCTCGGACGAAGTGGAACCCAAGGAAAGCGAGCTTACCAAAAAGACCAAGAAGGGTTTGAAAACAA
AAGGGGTGATCTACGAATGTAACATATGTGGTGCTCGGTACAAGAAAAGGGATAACTACGAAGCCCACAA
AAAATACTACTGCTCAGAGCTTCAGATCGCAAAGCCCATCTCTGCAGGCACCCACACATCTCCAGAAGCT
GAAAAGAGTCAGATTGAGCATGAGCCGTGGTCCCAAATGATGCATTACAAACTGGGAACCACCCTGGAAC
TCACTCCACTGAGGAAGAGGAGGAAAGAGAAGAGCCTTGGGGACGAGGAAGAGCCACCTGCCTTTGAGTC
CACAAAAAGTCAGTTTGGCAGCCCCGGGCCATCTGATGCTGCTCGGAACCTTCCCCTGGAGTCCACCAAG
TCACCAGCAGAACCAAGTAAATCAGTGCCCTCCTTGGAGGGACCCACGGGCTTCCAGCCAAGGACTCCCA
AGCCAGGGTCCGGTTCAGAATCAGGGAAGGAGGAGGAGAACAACGTCCAAAGAAATTTCTGTCATCCAGCA
CACCAGCTCCTTTGAGAAATCTGATTCTCTCGAGCAGCCGAGTGGCTTGGAAGGGGAAGACAAACCTCTG
GCCCAGTTCCCATCACCCCCACCTGCCCCACACGGACGCTCTGCTCACTCCCTGCAGCCTAAGTTGGTCC
GCCAGCCCAACATTCAGGTTCCTGAGATCCTAGTAACTGAGGAGCCTGACCGGCCGGACACAGAGCCAGA
GCCGCCCCCTAAGGAACCTGAGAAGACTGAGGAGTTCCAATGGCCCCAGCAGCCCAGACACTTGCCCAG
CTCCCAGCTGAGAAGCTGCCACCCAAAAAGAAGAGGTTGCGCCTGGCAGAGATGGCCCAATCATCAGGGG
AGTCCAGCTTCGAGTCCTCTGTGCCTCTGTCTCGCAGCCCGAGCCAGGAAAGCAATGTCTCTTTGAGTGG
GTCCAGCCGCTCAGCCTCGTTTGAGAGGGATGACCATGGGAAAGCCGAGGCCCCCAGTCCCTCATCTGAC
ATGCGCCCCAAACCCCTGGGCACCCACATGTTGACTGTCCCCAGCCACCACCCACATGCCCGAGAGATGC
GGAGGTCAGCCTCAGAGCAGAGCCCCAACGTTTCCCATTCTGCCCACATGACCGAGACACGCAGCAAATC
CTTTGACTATGGCAGCTTGTCCTTGACAGGCCCTTCTGCTCAGCCCCAGTGGCTCCACCAGCGCGGGTG
GCCCCGCCAGAGAGAAGAAAATGCTTCTTGGTGAGACAGGCCTCTCTGAGCAGGCCTCCAGAATCTGAGT
TGGAGGTTGCCCCCAAGGGAAGACAGGAGAGCGAAGAACCACAGCCCTCATCCAGTAAACCCTCTGCCAA
AAGCTCATTGTCCCAGATTTCCTCTGCGGCCACCTCACATGGTGGACCCCCGGGAGGCAAGGGCCCAGGG
CAGGACAGGCCCCCATTGGGGCCCACTGTGCCCTACACAGAAGCACTGCAAGTGTTCCACCACCCCGTTG
CCCAGACACCCCTGCATGAGAAGCCATACCTGCCCCCACCAGTCTCCCTTTTCTCCTTCCAGCATCTCGT
GCAGCATGAGCCAGGACAGTCTCCAGAATTCTTCTCCACCCAGGCCATGTCCAGCCTCCTGTCCTCACCA
TACTCCATGCCCCCACTTCCTCCCTCCTTATTTCAAGCCCCACCGCTTCCTCTCCAGCTACTGTTCTGC
ACCCAGGCCAACTCCATCTCCCCCAGCTCATGCCTCACCCAGCCAACATCCCCTTCAGGCAGCCCCCTTC
CTTCCTCCCCATGCCATACCCGACCTCCTCAGCACTGTCTTCTGGGTTTTTCCTGCCTCTGCAATCCCAG
TTTGCACTTCAGCTCCCTGGTGATGTGGAAAGCCATCTGCCCCAGATCAAAACCAGCCTGGCCCCACTGG
CAACAGGAAGTGCTGGCCTCTCCCCCAGCACAGAGTACAGCAGTGACATCCGGCTACCCCCTGTGGCTCC
CCCAGCCAGCTCCTCAGCACCTACATCAGCTCCTCCACTGGCCCTGCCTGCCTGTCCAGACACCATGGTG
TCCCTGGTTGTGCCTGTCCGTGTTCAGACCAATATGCCGTCCTATGGGAGCGCAATGTACACCACCCTTT
CCCAGATCTTGGTCACCCAGTCCCAAGGCAGCTCAGCAACTGTGGCACTTCCCAAGTTTGAGGAACCCCC
ATCAAAGGGGACGACTGTATGTGGTGCAGATGTGCATGAGGTTGGGCCGGCCCTTCTGGGTTAAGTGAA
GAGCAAAGCAGAGCTTTCCCAACTCCATACCTGAGAGTGCCTGTGACATTACCTGAAAGAAAAGGCACTT
CCCTGTCATCAGAGAGTATCTTGAGCCTGGAGGGGAGTTCATCAACAGCAGGGGAAGCAAACGTGTCCT
TTCACCAGCTGGCAGCCTTGAACTTACCATGGAAACCCAGCAGCAAAAAGAGTGAAGGAGGAGGAGGCT
TCCAAGGCAGATGAAAAACTTGAGCTGGTAAAACCATGCAGTGTGGTTCCTTACCAGCACCGAGGATGGGA
AGAGGCCAGAGAAATCCCACTTAGGCAACCAGGGCCAAGGCAGGAGGGAGCTAGAAATGCTGTCCAGCCT
GTCCTCAGATCCATCTGACACAAAGGAAATTCCTCCCCTCCCTCACCCTGCATTGTCCCATGGGACAGCC
CCAGGCTCAGAAGCTTTGAAGGAATATCCCCAGCCATCTGGCAAACCTCACCGAAGAGGGTTGACCCCAC
TGAGCGTGAAGAAAGAAGATTCCAAGGAACAACCTGATCTCCCCTCCTTGGCACCTCCGAGCTCTCTGCC
TCTGTCAGAAACGTCCTCCAGACCAGCCAAGTCACAAGAAGGTACGACTCAAAGAAGGTACTGCAGTTC
CCCAGCCTCCACACAACCACTAATGTCAGTTGGTGCTATTTAAACTACATTAAGCCAAATCACATCCAGC
ATGCAGATAGGAGGTCCTCTGTTTACGCTGGTTGGTGCATAAGTTTGTACAACCCCAACCTTCCGGGGGT
TTCCACTAAAGCTGCTTTGTCCCTCCTGAGGTCTAAGCAGAAAGTGAGCAAAGAGACATACACCATGGCC
ACAGCTCCGCATCCTGAGGCAGGAAGGCTTGTGCCATCCAGCTCCCGCAAGCCCCGCATGACAGAGGTTC
ACCTCCCTTCACTGGTTTCCCCGGAAGGCCAGAAAGATCTAGCTAGAGTGGAGAAGGAAGAAGAGAGGAG
AGGGGAGCCGGAGGAGGATGCTCCTGCCTCCCAGAGAGGGGAGCCGGCGAGGATCAAAATCTTCGAAGGA
GGGTACAAATCAAACGAAGAGTATGTATATGTGCGAGGCCGCGGCCGAGGGAAATATGTTTGTGAGGAGT
GTGGAATTCGCTGCAAGAAGCCCAGCATGCTGAAGAAACACATCCGCACCCACACTGACGTCCGGCCCTA
TGTGTGCAAGCACTGTCACTTTGCTTTTAAAACCAAAGGGAATCTGACTAAGCACATGAAGTCGAAGGCC
CACAGCAAAAGTGCCAAGAGACAGGGGTGCTGGAGGAGCTGGAAGCCGAAGAAGGAACCAGTGACGACC
TGTTCCAGGACTCGGAAGGACGAGAGGGTTCAGAGGCTGTGAGGAGCACCAGTTTTCGGACCTGGAGGA
CTCGGACTCAGACTCAGACCTGGACGAAGACGAGGATGAGGATGAGGAGGAGAGCCAGGATGAGCTGTCC
AGACCATCCTCAGAGGCGCCCCCGCCTGGCCCACCACATGCACTGCGGGCAGACTCCTCACCCATCCTGG
GCCCTCAGCCCCAGATGCCCCGCCTCTGGACGAGGAGGCTACACGAGGCAGCTCGGTCTCGGAAGCTGA
GCGCCTGACAGCCAGCAGCTGCTCCATGTCCAGCCAGAGCATGCCGGGCCTCCCCTGGCTGGGACCGGCC
CCTCTGGGCTCTGTGGAGAAAGACACAGGCTCAGCCTTGAGCTACAAGCCTGTCCCCAAGAAGACCGT
GGTCCCCAAGCAAAGAAGCAGGCAGCCGTCCACCACTAGCCCGCAAACACTCGCTAACCAAAAACGACTC
ATCTCCCCAGCGATGCTCCCCGGCCCGAGAACCACAGGCCTCAGCCCCAAGCCCACCTGGCCTGCACGTG
GACCCAGGAAGGGGCATGGGCGCTCTCCCTTGTGGGTCTCCAAGACTTCAGCTGTCTCCTCTCACCCTCT
```

SEQUENCE LISTING:

```
GCCCCCTGGGAAGAGAACTGGCCCCTCGAGCACATGTGCTCTCCAAACTCGAGGGTACCACCGACCCAGG
CCTCCCCAGATACTCGCCCACCAGGAGATGGTCTCCAGGTCAGGCCGAGTCACCACCACGGTCAGCGCCG
CCAGGGAAGTGGGCCTTGGCTGGGCCGGGCAGCCCCTCAGCGGGGGAGCATGGCCCAGGCTTGGGGGCTGG
ACCCACGGGTTCTCTTCCCGCCCGCGCCTCTACCTCACAAGCTCCTCAGCAGAAGCCCAGAGACCTGCGC
CTCCCCGTGGCAGAAGGCCGAGTCCCGAAGTCCCTCCTGCTCACCCGGCCCTGCTCATCCTCTCTCCTCC
CGACCCTTCTCCGCCCTCCATGACTTCCACGGCCACATCCTGGCCCGGACAGAGGAGAACATCTTCAGCC
ACCTGCCTCTGCACTCCCAGCACTTGACCCGTGCCCCATGTCCCTTGATTCCCATCGGTGGGATCCAGAT
GGTGCAGGCCCGGCCAGGAGCCCACCCCACCCTGCTGCCAGGGCCCACCGCAGCCTGGGTCAGTGGCTTC
TCCGGGGGTGGCAGCGACCTGACAGGGGCCCGGGAGGCCCAGGAGCGAGGCCGCTGGAGTCCCACTGAGA
GCTCGTCAGCCTCCGTGTCGCCTGTGGCTAAGGTCTCCAAATTCACACTCTCCTCAGAGCTGGAGGGCGG
GGACTACCCCAAGGAGAGGGAGAGGACCGGCGGAGGCCCGGGCAGGCCTCCTGACTGGACACCCCATGGG
ACCGGGGCACCTGCAGAGCCCACACCCACGCACAGCCCCTGCACCCCACCCGACACCTTGCCCCGGCCGC
CCCAGGGACGCCGGGCAGCGCAGTCCTGGAGCCCCGCTTGGAGTCCCCGCGTGCACCGACCAACCCCGA
GCCTTCTGCCACCCCGCCGCTGGACCGCAGCAGCTCTGTGGGCTGCCTGGCAGAGGCCTCTGCCCGCTTC
CCAGCCCGGACGAGGAACCTCTCCGGGGAACCCAGGACCAGGCAGGACTCCCCAAGCCCTCAGGAAGTG
GGGAGCCCAGGGCACATCCACATCAGCCTGAGGACAGGGTTCCCCCAACGCTTAGCCTCTCTCCAACTG
CTTCAGCATCTGGCTTCCAGTGTCCAGCAACAGACGTTTCCAGCCACTTTCCTCGAATCATCCCACTTCC
TCAGCCCCATCTGTCCCTCCGTCCAGGAGCTCTCACGGCCCCATCTGTTGTACCTTCCCATGTATGCAGT
TACCTGTGCCTTTTTCTACACCTTTTGTTGCTTAAAAAGAAACAAAACAAATCACATACATACATTTAAA
AAAAAAACAACAACCCACGAGGAGTCTGAGGCTGTGAATAGTTTATGGTTTTGGGGAAAGGCTGATGGTG
AAGCCTCCTGACCCTCCCCGCTGTGGTTGGCAGCCACCCACCCCAGAGGCTGGCAGAGGGAAAGGGGTAC
ACTGAGGGAGAAAGGAAAAGGAAACTTCAAACAATATAGAATTAAATGTAAAAGGAAGCACTCCTGTGTA
CAGATGCGATCAAGGTTCCTGTTTATTGCCACTTCACCCCCCTGCCCAGCTCGTAGCCACCCCTCTCTGC
CAGCAGAAAGGCCAGTGTCCCCAGGCAGAGGGGCACAAACACAGGCAGGTGACCCCCACCCAGGCCCCAG
CAGGCAGGCCCAGAAAACTAATCTTTTCCTTTTTTTTTTTTTTTTTTTTTGCAAGAAAATAAAATG
ATACTTTTCCTAGGATTTCAACACAAATAATAGGTGCAGGTAGAAGGAGGAGGGCTGGCTCCCAAGGG
CTCCTGGATACTCTGGTAGTCTGAGTCATGGGCCCATCCTGGCACTCCACAGGTGGGCAGGCCACCCCAC
CCACGCACCCCCACTCCAGACACCTCCCTTCTGCACCCCACCCTGGCCCCCTGGGCTGGGGAAGGAGCCC
TGACTGTCCGTCCCTGGCTCCCAAGCCCCTGACCGAGGCCTCACTCTCCTGTTGCCTCCTCTGTTCTAAA
ACCACCAAACCACCCACAAAGGCAGAAGTGGCAGGGCCCGAGCCCTAGCGGCCGTTCCTGAGACTGGGTT
TTGGGTTTTGTTTCATCTTGGTCCCTGGGGTACAAGGGAGCCTGTTCCCCTCATGGCTGGGTTTTTCCAG
TTCTCCACAGCAGAGGTTTGCGGGGAACTGTTTCAGGACCACTTTGCCACAGGACCGTTTCCCCCCGTCC
CTGCCCCTGTCTCCACTACCCCAAGGAAATACCCACAACTGTGGCTGGTGGATACGGCCTGGACCTGTTT
GCTGTCTTACACCTCTTTTTTAAAAGAGAGGATGGTGTTTGATACTTCACCCAGCCACCACAGATTC
TTTTGACCTAGAGGATTTTGAATTGTCCTAACTCGTTGGAATTCTCCAAAGCAATCAGTGTGAGCCAGT
GCCTCTTCCTTACCCACATCTCTACTTTCAAGAAGCTGCCCTGCATTTCCTGGGGCAAAACTCTACTTTG
TAAGAAAAATAATAGGACCAGAAATTTAAATCCCAAATTGAACTATGGAACTTGAACTCTAGCGTGTTCG
CCCCAACTGGGAGAGGTGAGCTTTTTCCCAGTGTTTCAGAACTGATTTTCTTTACTTTCTACAAGGGAGG
GCAGCACAGGGACTACGGTTGAGGCCCGTGAAGGCTGGGTTTGATGCCACCCTATACAGAGCAGGGACCT
CTCTGGCTAATCCCCAGTCCTCAGCCAGGCTGTGTGAATCAAGTGCCTGCCCCAGGGCTCTTGAGCTATT
GAAGCTGCTTGGGTACAGGACACAGTAGGTGGGGAGGGTTAAGACCCTTCTGTGAGTTCCCTGTGCGGGG
CTGTACTTGCCTCTTCCAATTCGTGGCCTTTCCCTGCTTGGTCCCTACTAGACAGACAAACCAGCCACAG
TCCAGCCTGCAGCCAGACCACCTTGTTCACTCATTCTCCTTTGCCTCAGAGCTAAGACAAAATGAGACA
GAAGGCAGGGCTCCCTGGGAGTCCACTGTGCTCCAGGGTTCTGGGGAATCAGGGTTAGCCAGCAGCTCCT
GGCTGCTTCCCTCAGAGACTAGGGCTCTCATCCTCCCCAAGAGAAGCAGCAAGCCCAGCCTGGACCACAC
TGTCCATATTGCTGGACAGTGGCCTGACAGAAAGTGACTCCTCCAAGTCCCAGGAGGCCAGGGCTTTTCT
CATCCTTGCCTTTCAGCCCTAACCCATGGGACTGCCCACGGATTGGAGACTTCAAGGGCTGAGGTCTGGG
AGCTGCATAAAGGGCATTGCTTCAGCCCAGGTTAGAAATCTGCCTGGGCAAGCTCTTCCTGCCCCAGACC
TACAAAGCAGCAGACCGGGGGCTCGGTGGACTAGCCCCTGACATTGGTGGGGGCCCCACACCACTCCA
CCCCACCCTGCCTTCCAGCTCTCCTGGGCATTTTTCTCCCTGTACTCAAACAGCCTACCCACCCAAGGTT
TCCTCCCTGGGCAGCCTAGCAATGAACAGTGCAGCCGGCAGGGCAGAGGCCGGCAGTCACCGGGCCCGT
CAGGCTCAGGCAGAGAAGCCACAGGGGCCAGGAGTCACTGGAGACTATTTCTAAATGATGGGGGTAAATG
CACAAATAGAATCTCACCAAAGGGCTGCCTCCACATTGATGCCGTGCCCAGAGGGACAGAACCAATGCCA
CCAGCCTGGGTATATGTCACTGGGCACAGCTCTAACCCCCTCCTCCGGACTCTAGTCCCGCTCCTCTGCG
CACAGAGCCCCCAGCCCACAGGTACACCTTCATGATTTGGAGAAAGACGCTCGCCCCATGCACGCCCTCC
TCTGGGCCTTCTGCCCTGCTCCCAGTCACTTCCAAGCTTCCTGTTTGCCTGTGATGTTATTGTGCCTGTT
GAGGGAAGCAGCAGAGGAGGCAGTGGCTGACTTGGCACAGATGCCTGCTACGTGCTCTGTTGAAATGCGC
GGGGTGGCCATTCCTCGGTACAGACTAGTCCTGGTCCTTGGGTGTGGGCAGTGGGGAGGAACCAACTGG
TCGAGGTTTCAGAGCCAAACCTTGCCTTTGGTTGGTGAGTCCTTGCCCCCCAGGCCTGCGCTCCACGATG
CCTTTCACCCTTGGCAATCTCAGGGCATCCTGGGTAGTAACCCACTCCTCTCTGCTCCCGCCCGCACC
TGTGGCTCTCACTCTGGGCTCAACCCCTGCAACCCTCCAGGAGCCCGACAGCAGCCAGCTGCCTGCACTG
TCGCCTCCGTAAGCTCCAACTTCCAGACCCAGAAGTCCCTCTGCTTCCCTCTGTTGGAAAAAGCCTAAAA
GAATTAGCTTCCAGATTCCTCTAGCCCCTGCTCCATTCCCACCCAGTCCTTCTGAAGAGGAATGAGCAAT
ACATCTGAGCTGGATTTCTCTCTAGTCCTTTCTCCAGACAAATCCTTCTTAAAGCAAAAGTCCTGGCTGA
GCACCTGTCCTTGGGGACCGATCTGCCGTGTGACCAGGGGAAGAAAGTTCCCGAAAGCCTGTTCCACCAA
TTCTGCTTCTGTGTTGTGAATCCAGTCTGCTTTCCATTAGAAAACCGCTTCGGCACTTATGGTCACTTTA
ATAAATCTAGTATGTAAAAAAGAAAGAAAAGAAAAGAAACAGAAAAAAAGAAACGTGCAGGCAAATGTAAA
ATACAATGCTCTCTGTAAGATAAATATTTGCCTTTTTTTCTAAAAGGTGTACGTATTCTGTATGTGAAAT
TGTCTGTAGAAAGTTTCTATGTTCTTAAATGGCAATACATTCCAAAAATTGTACTGTAGATATGTACAGC
AACCGCACTGGGATGGGGTAGTTTTGCCTGTAATTTTATTTAAACTCCAGTTTCCACACTTGCATCTTGC
AATGTTGGATTGGTATATATCAGTGCAAAAGAAAAAACAAAACAGAACAAACAAAAAAAAAAAAAAAA
ATCCACGCAGGTCTAAAGCACAGAGTCTGACGTACAAAAGGAAAAATGCTCAGTATTGATGTGTGTGACC
TTTGTTGTAAATTACATCTGTACTGTGAATGAGAAGTTTTTACAAGTATAATAATTGCCTTTATTACAGC
TCTGGCTGAGTGTTCAGCCTGAGGATATTTTTAAAAAAAAAAGAATTAGCATGTTGGAATAAATTTGAA
AATCCCAACATAAAAAAA
```

HOXA3 mRNA nucleic acid sequence

SEQUENCE LISTING:

SEQ ID NO: 22
```
TCTCACTAGCCTCAGAGCACTCTCAGAAGTTCAGAAACTAAGACCAGAAAAGAGAAGATTTTTAGACAGC
TCATGAAACGGTCTGCGCGGGGCGGCCATTGGCGGCGGAGTGTCACGTGACCGCGGGGGCGTGCCAATGT
GCGCCCTCACGGGTGTCAAACCCCTGTCAGAGTGTGCGATCAAGATCGTGAAACAACGCGATGCAAAAAG
CGACCTACTACGACAGCTCGGCGATCTACGGTGGCTACCCCTACCAGGCAGCCAACGGGTTCGCTTATAA
TGCCAATCAGCAGCCGTACCCGGCGTCCGCCGCTTTGGGCGCCGACGGCGAGTACCACCGACCCGCCTGC
TCCCTCCAGTCTCCCTCCAGCGCCGGGGGCCACCCCAAGGCACACGAACTGAGTGAGGCGTGCCTGCGCA
CCCTGAGCGCCCCACCTAGCCAGCCTCCAAGCCTGGGAGAGCCGCCCCTGCACCCGCCGCCGCCCCAGGC
CGCGCCCCTGCCCCACAGCCGCCTCAGCCCGCACCTCAGCCCCCTGCACCTACCCCTGCCGCGCCCCCG
CCTCCCTCTTCTGCCTCCCCTCCTCAGAATGCCAGCAACAACCCTACCCCTGCCAACGCGGCCAAGAGCC
CCCTGCTCAACTCACCCACAGTGGCCAAACAAATCTTCCCCTGGATGAAAGAGTCTCGACAAAACACAAA
GCAGAAAACCAGCAGCTCCAGCTCAGGCGAAAGCTGCGCTGGCGACAAGAGCCCGCCGGGGCAGGCTTCG
TCCAAGCGCGCGCGCACGGCCTACACGAGCGCGCAGCTGGTGGAGCTGGAGAAAGAGTTCCACTTCAACC
GCTACCTGTGCCGGCCGCGCCGGGTGGAGATGGCCAATCTGCTGAACCTCACTGAGCGCCAGATCAAGAT
CTGGTTCCAGAATCGCCGCATGAAGTACAAAAAGGATCAGAAAGGGCAGGGCATGCTAACGTCATCGGGG
GGCCAGTCTCCAAGTCGCAGCCCCGTGCCCCCCGGAGCCGGTGGCTATCTGAACTCTATGCATTCGCTGG
TCAACAGCGTCCCGTATGAGCCCCAGTCGCCCCCGCCCTTCTCCAAGCCCCCCCAGGGTACCTACGGGCT
GCCCCCCGCCTCCTACCCTGCGTCCCTGCCCAGCTGCGCACCCCCGCCACCCCCACAGAAGCGCTACACG
GCGGCAGGGCGGGCGCAGGGGGCACCCCCGACTATGACCCGCACGCTCATGGCCTGCAGGGCAACGGCA
GCTATGGGACCCCACACATACAGGGAAGCCCCGTCTTCGTGGGGGGCAGCTATGTGGAGCCCATGAGCAA
CTCCGGGCCAGCCCTCTTTGGTCTAACTCACCTCCCCCACGCTGCCTCGGGCGCCATGGACTATGGGGGT
GCCGGGCCGCTGGGCAGCGGCCACCACCACGGGCCGGGGCCTGGGGAGCCGCACCCCACCTACACGGACC
TTACCGGCCACCATCCTTCTCAGGGAAGAATTCAGGAAGCACCCAAGCTCACCCACCTGTGATAGTGGGC
TTGGGGCTACGCGCCAGGAGAGTCTCCCCCCACCCACCTTTTTTCTTTGGTTGCTTTTTTTTTTTTTTT
TTTTAGGTTCTTCCTGCCCTTTCCTTCCTTCCTTTTCTCTCTTCTCCGCCCCGCACTCCGTTTCCCGGTT
TCCCCCCTCGTTGGTAAGGCGTTTTTATAGTTTATGTGACGTAGCAATCTTGGTTGCTGGAATGGCTGTA
TCATAGCGATATTTATCTCTTCCTGCTCCTCGATAGGCCACTGGCCCTGCACCCTTTACCTTCTCCACTC
TTTGATCAGAAACAGGGTATATGAACAAATTTTCTAGTCGAGTTTTCAATGTGAATTTGTTCTTACATTA
TGGCTCCCGAGGGGAAGCGATTACTTTTTTTAATTTTAAATTTTTTTTTAATTGCACTTCTTGTAAAGA
GTGAGAAAAAAATCAAAGGCGCTTTGAAACAGGGGCTCTCTGTGCAAGGATGACTAAGTGTACGTCTTT
CCGTGTGTGTATGCTGGTGAACAGTCAGATTTATTTATATTTTTTGCAAGCATTGAATAATCTAAGTTT
TAAATATTATTTATCCCCATCCGTTCGTATTTATATTAAAGAATTCTGTACCCTGATGGTTCAGAAGGGT
TCTTGGGCCTTTTGTTCAATTGTGTATTGGCGTACTTAGAATTTTTTTTATTTGAAAGAGAAATATAATT
CCTTTAAACGGTAACGATACAATAAAACCAGAGAAGATCCAGTCTTTTGAAAACAGTGATTTAGGTTTGTA
ACATCCGGCAAAACTGAAAAAAAAAATCTGTAAACGCGAAAAATACTAGATTTGTTTTGAGAGTTCTTCA
TTCCTTGCTGCTCACATTCTGAGAAACAAAAAGAAATAAAGTTTTTATTCTGAATAATATCCGTGTTAAG
AAGGGGTTCTTTGGCCGAAGACGTGGGTCTGCGTGGAATTCAGGCCGAGGCGAGCCGGCAGAGCAGGCCG
GACGCAGCAGCCCTCTGGCTCCAGCATGGGGCCTGGCCAGGCTATTCGCCTGGAAGCTCGGCGAATTCTC
AGGATGGCGGCTGGGGCTCCAGGCGGCTGCGGCAGCTCTGGTAACGCCGTGCGGCGGGCCAGCTGGGCTG
CCCGGTTCCCAGCTGCTGCGGAGGCAGGCTGAGGGCGCAGGGGCTGCCGAGTGCTGTGCACGGAAGAAAC
AAAGACATCCCGGCCCAAGGCGCAGCGGGAGCGCACAGGTGCCCCGCGGCCCAGCCGGGGGATAACGCAG
GGCGGTCTTCTGCTCCATGCTCTTCCTCGGGTCAAAGCGGACCAACTAACGCCTAAACCTCGGTATTAGC
CAGCCGCGCAGAGGATGCCGAGCACTTTCCGGGAGCAATCGGACTCCTGGTCTCCTCCGGGGATGCTTCG
CGGTCTGTTATCGCGTCAGGAGGAAAGAATTGCTCCAAAAATCTGCACGCGGAGCGAAACAGTTTGAAAG
GGACTGAGGCTCACCCAGGTCTCCAGCAAACGGAGGACTGAACCTTGTTGCGACGTGAGTCACCCTGAGCCAGCCCT
TCCCTGGACTGCCGGAATCCCAGCATTAGCTTCCTGCTGAATGTAGTATTTGGCATTCTCTGAATTTATT
TCCTCTCCTTCCCCCACCCAGCTTTCTTTTTATGGCCCCAGGGGGAGGGGGAGAGAGCAAGGAGATCGGT
ATCTTTGTAATAAAACTGCAATTTTATAAATTTTTCA
```

HOXA5 mRNA nucleic acid sequence

SEQ ID NO: 23
```
GGGTGCTATAGACGCACAAACGACCGCGAGCCACAAATCAAGCACACATATCAAAAAACAAATGAGCTCT
TATTTTGTAAACTCATTTTGCGGTCGCTATCCAAATGGCCCGGACTACCAGTTGCATAATTATGGAGATC
ATAGTTCCGTGAGCGAGCAATTCAGGGACTCGGCGAGCATGCACTCGGCAGGTACGGCTACGGCTACAA
TGGCATGGATCTCAGCGTCGGCCGCTCGGGCTCCGGCCACTTTGGCTCCGGAGAGCGCGCCCGCAGCTAC
GCTGCCAGCGCCAGCGCGGCGCCCGCCGAGCCCAGGTACAGCCAGCCGGCCACGTCCACGCACTCTCCTC
AGCCCGATCCGCTGCCCTGCTCCGCCGTGGCCCCCTCGCCCGGCAGCGACAGCCATCCACGGCGGGAAAA
CTCCCTAAGCAACTCCAGCGGCGCCTCGGCCGACGCCGGCAGCACCCACATCAGCAGCAGAGAGGGGTT
GGCACGGCGTCCGGAGCCGAGGAGGACGCCCCTGCCAGCAGCGAGCAGGCGAGTGCGCAGAGCGAGCCGA
GCCCGGCGCCGCCCGCCCAACCCCAGATCTACCCCTGGATGCGCAAGCTGCACATAAGTCATGACAACAT
AGGCGGCCCGGAAGGCAAAAGGGCCCGGACGGCCTACACGCGCTACCAGACCCTGGAGCTGGAGAAGGAG
TTCCACTTCAACCGTTACCTGACCCGCAGAAGGAGGATTGAAATAGCACATGCTCTTTGCCTCTCCGAGA
GACAAATTAAAATCTGGTTCCAAAACCGGAGAATGAAGTGGAAAAAGATAATAAGCTGAAAAGCATGAG
CATGGCCGCGGCAGGAGGGCCTTCCGTCCCTGAGTATCTGAGCGTTTAAAGTACTGAGCAGTATTAGCG
GATCCCGCGTAGTGTCAGTACTAAGGTGACTTTCTGAAACTCCCTTGTGTTCCTTCTGTGAAGAAGCCCT
GTTCTCGTTGCCCTAATTCATCTTTTAATCATGAGCCTGTTTATTGCCATTATAGCGCCTGTATAAGTAG
ATCTGCTTTCTGTTCATCTCTTTGTCCTGAATGGCTTTGTCTTGAAAAAAAATAGATGTTTTAACTTATT
TATATGAAGCAAGCTGTGTTACTTGAAGTAACTATAACAAAAAAAGAAAAGAGAAAAAAAAACACACAAA
AAGTCCCCCTTCAATCTCGTTTAGTGCCAATGTTGTGTGTTGCACTCAAGTTGTTTAACTGTGCATGTGC
GTGGAAGTGTTCCTGTCTCAATAGCTCCAAGCTGTTAAAGATATTTTATTCAAACTACCTATATTCCTT
GTGTAATTAATGCTGTTGTAGAGGTGACTTGATGAGACACAACTTGTTCGACGTGTAGTGACTAGTGACT
CTGTGATGAAAACTGTGACTCCAAGCGGTGTGTCCCTGCGTGCCTTTATAGGACCCTTTGCACGAACTCT
GGAAGTGGCTCTTATAAGCGCAGCTTCAGTGATGTATGTTTTTGTGAACAAAGTTACAAATATTGTCCAA
GTCTGGCTGTTTAAGCAAACTGTGATCAGCTTTTTTTTTTTTTTTTTTTTTTGTATTTGTTTTAAG
GAAAAAATACTGACTGGAACAAAAAATAAACTTTCTATTGTAAGTTC
```

HOXB3 mRNA nucleic acid sequence

SEQUENCE LISTING:

SEQ ID NO: 24
CTGGGTAGGGCAGGGGGAACCGACAGGCCGGTGTCCCCAGCCGCAAAAGAGCTGCTGAACTGTCCGTTTA
AATGCTGCTGGGAGACTCGTAAAAAAATCATCGTGGACCTGGAGGATGAGAGGGGCGAGCTTTATTTCGG
TCGGATTGCGGTGTGGTGGTTTAGCTGCAAGGGGATGCCGCAGCCCCAGTTGAGGGGGAAAATAGTTCTT
AAAAAGCATATGCCCCCCTAAGGAATGTCTCTAAAGAACCAAATCAAAGCTGCTCTTTGGAAGGTATGAA
TAGAATTTAAAAAAAAAAGATTTCTATGGAGCTTAAAGTTCACAGCCATTCTGTGTAGACAAGAGCTAAG
AAAAATGTGAGAATTATACAGAAAACCATTAATCACTTCTTTTCTTTAAATACGTATCCTCTCTCCTTTG
TTATTATTCAACAGCAAATCTCCTTGGACCGGCTGTTGGGGAAAAAAGTGTTAGCCGTCTCTCCCGGAT
CTGCAAGGGGAAAAAATTTGGAACCATAAAGTTGAAAACTTTTTTCTCTCAGTTTGGAAGAAGCCCTTC
GTCATGAATGGGATCTGCAGAGTTCGGGCGAGAGGAGGCGAGAGGCGCAAAGGAGGGGAGATTTGTCGCC
TGCCGCTCGCTCTGGGGCTCGATGTGAATATATATTATGTCTGCCTGTTCTCCCCTCGTCGGTGGCTAAG
GTCAGCCGCTTGGAACAGACCCCGGAGGAGGGGGCAGAGAGGGGAGGTGGGGGGGGGGGTCGGGCGTG
TCACGTGACCCCCAGGGTTGCCAATGTCCGTCCTGAGGGTATCAGGCCTTTCCAAGTTGCCACCCACTG
CCCAGGCCTCACCCAGCGATGCAGAAAGCCACCTACTACGACAACGCCGCGGCTGCTCTCTTCGGAGGCT
ATTCCTCGTACCCTGGCAGCAATGGCTTCGGCTTCGATGTCCCCCCCCAACCCCCATTTCAGGCCGCCAC
GCACCTGGAGGGCGACTACCAGCGCTCAGCTTGCTCGCTGCAGTCCCTGGGCAACGCTGCCCCACATGCC
AAGAGCAAGGAGCTCAACGGCAGCTGCATGAGGCCGGGTCTGGCCCCCGAGCCCTGTCGGCCCCGCCTG
GCTCACCCCGCCCAGTGCCGCACCTACCAGTGCCACTAGCAACAGCAGTAATGGGGGCGGGCCCAGCAA
AAGTGGTCCCCCAAAGTGCGGTCCCGGCACCAACTCCACCCTCACCAAACAGATATTCCCCTGGATGAAA
GAGTCGAGGCAAACGTCCAAGCTGAAAAACAACTCCCCCGGCCACGCAGAGGCTGTGGTGGCGGCGGCG
GTGGCGGCGGCGGCGGAGGCAGTGGTGGCAGCGGGGCGGTGGCGGCGGCGGCGGGGGAGGGGACAAGAG
CCCCCCGGGGTCGGCGGCGTCCAAGCGGGCGCGGACGGCGTACACGAGCGCGCAGCTGGTGGAGCTGGAG
AAGGAGTTCCATTTTAACCGCTACCTGTGCCGGCCTCGCCGTGTAGAGATGGCCAACCTGCTGAACCTCA
GCGAGCGGCAGATCAAGATCTGGTTCCAGAACCGGCGCATGAAGTACAAGAAGGACCAGAAGGCCAAGGG
ATTGGCTCGTCGTCGGGGGGCCCATCTCCAGCCGGCAGCCCCCGCAGCCCATGCAGTCCACGGCCGGC
TTCATGAACGCCTTACACTCCATGACCCCCAGCTACGAGAGCCCGTCCCACCCGCCTTCGGTAAAGCCC
ACCAGAATGCCTACGCGCTGCCCTCCAACTACCAGCCCCTCTCAAAGGCTGCGGCGCCCCGCAGAAGTA
CCCTCCGACCCCGGCGCCCGAGTATGAGCCGCACGTCCTCCAAGCCAACGGGGGCGCCTACGGGACGCCC
ACCATGCAGGGCAGTCCGGTGTACGTGGGCGGGGCGGCTACGCGGATCCGCTGCCGCCCCCTGCCGGCC
CCTCCCTCTATGGCCTCAACCACCTTTCCCATCACCCTTCCGGGAACCTGGACTACAACGGGGCGCCCCC
TATGGCGCCCAGCCAGCACCACGGACCCTGCGAACCCCACCCCACCTACACAGACCTCTCCTCTCACCAC
GCGCCTCCTCCTCAGGGTAGAATCAAGAAGCGCCCAAATTAACACTCCTGTGATGGGAAAGGGCGAACG
AGGATTAGGGGATGGGGAGGAAGAGAGAGACTGTGGAGCTCTGGGGGGCAACCTGGAGGTCTGAAAAGAG
GAGCCAGAGAAGGTGGTACCCAGGCTTCCTGGTCAGAACCGGCCTGGAGCTCCTTCCCTTCCCCCTGGCC
TGAGAGGTTGCTTTTAAGTCTTCCACCCCTTGTTCCATCTGCCTGCCAACCCATCGGAAAGGAATCCACA
TCATATTGGAGATGACCCCATCAACCCCAGGGCTCCAGCACTACCAAGTTGGAATTCCACGCCCGGGAGT
GGGGTAGAGGAAGACGAGACAGGACGAGGCAGAAAAGCACATTTTAAAAACCAGACAAGATGGCTAGGCC
ATCACCAACCAACGGACTTACCTTACATCTTTGTAGGTAATTCCCCCAAATCTTGATTTTTTTTTTTCC
TCAATTATCCTTTAAAAAATAAGAAAACACATTTCAAACCCAAAAGGCACAAAACACGTTCCCTTCCAAC
TTTCCCAAAACCTCAAATTTGTTCCCATTTGAGGTTTATTGAGGTACACTTCTAGCCCCCGGTTTTTCTG
CTCTAGAACATTCATATCTATACATCCCACCCCCATCAATTACAGTTTTTAGAGGGCTCAGGGATGGTGA
GAGATCCTGAAAGAGCTGCCTATATTATAAATTATATACATTTTTTTTAAGGAAAAGTGTGGAGGCTAG
GGCAGGCAGGTTGTTAGGACTGAAGGTTTGCCCATTCTGCTGCCTCCATCTCAGCTCCAGCTCCATCCCC
CTCTCCACAGAAAGCAGTTGGTGACACGAGGTTCTATACTTTTCTTCTGTTGCTCTCTTGACTTAACGTG
AAAACAGGGTATATTTGAACAAACTGTCCCAGGCAGGGGCTGGCAGGGACATTGTGTGCCTTGCTCAGCCT
CCTGACAGGACACTTTTGTTGCACTTAGAATTTACATTTTAATGGATGTAAAAACAACTGTGAGAGATGT
CTGGGCCTGCAGAAGTCCAGCATTGCTCAAAAAAGCGTGTGTTCTAGTGAACATTTTCATATATATTTAT
TGGTTATAGCCTGTTAAAATATTTTCTTTTTTGTATTATTTATCCCCTACATTATGTATTTATATGAGG
GAAAAAAGGAAAAAATTGTACTTTTTTAGTATTTACCTGTTACAAAAGACATTGTGTTTCCTTGATGT
AAAACCAGCTATTTTAGTTACTATTGTACTCTAGAAAAGAGCTGTAGATTTATGTTAAACTCGTACTTAC
GAACAATTGTAATTAGTTCTAAAAGGCATGAACTCAGCTCCTAATCGTCACTGTATAGTCCTGAATTTGT
AGAACTAGAGTTAATTCCCTCTTGGAACTTTCTTTGTTCTTCAGTAGTTACTTTTTTCCTTACCTAAAAG
GGTTGTCTGTCAAACAATTCTTGAATAAACTTTCTGTTATCAATTTTAAAAAAAAAA

HOXB5 mRNA nucleic acid sequence

SEQ ID NO: 25
GTGAAGCACAGGGTTATAACGACCACGATCCACAAATCAAGCCCTCCAAAATCACCCAAATGAGCTCGTA
CTTTGTAAACTCCTTCTCGGGGCGTTATCCAAATGGCCCGGACTATCAGTTGCTAAATTATGGCAGTGGC
AGCTCTCTGAGCGGCTCTTACAGGGATCCCGCTGCCATGCACACCGGCTCTTACGGCTACAATTACAATG
GGATGGACCTCAGCGTCAACCGCTCCTCGGCCTCCTCCAGCCACTTTGGGCGGTGGGCGAGAGCTCGCG
CGCCTTCCCCGCGCCCGCCCAGGAGCCCCGCTTCAGGCAAGCGGCTTCGAGCTGCTCCCTGCTCCGCCC
GAGTCCCTGCCCTGCACCAACGGCGACAGCCACGGCGCCAAGCCCTCTGCTTCGTCCCCCTCCGACCAGG
CGACCTCAGCCAGCTCCAGCGCCAATTTCACCGAAATAGACGAGGCCAGCGCGTCCTCGGAGCCTGAGGA
AGCGGCAAGCCAGCTAAGCAGCCCCAGCCTAGCTCGGGCGCAGCCAGAGCCCATGGCCACCTCCACAGCC
GCGCCCGAGGGGCAGACTCCGCAAATATTCCCCTGGATGAGGAAGCTTCACATCAGCCATGATATGACCG
GGCCGGACGGGAAAAGGGCCCGGACGCGTATACCCGCTACCAGACCCTGGAGCTGGAAAAGGAGTTCCA
CTTCAACCGCTACCTGACCCGGCGACGGCGCATCGAGATCGCCCACGCACTCTGCCTGTCCGAGCGCCAG
ATCAAGATCTGGTTCCAGAACCGGCGCATGAAGTGGAAGAAGGACAACAAATTGAAAGTATGAGCCTGG
CTACAGCTGGCAGCGCCTTCCAGCCCTGAGCCCGCCCAGAGGAGCCCAGCGGCCCAAGAGCCCGTGCCAC
CCCCAGCCCTGGCCCCTCCAATCCTCCCCGCTCTGCCGCCGCCCGCTGGGGACCGGTTCCCACAAGCCTG
CCTCGCCTTGTGTTACGATATTCGTTTGGTCTTAGGTCTTCCTGGCCTCCCTCTCCTGGACTGGTT
ATCTTGTTATTATTGTTAATAATAATTATTATTATTTTCCTTCCATGCTCCCAACTCCCTTCTGCTT
GTCCCAAATCCGCCAGTGTTTCTGAATGTTTGTGTCTGTGGTTGCAGTCTTTCCCCAGGAAAAAAAAA
AAAGAAATTCGCATGTTTAATGTGAACTCTCCCCTCCCCATCTGTGTTCAACTTATTTATAAAAGATG
ATCGCTGTATTTTGAGTTTCAGCTGGAAACTTCTGTAAGGGGCAGCAGTTGAGGTGGGGTAGTGCCGCAG
TGGGGTCAAGCTGAGCTGGCTTCGGAGATGGAGTCCCTTTTCATTCTCCTCCTCCTCCTCCTCACTCCC
TAGGCCCAAGTCTCCTAGGGGCTTGGTCCTAGGGTGGGAAGGGGCTAGGGAGGACCAAAGGGATGGTATT

GAGAAGAGAGAAAGAAGATAGTGAGATTTAAGTTCCTGCTGCCTGGGTAGGCCCCACAAGGCCTGGTCTG
GGAGTATACGGAAACAAAAATGATCCTCAGTGCAAAATGTCTTGTGTATTTCTCTGTGAATCCATGGGTC
TGGCTAGAGGGCCCAAAGCTTGTAAATATGGGGATAGTCTGGGTCAGACCCATCTCTCCCTTACCCATCT
TGCTTCCAAGACCATTTGTAGTGAGCGAGTGGATGCTGTGCTACGTGTGAAATCTGTCTTTGCGGGGCCT
GTCTCAGTGATTCGCTTTTGGTATTTGTTTGTAGCTTTCCTGGAAGTCAAATAAATGTTTCCCCCACTCC
AAAAAAAAAA

HOXB6 mRNA nucleic acid sequence

SEQ ID NO: 26

CACCACACCTAGGTCGGAGCACTGTCGTCCTTCAGGGCTCCAGCCTCTTGATATTTTGTACTTCAGTAT
CAGCTCGATAGAGCAAAAGAGAGAGGACGAGAGAGGGGGTCAGAGAAGGGGAAGCAACGGCTCTCACG
TTGGGACAATATTATCTGGAAGCTGAAGAAGAAACTGAATACTCCTTCCTTCCTCCCCACCCATTCCTTT
AAATCCGGAGGGGGAAAAAATCCCAAGGTCTGCAAAGGCGCGGCGCTCGGACTATAAAACACAACAAATC
ATAAACCCGGCGGAGCAGCAGCGGCCGCGCGCGCCTCCCCTCCCAATGAGTTCCTATTTCGTGAACTCCA
CCTTCCCCGTCACTCTGGCCAGCGGGCAGGAGTCCTTCCTGGGCCAGCTACCGCTCGTATTCGTCGGGCTA
TGCGGACCCGCTGAGACATTACCCCGCGCCCTACGGGCCAGGGCCGGGCCAGGACAAGGGCTTTGCCACT
TCCTCCTATTACCCGCCGGCGGGCGGTGGCTACGGCCGAGCGGCGCCCTGCGACTACGGGCGGCGCCGG
CCTTCTACCGCGAGAAAGAGTCGGCCTGCGCACTCTCCGGCGCCGACGAGCAGCCCCGTTCCACCCCGA
GCCGCGAAGTCGGACTGCGCGCAGGACAAGAGCGTGTTCGGCGAGACAGAAGAGCAGAAGTGCTCCACT
CCGGTCTACCCGTGGATGCAGCGGATGAATTCGTGCAACAGTTCCTCCTTTGGGCCCAGCGGCCGGCGAG
GCCGCCAGACATACACACGTTACCAGACGCTGGAGCTGGAGAAGGAGTTTCACTACAATCGCTACCTGAC
GCGGCGGCGCGCATCGAGATCGCGCACGCCCTGTGCCTGACGGAGAGGCAGATCAAGATATGGTTCCAG
AACCGACGCATGAAGTGGAAAAAGGAGAGCAAACTGCTCAGCGCGTCTCAGCTCAGTGCCGAGGAGGAGG
AAGAAAAACAGGCCGAGTGAAGGTGCTGGAAAGGGAGGGAGGGACGCGAGGGGAAAGGCCTGTGGGGAGCC
GAGGGCGTCAGAGAGACCCGGGAAGGAAGGCTCTCGGGTGGGGGAGCCAGGAGACCTGCTCTCCGGCGCA
GACAGGCGGGGCCCAGCGCTCTCCTGGACGCCCCGCCCGCACAGCTCCCGGCGGGTGCTCTGAGGCCTC
ACTACTCGAGCCCACCCAGCATCCCGCGCGCCCTTCCTTCCCGAGGAACTCGCCTCAGCCTGATCAGGCT
TCCTGGTGAGAACTGAGGAGCGGACTCACTTGATGTTTCTGGAAGCAGAGCAAAATGCTCTTGTCCCTG
TCGCGTCTCATTTTGTCCATGTCCCCCGTGCACGGTTCAATGGTAGATTCGCTGTCCCCTCAGCGGGGGC
CTTGAAGACTCCCTGATCCCAGACCTGTCGTCTCTCCCACCCCCTCCCAAAGCCACTGGAAGGAGCACA
TACTACCTAGAAGTAAGAAGAGGAGCCTCAGAAGAAAACAAAGTTCTATTTTATTAATTTTCTATGTGTT
GTGTTTGTAGTCTTGTCTTAGCTCTGGACGTGAAATACTTCGATGATGATGATGATGATGATGATGATGAAA
TAATAATAATAACAACAACAACAACAATAATAAAGATGTGAAAACTCGACGCTCGGTCACCTCAAAA
AAAAAA

ITGA6 mRNA nucleic acid sequence

SEQ ID NO: 27

AACGGGCTCATTCAGCGGTCGCGAGCTGCCCGCGAGGGGAGCGGCCGGACGGAGAGCGCGACCCGTCCC
GGGGGTGGGGCCGGGCGCAGCGGCGAGAGGAGGCGAAGGTGGCTGCGGTAGCAGCAGCGCGGCAGCCTCG
GACCCAGCCCGAGCGCAGGGCGGCCGCTGCAGGTCCCCGCTCCCCTCCCCGTCGTCCGCCCATGGCCG
CCGCCGGGCAGCTGTGCTTGCTCTACCTGTCGGCGGGGCTCCTGTCCCGGCTCGGCGCAGCCTTCAACTT
GGACACTCGGGAGGACAACGTGATCCGGAAATATGGAGACCCCGGGAGCCTCTTCGGCTTCTCGCTGGCC
ATGCACTGGCAACTGCAGCCCGAGGACAAGCGGCTGTTGCTCGTGGGGGCCCCGCGGGCAGAAGCGCTTC
CACTGCAGAGAGCCAACAGAACGGGAGGGCTGTACAGCTGCGACATCACCGCCCGGGGGCCATGCACGCG
GATCGAGTTTGATAACGATGCTGACCCCACGTCAGAAAGCCAAGGAAGATCAGTGGATGGGGTCACCGTC
CAGAGCCAAGGTCCAGGGGCAAGGTCGTGACATGTGCTCACCGATATGAAAAAGGCAGCATGTTAATA
CGAAGCAGGAATCCCGAGACATCTTTGGCGGTGTTATGTCCTGAGTCAGAATCTCAGGATTGAAGACGA
TATGGATGGGGGAGATTGGAGCTTTTGTGATGGGCGATTGAGAGGCCATGAGAAATTTGGCTCTTGCCAG
CAAGGTGTAGCAGCTACTTTTACTAAAGACTTTCATTACATTGTATTTGGAGCCCCGGGTCTTTATACT
GGAAAGGGATTGTTCGTGTAGAGCAAAAGAATAACACTTTTTTTGACATGAACATCTTTGAAGATGGGCC
TTATGAAGTTGGTGGAGAGACTGAGCATGATGAAAGTCTCGTTCCTGTTCCTGCTAACAGTTACTTAGGT
TTTTCTTTGGACTCAGGGAAAGGTATTGTTTCTAAAGATGAGATCACTTTTGTATCTGGTGCTCCCAGAG
CCAATCACAGTGGAGCCGTGGTTTTGCTGAAGAGAGACATGAAGTCTGCACATCTCCTCCCTGAGCACAT
ATTCGATGGAGAAGGTCTGGCCTCTTCATTTGGCTATGATGTGGCGGTGGTGGACCTCAACAAGGATGGG
TGGCAAGATATAGTTATTGGAGCCCCACAGTATTTTGATAGAGATGGAGAAGTTGGAGGTGCAGTGTATG
TCTACATGAACCAGCAAGGCAGATGGAATAATGTGAAGCCAATTCGTCTTAATGGAACCAAAGATTCTAT
GTTTGGCATTGCAGTAAAAAATATTGGAGATATTAATCAAGATGGCTACCAGATATTGCAGTTGGAGCT
CCGTATGATGACTTGGGAAAGGTTTTTATCTATCATGGATCTGCAAATGGAATAAATACCAAACCAACAC
AGGTTCTCAAGGGTATATCACCTTATTTTGGATATTCAATTGCTGGAAACATGGACCTTGATCGAAATTC
CTACCCTGATGTTGCTGTTGGTTCCCTCTCAGATTCAGTAACTATTTTCAGATCCCGGCCTGTGATTAAT
ATTCAGAAAACCATCACAGTAACTCCTAACAGAATTGACCTCCGCCAGAAAACAGCGTGTGGGGCGCTA
GTGGGATATGCCTCCAGGTTAAATCCTGTTTTGAATATACTGCTAACCCCGCTGGTTATAATCCTTCAAT
ATCAATTGTGGGCACACTTGAAGCTGAAAAGAAAGAAGAAAATCTGGGCTATCCTCAAGAGTTCAGTTT
CGAAACCAAGGTTCTGAGCCCAAATATACTCAAGAACTAACTCTGAAGAGGCAGAAACAGAAAGTGTGCA
TGGAGGAAACCCTGTGGCTACAGGATAATATCAGAGATAAACTGCGTCCCATTCCCATAACTGCCTCAGT
GGAGATCCAAGAGCCAAGCTCTCGTAGGCGAGTGAATTCCAAGTTCTTCCAATTCTGAATTCA
GATGAACCCAAGACAGCTCATATTGATGTTCACTTCTTAAAAGAGGGATGTGGAGACGACAATGTATGTA
ACAGCAACCTTAAACTAGAATATAAATTTTGCACCCGAGAAGGAAATCAAGACAAATTTTCTTATTTACC
AATTCAAAAGGTGTACCAGAACTAGTTCTAAAAGATCAGAAGGATATTGCTTTAGAAATAACAGTGACA
AACAGCCCTTCCAACCCAAGGAATCCCACAAAAGATGGCGATGACGCCCATGAGGCTAAACTGATTGCAA
CGTTTCCAGACACTTTAACTATTCTGCATATAGAGAACTGAGGGCTTTCCCTGAGAAACAGTTGAGTTG
TGTTGCCAACCAGAATGGCTCGCAAGCTGACTGTGAGCTCGGAAATCCTTTTAAAAGAAATTCAAATGTC
ACTTTTTATTTGGTTTTAAGTACAACTGAAGTCACCTTTGACACCCCAGATCTGGATATTAATCTGAAGT
TAGAAACAACAAGCAATCAAGATAATTTGGCTCCAATTACAGCTAAAGCAAAAGTGGTTATTGAACTGCT
TTTATCGGTCTCGGGAGTTGCTAAACCTTCCCAGGTGTATTTTGGAGGTACAGTTGTGGCGAGCAAGCT
ATGAAATCTGAAGATGAAGTGGGAAGTTTAATAGAGTATGAATTCAGGGTAATAAACTTAGGTAAACCTC
TTACAAACCTCGGCACAGCAACCTTGAACATTCAGTGGCCAAAAGAAATTAGCAATGGGAAATGGTTGCT

```
TTATTTGGTGAAAGTAGAATCCAAAGGATTGGAAAAGGTAACTTGTGAGCCACAAAAGGAGATAAACTCC
CTGAACCTAACGGAGTCTCACAACTCAAGAAAGAAACGGGAAATTACTGAAAAACAGATAGATGATAACA
GAAAATTTTCTTTATTTGCTGAAAGAAAATACCAGACTCTTAACTGTAGCGTGAACGTGAACTGTGTGAA
CATCAGATGCCCGCTGCGGGGCTGGACAGCAAGGCGTCTCTTATTTTGCGCTCGAGGTTATGGAACAGC
ACATTTCTAGAGGAATATTCCAAACTGAACTACTTGGACATTCTCATGCGAGCCTTCATTGATGTGACTG
CTGCTGCCGAAAATATCAGGCTGCCAAATGCAGGCACTCAGGTTCGAGTGACTGTGTTTCCCTCAAAGAC
TGTAGCTCAGTATTCGGGAGTACCTTGGTGGATCATCCTAGTGGCTATTCTCGCTGGGATCTTGATGCTT
GCTTTATTAGTGTTTATACTATGGAAGTGTGGATTCTTTAAACGCTCTAGGTACGATGACAGTGTTCCCC
GATACCATGCTGTAAGGATCCGGAAAGAAGAGCGAGAGATCAAAGATGAAAGTATATTGATAACCTTGA
AAAAAAACAGTGGATCACAAAGTGGAACGAAAATGAAAGCTACTCATAGCGGGGGCCTAAAAAAAAAAG
CTTCACAGTACCCAAACTGCTTTTTCCAACTCAGAAATTCAATTTGGATTTAAAAGCCTGCTCAATCCCT
GAGGACTGATTTCAGAGTGACTACACACAGTACGAACCTACAGTTTTAACTGTGGATATTGTTACGTAGC
CTAAGGCTCCTGTTTTGCACAGCCAAATTTAAAACTGTTGGAATGGATTTTTCTTTAACTGCCGTAATTT
AACTTTCTGGGTTGCCTTTATTTTGGCGTGGCTGACTTACATCATGTGTTGGGGAAGGGCCTGCCCAGT
TGCACTCAGGTGACATCCTCCAGATAGTGTAGCTGAGGAGGCACCTACACTCACCTGCACTAACAGAGTG
GCCGTCCTAACCTCGGGCCTGCTGCGCAGACGTCCATCACGTTAGCTGTCCCACATCACAAGACTATGCC
ATTGGGGTAGTTGTGTTTCAACGGAAAGTGCTGTCTTAAACTAAATGTGCAATAGAAGGTGATGTTGCCA
TCCTACCGTCTTTTCCTGTTTCCTAGCTGTGTGAATACCTGCTCACGTCAAATGCATACAAGTTTCATTC
TCCCTTTCACTAAAACACACAGGTGCAACAGACTTGAATGCTAGTTATACTTATTTGTATATGGTATTTA
TTTTTTCTTTTCTTTACAAACCATTTTGTTATTGACTAACAGGCCAAAGAGTCTCCAGTTTACCCTTCAG
GTTGGTTTAATCAATCAGAATTAGAGCATGGGAGGTCATCACTTTGACCTAAATTATTTACTGCAAAAAG
AAAATCTTTATAAATGTACCAGAGAGAGTTGTTTTAATAACTTATCTATAAACTATAACCTCTCCTTCAT
GACAGCCTCCACCCCACAACCCAAAAGGTTTAAGAAATAGAATTATAACTGTAAAGATGTTTATTTCAGG
CATTGGATATTTTTACTTTAGAAGCCTGCATAATGTTTCTGGATTTCATACTGTAACATTCAGGAATTC
TTGGAGAAAATGGGTTTATTCACTGAACTCTAGTGCGGTTTACTCACTGCTGCAAATACTGTATATTCAG
GACTTGAAAGAAATGGTGAATGCCTATGGTGGATCCAAACTGATCCAGTATAAGACTACTGAATCTGCTA
CCAAAACAGTTAATCAGTGAGTCGATGTTCTATTTTTGTTTTGTTTCCTCCCCTATCTGTATTCCCAAA
AATTACTTTGGGGCTAATTTAACAAGAACTTTAAATTGTGTTTTAATTGTAAAAATGGCAGGGGGTGAAA
TTATTACTCTATACATTCAACAGAGACTGAATAGATATGAAAGCTGATTTTTTTAATTACCATGCTTCA
CAATGTTAAGTTATATGGGGAGCAACAGCAAACAGGTGCTAATTTGTTTTGGATATAGTATAAGCAGTGT
CTGTGTTTTGAAAGAATAGAACACAGTTTGTAGTGCCACTGTTGTTTTGGGGGGGCTTTTTCTTTTCGG
AAATCTTAAACCTTAAGATACTAAGGACGTTGTTTTGGTTGTACTTTGGAATTCTTAGTCACAAAATATA
TTTTGTTTACAAAAATTTCTGTAAAACAGGTTATAACAGTGTTTAAAGTCTCAGTTTCTTGCTTGGGGAA
CTTGTGTCCCTAATGTGTTTAGATTGCTAGATTGCTAAGGAGCTGATACTTTGACAGTGTTTTTAGACCT
GTGTTACTAAAAAAAAGATGAATGTCCTGAAAAGGGTGTTGGGAGGGTGGTTCAACAAAGAAACAAAGAT
GTTATGTGTTTAGATTTATGGTTGTTAAAAATGTCATCTCAAGTCAAGTCACTGGTCTGTTTGCATTTG
ATACATTTTTGTACTAACTAGCATTGTAAAATTATTTCATGATTAGAAATTACCTGTGGATATTTGTATA
AAAGTGTGAAATAAATTTTTATAAAAGTGTTCATTGTTTCGTAACACAGCATTGTATATGTGAAGCAAA
CTCTAAAATTATAAATGACAACCTGAATTATCTATTTCATCAAACCAAAGTTCAGTGTTTTATTTTGG
TGTCTCATGTAATCTCAGATCAGCCAAAGATACTAGTGCCAAAGCAATGGGATTCGGGGTTTTTTCTGT
TTTCGCTCTATGTAGGTGATCCTCAAGTCTTTCATTTTCCTTCTTTATGATTAAAAGAAACCTACAGGTA
TTTAACAACC

KIT mRNA nucleic acid sequence
                                                          SEQ ID NO: 28
TCTGGGGGCTCGGCTTTGCCGCGCTCGCTGCACTTGGGCGAGAGCTGGAACGTGGACCAGAGCTCGGATC
CCATCGCAGCTACCGCGATGAGAGGCGCTCGCGGCGCCTGGGATTTTCTCTGCGTTCTGCTCCTACTGCT
TCGCGTCCAGACAGGCTCTTCTCAACCATCTGTGAGTCCAGGGGAACCGTCTCCACCATCCATCCATCCA
GGGAAATCAGACTTAATAGTCGCGTGGGCGACGAGATTGAGTGTTATGCCATGCTATCCGGGCTTTGTCA
AATGGACTTTTGAGATCCTGGATGAAACGAATGAGAATAAGCAGAATGAATGGATCACGGAAAAGGCAGA
AGCCACCAACACCGGCAAATACACGTGCACCAACAAAACACGGCTTAAGCAATTCCATTTATGTGTTTGTT
AGAGATCCTGCCAAGCTTTTCCTTGTTGACCGCTCCTTGTATGGGAAAGAAGACAACGACACGCTGGTCC
GCTGTCCTCTCACAGACCCAGAAGTGACCAATTATTCCCTCAAGGGGTGCCAGGGGAAGCCTCTTCCCAA
GGACTTGAGGTTTATTCCTGACCCCAAGGCGGGCATCATGATCAAAAGTGTGAAACGCGCCTACCATCGG
CTCTGTCTGCATTGTTCTGTGGACCAGGAGGGCAAGTCAGTGCTGTCGGAAAAATTCATCCTGAAAGTGA
GGCCAGCCTTCAAAGCTGTGCCTGTTGTGTCTGTGTCCAAAGCAAGCTATCTTCTTAGGGAAGGGGAAGA
ATTCACAGTGACGTGCACAATAAAAGATGTGTCAGTTCTGTGTACTCAACGTGGGAAAAGAGAAACCAGT
CAGACTAAACTACAGGAGAAATATAATAGCTGGCATCACGGTGACTTCAATTATGAACGTCAGGCAACGT
TGACTATCAGTTCAGCGAGAGTTAATGATTCTGGAGTGTTCATGTGTTATGCCAATAATACTTTTGGATC
AGCAAATGTCACAACAACCTTGGAAGTAGTAGATAAAGGATTCATTAATATCTTCCCCATGATAAACACT
ACAGTATTTGTAAACGATGGAGAAAATGTAGATTTGATTGTTGAATATGAAGCATTCCCCAAACCTGAAC
ACCAGCAGTGGATCTATATGAACAGAACCTTCACTGATAAATGGGAAGATTATCCCAAGTCTGAGAATGA
AAGTAATATCAGATACGTAAGTGAACTTCATCTAACGAGATTAAAAGGCACCGAAGGAGGCACTTACACA
TTCCTAGTGTCCAATTCTGACGTCAATGCTGCCATAGCATTTAATGTTTATGTGAATACAAAACCAGAAA
TCCTGACTTACGACAGGCTCGTGAATGGCATGCTCCAATGTGTGGCAGCAGGATTCCCAGAGCCCACAAT
AGATTGGTATTTTTGTCCAGGAACTGAGCAGAGATGCTCTGCTTCTGTACTGCCAGTGGATGTGCAGACA
CTAAACTCATCTGGGCCACCGTTTGGAAAGCTAGTGGTTCAGAGTTCTATAGATTCTAGTGCATTCAAGC
ACAATGGCACGGTTGAATGTAAGGCTTACAACGATGTGGGCAAGACTTCTGCCTATTTTAACTTTGCATT
TAAAGGTAACAACAAAGAGCAAATCCATCCCCACACCCTGTTCACTCCTTTGCTGATTGGTTTCGTAATC
GTAGCTGGCATGATGTGCATTATTGTGATGATTCTGACCTACAAATATTTACAGAAACCCATGTATGAAG
TACAGTGGAAGGTTGTTGAGGAGATAAATGGAAACAATTATGTTTACATAGACCCAACACAACTTCCTTA
TGATCACAAATGGGAGTTTCCCAGAAACAGGCTGAGTTTTGGGAAAACCCTGGGTGCTGGAGCTTTCGGG
AAGGTTGTTGAGGCAACTGCTTATGGCTTAATTAAGTCAGATGCGGCCATGACTGTCGCTGTAAAGATGC
TCAAGCCGAGTGCCCATTTGACAGAACGGGAAGCCCTCATGTCTGAACTCAAAGTCCTGAGTTACCTTGG
TAATCACATGAATATTGTGAATCTACTTGGAGCCTGCACCATTGGAGGGCCCACCCTGGTCATTACAGAA
TATTGTTGCTATGGTGATCTTTTGAATTTTTTGAGAAGAAAACGTGATTCATTTATTTGTTCAAAGCAGG
AAGATCATGCAGAAGCTGCACTTTATAAGAATCTTCTGCATTCAAAGGAGTCTTCCTGCAGCGATAGTAC
```

SEQUENCE LISTING:

```
TAATGAGTACATGGACATGAAACCTGGAGTTTCTTATGTTGTCCCAACCAAGGCCGACAAAAGGAGATCT
GTGAGAATAGGCTCATACATAGAAAGAGATGTGACTCCCGCCATCATGGAGGATGACGAGTTGGCCCTAG
ACTTAGAAGACTTGCTGAGCTTTTCTTACCAGGTGGCAAAGGGCATGGCTTTCCTCGCCTCCAAGAATTG
TATTCACAGAGACTTGGCAGCCAGAAATATCCTCCTTACTCATGGTCGGATCACAAAGATTTGTGATTTT
GGTCTAGCCAGAGACATCAAGAATGATTCTAATTATGTGGTTAAAGGAAACGCTCGACTACCTGTGAAGT
GGATGGCACCTGAAAGCATTTTCAACTGTGTATACACGTTTGAAAGTGACGTCTGGTCCTATGGGATTTT
TCTTTGGGAGCTGTTCTCTTTAGGAAGCAGCCCCTATCCTGGAATGCCGGTCGATTCTAAGTTCTACAAG
ATGATCAAGGAAGGCTTCCGGATGCTCAGCCCTGAACACGCACCTGCTGAAATGTATGACATAATGAAGA
CTTGCTGGGATGCAGATCCCCTAAAAAGACCAACATTCAAGCAAATTGTTCAGCTAATTGAGAAGCAGAT
TTCAGAGAGCACCAATCATATTTACTCCAACTTAGCAAACTGCAGCCCCAACCGACAGAAGCCCGTGGTA
GACCATTCTGTGCGGATCAATTCTGTCGGCAGCACCGCTTCCTCCTCCCAGCCTCTGCTTGTGCACGACG
ATGTCTGAGCAGAATCAGTGTTTGGGTCACCCCTCCAGGAATGATCTCTTCTTTTGGCTTCCATGATGGT
TATTTTCTTTCTTTCAACTTGCATCCAACTCCAGGATAGTGGGCACCCCACTGCAATCCTGTCTTTCTG
AGCACACTTTAGTGGCCGATGATTTTTGTCATCAGCCACCATCCTATTGCAAAGGTTCCAACTGTATATA
TTCCCAATAGCAACGTAGCTTCTACCATGAACAGAAAACATTCTGATTTGGAAAAAGAGAGGGAGGTATG
GACTGGGGGCCAGAGTCCTTTCCAAGGCTTCTCCAATTCTGCCCAAAAATATGGTTGATAGTTTACCTGA
ATAAATGGTAGTAATCACAGTTGGCCTTCAGAACCATCCATAGTAGTATGATGATACAAGATTAGAAGCT
GAAAACCTAAGTCCTTTATGTGGAAAACAGAACATCATTAGAACAAAGGACAGAGTATGAACACCTGGGC
TTAAGAAATCTAGTATTTCATGCTGGGAATGAGACATAGGCCATGAAAAAATGATCCCCAAGTGTGAAC
AAAAGATGCTCTTCTGTGGACCACTGCATGAGCTTTTATACTACCGACCTGGTTTTTAAATAGAGTTTGC
TATTAGAGCATTGAATTGGAGAGAAGGCCTCCCTAGCCAGCACTTGTATATACGCATCTATAAATTGTCC
GTGTTCATACATTTGAGGGGAAAACACCATAAGGTTTCGTTTCTGTATACAACCCTGGCATTATGTCCAC
TGTGTATAGAAGTAGATTAAGAGCCATATAAGTTTGAAGGAAACAGTTAATACCATTTTTTAAGGAAACA
ATATAACCACAAAGCACAGTTTGAACAAAATCTCCTCTTTTAGTCTGATGAACTTATTCTGTAGATTCTGT
GGAACAAGCCTATCAGCTTCAGAATGGCATTGTACTCAATGGATTTGATGCTGTTTGACAAAGTTACTGA
TTCACTGCATGGCTCCCACAGGAGTGGGAAAACACTGCCATCTTAGTTTGGATTCTTATGTAGCAGGAAA
TAAAGTATAGGTTTAGCCTCCTTCGCAGGCATGTCCTGGACACCGGGCCAGTATCTATATATGTGTATGT
ACGTTTGTATGTGTAGACAAATATTTGGAGGGGTATTTTTGCCCTGAGTCCAAGAGGGTCCTTTAGTA
CCTGAAAAGTAACTTGGCTTTCATTATTAGTACTGCTCTTGTTTCTTTTCACATAGCTGTCTAGAGTAGC
TTACCAGAAGCTTCCATAGTGGTGCAGAGGAAGTGGAAGGCATCAGTCCCTATGTATTTGCAGTTCACCT
GCACTTAAGGCACTCTGTTATTTAGACTCATCTTACTGTACCTGTTCCTTAGACCTTCCATAATGCTACT
GTCTCACTGAAACATTTAAATTTTACCCTTTAGACTGTAGCCTGGATATTATTCTTGATGTTTACCTCTT
TAAAAACAAAACAAAACAAAACAAAAAACTCCCCTTCCTCACTGCCCAATATAAAAGGCAAATGTGTACA
TGGCAGAGTTTGTGTGTTGTCTTGAAAGATTCAGGTATGTTGCCTTTATGGTTTCCCCCTTCTACATTTC
TTAGACTACATTTAGAGAACTGTGGCCGTTATCTGGAAGTAACCATTTGCACTGGAGTTCTATGCTCTCG
CACCTTTCCAAAGTTAACAGATTTTGGGGTTGTGTTGTCACCCAAGAGATTGTTGTTTGCCATACTTTGT
CTGAAAAATTCCTTTGTGTTTCTATTGACTTCAATGATAGTAAGAAAAGTGGTTGTTAGTTATAGATGTC
TAGGTACTTCAGGGGCACTTCATTGAGAGTTTTGTCTTGGATATTCTTGAAAGTTTATATTTTTATAATT
TTTTCTTACATCAGATGTTTCTTTGCAGTGGCTTAATGTTTGAAATTATTTTGTGGCTTTTTTTGTAAAT
ATTGAAATGTAGCAATAATGTCTTTTGAATATTCCCAAGCCCATGAGTCCTTGAAAATATTTTTTATATA
TACAGTAACTTTATGTGTAAATACATAAGCGGCGTAAGTTTAAAGGATGTTGGTGTTCCACGTGTTTTAT
TCCTGTATGTTGTCCAATTGTTGACAGTTCTGAAGAATTCTAATAAAATGTACATATATAAATCAAAAAA
AAAAAAAAA
```

MEIS1 mRNA nucleic acid sequence

SEQ ID NO: 29

```
ATTTGAGGTGTTCTGACCAGAAGAAGACAGAGCGGATGATCATTCATTCACCACGTTGACAACCTCGCCT
GTGATTGACAGCTGGAGTGGCAGAAAGCCATGAGATTTGGTAGTGGGTCTGAGGGGCGCTCTTTTTTTT
CCTTTTCTTTCTTTCTTTTTTTTTTTTTAAACTGATTTTTGGGGGAGGAGAAGATCTGCTTTTTTTT
GCCCCCGCTGCTGTCTTGGAAACGGAGCGCTTTTATGCTCAGTGACTCGGGCGCTTTGCTTCAGGTCCCG
TAGACCGAAGATCTGGGACCAGTAGCTCACGTTGCTGGAGACGTTAAGGGATTTTTCGTCGTGCTTTTTT
TTTTTTTTTTTTTTTTCCGGGGGAGTTTGAATATTTGTTTCTTTTCACACTGGCCTTAAAGAGGATAT
ATTAGAAGTTGAAGTAGGAAGGGAGCCAGAGAGGCCGATGGCGCAAAGGTACGGACGATCTACCCCATTAC
GGGGGCATGGATGGAGTAGGCATCCCCTCCACGATGTATGGGGACCCGCATGCAGCCAGGTCCATGCAGC
CGGTCCACCACCTGAACCACGGGCCTCCTCTGCACTCGCATCAGTACCCGCACACAGCTCATACCAACGC
CATGGCCCCCAGCATGGGCTCCTCTGTCAATGACGCTTTAAAGAGAGATAAAGATGCCATTTATGGACAC
CCCCTCTTCCCTCTCTTAGCACTGATTTTTGAGAAATGTGAATTAGCTACTTTGTACCCCCGCGAGCCGG
GGGTGGCGGGCGGGACGTCTGCTCGTCAGAGTCATTCAATGAAGATATAGCCGTGTTCGCCAAACAGAT
TCGCGCAGAAAACCTCTATTTTCTTCTAATCCAGAACTGGATAACTTGATGATTCAAGCCATACAAGTA
TTAAGGTTTCATCTATTGGAATTAGAGAAGGTACACGAATTATGTGACAATTTCTGCCACCGGTATATTA
GCTGTTTGAAAGGGAAAATGCCTATCGATTTGGTGATAGACGATAGGAAGGAGGATCAAATTCAGACAG
TGAAGATATAACAAGATCAGCAAATCTAACTGACCAGCCCTCTTGGAACAGAGATCATGATGACACGGCA
TCTACTCGTTCAGGAGGAACCCCAGGCCCTTCCAGCGGTGGCCACACGTCACACAGTGGGACAACAGCA
GTGAGCAAGGTGATGGCTTGGACAACAGTGTAGCTTCCCCCAGCACAGGTGACGATGATGACCCTGATAA
GGACAAAAAGCGTCACAAAAAGCGTGGCATCTTTCCCAAAGTAGCCACAAATATCATGAGGGCGTGGCTG
TTCCAGCATCTAACACACCCTTACCCTTCTGAAGAACAGAAAAAGCAGTTGGCACAGGACACGGGACTCA
CCATCCTTCAAGTGAACAATTGGTTTATTAATGCCCGGAGAAGAATAGTGCAGCCCATGATAGACCAGTC
CAACCGAGCAGTAAGTCAAGGAACACCTTATAATCCTGATGGACAGCCCATGGGAGGTTTCGTAATGGAC
GGTCAGCAACATATGGGAATTAGAGCACCAGGACCTATGAGTGGAATGGGCATGAATATGGGCATGGAGG
GGCAGTGGCACTACATGTAACCTTCATCTAGTTAACCAATCGCAAAGCAAGGGGGAAGGCTGCAAAGTAT
GCCAGGGGAGTATGTAGCCCGGGGTGGTCCAATGGGTGTGAGTATGGGACAGCCCAAGTTATACCCAACCC
CAGATGCCCCCCATCCTGCTCAGCTGCGTCATGGGCCCCCATGCATACGTACATTCCTGGACACCCTC
ACCACCCAACAGTGATGATGCATGGAGGACCGCCCCACCCTGGAATGCCAATGTCAGCATCAAGCCCCAC
AGTTCTTAATCAGGAGACCCAACAATGAGTGGACAAGTCATGGACATTCATGCTCAGTAGCTTAAGGGA
ATATGCATTGTCTGCAATGGTGACTGATTTCAAATCATGTTTTTTCTGCAATGACTGTGGAGTTCCATTC
TTGGCATCTACTCTGGACCAAGGAGCATCCCTAATTCTTCATAGGGACCTTTAAAAAGCAGGAAATACCA
ACTGAAGTCAATTTGGGGGACATGCTAAATAACTATATAAGACATTAAGAGAACAAAGAGTGAAATATTG
```

```
TAAATGCTATTATACTGTTATCCATATTACGTTGTTTCTTATAGATTTTTTAAAAAAAATGTGAAATTTT
TCCACACTATGTGTGTTGTTTCCATAGCTCTTCACTTCCTCCAGAAGCCTCCTTACATTAAAAAGCCTTA
CAGTTATCCTGCAAGGGACAGGAAGGTCTGATTTGCAGGATTTTTAGAGCATTAAAATAACTATCAGGCA
GAAGAATCTTTCTTCTCGCCTAGGATTTCAGCCATGCGCGCGCTCTCTCTCTTTCTCTCTCTTTTCCTCT
CTCTCCCTCTTTCTAGCCTGGGGCTTGAATTTGCATGTCTAATTCATTTACTCACCATATTTGAATTGGC
CTGAACAGATGTAAATCGGGAAGGATGGGAAAAACTGCAGTCATCAACAATGATTAATCAGCTGTTGCAG
GCAGTGTCTTAAGGAGACTGGTAGGAGGAGGCATGGAAACCAAAAGGCCGTGTGTTTAGAGAGCCTAATTG
TCACATCAAGCATCATTGTCCCCATGCAACAACCACCACCTTATACATCACTTCCTGTTTTAAGCAGCTC
TAAAACATAGACTGAAGATTTATTTTTAATATGTTGACTTTATTTCTGAGCAAAGCATCGGTCATGTGTG
TATTTTTTCATAGTCCCACCTTGGAGCATTTATGTAGACATTGTAAATAAATTTTGTGCAAAAAGGACTG
GAAAAATGAACTGTATTATTGCAATTTTTTTTGTAAAAGTAGCAGTTTGGTATGAGTTGGCATGCATAC
AAGATTTACTAAGTGGGATAAGCTAATTATACTTTTTGTTGTGGATAAACAAATGCTTGTTGATAGCCTT
TTTCTATCAAGAAACCAAGGAGCTAATTATTAATAACAATCATTGCACACTGAGTCTTAGCGTTTCTGAT
GGAAACAGTTTGGATTGTATAATAACGCCAAGCCCAGTTGTAGTCGTTTGAGTGCAGTAATGAAATCTGA
ATCTAAAATAAAAACAAGATTATTTTTGTCAAAAAAAAAAAAAAAAAA
```

MYCN mRNA nucleic acid sequence
SEQ ID NO: 30
```
GCTTTCCTCTCCTTTCTCCCTCCCCCTTGTCTGCGCCACAGCCCCCTTCTCTCCCCGCCCCCGGGTGTG
TCAGATTTTTCAGTTAATAATATCCCCCGAGCTTCAAAGCGCAGGCTGTGACAGTCATCTGTCTGGACGC
GCTGGGTGGATGCGGGGGGCTCCTGGGAACTGTGTTGGAGCCGAGCAAGCGCTAGCCAGGCGCAAGCGCG
CACAGACTGTAGCCATCCGAGGACACCCCCGCCCCCCGGCCCACCCGGAGACACCCGCGCAGAATCGCC
TCCGGATCCCCTGCAGTCGGCGGGAGGTAAGGAGCAGGGCTTGCAAACCGCCCGGCGCCCAGGGAAGCGA
CGAGCGCCGGGGCAAGGCAAGCCCTGGACGGGATTGCGACGTGCGCACCGGGCGCCCTAATATGCCCGGG
GGACTGTTTCTGCTTCCGAAACAAAACCATCTCTGGGTTTTCCCAGAAAAGCCAGTTCCAGCCCCGAAGG
CATCCTGGCTAGAGGAGACCCGCCCTAATCCTTTTGCAGCCCTTACCGGGGGAGTAATGGCTTCTGCGA
AAAGAAATTCCCTCGGCTCTAGAAGATCTGTCTGTGTTTGAGCTGTCGGAGAGCCGTGTTGGAGGTCGGC
GCCGGCCCCCGCCTTCCGCGCCCCCACGGGAAGGAAGCACCCCCCGGTATTAAAACGAACGGGGCGGAAA
GAAGCCCTCCAGTCGCCGGCCGGGAGGCGAGCCGATGCCGAGCTGCTCCACGTCCACCATGCCGGGCATGA
TCTGCAAGAACCCAGACCTCGAGTTTGACTCGCTACAGCCCTGCTTCTACCCGGACGAAGATGACTTCTA
CTTCGGCGGCCCCGACTCGACCCCCCCGGGGGAGGACATCTGGAAGAAGTTTGAGCTGCTGCCCACGCCC
CCGCTGTCGCCCAGCCGTGGCTTCGCGGAGCACAGCTCCGAGCCCCCGAGCTGGGTCACGGAGATGCTGC
TTGAGAACGAGCTGTGGGGCAGCCCGGCCGAGGAGGACGCGTTCGGCCTGGGGGGACTGGGTGGCCTCAC
CCCCAACCCGGTCATCCTCCAGGACTGCATGTGGAGCGGCTTCTCCGCCCGCGAGAGCTGGAGCGCGCC
GTGAGCGAGAAGCTGCAGCACGGCCGCGGGCCGCCAACCGCCGGTTCCACCGCCCAGTCCCCGGGAGCCG
GCGCCGCCAGCCCTGCGGGTCGCGGGCACGGCCGGGCTGCGGGAGCGCCGCGCCGGGGCGCCCCTGCC
CGCCGAGCTCGCCCACCCGGCCGCCGAGTGCGTGGATCCCGCCGTGGTCTTCCCCTTTCCCGTGAACAAG
CGCGAGCCAGCGCCCGTGCCCGCAGCCCCGGCCAGTGCCCCGGCGGCGGGCCTGCGGTCGCCTCGGGGG
CGGGTATTGCCGCCCCAGCCGGGGCCCCCGGGGTCGCCCTCCGCGCCCAGGCGGCCGCCAGACCAGCGG
CGGCGACCACAAGGCCCTCAGTACCTCCGGAGAGGACACCCTGAGCGATTCAGATGATGAAGATGATGAA
GAGGAAGATGAAGAGGAAGAAATCGACGTGGTCACTGTGGAGAAGCGGCGTTCCTCCTCCAACACCAAGG
CTGTCACCACATTCACCATCACTGTGCGTCCCAAGAACGCAGCCCTGGGTCCCGGGAGGGCTCAGTCCAG
CGAGCTGATCCTCAAACGATGCCTTCCCATCCACCAGCAGCACAACTATGCCGCCCCCTCTCCCTACGTG
GAGAGTGAGGATGCACCCCCACAGAAGAAGATAAAGAGCGAGGCGTCCCCACGTCCGCTCAAGAGTGTCA
TCCCCCCAAAGGCTAAGAGCTTGAGCCCCCGAAACTCTGACTCGGAGGACAGTGAGCGTCGCAGAAACCA
CAACATCCTGGAGCGCCAGCGCCGCAACGACCTTCGGTCAGCTTTCTCACGCTCAGGGACCACGTGCCG
GAGTTGGTAAAGAATGAGAAGGCCGCCAAGGTGGTCATTTTGAAAAAGGCCACTGAGTATGTCCACTCCC
TCCAGGCCGAGGAGCACCAGCTTTTGCTGGAAAAGGAAAAATTGCAGGCAAGACAGCAGCAGTTGCTAAA
GAAAATTGAACACGCTCGGACTTGCTAGACGCTTCTCAAAACTGGACAGTCACTGCCACTTTGCACATTT
TGATTTTTTTTTAAACAAACATTGTGTTGACATTAAGAATGTTGGTTTACTTTCAAATCGGTCCCCTGT
CGAGTTCGGCTCTGGGTGGGCAGTAGGACCACCAGTGTGGGGTTCTGCTGGGACCTTGGAGAGCCTGCAT
CCCAGGATGCTGGGTGGCCCTGCAGCCTCCTCCACCTCACCTCCATGACAGCGCTAAACGTTGGTGACGG
TTGGGAGCCTCTGGGGCTGTTGAAGTCACCTTGTGTGTTCCAAGTTCCAAACAACAGAAAGTCATTCCT
TCTTTTTAAAATGGTGCTTAAGTTCCAGCAGATGCCACATAAGGGGTTTGCCATTTGATACCCCTGGGGA
ACATTTCTGTAAATACCATTGACACATCCGCCTTTTGTATACATCCTGGGTAATGAGAGGTGGCTTTTGC
GGCCAGTATTAGACTGGAAGTTCATACCTAAGTACTGTAATAATACCTCAATGTTTGAGGAGCATGTTTT
GTATACAAATATATTGTTAATCTCTGTTATGTACTGTACTAATTCTTCACTGCCTGTATACTTTAGTAT
GACGCTGATACATAACTAAATTTGATACTTATATTTTCGTATGAAAATGAGTTGTGAAAGTTTTGAGTAG
ATATTACTTTATCACTTTTTGAACTAAGAAACTTTTGTAAAGAAATTTACTATATATATATGCCTTTTC
CTAGCCTGTTTCTTCCTGTTAATGTATTTGTTCATGTTTGGTGCATAGAACTGGGTAAATGCAAAGTTCT
GTGTTTAATTTCTTCAAAATGTATATATTTAGTGCTGCATCTTATAGCACTTTGAAATACCTCATGTTTA
TGAAAATAAATAGCTTAAAATTAAATGAAAAAAAAA
```

NFIL3 mRNA nucleic acid sequence
SEQ ID NO: 31
```
AATTGTGCAGGGGCGGTGTTTGTGCGTGGAGCTTTCCCTCCCGGCTCCGGGCCGTCGCGGCTCTCGGGA
GAGGCGCCGGGACATTTTAATCGCTGCCTCCGCCGCGCAGCCCTGCCGCAGCTGCCCGGCCGCGCCAACCC
CTTCCCCGCCGCAGCGCGCCCCGAGTGTTGGCAGCTTGCCAGCCGCCACCCCCCGCCTTCCCTCCTGCCC
ACCCCAAGGTAGAGGGCTCCTCTCGGGAGTGTGCGGGGAAGGGGAGGCCGAGGTCCGGGCCACGCCCGGG
TAGCCGCAACCCGCAGTGCTCAGTCGGCAACAGGTAGCCCAGCAGGCTGCGGCTCTCAGGAAGACAAAAA
GCGCCTCTGCGAGCAAATAACGAAGGAGGCCCAACTTCATTCAATAAGGAGCCTGACGGATTTATCCCAG
ACGGTAGAACAAAAGGAAGAATATTGATGGATTTTAAACCAGAGTTTTTAAAGAGCTTGAGAATACGGGG
AAATTAAATTTGTTCTCCTACACACATAGATAGGGTAAGGTTGTTTCTGATGCAGCTGAGAAAAATGCAGA
CCGTCAAAAGGAGCAGGCGTCTCTTGATGCCAGTAGCAATGTGGACAAGATGATGGTCCTTAATTCTGC
TTTAACGGAAGTGTCAGAAGACTCCACAACAGGGTGAGGAGCTGCTTCTCAGTGAAGGAAGTGTGGGGAAG
AACAAATCTTCTGCATGTCGGAGGAAACGGGAATTCATTCCTGATGAAAAGAAAGATGCTATGTATTGGG
AAAAAAGGCGGAAAATAATGAAGCTGCCAAAAGATCTCGTGAGAAGCGTCGACTGAATGACCTGGTTTT
```

| SEQUENCE LISTING: |
|---|
| AGAGAACAAACTAATTGCACTGGGAGAAGAAAACGCCACTTTAAAAGCTGAGCTGCTTTCACTAAAATTA<br>AAGTTTGGTTTAATTAGCTCCACAGCATATGCTCAAGAGATTCAGAAACTCAGTAATTCTACAGCTGTGT<br>ACTTTCAAGATTACCAGACTTCCAAATCCAATGTGAGTTCATTTGTGGACGAGCACGAACCCTCGATGGT<br>GTCAAGTAGTTGTATTTCTGTCATTAAACACTCTCCACAAAGCTCGCTGTCCGATGTTTCAGAAGTGTCC<br>TCAGTAGAACACACGCAGGAGAGCTCTGTGCAGGGAAGCTGCAGAAGTCCTGAAAACAAGTTCCAGATTA<br>TCAAGCAAGAGCCGATGGAATTAGAGAGCTACACAAGGGAGCCAAGAGATGACCGAGGCTCTTACACAGC<br>GTCCATCTATCAAAACTATATGGGAATTCTTTCTCTGGGTACTCACACTCTCCCCCACTACTGCAAGTC<br>AACCGATCCTCCAGCAACTCCCCGAGAACGTCGGAAACTGATGATGGTGGTAGGAAAGTCATCTGATG<br>GAGAAGACGAGCAACAGGTCCCCAAGGGCCCCATCCATTCTCCAGTTGAACTCAAGCATGTGCATGCAAC<br>TGTGGTTAAAGTTCCAGAAGTGAATTCCTCTGCCTTGCCACACAAGCTCCGGATCAAAGCCAAAGCCATG<br>CAGATCAAAGTAGAAGCCTTTGATAATGAATTTGAGGCCACGCAAAAACTTTCCTCACCTATTGACATGA<br>CATCTAAAAGACATTTCGAACTCGAAAAGCATAGTGCCCCAAGTATGGTACATTCTTCTCTTACTCCTTT<br>CTCAGTGCAAGTGACTAACATTCAAGATTGGTCTCTCAAATCGGAGCACTGGCATCAAAAAGAACTGAGT<br>GGCAAAACTCAGAATAGTTTCAAAACTGGAGTTGTTGAAATGAAAGACAGTGGCTACAAAGTTTCTGACC<br>CAGAGAACTTGTATTTGAAGCAGGGGATAGCAAACTTATCTGCAGAGGTTGTCTCACTCAAGAGACTTAT<br>AGCCACACAACCAATCTCTGCTTCAGACTCTGGGTAAATTACTACTGAGTAAGAGCTGGGCATTTAGAAA<br>GATGTCATTTGCAATAGAGCAGTCCATTTTGTATTATGCTGAATTTTCACTGGACCTGTGATGTCATTTC<br>ACTGTGATGTGCACATGTTGTCTGTTTGGTGTCTTTTTGTGCACAGATTATGATGAAGATTAGATTGTGT<br>TATCACTCTGCCTGTGTATAGTCAGATAGTCCATGCGAAGGCTGTATATATTGAACATTATTTTTGTTGT<br>TCTATTATAAAGTGTGTAAGTTACCAGTTTCAATAAAGGATTGGTGACAAACACAGAAAAAAAAAAAAAA<br>AAAAAAA |

PTPN14 mRNA nucleic acid sequence

SEQ ID NO: 32

| ACTCGCACGGCCCCTTCCTCCCTCCTCTCCCGGCCGCTCGCATTTCCTGCCGCTCTGGCTCTCCCGGCCC<br>CTCAAAGTTCTTTCCAACTTTTTCTCGGCGGAGTGAGCGCAGCGGGCGCAGACTCGGGGCAGGTTGCTG<br>TGCTTCTCCGGGCTCAGCCGCCTGCTCTCCTGGCTCAGGTCCTCGGGGAGCCCTAGACAGACATCAAGTG<br>GCCACTGGCGCTCCTTCCCCTCCCAGCTGAGCCATCCTCCCCGGCCTCCTCGGGCGGGACAGCCCCGTGC<br>TTAGGTTTTTCTCCTTTTCTCCCCGGTGCGCCTCTGCTCGGACTCTCGCGCCGGGATCGCGGCGGAAAC<br>CTCCCTCCCCTTTCGCCTCCTGCGGCTCCTTCCCTTCGCCCCTCCTCCGCCAGTCACTGGAATCAATTCC<br>GTGGGGAATCGGCTCCGCCGCCGCGAAGGACAGCCTTTCCGCGCGGGACTCCGGGGCGCCACGGGGGCCA<br>TGTAAGCAGCTATCTTCCAGAGGGCCACACTGGGCATGGACACCCTTTTCCCTGCCTGGAGGAGCACAGG<br>TGATAGTGTAATTTTCCAGTCACGAAACTGCTAAGGCCATCTCAGGGGCGTGTGCGCAGGATAGGCGGG<br>CGGCGTCCGAGGACCACATAGCCATGCCTTTTGGTCTGAAGCTCCGCCGGACACGGCGCTACAACGTCCT<br>GAGCAAGAACTGCTTTGTCACACGGATTCGCCTGCTGGACAGCAATGTTATCGAGTGCACGCTGTCGGTG<br>GAAAGCACAGGGCAAGAATGCCTGGAGGCTGTGGCCCAGAGGCTGGAGCTGCGAGAGACGCACTACTTTG<br>GCCTTTGGTTTCTCAGCAAGACCAGCAAGCACGATGGGTGGAGCTGGAGAAACCTCTGAAGAAACATCT<br>GGACAAATTCGCTAATGAGCCTTTGCTTTTCTTTGGAGTCATGTTCTATGTGCCAAATGTGTCATGGCTT<br>CAGCAAGAGGCCACAAGATATCAGTATTACCTGCAAGTCAAAAAGATGTGCTTGAAGGGCGATTACGAT<br>GTACATTGGACCAGGTGATTCGGCTAGCCGGCCTAGCTGCAAGCTGATTTTGGAGACTATAATCAGTT<br>TGATTCTCAAGATTTCCTCAGAGTATGTGCTATTTCCTATGGATTTGGCCCTGGAAGAGGCTGTTCTG<br>GAGGGAGCTGACCCAGAAGGTAGCCCAAGAACACAAAGCCCACAGTGGAATCCTGCCAGCAGAAGCTGAAC<br>TGATGTACATCAATGAAGTTGAACGTTTGGATGGATTTGGACAGGAAATCTTCCCTGTAAAGGACAATCA<br>TGGAAACTGTGTACACCTTGGCATTTTCTTTATGGGATTTTCGTGAGGAACAGAATTGGAAGACAAGCG<br>GTAATATACAGGTGGAATGACATGGGAATATCACTCATAACGCTCGACCATTCTAGTGGAGCTCATCA<br>ACAAAGAAGAGACTGCCCTCTTTCACACGGATGATATCGAAAATGCCAAGTATATTTCTCGGTTGTTTGC<br>CACACGACACAAGTTTTACAAACAAAACAAAATCTGCACTGAACAGTCAAATTCTCCACCCCCCATCAGA<br>CGCCAGCCCACCTGGAGCCGATCCTCTCTGCCCAGGCAGCAGCCGTACATCCTGCCTCCCGTTCACGTCC<br>AGTGTGGTGGACTACTCGGAAACGCACACCTCGCAAGACAGCATTTTTCATGGGAATGAAGAAGCCTT<br>GTATTGCAACTCTCACAACAGCCTGGACTTAAATTATTTAAATGGCACTGTCACCAATGGCAGCGTGTGT<br>AGCGTTCACAGCGTCAACTCCCTCAACTGCTCGCAAAGTTTCATCCAGGCCTCCCCTGTATCCTCCAACC<br>TCAGTATCCCTGGGAGTGACATCATGCGGGCCGACTACATCCCGAGCCACCGGCACAGCGCGATCATCGT<br>GCCCTCGTACAGGCCAACCCCCGATTATGAGACAGTCATGCGCCAGATGAAGAGGGGGATCCTGCATACA<br>GACAGCCAGAGCCAGTCTCTGAGAAACCTCAACATTATCAACACCCATGCCTACAACCAGCCAGAGGATC<br>TGGTGTACAGCCAACCGGAGATGCGGGAGAGGCACCCCTACACTGTCCCTTATGGGCACAGGGGGTCTA<br>CAGCAACAAACTTGTCAGTCCATCTGACCAGAGGAACCCAAAGAATAATGTGGTACCAAGCAAGCCGGGG<br>GCAAGCGCCATCTCGCACACGGTGAGCACCCCAGAGCTGGCCAACATGCAGCTGCAGGGCAGCCATAACT<br>ACAGCACGGCCCACATGCTTAAGAACTATCTCTTCAGGCCACCGCCCCCTACCCACGGCCACGACCTGC<br>CACCAGCACCCCAGACCTGGCCAGCCACCGCCACAAGTACGTCAGCGGCAGCAGCCCGGACCTGGTGACC<br>CGGAAGGTGCAGCTCTCGGTGAAGACCTTCCAAGAGGACAGCTCTCCGGTGGTTCATCAGTCTCTCCAGG<br>AGGTGAGCGAGCCCCTCACGGCCACCAAGCACCACGGCACTGTGAACAAGCGCCACGACCTGGAGGTGAT<br>GAACAGCATGGTGCGGGCATGGAGGCCATGACGCTCAAGTCGCTCCACCTCCCCATGGCTCGCCGCAAC<br>ACGCTCCGGGAGCAGGGACCGCCCGAGGAGGGTCAGGCAGCCACGAGGTCCCCAGCTCCCTCAGTATC<br>ACCACAAGAAGACCTTCTCTGATGCCACTATGCTAATCCACAGCAGCGAGAGTGAGGAGGAGGAGGAGGA<br>GGCTCCAGAATCGGTGCCCCAGATCCCCATGCTCCGGGAGAAGATGGAGTACAGTGCCCAGCTGCAGGCG<br>GCCCTGGCCCGCATCCCCAACAAGCCCCCGCCTGAGTACCCCGGTCCAAGGAAGAGTGTGAGCAATGGGG<br>CTCTGAGGCAGGACCAAGCCAGCCTTCCTCCCGCCATGGCCCAGAGCCAGGGTGCTGAGGCATGGGCCAGC<br>CAAGGCCATCAGCATGTCTCGGACTGACCCGCCGGCTGTCAACGGGCCTCTCTCGGCCCATCCATCTCG<br>GAACCCCGACCTGACTAGTGTGAAGGAGCGGGTCAAAAAAGAGCCTGTGAAGGAGAGACCTGTGTCTGAAA<br>TGTTTTCCCTGGAAGACAGCATTATAGAGAGAGATGATGATCAGGAATCTAGAGAAGCAGAAGATGGC<br>AGGCCTGGAGGCACAGAAGAGGCCGCTGATGTTGGCAGCATTGAATTGGCTCTCGGTGGCTCGAGTCTCA<br>GGGCGGGAAGAGAATCGAGTTGATGCCACACCCGGGTTCCCATGGACGAGAGGTTCAGAACCCTGAAGAAGA<br>AACTAGAAGAGGGAATGGTGTTCACAGAATATGAGCAAATTCCAAAGAAAAAGGCGAATGGCATTTTCAG<br>CACAGCAGCTCTGCCAGAAAACGCCGAGCGCAGCCGAATCCGTGAAGTTGTCCCTATGAGGAGAATCGA<br>GTAGAGCTGATACCAACCAAAGAAAATAACACAGGATACATTAATGCCTCCCACATCAAGGTGGTGGTTG<br>GCGGGGCAGAATGGCACTACATAGCCACCCAGGGGCCCCTGCCACACACGTGCCACGACTTCTGGCAGAT<br>GGTGTGGGAGCAGGGAGTGAATGTGATTGCCATGGTCACTGCAGAGGAGGAGGGTGGACGAACCAAAAGC |

SEQUENCE LISTING:

```
CACCGATACTGGCCCAAACTAGGTTCAAAGCACAGCTCAGCCACCTATGGCAAGTTCAAGGTCACCACGA
AGTTTCGAACGGATTCTGTTTGCTATGCAACCACGGGCTTGAAGGTCAAGCACCTTTTGTCTGGGCAAGA
AAGGACGGTGTGGCATTTACAATATACTGACTGGCCAGATCACGGCTGTCCAGAAGATGTCCAAGGATTT
TTATCCTACTTGGAGGAGATCCAGTCGGTCCGTCGCCATACCAACAGCATGCTGGAAGGCACCAAGAACC
GGCACCCGCCCATCGTGGTCCACTGTAGTGCTGGGGTGGGAAGGACCGGCGTGCTCATTCTTTCTGAGCT
GATGATCTACTGCTTGGAACATAACGAAAAGGTGGAAGTGCCCATGATGCTGAGGCTCCTCAGGGAGCAG
AGGATGTTCATGATCCAGACTATCGCTCAGTACAAGTTTGTCTACCAAGTCCTCATCCAGTTCCTCCAAA
ACTCCAGACTCATTTAATCACCCCAATCCAGCTCCTGGAGGAGGGACCCAGCTCCATCGCGCTGGAGGAG
AGTCACCTCCAGACAACATCTGCTCCCCCCACAGGGGTGCAGGTGGCTGGCAGCAAACAGGCTCTCTGAA
GACAGTAGCCAAGATTATTCACACATACCATGTATTATTTTATATGAGATAATTTATTTTTTTCCCCTTT
GGAATAACTTTTGTGAATTATTATAATGCAGTTTCCCTAGTAATATAGTACTTTTCATTTGAACCACATC
TTGACTGATCTGTATTGTAATATATGTCAGCAGGTAAGGTTGCCTGCTGGATCATTTTGAGGACAGAGGC
ATGAGGGAGCACATCTCTTGTGAAGTTGCAGCCAGATTTGTAACCAACCCTGAAATTCATCAGCTTAATT
CATTTATCAGCTTGATTCATTCATCATTCATTGCTTATATCCAAAGCAAAGACGGTAAGAAAATGAATTC
ATCCTGAAATATAAAGAAAAGGGTCTGAAGGAACAAACACGATTCTCTTATATTTTGGGGCTCATGAGCC
TTGATAGACAGTTTCCTCTCGTCTTCATTTCCACCCCTCATCCTCAGTAGTCTCCTCTCCCCCACGCCCC
ACCCCAACTTCCCCCCCAAGCTTGAGTTAAAGACAGAATAGCTAAAGACAGTGCTGCCTTTACAATGCAG
TAATTGCCATCTTTGGGGCCGAAAGACAAGCTCTGTGTTGTGCTTTTCTTGACCACCCCTTATCCTGGGC
TCTGGAGCTTGTGTTTCCCTGCTGGCGACTGTACCTTGGGTATTTGTTGCTACCTCTCCTGTTTGCTCAG
TAGGACCCTGTCTGGTGGCATTGAGGCTCTGGACCAGACCATCTGTGCAGTTAAGGCTCTACCCTGATTG
AGAGAGGATAGCAGACCTAGAAAGAGAAAGGAGTTGGGCAGGGCCTTTGAGGATTGTGTTTTTCAGGCAG
GGCCTTGATGATCATTGTTTTTATTTAAATAAGATGTGTGTGCTGGACAGAGACCTAAAAGTTGAGGTC
ACTAAGTCATTGGAAAGGCCATCAAGGAAACAGATGGGGAAGCTGATTTATGGGAGCTGTAAGGCATTTA
GCTACATAACAGGGGTCCTGGCCAGGAAACACATCAAATGTGACCCCCGCTGTGCTGATATCATCTTCAG
GCTTTGGTCTGCAAGATCAGAATTAATCCCACTCGGGACCCCATAGTCCAAACTTGGGGCCACTTGATGA
ACGATGGTAGAATTGTCATTGGCAGAGCCCTGTGCTTCTTTCCTTTTCTTCATAAAATCCACTCGCTGGT
CAGTTATCTTCACTTTGAAGCCCAGTTCTTAGTTTCTTCCTATGGCTTCATTGGTCAGTGTCCTTCTGAA
TTTCCAAGGATGGTACACAATAAATCATGTTTTGTACTTTTTTCCTCTTACTGCATTTTGGGGATTTAT
CATTCTATGTCTACCTTTTCTTGAGTACAGCTTTGATATGCACCTGTTGTTACGTGGTGATGGGAAGTCA
CAGGCGTGCTCTTTCTAGTTAATTTGATGCCACATCTTCCTTGTCTTTTCAGCTTGGGAAAAAGGCGGCA
GTGGAGGAAGGCATGGAATGCCCACAGTGGTCAGTTCAAAGAACAAACGTGCAATTAAAAAACTGTAGTC
AGCCAGGCACGGTGGTTCACACCTGTAATCCCAGCACTTTGAAAGGCCAAGGCGGGCAGATTGCTTGAGC
TAAGGAGTTCGAGACCAGCCTGAGCAACATGATGAAACCCCGTCTCTACAAAAAGTACAAAAATTAGCCA
GGCGTGGTGGTATGCCCTGGTAGTCCCAGCTGCTCGGGAGGCTGAGGCAGGAGGATCACCTGATTCTAAG
AATTCGAGACTGCAGTGAGCCGTGATCTTGCCACTGTAGTCCAGGCTGGGCTACGGAGAGACCCTGCCTC
CAAAAAAAAAAAAAAAAAAAGGAAAAAAGGTTGTCAAGAAAAACTAGATGTTAGGAGAAAGGAAAAATTTAA
TTGCAGTTTTTTTTCTTAGAATTGACTGCTGTGAGAGTTCCATATGCCTTTCTTCATTGCTGCTTTTGTC
CCCCGTGAGCTAAAAAGATGGAGTGACATCAAATCAACCAGAAAAGTATGCCTTTGTGACATCCCATCA
CCACATGCCAACAGGTATATATTCCCCATTAAGTTCTTCGGAATAGGAATCCTCTGTTTCAACCTGGCCA
GGTGTTGTGGTGGCTGTACTCTAGTTAGACTCGGAATATCTGGGGATGGAGGGCTTCCCCTGTGTCTTCT
ACTTCAAGGTCTGAAGGCTCAGTGAAGGAGTATAATCTGCTGATCTTTGTAGATTCTGGAGTTTTGTTGT
ATGTCCTGGAAAGAAACCCATTAGTATTACATGTATTTTCAGTGAACAGAGCTTATAACCCTTATTATAA
GAAGCTCATCAATAAGCAAAAAGATACTTGTTTCCTTTCCTTGGAGGTTTTTCCATCCTTGGGATATTCT
GCTGTTAGGGATGTTTTAGCAAGTGGTCTCAGTTACTGGTTTATTGCGTGATGAACAACATCAGTATTTA
TCTTTTATCTCTAAGCCCCAAGGTGGGCACTGTTAGAATATGTCATGTGGACAGCATATAGATCTGGT
GCGTCTTTGAGGTCGTCAGAGCTCATGGGCTTCCCTGAAATTCATCCACTGTCCCTGCCGTATGCTACGG
GAATATTCATTAGTGTACAAAATGCAGGGAGGAAGTAGGTTTAATATTCAACTTTCTAGCCAAAGTTTAT
ATTGAAACCCAAAAGAAAACATTTAAGAGTTGTTCCACATATTTCACTTTTAAAAACAAATGCCTTTGGT
TCTTTAGCACATTTTGCATTCCTTTTCACATCTCCAGTAAATGCCAACATATCTCCTGTTAAATTAGCAG
CAGCCATTTAAAGTCCTTTCGGTGGCATCTGCATAATAATTGCCCAGAGATGCTTTATATCTGGGAAGCA
AGCCAAGGAATAAACCTTGAAGCAAAGTGTATTAAATTAGTTATCTAGTTAGAGCTTTTGGAATGATTTC
CTGATGATGTATCAAGTCTGAAGCTGGAGCTGTCAGTGTCTATTGCTGCAGTTTGGATTTGAAGGGAGAA
AATGTAAAATGGAGGAAAAAAAAGTTACCATCTCACAACAAGACATCAAACATTTTCCAGCCGCTGTTT
TCGAGGTTTTCCAGTTGAACTGTTTGGTTTCTTTCATCCACACTCATTTGGATACATTGACCCGAGGTAT
TCATCCTTGTTTACTGTGGTCCCTGAATCATGGGGGCTGAATTTGATGTCTTCATCCTTGAGATGAGCCT
GCTGGCTTAGCTGAGGAATGTCCTGCTGAGGTTTCTTAGGTTTCCTTGGGTTCTAAGGATATACTGGATA
TACCATCTTTTAGCAAGAGTATCTGGTAGCATTTACAGATAGACATTGGTATGCACTTCTTTCCC
CAGATAGGAAGTAAAGGAGGATTTAGTTGCATGAAAAAAGGATGTTAAACATTGATTACATAGGAGTAAA
GATGAATGAGCTGCAATATTCAGTCGGAGCTAAACAATAAGATCAGGGAAGGTAAAAATACCTATGTGGA
ATATTTTGAATCGTAAGCTTTTGAGGAGCTTAAATTGAGAGAATTTTACTTTTAATTTTGTAGATTGAGA
AGAGGAACCGCTTTTTAAAATTATAGCTAAACTGTCATTGTTTTCCTAAGAGTCACTTGGCCATCTCTGG
CCCCCTCTTTCATCAGCCTGAAGAGAGGGTCTTTGTAGACTGCTGAGGGTGGGCCTTGTAGGACTTGACC
ATGGCTTACACCTACTTAACCTTTATCCTGCTTTCTTTCAGCTTGTGCTTTTCAGTTATAAACTCCAGTG
GGTACAGCAGGCTGGCCTTTTCATCCAGCTGATTATTTTCCAGCTTAATATAGATTGACCCATATGAAA
TTTCCAATAATGGACCATATTTTCTGCAAATAGACAGTACTCGCATGGATCACCTATATCTTCCCCCTGA
TACACTGTGGGTCCCAACACCAGATGTCATTTCTCCAGAGCAGTGCTAATGACACACAAAAGGTATACCCT
GGGTGGCCCAGCTCTTTTCACGAACGTGCTGCCCTGCTCATGATGATCCTTGCATCACTTGGTGAATGGG
CCATCTCCTGGGACATGGAAGTTCAGAGGTAGATAGTGCACTGCAGCTTCTCTTAAGCCGGATTGGCCA
TCAGGCATATCACTCTGGAGTTTTTAGCTGCTGTCCTTTCCCGATGAACAGTCTGTATTAGCTGACCTCA
GCCTACTTGTTACGTGACGTATGGGTCCCAAAAGTGTCCTTTGTCAAAAAGCAGAATGTGCCTTCTAGTC
TCCCTTTCCCCATCTAATGGTGTATTCGATGGTGAAGATGAGTACAGTTGACCACCCCTATCTGTGGGTT
CCACATCCCTATATTCAACCAAGTACAGATTGAAAAATATTTGGGGAAGAGGGGAAACCCACAAAGTTCC
AAAAAGCAAAGTTGAATTTGCCACATGCTGAATACTACATTGAATTCACACAAATGAAGTGATGTGTAG
GCATTGAGTTAGGTATTGTAAATAATCTAGAGATGATTTAAAGTATGCAAGAGATGTGCATAGGTTATAT
GCAAATACTGTGCTATTTTATATAAAAGACTTGAACATCCATGGATTCTGGTATTCTCAGAGGGTCCTTG
ATTGCCCCCTTTGGTAAAGGACAACTATTTCGTTACTGATTTTCGTTTGGGGAAGATCTGTCAATCCCTT
GAGGTGCGGGGGTTGGGGGGATGGAGGGTACAGGGCATTCTAGGATGTGTGCCAGGGAGCACAGATTCAA
```

SEQUENCE LISTING:

```
GGGATGGGATTGAGTCAGACCTGTGTTCTTACTCAGTGTCAGAAATAACTCTGTGGAGCTCCTAGAGTAA
GACATTTCCGGAAGCACCACATAATTACTGTTGGGCTCTTAGGGTAGCCCTTTTAGGGAATTGAGCATTC
CCATGTTTTACCAACAATTATTCTGCTGCTGTGTTTTATTATATTGCCAATGGTTTTGAGACACTCATCA
TGCTCTTATTTAGTGATTTCTTTTCATGAGCAGAGCAACAGCTCATCCAGCATGGTTTCCAAATGGAGAA
ATTTGGGTCTTCTGTAGAAACCACACAAATTCTCCAATGGCCTACAGCCTTATGGTTGGCACACTAGTTG
GCCCTATAGGGTGGAAATAAAGCTGTAAGATGTTAAACTGCATTTGATACTTCTCTTGAACGCTGAGCAA
GGAAGCAAAATAGTTCTTGTCTTTACTTAAGCTTCTAAGACATTTTGGGGCAAAGGACCTTACAGATGGC
GTCTGTTGAAAGTAACAGCAACGTGCCAGGGAGAAATGTGGGGGAAATCTCATCAAATTCTGCCACCTCA
AATGTGTTGTCCAGAAGTCAGTGTTATTCAGGGGCCCTGTGAAACTTGACCACCAGCTTGCGCCATCAA
CACTCAGCCTTTATCCAGCCTGCTCTCAGCTTTTGTGTTTCTGTTAGAAACTCAGATAGGTAAGTATTTT
TATTCAGTAGACTACCTTTCTTATCTTTTCAGCTTAATATAGCTGCATCTTCTTTCTCAAAGCCAAACTA
AGATATTCTCTATTAAAATGTCCATGAGCCTAGCATTGAGTGTCTGGCATCCATCAATTTCATAGACTGG
AAAATGATTGTTGTTGGTACAGTAAAGAAGAGGATGTGCATCAGTTCCTACCGTTTGCAGCTTTGTTTT
TAGCCTTCCCATTTTAAAAATAAATTCAAGGACATTGAGTTACAAGGCAGGAGGGCTGGAGCTACTGGGC
AGCCTGAATATGACAAGCATTTGTGTGGAAAGTCATTGCTCCTTCTGCCACACTTTGGGCCATCAGGATC
ATTCTTTCCCAGAAGTGCCATAAACTTGCTCAAAAGTTTCTATAAATGGGAAGAGGGAGAGGAAGGATTT
TTGCATCAGTCCTGAAGTTGCTATCCAAAAGTTCTCTGTTTCACAAATAATTTTCTGAACTCTGGAATGC
CTCTCCTACTCCCTGCCTCCCTTTCTGTAATGTCAGAGTGATGGAAACCACCAAGTGGCATGCTAGGGAA
AGCCTGCAGCAGTGTTGGAGTCTATTTCACCCTAGCTCATAGTTTTAAACTGTCTTCACTGTTGAGGTAG
AGCTTGATGAATGTCATGGATTATGATGTGTGGTTTATCATATTTGCCTGGATTTGCTGATCAAAAGCAC
CATCTTCCCTCGCCTGCTGCTGGCAGCCTTTCCTTGCCTTGCTTGTTAGCAGAGCATTCTGCTTACCCAT
GTGGCTCCCAGAGTTAGCAGCCCCGGCTCTTGGATTTCTTGATTCTTCTCCCCTGTGATCTCAGAGGTGC
TGCAGAGGACATTCCCCTTTAGAGCAAGTCATGTTTCTATTCAGGCCACAAAACTGGGATGTACATGCAG
TGACTTTGGTGTTCCTTGCTTGTTCAGGGGAACGGGTGGACTGTTGTGTGCTGTCACCCTCTTCATTC
CATGAGCACCTTGTTCACTTAGGGTCTGCTGCCTTTTTTTTTTCTTTTTCTTTTTTTTTTTTTTTAG
TTTTTGAGATCGTGTCTCACTCCTGTTGCGCAGGCTGGAGTGCAGCCTCCAAAGTAGCTGGGATTATAGG
CGTGCACCACCACACCCGGCTAATTTTTATATTTTTAGTAGAGACGGGGTTTTGCCATGTTGGCCAGACT
GGTCTCAAACCTCTGACCTCGTGATGACCCCCCTCGGCCTCCCAAAGTGCTGGGATTACACCCAGCCTCT
GCTGCCTTTTCATATTTCCCCATCTGCTTTATGGATCAACTCTCAACAGTACACTTTTTCTTTTCTTTAC
CTACCCTATGAGTGCAACCCAGATGTAAGAGTTAATCCTCGTCAGAGAATCATTGCCTTAAACCTCTCAG
AAATATGTAATTAGGAAATCTTATTTTAATTTTTTAAAAATTGCTTGTATAGTTTCAAAGAATAAGATCT
GGCAAATGGCCAGATGTGGTGGCTCACACCTGTAATCAAACCAGCACTTTGGGAGGCTGAGGCAGGCAGA
TCACCTGAGGTCAGGCGTTCAAGACCAGCCTGGCCAACATGGTGAAATCCCGTCTCTACTAAAAATACAA
AAAAAAAAAAAAAAAAAAAAATTAGCCAGGCATGGTGGCACATGCCTGTAATCCCAGCTACTCAGGAGGC
TGAGGCAGGATAATTGCTTGAACCCGGGAGGTGGAGGTTGCAGTGAGCCGAGATCATGCCACTGCACTCC
AGCCTGGGCAACAGAGTGAGACTTTGTCTCAAAAAAAAAAAAAAAAAAAAAAAAGATCTGGCGGATGAA
AATAACCAGAATGAAAATAGCTAGAAAACTCAGCAAGCAGGAAGCTCCCTTTCTCACCCTTTTGTTCCCT
TGCCGATAGAATCAGTCACTATTAGAAAAAATGAAAGACGCTCTGTTTAAAACAATGATGACAGCAGTAC
TTAATATGTATTTCGAGGTGAACTTATATAGATTGAGAGAGGCTGCATTTGGCAGACTGATGTATAGGAA
GACCCATTTGTTTCTAGCTTCTCCCTGCAGGGAAAATGCTTTCGTCATTATAGCCTCTTTACACAGACTG
GCCATTCTAGTGAAACAGGTGGTAAACCTTTGGGCTGCCCAGAAACATTTTATCTGTTTTCACTTACCTA
GGAAGGGGAAAGATTAGCGGGTCATCCAAAATCTGTATGTAAGCTATCTTCATTTTCTTCCCCAACCTTC
TCCTCCTGGGAAACACAAATGCTATCTCATCGACAAAAGGTTTTAGAGGATAAAGCTGAAAAGATTGGA
TTGGGATCTTTTTGTGGCTTGGGCGGAGCCTTTTGCTAAAATCTCAAGAATGCTGCTTTGAGTTTAGCT
AGGGTGGCTCTCAGAACTGGGGTGCCTGGCATTCTCAGCATTTCTCAGGGGCCTCCCACCTCTGACAACT
GCAGTGTTAGCTAATACATACCTTGAGCATAGAACTGAATGCTGTAATTCAGAGCCATTTTTTTTTTCAA
CTTGAACATTGTACAATTTTACTGCAATTTCCTTTGAACTTTCTTGCCACTGTTTGGAATCTTAAAAATT
CATTAGCCTTCTCCTTTCTGACATAAAGCTACTCTTCATCAGAGATGAGTTCCTATGTATGTCCTTTGTT
CCTTCAATAGCTAATTAATGTGCTTGAGGATACTTCAGTGGAAAAAAGGTTTAAATATGCAAATTACTA
ATAAATGTGTAACCTTATGTAACTTGTGTTACATCAAGTAACAAGCTAATCTAGTTTGTTTCACTGGACT
AGGCTTGTGCTCCCTACTTCAGTATTTTGATGCTTTCCTTGATCTTTGTTTCACAAATGTTGTGAATTT
TGGTATCATTCAAAACAAATGACATTTATTAGGTTTCATTTTGAAACGATGTACAGACAAGTCCCCAACT
TAGAAACCGGTTTGTTCTTAAGGTTCTTGCGTCAGCCCATAGAAGCCCACTGACCTCCACCACAGCCCAA
ATGGAGGGCTGTGATAGCCAGATCGGTTGGCTTTTGTGGGCTGACCCAGACATTTAATCACCATCTCTT
ATGTTGTTGCCGTAAGAAATGCATTCCAGGTTGGGACTTGGGATCCTGAGAGCACATTCGCCCCTGTGG
TGGCCGCTTGCCACCTTGCAAGATGGAAGCCCAGTCTCCTTACTACCAAACTGTAGTTGTAAGCAGAGGG
AGGGGTGAGATGTTTATAGGACATTCCCTAAGCTGGGGAGTGATTTTTACTACTATTCATGTCAACTGTA
CTTTGGTATAGACTCCCTATCAATTTAATAATATGAAAAGCCTAAAATAAAACTATGCATGCTATTCTAT
GTGCTATTTTATATCAGTAAATAAGCTTATGCTTGCCAGTTGTATACACAGTTATGAGGTGTATAGAACT
GACTTTGACAGTATTTTTGCACTGTTTCCTATCTGTTTTTATAAAGTCTTATTTAGATATTGGACCTTG
TTGATGTTCTCACTGCCCTTGTGCTTGCTATAAAATGTTTCATATGTGCCTTTACAAATGTGAGATCTTT
ATTCTAACCTTTTTTTGTAAAAGATATCTATTGATTTCCATATGCAATAAACCTTTTTTTCAGAGAAAAG
TTA

RHOC mRNA nucleic acid sequence
                                           SEQ ID NO: 33
ATTGAAGGCTGGGCAGAGTCTGAGTCCACCCGGGTCGTGCTCCCCCGCTCGCCCGGCTCCTCCGCAGTC
CAGGAATCTCCCCGTGGCTCTCCCCGACCTGGAGGGGTGACGCCCCTGGCCCCAGTCCCCGGCCTGCG
GAGGGGGCCGGTGGCTGCGGCCCTGCGCGGGGCCGGGCGGGCCGAGCCAAGGGCCGCCCCGGCCGACC
CTCCCCCTGCCGGGCCCGCCCTCCCCGCCGCGGCGCTGGAGGAGGGCGGGCGGGCCCTGGGTCAGTC
TGAGCCTCCGGCACCGGCCGCGCAGCTGGAGGCGGCGGAGCGGAAGCCTTGACTTCATCTCAGCTCCAGA
GCCCGCCCTCTCTTCCTGCAGCCTGGGAACTTCAGCCGGCTGGAGCCCCACCATGGCTGCAATCCGAAAG
AAGCTGGTGATCGTTGGGGATGGTGCCTGTGGGAAGACCTGCCTCCTCATCGTCTTCAGCAAGGATCAGT
TTCCGGAGGTCTACGTCCCTACTGTCTTTGAGAACTATATTGCGGACATTGAGGTGGACGGCAAGCAGGT
GGAGCTGGCTCTGTGGGACACAGCAGGGCAGGAAGACTATGATCGACTGCGGCCTCTCTCCTACCCGGAC
ACTGATGTCATCCTCATGTGCTTCTCCATCGACAGCCCTGACAGCCTGGAAAACATTCCTGAGAAGTGGA
CCCCAGAGGTGAAGCACTTCTGCCCCAACGTGCCCATCATCCTGGTGGGGAATAAGAAGGACCTGAGGCA
```

-continued

SEQUENCE LISTING:

AGACGAGCACACCAGGAGAGAGCTGGCCAAGATGAAGCAGGAGCCCGTTCGGTCTGAGGAAGGCCGGGAC
ATGGCGAACCGGATCAGTGCCTTTGGCTACCTTGAGTGCTCAGCCAAGACCAAGGAGGGAGTGCGGGAGG
TGTTTGAGATGGCCACTCGGGCTGGCCTCCAGGTCCGCAAGAACAAGCGTCGGAGGGGCTGTCCCATTCT
CTGAGATCCCCAAGGCCTTTCCTACATGCCCCCTCCCTTCACAGGGGTACAGAAATTATCCCCCTACAAC
CCCAGCCTCCTGAGGGCTCCATGCTGAAGGCTCCCATTTTCAGTTCCCTCCTGCCCAGGACTGCATTGTT
TTCTAGCCCCGAGGTGGTGGCACGGGCCTCCCTCCCAGCGCTCTGGGAGCCACGCCTATGCCCTGCCCT
TCCTCAGGGCCCCTGGGGATCTTGCCCCCTTTGACCTTCCCCAAAGGATGGTCACACACCAGCACTTTAT
ACACTTCTGGCTCACAGGAAAGTGTCTGCAGTAGGGGACCCAGAGTCCCAGGCCCCTGGAGTTGTTTTCG
GCAGGGGCCTTGTCTCTCACTGCATTTGGTCAGGGGGGCATGAATAAAGGCTACAGGCTCCAACGTGAAA
AAAAAAAAAAAAAAA

WT1 mRNA nucleic acid sequence
SEQ ID NO: 34
AGCTGGGGTAAGGAGTTCAAGGCAGCGCCCACACCCGGGGGCTCTCCGCAACCCGACCGCCTGTCCGCTC
CCCCACTTCCCGCCCTCCCTCCCACCTACTCATTCACCCACCCACCCACCCAGAGCCGGGACGGCAGCCC
AGGCGCCCGGGCCCCGCCGTCTCCTCGCCGCGATCCTGGACTTCCTCTTGCTGCAGGACCCGGCTTCCAC
GTGTGTCCCGGAGCCGGCGTCTCAGCACACGCTCCGCTCCGGGCCTGGGTGCCTACAGCAGCCAGAGCAG
CAGGGAGTCCGGGACCCGGGCGGCATCTGGGCCAAGTTAGGCGCCGCCGAGGCCAGCGCTGAACGTCTCC
AGGGCCGGAGGAGCCGCGGGGCGTCCGGGTCTGAGCCGCAGCAAATGGGCTCCGACGTGCGGGACCTGAA
CGCGCTGCTGCCCGCCGTCCCCTCCCTGGGTGGCGGCGGCGTGTCCCTGCCTGTGAGCGGCGCGGCG
CAGTGGGCGCCGGTGCTGGACTTTGCGCCCCCGGGCGCTTCGGCTTACGGGTCGTTGGGCGGCCCCGCGC
CGCCACCGGCTCCGCCGCCACCCCCGCCGCCGCCGCCTCACTCCTTCATCAAACAGGAGCCGAGCTGGGG
CGGCGCGGAGCCGCACGAGGAGCAGTGCCTGAGCGCCTTCACTGTCCACTTTTCCGGCCAGTTCACTGGC
ACAGCCGGAGCCTGTCGCTACGGGCCCTTCGGTCCTCCTCCGCCCAGCCTGCATCCGGCCAGGCCA
GGATGTTTCCTAACGCGCCCTACCTGCCCAGCTGCCTCGAGAGCCAGCCCGCTATTCGCAATCAGGGTTA
CAGCACGGTCACCTTCGACGGGACGCCCAGCTACGGTCACACGCCCTCGCACCATGCGGCGCAGTTCCCC
AACCACTCATTCAAGCATGAGGATCCCATGGGCCAGCAGGGCTCGCTGGGTGAGCAGCAGTACTCGGTGC
CGCCCCCGGTCTATGGCTGCCACACCCCCACCGACAGCTGCACCGGCAGCCAGGCTTTGCTGCTGAGGAC
GCCCTACAGCAGTGACAATTTATACCAAATGACATCCCAGCTTGAATGCATGACCTGGAATCAGATGAAC
TTAGGAGCCACCTTAAAGGGCCACAGCACAGGGTACGAGAGCGATAACCACACAACGCCCATCCTCTGCG
GAGCCCAATACAGAATACACACGCACGGTGTCTTCAGAGGCATTCAGGATGCGACGTGTGCCTGGAGT
AGCCCCGACTCTTGTACGGTCGGCATCTGAGACCAGTGAGAACGCCCCTTCATGTGTGCTTACCCAGGC
TGCAATAAGAGATATTTTAAGCTGTCCCACTTACAGATGCACAGCAGGAAGCACACTGGTGAGAAACCAT
ACCAGTGTGACTTCAAGGACTGTGAACGAAGGTTTTCTCGTTCAGACCAGCTCAAAGACACCAAAGGAG
ACATACAGGTGTGAAACCATTCCAGTGTAAAACTTGTCAGCGAAAGTTCTCCCGGTCCGACCACCTGAAG
ACCCACACCAGGACTCATACAGGTGAAAAGCCCTTCAGCTGTCGGTGGCCAAGTTGTCAGAAAAAGTTTG
CCCGGTCAGATGAATTAGTCCGCCATCACAACATGCATCAGAGAAACATGACCAAACTCCAGCTGGCGT
TTGAGGGGTCTCCCTCGGGGACCGTTCAGTGTCCCAGGCAGCACAGTGTGTGAACTGCTTTCAAGTCTGA
CTCTCCACTCCTCCTCACTAAAAAGGAAACTTCAGTTGATCTTCTTCATCCAACTTCCAAGACAAGATAC
CGGTGCTTCTGGAAACTACCAGGTGTGCCTGGAAGAGTTGGTCTCTGCCCTGCCTACTTTTAGTTGACTC
ACAGGCCCTGGAGAAGCAGCTAACAATGTCTGGTTAGTTAAAAGCCCATTGCCATTTGGTGTGGATTTTC
TACTGTAAGAAGAGCCATAGCTGATCATGTCCCCCTGACCCTTCCCTTCTTTTTTTATGCTCGTTTTCGC
TGGGGATGGAATTATTGTACCATTTTCTATCATGGAATATTTATAGGCCAGGGCATGTGTATGTGTCTGC
TAATGTAAACTTTGTCATGGTTTCCATTTACTAACAGCAACAGCAAGAAATAAATCAGAGAGCAAGGCAT
CGGGGGTGAATCTTGTCTAACATTCCCGAGGTCAGCCAGGCTGCTAACCTGGAAAGCAGGATGTAGTTCT
GCCAGGCAACTTTTAAAGCTCATGCATTTCAAGCAGCTGAAGAAAAAATCAGAACTAACCAGTACCTCTG
TATAGAAATCTAAAAGAATTTTACCATTCAGTTAATTCAATGTGAACACTGGCACACTGCTCTTAAGAAA
CTATGAAGATCTGAGATTTTTTGTGTATGTTTTGACTCTTTTGAGTGGTAATCATATGTGTCTTTATA
GATGTACATACCTCCTTGCACAAATGGAGGGGAATTCATTTTCATCATCGGGAGTGTCCTTAGTGTATAA
AAACCATGCTGGTATATGGCTTCAAGTGTAAAAATGAAAGTGACTTTAAAAGAAAATAGGGGATGGTCC
AGGATCTCCACTGATAAGACTGTTTTTAAGTAACTTAAGGACCTTTGGGTCTACAAGTATATGTGAAAAA
AATGAGACTTACTGGGTGAGGAAATCCATTGTTTAAAGATGGTCGTGTGTGTGTGTGTGTGTGTGTGT
GTGTGTGTTGTGTGTTTTGTTTTTTAAGGGAGGGAATTTATTATTTACCGTTGCTTGAAATTACTGT
GTAAATATATGTCTGATAATGATTTGCTCTTTGACAACTAAAATTAGGACTGTATAAGTACTAGATGCAT
CACTGGGTGTTGATCTTACAAGATATTGATGATAACACTTAAAATTGTAACCTGCATTTTTCACTTTGCT
CTCAATTAAAGTCTATTCAAAGGAAAAAAAAAAAAA AEBP1 mRNA nucleic acid sequence
SEQ ID NO: 35
CGGCTATCCGCGCGGGAGTGCGCCACGCGGGGCCGGAGCGCCTATTAGCCGCCAGGACCTCGGAGCGCCC
CGACCACCCCTGAGCCCCTCTGGCTTCGGAGCCCCCCAGCACCCCCTTCCCGGGTCCCCTCGCCCACCCTA
ATCCACTCTCCCTCCCTTTCCCGGATTCCCTCGCTCACCCCATCCTCTCTCCCGCCCCTTCCTGGATTCC
CTCACCCGTCTCGATCCCCTCTCCGCCCTTTCCCAGAGACCCAGAGCCCCTGACCCCCCGCGCCCTCCCC
GGAGCCCCCCGCGCGTGCCGCGGCCATGGCGGCCGTGCGCGGGGCGCCCCTGCTCAGCTGCCTCCTGGCG
TTGCTGGCCCTGTGCCCTGGAGGGCGCCCGCAGACGGTGCTGACCGACGACGAGATCGAGGAGTTCCTCG
AGGGCTTCCTGTCAGAGCTAGAACCTGAGCCCCGGGAGGACGACGTGGAGGCCCGCGCCTCCCGAGCC
CACCCCGCGGGTCCGAAAAGCCCAGGCGGGGGCAAGCAGGGAAGCGGCCAGGGACGGCCGCAGAAGTG
CCTCCGGAAAAGACCAAAGACAAAGGGAAGAAAGCAAGAAAGACAAAGGCCCCAAGGTGCCCAAGGAGT
CCTTGGAGGGGTCCCCAGGCCGCCCAAGAAGGGAAGGAGAAGCCACCCAAGGCCACCAAGAAGCCCAA
GGAGAAGCCACCTAAGGCCACCAAGAAGCCCAAGGAGAAGCCACCCAAGGCCACCAAGAAGCCCAAAGAG
AAGCCACCCAAGGCCACCAAGAAGCCCCCGTCAGGGAAGGAGCCCCCATTCTGGCTCCTCAGAAACCC
TGGAGTGGCCACTGCCCCCACCCCCCAGCCCTGGCCCTCCGAGGAGCTACCCCAGGAGGGAGGGGCGCCCT
CTCAAATAACTGGCAGAATCCAGGAGAGGAGACCCATGTGGAGGCACGGGAGCACCAGCCTGAGCCGGAG
GAGGAGACCGAGCAACCCACACTGGACTACAATGACCAGATCGAGGGGAGGACTATGAGGACTTTGAGT
ACATTCGGCGCCAGAAGCAACCCAGGCCACCCCCAAGCAGAAGGAGGAGGCCCGAGCGGGTCTGGCAGA
GCCCCCTGAGGAGAAGGCCCCGGCCCCAGCCCGGAGGAGAGGATTGAGCCTCCTGTGAAGCCTCTGCTG
CCCCCGCTGCCCCCTGACTATGGTGATGGTTACGTGATCCCCAACTACGATGACATGGACTATTACTTTG

SEQUENCE LISTING:

```
GGCCTCCTCCGCCCCAGAAGCCCGATGCTGAGCGCCAGACAGACGAAGAGAAGGAGGAGCTGAAGAAACC
CAAAAAGGAGGACAGCAGCCCCAAGGAGGAGACCGACAAGTGGGCAGTGGAGAAGGGCAAGGACCACAAA
GAGCCCCGAAAGGGCGAGGAGTTGGAGGAGGAGTGGACGCTACGGAGAAAGTCAAGTGTCCCCCCATTG
GGATGGAGTCACACCGTATTGAGGACAACCAGATCCGAGCCTCCTCCATGCTGCGCCACGGCCTGGGGGC
ACAGCGCGGCCGGCTCAACATGCAGACCGGTGCCACTGAGGACGACTACTATGATGGTGCGTGGTGTGCC
GAGGACGATGCCAGGACCCAGTGGATAGAGGTGGACACCAGGAGGACTACCCGGTTCACAGGCGTCATCA
CCCAGGGCAGAGACTCCAGCATCCATGACGATTTTGTGACCACCTTCTTCGTGGGCTTCAGCAATGACAG
CCAGACATGGGTGATGTACACCAACGGCTATGAGGAAATGACCTTTCATGGGAACGTGGACAAGGACACA
CCCGTGCTGAGTGAGCTCCCAGAGCCGGTGGTGGCTCGTTTCATCCGCATCTACCCACTCACCTGGAATG
GCAGCCTGTGCATGCGCCTGGAGGTGCTGGGGTGCTCTGTGCCCCTGTCTACAGCTACTACGCACAGAA
TGAGGTGGTGGCCACCGATGACCTGGATTTCCGGCACCACAGCTACAAGGACATGCGCCAGCTCATGAAG
GTGGTGAACGAGGAGTGCCCCACCATCACCCGCACTTACAGCCTGGGCAAGAGCTCACGAGGCCTCAAGA
TCTATGCCATGGAGATCTCAGACAACCCTGGGGAGCATGAACTGGGGGAGCCCGAGTTCCGCTACACTGC
TGGGATCCATGGCAACGAGGTGCTGGGCCGAGAGCTGTTGCTGCTGCTCATGCAGTACCTGTGCCGAGAG
TACCGCGATGGGAACCCACGTGTGCGCAGCCTGGTGCAGGACACACGCATCCACCTGGTGCCCTCACTGA
ACCCTGATGGCTACGAGGTGGCAGCGCAGATGGGCTCAGAGTTTGGGAACTGGGCGCTGGGACTGTGGAC
TGAGGAGGGCTTTGACATCTTTGAAGATTTCCCGGATCTCAACTCTGTGCTCTGGGGAGCTGAGGAGAGG
AAATGGGTCCCCTACCGGGTCCCCAACAATAACTTGCCCATCCTGAACGCTACCTTTCGCCAGATGCCA
CGGTATCCACGGAGGTCCGGGCCATCATTGCCTGGATGGAGAAGAACCCCTTCGTGCTGGGAGCAAATCT
GAACGGCGGCGAGCGGCTAGTATCCTACCCCTACGATATGGCCCTGGAGCTCCGCTACCCAGGAGCAGCTGCTG
GCCGCAGCCATGGCAGCAGCCCGGGGGGAGGATGAGGACGAGGTCTCCGAGGCCCAGGAGACTCCAGACC
ACGCCATCTTCCGGTGGCTTGCCATCTCCTTCGCCTCCGCACACCTCACCTTGACCGAGCCCTACCGCGG
AGGCTGCCAAGCCCAGGACTACACCGGCGGCATGGGCATCGTCAACGGGGCCAAGTGGAACCCCCGGACC
GGGACTATCAATGACTTCAGTTACCTGCATACCAACTGCCTGGAGCTCTCCTTCTACCTGGGCTGTGACA
AGTTCCCTCATGAGAGTGAGCTGCCCCGCGAGTGGGAGAACAACAAGGAGGCGCTGCTCACCTTCATGGA
GCAGGTGCACCGCGGCATTAAGGGGGTGGTGACGGACGAGCAAGGCATCCCCATTGCCAACGCCACCATC
TCTGTGAGTGGCATTAATCACGGCGTGAAGACAGCCAGTGGTGGTGATTACTGGCGAATCTTGAACCCGG
GTGAGTACCGCGTGACAGCCCACGCGGAGGGCTACACCCCGGACGCCAAGACCTGCAATGTTGACTATGA
CATCGGGGCCACTCAGTGCAACTTCATCCTGGCTCGCTCCAACTGGAAGCGCATCCGGGAGATCATGGCC
ATGAACGGGAACCGGCCTATCCCACACATAGACCCATCGCGCCCTATGACCCCCAACAGCGACGCCTGC
AGCAGCGACGCCTACAACACCGCCTGCGGCTTCGGGCACAGATGCGGCTGCGGCGCCTCAACGCCACCAC
CACCCTAGGCCCCCACACTGTGCCTCCCACGCTGCCCCCTGCCCCTGCACCACCCTGAGCACTACCATA
GAGCCCTGGGGCCTCATACCGCCAACCACCGCTGGCTGGGAGGAGTCGGAGACTGAGACCTACACAGAGG
TGGTGACAGAGTTTGGGACCGAGGTGGAGCCCGAGTTTGGGACCAAGGTGGAGCCCGAGTTTGAGACCCA
GTTGGAGCCTGAGTTTGAGACCCAGCTGGAACCCGAGTTTGAGGAAGAGGAGGAGGAGGAGAAAGAGGAG
GAGATAGCCACTGGCCAGGCATTCCCCTTCACAACAGTAGAGACCTACACAGTGAACTTTGGGGACTTCT
GAGATCAGCGTCCTACCAAGACCCCAGCCCAACTCAAGCTACAGCAGCACTTCCCAAGCCTGCTGAC
CACAGTCACATCACCCATCAGCACATGGAAGGCCCCTGGTATGGACACTGAAAGGAAGGGCTGGTCCTGC
CCCTTTGAGGGGGTGCAAACATGACTGGGACCTAAGAGCCAGAGGCTGTGTAGAGGCTCCTGCTCCACCT
GCCAGTCTCGTAAGAGATGGGGTTGCTGCAGTGTTGGAGTAGGGCAGAGGGAGGGAGCCAAGGTCACTC
CAATAAAACAAGCTCATGGCACGGACAAAAAAAAAAAAAAAA
```

CREB5 mRNA nucleic acid sequence

SEQ ID NO: 36

```
AACATTTACAACAAAGTTGATTCTGTGTAGGGTTGGAGGCTAGACAGTTCCACAAATTTTTAGTCACATT
TTCCATGTCAGTTAAATCTAGGGAGTTCAAGACTACTGGAAAAATTAGTCTCATTACTAAAAGAAACTTA
GAGACCGAGGGAGGTACCAGAGTCTAGGAGGTACCTCTGGGTTGCAGAAGTAATTGTAAAATACCAGACC
TGTTCTTTTTACTAAAAGCTAGTTTCACTATCTTCTGGTCTGAAATACTGAGGCAAATACTCAAGACTTA
TTTTCTTCCTAATCTTGCTGGTGAAACAGAAGTTACTAGAAAGAAAGGAAGAAAAAACTTGATTTGGTGA
CTGCAGGAAGCAACACGTTGCTGCTTTTATTCTACAGATAATGATTTATGAGGAATCCAAGATGAATTTG
GAGCAGGAGAGGCCGTTTGTCTGCAGTGCCCCAGGCTGCTCCCAGCGCTTCCCAACAGAGGACCATCTGA
TGATTCATAGGCACAAACATGAAATGACTTTGAAGTTTCCTTCAATAAAAACAGACAATATGTTATCAGA
TCAAACTCCGACCCCAACGAGATTCCTGAAGAACTGCGAGGAGGTGGGCCTCTTCAGCGAGCTGGACTGC
TCCCTGGAGCACGAGTTCAGGAAGGCTCAGGAAGAGGAGAGCAGCAAGCGGAATATCTCGATGCATAATG
CAGTTGGTGGGGCCATGACGGGGCCCGGAACTCACCAGCTTAGCAGCGCTCGGCTGCCCAACCATGACAC
CAACGTTGTGATTCAGCAAGCCATGCCGTCGCCTCAGTCCAGCTCTGTCATCACTCAGGCACCTTCCACC
AACCGCCAGATCGGGCTGTCCCAGGCTCTCTATCTTCTCTGCTACATCTCCACAACAGACAGAGACAGC
CCATGCCAGCCTCCATGCCTGGGACCCTGCCCAACCCTACAATGCCAGGATCTTCCGCCGTCTTGATGCC
AATGGAGCGACAAATGTCAGTGAACTCCAGCATCATGGGGATGCAAGGTCCAAATCTCAGCAACCCCTGT
GCTTCTCCCCAGGTCCAGCCAATGCATTCAGAAGCCAAAATGAGGTTGAAGGCTGCATTGACTCACCACC
CTGCTGCCATGTCAAATGGGAACATGAACACCATGGGACACATGATGGAGATGATGGGCTCCCGGCAGGA
CCAGACGCCACACCATCACATGCACTCGCACCCGCATCAGCACCAGACACTGCCACCCCATCACCCTTAC
CCACACCAGCACCAGCACCCAGCACACCATCCTCACCCTCAACCCCATCACCAGCAGAACCATCCACATC
ACCACTCCCATTCCCACCTTCATGCACACCCAGCACATCACCAGACCTCGCCACATCCGCCCCTGCACAC
CGGCAACCAAGCACAGGTTTCACCAGCAACACAACAGATGCAGCCAACCCAGACAATACAGCCACCCCAG
CCCACAGGGGGCGCCGGCGAAGGGTGGTAGACGAGGATCCGGAGGCGGCGGAAATTTCTGGGAAC
GGAACCGGGCAGCTGCCACCCGCTGCAGACAGAAGAGGAAGGTCTGGGTGATGTCATTGGAAAAGAAAGC
AGAAGAACTCACCCAGACAAACATGCAGCTTCAGAATGAAGTGTCTATGTTGAAAAATGAGGTGGCCCAG
CTGAAACAGTTGTTGTTAACACATAAAGACTGCCCAATAACAGCCATGCAGAAAGAATCACAAGGATATC
TAAGTCCAGAGAGTAGCCCTCCTGCTAGTCCTGTCCCAGCTTGCTCCCAGCAACAAGTCATCCAGCATAA
TACCATCACTACTTCCTCATCGGTCAGCGAGGTGGTAGGAAGCTCCACCCTCAGCCAGCTCACCACTCAC
AGAACAGACCTGAATCCGATTCTTTAAAATGCACCATCAGACCTGGCCTCCAAGAAGAGCTGTAGCGTAC
CATGCGTCCTTTCTTTTAAGGGCATTTTTAGAATTAACTCAGACCTGGAAGACTCCTCAGTTCTTCAAAG
ACTGGCTTTCATTTTTATAGTTATTATGGAAATGTTGTCTTTTATCTTAGTTATATAAGAAAAAGGGA
GTTATGCAATTAATATCTATCAGCTTGGGAAACGCTTTGGTGCTTTTCTCCAGTTTTCTGGTACCAGTTA
CTTGTTTATAAACTGAACCTTTTCTGTATATAGCCATGGTTTCATTCTTATCAGTCCAACCCTTTGCCTG
AAACATTGAATCTTGTTAAACCACAGCTTTTAGCTAAAATGAGGGTATACCTAGATGTCAAGTAAGACAGA
```

SEQUENCE LISTING:

```
TCCAAGGTAACTGGGTAGGAAATCTTTTGACATCTTAACTCATGTTGAGTTTGTGCTGTGGTGTCACCAG
AATTCCAGATAAACACACAGCCTTTCCCATACCTTTTTTTTCTTACTATAAAATATTATAAGATCCATT
GATGTCCAAATAATACCACCAAGCATCTCTTCACCTCTCCTCCTCTTGGTCCACTTGCTAATGCCCAGTT
TTCTTCTCCATTTCCACTTTTTCTTAGGCTCCCTATTTACTATTCATTTTGACTTCCTTCTGTTTTATTT
TTTTCCCTTTAGCATTGCATGTGAATAAGAAAATAATGTTTAAAGAAAAAAAAAAAAAAGCAAACCTCCA
AAACGTGGACCTAACCATTGCTTCACTTACACTTCACCCACAGCTGGAGTTCATTCAACTCTTGCTTTTC
ACAAAATAGTAACCAGGAGATGTTTAATGTGCCTGATTTAATGTTTTTAATAATCACAGCAAATGAAAGG
TGGTTTAGTTATAAGTGAAGCATGGTTGAATACCAGCTGGGGAGACACTAGGGAAGGGAGCTTTGTAAGC
CTTGATTGCGAAAGTCCAAATTTTGATGTGGGCTATAACATGACACCCTTGGATTGCGACTGGTTTTAT
ACGGCCTGCCTATAACGTTGAAAATCCATGTACTACATAATAATTCAGAAGGGCTCTATTCACTACACAG
ATTACATTGTTCAATCATCAGCTGCTAATAGCCTAAGATTTATTTTTTTTTTTTCTTAAGCCTATGGAA
CCGGCTTTGCTGTTCTGGGGGGTGAAAATAGACTAACTACTGGAGAAACAAAGAGAGAAAGAAAACCCAG
TGTTTCCATAGGGGCACTTTTAGCCTTCCCACAACAGTTAAGCACTCTTTGACTGCTGAAGGAACCCCAT
GGATGAGGTGCAGGCTACTTCACTCTTTTTTTTTCTTTTTGAGACAGAGTCTCACCTATTGCCCAGACT
GAAGTGCAGTGGTGCGATCATGGATCACTGCAGCAGCATCCTCCGAGTTCAAGCTATCCTTCCACCTCCG
CCTCCTGAGTAGCTGGGACCACAGGTTCACATAACCATGCCTGGCTAATTTATTTTTACTTTTATTTTAA
AATAAAAGATGAGGTC+32CTTATGTTGCCCAGGCTGGTCTCAAACTATCCTACTTCTTCCTCCCAAAGT
GTTGGGATTATAGGTGTGAGCCACTGCACCCAGCCTACTTCACTCTTCTGAATTATTCTGATTTATTTTC
AACAACTTTTGTGAACTTGCCCGTGATACAAAGCAGATAGTCCCTGAACCACAGTCGTGCCTCCTTGAAA
CAAGCCATTCTACTGTGCTAATGTTTTAATATCACATCTCACAAATAACAGGGGTGAATGTTTCTCTCTA
GCAATCTAGGCAGGTGCTGGTGTTTCATCTCCATTTGAATGCTTGACCTCTTAATGTGTGTGTGTGTGTG
TGTGTGTGTGTGTGTTCATGGGTTTTAAAAGAACAGTATTTTACAAAAGGTGTAGCTTTTATAAGAGT
GCAGAAAAGGGAAGGATGTGTTTTTTTCTCTCACTATAGTATAAGAATCTATTTGGAGAAAAAAAGAAA
ATATGAGGGTCTCGAAGCATGATTTTTATATAACTAGTTTCAGTTTTATCTAATAACTTACTTTTTAAAT
CAATATTTATCAACAATCTTTCCTTGTATGCAGTGCTTTCAAAAGATGGTTTTGAGTGTCCAGTGAAACT
TATGACTTGGATATATGGTTGAAGAATCAAACAAAAGCAAAAAAAAAAAGCAAAAAAAGAAAGAGAAA
AAAAGAAAAAATGCAAATGGAATAATTTTCTATTATATTTTAGACAAACATATCATTTTCGAGTATTTA
AATACTGAATTCATAGTTGTTGTTTTTTAAATTCCAACAGTAACAGCTGAATGGTTTAATCTGACTGGCT
TCCTAAGAAATGTTTAAGACTCAGCTTTAAAAAGAAGTTAACATTCATATCTCTGTTTTGAAATCAAAAA
TCATATTTCAAAATTCTTTCCTAGGACCATCTATGTGTCTCCCCTCCCCTCCACAAAAAGGAGAAAGAGT
GCATTAAAATGTTTAGTTGGGTTTTTAATTTTTAATTTTTATGTTATGTTTTGCTTTGTTTTAAGTAAA
CAAAAATTTTTCTTTCTTTACTGCATGCATAGCACTTAATAAAATGGATTTTTAAAAAATCCACTAGTAA
TATCAGAATGTCCAGGGAGTGACTGTCACTACAATGATGGTTTAGTTTACTTCTGTTCCACCTTTTGATT
GAAATATTTAGTTGTTAGGCTGAAAGCCTCGGCAGTTAAGAACTTGCCTGAGTTTTCTTCGTTCAGCAAC
TTGACAGTTTGACTGATGTGCATTATATATAGCTCAATTATGTCTGTTTTTTATGCTAAGTAGGAAAACC
AACCACACACATTAGCAAACCGGCCTCAACATATAATTAGAATAAACTGTCTTCTTGTTCTACTCAGGGC
CTTTAGGTGTGTTCATTCACGGTATGGAAATACAGTAAATGAAAGATTCCAACTAGTTGTCAGTGCTTCT
TGAAATTCCAAACAGAAAGATACATTGGTCAAATCCAACACTTGGCTTATCAATATTAAGTCTTTTACCT
AAAGGCCCAGCCGTCACCAGACAACAGAATAATCAATCTGCCTGAAAATCCCTCCTCCTTGTCCTACACT
TTTTGCCTGTTTGGGAGAATATCTTTGTACTCCATTCTCCTCCCTCAGCCAGTTACTGGGTCACCCATCC
ATGTGTTCATGAATCAATCATCGGCCTGCAGAGCACCTGTCCTAAGGAGGGAAAATCCTGTCACACTG
CCTCTCCCCATTCGTGTGTGGTTTTCTTGATCGGTGAGATCTGTCTCTGAAGTCACTGCCAGCCTCCCTG
GGAACGTCTATAGTGCCTCCCCTGCCTTATGTGATGGGAGTTAACAACTCAGATAAGTACACCTGAGAGC
ATTTCTATCAGGTAAACTGTCACTTAAATGGAGGTGTCCACATCTTAATTGTTTCTCCTTGACACATTTC
TCAATCCACGAAGCCAGGAGAGGTAGAGTGAAAATCCCAGCTGGTGAATGTACTAATTTGAAAGCCA
AGTGTTAAGTCGGATGTTTTCCCGTTACACTACTACTCAGCCCTCTCCTGCGGCCACATCAACGGATGCA
AGTCACAGTCTTAACACAGCCTGTGGGAGACAAGCAGTTTGTGTGCTCACAGTATATATTATAGTAATTA
GGGTGACTTAGAGCAAATACTCTTCAGATCCTATGTAGTCAGTGAAACAAAATGGAGAGCGTATTCTGAT
AGAAGGACGTCGACGGTGAATGTTCTGGTGGTTGTTGCCTGTTAAGTAAACTTTAGTGTGTAAGTTGAGT
TTGTCATTAAAATCATAAACCAGCTGCGGTAACAGACAAGCCTTTGGCTGGGGAGTTTTAAGCCTCGGTA
ACTGCTATAAAACTAGCCATCCAGTTAGGATAGAATGTGTTTCTTTCTGGTTAAAAAAAGGAAAACCAT
CTAAGAAAATATATATGTATGTATGTGTATACAGTGGAATTCAAAGGACCAAAGCAAAATTTGAACAG
GAATCTATTAATTTAGAATTTTATAAGATATTTATTAATAAAATGTTATTTTTAAACATTCCATTTGAACA
GTATTCTGTAGGATCTACTTGTTTTTAAAGTGTTAGTCCATAATAAACTACTATAGTTATGTGTATTTTC
ATTTTTTCAGGGTTTCAAATGGCTATTCTCCATCATTTGGTGGAAATGTTTGCTTAGATCTCTGTGCATAG
ACATTTCAAGGATTTTTATTGCTCTGTGAGTTATTTTTAATCAACATTCTGAACAGTTTTTTTTAAACA
TTTATTTCTGTGTGTTCATTTTTAAAGTAAGCTCTTTCATTTAGGAAGCAGAGTTCAGCTAAAGGGAATC
AGTAACTCTAACTGGAACAGCTTTCTTGTAGAAGTGTAAAAACAGCTTCATCTCTGCCTCTCTCCACCCC
ACCCCAATTTCCTAGAAAGCCTTGCACTATTCAGCTCCCTTAGTGCTTTTTGTCCCTTCCCGAACAATAT
GCAGTAGCTTTAAGCCATTCAAGCTCCATTATGCAGTATATCTGAGAAGGGAAAGGAAACAACCCATTTA
AATTTGAATAAAACCGTGCCTATGCGAACAGTAGCAATTTAGAATCTCTTTTCTGCTTTTAAATAATTT
ATATTTAAAAATTGCACTTTAGCTTTTTGATCCCTTTGTATTTCTCTTATTCTCTTTCTAACCTCTTCTC
TGTCCTCAAACTTGCCTTTGCTCTCCTTTACAATACCCCCACCCCTCCTCCAAGGCTCTGAGCGGCATC
ATTTAAAATACTTTACAGATATTTGCACCAGGTACATTTATGTGCGTCCATTGGTAGCACAGCTGAGACC
TGTGTCTCACATCAGCCTAGGTGAAGCCTACTACAAGAATGCCAAGGAGAAGAGCCAGTACACTATATGG
TTTATACTCTTTTATCCCTTTATTCATAGCATGTTTTTTAAAAATGTTATATTATGCAACAGATGTGAGGC
AGCAGCTAAGCTATACTTAAGAATTTTCTCTCACCTTCCAAACCAAAGTGTCCTGAATAAGCCAGGAGAC
TTATTCTTTTGTGCACCCTGGTGCACATCTGACTGTTGTCCTAGCCATAGACTCTCTGAGGCCACTGAAA
GAACAGTGGCCCTATCGATTTCATTCCTAGGTCTCAAAAATACAATGTTGCCTTGTAACATAATTAGGGA
CAGCACCTCTATTTCACAATTATAATCTAAGGTAGGATAAGACGACACAGCAGCAATAAACTTACAAGTA
AAATTCAATACCAAAACAAAACACAAAGAAATTTAAAAAACAAAAAACCTAGCTCATCATGTTGTGAAAT
GAAAAGTGAATGTCCATTCAAAATATTTTACTATTTCTTGTGGAGTTTTTCAGTGATGTAATGCTTGTA
GCCAAATTGCTTAAAGAGTGTTTATATATTTTTTCCTTATAAATTGTCTATTTTTAAAAAAGCTATTT
AACCACAGCTGAAGTGGGGGTAAGGCCAAATTGCCAACACTTGTTAAAAGATTAATACTCTTAAGTGGC
ACTCTGATACCTTTCCAACTTGTCATCAGAAAGGAATCAATAATTACCAACTGTTGTATTTAGACCAACT
TACAATATCTAGCTCATTAGAAGCCAGGATCTAGAAAGCTCCTTCTAAGCCATTTAAGATATTCTTACAT
TGAGCTTCATATTATAGAACTTTATAGGATTGGATATTTTACAATAGAATAATTTAGCCTCAGGACTGAG
```

SEQUENCE LISTING:

AATGTGGAAGCTGAATAAATTAGCTTTAAATACATCATTAAAATCTTATGCACAATAAGCTCATTAGATT
CTAGTTTTCTCCTTTAGAATACCAATGCCACAGACACTACAGGAGATAATGAAAGGTATCAGTTGTGTTG
AGTGGAGGGAGTTTAAGAGAAAGGACCCTTCCCAACCAGCAGCCAGTAGAAAATACAACCTACTCACCTT
TTTCCCTTCTAAGTTCTGCTAAATCACATCTGCCTCATAGAGAAAGGAATGTTGCCTTTGAGAACTGTCT
TGGAGAACAGATAAGCTTGAAATGTTCTCTCTAGAGAGGACATAGGGTTTGGGATCCTCTGAAAAGGCCC
AGAAAAATAGCTCAGTTCAAATACAATGTTCTAGGACAATTGGAATATAAATATTGTCCAAAAATATAAT
TAAAAGAAAAAAGTTTAGCACTGTGTAAAGTAAGTGTTAACTGAGGAAGTCCCAAAAAGGTGCTGTCACT
TTAAGTTCTGGACTTGGGGTTCTTTGTATTTGTAAACAGCAAAGCATTTGTGTTTGTTTGTCTATTTGTA
AAGCAACCACCTTCCTTATTGGAAGGAGAAAAAAGGGGTACATACATGTAAATACTTGCTGCAGCATTT
AATATGTTTAATTTTGTGTTAAGCTTTTTGTTGCATCGTGAACACATTTATTGTTACCAATGGACAATGA
GTTCATTAAGACTGTTCAACTAGGTCAGATTTTTACATCTCTTTCTAGCAAGAAGAGACAAGATTTTGTG
CATTTGTACAAATGTTAATATCACTGCAATTCCAATATAATAAAGCACTCAAATGCAAATAA

ERG mRNA nucleic acid sequence
SEQ ID NO: 37
TTCATTTCCCAGACTTAGCACAATCTCATCCGCTCTAAACACCTCATCAAAACTACTTTCTGGTCAGAG
AGAAGCAATAATTATTATTAACATTTATTAACGATCAATAAACTTGATCGCATTATGGCCAGCACTATTA
AGGAAGCCTTATCAGTTGTGAGTGAGGACCAGTCGTTGTTTGAGTGTGCCTACGGAACGCCACACCTGGC
TAAGACAGAGATGACCGCGTCCTCCTCCAGCGACTATGGACAGACTTCCAAGATGAGCCCACGCGTCCCT
CAGCAGGATTGGCTGTCTCAACCCCCAGCCAGGGTCACCATCAAAATGGAATGTAACCCTAGCCAGGTGA
ATGGCTCAAGGAACTCTCCTGATAATGCAGTGTGGCCAAAGGCGGGAAGATGGTGGGCAGCCCAGACAC
CGTTGGGATGAACTACGGCAGCTACATGGAGGAGAAGCACATGCCACCCCCAAACATGACCACGAACGAG
CGCAGAGTTATCGTGCCAGCAGATCCTACGCTATGGAGTACAGACCATGTGCGGCAGTGGCTGGAGTGGG
CGGTGAAAGAATATGGCCTTCCAGACGTCAACATCTTGTTATTCCAAGAACATCGATGGGAAGGAACTGTG
CAAGATGACCAAGGACGACTTCCAGAGGCTCACCCCCAGCTACAACGCCGACATCCTTCTCTCACATCTC
CACTACCTCAGAGAGACTCCTCTTCCACATTTGACTTCAGATGATGTTGATAAAGCCTTACAAAACTCTC
CACGGTTAATGCATGCTAGAAACACAGGGGGTGCAGCTTTTATTTTCCCAAATACTTCAGTATATCCTGA
AGCTACGCAAAGAATTACAACTAGGCCAGATTTACCTATAGAGCCCCCCAGGAGATCAGCCTGGACCGGT
CACGGCCACCCCACGCCCCAGTCGAAAGCTGCTCAACCATCTCCTTCCACAGTGCCCAAAACTGAAGACC
AGCGTCCTCAGTTAGATCCTTATCAGATTCTTGGACCAACAAGTAGCCGCCTTGCAAATCCAGGCAGTGG
CCAGATCCAGCTTTGGCAGTTCCTCCTGGAGCTCCTGTCGGACAGCTCCAACTCCAGCTGCATCACCTGG
GAAGGCACCAACGGGGAGTTCAAGATGACGGATCCCGACGAGGTGGCCCGGCGCTGGGGAGAGCGGAAGA
GCAAACCCAACATGAACTACGATAAGCTCAGCCGCGCCCTCCGTTACTACTATGACAAGAACATCATGAC
CAAGGTCCATGGGAAGCGCTACGCCTACAAGTTCGACTTCCACGGGATCGCCCAGGCCCTCCAGCCCCAC
CCCCCGGAGTCATCTCTGTACAAGTACCCCTCAGACCTCCCGTACATGGGCTCCTATCACGCCCACCCAC
AGAAGATGAACTTTGTGGCGCCCCACCCTCCAGCCCTCCCCGTGACATCTTCCAGTTTTTTGCTGCCCC
AAACCCATACTGGAATTCACCAACTGGGGGTATATACCCCAACACTAGGCTCCCCACCAGCCATATGCCT
TCTCATCTGGGCACTTACTACTAAAGACCTGGCGGAGGCTTTTCCCATCAGCGTGCATTCACCAGCCCAT
CGCCACAAACTCTATCGGAGAACATGAATCAAAGTGCCTCAAGAGGAATGAAAAAAGCTTTACTGGGGC
TGGGGAAGGAAGCCGGGGAAGAGATCCAAAGACTCTTGGGAGGGAGTTACTGAAGTCTTACTACAGAAAT
GAGGAGGATGCTAAAAATGTCACGAATATGGACATATCATCTGTGGACTGACCTTGTAAAAGACAGTGTA
TGTAGAAGCATGAAGTCTTAAGGACAAAGTGCCAAAGAAAGTGGTCTTAAGAAATGTATAAACTTTAGAG
TAGAGTTTGGAATCCCACTAATGCAAACTGGGATGAAACTAAAGCAATAGAAACAACACAGTTTTGACCT
AACATACCGTTTATAATGCCATTTTAAGGAAAACTACCTGTATTTAAAAATAGAAACATATCAAAAACAA
GAGAAAAGACACGAGAGAGACTGTGGCCCATCAACAGACGTTGATATGCAACTGCATGGCATGTGCTGTT
TTGGTTGAAATCAAATACATTCCGTTTGATGGACAGCTGTCAGCTTTCTCAAACTGTGAAGATGACCCAA
AGTTTCCAACTCCTTTACAGTATTACCGGGACTATGAACTAAAAGGTGGGACTGAGGATGTGTATAGAGT
GAGCGTGTGATTGTAGACAGAGGGGTGAAGAAGGAGGAGGAAGAGGCAGAGAAGGAGGAGACCAGGGCTG
GGAAAGAAACTTCTCAAGCAATGAAGACTGGACTCAGGACATTTGGGGACTGTGTACAATGAGTTATGGA
GACTCGAGGGTTCATGCAGTCAGTGTTATACCAAACCCAGTGTTAGGAGAAAGGACACAGCGTAATGGAG
AAAGGGGAAGTAGTAGAATTCAGAAACAAAATGCGCATCTCTTTCTTTGTTTGTCAAATGAAATTTTA
ACTGGAATTGTCTGATATTTAAGAGAAACATTCAGGACCTCATCATTATGTGGGGCTTTGTTCTCCACA
GGGTCAGGTAAGAGATGGCCTTCTTGGCTGCCACAATCAGAAATCACGCAGGCATTTTGGGTAGGCGGCC
TCCAGTTTTCCTTTGAGTCGCGAACGCTGTGCGTTTGTCAGAATGAAGTATACAAGTCAATGTTTTCCC
CCTTTTTATATAATAATTATATAACTTATGCATTTATACACTACGAGTTGATCTCGGCCAGCCAAAGACA
CACGACAAAAGAGACAATCGATATAATGTGGCCTTGAATTTTAACTCTGTATGCTTAATGTTTACAATAT
GAAGTTATTAGTTCTTAGAATGCAGAATGTATGTAATAAAATAAGCTTGGCCTAGCATGGCAAATCAGAT
TTATACAGGAGTCTGCATTTGCACTTTTTTAGTGACTAAAGTTGCTTAATGAAAACATGTGCTGAATGT
TGTGGATTTTGTGTTATAATTTACTTTGTCCAGGAACTTGTGCAAGGGAGCCAAGGAAATAGGATGTT
TGGCACCCAAATGGCGTCAGCCTCTCCAGGTCCTTCTTGCCTCCCCTCCTGTCTTTTATTTCTAGCCCCT
TTTGGAACAGAAGGACCCCGGGTTTCACATTGGAGCCTCCATATTTATGCCTGGAATGGAAAGAGGCCTA
TGAAGCTGGGGTTGTCATTGAGAAATTCTAGTTCAGCACCTGGTCACAAATCACCCTTAATTCCTGCTAT
GATTAAAATACATTTGTTGAACAGTGAACAAGCTACCACTCGTAAGGCAAACTGTATTATTACTGGCAAA
TAAAGCGTCATGGATAGCTGCAATTTCTCACTTTACAGAAACAAGGGATAACGTCTAGATTTGCTGCGGG
GTTTCTCTTTCAGGAGCTCTCACTAGGTAGACAGCTTTAGTCCTGCTACATCAGAGTTACCTGGGCACTG
TGGCTTGGGATTCACTAGCCCTGAGCCTGATGTTGCTGGCTATCCCTTGAAGACAATGTTTATTTCCATA
ATCTAGAGGTCAGTTTCCCTGGGCATCTTTTCTTTGAATCACAAATGCTGCCAACCTTGGTCAGGTGAAG
GCAACTCAAAAGGTGAAAATACAAGGTGACCGTGCGAAGGCGCTAGCCGAAACATCTTAGCTGAATAGGT
TTCTGAACTGGCCCTTTTCATAGCTGTTTCAGGGCCTGTTTTTTTCACGTTGCAGTCCTTTTGCTATGAT
TATGTGAAGTTGCCAAACCTCTGTGCTGTGGATGTTTTGGCAGTGGGCTTTGAAGTCGGCAGGACACGAT
TACCAATGCTCCTGACACCCCGTGTCATTTGGATTAGACGGAGCCCAACCATCCATCATTTTTGCAGCAGC
CTGGGAAGGCCCACAAAGTGCCCGTATCTCCTTAGGGAAATAAATAAATACAATCATGAAAGCTGGCAG
TTAGGCTGACCCAAACTGTGCTAATGAAAAGATCAGTCATTTTTATTTTGGAATGCAAAGTCAAGACAC
ACCTACATTCTTCATAGAAATACACATTTACTTGGATAATCACTCAGTTCTCTCTTCAAGACTGTCTCAT
GAGCAAGATCATAAAAACAAGACATGATTATCATATTCAATTTTAACAGATGTTTTCCATTAGATCCCTC
AACCCTCCACCCCAGTCCAGGTTATTAGCAAGTCTTATGAGCAACTGGGATAATTTTGGATAACATGAT
AATACTGAGTTCCTTCAAATACATAATTCTTAAATTGTTTCAAAATGGCATTAACTCTCTGTTACTGTTG

```
TAATCTAATTCCAAAGCCCCCTCCAGGTCATATTCATAATTGCATGAACCTTTTCTCTCTGTTTGTCCCT
GTCTCTTGGCTTGCCCTGATGTATACTCAGACTCCTGTACAATCTTACTCCTGCTGGCAAGAGATTTGTC
TTCTTTTCTTGTCTTCAATTGGCTTTCGGGCCTTGTATGTGGTAAAATCACCAAATCACAGTCAAGACTG
TGTTTTGTTCCTAGTTTGATGCCCTTATGTCCCGGAGGGGTTCACAAAGTGCTTTGTCAGGACTGCTGC
AGTTAGAAGGCTCACTGCTTCTCCTAAGCCTTCTGCACAGATGTGGCACCTGCAACCCAGGAGCAGGAGC
CGGAGGAGCTGCCCTCTGACAGCAGGTGCAGCAGAGATGGCTACAGCTCAGGAGCTGGGAAGGTGATGGG
GCACAGGGAAAGCACAGATGTTCTGCAGCGCCCCAAAGTGACCCATTGCCTGGAGAAAGAGAAGAAAATA
TTTTTTAAAAAGCTAGTTTATTTAGCTTCTCATTAATTCATTCAAATAAAGTCGTGAGGTGACTAATTAG
AGAATAAAAATTACTTTGGACTACTCAAAAATACACCAAAAAAAA
```

FOSL2 mRNA nucleic acid sequence

SEQ ID NO: 38

```
CGAACGAGCGGCGCTCGGCGGGGACAGAAAGAGGGGAGAGAGAGAGAGAGAGGGGAGAGGCGCGGCCG
GGCGAGGCGGGCCCGTCCGGGAGCGGGCTCCGGGGAAGGGGTGCGGGTCTGGGCGCCGGAGCGGGGAGCG
GGGCCGCGTCCCTCTCAGCGCCAGCTCTACTTGAGCCCCACGAGCCGCTGTCCCCCTGGCGCGCTCGGGG
CCGCGGGACGGGCGCACGCCGCCTTCTCCTAGTCAAGTATCCGAGCCGCCCCGAAACTCGGGCGGCGAGT
CGGCCACGGGAAGTTTATTCTCCGGCTCCTTTTCTAAAAGGAAGAAACAGAAGTTTCTCCCAGCGGACAG
CTTTTCTTTCCGCCTTTTTGGCCCTGTCTGAAATCGGGGGTCCCCAGGGCTGGCAGGCCAGGCTCGCTGG
GCTCCTAATCTTTTTTTTAATTTCCAATTTTTGATTGGGCCGTGGGTCCCCGCTGAGCTCCGGCTGCGCG
CGGGGCGGGAGGGCGCGCCAGGGGAGGGACCGAGAGACGCGCCGACTTTTTAGAGGGAGGGATCGGGT
GGACAACTGGTCCCGCGGCGCTCGCAGAGCCGGAAAGAAGTGCTGTAAGGGACGCTCGGGGGACGCTGTT
CCTGAGGTGTCGCCGCCTCCCTGTCCTCGCCCTCCGCGGTGGGGGAGAAACCCAGGAGCGAAGCCCAGAG
CCCGCGGCGCGGCCGGCGGACGAACGAGCGCGCAGCAGCCGGTGCGCGGCCGCGGCGAGGGCGGGGAAG
AAAAACACCCTGTTTCCTCTCCGGGCCCCACCGCGGATCATGTACCAGGATTATCCGGAACTTTGACA
CCTCGTCCCGGGGCAGCAGCGGCTCTCCTGCGCACGCCGAGTCCTACTCCAGCGGCGGCGGCGGCCAGCA
GAAATTCCGGGTAGATATGCCTGGCTCAGGCAGTGCATTCATCCCCACCATCAACGCCATCACGACCAGC
CAGGACCTGCAGTGGATGGTGCAGCCCACAGTGATCACCTCCATGTCCAACCCATACCCTCGCTCGCACC
CCTACAGCCCCCTGCCGGGCCTGGCCTCTGTCCCTGGACACATGGCCCTCCCAAGACCTGGCGTGATCAA
GACCATTGGCACCACCGTGGGCCGCAGGAGGAGAGATGAGCAGCTGTCCTGAAGAGGAGGAGAAGCGT
CGCATCCGGCGGGAGAGGAACAAGCTGGCTGCAGCCAAGTGCCGGAACCGACGCCGGGAGCTGACAGAGA
AGCTGCAGGCGGAGACAGAGGAGCTGGAGGAGGAGAAGTCAGGCCTGCAGAAGGAGATTGCTGAGCTGCA
GAAGGAGAAGGAGAAGCTGGAGTTCATGTTGGTGGCTCACGGCCCAGTGTGCAAGATTAGCCCCGAGGAG
CGCCGATCGCCCCCAGCCCTGGGCTGCAGCCCATGCGCAGTGGGGGTGGCTCGGTGGGCCTGTAGTGG
TGAAACAGGAGCCCCTGGAAGAGGACAGCCCCTCGTCCTCGTCGGCGGGGCTGGACAAGGCCCAGCGCTC
TGTCATCAAGCCCATCAGCATTGCTGGGGGCTTCTACGGTGAGGAGCCCCTGCACACCCCCATCGTGGTG
ACCTCCACACCTGCTGTCACTCCGGGCACCTCGAACCTCGTCTTCACCTATCCTAGCGTCCTGGAGCAGG
AGTCACCCGCATCTCCCTCCGAATCCTGCTCCAAGGCTCACCGCAGAAGCAGTAGCAGCGGGGACCAATC
ATCAGACTCCTTGAACTCCCCCACTCTGCTGGCTCTGTAACCCAGTGCACCTCCCTCCCCAGCTCCGGAG
GGGGTCCTCCTCGCTCCTCCTTCCCAGGGACCAGCACCTTCAAGCGCTCCAGGGCCGTGAGGGCAAGAGG
GGGACCTGCCACCAGGGAGCTTCCTGGCTCTGGGGGACCCAGGTGGGACTTAGCAGTGAGTATTGGAAGA
CTTGGGTTGATCTCTTAGAAGCCATGGGACCTCCTCCCTCATTCATCTTGCAAGCAAATCCCATTTCTTG
AAAAGCCTTGGAGAACTCGGTTTGGTAGACTTGGACATCTCTCTGGCTTCTGAAGACCTGAAGCTGGCC
TGGACCATTCCTGTCCCTTTGTTACCATACTGTCTCTGGAGTGATGGTGTCCTTCCCTGCCCCACCACGC
ATGCTCAGTGCCTTTTGGTTTCACCTTCCCTGACTTGACCCCTTTCCTCCCCCAGCGTCAGTTTCACTCC
CTCTTGGTTTTTATCAAATTTGCCATGACATTTCATCTGGGTGGTCTGAATATTAAAGCTCTTCATTTCT
GGAGATGGGGCAGCAGGTGGCTCTTCTGCTGGGGCTGACTTGTCCAGAAGGGGACAAAGTGCAATACAGA
GCCTTCCCTACCCTGACGCCTCCCAGTCATCATCTCCAGAACTCCCAGCGGGCTCCCTGAGCTCTCAAG
GAGATGCTGCCATCACTGGGAGGCTCAGAGGACCCTTCCTGCCCACCTTCGGAGACGGCTTCTGGAGGAA
CGGCTTGGCCAGAAGACAGGGTGTGAGTGAGACAGTGGGGCACAGGTTGGGTTTGCCAAACGCCTAATTA
CCAGGCCAGGAAGCATGCCAACAAAGCCACACGGGTGTCCTAGCCAGCTTCCCTTCACCTGGTGTCTTGA
GTAGGGCGTCTCCTGTAATTACTGCCTTGCCATTCTGCCCCTGGACCCTTCTCTCCGGACCAGGGAGGCG
TCCCTCCCTAGGAGCCACACATTATACTCCAAGTCCCTGCCGGGCTCCGCCTTTCCCCCACCCTGGCTCT
CAGGGTGACGCCACCCACAGAGATTTAATGAGCGTGGGCCTGGACCTTCCCCAGATGCTGCCAGGCAGCC
CCTCCCCAAGCCTCAAAGAAGCATTTGCTGAGGATGGAGAGGCAGGGGAGGGAGGCGGGAGGCCGTCACT
GGAGTGGCGTCTGCAGCAGCTGCTGCCCCAGCACCCGCTCAGCCTGTCCTGGCTGCTCACCTCCCCGCAG
GGCACCGGGCCTTTCCTGCCCTCTGTGGTCATCTGCCACCTGCTGGATCAAGTGCTTTCTCTTTTACACT
CCCCTGTCCCCACCCCAGTGCACTCTTCTGGCCCAGGCAGCAAGCTGTGAACAGCTGGCCTGAGCT
GTCGCTGTGGCTTGTGGCTCATGCGCCATTCCTGGTTGTCTGTTGAATCTTTCTGGCTGCTGGAATTGGA
GATAGGATGTTTTGCTTCCCACTGCAGGAGAGCTGCCCCCTTTCACGGGGTTGGGGAAGGGTCCCCCTGG
CCTCCAGCAGGAGCACAGCTCAGCAGGGTCCCTGCTGCCCACCCCTCTGAGCCTTTTCTCCCCAGGGTAT
GGCTCCTGCTGAGTTTCTTGTCCAGCAGGGCCTTGACAGGAATCCAGGGAGTAGCTCTGGCCAGACCA
GCCTCTGCGGGCTTGTGCTCTGCAAAGACTCTGCTGCTGGGGATTCAGCTCTAGAGGTCACAGTATCCT
CGTTTGAAAGATAATTAAGATCCCCGTGGAGAAAGCAGTGACACATTCACACAGCTGTTCCCTCGCATG
TTATTTCATGAACATGACCTGTTTTCGTGCACTAGACACACAGAGTGGAACAGCCGTATGCTTAAAGTAC
ATGGGCCAGTGGGACTGGAAGTGACCTGTACAAGTGATGCAGAAAGGAGGGTTTCAAAGAAAAAGGATTT
TGTTTAAAATACTTTAAAAATGTTATTTCCTGCATCCCTTGTGATGCCCCTCTCCCGATTTCCAG
GGGCTCTGGGAGGGACCCTTCAAGAAGATTGGGCAGTTGGGTTTCTGGCTTGAGATGAATCCAAGCAGC
AGAATGAGCCAGGAGTAGCAGGAGATGGGCAAAGAAAACTGGGGTGCACTCAGCTCTCACAGGGGTAATC
ATCTCAAGTGGTATTTGTAGCCAAGTGGGAGCTATTTTCTTTTTTGTGCATATAGATATTTCTTAAATGA
AAAAAAAAAAAAAAAAAAAAAAAA
```

HOXA7 mRNA nucleic acid sequence

SEQ ID NO: 39

```
GTGCTGCGGCGAGCTCCGTCCAAAAGAAATGGGGTTTGGTGTAAATCTGGGGGTGTAATGTTATCATAT
ATCACTCTACCTCGTAAAACCGACACTGAAAGCTGCCGGACAACAAATCACAGGTCAAAATTATGAGTTC
TTCGTATTATGTGAACGCGCTTTTTAGCAAATATACGGCGGGGCTTCTCTGTTCCAAAATGCCGAGCCG
ACTTCTTGCTCCTTTGCTCCCAACTCACAGAGAAGCGGCTACGGGGCGGGCGCCGGCGCCTTCGCCTCGA
```

```
CCGTTCCGGGCTTATACAATGTCAACAGCCCCCTTTATCAGAGCCCCTTTGCGTCCGGCTACGGCCTGGG
CGCCGACGCCTACGGCAACCTGCCCTGCGCCTCCTACGACCAAAACATCCCCGGGCTCTGCAGTGACCTC
GCCAAAGGCGCCTGCGACAAGACGACGAGGGCGCGCTGCATGGCGCGGCTGAGGCGCAATTTCCGCATCT
ACCCCTGGATGCGGTCTTCAGGACCTGACAGGAAGCGGGGCCGCCAGACCTACACGCGCTACCAGACGCT
GGAGCTGGAGAAGGAGTTCCACTTCAACCGCTACCTGACGCGGCGCCGCCGCATTGAAATCGCCCACGCG
CTCTGCCTCACCGAGCGCCAGATTAAGATCTGGTTCCAGAACCGCCGCATGAAGTGGAAGAAAGAGCATA
AGGACGAAGGTCCGACTGCCGCCGCAGCTCCCGAGGGCGCCGTGCCCTCTGCCGCCGCCACTGCTGCCGC
GGACAAGGCCGACGAGGAGGACGATGATGAAGAAGAGGAAGACGAGGAGGAATGAGGGGCCGATCCGGGG
CCCTCTCTGCACCGGACAGTCGGAAAAGCGTCTTTAAGAGACTCACTGGTTTTACTTACAAAATGGGAA
AAATAAAAGAAAATGTAAAAAACAAAAACAAAAACAAAAAAGCAACCCAGTCCCCAACCTGCACTCTACC
CACCCCCATCACCTACTCCAGCTCCCAACTTTTGTGGACTGAGCGGCCGCAGAGACTGGGTCGCCTTGGA
TTCCCTCTGCCTCCGAGGACCCCAAAAGACACCCCCAACCCCAGGCCAGCCGGCCCTGCTCTGGCGCGTC
CAAAATACTACCTAGCACAGGCCTCTGCTCGAGGCACCCCCAAACTACCTATGTATCCAGCCCCAGAGGG
CCTCCATTCCCAGGAAGTCCCTATGTATCCCAACACTGGCAGACACCCAGCACCACCCTCCCAGACCCGC
AAGAAAGTGAATCTCACTACTACTACTCCCCTAAAACTACCTATTTTGTGCTGGCTGGCTTGCCTGCTA
CCTAGTGCCGACTGCTCCCAGGCAAGTCCCCTGCTGCTTACAGCCCGCAGCTTTTGGGGTCCCTGAGGCT
GCCCTGAGAATGTGCTGAGGTCCAGGATCAGGGTATTGGCATCTATTTAAATCGAAAAATAATATATTTA
TTCCAAAAGCATCCTAAGTGCTTGCACCCTAGAATCAATCCCTCCTTCTCTGGCTTGGCACCCACAGCT
CAGGCCCATCAACCCCCACTTCTGGAGGGGAATGTTCCTGAGCTGGCTGCAGATCTGTGGGTTAGCTTCT
GCTTAGCAGGACTGTGGAGATGCTTCCAGCTTCGCTGTCCTTTCCTCTGGCTCCTCTGTATCTTACTGTTCA
GCTGTGTTAAATATGTACGCCCTGATGTTTCCTATAATAGCAGATACTGTATATTTGAACAAGATTTTTT
TTTATCATTTCTATAGTCTTGGAGTTCATTTGTAAGGCAGTGTCTTGACTTGGAAAGGATGTGTTAATGG
GGTGACTTTGTAGCATGGTATGTTGTCTTGAGTTAACTGTAGTGGGTGGGAGGTCCAATGCCCTCCGCA
ATGCCCTTCATCTCCTGTGTTGTCCTGTACCCTGCTCAGCTCCATCCTGGGGTTCAGGGAAGGCACACTT
CCCAGCCCAGCTGTGTTTTATGTAACCGAAAATAAAGATGCGTGGTGACAAAGAAAAA
```

IL11RA mRNA nucleic acid sequence
SEQ ID NO: 40
```
AGAGGGCGAGGGCGAGGGCAGAGGGCGCTGGCGGCAGCGGCCGCGGAAGATGAGCAGCAGCTGCTCAGGG
CTGAGCAGGGTCCTGGTGGCCGTGGCTACAGCCCTGGTGTCTGCCTCCTCCCCCTGCCCCAGGCCTGGG
GCCCCCAGGGGTCCAGTATGGGCAGCCAGGCAGGTCCGTGAAGCTGTGTTGTCCTGGAGTGACTGCCGG
GGACCCAGTGTCTCTGGTTTCGGGATGGGGAGCCAAAGCTGCTCCAGGGACCTGACTCTGGGCTAGGGCAT
GAACTGGTCCTGGCCCAGGCAGACAGCACTGATGAGGGCACCTACATCTGCCAGACCCTGGATGGTGCAC
TTGGGGGCACAGTGACCCTGCAGCTGGGCTACCCTCCAGCCCGCCCTGTTGTCTCCTGCCAAGCAGCCGA
CTATGAGAACTTCTCTTGCACTTGGAGTCCCAGCCAGATCAGCGGTTTACCCACCCGCTACCTCACCTCC
TACAGGAAGAAGACAGTCCTAGGAGCTGATAGCCAGAGGAGGGAGTCCATCCACAGGGCCCTGGCCATGCC
CACAGGATCCCCTAGGGGCTGCCCGCTGTGTTGTCCACGGGGCTGAGTTCTGGAGCCAGTACCGGATTAA
TGTGACTGAGGTGAACCCACTGGGTGCCAGCACACGCCTGCTGGATGTGAGCTTGCAGAGCATCTTGCGC
CCTGACCCACCCCAGGGCCTGCGGGTAGAGTCAGTACCAGGTTACCCCGACGCCTGCGAGCCAGCTGGA
CATACCCTGCCTCCTGGCCGTGCCAGCCCCACTTCCTGCTCAAGTTCCGTTTGCAGTACCGTCCGGCGCA
GCATCCAGCCTGGTCCACGGTGGAGCCAGCTGGACTGGAGGAGGTGATCACAGATGCTGTGGCTGGGCTG
CCCCATGCTGTACGAGTCAGTGCCCGGGACTTTTAGATGCTGGCACCTGGAGCACCTGGAGCCCGGAGG
CCTGGGGAACTCCGAGCACTGGGACCATACCAAAGGAGATACCAGCATGGGGCCAGCTACACACGCAGCC
AGAGGTGGAGCCTCAGGTGGACAGCCCTGCTCCTCCAAGGCCCTCCCTCCAACCACACCCTCGGCTACTT
GATCACAGGGACTCTGTGGAGCAGGTAGCTGTGCTGGCGTCTTTGAGGAATCCTTTCTTTCCTGGGACTGG
TGGCTGGGGCCCTGGCACTGGGGCTCTGGCTGAGGCTGAGACGGGGTGGGAAGGATGGATCCCCAAAGCC
TGGGTTCTTGGCCTCAGTGATTCCAGTGGACAGGCGTCCAGGAGCTCCAAACCTGTAGAGGACCCAGGAG
GGCTTCGGCAGATTCCACCTATAATTCTGTCTTGCTGGTGTGGATAGAAACCAGGCAGGACAGTAGATCC
CTATGGTTGGATCTCAGCTGGAAGTTCTGTTTGGAGCCCATTTCTGTCAGACCCTGTATTTCAAATTTGC
AGCTGAAAGGTGCTTGTACCTCTGATTTCACCCCAGAGTTGGAGTTCTGCTCAAGGAACGTGTGTAATGT
GTACATCTGTGTCCATGTGTGACCATGTGTCTGTGAGGCAGGGAACATGTATTCTCTGCATGCATGTATG
TAGGTGCCTGGGGAGTGTGTGTGGGTCCTTGGCTCTTGGCCTTTCCCCTTGCAGGGGTTGTGCAGGTGTG
AATAAAGAGAATAAGGAAGTTCTTGGAGATTATACTCAGAAAAAAAAA
```

KDM7A mRNA nucleic acid sequence
SEQ ID NO: 41
```
AAAGATGGCCGGAGCGGCGGCGGCGGTGGCCGCGGGAGCAGCAGCTGGAGCCGCCGCCGCGGCAGCCGTGTCG
GTGGCGGCTCCCGGCCGGGCCTCGGCGCCTCCGCCGCCCCCGCCCGTGTACTGTGTGTGCCGGCAGCCGT
ACGACGTGAACCGCTTCATGATCGAGTGCGATATCTGCAAGGACTGGTTCCACGGCAGCTGTGTTGGAGT
AGAAGAACATCATGCTGTTGACATTGACCTGTATCACTGTCCCAACTGTGCAGTTTTACATGGTTCCTCC
TTGATGAAAAAAAGGAGGAACTGGCACAGACATGACTACACAGAAATTGATGATGGTTCCAAACCAGTGC
AAGCTGGAACTAGAACTTTCATTAAGGAATTACGCTCTCGAGTCTTCCCAAGTGCCGATGAAATAATTAT
AAAGATGCATGGCAGCCAGCTGACACAAAGATATCTGGAGAAACATGGATTTGATGTCCCTATTATGGTC
CCAAAATTAGATGATCTAGGACTCAGGCTCCCTTCACCTACATTTTCTGTGATGGATGTGGAACGTTATG
TAGGTGGTGACAAAGTGATAGATGTCATTGATGTGGCGAGGCAGGCAGACAGCAAAATGACACTTCACAA
TTATGTTAAATACTTCATGAATCCTAACAGACCAAAAGTGCTTGATTGATCAGCCTTGAATTTTCAGAT
ACAAAGATGTCTGAATTGGTGGAGGTCCCTGATATAGCCAAAAAACTTTCCTGGGTGGAAAATTATTGGC
CAGATGATTCAGTCTTTCCCAAGCCATTTGTTCAGAAATATTGCTTAATGGGAGTTCAAGACAGCTATAC
AGATTTCCACATTGACTTCGGTGGAACTTCAGTCTGGTACCATGTCCTCTGGGGTGAGAAGATTTTTTAT
TTAATAAAGCCAACAGATGAAAATTTGGCACGTTATGAATCTTGAGTTCATCTGTGACCCAGAGTGAGG
TGTTCTTTGGAGATAAGGTGGATAAATGCTACAAATGTGTACAGGGAGCATACCTTATTTGTTCC
TACAGGGTGGATCCATGCTGTGCTCACTTCTCAGGACTGTATGCGTTTGGGGGGAACTTCCTGCACAAC
CTTAACATTGGCATGCAGCTCAGGTGTTATGAGATGGAGAAAAGGCTAAAAACACCAGATCTTTTCAAAT
TCCCTTTCTTTGAAGCCATATGTTGGTTTGTAGCCAAAAACTTGCTGGAAACCCTGAAAGAACTGAGAGA
AGATGGTTTCCAGCCTCAAACTTACCTAGTACAGGGAGTGAAAGCACTGCATACTGCTTTAAAATTATGG
ATGAAAAAAGAACTTGTATCTGAACATGCCTTTGAAATTCCAGACAATGTTAGACCTGGACACCTTATTA
AAGAACTTTCTAAAGTAATTCGAGCAATAGAGGAGGAAAACGGCAAACCAGTTAAATCTCAGGGAATTCC
```

SEQUENCE LISTING:

```
TATTGTGTGTCCAGTTTCACGATCCTCAAATGAAGCAACTTCCCCATACCATTCCCGAAGAAAGATGAGG
AAACTTCGAGATCATAATGTCCGAACTCCTTCTAACCTAGACATCCTAGAGCTCCACACAAGGGAGGTCC
TCAAAAGATTAGAGATGTGTCCATGGGAAGAGGACATCTTGAGCTCTAAACTGAATGGAAAATTCAACAA
ACATCTCCAACCATCCTCCACAGTACCTGAATGGAGAGCGAAAGATAATGATCTACGATTACTGCTGACA
AATGGAAGAATAATTAAAGATGAAAGGCAGCCCTTTGCAGATCAAAGTCTTTATACAGCAGATAGTGAAA
ATGAAGAGGATAAAAGAAGGACAAAAAAGGCAAAAATGAAGATAGAAGAGAGTTCAGGAGTAGAGGGAGT
GGAACATGAAGAATCTCAAAAACCACTGAATGGGTTTTTTACACGTGTGAAATCAGAACTCAGGAGTAGA
TCATCAGGATATTCTGATATTTCTGAGTCAGAAGACTCCGGACCCGAGTGCACTGCACTGAAAAGTATCT
TTACCACTGAAGAGTCTGAAAGTTCAGGTGATGAAAAGAAACAAGAATAACATCCAACTTTAAGGAGGA
ATCTAATGTGATGAGGAACTTCCTTCAAAAGAGCCAGAAGCCATCTAGAAGTGAAATTCCAATTAAAAGG
GAATGTCCTACCTCGACGAGCACAGAGGAAGAAGCTATTCAGGGCATGCTGTCTATGGCAGGGTTGCACT
ATTCCACGTGTTTACAAAGGCAAATACAAAGCACAGACTGCAGTGGTGAAAGAAACTCTCTCCAGGATCC
CAGCAGCTGCCATGGCAGTAACCATGAGGTTAGGCAGTTGTATCGCTATGATAAACCAGTGGAATGTGGA
TACCATGTCAAGACTGAAGATCCAGACTTGAGGACTTCCTCCTGGATTAAACAGTTTGATACTTCCAGAT
TTCATCCTCAGGATCTAAGTAGAAGCCAGAAATGCATCAGAAAGGAAGGTTCATCAGAAATTAGTCAGAG
GGTACAAAGTAGGAATTATGTGGACAGCAGCGGCTCAAGCCTTCAGAATGGAAAGTATATGCAGAATTCA
AACCTGACTTCGGGGGCGTGCCAGATAAGTAATGGCAGTCTAAGCCCAGAAAGGCCAGTTGGTGAAACTT
CCTTCTCGGTGCCCCTTCACCCCACCAAGAGACCGGCATCAAATCCACCACCTATCAGCAACCAGGCAAC
AAAAGGTAAACGTCCAAAAAAAGGAATGGCAACAGCCAAACAACGTCTTGGGAAGATCCTTAAGTTGAAC
AGAAATGGCCATGCACGTTTCTTTGTGTGACAGAGCTGCTGTTGCAGCCATTCTTCCCTTTGGAGACCAG
TCTAGGGGTGCAGGAGCCTGGAGCTTCCGCTGTCCCCCTGCCTGGAGCAGTTTGTGTGTATAGTAAGAAC
ACTGCCCGAAGAACAGAATGAACCTGATGCTGCATTTTCACTGTGCCACACCCACTCAGCAATAACCATT
TTGGACCTGGTGGGGAGAGGAAGAAGGAGGGTAGAACCTTAAAAAGAGACCTTGAACTGGAAAGGGTCT
CTTGTCAGGGCTTGAATTTTATTTTGTTGTTGGTAGTGTCTTGATGTATTTTCAGTGGTAGGGTAAAGAA
TTATCAATAATTTATTTAACAGATTTTTTTTAAAGTTAACAGCTTTTAAATTCTTTTTTAAAGCTATT
TATTTGGAAGATTTCTGGAGAAATATCTCACTAATTTAGATGTAAGAATGTGAAGGTTTTAAATTATTT
TTGATAGTGTGTGTGTTACATGTGGGGAAGGGCCACAGTAACAGTAACTAGTCTGGACTCTTAAATTTGA
TATTCAGGTTAAAGTCTTAAACAGGGATTTGATGCATTAATTATTTTAAATTAAGATGTATATGAAAATC
ATTTTATTTTATATATTTCATGTGTTTTTTATAAGCTATTAGCTTCGCTTTTGCTAACATCCAAGGTGCA
TACTGTTATCCAGGTTGATTACCTTATATCCCACCTTCCCTCTGCACTCCCCATCATTTTGTGATGACCC
AGTAAGACTCTTCTCTTTGCAGGGAAACACTTTCGTAGCCAATGTGTAAGAACTCCATGAAAGATCCCTC
ATTTCTCATTTCGTTTGACATTGTGATTTTCTTCTCAACATTAAAAAAAATAGGCTTTTGCATTTTCATT
TCTGCTGATGATATCTGGGTCCCAAAGAGAGCAGCTTTAATATATTTTTCCTACTTGTGGGAAAAGTATT
ATAAGTTTGGTTAAATTGTCATGTTTATAGTTTTTCCAAGTACATTTGTAACTACAGCAGGCCTTCTTCG
TACTGCTGCTGTTGGACAACAGGACTGGCACCTGCTGCAGAGGTTATACCTTATGATACTTTTATGCTCC
ATACCTGATTTGTTGGGAAATGTTATTTAGGATATTCAAATCTGCATCATAAGCCGTAATATAATAGGAT
TAATACTACATTAAGTTGTATAGAAGCAAGCATGTTGGAATAGATCTTTTGTGTGTATTTACTTTTTTTA
TTTCTTAATTTTCTAAAGAATTACTTAAGATATGGATTTGGAGTAAAATGGGTGCTTTTGGCAGTTTCTT
CCATCTATCCTAACCTGACCAGTACATATTGAGGTTAAGTATCTGGTTAAACTTTAAGGTATTCATTTAT
CTCCTTTATGTATGATTTTTACTAAATGCCAGTTTTCATTTGTCTTATAGTAGCTTCTATTTTCCCTTTTT
TCCATCCATGGCATAAAAATAAGTGATTTCTGGGGGTGGGGCAGAAATGTTCCCAAGTCTGACAATAGAG
CATTTTACAAATTCCTACAAAGAAAATATAGGCAAATAGATAAAATTTATTTTTATGGAGAAGAAATATG
GCCATATTATGGATTTGTCTTTTTTTTACTCAGCAAGATAGCAGGACTTACCCTTCTCTATTAAGTATCA
CTTGAATTGCTAAGAAGAAAAAGTCTGTACCATCATCTTTCATGGTTGCATTCAAATGTATATTTTCAA
AGAGAAATACTTCTTGTGTCCCCATTCCAAAATGTCATGGGATAAATATGAAATAGTTTATGAAGTAGCC
TTTCTGGTTCAGAGTGACTGGACCAAAGTCTGAATCTTATCTGGGTATCAGGAAAAAGAATTTTTATGGA
AATCCTTAGTGTCTATAAACAACCCGTGTAAACCCTGTCTACACTATGCCAAAACCAGTGGAAAGATGGG
TAGAGTCATCTTATCTCAGGATGTCAAAAATCTGGGTTTGACTGATTCCCCTACCTTCCCACACAGTATA
TTCTTGTGATTTTTGCTTTTCTGTAGATCCTGAGTCGGTGTTTACAATAGTCATGTTTTTATTTTGGGTTA
AGAAATACGAGGTGTAAGAGCTATAATTTCCTTTTCGTGTTATATCATGATCTGGGTTTTCTTTTTTCCT
TTACGTTTTTCACAGCTCTTGAGTATTTTCTATTTTTTTCTTTAGTCACAAAAATTAAAATTAAACTTTA
TTTTTATGAATTAAAATGAAATTTAATTTATTTTTATGAATTAAAATTGTGGCCAGTATCCACTGTGTCC
TTAGGCTGAGAAGTACTAATTTGGAGTAGCCCGTGTGTGAATTCTAAAGTGAAGGTACTGTGGATTCAT
TTTTAGTAGTTTTAGCCCCTTAATAAGTGGCTAAGTTAGAAAACTTTCAGCGAGGTAATAGAACCACTTG
AATAGAATCCATGTGTCTTTTTCTGAATTGGTGAAAATTCGGCCACTGATCCAGTGACTCCTGGTCAAAC
GTCTTATAACATTACTGGCCATAATGCATCCCTTTATCTCATGGAAATGGCTGAACTTTGTGGTAGCTGC
TGCGAGTACCTGGGCTTAACAGTAATAGAGAACCTCATTTATACCATACAGACACAGCAACTTAGGAAGA
CAGCACTGATAGCATTTAGCTAGTTGTAACCAAATACAAATATGTAAATTGAGAATTATGATTAACATA
TGCAACTTTAGTAATAGGAATAGATGATAATTTTCCTGTATTGTTTCAAATAAGTGACTGTTCAGCTGGG
ATCCATTGGATTATAATTTACAATGTCACATAATATTATGCTTTTCAATATTGATGAGTGATGTAAACAA
TATAAAGTTGGCAGTTTGTAGTAGTTCAGTATCCTAGAAATACATTGAACTTCATAAGTATCAGTTCATT
TTTAAGCATACAGAATTGAAGATTCTGACTGAAATCATAAACTCAGAGGAAACAAGCCCATCTTTATCAC
TAATTACTTAGCTTGAATACTTTTCTATTTTAAATAATCCTAATTATTGCCTTTTCAATTATAGTCTAC
TGTATTTATTTATATGGGATCAACAGGTATTTATCAAACATCTACTGTGTGCCCAGCACTACCTAGTACT
GTTGGGGAACATCAATTTGCAGTTGTGGTCTCTGCCCTTGAAGGTATCTTCTCCAGGAAATTAGCAGTAT
TATTTTCACTTCTAAGCAAACATGAGCAAAAGAGGACCTTGTCATTAAAAAACATGCTGACTTTTTAGT
TTCAACTGAGATATGCCACTGTAGAAGTGAAAGTAATTTCACAATTAAAGAAATGCTTCAACTTGGTAAT
TAATATGGTCATACAGGGACTTGGTGTAGCATGCAAGGAAGCAGAAGACCTGGGCTTTTGTCGAAGTTCT
GCCATTTAGGTATCAGCTGTGTAACCTTGAATAAGTCACTTAACTCTTTCTCTTAGTTTTCTCATTTGTA
AATTTGGATTAAAGTGTTTATTATGATAATCAATTAAGAAAATCTCTTAACACTTCATACATACAGAGAA
CTTATCATTAAGTTAAAACTGGCAATTAATGCACCTTTATATATTTTTAAATGAAAACTAATACTATT
CATGATGTTTATTTTATATCAAATATATGCCCAGGGCATGCTACTTTAAAAATCCGAGGAATCTCCAACA
AGGTGCTGGATTAAAATCAGATTTCGTGCTTGAAGTGGAAGAAAATGAAGTTGTTTATGGATAAGAGAG
TGAGAATGTGTATCCTCAAGTACGTTAAGATGATTTAACTGAAAGATGGCTTTAGGTTTTCTTGAAGAA
TTAGGAAAGTACCATCCCCACAGATTCAGCATACTCTTCAGGTACTAGATAAAGGTGAAGGAAGTCATGG
AATTAAAATGACTTAGCAACTCCCCAGGGAACTTGTGGGAGAATGAGGTGGTTAGAAAGGTGAGAATGC
ACAAAGACAGCTCTGGGTTGGGTACCAACAGTTTGCTTGGTAGAAAGAAACCAGTGTAGGAAAGGAGACG
```

SEQUENCE LISTING:

```
CCACCAGACATCTTCAACAGACAAGATTCTTTCTGCCTTTTTCAAAAGATGCTCTCTGCAGCAGTAAGAC
TATAGATAGAGTTGATTGGAATATCATGTGACCCAGTATGCTACTGCTAGGCATAATTATCAAAAATTCA
TTTTTCTCATTAAATATTGTTAATTGCTCGCCACATAAAGAGAAGCTAGAGCTCACCAGTCTTGGTGGTG
TCCTAGACCTTCCTCTAAAGCAGTCTTGGGAAGCTGGATCATCAGATCTTTAGCCTAGACAGAGTGTCGC
TGGTAAATAAAGGAGACACAGGTAACCCAGAGTGGACAGTGATTTGCGTGGGGAGACACAGTGGATCTGG
GGCCTCTGATACTTTGCTTCCTAAAACAGCCCCCAGTTTTCGGCTTGCCCTATGAGATGATGTTCATGTG
CTTCCTTGAAACCAGGTGGAAAGAAAGGGGAAGAATTAATTTTCTCATTCTGTTGCTGTTGAACGTAATG
TAATCTTAATACTGTAGCCTTCCTAGAAGCCCTTCCCTCTTTTTCATGCTGTAAAGTCAAATATTTGATA
TCCTTAACATAAATTTTAAAAATTAAGGTCATTAGGAAGCAAATGTCTATTTCCAAAGCAATGAGCTTGT
TGTGACTGTGATTTTATTCTTCTATAGTATTTTTTCCTCATTTTAACTGAGAGGAGAAAATAATACTCT
TTTGCAATATCCTTAGGTTCTCCCCTTCCCCTGGTGCCCCTTCTAGTGTCTTAAGACTTTGTCTTAACA
AGTATAACATTACATTTTGTTGTTAAAACCTTTCGAAACTGTATTCAGTGATTCTTCCAAGTTTATCTGC
TCTGCACTATTTCACTAATAAACCCTGGCTACCACGTAGCCCTTGATCTCCAAGTAGTTTACCTATGCAA
GACCTGTGACACTCTGAATTCACTTCTCTTTCTTTCAGAAAGTAGTCATAAATGGAGCTTAATTATAAAG
GTAAAACTTGTCTCCAACCAGTTTCATTTTGGCCATTTCTTTTTCAAAATGTCAGCTGTTTTCCTCCAAG
ATTTTTCACCAAAACAATGATCATAAGTGCTGGAATATATAATACTTTGCAGGCATAAAATAACCCAGAC
ATACTCTCATATTTCTTTGTGTATTTTGGTTGGTAAAACTTACCAGCATTAAATGTAAAATATAATGAG
GAGTTAATTCCTTACCTAGAACTATTTCTTCCTTTTAAGATTCATAAGTAACCTTTTATTTTTACAGAGC
TACGTATAACTTCCACATTACAGTCAGGGACCTGAGGTGTAACTTACTAAGTGAACCCCAAGGTTATTTT
ATCTTGCAAAAGAAACCTAAACCAAACTAAGGGCCTTACAGTTTATGTTGACTGAATCAAAAGCTATA
ACCTCAATTTTTCCAAAAACAGCTTCTGACTGCAAAAGCAAGTCATACAGTTGTTAGGTATGAAATAGCA
CTGATCAGGAAATGCATCTTCGCAGATGGTATTTCCTTCAGAAAAGACTTTTCTACTTTTAATATAAATT
AAGCCATAACAGTTTCATGCTGTGGAAAGAGGGTGAAAAGGTTCATTTTAAGAGATTATATAATATGAAC
TTTCACATTTACTGTGAAATGTCTAACTTTGCCAGTGCTTCAGCAAGTTTTTTTGGGGGGTGATGGGGAG
GGGTAGTATTGGTTTTAGAGGTTTCAAATCTGTGAACTTTGGAGAGGGGACAGTTGTTGGCTCTGGTATT
TACTAGTTTTGTAGTAACGTTTTGCTAGCCTGACTGACTTTTCTTACTGGTTTTTATGCCCACGGTCCGA
GGGGACTGTTCTTCTTGTTGGGGGTGTCTGCGGAATAGCGTCTCGTCTTGTTTGTATAGGCAGTCAATGT
GTGTGACATGTGTGTCCTTTCAGTCCGGAAGCCCACTGTGTGACAATGGCGTGGGGTGTGGCTGGGAGGT
GGGGTGCTGAAGCTTGAAGAGCATTTCTTTGCTGATTCATAACAGTATTTCCCATCTTTTGCCTGCAGGC
AGGGAAAGTGTACAGTATTTATTTTGTTTCTGTTTTACTTTAAATTTGTAAGTCTTTAAGTAGCTTACAT
TGATTATATAGGGGAGGACAAGTGACTTGTTTAAAGTTGTATTTAGTATTCTTTCCAATTTCTGTATTT
TAAAATATTGAAATTAAAATTGTATTACTTCTGTTTTGATTTTTTTAGCACTTAGTGTATTTTTTGCTCA
TTTTGTTTGAAAGTATAAATGTTGAAAATTGTATAAAATGCGTCCTTGAAAGAAAAAGAATCTGAATTCT
ATATCCAA
```

KLF7 mRNA nucleic acid sequence

SEQ ID NO: 42

```
AGAGAAGCGATCGCGAGAGAAAAAAATGCAACCTCCCAAAATAAAGAGCAAAGATTGCATTAGGAGCGAA
CAGCGCTGCAGAAATAGATGGCAGCTTCGTGTCAGTGAGTTTGCATCCCCCTTCCTGATCCACGAGCTGG
AGTGATTAGAGCCCTGGAAGGGAATTGTTACTCCCGTGGAGAAGTCCCCTTTTCCTGGCAGTCGTCTGCA
CTGTACACGCTGGATGCCTCTCTCCATCCACCCCACTCACTCGCTCCTCTTCCACCTCCTCTCTCCCTCT
CCTGCATTGATTTTTTTTTTCCTTTTTAGTTGACTGAAACAAAACAAAACAAAAGGGCCACTGGATGTC
TGCCTTCTTGGGGGGTGAGCCAGACAGACTGACAAACAAACAGCCCCAACTGTGTTCGGGGGAGGGTTTC
GCCTCCCGTTTTGCCCGGCAGCAGCAGCATGGACGTGTTGGCTAGTTATAGTATATTCCAGGAGCTACAA
CTTGTCCACGACACCGGCTACTTCTCAGCTTTACCATCCCTGGAGGAGACCTGGCAGCAGACATGCCTTG
AATTGGAACGCTACCTACAGACGGAGCCCCGGAGGATCTCAGAGACCTTTGGTGAGGACTTGGACTGTTT
CCTCCACGCTTCCCCTCCCCCGTGCATTGAGGAAAGCTTCCGTCGCTTAGACCCCCTGCTGCTCCCGTG
GAAGCGGCCATCTGTGAGAAGAGCTCGGCAGTGGACATCTTGCTCTCTCGGGACAAGTTGCTATCTGAGA
CCTGCCTCAGCCTCCAGCCGGCCAGCTCTTCTCTAGACAGCTACACAGCCGTCAACCAGGCCCAGCTCAA
CGCAGTGACCTCATTAACGCCCCCATCGTCCCCTGAGCTCAGCCGCCATCTGGTCAAAACCTCACAAACT
CTCTCTGCCGTGGATGGCACGGTGACGTTGAAACTGGTGGCCAAGAAGGCTGCTCTCAGCTCCGTAAAGG
TGGGAGGGGTCGCAACAGCTGCAGCAGCCGTGACGGCTGCGGGGCCGTTAAGAGTGGACAGAGCGACAG
TGACCAAGGAGGGCTAGGGGCTGAAGCATGTCCCGAAAACAAGAAGAGGGTTCACCGCTGTCAGTTTAAC
GGGTGCCGGAAAGTTTATACAAAAAGCTCCCACTTAAAGGCCCACCAGAGGACTCACACAGGTGAGAAGC
CTTATAAGTGCTCATGGGAGGGATGTGAGTGGCGTTTTGCACGAAGCGATGAGCTCACGAGGCACTACAG
GAAACACACAGGTGCAAAGCCCTTCAAATGCAACCACTGCGACAGGTGTTTTTCCAGGTCTGACCATCTT
GCCCTCCACATGAAGACATATCTAAAAAACCGAAAGGCCAAGGTTGCCATGGCATCGGCTAGTGTCTA
AAGGAAACGCCATGAGGCAGGGGCTGGACTTCAGGCGGGGACCCCATTGCCTCGCAGAAGAAAGTTCTCA
CTTATAAACCTCTGTACACACACACACACACACACATATACACACTCACAGACCCACACACATACA
CACTGTCATGCACTCAACTATATTTAAAATATACGTCTATTCTTTATGCCTTGCCCTAGCCAGATGGA
AGAAGATGAAGAAGGAAACCAGGTGAACTCAGCAAGGCAGACTGGCTGCTTACTTCAGCACTATTGGAAT
TATTTCCCGCTGTTGCCAATGGAAATCAAAGAAAATGGATGTGACGTCTGTGCAGGTGGACGGCAGTCCG
AGGGGCTTATTTCACTTGCTTCTCAGTGCAACTTGATAGGAGAATCCAGCATCTTAAAGTTGCATATGTG
TAGCACTAATGTTTCTTTTAAATAGTTGGGGGAAAATGACCTAGAAAACCAAATTGCAGTTTGGTAGCC
AAAATTAACTCTTGGTTTATTTGTCCTTTGTGTGAAAAGTCCTACTATTCCGTGCGTCAGACTTCCTC
ACAGAACTGTTGACTGGTTTTGGTTCTTAGTACTATTGAGATCTTTCGCGTCGATCCCAACGGCCTTAGC
GGCGGCAGACTGGAATAACACCTTACACCTTTCTGGCCTGCATTTCTGTAGACTTCACTCTCAAGGGAGG
AGTTTTCTTTTCTTACGTTTTGACTTTTGCACACCATATGCACTAGGGATTCTGGAAACTTCTAGCATGA
CTGCAAAGTGGCCAAGAGAATAAAGTCCTTGATGATAAATCACAGTATATCCCTTGAGCCTCACCTTATT
GCCAGTGCTAGATTTTTCTTTTAATCTCTCCGTTTTGCTAACGAAAACTTGAAAAGCTTATTTGGAA
GCTTAAATGTTTTATCTTTTCTCCATGGACTAAACCTCTCCAGGCTCTCTCGGCACCTGGATGTCCAGC
TCTCGAAGCAGCCAGTCAGATGGGACATCACAGTTCTCTCATCCTCCTTGAGGCATGATGACCTCAGCTC
ATAGTGATCAACCGTTGTGCTGTGTGTCATTGCTACCCCATAACCAGTTACAGCATAGATGTCGCTAGTC
TCAGAGGGCAGCTGCGTATTTAATTAACTCTGGTTTATGACCTGACAAAAGCCAAAAATATCACTCTT
TCCAGGAGTGGGGAAAACTGAGGATGCCTCCCAAGTCTAGTGGCTTCACAAAAGATCATCCTGTCTTCTC
TGTCATGCCCACTGAGCTCCTATTCCCCTACGTGTTACAATACACAATTTAAAACGCCATTGTGGGAGTG
AAGGGTTGACATTTAAGGAAAAGGTTGAGGTGTTTCTCTCATGGGCTGTCTAAAAGGAGAGACACGTTTC
```

SEQUENCE LISTING:

```
TTTCTTTCCTTTTTTTTTGGCTAGGCCCACCATGACTTGTGACCTAGAACCCCCAGGATTAACAGAGGC
CTCACATTTACTCTGCAAGCTGACTCCAAAGGAGTCTACAGTCCTTACTTGTCATGCCACACTCACACAT
CCAGTAGTGGTCTCTATCTACCCGCATTCCTAGCTAGCTGGCACTGGCCTCAACTCCAAAGACTGCCTTT
AGGACCATCAAATGGCCTATGCAAGCAAGCGGGGTGGTTATTAGGACAGATTGTATATTTTGTATATTCT
GGGACCATCCCTTCAAGACACGTCTATAAAACAAAAATGGCGCTTGGTCCACACACGGTTGCTGCTCCCT
CCTACCAGCTGGCTCCCCTCCTGTCCTCCTTTGACTGTTTGACTCATTGACTGTTAAAATGCCACCCCAT
ACATATTTGGGATGCAAAACTGAAGTCAAAAGGAAATAATATAAGAAACACAAACACATATATGACAGCA
ACCTTCAAGATCTGGGTTTTCAGCTTTCTGCAACCTTTGTTTTCACTGAAATGTTGAAACTACTCGTCTG
AGGGCAAAGGAACCTCCTCACAAATGCTATAGCTGCCAATTGGACACTTGGGGCATTTCGAGGTCTGGCC
CTAAGAATTTACTTTCTCCTTTTCCTTTTTTCTATTTAGACCAAAAAAAACAAAAACAAAAACAAAAAAA
AAAACAAAATAATACAAAACGAAAAAAAAAGAAAGAACACCCGTTAACACACACGCGCACACACACACAA
AATCTGTCCATTTGCCGGAGGCAATTGTATGTATGTTAGTTGGAGGGTATTAAAAATCAGTTTTATTCCA
AAGATTTAAAACTAGACATGACTTAAAAACAATTTCTGGAGCACTGCTTGCTGACAATCTCGTAGTTCTC
TGCTGCATTTGAGTGCATTTTGTGGCCAGTCCATCAGGGCGTACCATGGGATTATATTTGAATGTGTGGT
GCATCCTTCCTGGATGAAGGATGTGTGAGGGACCTTGAACCTCAGCTGTATTAAACTGTAGCGCCTCCAG
TCAGTGCACTAGATGAAACTTTTAGACACCCTGAATTCTGTTGGTTCCTTTCTTTTCCTTTATGTAGCAG
CCTCCAGCATGAATGCACGCACACGCCAGTGATGGCATTAAGCCATGGCCACCACGATTTGCAAATGTTC
TCTCCCAAGCTGGAGCTGCTCTTGCCTCTCGAATGCTATTATTAAGGGTTTATAATACTTAATTTAATTT
TCGAACTGACCAATGCAAGGCTCTATTAAAAAGAAAGTTTAAAAAAATGCAAAAGAGTAATCATTGCTTGT
TTGCTCCCTATTTTCATCTGTGGTCTCATTTGAATGTGGCAGAACAAAGGCCCTTTGGTCCTCATCAGTG
TCTGAAATGTTCAGTAATTTCTCTCTCTTTTGTATCAGTGAGGTCCTTTGTAATCTGCTCCTGACCTTTC
TTGGAGCAGGGTGCATTGAAACTCAATGGTGGTGCTTGCTTGCTTCAGAGTCATTTGTTGACTGTGAGAA
TTGGCCTAAGAATTTGGTGGGTGCTAAGTGGATGGCTTTGAAACTGTTCTTCTTTAGCCGAGTTGACACC
TGTGAATGATGACCAGTCCTGATCATTTTGGAAATGGATTTGTAATAAAACGTCATCACCTCTGCAGTG
GCAGAGATGGTTACTAAGAGCCGCTAGAGCGAGCAGGTTTTCCAAGAAGTAACCTGAAGACATTTTGCTC
CCAAGAGGACTGGTTATTTAAAACAGTGCATTAATGGACATTTGAAACACATTAAACCCCTTTCTCATTT
CAGTTGTTACCTCCTAACCCTCCAGGGGATCCCAAATTTGAAAGGAAAAACCCGGCCTGGTGTTTCTGGT
GGTGTCCTAACAAGCACGCTTTTATCCAGGGTTCAGATTTGTTCATGTAGAAAAAGAGTTTCTAAGCCAC
TGACAATTTTTTTTTTGTAATTTCAAATTATACTTCTTTCTCCTGCCACATGACTGTAAGTCATAGAC
ATGGAAACCTGAATTATAATGCTGCTCCTAGCTACTGGCCTCCTGCCCCACCCATGGTTAATGGCTCAG
CTCAATGCCTGGTGGTAATGAGTATTATGTCCAGAAAAGAGATGTTCAGATTCCATGACAAAGCTGCAT
TTTTGTAAAAATATTGGAGACCCCAAAATGAACTTCATGCTGACCATTTTCCTCCTCTCTGTGTGCTTTCC
CTTGCAAAGCCCTTCAAATATCCTCTTCTCTCGACGCCATCTCCTCTCCACCTGCACCTCTTGTGCCCTT
TGTACATCTTTGATTGCCTGATGATAACAGGGTAAAAGGACAGCCAACCTCATGCCTGATTAGCAGAACT
GAATCCTAGTTTTAAAAAATCTTCTCTGGCTTCAGAGAAGATTTTATAAGGACTTTTGTTTGGGATAAGC
TTTCCAGATTATCCATGTCTATTTGCATCAAAGGGGAAAGAAATGGGGCTTTTGGATGGCTCTTCCAGTG
CATTCGGAACATTGCCTCTTGCCTTTATTCCTGCATTTTATGGCAAAGCCAAAAGAAACTCAAGTTGCAA
GAACAAAACCCAGTGACTCGTTTTGATGGTTCAAAATGGTTTCCTTTATGGAAGTCACTTCATAAAATGT
TAAGTAAAAAGTGGGAAGTGCTTCTGTCTTCTCTTTTGCATGAGTTGCTTTTAGGAGCAGGAAGAAGGTA
GGCAAAGTAAGATAAAGATGCAACACATTTAACTACAAAAATCAAGTTCATTTTTTAGTTTATTAGAATT
TTTTTGAAATCTTAAGAGGGCCAGCATTTCTGGCTACAATTTTGCACCCAGAACATTGCCAAAATGAACA
TTCAGTAAATAGAACCTGATTGAAATTTACTCCTGGAAGCTTTCCTTTGCATTTTCGGGAAGTGGCCACC
TGCCAAGCGCAAGAGTTGGGGGCAGGAGGGGAGGACTCAAATTCAGGGTGTCTGGATTAAATTTCGGTG
AACATGGTGATATCTCAGTTTGAAAACTAGAGGGCCTATCCTGAGTATACATCAATGTCTCTTTGATGGC
CTACTTTCCTCAGTGAGGATCTTTGGGAATACTTGAAGGAGCAACAGAAATGTGTGAAAGGAAGCAGA
AACTTCTTGTAAATAACGTGACCTCCCACGACGAACTGCCTGAGGCTTCAGGGTTTTTTCTTGCTTTTAA
CACTCTTAAATCTCCTCTGTTGGTTCCTAATAGATCCCAGAAAAGGGAAAAATAAAGCTGCAGTTAACTT
TCTTATGTGCATCCTTCCAATAGAGTACTGTATTTTCAGGTGTTTTGCATTTAACATAAAAGTCCTCGG
GAAACAGGTGTCAAAAACAGAGAGAGAAATCCTGGGCCATCACTTCACAAATATCCCAAACAAGATATTC
TTTTCAAACAGGGCTCCCTCTCAGTGGTCATGAGGGAAGGTTGATAATGTTCTTTGTTGGGGACTGTTTA
TACAATTTTTTTCAACTGTGAGCTTTGGAATCGTAACTTGCTGTGAGTCCAGCTTCGTCTACTGCCAT
AAGATGGACCCCACGTCAGCATAATGAGGGTGGTATATATGCTCGCACCTAGACATGCGCATATGTACCT
GTCGTACCTTCACGGAAGGAAAACAGGCTACTGACGTTTCGGAGGAGTAGCCACCAGTGCCTAATATCTT
TTGGGGGGGATGGATGCTTATAATTGCCAGTATATCGAAACCACACTGGGAGTTCCACATAGCGGGAGG
GGTTGGGGGTGGGCAGAGGGGACATTTTAAACCTAGGCCTTTGGACTGGAGGCAGAACGATTTCTGCAAA
CCTAGGTCCTGAAGGCTTTGGGGCTTATTGGCTGGTTCTCAACCTTTTTGTTTTTCTTCCCAGCATGCA
TTTCCTATCTAAACCCAGACTTAGTTTAATTTCCTTATCTTTCACTTCTGCTTCATTCCAGGGAGGAAAA
ATACACCTGTTAATGGCCAAGATCTCCTTGCTAACACAGAGGCAAAAATAAATGTCTAATGTTTTTGAAG
CCTCCCCTTCCTTTCCACAAGCCCCACCCGCCCCGCGTCAAGCTCCTTCTCCCACTTCCTACTCCCAC
ACAACTTCCCAGCCACTGAAACTTTTCTTTCAAATCTCTATTATCCTCTTAACAGTTGCTTGAATAAATT
TATTTTTGCACTATACATTTTCTTTTTGCCAGATGTGTCTAACAAGTGTGTTTGGAGAGACCTACTCCCA
GCCCCGTCTCCTTCCCCGCCTCCCCCCGTCACATTCTCTCAGGCCTTCTCTGGTATTTATAATATATCAC
AGAAGTACCCAGTCTTATAGCCCTCGGTTATGCCTTTTTTGACATTTTATTTTTTTAAGCTTTTTATA
TATATATATATAAATATATTACTTTGTCAAGTTTTTTTGCTGTACAAAAGTCTTAAGATTTAAAACTA
TTATTTGTATTATATGATGGTGGTATGTTAATGTTACAAAATTATTAATGAAGAAAAATTTATTTTGT
TACTGGTCTGTTTCATAATTCTTTTTTAAATTGGTATATTGTAAGATATCTATGCAAAAAATGTTATGTG
ACGCATTTTTATTTAAGAATGTAATATGTGTAATAAACAGTAGAATGTGTTTGGCCTTGGAATACTTTAC
TGTATTTCTCCTTAGCTTGTTTCACTGGGGAAAAAAATCTTCGAAAGACGCAAGTGGGTACTTACATACT
TCGTGAAAGTTTTCTTTCTTGGAGAAAGGGAAAGCAAAAGGTTGTATTAGGTTATCTTCGTTTGGGAAGT
TGTGTGTGTGTGCGTATGTGTGTATTTTATAGTTTCATTGAGGCAGCTCAATGCCCAAATAAGGGTCA
CTGAGTTTATTTCTTCAAGGGGAAAAAGGGAGCCAATATTTGAAAAGCAATATTTTAGAAT
GATAGAGATTACAAGATGTTATTTGTTTAGGGGGTTGGGAGAGGCTTATTGAAAGCGGTTTATTTGGCGA
GAGAAGGAGGCAGTTTGTTCTGGGATGGTGTTTAATAGGAACCTATTGGGAAGGATCTTTGAAGCAGTC
TGTGAAGGAGGAAGGGTAAAGATCAGAGGGAATAATTTAGGTGAGGGGTAGGGGCAGTAAAATGACAGG
AGGTGGTTGGAGTGGGGAGGAAATGGGTAACCGGAAGCCAGGAAATCCAGCTGGCTGTGAGAGTACAAA
AAACTAGATGGAAATACAAGCAGCTTCAGACCCAGAGAAGAGAGGGAGATGAAAGCCCCAGGGAAAATTC
TCAGAACTGAAAAGAAAAGTACTAAAATCTCTGCCACACACGACTTCCAGGAAAGAGCATCACCAGTAAG
```

GAGGAAGGTAGAGAACCCAGCTGGTGGTGTCGCCTCAGCATCCCGAGCTCAGCGATTCCCCGAGAGAAGT
GGTGTCATTCACAGGAAACAGCAGTAAAACACATTTGTCACATGGGACACAGCAGTAGTCAAGCTTTCTT
TGCATTCTTTGGACTTACAGAAGTGGATACGGTGGTGAATAACCTCTATCCCTAATCAAATGAATCTGAC
AAGAAACTTTCCAATAAATGTTTACTTTAGAAA

KLF9 mRNA nucleic acid sequence
SEQ ID NO: 43
CTTACTCATTTGTGTTTATTCTTGGACTTATCCTGACATAATGGGGTTTTTTTAATTATAGATTCACACT
GCATTTATTCATCACCCCTGTCCTCTCATCCATAACTCAAATTTACTACCAGCAACACAAAATACAAAGA
TGTGTCCAGTTTCACTACAGCTCTTCGCGTTTACAAGTGTCGAGCGCTTGCTTTCGGAACGCCCTTGTGA
TTGGCCGAGCCAATGCCAGTGACATCAACCAACTTACTTTTGATTGGAAGGCTGGTTGCTGGGACTGTAG
CGTTTGCAGGAAGTCACTTAACTGTTTGGGAGCTGGAAAACCGAAGCTGAAGTTCTCTTTTGCCATAGGA
ACGAGCGCAACTGACTAGGAAAGATGTGTCCCAAAGCTCCGCAAGCTGGAACGTGAGCCAGGAGGCCCGG
ACCGGCCACGGGACCGCGAGGCACTCCGAAAGTGTGCGGCTGCCCCTTCCCTGCCTCCCAGCTGTTACCC
TTTTAAATGTCAGTGTTCGAGGCTGTAGGGGTAGCACGAGGCAGCGAAACGGAACAGTCGGATTGGCCGC
ACGCCTCAGTTCTAGACGCACCTCTCCACCGAAGGCCGTTCTGACTGGCAGGGGGAGAAAGTAAACAGAG
TTGAATCACCCTCCCCACTGGCCAATTGGAGGGGGTTTGGTTTGTGACGTGATGGGATTCTGCGAAATTG
TTACTGAGCAAGAGAATGCCGGAACGGTGCGGACCGGCCGGAGCAGGGGTTCAGAAGCCGTCAGTGGACT
CGGGAAAAAGTGTCTCTTAGACCTGGCGCTCGGCGGGACCCTCGCCACCCGCGTCGGGGTGATCGGGTGA
ATGTCCTGGGGCTTTGGCTCGACGGCGAGGCGGCCGAGGGCGTGCACCTCTCTTGCAGTTTCCTCTCCCA
GCGCCTCGGGGCGTTTTCAGTCGAATAAACTTGCGACCGCCACGTGTGGCATCTTTCCAAGGGAGCCGG
CTCAGAGGGGCCGGCGCGCCCGTCGGGGATCGCGGCCGGCGCGGGGCAGGGCGGCGGCTAGAGGCGGC
GGCGCGGCGGAGCCCGGGGCCGTGGATGCTGCGTGCGGAGGCGCTGCCGGTTACGTAAAGATGAGGGGCT
GAGGTCGCCTCGGCGCTCCTGCGAGTCGGAAGCGCCCCGCGCCCCGCAGCCCCCCTTGGCCGCCGCCGTGC
CGCGCCGCGCCGCGCTCGTCGTCCGAGGCCAGGGCAGGGCGAGCCGAACCTCCGCAGCCACCGCCAAGTT
TGTCCGCGCCGCCTGGGCTGCCGTCGCCCGCACCATGTCCGCGGCCGCCTACATGGACTTCGTGGCTGCC
CAGTGTCTGGTTTCCATTTCGAACCGCGCTGCGGTGCCGAGCATGGGGTCGCTCCGGACGCCGAGCGGC
TGCGACTACCTGAGCGCGAGGTGACCAAGGAGCACGGTGACCCGGGGACACCTGGAAGGATTACTGCAC
ACTGGTCACCATCGCCAAGAGCTTGTTGGACCTGAACAAGTACCGACCCATCCAGACCCCCTCCGTGTGC
AGCGACAGTCTGGAAAGTCCAGATGAGGATATGGGATCCGACAGCGACGTGACCACCGAATCTGGGTCGA
GTCCTTCCCACAGCCCGGAGGAGAGACAGGATCCTGGCAGCGCGCCCAGCCCGCTCTCCCTCCTCCATCC
TGGAGTGGCTGCGAAGGGGAAACACGCCTCCGAAAAGAGGCACAAGTGCCCCTACAGTGGCTGTGGGAAA
GTCTATGGAAAATCCTCCCATCTCAAAGCCCATTACAGAGTGCATACAGGTGAACGGCCCTTTCCCTGCA
CGTGGCCAGACTGCCTTAAAAAGTTCTCCCGCTCAGACGAGCTGACCCGCCACTACCGGACCCACACTGG
GGAAAAGCAGTTCCGCTGTCCGCTGTGTGAGAAGCGCTTCATGAGGAGTGACCACCTCACAAAGCACGCC
CGGCGGCACACCGAGTTCCACCCCAGCATGATCAAGCGATCGAAAAAGGCGCTGGCCAACGCTTTGTGAG
GTGCTGCCCGTGGAAGCCAGGGAGGGATGGACCCCGAAAGGACAAAAGTACTCCCAGGAAACAGACGCGT
GAAAACTGAGCCCCAGAAGAGGCACACTTGACGGCACAGGAAGTCACTGCTCTTTGGTCAATATTCTGAT
TTTCCTCTCCCTGCATTGTTTTAAAAAGCACATTGTAGCCTAAGATCAAAGTCAACAACACTCGGTCCC
CTTGAAGAGGCAACTCTCTGAACCCGTCTCTGACTGTTGGAGGGAAGGCAAATGCTTTTGGGTTTTTGG
TTTTTGTTTTTGTTTTTTTTCTCCTTTTATTTTTTTGCGGGGGAGGGTAGGGAGTGGGTGGGGGGGAG
GGGGTAAGGCCAAGACTGGGGTAGAATTTTAAAGATTCAACACTGGTGTACATATGTCCGCTGGGTGAGT
TGACCTGTGGCCTCGCACAGTGATTCTGGGCCCTTTATGCTTGCTGTCTCTCAGAATTGTTTTCTTACCT
TTTAATGTAATGACGAGTGTGCTTCAGTTTGTTTAGCAAAACCACTCTCTTGAATCACGTTAACTTTTGA
GATTAAAAAAAAAACGCCATAGCACAGCTGTCTTTATGCAAGCAAGGACATCTACTCCAGCATGATC
TGTCATCTAAAGACTTGAAAACAAAAAACAGTTACTTATAGTCAATGGGTAAGCAGAGTCTGAATTTATA
CTAATCAAGACAAACCTTTGAAAGGTTACACTAAGTACAGAACTTTTAAACCTTGCTTTGTATGAGTTGT
ACTTTTTGAACATAAGCTGCACTTTTATTTTCTAATGCAGAGGATGAATAAGTTAAATACATGCTTTGAG
GATAGAAGCAGATGTTCTGTTTGGCACCACGTTATAATCTGCTTATTTTACAATATACACGTTTCCCTAA
GAAATCATGGCAGAGATGTGAGGGCAGAATATACACAACAGATGCTGAAGGAGAAGGAGGGTAGTGTTTT
GCAAAAGAAAAGAAAAGAACCAACAGAATTTTAACTCTATTAACTTTTCCAAATTTTCCTATGCTTTTA
GTTAACATCATTATTGTATCCTAATGCCACTAGGGGAGAGAGCTTTTGACTCTGTTGGGTTTATTTGAA
TGTGTGCATAACAGTAATGAGATCTGGAAACACCTATTTTTTGGGGAAAAAGGTTTGTTGGTCTCCTTCC
TGTGTTCCTACAAAACTCCCACTCTCAGGTGCAAGAGTTATGTAGAAGGAAAGGGAGCTGAAATAGGAAC
AGAAAAATCAACCCCTATAACTAGTGAACACCAAGGGAAAATACCACAATGATTTCAGAGGAGACTCTGC
AAAATCGTCCCTTGTGGAGAATGCAGGCAACATGGAATACTAGGAATGAAATCACATCACTGTATCTTTT
ACATCAATAGCCTCACCACTAATATATCTTGTATCTAGGTGTCTATAATGGCTGAAACCACTACATCCAT
CTATGCCATTTACCTGAAAACTTAACTGTGGCCTTTATGAGGCCAGAAAGTGAACTGAGTTTTCGTAGT
TAAGACCTCAAATGAGGGGAGTCAGCAGTGATCATGGGGAAATGTTTACATTTTTTTTTCTTCAGAAG
TAACGCTTTCTGATGATTTATCTGATATTTAAAACAGGGAGCTATGGTGCACTCTAGTTTATACTTGCG
CTCTGAAATGTGTAAACATAGGGTGCCTACCTATTTCACCTGACCCATACTCGTTTCTGATTCAGAATCA
GTGTGGGCTCCTGCAGTGGGCGCGGGTCACGGCTGACTCCAACTTCCAATACAACAGCCATCACTAGCAC
AGTGTTTTTTGTTTAACCAACGTAGTTGTATTAGTAGTTCTATAAAGAGAACTGCTTTTAACATTAGGG
ACTGGGAGCAGTCCATGGGATAAAAGGAAAGTGTTTTCTCACGAGAAAACATGTCAGGAAAATAAAGA
ACACTTTCTACCTCTGTTTCAGATTTTTGAAACACTTATTTTAAACCAAATTTTAATTTCTGTGTCCAAA
ATAAGTTTAAGGACATCTGTTCTTCCATACGAAATAGGTTAGGCTGCCTATTTCTCACTGAGCTCATGG
AATGGTTCTGCTTATGATACTCTGCACGCTGCCTTTAGTGAGTGAGGAGTTTGGGGTTGCCTAGCAACT
TGCTAACTTGTAAAAGTCATCTTTCCCTCACAGAAAGAAACGAAAGAAAGCAAAGTCAGTGAAA
GACAATCTTTATAGTTTCAGGAGTAAATCTAAATGTGGCTTTTGTCAAGCACTTAGATGGATATAAATGC
AGCAACTTGTTTTAAAAAAATGCACAATTTACTTCCCAAAAAAGTTGTTACTTGCCTTTTCAAGTTGTTG
ACAAACACACATTTGATATTCTCTTATATGTTATAGTAATGTAACGTATAAACTCAAGCCTTTTTATTCT
TTGTGATTAAATCCTGTTTTAAAATGTCACAAAACAGGAACCAGCATTCTAATTAGATTTACTATATCAA
GATATGGTTCAAATAGGACTACTAGAGTTCATTGAACACTAAAACTATGAAACAATTACTTTTTATATTA
AAAAGACCATGGATTTAACTTATGAAAATCCAAATGCAGGATAGTAATTTTGTTTACTTTTTTAACCAA
ACTGAATTTTTGAAAGACTATTGCAGGTGTTTAAAAAGAAAGAAAAGTTGTTTTATCTAATACTGTAAGT
AGTTGTCATATTCTGGAAAATTTAATAGTTTTAGAGTTAAGATATCTCCTCTCTTTGGTTAGGGAAGAAG
AAAGCCCTTCACCATTGTGGAATGATGCCCTGGCTTTAAGGTTTAGCTCCACATCATGCTTCTCTTGAGA

```
ATTCTATTTGGTAGTTACAATTACAGAAACTGATTAGTTTGTCAGTTTGCAGATAGATTTAGCACAGTAC
TCATCACTCGGATAGATTGAGATGTTCTTTCACATCAGATGATCTGTAACACTGTAAGATACTGATCTTT
ACAACTGTTTAATCAGTTTTATTTTTGTACAGTATTAGTGACCTAAGTTATTTTGCTGTCCCGTTTTTGT
AAATCAAATGAAATTATAAAAGAGGATTCTGACAGTAGGTATTTTGTACATATGTATATATGTTGTCCAA
ATAAAAATAATAAATGATAAAGACTGAA
```

MAFF mRNA nucleic acid sequence

SEQ ID NO: 44
```
CGGGTCGGTGACGTCACCGCATGACTGGGTTTTTATGAATGAAAGGAATCCTGTGAGTGAGTAATTCCGG
GAAGCTCGCCTTACAACTCCGCGCGGCCTCGGCCCCCTGCGCCGCCCGCCCCACAACAAAACTCAGCGCA
GCGCTCCCGGGCGCCCGGTTCAGAGCGACCTGCGGCTCAGAGCGGAGGGGAGACTGACCGGAGCGCGGAT
CGGGACAGCGGCCGGGACAGCGGCGAGACGCGCGTGTGAGCGCGCCGGACCAAGCGGGCCCAGAAGCG
GATCAAGCGAGAGCTGAGCGAGAACACGCCGCACCTGTCGGACGAGGCGCTGATGGGGCTGTCGGTGCGC
GAGCTGAACCGGCATCTGCGCGGGCTCTCCGCCGAGGAGGTGACACGGCTCAAGCAGCGGCGCCGCACAC
TCAAAAACCGTGGCTACGCCGCCAGCTGCCGCGTGAAGCGCGTGTGCCAGAAGGAGGAGCTGCAGAAGCA
GAAGTCGGAGCTGGAGCGCGAGGTGGACAAGCTGGCGCGCGAGAACGCCGCCATGCGCCTGGAGCTCGAC
GCGCTGCGCGGCAAGTGCGAGGCGCTGCAGGGCTTCGCGCGCTCCGTGGCCGCCGCCCGCGGGCCCGCCA
CGCTCGTGGCGCCGGCCAGCGTCATCACCATCGTCAAGTCCACCCCGGGCTCGGGTCTGGCCCCGCCCA
CGGCCCCGGACCCCGCCCACGGCCCGGCCTCCTGCTCCTAGTGCCCGCCCCGCCATGCCTCAGCCACGCC
CCTCCGGCCTCAGCTCCCTCCCCAAAGTGCCTGAGCGCCGCCTCTGTGCCCAGGTCCCATTTCTCTGCAG
CACTGGCCCCTTGGTGCACACACATTCCCTTCGTGGGCCCTGTCTTCCTCTTGCAGCCCCCCAAACTGGG
ACCGAATGACCCTGGGAAGGGGAACTTGGGTAGGTTGGGGATGGGGCAGAGGTCTGGATCTGGGATCGCC
CTTGGCTGAAAGTTTAGCCTTTTTAGATTGAGAGATACAGAGCCGGCTTAGAGAACAGCTGTTGGGGGAG
AAGAGGGCACCCCTCATCTTGGAAACTGCTCCTTATTGTGCCAATATGCCCTCCAAACCCTCCCAGGATTC
AAAGCTAGGTTTGGCTGTCTGTGACTTACGGGACCGTCCTGCTGAGAAATTGCACTGAAGAGATGCCCCC
ACCTCTGGTTGGGCCTGGGGGTGCCTGGCCTTCCGAAACTAAAAGAGTGGGTGGGAAGACTAGTGAAACC
CAGTTCACGGATGGGGAAACAGGCCTGAGGTCACATTTCACTTAGTGGTTGTGTTGGGACCAAAACCTGG
GTGTCCTCACTGCTGCCCTGAGTCCAGCCATGGTTTTCAGGGGGACAGTGGACAGGGACTCAGAAATGTG
GTGGGAGGGCCTCCCTGGCTTGGGAGACCGCTCTCTGCAAGGGAGGGGGAGAGAAGCAGAGGGAGAGAGA
AGGTGACACGGATGGAAGAGTGGGAAGGAGCTGGCCTGGCTCAGCCCTAGGCTGTCCCTGCAGCCAGGGT
GTCCGGGGGCTGGCCAGTCAGAGAAAGGGGGCCATGGACTGCTGTGGCAAATAGGGAGACAAGGAGACAG
ACCCTGCAGTCCTACTACAGTCTGGAGTGGGGTCCTAAGAAGAAGGGTCCCACCTCAACCCCTGTCAGTG
TCCACTGTGGGGTGGGGCTGACCCCTGCCTTTGATTGTCATTCTCCTGGGAAGCCCAGTCTCAGTCCCT
CCCCCAACACTGTCCACACTGCCCCTCCCCACTGTTTATTTATTGCACGGATCTAAGTTATTCTCCCCAG
CCAGAGCCCGAGCTCCTGCTCCCTGGGAAAAGTGGCGTATGCCCTGAGCTGGGCTTTATATTTTATATC
TGCAAATAAATCACATTTTATCTTATATTTAGGGAAAGCCGGAGAGCAACACAAAAAATGTTTAAGCCG
GGCGCGGTGGCTCACATCTGTAATCCCAGCACTTTGGGAGTCCAAGGAGGGGGATCGCTTGAGTCCAGGA
GTTTGAGACCAGCCTGGACAACATGGTGAAACCCCATCTCTACAAAAAATACAAAAATTAGCCATGCATG
GTGGCTCATGCCTGTAGTCCCAGCTACTTGGGAGGCTGAGGCAGGAGGATCACTTAAGCCCAGAAGGCAG
AGGTTGTAGTGAGCTGAGATCGCACCACTGCACTCCAGCCTGGGCAACATAGCAAATCCTGTCTCAAAA
AAAAGTTAAAAAATATTGCCCGGCTCCTAGAATTTATTTATTTCCTGACTTACAGCAAGCGAGTTATCG
TCTTCGTGTATTTTGTAGACTTTCTAAATAAAGTCAAATTCTTTCTTTTTCCACAGAGAATAAAAAAAAAA
AAA
```

STAT4 mRNA nucleic acid sequence

SEQ ID NO: 45
```
TTTTTCCTGGCACTGCTGAGCCACCTGCAGTTGCGAGAGCCGCTGGGAGGGATAAGAGGGAAGAGGACGC
CCGGTGAAGGGGCTCCAGCCTGGCAGTTTCTGCGTGTTAGCATTTCTAGAATAGAGTGGGTGGGAACTGA
CCCAAGTAAAGTCCCAGAGACTCGAACACTGACGCACAGGAAAGCCTCAAGTGGGAGGGAGAAATGCAAT
CCCCTACTGATGATGGCGTCAGCGGCTTTCTCCTAGGGACTGTGAGGGGCGCTTCTGACTTTGGACTTGA
GCACTGCCTGGGACCTGTGCTGAGAGAGCGCTAGCATGTCTCAGTGGAATCAAGTCCAACAGTTAGAAAT
CAAGTTTTTGGAGCAGGTGGATCAATTCTATGATGACAACTTTCCCATGGAAATTCGGCATCTGTTGGCC
CAATGGATTGAAAATCAAGACTGGGAGGCAGCTTCTAACAATGAAACCATGGCAACGATTCTTCTTCAA
ACTTGTTAATACAACTGGATGAACAGTTAGGTCGTGTTTCCAAAGAGAAAACCTACTCTTGATACACAA
TCTAAAAAGAATTAGGAAGGTCCTTCAGGGAAATTTCATGAAATCCAATGCATGTAGCTGTGGTTATT
TCAAACTGTTTAAGGGAAGAGAGGAGAATATTGGCTGCAGCCAACATGCCTGTCAGGGGCCTCTAGAGA
AATCCTTACAAAGTTCTTCAGTTTCAGAAAGACAGAGGAATGTGGAGCACAAAGTGGCTGCCATTAAAA
CAGTGTGCAGATGACAGAACAAGATACCAAATACTTAGAAGATCTGCAAGACGAATTTGACTACAGGTAT
AAAACAATTCAGACAATGGATCAGAGTGACAAGAATAGTGCCATGGTGAATCAGGAAGTTTTGACACTGC
AGGAAATGCTTAACAGCCTCGATTTCAAGAGAAAGGAGGCTCTCAGTAAAATGACCCAAATCATCCATGA
GACAGACCTGTTAATGAACACCATGCTCATAGAAGAGCTGCAAGACTGGAAGCGGAGGCAGCAACTCGC
TGCATCGGGGGTCCACTCCACAATGGGCTCGACCAGCTTCAGAACTGCTTTACACTATTGGCAGAAAGTC
TTTTCCAACTGAGAAGGCAATTGGAGAAACTAGAGGAGCAATCTACCAAAATGACATATGAAGGTGATCC
CATTCCAATGCAAAGAACTCACATGCTAGAAAGAGTCACCTTCTTGATCTACAACCTTTTCAAGAACTCA
TTTGTGGTTGAGCGACAGCCATGTATGCCAACCCACCCTCAGAGGCCGTTGGTACTTAAAACCCTAATTC
AGTTCACTGTAAAACTAAGGCTACTAATAAAATTGCCAGAACTAAACTATCAGGTAAAGGTTAAGGCATC
AATTGACAAGAATGTTTCAACTCTAAGCAACCGAAGATTTGTACTTTGTGGAACTAATGTCAAAGCCATG
TCTATTGAAGAATCTTCCAATGGGAGTCTCTCAGTAGAATTTCGACATTTGCAACCAAAGGAAATGAAGT
CCAGTGCTGGAGGTAAAGGAAATGAGGGCTGTCACATGGTGACTGAAGAACTTCATTCCATAACGTTTGA
AACACAGATCTGCCTCTATGGCCTGACCATAGATTTGGAGACCAGCTCATTGCCTGTGGTGATGATTTCC
AATGTCAGTCAGTTACCTAATGCTTGGGCATCCATCATTTGGTACAACACGTGACAACAGATTCCCAGA
ACTTGGTTTTCTTTAATAATCCTCCACCTGCCACATTGAGTCAACTACTGGAGGTGATGAGCTGGCAGTT
TTCATCGTACGTTGGTCGTGGTCTTAACTCAGATCAACTCCATATGCTGGCAGAGAAGCTTACAGTCCAA
TCTAGCTACAGTGATGGTCACCTCACCTGGGCCAAGTTCTGCAAGGAACATTTACCTGGTAAATCATTTA
CCTTTTGGACATGGCTTGAAGCAATATTGGATCTAATTAAGAAACACATTCTTCCCCTTTGGATTGATGG
GTATGTCATGGGCTTTGTTAGCAAAGAGAAGGAACGGCTGTTGCTAAAGGATAAATGCCTGGCACCTTT
TTATTAAGATTCAGTGAAAGCCATCTCGGAGGAATAACTTTCACCTGGGTGGACCATTCTGAAAGTGGGG
```

AAGTGAGATTCCACTCTGTAGAACCCTACAATAAAGGCCGGTTGTCTGCTCTGCCATTCGCTGACATCCT
GCGAGACTACAAAGTTATTATGGCTGAAAACATTCCTGAAAACCCTCTGAAGTACCTATATCCTGACATT
CCCAAAGACAAAGCCTTCGGTAAACACTACAGCTCTCAGCCTTGCGAAGTTTCAAGACCAACAGAAAGGG
GTGACAAAGGTTATGTTCCTTCTGTTTTTATCCCCATCTCAACAATCCGAAGTGATTCAACAGAGCCACA
TTCTCCATCAGACCTTCTTCCCATGTCTCCAAGTGTGTATGCGGTGTTGAGAGAAAACCTGAGTCCCACA
ACAATTGAAACTGCAATGAAGTCTCCTTATTCTGCTGAATGACAGGATAAACTCTGACGCACCAAGAAAG
GAAGCAAATGAAAAAGTTTAAAGACTGTTCTTTGCCCAATAACCACATTTTATTTCTTCAGCTTTGTAAA
TACCAGGTTCTAGGAAATGTTTGACATCTGAAGCTCTCTTCACACTCCCGTGGCACTCCTCAATTGGGAG
TGTTGTGACTGAAATGCTTGAAACCAAAGCTTCAGATAAACTTGCAAGATAAGACAACTTTAAGAAACCA
GTGTTAATAACAATATTAACAGAAGAAAAAAAAAAAAAAA

TOX mRNA nucleic acid sequence
SEQ ID NO: 46
GGTGCGCGCCGCGGCTTGGGGGAGAGTTGAGCGCTTTTCCCCCCTCTTTTTTTTTTTTCCTCTTCTTC
TTAAACAAACCACAAACGGATGTGAGGGAAGGAAGGTGTTTCTTTTACTCCTGAGCCCAGACACCTCACT
CTGTTCCGTCTAAGCTTGTTTTGCTGAACACTTTTTTTTAAAAAAGGAAAAAGAAAAGGAGTTGCTTGAT
GTGAGAGTGAAATGGACGTAAGATTTTATCCACCTCCAGCCCAGCCCGCCGCTGCGCCCGACGCTCCCTG
TCTGGGACCTTCTCCCTGCCTGGACCCCTACTATTGCAACAAGTTTGACGGTGAGAACATGTATATGAGC
ATGACAGAGCCGAGCCAGGACTATGTGCCAGCCAGCCAGTCCTACCCTGGTCCAAGCCTGGAAAGTGAAG
ACTTCAACATTCCACCAATTACTCCTCCTTCCCTCCCAGACCACTCGCTGGTGCACCTGAATGAAGTTGA
GTCTGGTTACCATTCTCTGTGTCACCCCATGAACCATAATGGCCTGCTACCATTTCATCCACAAAACATG
GACCTCCCTGAAATCACAGTCTCCAATATGCTGGGCAGGATGGAACACTGCTTTCTAATTCCATTTCTG
TGATGCCAGATATACGAAACCCAGAAGGAACTCAGTACAGTTCCCATCCTCAGATGGCAGCCATGAGACC
AAGGGGCCAGCCTGCAGACATCAGGCAGCAGCCAGGAATGATGCCACATGGCCAGCTGACTACCATTAAC
CAGTCACAGCTAAGTGCTCAACTTGGTTTGAATATGGGAGGAAGCAATGTTCCCCACAACTCACCATCTC
CACCTGGAAGCAAGTCTGCAACTCCTTCACCATCCAGTTCAGTGCATGAAGATGAAGGCGATGATACCTC
TAAGATCAATGGTGGAGAGAAGCGGCCTGCCTCTGATATGGGGAAAAAACCAAAAACTCCCAAAAAGAAG
AAGAAGAAGGATCCCAATGAGCCCCAGAAGCCTGTGTCTGCCTATGCGTTATTCTTTCGTGATACTCAGG
CCGCCATCAAGGGCCAAAATCCAAACGCTACCTTTGGCGAAGTCTCTAAAATTGTGGCTTCAATGTGGGA
CGGTTTAGGAGAAGAGCAAAACAGGTCTATAAAAAGAAAACCGAGGCTGCGAAGAAGGAGTACCTGAAG
CAACTCGCAGCATACAGAGCCAGCCTTGTATCCAAGAGCTACAGTGAACCTGTTGACGTGAAGACATCTC
AACCTCCTCAGCTGATCAATTCGAAGCCGTCGGTGTTCCATGGGCCCAGCCAGGCCCACTCGGCCCTGTA
CCTAAGTTCCCACTATCACCAACAACCGGGAATGAATCCTCACCTAACTGCCATGCATCCTAGTCTCCCC
AGGAACATAGCCCCCAAGCCGAATAACCAAATGCCAGTGACTGTCTCTATAGCAAACATGGCTGTGTCCC
CTCCTCCTCCCCTCCAGATCAGCCCGCCTCTTCACCAGCATCTCAACATGCAGCAGCACCAGCCGCTCAC
CATGCAGCAGCCCCTTGGGAACCAGCTCCCCATGCAGGTCCAGTCTGCCTTACACTCACCCACCATGCAG
CAAGGATTTACTCTTCAACCCGACTATCAGACTATTATCAATCCTACATCTACAGCTGCACAAGTTGTCA
CCCAGGCAATGGAGTATGTGCGTTCGGGGTGCAGAAATCCTCCCCCACAACCGGTGACTGGAATAACGA
CTACTGCAGTAGTGGGGCATGCAGAGGGACAAAGCACTGTACCTTACTTGAGAATCTGAACACCTCTTC
TTTCCACTGAGGAATTCAGGGAAGTGTTTTCACCATGGATTGCTTTGTACAGTCAAGGCAGTTCTCCATT
TTATTAGAAAATACAAGTTGCTAAGCACTTAGGACCATTTGAGCTTGTGGGTCACCCACTCTGGAAGAAA
TAGTCATGCTTCTTTATTATTTTTTAATCCTTTATGGACATTGTTTTTCTTCTTCCCTGAAGGAAATTT
GGACCATTCAGATTTTATGTTGGTTTTTTGCTGTGAAGTGCTGCGCTCTAGTAACTGCCTTAGCAACTGT
AGATGTCTCGGATAAAAGTCCTGGATTTTCCATTGGTTTTCATAATGGGTGTTTATATGAAACTACTAAA
GACTTTTTAAATGGCTTGATGTAGCAGTCATAGCAAGTTTGTAAATAGCATCTATGTTACACTCTCCTAG
AGTATAAAATGTGAATGTTTTTGTAGCTAAATTGTAATTGAAACTGGCTCATTCCAGTTATTGATTTCA
CAATAGGGGTTAAATTGGCAAACATTCATATTTTTACTTCATTTTTAAAACAACTGACTGATAGTTCTAT
ATTTTCAAATATTTGAAATAAAAAGTATTCCCAAGTGATTTTAAATTTAAAAACAAATTGGCTTTGTCT
CATTGATCAGACAAAAAGAAACTAGTATTAAGGGAAGCGCAAACACATTTATTTTGTACTGCAGAAAAAT
TGCTTTTTTGTATCACTTTTTGTGTAATGGTTAGTAAATGTCATTTAAGTCCTTTTATGTATAAAACTGC
CAAATGCTTACCTGGTATTTTATTAGATGCAGAAACAGATTGGAAACAGCTAAATTACAACTTTTACATA
TGGCTCTGTCTTATTGTTTCTTCATACTGTGTCTGTATTTAATCTTTTTTTATGGAACCTGTTGCGCCTA
TTTATGAAATAAATATAGGTGTTTGTAAGTAAATTTGTTAGTATTTGAAAGAGGTTTCTTTGATGTT
TTAACTTTTGCTGGCAAAAAAAATTCACGCTTGGTGTGAATACTTTATTAGTTTTTACAGTAACA
TGAATAAAGCCAAACCTGCTTTTCATTTAGCAGCAAATTAAAGTAACCAGTCCTTATTTCTGCATTTCTT
TGGTTGATGCAAACAAAAACTATTATATTTAAGAACTTTATTTCTTCATACGACATAACAGAATTGCCC
TCCAAGTCACACAAGCTCCAAGACTAAACAAACAGACAGGTCCTCTGTCTTAAAAAGGTTACTTCTTGGT
TCTCAGCTGGTTCTAGTCAATTCTGAACCACCACCCCCCGCCCCCGCAAAAAGTAAAGTCAAACCAA
ACTTCCTCAAGCTGCATGCTTTTCACAAAATCCAGAAAGCATTTAAGAATTGACTAGGGGCTGGAAGAA
GTGAAAGGGAAGCATCTAAAAATGAAAGGTGAGTAACCAGATAGCAAAAGAAAAGGGAAAGCCATCCAAA
TTTGAAAGCTGTTGATAGAAATTGAGATTCTTGCTGTCTTTTGTGCCTCTACAAGCTACTACTCATTCCA
GAATTCCTGGGTCTTCCAAGAGGATTCTTAAGGTACCAGAGATTTGCTAGGGAACCAAAAGTGCTTGAGA
ATCTGCCTGAGGGCTTGCATAGCTTTCACATTAAAAAAGAAAAAGCTAGCAGATTTACTCCTTTTTAGG
GGATCATATCAAGAAAGTTAGTCTGGTTGGAAACCAAGAGAATGGCTGATGTCTCTTTCTTGGAATATGT
GAAATAAATTTAGCAGTTTAACTAAATACAAATATATGCATTGTGTAATCCACTCAGAATTAAACAGACA
AAAGGTATGCTTGCTTTGGAATGATTTTAGGCATTGTACAACCTTGAATCACTTGAGCATGTAATAACTA
ATAAATAATGCAGATCCATGTGATTATTAAAATGACTGTAGCTGAGAGCTCTAATTTTCCTGTCTTGAAA
CTGTATAAGAACTCATGTGATTAAGTTCACAGTTTATTGTTTGTCTGTTTAGTATTTTAGAAATATACCA
GCACTACTAATTAACTAATGTCTTTTATTTATTATATTATGATAAAGTAAAAATTTCACTTGCATTAAGT
CTAAACTGAGAAGGTAATTACTGGGAGGAGAATGAGCAGCTTTGACTTTGACAGGCGGTTTGTGCAGGAA
AGCACAGTGCCGTGTTGTTTACAGCTTTTCTAGAGCAGCTGTGCGACCAGGGTAGAGAGTGTTGAAATTC
AATACCAAATACAGTAAAAACAAATGTAAATAAAAGAAAACACATCATCAATAAAACTGTTATTATGCGT
G ZBTB16 mRNA nucleic acid sequence

SEQUENCE LISTING:

SEQ ID NO: 47
```
GCAGCAGAGAGGAGTTGAGGGCGATGAGAGCGGGTACTGCGAACTGCCGGGCGATGCGTCGCTGCCGCC
GTGATACGGAGAGCAACAGTTCCCCAGCAACACCCCTCCCCGACACGACACACCCCCGACAGGCAC
GCACACCCACCCCACAGTGCCCGGCTCGGCTGCGCCTCCTCTATTGGCCCAGGAAGCCCACCCAGCCCCG
CCACGCAGAGCCCAGAAGGAAAGAAAGCCTCATGCCTGAGCCGAGGGGAGCACCATGGATCTGACAAAAA
TGGGCATGATCCAGCTGCAGAACCCTAGCCACCCCACGGGGCTACTGTGCAAGGCCAACCAGATGCGGCT
GGCCGGGACTTTGTGCGATGTGGTCATCATGGTGGACAGCCAGGAGTTCCACGCCCACCGGACGGTGCTG
GCCTGCACCAGCAAGATGTTTGAGATCCTCTTCCACCGCAATAGTCAACACTATACTTTGGACTTCCTCT
CGCCAAAGACCTTCCAGCAGATTCTGGAGTATGCATATACAGCCACGCTGCAAGCCAAGGCGGAGGACCT
GGATGACCTGCTGTATGCGGCCGAGATCCTGGAGATCGAGTACCTGGAGGAACAGTGCCTGAAGATGCTG
GAGACCATCCAGGCCTCAGACGACAATGACACGGAGGCCACCATGGCCTGATGGCGGGGCCGAGGAAGAAG
AGGACCGCAAGGCTCGGTACCTCAAGAACATCTTCATCTCGAAGCATTCCAGCGAGGAGAGTGGGTATGC
CAGTGTGGCTGGACAGAGCCTCCCTGGGCCCATGGTGGACCAGAGCCCTTCAGTCTCCACTTCATTTGGT
CTTTCAGCCATGAGTCCCACCAAGGCTGCAGTGGACAGTTTGATGACCATAGGACAGTCTCCTGCAGG
GAACTCTTCAGCCACCTGCAGGGCCCGAGGAGCCAACTCTGGCTGGGGGTGGGCGGCACCCTGGGGTGGC
TGAGGTGAAGACGGAGATGATGCAGGTGGATGAGGTGCCCAGCCAGGACAGCCCTGGGGCAGCCGAGTCC
AGCATCTCAGGAGGGATGGGGGACAAGGTTGAGGAAAGAGGCAAAGAGGGGCCTGGGACCCCGACTCGAA
GCAGCGTCATCACCAGTGCTAGGGAGCTACACTATGGGCGAGAGGAGAGTGCCGAGCAGGTGCCACCCCC
AGCTGAGGCTGGCCAGGCCCCACTGGCCGACCTGAGCACCCAGCACCCCCGCCTGAGAAGCATCTGGGC
ATCTACTCCGTGTTGCCCAACCACAAGGCTGACGCTGTATTGAGCATGCCGTCTTCCGTGACCTCTGGCC
TCCACGTGCAGCCTGCCCTGGCTGTCTCCATGGACTTCAGCACCTATGGGGGGCTGCTGCCCCAGGGCTT
CATCCAGAGGGAGCTGTTCAGCAAGCTGGGGGAGCTGGCTGTGGGCATGAAGTCAGAGAGCCGGACCATC
GGAGAGCAGTGCAGCGTGTGTGGGGTCGAGCTTCCTGATAACGAGGCTGTGGAGCAGCACAGGAAGCTGC
ACAGTGGGATGAAGACGTACGGGTGCGAGCTCTGCGGGAAGCGGTTCCTGGATAGTTTGCGGTGCACAGT
GCACTTACTGGCTCATTCAGCGGGTGCCAAAGCCTTTGTCTGTGATCAGTCGGTGCACAGTTTTCGAAG
GAGGATGCCCTGGAGACACACAGGCAGACCCATACTGGCACTGACATGGCCGTCTTCTGTCTGCTGTGTG
GGAAGCGCTTCCAGGCGCAGAGCGCACTGCAGCAGCACATGGAGGTCCACGCGGGCGTGCGCAGCTACAT
CTGCAGTGAGTGCAACCGCACCTTCCCCAGCCACACGGCTCTCAAACGCCACCTGCGCTCACATACAGGC
GACCACCCCTACGAGTGTGAGTTCTGTGGCAGCTGCTTCCGGGATGAGAGCACACTCAAGAGCCACAAAC
GCATCCACACGGGTGAGAAACCCTACGAGTGCAATGGCTGTGGCAAGAAGTTCAGCCTCAAGCATCAGCT
GGGAGACGCACTATAGGGTGCACACAGGTGAGAAGCCCTTTGAGTGTAAGCTCTGCCACCAGCGCTCCCGG
GACTACTCGGCCATGATCAAGCACCTGAGAACGCACAACGGCGCCTCGCCCTACCAGTGCACCATCTGCA
CAGAGTACTGCCCCAGCCTCTCCTCCATGCAGAAGCACATGAAGGGCCACAAGCCCGAGGAGATCCCGCC
CGACTGGAGGATAGAGAAGACGTACCTCTACCTGTGCTATGTGTGAAGGGAGGCCCGCGGCGGTGGAGCC
GAGCGGGGAGCCAGGAAAGAAGAGTTGGAGTGAGATGAAGGAAGGACTATGACAAATAAAAAAGGAAAAG
AAAAAAAAAACAGAAGGAAAAGGAAAAAAAAAAAAA
```

ARID5B amino acid sequence
SEQ ID NO: 48
```
MEPNSLQWVGSPCOLHOPYIFYKAFQFHLEGKPRILSLGDFFFVRCTPKDPICIAELQLLWEERTSRQLL
SSSKLYFLPEDTPQGRNSDHGEDEVIAVSEKVIVKLEDLVKWVHSDFSKWRCGFHAGPVKTEALGRNGQK
EALLKYRQSTLNSGLNFKDVLKEKADLGEDEEETNVIVLSYPQYCRYRSMLKRIQDKPSSILTDQFALAL
GGIAVVSRNPQILYCRDTFDHPTLIENESICDEFAPNLKGRPRKKPCPQRRDSFSGVKDSNNNSDGKAV
AKVKCEARSALTKPKNNHNCKKVSNEEKPKVAIGEECRADEQAFLVALYKYMKERKTPIERIPYLGFKQI
NLWTMFQAAQKLGGYETITARRQWKHIYDELGGNPGSTSAATCTRRHYERLILPYERFIKGEEDKPLPPI
KPRKQENSSQENENKTKVSGTKRIKHEIPSKKEKENAPKPQDAAEVSSEQEKEQETLISQKSIPEPLPA
ADMKKKIEGYQEFSAKPLASRVDPEKDNETDQGSNSEKVAEEAGEKGPTPPLPSAPLAPEKDSALVPGAS
KQPLTSPSALVDSKQESKLCCFTESPESEPQEASFPSFPTTQPPLANQNETEDDKLPAMADYIANCTVKV
DQLGSDDIHNALKQTPKVLVVQSFDMFKDKDLTGPMNENHGLNYTPLLYSRGNPGIMSPLAKKKLLSQVS
GASLSSSYPYGSPPPLISKKKLIARDDLCSSLSQTHHGQSTDHMAVSRPSVIQHVQSFRSKPSEERKTIN
DIFKHEKLSRSDPHRCSFSKHHLNPLADSYVLKQEIQEGKDKLLEKRALPHSHMPSFLADFYSSPHLHSL
YRHTEHHLHNEQTSKYPSRDMYRESENSSFPSHRHQEKLHVNYLTSLHLQDKKSAAAEAPTDDQPTDLSL
PKNPHKPTGKVLGLAHSTTGPQESKGISQFQVLGSQSRDCHPKACRVSPMTMSGPKKYPESLSRSGKPHH
VRLENFRKMEGMVHPILHRKMSPQNIGAARPIKRSLEDLDLVIAGKKARAVSPLDPSKEVSGKEKASEQE
SEGSKAAHGGHSGGGSEGHKLPLSSPIFPGLYSGSLCNSGLNSRLPAGYSHSLQYLKNQTVLSPLMQPLA
FHSLVMQRGIFTSPTNSQQLYRHLAAATPVGSSYGDLLHNSIYPLAAINPQAAFPSSQLSSVHPSTKL
```

ATF3 amino acid sequence
SEQ ID NO: 49
```
MMLQHPGQVSASEVSASAIVPCLSPPGSLVFEDFANLTPFVKEELRFAIQNKHLCHRMSSALESVTVSDR
PLGVSITKAEVAPEEDERKKRRRERNKIAAAKCRNKKKEKTECLQKESEKLESVNAELKAQIEELKNEKQ
HLIYMLNLHRPTCIVRAQNGRTPEDERNLFIQQIKEGTLQS
```

AZU1 amino acid sequence
SEQ ID NO: 50
```
MTRLTVLALLAGLLASSRAGSSPLLDIVGGRKARPRQFPFLASIQNQGRHFCGGALIHARFVMTAASCFQ
SQNPGVSTVVLGAYDLRRREROSRQTFSISSSMSENGYDPQQNLNDLMLLQLDREANLTSSVTILPLPLQN
ATVEAGTRCQVAGWGSQRSGGRLSRFPRFVNVTVTPEDQCRPNNVCTGVLTRRGGICNGDGGTPLVCEGL
AHGVASFSLGPCGROPDFFTRVALFRDWIDGVLNNPGPGPA
```

BMI1 amino acid sequence
SEQ ID NO: 51
```
MHRTTRIKITELNPHLMCVLCGGYFIDATTIIECLHSFCKTCIVRYLETSKYCPICDVQVHKTRPLLNIR
SDKTLQDIVYKLVPGLFKNEMKRRRDFYAAHPSADAANGSNEDRGEVADEDKRIITDDEIISLSIEFFDQ
NRLDRKVNKDKEKSKEEVNDKRYLRCPAAMTVMHLRKFLRSKMDIPNTFQIDVMYEEEPLKDYYTLMDIA
```

YIYTWRRNGPLPLKYRVRPTCKRMKISHQRDGLTNAGELESDSGSDKANSPAGGIPSTSSCLPSPSTPVQ
SPHPQFPHISSTMNGTSNSPSGNHQSSFANRPRKSSVNGSSATSSG

CLEC11A amino acid sequence

SEQ ID NO: 52

MQAAWLLGALVVPQLLGFGHGARGAEREWEGGWGGAQEEEREREALMLKHLQEALGLPAGRGDENPAGTV
EGKEDWEMEEDQGEEEEEEATPTPSSGPSPSPTPEDIVTYILGRLAGLDAGLHQLHVRLHALDTRVVELT
QGLRQLRNAAGDTRDAVQALQEAQGRAEREHGRLEGCLKGLRLGHKCFLLSRDFEAQAAAQARCTARGGS
LAQPADRQQMEALTRYLRAALAPYNWPVWLGVHDRRAEGLYLFENGQRVSFFAWHRSPRPELGAQPSASP
HPLSPDQPNGGTLENCVAQASDDGSWWDHDCQRRLYYVCEFPF

CSTA amino acid sequence

SEQ ID NO: 53

MIPGGLSEAKPATPEIQEIVDKVKPQLEEKTNETYGKLEAVQYKTQVVAGTNYYIKVRAGDNKYMHLKVF
KSLPGQNEDLVLTGYQVDKNKDDELTGF

ETV5 amino acid sequence

SEQ ID NO: 54

MDGFYDQQVPFMVPGKSRSEECRGRPVIDRKRKFLDTDLAHDSEELFQDLSQLQEAWLAEAQVPDDEQFV
PDFQSDNLVLHAPPPTKIKRELHSPSSELSSCSHEQALGANYGEKCLYNYCAYDRKPSGFKPLTPPTTP
LSPTHQNPLFPPPQATLPTSGHAPAAGPVQGVGPAPAPHSLPEPGPQQQTFAVPRPPHQPLQMPKMMPEN
QYPSEQRFQRQLSEPCHPFPPQPGVPGDNRPSYHRQMSEPIVPAAPPPPQGFKQEYHDPLYEHGVPGMPG
PPAHGFQSPMGIKQEPRDYCVDSEVPNCQSSYMRGGYFSSSHEGFSYEKDPRLYFDDTCVVPERLEGKVK
QEPTMYREGPPYQRRGSLQLWQFLVTLLDDPANAHFIAWTGRGMEFKLIEPEEVARRWGIQKNRPAMNYD
KLSRSLRYYYEKGIMQKVAGERYVYKFVCDPDALFSMAFPDNQRPFLKAESECHLSEEDTLPLTHFEDSP
AYLLDMDRCSSLPYAEGFAY

HIVEP3 amino acid sequence

SEQ ID NO: 55

MDPEQSVKGTKKAEGSPRKRLTKGEAIQTSVSSSVPYPGSGTAATQESPAQELLAPQPFPGPSSVLREGS
QEKTGQQQKPPKRPPIEASVHISQLPQHPLTPAFMSPGKPEHLLEGSTWQLVDPMRPGPSGSFVAPGLHP
QSQLLPSHASIIPPEDLPGVPKVFVPRPSQVSLKPTEEAHKKERKPQKPGKYICQYCSRPCAKPSVLQKH
IRSHTGERPYPCGPCGFSFKTKSNLYKHRKSHAHRIKAGLASGMGGEMYPHGLEMERIPGEEFEEPTEGE
STDSEEETSATSGHPAELSPRPKQPLLSSGLYSSGSHSSSHERCSLSQSSTAQSLEDPPPFVEPSSEHPL
SHKPEDTHTIKQKLALRLSERKKVIDEQAFLSPGSKGSTESGYFSRSESAEQQVSPPNTNAKSYAEIIFG
KCGRIGQRTAMLTATSTQPLLPLSTEDKPSLVPLSVPRTQVIEHITKLITINEAVVDTSEIDSVKPRRSS
LSRRSSMESPKSSLYREPLSSHSEKTKPEQSLLSLQHPPSTAPPVPLLRSHSMPSAACTISTPHHPFRGS
YSFDDHITDSEALSHSSHVFTSHPRMLKRQPAIELPLGGEYSSEEPGPSSKDTASKPSDEVEPKESELTK
KTKKGLKTKGVIYECNICGARYKKRDNYEAHKKYYCSELQIAKPISAGTHTSPEAEKSQIEHEPWSQMMH
YKLGTTLELTPLRKRRKEKSLGDEEEPPAFESTKSQFGSPGPSDAARNLPLESTKSPAEPSKSVPSLEGP
TGFQPRTPKPGSGSESGKERRTTSKEISVIQHTSSFEKSDSLEQPSGLEGEDKPLAQFPSPPPAPHGRSA
HSLQPKLVRQPNIQVPEILVTEEPDRPDTEPEPPPKEPEKTEEFQWPQRSQTLAQLPAEKLPPKKKRLRL
AEMAQSSGGESSFESSVPLSRSPSQESNVSLSGSSRSASFERDDHGKAEAPSSSDMRPKPLGTHMLTVPS
HHPHAREMRRSASEQSPNVSHSAHMTETRSKSFDYGSLSLTGPSAPAPVAPPARVAPPERRKCFLVRQAS
LSRPPESELEVAPKGRQESEEPQPSSSKPSAKSSLSQISSAHPVSPPGGKGPGQDRPPLGPTVPYTEA
LQVFHHPVAQTPLHEKPYLPPPVSLFSFQHLVQHEPGQSPEFFSTQAMSSLLSSPYSMPPLLPPSLFQAPP
LPLQPTVLHPGQLHLPQLMPHPANIPFRQPPSFLPMPYPTSSALSSGFFLPLQSQFALQLPGDVESHLPQ
IKTSLAPLATGSAGLSPSTEYSSDIRLPPVAPPASSSAPTSAPPLALPACPDTMVSLVVPVRVQTNMPSY
GSAMYTTLSQILVTQSQGSSATVALPKFEEPPSKGTTVCGADVHEVGPGPSGLSEEQSRAFPTPYLRVPV
TLPERKGTSLSSESILSLEGSSSTAGGSKRVLSPAGSLELTMETQQQKRVKEEEASKADEKLELVKPCSV
VLTSTEDGKRPEKSHLGNQGQGRRELEMLSSLSSDPSDTKEIPPLPHPALSHGTAPGSEALKEYPQPSOK
PHRRGLTPLSVKKEDSKEQPDLPSLAPPSSLPLSETSSRPAKSQEGTDSKKVLQFPSLHTTTNVSWCYLN
YIKPNHIQHADRRSSVYAGWCISLYNPNLPGVSTKAALSLLRSKQKVSKETYTMATAPHPEAGRLVPSSS
RKPRMTEVHLPSLVSPEGQKDLARVEKEEERRGEPEEDAPASQRGEPARIKIFEGGYKSNEEYVYVRGRG
RGKYVCEECGIRCKKPSMLKKHIRTHTDVRPYVCKHCHFAPKTKONLTKHMKSKAHSKKCQETGVLEELE
AEEGTSDDLFQDSEGREGSEAVEEHQFSDLEDSDSDSDLDEDEDEDEEESQDELSRPSSEAPPPGPPHAL
RADSSPILGPQPPDAPASGTEATRGSSVSEAERLTASSCSMSSQSMPGLPWLGPAPLGSVEKDTGSALSY
KPVSPRRPWSPSKEAGSRPPLARKHSLTKNDSSPQRCSPAREPQASAPSPPGLHVDPGRGMGALPCGSPR
LQLSPLTLCPLGRELAPRAHVLSKLEGTTDPGLPRYSPTRRWSPGQAESPPRSAPPGKWALAGPGSPSAG
EHGPGLGLDPRVLFPPAPLPHKLLSRSPETCASPWQKAESRSPSCSPGPAHPLSSRPFSALHDFHGHILA
RTEENIFSHLPLHSQHLTRAPCPLIPIGGIQMVQARPGAHPTLLPGPTAAWVSGFSGGGSDLTGAREAQE
RGRWSPTESSSASVSPVAKVSKFTLSSELEGGDYPKERERTGGGPGRPPDWTPHGTGAPAEPTPTHSPCT
PPDTLPRPPQGRRAAQSWSPRLESPRAPTNPEPSATPPLDRSSSVGCLAEASARFPARTRNLSGEPRTRQ
DSPKPSGSGEPRAHPHQPEDRVPPNA

HOXA3 amino acid sequence

SEQ ID NO: 56

MQKATYYDSSAIYGGYPYQAANGFAYNANQQPYPASAALGADGEYHRPACSLQSPSSAGGHPKAHELSEA
CLRTLSAPPSQPPSLGEPPLHPPPPQAAPPAPQPPQPAPQPPAPTPAAPPPPSSASPPQNASNNPTPANA
AKSPLLNSPTVAKQIFPWMKESRQNTKQKTSSSSSGESCAGDKSPPGQASSKRARTAYTSAQLVELEKEF
HFNRYLCRPRRVEMANLLNLTERQIKIWFQNRRMKYKKDQKGKGMLTSSGGQSPSRSPVPPGAGGYLNSM
HSLVNSVPYEPQSPPPFSKPPQGTYGLPPASYPASLPSCAPPPPPQKRYTAAGAGAGGTPDYDPHAHGLQ
GNGSYGTPHIQGSPVFVGGSYVEPMSNSGPALFGLTHLPHAASGAMDYGGAGPLGSGHHHGPGPGEPHPT
YTDLTGHHPSQGRIQEAPKLTHL

HOXA5 amino acid sequence

SEQUENCE LISTING:

SEQ ID NO: 57
MSSYFVNPTFPGSLPSGQDSFLGQLPLYQAGYDALRPFPASYGASSLPDKTYTSPCFYQQSNSVLACNRA
SYEYGASCFYSDKDLSGASPSGSGKQRGPGDYLHFSPEQQYKPDSSSGQQKALHDEGADRKYTSPVYPWM
QRMNSCAGAVYGSHGRRGRQTYTRYQTLELEKEFHFNRYLTRRRRIEIANALCLTERQIKIWFQNRRMKW
KKENKLINSTQPSGEDSEAKAGE

HOXB3 amino acid sequence
SEQ ID NO: 58
MQKATYYDNAAAALFGGYSSYPGSNGFGFDVPPQPPFQAATHLEGDYQRSACSLQSLGNAAPHAKSKELN
GSCMRPGLAPEPLSAPPGSPPPSAAPTSATSNSSNGGGPSKSGPPKCGPGTNSTLTKQIFPWMKESRQTS
KLKNNSPGTAEGCOGGGGGGGGGGSGGSGGGGGGGGGDKSPPGSAASKRARTAYTSAQLVELEKEFHFN
RYLCRPRRVEMANLLNLSERQIKIWFQNRRMKYKKDQKAKGLASSSGOPSPAGSPPQPMQSTAGFMNALH
SMTPSYESPSPPAFGKAHQNAYALPSNYQPPLKGCGAPQKYPPTPAPEYEPHVLQANGGAYGTPTMQGSP
VYVGGGGYADPLPPPAGPSLYGLNHLSHHPSGNLDYNGAPPMAPSQHHGPCEPHPTYTDLSSHHAPPPQG
RIQEAPKLTHL HOXB5 amino acid sequence
SEQ ID NO: 59
MSSYFVNSFSGRYPNGPDYQLLNYGSGSSLSGSYRDPAAMHTGSYGYNYNGMDLSVNRSSASSSHFGAVG
ESSRAFPAPAQEPRFRQAASSCSLSSPESLPCTNGDSHGAKPSASSPSDQATSASSSANFTEIDEASASS
EPEEAASQLSSPSLARAQPEPMATSTAAPEGQTPQIFPWMRKLHISHDMTGPDGKRARTAYTRYQTLELE
KEFHFNRYLTRRRRIEIAHALCLSERQIKIWFQNRRMKWKKDNKLKSMSLATAGSAFQP HOXB6 amino acid sequence
SEQ ID NO: 60
MSSYFVNSTFPVTLASGQESFLGQLPLYSSGYADPLRHYPAPYGPGPGQDKGFATSSYYPPAGGGYGRAA
PCDYGPAPAFYREKESACALSGADEQPPFHPEPRKSDCAQDKSVFGETEEQKCSTPVYPWMQRMNSCNSS
SFGPSGRRGRQTYTRYQTLELEKEFHYNRYLTRRRRIEIAHALCLTERQIKIWFQNRRMKWKKESKLLSA
SQLSAEEEEEKQAE ITGA6 amino acid sequence
SEQ ID NO: 61
MAAAGQLCLLYLSAGLLSRLGAAFNLDTREDNVIRKYGDPGSLFGFSLAMHWQLQPEDKRLLLVGAPRAE
ALPLQRANRTGGLYSCDITARGPCTRIEFDNDADPTSESKEDQWMGVTVQSQGPGGKVVTCAHRYEKRQH
VNTKQESRDIFGRCYVLSQNLRIEDDMDGGDWSFCDGRLRGHEKFGSCQQGVAATFTKDFPHYIVFGAPGT
YNWKGIVRVEQKNNTFFDMNIFEDGPYEVGGETEHDESLVPVPANSYLGFSLDSGKGIVSKDEITFVSGA
PRANHSGAVVLLKRDMKSAHLLPEHIFDGEGLASSFGYDVAVVDLNKDGWQDIVIGAPQYFDRDGEVGGA
VYVYMNQQGRWNNVKPIRLNGTKDSMFGIAVKNIGDINQDGYPDIAVGAPYDDLGKVFIYHGSANGINTK
PTQVLKGISPYFGYSIAGNMDLDRNSYPDVAVGSLSDSVTIFRSRPVINIQKTITVTPNRIDLRQKTACG
APSGICLQVKSCFEYTANPAGYNPSISIVGTLEAEKERRKSGLSSRVQFRNQGSEPKYTQELTLKRQKQK
VCMEETLWLQDNIRDKLRPIPITASVEIQEPSSRRRVNSLPEVLPILNSDEPKTAHIDVHFLKEGCGDDN
VCNSNLKLEYKFCTREGNQDKFSYLPIQKGVPELVLKDQKDIALEITVTNSPSNPRNPTKDGDDAHEAKL
IATFPDTLTYSAYRELRAFPEKQLSCVANQNGSQADCELGNPFKRNSNVTFYLVLSTTEVTFDTPDLDIN
LKLETTSNQDNLAPITAKAKVVIELLLSVSGVAKPSQVYFGGTVVGEQAMKSEDEVGSLIEYEFRVINLG
KPLTNLGTATLNIQWPKEISNGKWLLYLVKVESKGLEKVTCEPQKEINSLNLTESHNSRKKREITEKQID
DNRKFSLFAERKYQTLNCSVNVNCVNIRCPLRGLDSKASLILRSRLWNSTFLEEYSKLNYLDILMRAFID
VTAAAENIRLPNAGTQVRVTVFPSKTVAQYSGVPWWIILVAILAGILMLALLVFILWKCGFFKRSRYDDS
VPRYHAVRIRKEEREIKDEKYIDNLEKKQWITKWNENESYS KIT amino acid sequence
SEQ ID NO: 62
MRGARGAWDFLCVLLLLLRVQTGSSQPSVSPGEPSPPSIHPGKSDLIVRVGDEIRLLCTDPGFVKWTFEI
LDETNENKQNEWITEKAEATNTGKYTCTNKHGLSNSIYVFVRDPAKLFLVDRSLYGKEDNDTLVRCPLTD
PEVTNYSLKGCQGKPLPKDLRFIPDPKAGIMIKSVKRAYHRLCLHCSVDQEGKSVLSEKFILKVRPAFKA
VPVVSVSKASYLLREGEEFTVTCTIKDVSSSVYSTWKRENSQTKLQEKYNSWHHGDFNYERQATLTISSA
RVNDSGVFMCYANNTFGSANVTTTLEVVDKGFINIFPMINTTVFVNDGENVDLIVEYEAFPKPEHQQWIY
MNRTFTDKWEDYPKSENESNIRYVSELHLTRLKGTEGGTYTFLVSNSDVNAAIAFNVYVNTKPEILTYDR
LVNGMLQCVAAGFPEPTIDWYFCPGTEQRCSASVLPVDVQTLNSSGPPFGKLVVQSSIDSSAFKHNGTVE
CKAYNDVGKTSAYFNFAFKGNNKEQIHPHTLFTPLLIGFVIVAGMMCIIVMILTYKYLQKPMYEVQWKVV
EEINGNNYVYIDPTQLPYDHKWEFPRNRLSFGKTLGAGAFGKVVEATAYGLIKSDAAMTVAVKMLKPSAH
LTEREALMSELKVLSYLGNHMNIVNLLGACTIGOPTLVITEYCCYGDLLNFLRRKRDSFICSKQEDHAEA
ALYKNLLHSKESSCSDSTNEYMDMKPGVSYVVPTKADKRRSVRIGSYIERDVTPAIMEDDELALDLEDLL
SFSYQVAKGMAFLASKNCIHRDLAARNILLTHGRITKICDFGLARDIKNDSNYVVKGNARLPVKWMAPES
IFNCVYTFESDVWSYGIFLWELFSLGSSPYPGMPVDSKFYKMIKEGFRMLSPEHAPAEMYDIMKTCWDAD
PLKRPTFKQIVQLIEKQISESTNHIYSNLANCSPNRQKPVVDHSVRINSVGSTASSSQPLLVHDDV MEIS1 amino acid sequence
SEQ ID NO: 63
MAQRYDDLPHYGGMDGVGIPSTMYGDPHAARSMQPVHHLNHGPPLHSHQYPHTAHTNAMAPSMGSSVNDA
LKRDKDAIYGHPLFPLLALIFEKCELATCTPREPGVAGGDVCSSESFNEDIAVFAKQIRAEKPLFSSNPE
LDNLMIQAIQVLRFHLLELEKVHELCDNFCHRYISCLKGKMPIDLVIDDREGGSKSDSEDITRSANLTDQ
PSWNRDHDDTASTRSGGTPGPSSGGHTSHSGDNSSEQGDGLDNSVASPSTGDDDDPKDKKRHHKKRGIFP
KVATNIMRAWLFQHLTHPYPSEEQKKQLAQDTGLTILQVNNWFINARRRIVQPMIDQSNRAVSQGTPYNP
DGQPMGGFVMDGQQHMGIRAPGPMSGMGMNMGMEGQWHYM MYCN amino acid sequence

SEQUENCE LISTING:

```
                                                            SEQ ID NO: 64
MPSCSTSTMPGMICKNPDLEFDSLQPCFYPDEDDFYGGPDSTPPGEDIWKKFELLPTPPLSPSRGFAEH
SSEPPSWVTEMLLENELWGSPAEEDAFGLGGLGGLTPNPVILQDCMWSGFSAREKLERAVSEKLQHGRGP
PTAGSTAQSPGAGAASPAGRGHGGAAGAGRAGAALPAELAHPAAECVDPAVVFPFPVNKREPAPVPAAPA
SAPAAGPAVASGAGIAAPAGAPGVAPPRPGGRQTSGGDHKALSTSGEDTLSDSDDEDDEEEDEEEEIDVV
TVEKRRSSSNTKAVTTFTITVRPKNAALGPGRAQSSELILKRCLPIHQQHNYAAPSPYVESEDAPPQKKI
KSEASPRPLKSVIPPKAKSLSPRNSDSEDSERRRNHNILERQRRNDLRSSFLTLRDHVPELVKNEKAAKV
VILKKATEYVHSLQAEEHQLLLEKEKLQARQQQLLKKIEHARTC

NFIL3 amino acid sequence
                                                            SEQ ID NO: 65
MQLRKMQTVKKEQASLDASSNVDKMMVLNSALTEVSEDSTTGEELLLSEGSVGKNKSSACRRKREFIPDE
KKDAMYWEKRRKNNEAAKRSREKRRLNDLVLENKLIALGEENATLKAELLSLKLKFGLISSTAYAQEIQK
LSNSTAVYFQDYQTSKSNVSSFVDEHEPSMVSSSCISVIKHSPQSSLSDVSEVSSVEHTQESSVQGSCRS
PENKFQIIKQEPMELESYTREPRDDRGSYTASIYQNYMGNSFSGYSHSPPLLQVNRSSSNSPRTSETDDG
VVGKSSDGEDEQQVPKGPIHSPVELKHVHATVVKVPEVNSSALPHKLRIKAKAMQIKVEAFDNEFEATQK
LSSPIDMTSKRHFELEKHSAPSMVHSSLTPFSVQVTNIQDWSLKSEHWHQKELSGKTQNSFKTGVVEMKD
SGYKVSDPENLYLKQGIANLSAEVVSLKRLIATQPISASDSG PTPN14 amino acid sequence
                                                            SEQ ID NO: 66
MPFGLKLRRTRRYNVLSKNCFVTRIRLLDSNVIECTLSVESTGQECLEAVAQRLELRETHYFGLWFLSKS
QQARWVELEKPLKKHLDKFANEPLLFFGVMFYVPNVSWLQQEATRYQYYLQVKKDVLEGRLRCTLDQVIR
LAGLAVQADFGDYNQFDSQDFLREYVLFPMDLALEAEVLEELTQKVAQEHKAHSGILPAEAELMYINEVE
RLDGFGQEIFPVKDNHGNCVHLGIFFMGIFVRNRIGRQAVIYRWNDMGNITHNKSTILVELINKEETALF
HTDDIENAKYISRLFATRHKFYKQNKICTEQSNSPPPIRRQPTWSRSSLPRQQPYILPPVHVQCGEHYSE
THTSQDSIFHGNEEALYCNSHNSLDLNYLGTVTNGSVCSVHSVNSLNCSQSFIQASPVSSNLSIPGSDI
MRADYIPSHRHSAIIVPSYRPTPDYETVMRQMKRGILHTDSQSQSLRNLNIINTHAYNQPEDLVYSQPEM
RERHPYTVPYGPQGVYSNKLVSPSDQRNPKNNVVPSKPGASAISHTVSTPELANMQLQGSHNYSTAHMLK
NYLFRPPPPYPRPRPATSTPDLASHRHKYVSGSSPDLVTRKVQLSVKTFQEDSSPVVHQSLQEVSEPLTA
TKHHGTVNKRHSLEVMNSMVRGMEAMTLKSLHLPMARRNTLREQOPPEEGSGSHEVPQLPQYHHKKTFSD
ATMLIHSSESEEEEEEAPESVPQIPMLREKMEYSAQLQAALARIPNKPPPEYPGPRKSVSNGALRQDQAS
LPPAMARARVLRHGPAKAISMSRTDPPAVNGASLGPSISEPDLTSVKERVKKEPVKERPVSEMFSLEDSI
IEREMMIRNLEKQKMAGLEAQKRPLMLAALNGLSVARVSGREENRVDATRVPMDERFRTLKKKLEEGMVF
TEYEQIPKKKANGIFSTAALPENAERSRIREVVPYEENRVELIPTKENNTGYINASHIKVVVGGAEWHYI
ATQGPLPHTCHDFWQMVWEQGVNVIAMVTAEEEGGRTKSHRYWPKLGSKHSSATYGKFKVTTKFRTDSVC
YATTGLKVKHLLSGQERTVWHLQYTDWPDHGCPEDVQGFLSYLEEIQSVRRHTNSMLEGTKNRHPPIVVH
CSAGVGRTGVLILSELMIYCLEHNEKVEVPMMLRLLREQRMFMIQTIAQYKFVYQVLIQFLQNSRLI RHOC amino acid sequence
                                                            SEQ ID NO: 67
MAAIRKKLVIVGDGACGKTCLLIVFSKDQFPEVYVPTVFENYIADIEVDGKQVELALWDTAGQEDYDRLR
PLSYPDTDVILMCFSIDSPDSLENIPEKWTPEVKHFCPNVPIILVGNKKDLRQDEHTRRELAKMKQEPVR
SEEGRDMANRISAFGYLECSAKTKEGVREVFEMATRAGLQVRKNKRRRGCPIL WT1 amino acid sequence
                                                            SEQ ID NO: 68
MGHHHHHHHHHHSSGHIEGRHMRRVPGVAPTLVRSASETSEKRPFMCAYPGCNKRYFKLSHLQMHSRKHT
GEKPYQCDFKDCERRFFRSDQLKRHQRRHTGVKPFQCKTCQRKFSRSDHLKTHTRTHTGEKPFSCRWPSC
QKKFARSDELVRHHNMHQRNMTKLQLAL AEBP1 amino acid sequence
                                                            SEQ ID NO: 69
MAAVRGAPLLSCLLALLALCPGGRPQTVLTDDEIEEFLEGFLSELEPEPREDDVEAPPPPEPTPRVRKAQ
AGGKPGKRPGTAAEVPPEKTKDKGKKGKKDKGPKVPKESLEGSPRPPKKGKEKPPKATKKPKEKPPKATK
KPKEKPPKATKKPKEKPPKATKKPPSGKRPPILAPSETLEWPLPPPPSPGPEELPQEGGAPLSNNWQNPG
EETHVEAREHQPEPEEETEQPTLDYNDQIEREDYEDFEYIRRQKQPRPPPSRRRRPERVWPEPPEEKAPA
PAPEERIEPPVKPLLPPLPPDYGDGYVIPNYDDMDYYFGPPPPQKPDAERQTDEEKEELKKPKKEDSSPK
EETDKWAVEKGKDHKEPRKGEELEEEWTPTEKVKCPPIGMESHRIEDNQIRASSMLRHGLGAQRGRLNMQ
TGATEDDYYDGAWCAEDDARTQWIEVDTRRTRFTGVITQGRDSSIHDDFVTTFFVGFSNDSQTWVMYTN
GYEEMTFHGNVDKDTPVLSELPEPVVARFIRIYPLTWNGSLCMRLEVLGCSVAPVYSYYAQNEVVATDDL
DFRHHSYKDMRQLMKVVNEECPTITRTYSLGKSSRGLKIYAMEISDNPGEHELGEPEFRYTAGIHGNEVL
GRELLLLLMQYLCREYRDGNPRVRSLVQDTRIHLVPSLNPDGYEVAAQMOSEFGNWALGLWTEEGFDIFE
DFPPDLNSVLWGAEERKWVPYRVPNNNLPIPERYLSPDATVSTEVRAIIAWMEKNPFVLGANLNGGERLVS
YPYDMARTPTQEQLLAAAMAAARGEDEDEVSEAQETPDHAIFRWLAISFASAHLTLTEPYRGGCQAQDYT
GGMGIVNGAKWNPRTGTINDFSYLHTNCLELSFYLGCDKFPHESELPREWENNKEALLTFMEQVHRGIKG
VVTDEQGIPIANATISVSGINHGVKTASGGDYWRILNPGEYRVTAHAEGYTPSAKTCNVDYDIGATQCNF
ILARSNWKRIREIMAMNGNRPIPHIDPSRPMTPQQRRLQQRRLQHRLRLRAQMRLRRLNATTTLGPHTVP
PTLPPAPATTLSTTIEPWGLIPPTTAGWEESETETYTEVVTEFGTVEPEPEFGTKVEPEFETQLEPEFETQ
LEPEFEEEEEEKEEEIATGQAFPFTTVETYTVNFGDF CREB5 amino acid sequence
                                                            SEQ ID NO: 70
MNLEQERPFVCSAPGCSQRFPTEDHLMIHRHKHEMTLKFPSIKTDNMLSDQTPTPTRFLKNCEEVGLFSE
LDCSLEHEFRKAQEEESSKRNISMHNAVGGAMTGPGTHQLSSARLPNHDTNVVIQQAMPSPQSSSVITQA
PSTNRQIGPVPGSLSSLLHLHNRQRQPMPASMPGTLPNPTMPGSSAVLMPMERQMSVNSSIMGMQGPNLS
NPCASPQVQPMHSEAKMRLKAALTHHPAAMSNGNMNTMGHMMEMMGSRQDQTPHHHMHSHPHQHQTLPPH
```

```
HPYPHQHQHPAHHPHPQPHHQQNHPHHHSHSHLHAHPAHHQTSPHPPLHTGNQAQVSPATQQMQPTQTIQ
PPQPTGGRRRRVVDEDPDERRRKFLERNRAAATRCRQKRKVWVMSLEKKAEELTQTNMQLQNEVSMLKNE
VAQLKQLLLTHKDCPITAMQKESQGYLSPESSPPASPVPACSQQQVIQHNTITTSSSVSEVVGSSTLSQL
TTHRTDLNPIL

ERG amino acid sequence
                                                           SEQ ID NO: 71
MASTIKEALSVVSEDQSLFECAYGTPHLAKTEMTASSSSDYGQTSKMSPRVPQQDWLSQPPARVTIKMEC
NPSQVNGSRNSPDECSVAKGGKMVGSPDTVGMNYGSYMEEKHMPPPNMTTNERRVIVPADPTLWSTDHVR
QWLEWAVKEYGLPDVNILLFQNIDGKELCKMTKDDFQRLTPSYNADILLSHLHYLRETPLPHLTSDDVDK
ALQNSPRLMHARNTGGAAFIFPNTSVYPEATQRITTRPDLPYEPPRRSAWTGHGHPTPQSKAAQPSPSTV
PKTEDQRPQLDPYQILGPTSSRLANPGSGQIQLWQFLLELLSDSSNSSCITWEGTNGEFKMTDPDEVARR
WGERKSKPNMNYDKLSRALRYYYDKNIMTKVHGKRYAYKFDFHGIAQALQPHPPESSLYKYPSDLPYMGS
YHAHPQKMNFVAPHPPALPVTSSSFFAAPNPYWNSPTGGIYPNTRLPTSHMPSHLGTYY FOSL2 amino acid sequence
                                                           SEQ ID NO: 72
MYQDYPGNFDTSSRGSSGSPAHAESYSSGGGGQQKFRVDMPGSGSAFIPTINAITTSQDLQWMVQPTVIT
SMSNPYPRSHPYSPLPGLASVPGHMALPRPGVIKTIGTTVGRRRDEQLSPEEEEKRRIRRERNKLAAAK
CRNRRRELTEKLQAETEELEEEKSGLQKEIAELQKEKEKLEFMLVAHGPVCKISPEERRSPPAPGLQPMR
SGGGSVGAVVVKQEPLEEDSPSSSSAGLDKAQRSVIKPISIAGGFYGEEPLHTPIVVTSTPAVTPGTSNL
VFTYPSVLEQESPASPSESCSKAHRRSSSSGDQSSDSLNSPTLLAL HOXA7 amino acid sequence
                                                           SEQ ID NO: 73
MSSSYYVNALFSKYTAGASLFQNAEPTSCSFAPNSQRSGYGAGAGAFASTVPGLYNVNSPLYQSPFASGY
GLGADAYGNLPCASYDQNIPGLCSDLAKGACDKTDEGALHGAAEANFRIYPWMRSSGPDRKRGRQTYTRY
QTLELEKEFHFNRYLTRRRRIEIAHALCLTERQIKIWFQNRRMKWKKEHKDEGPTAAAAPEGAVPSAAAT
AAADKADEEDDDEEEEDEEE IL11RA amino acid sequence
                                                           SEQ ID NO: 74
MSSSCSGLSRVLVAVATALVSASSPCPQAWGPPGVQYGQPGRSVKLCCPGVTAGDPVSWFRDGEPKLLQG
PDSGLGHELVLAQADSTDEGTYICQTLDGALGGTVTLQLGYPPARPVVSCQAADYENFSCTWSPSQISGL
PTRYLTSYRKKTVLGADSQRRSPSTGPWPCPQDPLGAARCVVHGAEFWSQYRINVTEVNPLGASTRLLDV
SLQSILRPDPPQGLRVESVPGYPRRLRASWTYPASWPCQPHFLLKFRLQYRPAQHPAWSTVEPAGLEEVI
TDAVAGLPHAVRVSARDFLDAGTWSTWSPEAWGTPSTGTIPKEIPAWGQLHTQPEVEPQVDSPAPPRPSL
QPHPRLLDHRDSVEQVAVLASLGILSFLGLVAGALALGLWLRLRRGGKDGSPKPGFLASVIPVDRRPGAP
NL KDM7A amino acid sequence
                                                           SEQ ID NO: 75
MAGAAAAVAAGAAAGAAAAAVSVAAPGRASAPPPPPPVYCVCRQPYDVNRFMIECDICKDWFHGSCVGVE
EHHAVDIDLYHCPNCAVLHGSSLMKKRRNWHRHDYTEIDDGSKPVQAGTRTFIKELRSRVFPSADEIIIK
MHGSQLTQRYLEKHGFDVPIMVPKLDDLGLRLPSPTFSVMDVERYVGGDKVIDVIDVARQADSKMTLHNY
VKYFMNPNRPKVLNVISLEFSDTKMSELVEVPDIAKKLSWVENYWPDDSVFPKPFVQKYCLMGVQDSYTD
FHIDFGGTSVWYHVLWGEKIFYLIKPTDENLARYESWSSSVTQSEVFFGDKVDKCYKCVVKQGHTLFVPT
GWIHAVLTSQDCMAFGGNFLHNLNIGMQLRCYEMEKRLKTPDLFKPFFFEAICWFVAKNLLETLKELRED
GFQPQTYLVQGVKALHTALKLWMKKELVSEHAFEIPDNVRPGHLIKELSKVIRAIEEENGKPVKSQGIPI
VCPVSRSSNEATSPYHSRRKMRKLRDHNVRTPSNLDILELHTREVLKRLEMCPWEEDILSSKLNGKFNKH
LQPSSTVPEWRAKDNDLRLLLTNGRIIKDERQPFADQSLYTADSENEEDKRRTKKAKMKIEESSGVGVE
HEESQKPLNGFFTRVKSELRSRSSGYSDISESEDSGPECTALKSIFTTEESESSGDEKKQEITSNFKEES
NVMRNFLQKSQKPSRSEIPIKRECPTSTSTEEEAIQGMLSMAGLHYSTCLQRQIQSTDCSGERNSLQDPS
SCHGSNHEVRQLYRYDKPVECGYHVKTEDPDLRTSSWIKQFDTSRFHPQDLSRSQKCIRKEGSSEISQRV
QSRNYVDSSGSSLQNGKYMQNSNLTSGACQISNGSLSPERPVGETSFSVPLHPTKRPASNPPPISNQATK
GKRPKKGMATAKQRLGKILKLNRNGHARFFV KLF7 amino acid sequence
                                                           SEQ ID NO: 76
MDVLASYSIFQELQLVHDTGYFSALPSLEETWQQTCLELERYLQTEPRRISETFGEDLDCFLHASPPPCI
EESFRRLDPLLLPVEAAICEKSSAVDILLSRDKLLSETCLSLQPASSSLDSYTAVNQAQLNAVTSLTPPS
SPELSRHLVKTSQTLSAVDGTVTLKLVAKKAALSSVKVGGVATAAAAVTAAGAVKSGQSDSDQGGLGAEA
CPENKKRVHRCQFNGCRKVYTKSSHLKAHQRTHTGEKPYKCSWEGCEWRFARSDELTRHYRKHTGAKPFK
CNHCDRCFSRSDHLALHMKRHI KLF9 amino acid sequence
                                                           SEQ ID NO: 77
MSAAAYMDFVAAQCLVSISNRAAVPEHGVAPDAERLRLPEREVTKEHGDPGDTWKDYCTLVTIAKSLLDL
NKYRPIQTPSVCSDSLESPDEDMGSDSDVTTESGSSPSHSPEERQDPGSAPSPLSLLHPGVAAKGKHASE
KRHKCPYSGCGKVYGKSSHLKAHYRVHTGERPFPCTWPDCLKKFSRSDELTRHYRTHTGEKQFRCPLCEK
RFMRSDHLTKHARRHTEFHPSMIKRSKKALANAL MAFF amino acid sequence
```

SEQUENCE LISTING:

```
                                                              SEQ ID NO: 78
MSVDPLSSKALKIKRELSENTPHLSDEALMGLSVRELNRHLRGLSAEEVTRLKQRRRTLKNRGYAASCRV
KRVCQKEELQKQKSELEREVDKLARENAAMRLELDALRGKCEALQGFARSVAAARGPATLVAPASVITIV
KSTPGSGSGPAHGPDPAHGPASCS
```

STAT4 amino acid sequence

```
                                                              SEQ ID NO: 79
MSQWNQVQQLEIKFLEQVDQFYDDNFPMEIRHLLAQWIENQDWEAASNNETMATILLQNLLIQLDEQLGR
VSKEKNLLLIHNLKRIRKVLQGKFHGNPMHVAVVISNCLREERRILAAANMPVQGPLEKSLQSSSVSERQ
RNVEHKVAAIKNSVQMTEQDTKYLEDLQDEFDYRYKTIQTMDQSDKNSAMVNQEVLTLQEMLNSLDFKRK
EALSKMTQIIHETDLLMNTMLIEELQDWKRRQQIACIGOPLHNGLDQLQNCFTLLAESLFQLRRQLEKLE
EQSTKMTYEGDPIPMQRTHMLERVTFLIYNLFKNSFVVERQPCMPTHPQRPLVLKTLIQFTVKLRLLIKL
PELNYQVKVKASIDKNVSTLSNRRFVLCGTNVKAMSIEESSNGSLSVEFRHLQPKEMKSSAGGKGNEGCH
MVTEELHSITFETQICLYGLTIDLETSSLPVVMISNVSQLPNAWASIIWYNVSTNDSQNLVFFNNPPPAT
LSQLLEVMSWQFSSYVGRGLNSDQLHMLAEKLTVQSSYSDGHLTWAKFCKEHLPGKSFTFWTWLEAILDL
IKKHILPLWIDGYVMGFVSKEKERLLLKDKMPGTFLLRFSESHLGGITFTWVDHSESGEVRFHSVEPYNK
GRLSALPFADILRDYKVIMAENIPENPLKYLYPDIPKDKAFGKHYSSQPCEVSRPTERGDKGYVPSVFIP
ISTIRSDSTEPHSPSDLLPMSPSVYAVLRENLSPTTIETAMKSPYSAE
```

TOX amino acid sequence

```
                                                              SEQ ID NO: 80
MDVRFYPPPAQPAAAPDAPCLOPSPCLDPYYCNKFDGENMYMSMTEPSQDYVPASQSYPGPSLESEDFNI
PPITPPSLPDHSLVHLNEVESGYHSLCHPMNHNGLLPFHPQNMDLPEITVSNMLGQDGTLLSNSISVMPD
IRNPEGTQYSSHPQMAAMRPRGQPADIRQQPGMMPHGQLTTINQSQLSAQLGLNMGGSNVPHNSPSPPGS
KSATPSPSSSVHEDEGDDTSKINGGEKRPASDMGKKPKTPKKKKKKDPNEPQKPVSAYALFFRDTQAAIK
GQNPNATFGEVSKIVASMWDOLGEEQKQVYKKKTEAAKKEYLKQLAAYRASLVSKSYSEPVDVKTSQPPQ
LINSKPSVFHGPSQAHSALYLSSHYHQQPGMNPHLTAMHPSLPRNIAPKPNNQMPVTVSIANMAVSPPPP
LQISPPLHQHLNMQQHQPLTMQQPLGNQLPMQVQSALHSPTMQQGFTLQPDYQTIINPTSTAAQVVTQAM
EYVRSGCRNPPPQPVDWNNDYCSSGGMQRDKALYLT
```

ZBTB16 amino acid sequence

```
                                                              SEQ ID NO: 81
MDLTKMGMIQLQNPSHPTGLLCKANQMRLAGTLCDVVIMVDSQEFHAHRTVLACTSKMFEILFHRNSQHY
TLDFLSPKTFQQILEYAYTATLQAKAEDLDDLLYAAEILEIEYLEEQCLKMLETIQASDDNDTEATMADG
GAEEEEDRKARYLKNIFISKHSSEESGYASVAGQSLPGPMVDQSPSVSTSFGLSAMSPTKAAVDSLMTIG
QSLLQGTLQPPAGPEEPTLAGGGRHPGVAEVKTEMMQVDEVPGQDSPGAAESSISGGMGDKVEERGKEGP
GTPTRSSVITSARELHYGREESAEQVPPPAEAGQAPTGRPEHPAPPPEKHLGIYSVLPNHKADAVLSMPS
SVTSGLHVQPALAVSMDFSTYGGLLPQGFIQRELFSKLGELAVGMKSESRTIGEQCSVCGVELPDNEAVE
QHRKLHSGMKTYGCELCGKRFLDSLRLRMHLLAHSAGAKAFVCDQCGAQFSKEDALETHRQTHTGTDMAV
FCLLCGKRFQAQSALQQHMEVHAGVRSYICSECNRTFPSHTALKRHLRSHTGDHPYECEFCGSCFRDEST
LKSHKRIHTGEKPYECNGCGKKFSLKHQLETHYRVHTGEKPFECKLCHQRSRDYSAMIKHLRTHNGASPY
QCTICTEYCPSLSSMQKHMKGHKPEEIPPDWRIEKTYLYLCYV
```

EXAMPLES

Example 1—Characterization of AML LSC

Patient Samples

Bone marrow (BM) or peripheral blood (PB) samples from normal donors undergoing orthopaedic procedures or bone marrow harvest and AML patients were obtained with informed consent (MREC #06/Q1606/110, #09/H0606/11, MREC 08/MRE09/29). Mononuclear cells were isolated by Ficoll density gradient. In normal BM samples, CD34+ cells were purified using CD34 Microbead Kit and MACS separation columns (Miltenyi Biotec, Bisley UK). Unseparated, CD34+ and CD34-deplete fractions were frozen in 90% FCS/10% DMSO and stored in liquid nitrogen, and subsequently thawed on the day of the experiment.

FACS Protocols

The antibodies used in the lineage depletion cocktail for purification of: (i) CD34− normal and CD34− AML samples were CD2, CD3, CD4, CD8a, CD10, CD19, CD20 and CD235a. Normal CD34− BM and CD34− AML samples were analysed and sorted using Lin depletion and antibodies to CD34, CD150, CD48, CD244 and CD117. Engraftment was assayed using antibodies to human CD45 (hCD45), CD19 and CD33. Bone marrow harvested from engrafted mice were analysed and sorted using antibodies to hCD45, CD33, CD19, CD34, CD150, CD48, CD244 and CD117.

FACS analysis was carried out on either a Cyan ADP (Dakocytomation, Ely UK) or a BD LSR Fortessa (Becton Dickinson, Oxford UK). Flow sorts were carried out on a BD Aria III SORP (Becton Dickinson, Oxford UK).

Calculating Frequency of Leukaemic Stem Cells

LSC frequency was calculated using L-Calc software (Stem Cell Technologies) using data from injecting variable numbers of leukaemia cells in limit dilution xenotransplantation assays (LDA). Percentages of sorted subpopulations of each sample used in LDA experiments were expressed as a % of live MNC. The LSC frequency of sorted subpopulation $\mathcal{H}$ per live MNCs was calculated as:

$$\text{LSC frequency (MNC)} = \text{LSC frequency } (\mathcal{H}) \times 100 / \mathcal{H} \text{ (\% of live MNC)}$$

The value of $100/\mathcal{H}$ (% of live MNC) represents the fold change enrichment over bulk live MNC Absolute no. of LPC per million bulk cells=1,000,000/LSC frequency (MNC)

Nucleic Acid Manipulation

DNA extraction was performed using DNeasy Blood and Tissue extraction kit (#69506) and RNA extraction using RNeasy Micro Kit (#74004) (QIAgen, Crawley UK). Whole genome amplification (WGA) was carried out using 3-10 ng of extracted genomic DNA or 3×10³-10⁴ sorted AML cells using Illustrate GenomiPhiV2 Amplification kit (GE Healthcare, Chalfont St Giles, UK). Nucleic acids were analysed quantified using Qubit assay (Invitrogen, Pailsey UK) or the appropriate Bioanalyser chip (Agilent, Wokingham, UK).

Gene Expression by Dynamic Arrays

Q RT-PCR analysis was performed with nanofluidic Bio-Mark 48.48 Dynamic Array (Fluidigm, San Francisco, USA) and TaqMan Gene Expression Assays (see list below; Life Technologies, Carlsbad, USA). cDNA generation and gene specific pre-amplification were carried out using CellsDirect One-Step qRT-PCR Kit (Life Technologies, Carlsbad, USA). 500 cells (>99% purity) were FACS-sorted into 96 well plates with 10 ul reaction buffer (5 µl CellsDirect 2× Reaction Mix, 1 µl of CellsDirect RT/Taq Mix, 0.4 µl water, 0.1 µl SUPERase-In RNase Inhibitor and 2.5 µl of a mix of 0.2× TaqMan Gene Expression Assays. Reverse transcription and specific target pre-amplification conditions were; 15 min @ 50° C.; 2 min 95° C.; 22 cycles 95° C. 15 s and 60° C. 4 min. Pre-amplified samples were diluted 1:4 and analysed on a 48.48 dynamic array (Fluidigm, San Francisco, USA). PCR cycling condition: 10 minutes @95° C.; 40 cycles of (15 seconds @95° C.; 60 seconds @ 60° C.). All reactions were carried out in 3 technical replicates. Data was analyzed using the Ct method; results were normalized to GAPDH expression and expressed as mean expression level relative to GAPDH.

| Gene Expression Assay | TaqMan Assay ID |
|---|---|
| GAPDH | Hs02758991_g1 |
| ELANE | Hs00975994_g1 |
| EPOR | Hs00959427_m1 |
| MPO | Hs00924296_m1 |
| PF4 | Hs00427220_g1 |
| SPI1 | Hs02786711_m1 |
| SPTB | Hs01024103_m1 |
| CSF3R | Hs00167918_m1 |
| ITGAM | Hs00355885_m1 |
| IL3RA | Hs00608141_ |

RNA Sequencing

Total RNA was extracted from 5×103-4×104 sorted cells, quantified using the total RNA Pico or Nano Bioanalyzer chip (Agilent, Wokingham UK). All samples had a RIN score of ≥7.0. 20 pg to 4 ng of total RNA was used for cDNA synthesis (SMARTer Ultra Low input RNA kit (Clontech, St Germain-en-Laye France). cDNA libraries were amplified and sequenced on the Illumina HiSeq 2000 and 2500 (paired end, read length: 50 base pairs; Illumina, Saffron Walden, UK). Sequences were aligned to human reference genome genome (hg19/GRCh37) using TopHat v2.0.8 [http://tophat.cbcb.umd.edu/]. PCR duplicates were removed and reads were filtered for uniquely mapping reads (MAPQ>3) using SAMtools version 0.1.19. Data analyses were performed using the R software environment for statistical computing, version 3.0.1 http://www.R-project.org. Gene-level read summarization was carried out using the R package Genomic ranges (http://www.bioconductor.org/packages/release/bioc/html/GenomicRanges.html) and gene expression analysis was conducted using edgeR.

Gene Expression Profiling

We used a filtering strategy to eliminate non-expressed or only marginally expressed genes from the 59689 genes defined in Ensembl. We retained the genes that have a cpm (counts per million)>2 in at least half of the samples of at least one of the experimental conditions considered. Thus, for example in the non-leukaemic samples we retained 16284 genes for further analysis.

We generated gene expression profiles by computing differential gene expression. Our experimental design included comparisons of (a) all populations using an ANOVA approach (b) single populations against other single populations (c) single populations against the average of the remaining populations. Differential gene expression was computed using generalized linear models. Where appropriate, we included the donor as an additive covariate to correct for donor specific effects. We calculated the log 2 fold-changes, the p-values of differential expression and the FDR-adjusted pvalues of differential expression of all genes in all the profiles. To perform Principal Component Analysis (PCA) we used the ANOVA expression profile (11049 genes at FDR<0.05) and selected the 300 genes with the highest significance (FDR p-value <3.3e—39). The read counts of these genes were normalised as counts per million (cpm) and log 2—transformed. Based on these expression values we performed PCA of (a) normal samples (b) normal and leukaemic samples. We computed the Pearson correlation of the normal and leukaemic samples and generated a correlation matrix. In addition, we selected the 1000 and 3000 most significant genes based on their FDR p-value to perform PCA.

Gene Set Enrichment Analysis

We used gene set enrichment analysis (GSEA) to test the enrichment of specific population signatures in our expression profiles. Population specific signatures were computed from a subset of the gene expression values described above by selecting genes that are upregulated with an FDR adjusted p-value <0.05. Among these, the 250 with the highest fold-changes were selected and the Ensembl gene identifiers were translated to HGNC symbols in order to be used as gene sets in GSEA.

Results

Figure 1C:
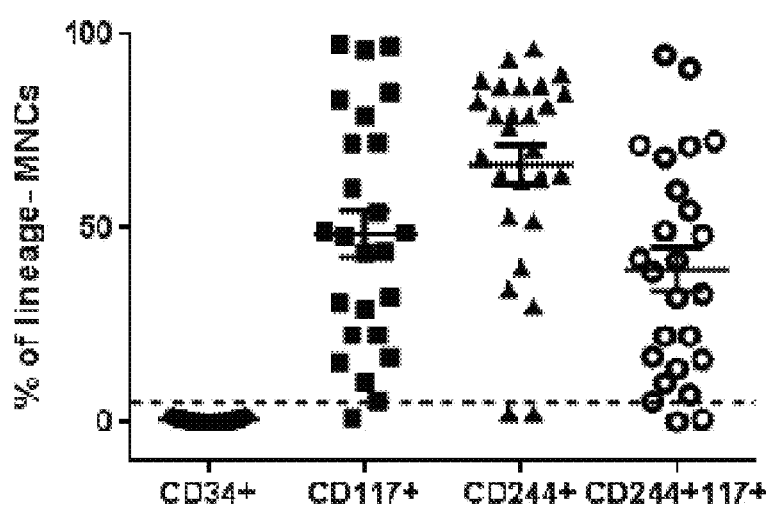
Figure 2A:
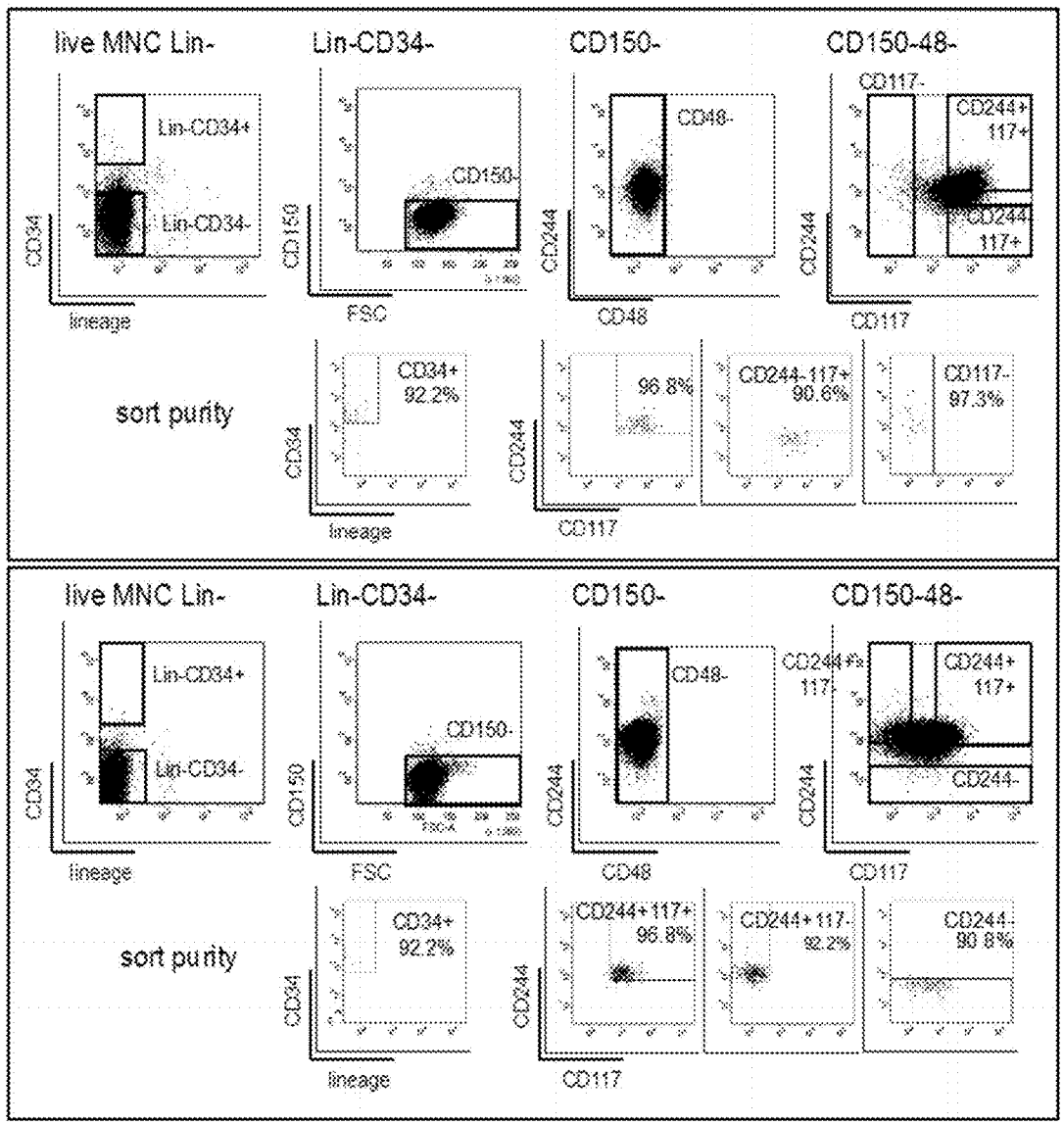
Figure 2B:
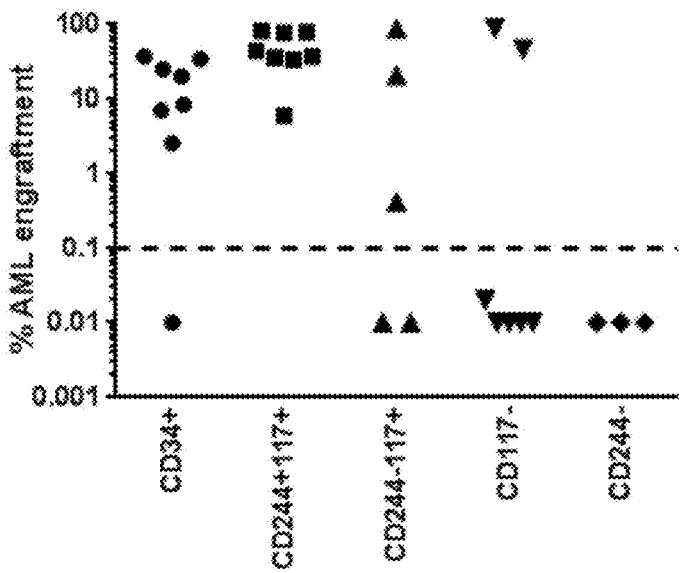
Figure 2C:
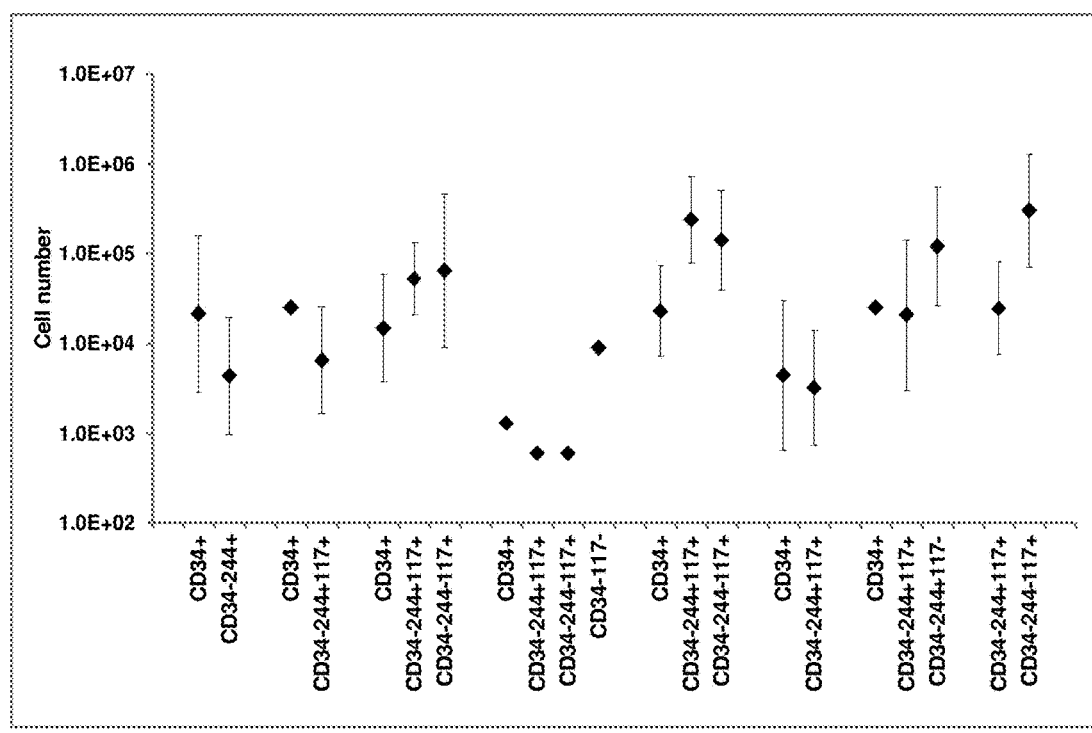

We screened 49 randomly selected AML samples where 0.0-1.5% (mean 0.5%) of mononuclear cells (MNCs) expressed CD34, of which 29 samples were mutated for NPM1 (FIG. 1A). 28/49 samples were tested for leukaemia propagation in vivo in immunodeficient mice. In addition to CD34, we further immunophenotyped samples with CD117; and the SLAM markers CD150, CD48 and CD244. Of these, only CD244 was significantly expressed by our cohort (FIG. 1B). Most of the injected samples expressed CD117, the majority of which also co-expressed CD244 (FIG. 1C). 11 samples, FACS sorted using CD34+/−CD244 and CD117, showed long-term engraftment with AML (defined by detection of >0.1% human CD45+33+19-blasts, harbouring AML-associated mutations). For engrafting populations, LSC activity was confirmed by serial transplantation assays, cell numbers permitting. We were able to perform further detailed analysis in 8/11 engrafting samples. In 7/8 cases sortable CD34+ fractions had LSC activity. Within the CD34− fraction, CD117 expression, especially when co-expressed with CD244 predicted LSC activity. There were 2 exceptional samples where CD34− 117− cells had LSC activity, #1037 where all sorted subpopulations engrafted mice aggressively; and #001 where the level of engraftment of cell equivalent CD117-population was 40-70× lower compared with CD117+ counterparts (FIG. 2B). Engrafting populations did so at cell doses equivalent or lower than non-engrafting populations (data not shown). LSC frequencies (range 0.07-237 cells/$10^6$) were similar between CD34+ and CD34− LSCs within a patient sample (FIG. 2C). In all 8 engrafting AML samples, CD34− 244+117+ fractions constituted the majority and accounted for 69.4-99.9% of total LSCs of the bulk sample. Accordingly the fold enrichment of LSCs in this compartment was modest (1.1-4.6×) whereas that seen in the smaller fractions CD34+(42-477×) and CD34− 244-117+(6.8-232×) were greater.

Figure 2D:
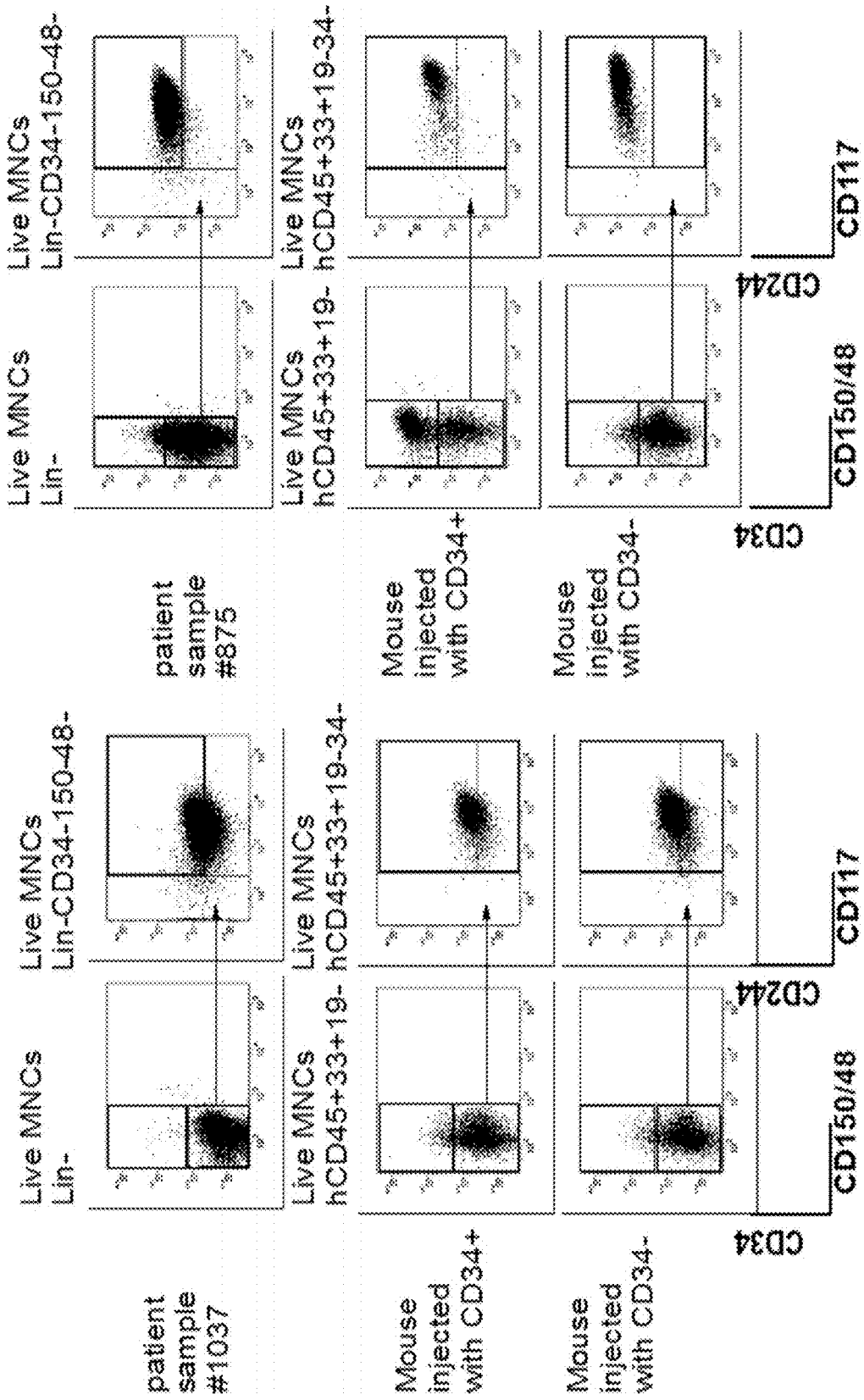

Engrafted LSCs recapitulated the immunophenotype of the patient's leukemia. The detection of CD34+ and CD34− engrafted leukaemia was independent of the CD34 expressing status of the injected parent population (FIG. 2D). This suggests that there is no hierarchy between CD34+ and CD34− LSC populations. Primary engrafted CD34+ and CD34− progeny of patient CD34+ and CD34− populations propagated leukemia in secondary transplantation experiments (data not shown). We also compared RNA sequencing profiles of CD34+LSC and CD34− LSC. Out of 15539 expressed genes, only 8 protein coding genes were significantly differentially expressed, of which 6 (including CD34) had >2-fold difference between the two LSC populations (p<0.05). In summary, non-hierarchically arranged CD34+ and CD34− populations with similar global gene expression have LSC function. Within the CD34− population, CD117 expression marks LSC populations enriching for LSC activity in some samples.

Figure 3B:
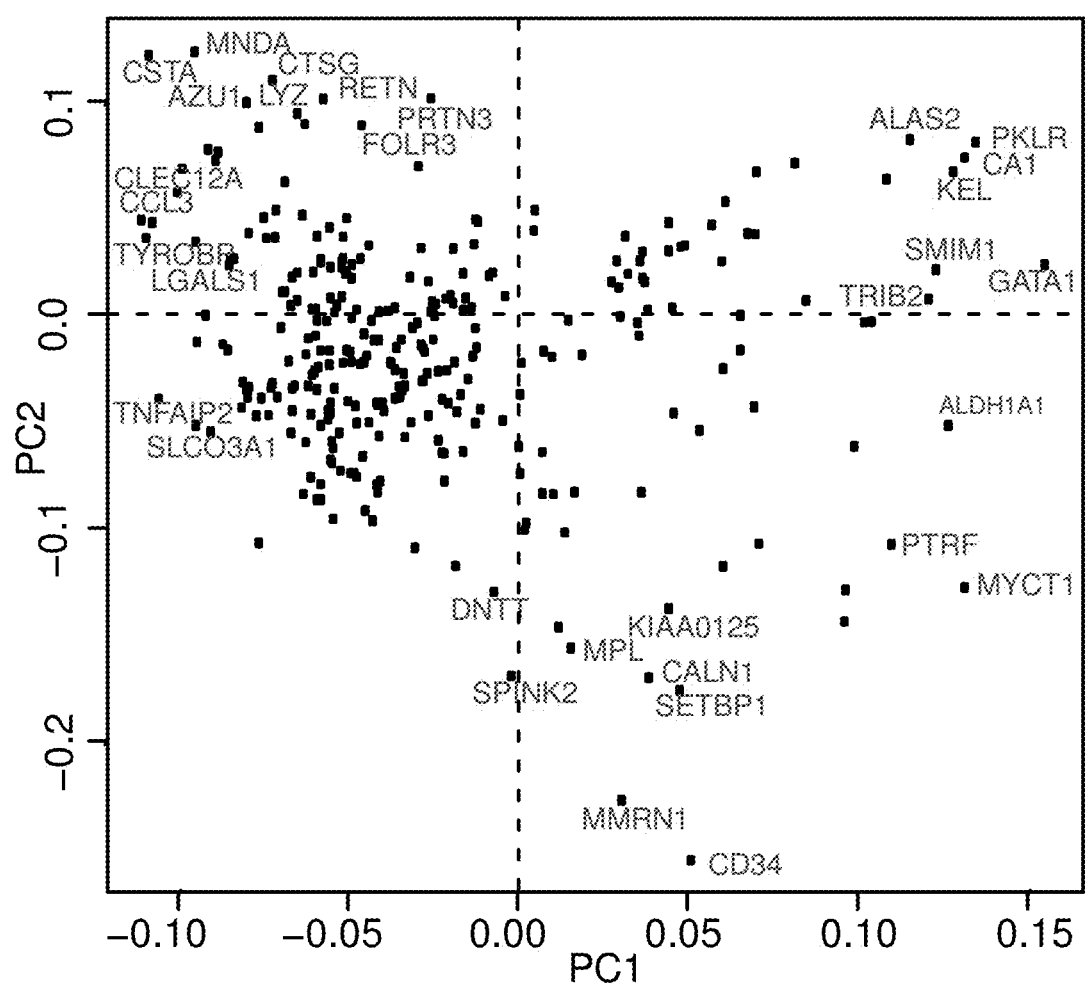
FIG. 3B Loadings plot for PCA in FIG. 3A. Genes contributing most to variability in PC1 and PC2 are annotated.

Finally we addressed the question of how CD34-negative AML LSCs relate to normal haematopoeitic populations. In addition to CD34− precursor populations, we purified normal CD34+HSPC: haematopoietic stem cells (HSC), multipotent (MPP), lymphoid-primed multipotent (LMPP), common myeloid (CMP), granulocyte-macrophage (GMP) and megakaryocyte-erythroid (MEP) progenitors (FIG. 3A-3F) and both CD34+ and CD34− CD34-negative AML LSCs in order to perform mRNA sequencing (RNAseq). Using ANOVA, we defined 11049 genes differentially expressed between functionally distinct normal cell populations (p<0.05). We then performed Principle Component Analyses (PCA) of 300, 1000 and 3000 of the most significantly differentially expressed genes ranked by p-value. The 300-gene set resulted in the best spatial segregation of the normal populations (adjusted p≤3.3$^{-39}$) and the best clustering of biologic replicates. The topology of the PCA shows the close clustering of HSC and MPP populations, and a bifurcation of erythroid and myeloid populations of increasing maturity. PCA with both normal and LSC populations shows clustering of LSCs, closest to normal myeloid precursors. There is neither segregation of CD34+ and CD34− LSCs within CD34-negative AML group nor was clustering affected by NPM1 mutation status (FIG. 3A). In contrast, CD34+ progenitor-like LSCs clustered separately, lying closest to normal GMP/LMPP. Pearson correlation test using the 300-gene set confirms the clustering pattern seen in PCA (data not shown).

Given that CD34− AML LSCs are most closely related to normal myeloid precursors but are functional stem cells, we tested whether CD34-negative LSC have a hybrid expression signature encompassing profiles of both normal HSCs and myeloid precursors. We derived signatures for normal HSPC populations and validated them. Our HSC/MPP signature is highly enriched in CD34-LSC compared to normal GMP and CD34− 244+117+ fractions (NES 2.75, FIG. 3C). The enrichment of a myeloid precursor signature in the LSCs is also marked (NES 2.8, FIG. 3D), and more significant than that seen with a GMP signature (NES 1.8, FIG. 3E).

Figure 3H:
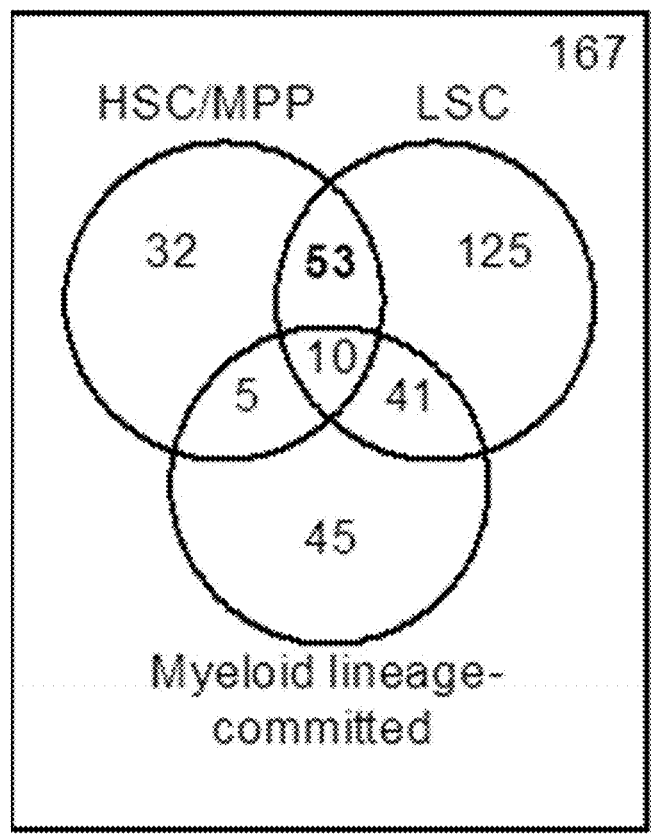
FIG. 3H Venn diagram showing overlap of differentially expressed TFs (versus average level of expression; p<0.05) in each of the indicated populations: normal HSC/MPP, normal GMP/CD244+117+/CD34− 244+117− (myeloid cells) and CD34− AML LSCs. 53 TF genes were shared exclusively by HSC/MPP and LSCs. 16/53 differentially expressed TF expressed in HSC/MPP and LSC are shown.

Next, we addressed the relationship of transcription factor (TF) expression in CD34− AML LSCs and normal haematopoietic populations. PCA with 525 curated TF genes shows that CD34-negative LSCs occupy a unique position reflecting its hybrid stem and myeloid nature, distinct from CD34-positive progenitor-like LSCs (FIG. 3F). TF genes most important in the clustering of CD34-negative LSCs include HOX genes (HOXA5, A7, B3, B5 and B6), the HOX cofactor MEIS1 and oncogenic TFs MYCN and ERG (FIG. 3G). Finally, there is significant overlap of differentially expressed TFs in CD34-negative LSCs with normal HSC/MPP and myeloid-lineage populations (FIG. 3H). TFs shared by both HSC/MPP and LSC populations include AFF1, KMT2A, ETV5, GATA2, MEIS1, MYCN and ZBTB16/PLZF and multiple HOX genes.

CD34-negative AML is genetically and functionally distinct. We now demonstrate that: (i) Experimentally defined LSC function in the CD34− fraction is more commonly present in CD117-expressing cells that can either be CD244+117+ or CD244−117+. (ii) There is no hierarchy between CD34+ and CD34− LSC as each immunophenotypic population gives rise to the other during serial transplantation. Thus, CD34+ expression is not a fixed maturation-associated marker. (iii) Concordant with this only 8 genes are differentially expressed between CD34+ and CD34− LSC populations. Global gene expression and PCA analysis confirms that CD34+ and CD34− LSC populations in CD34 negative AML are highly related and their closest normal counterparts are CD34− myeloid precursors. This suggests to differentiation arrest has occurred in these LSC populations at a more mature stage than CD34-positive progenitor-like LSCs. However, LSCs have aberrant self-renewal and this is reflected in their expression of HSC-associated genes.

Evaluation of transcriptional programmes of CD34− AML LSC populations also shows that unlike normal myeloid lineage-committed populations, these LSC express HSC/MPP genes. These include TFs implicated in stem cell function and myeloid leukemia, e.g. GATA2, PLZF and MYCN. Though, it is unclear if their expression in CD34− AML LSCs is mechanistically important for leukemogenesis, overexpression of Mycn can lead to rapidly fatal AML. Aberrant expression of KMT2A (or MLL), the MLL-translocation partner protein AFF1 (also known as AF4), MLL target genes—the HOX family and HOX co-factor MEIS1 in CD34− LSC compared to normal myeloid precursors is noteworthy. Increased Hox gene expression occurs in Lin− haematopoietic progenitors of knock-in Npm1c mutant mice suggesting mutant NPM1 expression may directly cause the increased of these TF in human CD34− AML. It also raises the hypothesis that AML associated with mutant MLL and mutant NPM1 (both of which are often CD34−) may share some overlapping oncogenic mechanisms.

Example 2—Prognostic Application of Diagnostic Screen of the Present Invention

A 62 year old male suffering from symptoms of pancytopenia presents himself to hospital. 10 ml of blood and/or 2 mls of bone marrow is removed for diagnostic and for flow cytometery evaluation. The biological samples are treated either as in Example 1 or with red cell lysis buffer to remove red cells. Then the nucleated cells are incubated with antibodies as described in Example 1 that are either directly conjugated or indirectly conjugated. Excess unbound antibody is washed off. The stained cells are then put through a flow cytometer. Data is then collected and prognosis is made.

Example 3—Use of the Diagnostic Screen of the Present Invention in an In Vitro Assay to Identify a Therapeutic Candidate A 33 year old with known Acute Myeloid Leukaemia presents himself to hospital. 10 ml of blood and/or 2 mls of bone marrow is removed to monitor residual leukaemia stem cells for flow cytometry evaluation. The biological samples are treated either as in Example 1 or with red cell lysis buffer to remove red cells. Then the nucleated cells are incubated with antibodies as described in Example 1 that are either directly conjugated or indirectly conjugated. Excess unbound antibody is washed off. The stained cells are then put through a flow cytometer. Data is then collected and the effect of a therapeutic candidate assessed.

Example 4—Prognostic Application of Gene Expression Profile of the Present Invention A 67 year old female suffering from symptoms of pancytopenia presents herself to hospital. 2 mls of bone marrow is removed. Total RNA is extracted from the sample and in toto RNA sequencing is performed (RNA-Seq) and the sample is analysed to determine whether the gene profile of the present invention is present i.e. the genes are differentially expressed relative to a non-acute myeloid leukaemia leukaemic stem cell population. A positive test result confirms the presence of AML LSC and prognosis is made.

Example 5—AML Therapy

Following the prognosis made as described in inter alia Examples 2 and 4 above, an AML treatment regimen is initiated comprising chemotherapy and/or stem cell transplant therapy.

The invention claimed is:

1. A method for detecting acute myeloid leukaemia (AML) leukaemic stem cells (LSCs) comprising:
   i. contacting an isolated sample containing a blood cell population with:
      a first antibody that specifically binds to CD34;
      a second antibody that specifically binds to CD48;
      a third antibody that specifically binds to CD117;
      a fourth antibody that specifically binds to CD150; and
      a fifth antibody that specifically binds to CD244; and
   ii. detecting:
      the absence of binding between the first, second, and fourth antibodies and a blood cell comprised in said isolated sample, and the presence of binding between the third and fifth antibodies and said blood cell; or
      the absence of binding between the first, second, fourth, and fifth antibodies and said blood cell, and the presence of binding between the third antibody and said blood cell;
   thereby confirming that said blood cell is an AML LSC; or
   iii. not detecting:
      the absence of binding between the first, second, and fourth antibodies and a blood cell comprised in said isolated sample, and the presence of binding between the third and fifth antibodies and said blood cell; or
      the absence of binding between the first, second, fourth, and fifth antibodies and said blood cell, and the presence of binding between the third antibody and said blood cell;
   thereby confirming that said blood cell is not an AML LSC.

2. The method according to claim 1 further comprising contacting the isolated sample with one or more selected from the group consisting of:
   an antibody that specifically binds to CD2;
   an antibody that specifically binds to CD3;
   an antibody that specifically binds to CD4;
   an antibody that specifically binds to CD8a;
   an antibody that specifically binds to CD10;
   an antibody that specifically binds to CD19;
   an antibody that specifically binds to CD20; and
   an antibody that specifically binds to CD235a.

3. A method for determining the prognosis and treatment of acute myeloid leukaemia and/or a symptom thereof, comprising:
   i. contacting an isolated sample obtained from a patient containing a blood cell population with:
      a first antibody that specifically binds to CD34;
      a second antibody that specifically binds to CD48;
      a third antibody that specifically binds to CD117,
      a fourth antibody that specifically binds to CD150; and
      a fifth antibody that specifically binds to CD244;
   ii. detecting:
      the absence of binding between the first, second, and fourth antibodies and a blood cell comprised in said isolated sample, and the presence of binding between the third and fifth antibodies and said blood cell; or
      the absence of binding between the first, second, fourth, and fifth antibodies and said blood cell, and the presence of binding between the third antibody and said blood cell; and
   iii. administering to said patient a therapy for acute myeloid leukaemia and/or a symptom thereof.

4. The method according to claim 3 further comprising contacting the isolated sample with one or more selected from the group consisting of:
   an antibody that specifically binds to CD2;
   an antibody that specifically binds to CD3;
   an antibody that specifically binds to CD4;
   an antibody that specifically binds to CD8a;
   an antibody that specifically binds to CD10;
   an antibody that specifically binds to CD19;
   an antibody that specifically binds to CD20; and
   an antibody that specifically binds to CD235a.

5. A method of treating acute myeloid leukaemia in a patient comprising:
   i. requesting performance of the method of claim 1 and/or obtaining the results of the method of claim 1; and
   ii. administering to said patient a therapy for acute myeloid leukaemia (AML) if the presence of acute myeloid leukaemia (AML) leukaemic stem cells (LSC) is confirmed.

* * * * *